United States Patent
Itoh et al.

(10) Patent No.: US 8,278,473 B2
(45) Date of Patent: Oct. 2, 2012

(54) ALPHA, BETA-UNSATURATED IMIDATE COMPOUND AND PESTICIDAL COMPOSITION CONTAINING THE SAME

(75) Inventors: Shigeyuki Itoh, Oita (JP); Tomohiro Araki, Toyonaka (JP)

(73) Assignee: Sumitomo Chemical Company, Limited, Tokyo (JP)

(*) Notice: Subject to any disclaimer, the term of this patent is extended or adjusted under 35 U.S.C. 154(b) by 118 days.

(21) Appl. No.: 12/741,783

(22) PCT Filed: Nov. 14, 2008

(86) PCT No.: PCT/JP2008/071170
§ 371 (c)(1),
(2), (4) Date: May 6, 2010

(87) PCT Pub. No.: WO2009/064031
PCT Pub. Date: May 22, 2009

(65) Prior Publication Data
US 2010/0240729 A1  Sep. 23, 2010

(30) Foreign Application Priority Data

Nov. 16, 2007 (JP) ................... 2007-297731
Feb. 28, 2008 (JP) ................... 2008-047415

(51) Int. Cl.
*C07C 331/00* (2006.01)
*A61K 31/38* (2006.01)

(52) U.S. Cl. ............... 558/2; 558/6; 514/438; 514/508

(58) Field of Classification Search ............ 514/438, 514/508; 558/2, 6
See application file for complete search history.

(56) References Cited

FOREIGN PATENT DOCUMENTS

| JP | 9-202766 A | 8/1997 |
|---|---|---|
| WO | 96/16026 A1 | 5/1996 |
| WO | 2007/063702 A2 | 6/2007 |

OTHER PUBLICATIONS

Minami et al. CAS:153:358347, 2010.*
Fujita et al. CAS: 77:74988, 1972.*
M. Bluhm, et al., "3-Aminoiminoacrylate, 3-Aminoacrylate, and 3-Amidoiminomalonate Complexes as Catalysts for the Dimerization of Olefins," Organometallics, 2005, pp. 4139-4152, vol. 24, No. 17.
Z. Yoshida, et al., "Trithiocyclopropenium Ion as a Building Block for Nitrogen Heterocycle Synthesis," Tetrahedron, 1989, pp. 3217-3231, vol. 45, No. 10.
Hiroshi Fujita, et al., "A Novel Cleavage of Carbon-Carbon Triple Bond", Bulletin of the Chemical Society of Japan, May 1972, p. 1581.

* cited by examiner

*Primary Examiner* — Rei-tsang Shiao
(74) *Attorney, Agent, or Firm* — Sughrue Mion, PLLC

(57) ABSTRACT

There is provided a compound having an excellent controlling effect on pests, represented by the formula (I):

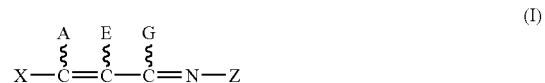

wherein,

A and E independently represent a —$R^1$ group, a -$L^1$-$R^1$ group, etc.; G represents a -$L^2$-$R^1$ group, a —$S(O)_2$—$R^4$ group, etc.; X represents a —S—$R^5$ group or a —O—$R^6$ group; Z represents an optionally substituted carbocyclic group or an optionally substituted heterocyclic group; $R^1$ represents an optionally substituted C1-C20 chain hydrocarbon group, etc.; $R^5$ represents a substituted C1-C4 alkyl group, an optionally substituted C5-C10 alkyl group, etc.; $R^6$ represents a substituted C1-C2 alkyl group, an optionally substituted C3-C10 alkyl group, etc.; $L^1$ represents a an oxygen atom, a sulfur atom, a —S(O)— group, or a —$S(O)_2$— group; and $L^2$ represents an oxygen atom or a sulfur atom.

17 Claims, No Drawings

ALPHA, BETA-UNSATURATED IMIDATE COMPOUND AND PESTICIDAL COMPOSITION CONTAINING THE SAME

TECHNICAL FIELD

The present invention relates to an α,β-unsaturated imidate compound and a pesticidal composition containing the same.

BACKGROUND ART

For controlling pests, various kinds of compounds have been developed and used practically.

A thioimidate compound is described in JP-A 09-202766.

DISCLOSURE OF THE INVENTION

An object of the present invention is to provide a compound having an excellent controlling effect on pests.

The present inventors have intensively studied so as to achieve the above object, and as a result, they found that an α,β-unsaturated imidate compound represented by the following formula (I) has an excellent pest controlling effect. Thus, the present invention has been completed.

The present invention includes:
[1] A compound represented by the formula (I):

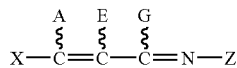

(I)

wherein,

A and E independently represent a —$R^1$ group, a -$L^1$-$R^1$ group, a —S—C(=O)—$R^1$ group, a —O—C(=O)—$R^1$ group, a —O—S(O)$_2$—$R^1$ group, a —C(=O)—$R^1$ group, a —C(=O)—O—$R^1$ group, a —N($R^2$)—$R^3$ group, a halogen atom, a cyano group, a nitro group, or a hydrogen atom, provided that at least one of A and E is a —$R^1$ group, a -$L^1$-$R^1$ group, a —S—C(=O)—$R^1$ group, a —O—C(=O)—$R^1$ group, a —O—S(O)$_2$—$R^1$ group, a —C(=O)—$R^1$ group, a —C(=O)—O—$R^1$ group, a —N($R^2$)—$R^3$ group, a halogen atom, a cyano group, or a nitro group;

G represents a -$L^2$-$R^1$ group, a —S(O)$_2$—$R^4$ group, or a —N($R^2$)—$R^3$ group;

X represents a —S—$R^5$ group or a —O—$R^6$ group;

Z represents a carbocyclic group having 3 to 14 ring-constituting atoms which is optionally substituted with a group selected from the group a, or a heterocyclic group having 3 to 14 ring-constituting atoms which is optionally substituted with a group selected from the group a;

$R^1$ represents a C1-C20 chain hydrocarbon group which is optionally substituted with a group selected from the group b, a carbocyclic group having 3 to 14 ring-constituting atoms which is optionally substituted with a group selected from the group a, or a heterocyclic group having 3 to 14 ring-constituting atoms which is optionally substituted with a group selected from the group a;

$R^2$ represents a hydrogen atom or a —$R^1$ group;

$R^3$ represents a —$R^1$ group, a —O—$R^1$ group, a mono(C1-C6 alkyl)amino group, a di(C1-C6 alkyl)amino group, a (C1-C6 alkyl)phenylamino group, a —C(=O)—$R^1$ group, or a —C(=O)—O—$R^1$ group;

$R^4$ represents a C1-C10 hydrocarbon group;

$R^5$ represents a C1-C4 alkyl group substituted with a group selected from the group b, a C5-C10 alkyl group which is optionally substituted with a group selected from the group b, a C3-C10 alkenyl group which is optionally substituted with a group selected from the group c, a C3-C10 alkynyl group which is optionally substituted with a group selected from the group c, a carbocyclic group having 3 to 14 ring-constituting atoms which is optionally substituted with a group selected from the group a, or a heterocyclic group having 3 to 14 ring-constituting atoms which is optionally substituted with a group selected from the group a;

$R^6$ represents a C1-C2 alkyl group substituted with a group selected from the group b, a C3-C10 alkyl group which is optionally substituted with a group selected from the group b, a C3-C10 alkenyl group which is optionally substituted with a group selected from the group c, a C3-C10 alkynyl group which is optionally substituted with a group selected from the group c, a carbocyclic group having 3 to 14 ring-constituting atoms which is optionally substituted with a group selected from the group a, a heterocyclic group having 3 to 14 ring-constituting atoms which is optionally substituted with a group selected from the group a, or a —S(O)$_2$—$R^1$ group;

$L^1$ represents a an oxygen atom, a sulfur atom, a —S(O)— group, or a —S(O)$_2$— group;

$L^2$ represents an oxygen atom or a sulfur atom;

the group a represents the group consisting of a halogen atom, a cyano group, a nitro group, a -$Q^3$ group, a -$L^1$-$Q^3$ group, a —C(=O)-$Q^3$ group, a —C(=O)—O-$Q^3$ group, a —C(=O)—N ($Q^1$)-$Q^3$ group, a —O—C(=O)-$Q^3$ group, a —N ($Q^3$)-C(=O)-$Q^3$ group, a —N($Q^1$)-$Q^3$ group, and a -$L^1$-T-$Q^3$ group;

the group b represents the group consisting of a halogen atom, a cyano group, a nitro group, a -$Q^2$ group, a -$L^1$-$Q^3$ group, a —C(=O)-$Q^3$ group, a —C(=O)—O-$Q^3$ group, a —C(=O)—N ($Q^1$)-$Q^3$ group, a —O—C(=O)-$Q^3$ group, a —N ($Q^3$)-C(=O)-$Q^3$ group, a —N($Q^1$)-$Q^3$ group, and a -$L^1$-T-$Q^3$ group;

the group c represents the group consisting of a halogen atom, a -$Q^2$ group, a —C(=O)-$Q^3$ group, a —C(=O)—O-$Q^3$ group, and a —C(=O)—N($Q^1$)-$Q^3$ group;

$Q^1$ represents a C1-C6 chain hydrocarbon group which is optionally substituted with a halogen atom;

$Q^2$ represents a carbocyclic group having 3 to 14 ring-constituting atoms which is optionally substituted with a group selected from the group d, or a heterocyclic group having 3 to 14 ring-constituting atoms which is optionally substituted with a group selected from the group d;

the group d represents the group consisting of a C1-C6 chain hydrocarbon group which is optionally substituted with a halogen atom, a phenyl group which is optionally substituted with a halogen atom, a C1-C6 alkoxy group which is optionally substituted with a halogen atom, a C1-C6 alkylthio group which is optionally substituted with a halogen atom, a halogen atom, a cyano group, and a nitro group;

$Q^3$ represents a -$Q^1$ group or a -$Q^2$ group; and

T represents a C1-C6 alkanediyl group which is optionally substituted with a halogen atom;

[2] The compound according to the above [1], wherein
E is a hydrogen atom; and
A is a —$R^1$ group, a -$L^1$-$R^1$ group, a —S—C(=O)—$R^1$ group, a —O—C(=O)—$R^1$ group, a —O—S(O)$_2$—$R^1$ group, a —C(=O)—$R^1$ group, a —C(=O)—O—$R^1$ group, a —N($R^2$)—$R^3$ group, a halogen atom, a cyano group, or a nitro group;

[3] The compound according to the above [1], wherein
A is a hydrogen atom; and
E is a —$R^1$ group, a -$L^1$-$R^1$ group, or a halogen atom;

[4] The compound according to the above [1], wherein
A is a hydrogen atom; and
E is a methyl group, an ethyl group, or a propyl group;

[5] The compound according to the above [1], wherein
G is a —S—$R^{1g}$ group or a —O—$R^{1g}$ group;
X is a —S—$R^{5x}$ group or a —O—$R^{R6x}$ group;
Z is a phenyl group which is optionally substituted with a group selected from the group a;
A is a hydrogen atom;
E is a —$R^1$ group or a -$L^1$-$R^1$ group;
$L^1$ is an oxygen atom or a sulfur atom;
$R^1$ is a C1-C10 alkyl group which is optionally substituted with a group selected from the group b, a phenyl group which is optionally substituted with a group selected from the group a, or a thienyl group which is optionally substituted with a group selected from the group a;
$R^{1g}$ is a C1-C10 alkyl group which is optionally substituted with a group selected from the group b, a phenyl group which is optionally substituted with a group selected from the group a, a naphthyl group which is optionally substituted with a group selected from the group a, or a thienyl group which is optionally substituted with a group selected from the group a; and
$R^{6x}$ and $R^{5x}$ independently represent a phenyl group which is optionally substituted with a group selected from the group a, or a naphthyl group which is optionally substituted with a group selected from the group a;

[6] The compound according to the above [1], wherein
G is a —S—$R^{1g}$ group or a —O—$R^{1g}$ group;
X is a —O—$R^{6x}$ group;
Z is a phenyl group which is optionally substituted with a group selected from the group a;
A is a hydrogen atom;
E is a —$R^1$ group;
$R^1$ is a C1-C10 alkyl group which is optionally substituted with a group selected from the group b, a phenyl group which is optionally substituted with a group selected from the group a, or a thienyl group which is optionally substituted with a group selected from the group a;
$R^{1g}$ is a C1-C10 alkyl group which is optionally substituted with a group selected from the group b, a phenyl group which is optionally substituted with a group selected from the group a, a naphthyl group which is optionally substituted with a group selected from the group a, or a thienyl group which is optionally substituted with a group selected from the group a; and
$R^{6x}$ is a phenyl group which is optionally substituted with a group selected from the group a, or a naphthyl group which is optionally substituted with a group selected from the group a;

[7] The compound according to the above [1], wherein
G is a —S—$R^{1g}$ group;
X is a —O—$R^{6x}$ group;
Z is a phenyl group which is optionally substituted with a group selected from the group a;
A is a hydrogen atom;
E is a —$R^1$ group;
$R^1$ is a C1-C10 alkyl group which is optionally substituted with a group selected from the group b, a phenyl group which is optionally substituted with a group selected from the group a, or a thienyl group which is optionally substituted with a group selected from the group a;
$R^{1g}$ is a C1-C10 alkyl group which is optionally substituted with a group selected from the group b, a phenyl group which is optionally substituted with a group selected from the group a, a naphthyl group which is optionally substituted with a group selected from the group a, or a thienyl group which is optionally substituted with a group selected from the group a; and
$R^{6x}$ is a phenyl group which is optionally substituted with a group selected from the group a, or a naphthyl group which is optionally substituted with a group selected from the group a;

[8] The compound according to the above [1], wherein
G is a —O—$R^{1g}$ group;
X is a —O—$R^{6x}$ group;
Z is a phenyl group which is optionally substituted with a group selected from the group a;
A is a hydrogen atom;
E is a —$R^1$ group;
$R^1$ is a C1-C10 alkyl group which is optionally substituted with a group selected from the group b, a phenyl group which is optionally substituted with a group selected from the group a, or a thienyl group which is optionally substituted with a group selected from the group a;
$R^{1g}$ is a C1-C10 alkyl group which is optionally substituted with a group selected from the group b, a phenyl group which is optionally substituted with a group selected from the group a, a naphthyl group which is optionally substituted with a group selected from the group a, or a thienyl group which is optionally substituted with a group selected from the group a; and
$R^{6x}$ is a phenyl group which is optionally substituted with a group selected from the group a, or a naphthyl group which is optionally substituted with a group selected from the group a;

[9] The compound according to the above [1], wherein
G is a —S—$R^{1g}$ group;
X is a —O—$R^{6x}$ group;
Z is a phenyl group which is optionally substituted with a group selected from the group a;
A is a hydrogen atom;
E is a methyl group, an ethyl group, or a propyl group; is a C1-C10 alkyl group which is optionally substituted with a group selected from the group b, a phenyl group which is optionally substituted with a group selected from the group a, a naphthyl group which is optionally substituted with a group selected from the group a, or a thienyl group which is optionally substituted with a group selected from the group a; and
$R^{6x}$ is a phenyl group which is optionally substituted with a group selected from the group a; or a naphthyl group which is optionally substituted with a group selected from the group a;

[10] The compound according to the above [1], wherein
G is a —S—$R^{1g}$ group;
X is a —O—$R^{6x}$ group;
Z is a phenyl group which is optionally substituted with a group selected from the group a;
A is a hydrogen atom;
E is a —$R^1$ group;
$R^1$ is a C1-C10 alkyl group which is optionally substituted with a group selected from the group b, a phenyl group which is optionally substituted with a group selected from the group a, or a thienyl group which is optionally substituted with a group selected from the group a;
$R^{1g}$ is a phenyl group which is optionally substituted with a group selected from the group a, or a naphthyl group which is optionally substituted with a group selected from the group a; and
$R^{6x}$ is a phenyl group which is optionally substituted with a group selected from the group a, or a naphthyl group which is optionally substituted with a group selected from the group a;

[11] The compound according to the above [1], wherein
G is a —S—$R^{1g}$ group;
X is a —O—$R^{6x}$ group;
Z is a phenyl group which is optionally substituted with a group selected from the group a;
A is a hydrogen atom;
E is a methyl group, an ethyl group, or a propyl group;
$R^{1g}$ is a phenyl group which is optionally substituted with a group selected from the group a, or a naphthyl group which is optionally substituted with a group selected from the group a; and
$R^{6x}$ is a phenyl group which is optionally substituted with a group selected from the group a; or a naphthyl group which is optionally substituted with a group selected from the group a;

[12] The compound according to the above [1], wherein
G is a —O—$R^{1g}$ group;
X is a —O—$R^{6x}$ group;
Z is a phenyl group which is optionally substituted with a group selected from the group a;
A is a hydrogen atom;
E is a methyl group, an ethyl group, or a propyl group;
$R^{1g}$ is a C1-C10 alkyl group which is optionally substituted with a group selected from the group b, a phenyl group which is optionally substituted with a group selected from the group a, a naphthyl group which is optionally substituted with a group selected from the group a, or a thienyl group which is optionally substituted with a group selected from the group a; and
$R^{6x}$ is a phenyl group which is optionally substituted with a group selected from the group a, or a naphthyl group which is optionally substituted with a group selected from the group a;

[13] The compound according to the above [1], wherein
G is a —O—$R^{1g}$ group;
X is a —O—$R^{6x}$ group;
Z is a phenyl group which is optionally substituted with a group selected from the group a;
A is a hydrogen atom;
E is a —$R^1$ group;
$R^1$ is a C1-C10 alkyl group which is optionally substituted with a group selected from the group b, a phenyl group which is optionally substituted with a group selected from the group a, or a thienyl group which is optionally substituted with a group selected from the group a;
$R^{1g}$ is a phenyl group which is optionally substituted with a group selected from the group a, or a naphthyl group which is optionally substituted with a group selected from the group a; and
$R^{6x}$ is a phenyl group which is optionally substituted with a group selected from the group a, or a naphthyl group which is optionally substituted with a group selected from the group a;

[14] The compound according to the above [1], wherein
G is a —O—$R^{1g}$ group;
X is a —O—$R^{6x}$ group;
Z is a phenyl group which is optionally substituted with a group selected from the group a;
A is a hydrogen atom;
E is a methyl group, an ethyl group, or a propyl group;
$R^{1g}$ is a phenyl group which is optionally substituted with a group selected from the group a; or a naphthyl group which is optionally substituted with a group selected from the group a; and
$R^{6x}$ is a phenyl group which is optionally substituted with a group selected from the group a; or a naphthyl group which is optionally substituted with a group selected from the group a;

[15] The compound according to the above [1], wherein
A is a hydrogen atom;
E is a —$R^1$ group, a —S—$R^1$ group, or a halogen atom;
G is a —S—$R^{1g}$ group or a —O—$R^{1g}$ group;
X is a —S—$R^{5x}$ group or a —O—$R^{6x}$ group;
Z is a phenyl group which is optionally substituted with a group selected from the group a;
$R^1$ is a C1-C10 alkyl group, a phenyl group, or a thienyl group;
$R^{1g}$ is a C1-C20 chain hydrocarbon group which is optionally substituted with a group selected from the group b, or a phenyl group which is optionally substituted with a group selected from the group a; and
$R^{6x}$ and $R^{5x}$ independently represent a phenyl group which is optionally substituted with a group selected from the group a;

[16] A pesticidal composition comprising the compound according to any one of the above [1] to [15] as an active ingredient;

[17] A method of controlling a pest, which comprises applying the compound according to any one of the above [1] to [15] to the pest or a place where the pest inhabits.

BEST MODE FOR CARRYING OUT THE INVENTION

Various substituents mentioned in the present specification will be described by way of examples. In the present invention, the "halogen atom" means a fluorine atom, a chlorine atom, a bromine atom, or an iodine atom.

Examples of the carbocyclic group having 3 to 14 ring-constituting atoms, as used herein, include a monocyclic saturated carbocyclic group having 3 to 8 ring-constituting atoms, such as a cyclopropyl group, a cyclobutyl group, a cyclopentyl group, a cyclohexyl group, etc.; a monocyclic unsaturated carbocyclic group having 5 to 8 ring-constituting atoms, such as a cyclobutenyl group, a cyclopentenyl group, a cyclohexenyl group (e.g., a 2-cyclohexen-1-yl group, a 3-cyclohexen-1-yl group, etc.), a phenyl group, etc.; a condensed polycyclic saturated carbocyclic group having 8 to 14 ring-constituting atoms, such as a bicyclo[3.1.0]hexyl group, a bicyclo[4.1.0]heptyl group, a bicyclo[3.2.0]heptyl group, a bicyclo[2.2.1]heptyl group, a bicyclo[4.2.0]octyl group, a bicyclo[3.3.0]octyl group, a bicyclo[4.3.0]nonyl group, a bicyclo[4.4.0]decyl group (also referred to as a perhydronaphthyl group), etc.; and a condensed polycyclic unsaturated carbocyclic group having 8 to 14 ring-constituting atoms, such as a naphthyl group, an anthryl group, an indanyl group, a 1,2,3,4-tetrahydronaphthyl group, a fluorenyl group, etc.

Examples of the heterocyclic group having 3 to 14 ring-constituting atoms, as used herein, include a monocyclic saturated heterocyclic group having 3 to 8 ring-constituting atoms which is composed of a heteroatom(s) and a carbon atom(s); a monocyclic unsaturated heterocyclic group having 5 to 8 ring-constituting atoms which is composed of a heteroatom(s) and carbon atoms; and a condensed polycyclic heterocyclic group having 8 to 14 ring-constituting atoms which is composed of a heteroatom(s) and carbon atoms.

The heteroatom means an oxygen atom, a sulfur atom, or a nitrogen atom.

Examples of the monocyclic saturated heterocyclic group include a pyrrolidinyl group, an imidazolidinyl group, a piperidyl group, a piperidino group, a piperazinyl group, a morpholinyl group, a sydnonyl group, a morpholino group, a thiazolidinyl group, a thiomorpholinyl group, a thiomorpholino group, a tetrahydrothienyl group, a dithianyl group, a tetrahydrofuryl group, a tetrahydropyranyl group, and a dioxanyl group.

Examples of the monocyclic unsaturated heterocyclic group include a pyrrolyl group, a pyrrolinyl group, an imidazolyl group, a pyrazolyl group, a pyridyl group, a dihydropyridyl group, a pyrimidinyl group, a pyrazinyl group, a pyridazinyl group, a triazolyl group (e.g., a 4H-1,2,4-triazolyl group, a 1H-1,2,3-triazolyl group, a 2H-1,2,3-triazolyl group, etc.), a tetrazolyl group (e.g., a 1H-tetrazolyl group, a 2H-tetrazolyl group, etc.), an oxazolyl group, an isoxazolyl group, an oxadiazolyl group (e.g., a 1,2,4-oxadiazolyl group, a thienyl group, a dihydrodithiinyl group, a dihydrodithionyl group, a 1,3,4-oxadiazolyl group, a 1,2,5-oxadiazolyl group, etc.), a triazolyl group, an isothiazolyl group, a thiadiazolyl group (e.g., a 1,2,3-thiadiazolyl group, a 1,2,4-thiadiazolyl group, a 1,3,4-thiadiazolyl group, a 1,2,5-thiadiazolyl group, etc.), a dihydrothiazinyl group, a furyl group, a dihydropyranyl group, a dioxynyl group, and a dihydrooxathiinyl group.

Examples of the condensed polycyclic heterocyclic group include an indolyl group, an isoindolyl group, an indolinyl group, an indolydinyl group, a benzimidazolyl group, a quinolyl group, an isoquinolyl group, an indazolyl group, a benzotriazolyl group, an imidazopyridyl group, a pyrazolopyridyl group, a benzoxazolyl group, a benzoxadiazolyl group, a benzothiazolyl group, a benzothiadiazolyl group, an imidazothiadiazolyl group, a benzofuranyl group, a benzodioxolyl group, a 1,4-benzodioxanyl group, a dibenzofuranyl group, a benzothienyl group, a benzodithiinyl group, a dibenzothienyl group, and a benzoxathiinyl group.

Examples of the C1-C20 chain hydrocarbon group, as used herein, include a C1-C20 alkyl group such as a methyl group, an ethyl group, a propyl group, an isopropyl group, a butyl group, an isobutyl group, a sec-butyl group, a tert-butyl group, a pentyl group, a sec-pentyl group, an isopentyl group, a neopentyl group, a hexyl group, an isohexyl group, a heptyl group, an octyl group, a 3-methyl-1-propylbutyl group, a nonyl group, a 1-propylhexyl group, a decyl group, a 3,5-dimethyloctyl group, a 3,7-dimethyloctyl group, an undecyl group, a dodecyl group, a tridecyl group, a tetradecyl group, a hexadecyl group, a heptadecyl group, an octadecyl group, a nonadecyl group, an icosyl group, etc.; a C3-C20 alkenyl group such as a 2-propenyl group, an isopropenyl group, a 2-butenyl group, a 3-methyl-2-butenyl group, an isobutenyl group, a 1-methylallyl group, a 2-pentenyl group, a 2-hexenyl group, a heptenyl group, an octenyl group, a 3,5-dimethyloctenyl group, a 3,7-dimethyloctenyl group, etc.; and a C3-C12 alkynyl group such as a propargyl group, a 2-butynyl group, a 3-butynyl group, a 3-pentynyl group, a 3-hexynyl group, a 6-heptynyl group, a 7-octynyl group, a 3,5-dimethyl-7-octynyl group, and a 3,7-dimethyl-4-octynyl group.

Examples of the "mono(C1-C7 alkyl)amino group" include a methylamino group, an ethylamino group, propylamino group, and a butylamino group.

Examples of the "di(C1-C7 alkyl)amino group" include a dimethylamino group, a diethylamino group, a methylethylamino group, a methylpropylamino group, and an ethylpropylamino group.

Examples of the "(C1-C7 alkyl)phenylamino group" include an N-methyl-N-phenylamino group, and an N-ethyl-N-phenylamino group.

Examples of the "C1-C10 hydrocarbon group" include a C1-C10 alkyl group such as a methyl group, an ethyl group, a propyl group, an isopropyl group, a butyl group, an isobutyl group, a sec-butyl group, a tert-butyl group, a pentyl group, a sec-pentyl group, an isopentyl group, a neopentyl group, a hexyl group, an isohexyl group, a heptyl group, an octyl group, a 3-methyl-1-propylbutyl group, an nonyl group, a 1-propylhexyl group, a decyl group, a 3,5-dimethyloctyl group, a 3,7-dimethyloctyl group, etc.; a C3-C10 alkenyl group such as a 2-propenyl group, an isopropenyl group, a 2-butenyl group, a 3-methyl-2-butenyl group, an isobutenyl group, a 1-methylallyl group, a 2-pentenyl group, a 2-hexenyl group, a heptenyl group, an octenyl group, a 3,5-dimethyloctenyl group, a 3,7-dimethyloctenyl group, etc.; a C3-C10 alkynyl group such as a propargyl group, a 2-butynyl group, a 3-butynyl group, a 3-pentynyl group, a 3-hexynyl group, a 6-heptynyl group, a 7-octynyl group, a 3,5-dimethyl-7-octynyl group, a 3,7-dimethyl-4-octynyl group, etc.; a monocyclic saturated carbocyclic group having 3 to 8 ring-constituting atoms, such as a cyclopropyl group, a cyclobutyl group, cyclopentyl group, a cyclohexyl group etc.; a monocyclic unsaturated a carbocyclic group having 5 to 8 ring-constituting atoms, such as a cyclobutenyl group, a cyclopentenyl group, a cyclohexenyl group (e.g., a 2-cyclohexen-1-yl group, a 3-cyclohexen-1-yl group, etc.), a phenyl group, etc.; a condensed polycyclic saturated carbocyclic group having 8 to 10 ring-constituting atoms, such as a bicyclo[3.1.0]hexyl group, bicyclo[4.1.0]heptyl group, bicyclo[3.2.0]heptyl group, a bicyclo[2.2.1]heptyl group, a bicyclo[4.2.0]octyl group, a bicyclo[3.3.0]octyl group, a bicyclo[4.3.0]nonyl group, a bicyclo[4.4.0]decyl group (also referred to as a perhydronaphthyl group), etc.; and a condensed polycyclic unsaturated carbocyclic group having 8 to 10 ring-constituting atoms, such as a naphthyl group, an indanyl group, a 1,2,3,4-tetrahydronaphthyl group, etc.

Examples of the C1-C4 alkyl group include a methyl group, an ethyl group, a propyl group, an isopropyl group, a butyl group, an isobutyl group, a sec-butyl group, and a tert-butyl group.

Examples of the C5-C10 alkyl group include a pentyl group, a sec-pentyl group, an isopentyl group, a neopentyl group, a hexyl group, an isohexyl group, a heptyl group, an octyl group, a 3-methyl-1-propylbutyl group, a nonyl group, a 1-propylhexyl group, a decyl group, a 3,5-dimethyloctyl group, and a 3,7-dimethyloctyl group.

Examples of the C3-C10 alkenyl group include a 2-propenyl group, an isopropenyl group, a 2-butenyl group, a 3-methyl-2-butenyl group, an isobutenyl group, a 1-methylallyl group, a 2-pentenyl group, a 2-hexenyl group, a heptenyl group, an octenyl group, a 3,5-dimethyloctenyl group, and a 3,7-dimethyloctenyl group.

Examples of the C3-C10 alkynyl group include a propargyl group, a 2-butynyl group, a 3-butynyl group, a 3-pentynyl group, a 3-hexynyl group, a 6-heptynyl group, a 7-octynyl group, a 3,5-dimethyl-7-octynyl group, and a 3,7-dimethyl-4-octynyl group.

Examples of the C1-C2 alkyl group include a methyl group and an ethyl group.

Examples of the C3-C10 alkyl group include a propyl group, an isopropyl group, a butyl group, an isobutyl group, a sec-butyl group, a tert-butyl group, a pentyl group, a sec-pentyl group, an isopentyl group, a neopentyl group, a hexyl group, an isohexyl group, a heptyl group, an octyl group, a 3-methyl-1-propylbutyl group, a nonyl group, a 1-propylhexyl group, a decyl group, a 3,5-dimethyloctyl group, and a 3,7-dimethyloctyl group.

Examples of the "C1-C6 chain hydrocarbon group which is optionally substituted with a halogen atom" include a C1-C6 alkyl group such as a methyl group, a fluoromethyl group, a difluoromethyl group, a trifluoromethyl group, a chloromethyl group, a bromomethyl group, an iodomethyl group, an ethyl group, a pentafluoroethyl group, a 2,2,2-trifluoroethyl group, a 2,2,2-trifluoro-1-(trifluoromethyl)ethyl group, etc.; a $C_2$-$C_6$ alkenyl group such as a vinyl group, a 2-fluorovinyl group, a 2-propenyl group, a 3,3-dichloropropenyl group, etc.; and a $C_2$-$C_6$ alkynyl group such as an ethynyl group, a propargyl group, a 4,4,4-trifluoro-2-butynyl group, etc.

Examples of the "phenyl group which is optionally substituted with a halogen atom" include a 2-fluorophenyl group, a 3-fluorophenyl group, a 4-fluorophenyl group, a 2-chlorophenyl group, a 3-chlorophenyl group, and a 4-chlorophenyl group.

Examples of the "C1-C6 alkoxy group which is optionally substituted with a halogen atom" include a methoxy group, a trifluoromethoxy group, an ethoxy group, and a 2,2,2-trifluoroethoxy group.

Examples of the "C1-C6 alkylthio group which is optionally substituted with a halogen atom" include a methylthio group, a trifluoromethylthio group, and an ethylthio group.

Examples of the "C1 to C6 alkanediyl group which is optionally substituted with a halogen atom" include a methylene group, an ethane-1,1-diyl group, a 2,2,2-trifluoroethane-1,1-diyl group, an ethane-1,2-diyl group, a propane-1,1-diyl group, a propane-1,2-diyl group, a propane-1,3-diyl group, a butane-1,4-diyl group, a pentane-1,5-diyl group, and a hexane-1,6-diyl group.

Examples of the compound of the present invention include the following compounds.

A compound represented by the formula (I) wherein Z is a carbocyclic group having 3 to 14 ring-constituting atoms which is optionally substituted with a group selected from the group a.

A compound represented by the formula (I) wherein Z is a heterocyclic group having 3 to 14 ring-constituting atoms which is optionally substituted with a group selected from the group a.

A compound represented by the formula (I) wherein Z is a phenyl group which is optionally substituted with a group selected from the group a, or a naphthyl group which is optionally substituted with a group selected from the group a.

A compound represented by the formula (I) wherein Z is a phenyl group which is optionally substituted with a group selected from the group a.

A compound represented by the formula (I) wherein Z is a monocyclic saturated carbocyclic group having 3 to 8 ring-constituting atoms which is optionally substituted with a group selected from the group a.

A compound represented by the formula (I) wherein Z is a condensed polycyclic saturated carbocyclic group having 8 to 14 ring-constituting atoms which is optionally substituted with a group selected from the group a.

A compound represented by the formula (I) wherein Z is an indanyl group which is optionally substituted with a group selected from the group a.

A compound represented by the formula (I) wherein Z is a phenyl group, a 4-methylphenyl group, a 4-ethylphenyl group, a 4-isopropylphenyl group, a 4-(2-pyridyl)phenyl group, a 4-phenylphenyl group, a 4-chlorophenyl group, a 4-nitrophenyl group, a 3-methylphenyl group, a 3-ethylphenyl group, a 3-isopropylphenyl group, a 3-phenylphenyl group, a 3-chlorophenyl group, a 3,4-dimethylphenyl group, a 4-fluorophenyl group, a 4-methoxyphenyl group, or a 5-indanyl group.

A compound represented by the formula (I) wherein G is a -$L^2$-$R^1$ group or a —N($R^2$)—$R^3$ group (wherein $L^2$, $R^1$, $R^2$ and $R^3$ are as defined above).

A compound represented by the formula (I) wherein G is a -$L^2$-$R^1$ group (wherein $L^2$ and $R^1$ are as defined above);

A compound represented by the formula (I) wherein G is a -$L^2$-$R^1$ group, $L^2$ is a sulfur atom, and $R^1$ is as defined above.

A compound represented by the formula (I) wherein G is a -$L^2$-$R^1$ group, $L^2$ is an oxygen atom, and $R^1$ is as defined above.

A compound represented by the formula (I) wherein G is a -$L^2$-$R^1$ group, $L^2$ is the same the same as defined above, and $R^1$ is a C1-C20 chain hydrocarbon group which is optionally substituted with a group selected from the group b.

A compound represented by the formula (I) wherein G is a -$L^2$-$R^1$ group, $L^2$ is a sulfur atom, and $R^1$ is a C1-C20 chain hydrocarbon group which is optionally substituted with a group selected from the group b.

A compound represented by the formula (I) wherein G is a -$L^2$-$R^1$ group, $L^2$ is a sulfur atom, and $R^1$ is a C1-C20 chain hydrocarbon group.

A compound represented by the formula (I) wherein G is a -$L^2$-$R^1$ group, $L^2$ is a sulfur atom, and $R^1$ is a C1-C20 alkyl group which is optionally substituted with a group selected from the group b.

A compound represented by the formula (I) wherein G is a -$L^2$-$R^1$ group, $L^2$ is as defined above, and $R^1$ is a carbocyclic group having 3 to 14 ring-constituting atoms which is optionally substituted with a group selected from the group a, or a heterocyclic group having 3 to 14 ring-constituting atoms which is optionally substituted with a group selected from the group a.

A compound represented by the formula (I) wherein G is a -$L^2$-$R^1$ group, $L^2$ is a sulfur atom, and $R^1$ is a carbocyclic group having 3 to 14 ring-constituting atoms which is optionally substituted with a group selected from the group a, or a heterocyclic group having 3 to 14 ring-constituting atoms which is optionally substituted with a group selected from the group a.

A compound represented by the formula (I) wherein G is a -$L^2$-$R^1$ group, $L^2$ is an oxygen atom, and $R^1$ is a carbocyclic group having 3 to 14 ring-constituting atoms which is optionally substituted with a group selected from the group a, or a heterocyclic group having 3 to 14 ring-constituting atoms which is optionally substituted with a group selected from the group a.

A compound represented by the formula (I) wherein G is a -$L^2$-$R^1$ group and $R^1$ is a carbocyclic group having 3 to 14 ring-constituting atoms which is optionally substituted with a group selected from the group a.

A compound represented by the formula (I) wherein G is a -$L^2$-$R^1$ group, $L^2$ is a sulfur atom, and $R^1$ is a carbocyclic group having 3 to 14 ring-constituting atoms which is optionally substituted with a group selected from the group a.

A compound represented by the formula (I) wherein G is a -$L^2$-$R^1$ group, $L^2$ is an oxygen atom, and $R^1$ is a carbocyclic group having 3 to 14 ring-constituting atoms which is optionally substituted with a group selected from the group a.

A compound represented by the formula (I) wherein G is a -$L^2$-$R^1$ group, $L^2$ is as defined above, and $R^1$ is a phenyl group which is optionally substituted with a group selected from the group a or a naphthyl group which is optionally substituted with a group selected from the group a.

A compound represented by the formula (I) wherein G is a -$L^2$-$R^1$ group, $L^2$ is a sulfur atom, and $R^1$ is a phenyl group which is optionally substituted with a group selected from the group a or a naphthyl group which is optionally substituted with a group selected from the group a.

A compound represented by the formula (I) wherein G is a -$L^2$-$R^1$ group, $L^2$ is an oxygen atom, and $R^1$ is a phenyl group which is optionally substituted with a group selected from the group a or a naphthyl group which is optionally substituted with a group selected from the group a.

A compound represented by the formula (I) wherein G is a -$L^2$-$R^1$ group, $L^2$ is as defined above, and $R^1$ is a monocyclic saturated carbocyclic group having 3 to 8 ring-constituting atoms which is optionally substituted with a group selected from the group a, or a condensed polycyclic saturated carbocyclic group having 8 to 10 ring-constituting atoms which is optionally substituted with a group selected from the group a.

A compound represented by the formula (I) wherein G is a -$L^2$-$R^1$ group, $L^2$ is a sulfur atom, and $R^1$ is a monocyclic saturated carbocyclic group having 3 to 8 ring-constituting atoms which is optionally substituted with a group selected from the group a, or a condensed polycyclic saturated carbocyclic group having 8 to 10 ring-constituting atoms which is optionally substituted with a group selected from the group a.

A compound represented by the formula (I) wherein G is a -$L^2$-$R^1$ group, $L^2$ is an oxygen atom, and $R^1$ is a monocyclic saturated carbocyclic group having 3 to 8 ring-constituting atoms which is optionally substituted with a group selected from the group a, or a condensed polycyclic saturated carbocyclic group having 8 to 10 ring-constituting atoms which is optionally substituted with a group selected from the group a.

A compound represented by the formula (I) wherein G is a —N($R^2$)—$R^2$ group (wherein $R^2$ and $R^3$ are as defined above).

A compound represented by the formula (I) wherein G is a —N($R^2$)—$R^2$ group, and $R^2$ and $R^3$ are independently a C1-C20 chain hydrocarbon group which is optionally substituted with a group selected from the group b, a carbocyclic group having 3 to 14 ring-constituting atoms which is optionally substituted with a group selected from the group a, or a heterocyclic group having 3 to 14 ring-constituting atoms which is optionally substituted with a group selected from the group a.

A compound represented by the formula (I) wherein G is a phenylthio group, a 4-methylphenylthio group, a 4-ethylphenylthio group, a 4-isopropylphenylthio group, a 4-methoxyphenylthio group, a 4-(2-pyridyl)phenylthio group, a 4-phenylphenylthio group, a 4-chlorophenylthio group, a 4-nitrophenylthio group, a 3-methylphenylthio group, a 3-ethylphenylthio group, a 3-isopropylphenylthio group, a 3-phenylphenylthio group, a 3-chlorophenylthio group, a 3,4-dimethylphenylthio, a 1-naphthylthio group, a 2-naphthylthio group, a 5-indanylthio group, a cyclopropylthio group, a cyclopentylthio group, a cyclohexylthio group, a 2-perhydronaphthylthio group, a benzylthio group, a phenethylthio group, an α-methylbenzylthio group, a cyclopropylmethylthio group, a cyclopentylmethylthio group, a cyclohexylmethylthio group, an isopropylthio group, a sec-butylthio group, a 3-methyl-1-propylbutylthio group, an allylthio group, a propargylthio group, a phenoxy group, a 4-methylphenoxy group, a 4-ethylphenoxy group, a 4-isopropylphenoxy group, a 4-methoxyphenoxy group, a 4-phenylphenoxy group, a 4-chlorophenoxy group, a 3-methylphenoxy group, a 3-ethylphenoxy group, a 3-isopropylphenoxy group, a 3-phenylphenoxy group, a 3-chlorophenoxy group, a 3,4-dimethylphenoxy group, a 3,5-dimethylphenoxy group, a 3-methoxyphenoxy group, a 3-ethoxyphenoxy group, a 3-trifluoromethylphenoxy group, a 3-trifluoromethoxyphenoxy group, a 1-naphthyloxy group, a 2-naphthyloxy group, a 5-indanyloxy group, or an N-methyl-N-phenylamino group.

A compound represented by the formula (I) wherein X is a —S—$R^5$ group (wherein $R^5$ is as defined above).

A compound represented by the formula (I) wherein X is a —S—$R^5$ group, $R^5$ is a carbocyclic group having 3 to 14 ring-constituting atoms which is optionally substituted with a group selected from the group a, or a heterocyclic group having 3 to 14 ring-constituting atoms which is optionally substituted with a group selected from the group a.

A compound represented by the formula (I) wherein X is a —S—$R^5$ group, $R^5$ group is a carbocyclic group having 3 to 14 ring-constituting atoms which is optionally substituted with a group selected from the group a.

A compound represented by the formula (I) wherein X is a —S—$R^5$ group, $R^5$ is a phenyl group which is optionally substituted with a group selected from the group a or a naphthyl group which is optionally substituted with a group selected from the group a.

A compound represented by the formula (I) wherein X is a —S—$R^5$ group, and $R^5$ is a monocyclic saturated carbocyclic group having 3 to 8 ring-constituting atoms which is optionally substituted with a group selected from the group a, or a condensed polycyclic saturated carbocyclic group having 8 to 10 ring-constituting atoms which is optionally substituted with a group selected from the group a.

A compound represented by the formula (I) wherein X is a —O—$R^6$ group (wherein $R^6$ is as defined above).

A compound represented by the formula (I) wherein X is a —O—$R^6$ group and $R^6$ is a carbocyclic group having 3 to 14 ring-constituting atoms which is optionally substituted with a group selected from the group a, or a heterocyclic group having 3 to 14 ring-constituting atoms which is optionally substituted with a group selected from the group a.

A compound represented by the formula (I) wherein X is a —O—$R^6$ group and $R^6$ is a carbocyclic group having 3 to 14 ring-constituting atoms which is optionally substituted with a group selected from the group a.

A compound represented by the formula (I) wherein X is a —O—$R^6$ group and $R^6$ is a phenyl group which is optionally substituted with a group selected from the group a, or a naphthyl group which is optionally substituted with a group selected from the group a.

A compound represented by the formula (I) wherein X is a —O—$R^6$ group and $R^6$ is a monocyclic saturated carbocyclic group having 3 to 8 ring-constituting atoms which is optionally substituted with a group selected from the group a, or a condensed polycyclic saturated carbocyclic group having 8 to 10 ring-constituting atoms which is optionally substituted with a group selected from the group a.

A compound represented by the formula (I) wherein X is a phenylthio group, a 4-methylphenylthio group, a 4-ethylphenylthio group, a 4-isopropylphenylthio group, a 4-methoxyphenylthio group, a 4-(2-pyridyl)phenylthio group, a 4-phenylphenylthio group, a 4-chlorophenylthio group, a 4-fluorophenylthio group, a 4-nitrophenylthio group, 3-methylphenylthio group, a 3-ethylphenylthio group, a 3-isopropylphenylthio group, a 3-phenylphenylthio group, a 3-chlorophenylthio group, a 3-fluorophenylthio group, a 3-(trifluoromethyl)phenylthio group, a 3,4-dimethylphenylthio, a 5-benzodioxolanylthio group, a 1-naphthylthio group, a 2-naphthylthio group, a 5-indanylthio group, a cyclopropylthio group, a cyclopentylthio group, a cyclohexylthio group, a 2-perhydronaphthylthio group, benzylthio group, a phenethylthio group, an α-methylbenzylthio group, a cyclopropylmethylthio group, a cyclopentylmethylthio group, a cyclohexylmethylthio group, a phenoxy group, a 4-methylphenoxy group, a 4-ethylphenoxy group, a 4-isopropylphenoxy group, a 4-methoxyphenoxy group, a 4-ethoxyphenoxy group, a 4-phenylphenoxy group, a 4-chlorophenoxy group, a 3-methylphenoxy group, a 3-ethylphenoxy group, a 3-isopropylphenoxy group, a 3-phenylphenoxy group, a 3-chlorophenoxy group, a 3-methoxyphenoxy group, a 3-ethoxyphenoxy group, a 2-methylphenoxy group, a 2-methoxyphenoxy group, a 2-ethoxyphenoxy group, a 2,4-dimethylphenoxy group, a 2,6-dimethylphenoxy group, a 3,4-dimethylphenoxy group, a 3,5-dimethylphenoxy group, a 2,3-dimethoxyphenoxy group, a 2,4-dimethoxyphenoxy group, a 2,6-dimethoxyphenoxy group, a 3,4-dimethoxyphenoxy group, a 5-benzodioxolyloxy group, a (1,4-benzodioxan)-6-yloxy group, a 1-naphthyloxy group, a 2-naphthyloxy group, or a 5-indanyloxy group.

A compound represented by the formula (I) wherein A is a hydrogen atom, a halogen atom, a cyano group, a nitro group, a —$R^1$ group, a -$L^1$-$R^1$ group, a —S—C(=O)—$R^1$ group, a —O—C(=O)—$R^1$ group, a —O—$SO_2$—$R^1$ group, a —C(=O)—$R^1$ group, a —C(=O)—O—$R^1$ group, or a —N($R^2$)—$R^3$ group, and E is a halogen atom, a cyano group, a nitro group, a —$R^1$ group, a -$L^1$-$R^1$ group, a —S—C(=O)—$R^1$ group, a —O—C(=O)—$R^1$ group, a —O—$SO_2$—$R^1$ group, a —C(=O)—$R^1$ group, a —C(=O)—O—$R^1$ group, or a —N($R^2$)—$R^2$ group (wherein $L^1$, $R^1$, $R^2$ and $R^3$ are as defined above).

A compound represented by the formula (I) wherein A is a hydrogen atom and E is a halogen atom, a cyano group, a nitro group, a —$R^1$ group, a -$L^1$-$R^1$ group, a —S—C(=O)—$R^1$ group, a —O—C(=O)—$R^1$ group, a —O—$SO_2$—$R^1$ group, a —C(=O)—$R^1$ group, a —C(=O)—O—$R^1$ group, or a —N($R^2$)—$R^3$ group (wherein $L^1$, $R^1$, $R^2$ and $R^3$ are as defined above).

A compound represented by the formula (I) wherein A is a hydrogen atom and E is a halogen atom, a cyano group, a nitro group, a —$R^1$ group, or a -$L^1$-$R^1$ group (wherein $L^1$ and $R^1$ are as defined above).

A compound represented by the formula (I) wherein A is a hydrogen atom and E is a halogen atom, a —$R^1$ group, or a -$L^1$-$R^1$ group (wherein $L^1$ and $R^1$ are as defined above).

A compound represented by the formula (I) wherein A is a hydrogen atom and E is a methyl group, an ethyl group, a propyl group, a butyl group, a phenyl group, a 2-methylphenyl group, a 3-methylphenyl group, a 4-methylphenyl group, a 2-fluorophenyl group, a 3-fluorophenyl group, a 4-fluorophenyl group, a 2-chlorophenyl group, a 3-chlorophenyl group, a 4-chlorophenyl group, a methoxy group, an ethoxy group, a propoxy group, a phenoxy group, a 2-methylphenoxy group, a 3-methylphenoxy group, a 4-methylphenoxy group, a 2-fluorophenoxy group, a 3-fluorophenoxy group, a 4-fluorophenoxy group, a 2-chlorophenoxy group, a 3-chlorophenoxy group, a 4-chlorophenoxy group, a methylthio group, an ethylthio group, a propylthio group, a butylthio group, a phenylthio group, a 2-methylphenylthio group, a 3-methylphenylthio group, a 4-methylphenylthio group, a 2-fluorophenylthio group, a 3-fluorophenylthio group, a 4-fluorophenylthio group, a 2-chlorophenylthio group, a 3-chlorophenylthio group, a 4-chlorophenylthio group, a 2-thienyl group, a 3-thienyl group, a 2-furyl group, a 3-furyl group, a 1-naphthyl group, a 2-naphthyl group, a fluorine atom, a methoxycarbonyl group, an ethoxycarbonyl group, a tert-butoxycarbonyl group, or a dimethylaminocarbonyl group.

A compound represented by the formula (I) wherein A is a hydrogen atom and E is a C1-C10 alkyl group.

A compound represented by the formula (I) wherein A is a hydrogen atom and E is a methyl group, an ethyl group or a propyl group.

A compound represented by the formula (I) wherein A is a halogen atom, a cyano group, a nitro group, a —$R^1$ group, a -$L^1$-$R^1$ group, a —S—C(=O)—$R^1$ group, a —O—C(=O)—$R^1$ group, a —O—$SO_2$—$R^1$ group, a —C(=O)—$R^1$ group, a —C(=O)—O—$R^1$ group, or a —N($R^2$)—$R^2$ group, and E is a hydrogen atom, a halogen atom, a cyano group, a nitro group, a —$R^1$ group, a -$L^1$-$R^1$ group, a —S—C(=O)—$R^1$ group, a —O—C(=O)—$R^1$ group, a —O—$SO_2$—$R^1$ group, a —C(=O)—$R^1$ group, a —C(=O)—O—$R^1$ group, or a —N($R^2$)—$R^2$ group (wherein $L^1$, $R^1$, $R^2$ and $R^3$ are as defined above). A compound represented by the formula (I) wherein A is a —$R^1$ group or a -$L^1$-$R^1$ group (wherein $L^1$ and $R^1$ are as defined above) and E is a hydrogen atom.

A compound represented by the formula (I) wherein A is a methyl group, an ethyl group, a propyl group, a phenyl group, a 2-methylphenyl group, a 3-methylphenyl group, a 4-methylphenyl group, a methoxy group, an ethoxy group, a propoxy group, a phenoxy group, a methylthio group, a phenylthio group, or a trifluoromethyl group and E is a hydrogen atom.

A compound represented by the formula (I) wherein A is a methyl group, a phenyl group, a methoxy group, a phenoxy group, a methylthio group, a phenylthio group, or a trifluoromethyl group, and E is a methyl group, an ethyl group, a propyl group, a phenyl group, a methoxy group, a phenoxy group, a methylthio group, or a phenylthio group.

A compound represented by the formula (I) wherein G is a -$L^2$-$R^1$ group and X is a —S—$R^5$ group or a —O—$R^6$ group (wherein $L^2$, $R^1$, $R^5$ and $R^6$ are as defined above);

A compound represented by the formula (I) wherein G is a -$L^2$-$R^1$ group, X is a —S—$R^5$ group or a —O—$R^6$ group, $L^2$ is a sulfur atom, and $R^1$, $R^5$ and $R^6$ are as defined above.

A compound represented by the formula (I) wherein G is a -$L^2$-$R^1$ group, X is a —S—$R^5$ group or a —O—$R^6$ group, $R^2$ is a C1-C20 chain hydrocarbon group which is optionally substituted with a group selected from the group b, a carbocyclic group having 3 to 14 ring-constituting atoms which is optionally substituted with a group selected from the group a, or a heterocyclic group having 3 to 14 ring-constituting atoms which is optionally substituted with a group selected from the group a, $L^2$ is as defined above, $R^5$ and $R^6$ are independently a carbocyclic group having 3 to 14 ring-constituting atoms which is optionally substituted with a group selected from the group a, or a heterocyclic group having 3 to 14 ring-constituting atoms which is optionally substituted with a group selected from the group a.

A compound represented by the formula (I) wherein G is a -$L^2$-$R^1$ group, X is a —S—$R^5$ group or a —O—$R^6$ group, $L^2$ is a sulfur atom, $R^1$ is a C1-C20 chain hydrocarbon group which is optionally substituted with a group selected from the group b, a carbocyclic group having 3 to 14 ring-constituting atoms which is optionally substituted with a group selected from the group a, or a heterocyclic group having 3 to 14 ring-constituting atoms which is optionally substituted with a group selected from the group a, $R^5$ and $R^6$ are independently a carbocyclic group having 3 to 14 ring-constituting atoms which is optionally substituted with a group selected from the group a, or a heterocyclic group having 3 to 14 ring-constituting atoms which is optionally substituted with a group selected from the group a (wherein $L^2$ is as defined above).

A compound represented by the formula (I) wherein G is a -$L^2$-$R^1$ group, X is a —S—$R^5$ group, $L^2$ is a sulfur atom, $R^1$ is a C1-C20 chain hydrocarbon group which is optionally substituted with a group selected from the group b, a carbocyclic group having 3 to 14 ring-constituting atoms which is optionally substituted with a group selected from the group a, or a heterocyclic group having 3 to 14 ring-constituting atoms which is optionally substituted with a group selected from the group a, $R^5$ is a carbocyclic group having 3 to 14 ring-constituting atoms which is optionally substituted with a group selected from the group a, or a heterocyclic group having 3 to 14 ring-constituting atoms which is optionally substituted with a group selected from the group a.

A compound represented by the formula (I) wherein G is a -$L^2$-$R^1$ group, X is a —O—$R^6$ group, $L^2$ is a sulfur atom, $R^1$ is a C1-C20 chain hydrocarbon group which is optionally substituted with a group selected from the group b, a carbocyclic group having 3 to 14 ring-constituting atoms which is optionally substituted with a group selected from the group a, or a heterocyclic group having 3 to 14 ring-constituting atoms which is optionally substituted with a group selected from the group a, and $R^6$ is a carbocyclic group having 3 to 14 ring-constituting atoms which is optionally substituted with a group selected from the group a, or a heterocyclic group having 3 to 14 ring-constituting atoms which is optionally substituted with a group selected from the group a.

A compound represented by the formula (I) wherein G is a -$L^2$-$R^1$ group, X is a —O—$R^6$ group, $L^2$ is an oxygen atom, $R^1$ is a C1-C20 chain hydrocarbon group which is optionally substituted with a group selected from the group b, a carbocyclic group having 3 to 14 ring-constituting atoms which is optionally substituted with a group selected from the group a, or a heterocyclic group having 3 to 14 ring-constituting atoms which is optionally substituted with a group selected from the group a, and $R^6$ is a carbocyclic group having 3 to 14 ring-constituting atoms which is optionally substituted with a group selected from the group a, or a heterocyclic group having 3 to 14 ring-constituting atoms which is optionally substituted with a group selected from the group a.

A compound represented by the formula (I) wherein G is a -$L^2$-$R^1$ group, X is a —S—$R^5$ group or a —O—$R^6$ group, A is a hydrogen atom, a —$R^1$ group, or a -$L^1$-$R^1$ group, and E is a halogen atom, a cyano group, a nitro group, a —$R^1$ group, or a -$L^1$-$R^1$ group (wherein $L^1$, $L^2$, $R^1$, $R^5$ and $R^6$ are as defined above).

A compound represented by the formula (I) wherein G is a -$L^2$-$R^1$ group, X is a —S—$R^5$ group or a —O—$R^6$ group, A is a hydrogen atom, and E is a —$R^1$ group (wherein $L^2$, $R^2$, $R^5$ and $R^6$ are as defined above).

A compound represented by the formula (I) wherein G is a -$L^2$-$R^1$ group, X is a —S—$R^5$ group or a —O—$R^6$ group, A is a hydrogen atom, and E is a C1-C10 alkyl group (wherein $L^2$, $R^1$, $R^5$ and $R^6$ are as defined above).

A compound represented by the formula (I) wherein G is a -$L^2$-$R^1$ group, X is a —S—$R^5$ group or a —O—$R^6$ group, A is a —$R^1$ group or a -$L^2$-$R^2$ group, and E is a hydrogen atom, a halogen atom, a cyano group, a nitro group, a —$R^1$ group, or a -$L^1$-$R^1$ group (wherein $L^1$, $L^2$, $R^1$, $R^{5x}$ and $R^6$ are as defined above).

A compound represented by the formula (I) wherein A is a hydrogen atom, E is a —$R^1$ group, a -$L^1$-$R^1$ group, a —S—C(=O)—$R^1$ group, a —O—C(=O)—$R^1$ group, a —O—S(O)$_2$—$R^1$ group, a —C(=O)—$R^1$ group, a —C(=O)—O—$R^1$ group, a —N($R^2$)—$R^3$ group, a halogen atom, a cyano group, or a nitro group, $R^2$ is a —$R^1$ group, $R^3$ is a —$R^1$ group or a —O—$R^1$ group, $R^1$ is a C1-C20 alkyl group which is optionally substituted with a group selected from the group b, a phenyl group which is optionally substituted with a group selected from the group a, or a thienyl group which is optionally substituted with a group selected from the group a, $R^4$ is a C1-C10 hydrocarbon group, $R^5$ is a carbocyclic group having 3 to 14 ring-constituting atoms which is optionally substituted with a group selected from the group a, or a heterocyclic group having 3 to 14 ring-constituting atoms which is optionally substituted with a group selected from the group a, $R^6$ is a carbocyclic group having 3 to 14 ring-constituting atoms which is optionally substituted with a group selected from the group a, or a heterocyclic group having 3 to 14 ring-constituting atoms which is optionally substituted with a group selected from the group a, and $L^1$ is an oxygen atom or a sulfur atom.

A compound represented by the formula (I) wherein A is a hydrogen atom, E is a —$R^1$ group, a $L^1$-$R^1$ group, a —S—C(=O)—$R^1$ group, a —O—C(=O)—$R^1$ group, a —O—S(O)$_2$—$R^1$ group, a —C(=O)—$R^1$ group, a —C(=O)—O—$R^1$ group, a —N($R^2$)—$R^3$ group, a halogen atom, a cyano group, or a nitro group, $R^2$ is a —$R^1$ group, $R^3$ is a —$R^1$ group or a —O—$R^1$ group, $R^1$ is a C1-C20 alkyl group which is optionally substituted with a group selected from the group b, a phenyl group which is optionally substituted with a group selected from the group a, or a thienyl group which is optionally substituted with a group selected from the group a, X is a —S—$R^5$ group or —O—$R^6$ group, $R^5$ and $R^6$ are independently a carbocyclic group having 3 to 14 ring-constituting atoms which is optionally substituted with a group selected from the group a, or a heterocyclic group having 3 to 14 ring-constituting atoms which is optionally substituted with a group selected from the group a, and $L^1$ is an oxygen atom or a sulfur atom.

A compound represented by the formula (I) wherein A is a hydrogen atom, E is a —$R^1$ group, a -$L^1$-$R^1$ group, or a halogen atom, G is a —S—$R^{1g}$ group, X is a —S—$R^{5x}$ group, Z is a phenyl group which is optionally substituted with a group selected from the group a, $R^1$ is a C1-C20 alkyl group which is optionally substituted with a group selected from the group b, a phenyl group which is optionally substituted with a group selected from the group a, or a thienyl group which is optionally substituted with a group selected from the group a, $R^{1g}$ and $R^{5x}$ represent a phenyl group which is optionally substituted with a group selected from the group a, and $L^1$ is an oxygen atom or a sulfur atom.

A compound represented by the formula (I) wherein A is a hydrogen atom, E is a —$R^1$ group, a -$L^1$-$R^1$ group, or a halogen atom, G is a —S—$R^{1g}$ group, X is a —O—$R^{6x}$ group, Z is a phenyl group which is optionally substituted with a group selected from the group a, $R^1$ is a C1-C20 alkyl group which is optionally substituted with a group selected from the group b, a phenyl group which is optionally substituted with a group selected from the group a, or a thienyl group which is optionally substituted with a group selected from the group a, and $R^{6x}$ are a phenyl group which is optionally substituted with a group selected from the group a.

A compound represented by the formula (I) wherein A is a hydrogen atom, E is a C1-C10 alkyl group, G is a —S—$R^{1g}$ group or a —O—$R^{1g}$ group, X is a —S—$R^{5x}$ group, Z is a phenyl group which is optionally substituted with a group selected from the group a, and $R^{5x}$ are a C1-C10 alkyl group or a phenyl group which is optionally substituted with a group selected from the group a.

A compound represented by the formula (I) wherein A is a hydrogen atom, E is a C1-C10 alkyl group, G is a —S—$R^{1g}$ group or a —O—$R^{1g}$ group, X is a —O—$R^{6x}$ group, Z is a phenyl group which is optionally substituted with a group selected from the group a, and $R^{1g}$ and $R^{6x}$ are a C1-C10 alkyl group or a phenyl group which is optionally substituted with a group selected from the group a.

A compound represented by the formula (I) wherein A is a hydrogen atom, E is a thienyl group, G is a —S—$R^{1g}$ group, X is a —S—$R^{5x}$ group, Z is a phenyl group which is optionally substituted with a group selected from the group a, and $R^{1g}$ and $R^{5x}$ are a phenyl group which is optionally substituted with a group selected from the group a.

A compound represented by the formula (I) wherein A is a hydrogen atom, E is a halogen atom, G is a —S—$R^{1g}$ group, X is a —S—$R^{5x}$ group, Z is a phenyl group which is optionally substituted with a group selected from the group a, and $R^{1g}$ and $R^{5x}$ are a phenyl group which is optionally substituted with a group selected from the group a.

A compound represented by the formula (I) wherein A is a hydrogen atom, E is a —S—$R^{1e}$ group or a —O—$R^{1e}$ group, G is a —S—$R^{1g}$ group, X is a —S—$R^{5x}$ group, Z is a phenyl group which is optionally substituted with a group selected from the group a, $R^{1e}$ is a C1-C10 alkyl group or a phenyl group which is optionally substituted with a group selected from the group a, and $R^{1g}$ and $R^{5x}$ are a C1-C10 alkyl group, or a phenyl group which is optionally substituted with a group selected from the group a.

A compound represented by the formula (I) wherein
$R^1$ is a C1-C20 alkyl group which is optionally substituted with a group selected from the group b, a phenyl group which is optionally substituted with a group selected from the group a, or a thienyl group which is optionally substituted with a group selected from the group a,
$R^2$ is a —$R^1$ group,
$R^3$ is a —$R^1$ group or a —O—$R^1$ group,
$R^4$ is a C1-C10 hydrocarbon group,
$R^5$ is a carbocyclic group having 3 to 14 ring-constituting atoms which is optionally substituted with a group selected from the group a, or a heterocyclic group having 3 to 14 ring-constituting atoms which is optionally substituted with a group selected from the group a,
$R^6$ is a carbocyclic group having 3 to 14 ring-constituting atoms which is optionally substituted with a group selected from the group a, or a heterocyclic group having 3 to 14 ring-constituting atoms which is optionally substituted with a group selected from the group a, and
$L^1$ is an oxygen atom or a sulfur atom.

A compound represented by the formula (I) wherein
G is a —S—$R^{1g}$ group or a —O—$R^{1g}$ group,
X is a —S—$R^{5x}$ group or a —O—$R^{6x}$ group,
Z is a phenyl group which is optionally substituted with a group selected from the group a,
A is a hydrogen atom,
E is a —$R^1$ group or a -$L^1$-$R^1$ group, $L^1$ is an oxygen atom or a sulfur atom,
$R^1$ is a C1-C10 alkyl group which is optionally substituted with a group selected from the group b, a phenyl group which is optionally substituted with a group selected from the group a, or a thienyl group which is optionally substituted with a group selected from the group a,
$R^{1g}$ is a C1-C10 alkyl group which is optionally substituted with a group selected from the group b, a phenyl group which is optionally substituted with a group selected from the group a, a naphthyl group which is optionally substituted with a group selected from the group a, or a thienyl group which is optionally substituted with a group selected from the group a, and
$R^{6x}$ and $R^{5x}$ are a phenyl group which is optionally substituted with a group selected from the group a, or a naphthyl group which is optionally substituted with a group selected from the group a.

A compound represented by the formula (I) wherein
G is a —S—$R^{1g}$ group or a —O—$R^{1g}$ group,
X is a —S—$R^{5x}$ group or a —O—$R^{6x}$ group,
Z is a phenyl group which is optionally substituted with a group selected from the group a,
A is a hydrogen atom,
E is a —$R^1$ group,
$R^1$ is a C1-C10 alkyl group which is optionally substituted with a group selected from the group b, a phenyl group which is optionally substituted with a group selected from the group a, or a thienyl group which is optionally substituted with a group selected from the group a,
$R^{1g}$ is a C1-C10 alkyl group which is optionally substituted with a group selected from the group b, a phenyl group which is optionally substituted with a group selected from the group a, a naphthyl group which is optionally substituted with a group selected from the group a, or a thienyl group which is optionally substituted with a group selected from the group a, and
$R^{6x}$ and $R^{5x}$ are a phenyl group which is optionally substituted with a group selected from the group a, or a naphthyl group which is optionally substituted with a group selected from the group a.

A compound represented by the formula (I) wherein
G is a —S—$R^{1g}$ group or a —O—$R^{1g}$ group,
X is a —O—$R^{6x}$ group,
Z is a phenyl group which is optionally substituted with a group selected from the group a,
A is a hydrogen atom,
E is a —$R^1$ group,
$R^1$ is a C1-C10 alkyl group which is optionally substituted with a group selected from the group b, a phenyl group which is optionally substituted with a group selected from the group a, or a thienyl group which is optionally substituted with a group selected from the group a,
$R^{1g}$ is a C1-C10 alkyl group which is optionally substituted with a group selected from the group b, a phenyl group which is optionally substituted with a group selected from the group a, a naphthyl group which is optionally substituted with a group selected from the group a, or a thienyl group which is optionally substituted with a group selected from the group a, and
$R^{6x}$ is a phenyl group which is optionally substituted with a group selected from the group a, or a naphthyl group which is optionally substituted with a group selected from the group a.

A compound represented by the formula (I) wherein
G is a —S—$R^{1g}$ group,
X is a —O—$R^{6x}$ group,
Z is a phenyl group which is optionally substituted with a group selected from the group a,
A is a hydrogen atom,
E is a —$R^1$ group,
$R^1$ is a C1-C10 alkyl group which is optionally substituted with a group selected from the group b, a phenyl group which is optionally substituted with a group selected from the group a, or a thienyl group which is optionally substituted with a group selected from the group a,
$R^{1g}$ is a C1-C10 alkyl group which is optionally substituted with a group selected from the group b, a phenyl group which is optionally substituted with a group selected from the group a, a naphthyl group which is optionally substituted with a group selected from the group a, or a thienyl group which is optionally substituted with a group selected from the group a, and
$R^{6x}$ is a phenyl group which is optionally substituted with a group selected from the group a, or a naphthyl group which is optionally substituted with a group selected from the group a.

A compound represented by the formula (I) wherein
G is a —O—$R^{1g}$ group,
X is a —O—$R^{6x}$ group,
Z is a phenyl group which is optionally substituted with a group selected from the group a,
A is a hydrogen atom,
E is a —$R^1$ group, $R^1$ is a C1-C10 alkyl group which is optionally substituted with a group selected from the group b, a phenyl group which is optionally substituted with a group selected from the group a, or a thienyl group which is optionally substituted with a group selected from the group a, $R^{1g}$ is a C1-C10 alkyl group which is optionally substituted with a group selected from the group b, a phenyl group which is optionally substituted with a group selected from the group a, a naphthyl group which is optionally substituted with a group selected from the group a, or a thienyl group which is optionally substituted with a group selected from the group a, and $R^{6x}$ is a phenyl group which is optionally substituted with a group selected from the group a, or a naphthyl group which is optionally substituted with a group selected from the group a.

A compound represented by the formula (I) wherein
G is a —S—$R^{1g}$ group,
X is a —O—$R^{6x}$ group,
Z is a phenyl group which is optionally substituted with a group selected from the group a,
A is a hydrogen atom,
E is a methyl group, an ethyl group, or a propyl group,
$R^{1g}$ is a C1-C10 alkyl group which is optionally substituted with a group selected from the group b, a phenyl group which is optionally substituted with a group selected from the group a, a naphthyl group which is optionally substituted with a group selected from the group a, or a thienyl group which is optionally substituted with a group selected from the group a, and
$R^{6x}$ is a phenyl group which is optionally substituted with a group selected from the group a, or a naphthyl group which is optionally substituted with a group selected from the group a.

A compound represented by the formula (I) wherein
G is a —S—$R^{1g}$ group,
X is a —O—$R^{6x}$ group,
Z is a phenyl group which is optionally substituted with a group selected from the group a,
A is a hydrogen atom,
E is a —$R^1$ group,
$R^1$ is a C1-C10 alkyl group which is optionally substituted with a group selected from the group b, a phenyl group which is optionally substituted with a group selected from the group a, or a thienyl group which is optionally substituted with a group selected from the group a,
$R^{1g}$ is a C1-C10 alkyl group which is optionally substituted with a group selected from the group b, and
$R^{6x}$ is a phenyl group which is optionally substituted with a group selected from the group a, or a naphthyl group which is optionally substituted with a group selected from the group a.

A compound represented by the formula (I) wherein
G is a —S—$R^{1g}$ group,
X is a —O—$R^{6x}$ group,
Z is a phenyl group which is optionally substituted with a group selected from the group a,
A is a hydrogen atom,
E is a methyl group, ethyl group or propyl group,
$R^{1g}$ is a C1-C10 alkyl group which is optionally substituted with a group selected from the group b, and
$R^{6x}$ is a phenyl group which is optionally substituted with a group selected from the group a, or a naphthyl group which is optionally substituted with a group selected from the group a.

A compound represented by the formula (I) wherein
G is a —S—$R^{1g}$ group,
X is a —O—$R^{6x}$ group,
Z is a phenyl group which is optionally substituted with a group selected from the group a,
A is a hydrogen atom,
E is a —$R^1$ group,
$R^1$ is a C1-C10 alkyl group which is optionally substituted with a group selected from the group b, a phenyl group which is optionally substituted with a group selected from the group a, or a thienyl group which is optionally substituted with a group selected from the group a,
$R^{1g}$ is a phenyl group which is optionally substituted with a group selected from the group a, or a naphthyl group which is optionally substituted with a group selected from the group a, and
$R^{6x}$ is a phenyl group which is optionally substituted with a group selected from the group a, or a naphthyl group which is optionally substituted with a group selected from the group a.

A compound represented by the formula (I) wherein
G is a —S—$R^{1g}$ group,
X is a —O—$R^{6x}$ group,
Z is a phenyl group which is optionally substituted with a group selected from the group a,
A is a hydrogen atom,
E is a methyl group, an ethyl group, or a propyl group,
$R^{1g}$ is a phenyl group which is optionally substituted with a group selected from the group a, or a naphthyl group which is optionally substituted with a group selected from the group a, and
$R^{6x}$ is a phenyl group which is optionally substituted with a group selected from the group a, or a naphthyl group which is optionally substituted with a group selected from the group a.

A compound represented by the formula (I) wherein
G is a —O—$R^{1g}$ group,
X is a —O—$R^{6x}$ group,
Z is a phenyl group which is optionally substituted with a group selected from the group a,
A is a hydrogen atom,
E is a methyl group, an ethyl group, or a propyl group,
$R^{1g}$ is a C1-C10 alkyl group which is optionally substituted with a group selected from the group b, a phenyl group which is optionally substituted with a group selected from the group a, a naphthyl group which is optionally substituted with a group selected from the group a, or a thienyl group which is optionally substituted with a group selected from the group a, and
$R^{6x}$ is a phenyl group which is optionally substituted with a group selected from the group a, or a naphthyl group which is optionally substituted with a group selected from the group a.

A compound represented by the formula (I) wherein
G is a —O—$R^{1g}$ group,
X is a —O—$R^{6x}$ group,
Z is a phenyl group which is optionally substituted with a group selected from the group a,
A is a hydrogen atom,
E is a —$R^1$ group,
$R^1$ is a C1-C10 alkyl group which is optionally substituted with a group selected from the group b, a phenyl group which is optionally substituted with a group selected from the group a, or a thienyl group which is optionally substituted with a group selected from the group a,
$R^{1g}$ is a C1-C10 alkyl group which is optionally substituted with a group selected from the group b, and $R^{6x}$ is a phenyl group which is optionally substituted with a group selected from the group a, or a naphthyl group which is optionally substituted with a group selected from the group a.

A compound represented by the formula (I) wherein
G is a —O—$R^{1g}$ group,
X is a —O—$R^{6x}$ group,
Z is a phenyl group which is optionally substituted with a group selected from the group a,
A is a hydrogen atom,
E is a methyl group, an ethyl group, or a propyl group,
$R^{1g}$ is a C1-C10 alkyl group which is optionally substituted with a group selected from the group b, and
$R^{6x}$ is a phenyl group which is optionally substituted with a group selected from the group a, or a naphthyl group which is optionally substituted with a group selected from the group a.

A compound represented by the formula (I) wherein
G is a —O—$R^{1g}$ group,
X is a —O—$R^{6x}$ group,
Z is a phenyl group which is optionally substituted with a group selected from the group a,
A is a hydrogen atom,
E is a —$R^1$ group,
$R^1$ is a C1-C10 alkyl group which is optionally substituted with a group selected from the group b, a phenyl group which is optionally substituted with a group selected from the group a, or a thienyl group which is optionally substituted with a group selected from the group a,
$R^{1g}$ is a phenyl group which is optionally substituted with a group selected from the group a, or a naphthyl group which is optionally substituted with a group selected from the group a, and
$R^{6x}$ is a phenyl group which is optionally substituted with a group selected from the group a, or a naphthyl group which is optionally substituted with a group selected from the group a.

A compound represented by the formula (I) wherein
G is a —O—$R^{1g}$ group,
X is a —O—$R^{6x}$ group,
Z is a phenyl group which is optionally substituted with a group selected from the group a,
A is a hydrogen atom,
E is a methyl group, an ethyl group or a propyl group, $R^{1g}$ is a phenyl group which is optionally substituted with a group selected from the group a, or a naphthyl group which is optionally substituted with a group selected from the group a, and
$R^{6x}$ is a phenyl group which is optionally substituted with a group selected from the group a, or a naphthyl group which is optionally substituted with a group selected from the group a.

A compound represented by the formula (I) wherein
$R^1$ is a C1-C20 alkyl group which is optionally substituted with a group selected from the group p, a phenyl group which is optionally substituted with a group selected from the group q, or a thienyl group which is optionally substituted with a group selected from the group q,
$R^2$ is a —$R^1$ group,
$R^3$ is a —$R^1$ group or a —O—$R^1$ group,
$R^4$ is a C1-C10 hydrocarbon group,
$R^5$ is a carbocyclic group having 3 to 14 ring-constituting atoms which is optionally substituted with a group selected from the group q, or a heterocyclic group having 3 to 14 ring-constituting atoms which is optionally substituted with a group selected from the group q, $R^6$ is a carbocyclic group having 3 to 14 ring-constituting atoms which is optionally substituted with a group selected from the group q, or a heterocyclic group having 3 to 14 ring-constituting atoms which is optionally substituted with a group selected from the group q, and
$L^1$ is an oxygen atom or a sulfur atom,
wherein the group p consists of a halogen atom, a cyano group, a nitro group, a phenyl group which is optionally substituted with a halogen atom, a naphthyl group which is optionally substituted with a halogen atom, a monocyclic saturated hydrocarbocyclic group having having 3 to 8 ring-constituting atoms which is optionally substituted with a C1-C4 alkyl group, and a condensed polycyclic saturated carbocyclic group having 8 to 14 ring-constituting atoms which is optionally substituted with a C1-C4 alkyl group, and
the group q consists of a halogen atom, a cyano group, a nitro group, a C1-C10 alkyl group which is optionally substituted with a halogen atom, a phenyl group which is optionally substituted with a halogen atom, and a monocyclic saturated hydrocarbocyclic group having 3 to 8 ring-constituting atoms which is optionally substituted with a C1-C4 alkyl group.

The above definitions of the group p and the group q are the same for compounds described below.

A compound represented by the formula (I) wherein
G is a —S—$R^{1g}$ group or a —O—$R^{1g}$ group,
X is a —S—$R^{5x}$ group or a —O—$R^{6x}$ group,
Z is a phenyl group which is optionally substituted with a group selected from the group q,
A is a hydrogen atom,
E is a —$R^1$ group or a -$L^1$-$R^1$ group,
$L^1$ is an oxygen atom or a sulfur atom,
$R^1$ is a C1-C10 alkyl group which is optionally substituted with a group selected from the group p, a phenyl group which is optionally substituted with a group selected from the group q, or a thienyl group which is optionally substituted with a group selected from the group q,
$R^{1g}$ is a C1-C10 alkyl group which is optionally substituted with a group selected from the group p, a phenyl group which is optionally substituted with a group selected from the group q, a naphthyl group which is optionally substituted with a group selected from the group q, or a thienyl group which is optionally substituted with a group selected from the group q, and
$R^{6x}$ and $R^{5x}$ represent a phenyl group which is optionally substituted with a group selected from the group q, or a naphthyl group which is optionally substituted with a group selected from the group q.

A compound represented by the formula (I) wherein
G is a —S—$R^{1g}$ group or a —O—$R^{1g}$ group,
X is a —S—$R^{5x}$ group or a —O—$R^{6x}$ group,
Z is a phenyl group which is optionally substituted with a group selected from the group q,
A is a hydrogen atom,
E is a —$R^1$ group,
$R^1$ is a C1-C10 alkyl group which is optionally substituted with a group selected from the group p, a phenyl group which is optionally substituted with a group selected from the group q, or a thienyl group which is optionally substituted with a group selected from the group q,
$R^{1g}$ is a C1-C10 alkyl group which is optionally substituted with a group selected from the group p, a phenyl group which is optionally substituted with a group selected from the group q, a naphthyl group which is optionally substituted with a group selected from the group q, or a thienyl group which is optionally substituted with a group selected from the group q, and $R^{6x}$ and $R^{5x}$ represent a phenyl group which is optionally substituted with a group selected from the group q, or a naphthyl group which is optionally substituted with a group selected from the group q.

A compound represented by the formula (I) wherein
G is a —S—$R^{1g}$ group or a —O—$R^{1g}$ group,
X is a —O—$R^{6x}$ group,
Z is a phenyl group which is optionally substituted with a group selected from the group q,
A is a hydrogen atom,
E is a —$R^1$ group,
$R^1$ is a C1-C10 alkyl group which is optionally substituted with a group selected from the group p, a phenyl group which is optionally substituted with a group selected from the group q, or a thienyl group which is optionally substituted with a group selected from the group q,
$R^{1g}$ is a C1-C10 alkyl group which is optionally substituted with a group selected from the group p, a phenyl group which is optionally substituted with a group selected from the group q, a naphthyl group which is optionally substituted with a group selected from the group q, or a thienyl group which is optionally substituted with a group selected from the group q, and
$R^{6x}$ represents a phenyl group which is optionally substituted with a group selected from the group q, or a naphthyl group which is optionally substituted with a group selected from the group q.

A compound represented by the formula (I) wherein
G is a —S—$R^{1g}$ group,
X is a —O—$R^{6x}$ group,
Z is a phenyl group which is optionally substituted with a group selected from the group q,
A is a hydrogen atom,
E is a —$R^1$ group,
$R^1$ is a C1-C10 alkyl group which is optionally substituted with a group selected from the group p, a phenyl group which is optionally substituted with a group selected from the group q, or a thienyl group which is optionally substituted with a group selected from the group q,
$R^{1g}$ is a C1-C10 alkyl group which is optionally substituted with a group selected from the group p, a phenyl group which is optionally substituted with a group selected from the group q, a naphthyl group which is optionally substituted with a group selected from the group q, or a thienyl group which is optionally substituted with a group selected from the group q, and
$R^{6x}$ is a phenyl group which is optionally substituted with a group selected from the group q, or a naphthyl group which is optionally substituted with a group selected from the group q.

A compound represented by the formula (I) wherein
G is a —O—$R^{1g}$ group,
X is a —O—$R^{6x}$ group,
Z is a phenyl group which is optionally substituted with a group selected from the group q,
A is a hydrogen atom,
E is a —$R^1$ group,
$R^1$ is a C1-C10 alkyl group which is optionally substituted with a group selected from the group p, a phenyl group which is optionally substituted with a group selected from the group q, or a thienyl group which is optionally substituted with a group selected from the group q,
$R^{1g}$ is a C1-C10 alkyl group which is optionally substituted with a group selected from the group p, a phenyl group which is optionally substituted with a group selected from the group q, a naphthyl group which is optionally substituted with a group selected from the group q, or a thienyl group which is optionally substituted with a group selected from the group q, and
$R^{6x}$ is a phenyl group which is optionally substituted with a group selected from the group q, or a naphthyl group which is optionally substituted with a group selected from the group q.

A compound represented by the formula (I) wherein
G is a —S—$R^{1g}$ group,
X is a —O—$R^{6x}$ group,
Z is a phenyl group which is optionally substituted with a group selected from the group q,
A is a hydrogen atom,
E is a methyl group, an ethyl group, or a propyl group,
$R^{1g}$ is a C1-C10 alkyl group which is optionally substituted with a group selected from the group p, a phenyl group which is optionally substituted with a group selected from the group q, a naphthyl group which is optionally substituted with a group selected from the group q, or a thienyl group which is optionally substituted with a group selected from the group q, and
$R^{6x}$ is a phenyl group which is optionally substituted with a group selected from the group q, or a naphthyl group which is optionally substituted with a group selected from the group q.

A compound represented by the formula (I) wherein
G is a —S—$R^{1g}$ group,
X is a —O—$R^{6x}$ group,
Z is a phenyl group which is optionally substituted with a group selected from the group q,
A is a hydrogen atom,
E is a —$R^1$ group,
$R^1$ is a C1-C10 alkyl group which is optionally substituted with a group selected from the group p, a phenyl group which is optionally substituted with a group selected from the group q, or a thienyl group which is optionally substituted with a group selected from the group q,
$R^{1g}$ is a C1-C10 alkyl group which is optionally substituted with a group selected from the group p, and
$R^{6x}$ is a phenyl group which is optionally substituted with a group selected from the group q, or a naphthyl group which is optionally substituted with a group selected from the group q.

A compound represented by the formula (I) wherein
G is a —S—$R^{1g}$ group,
X is a —O—$R^{6x}$ group,
Z is a phenyl group which is optionally substituted with a group selected from the group q,
A is a hydrogen atom,
E is a methyl group, an ethyl group, or a propyl group,
$R^{1g}$ is a C1-C10 alkyl group which is optionally substituted with a group selected from the group p, and
$R^{6x}$ is a phenyl group which is optionally substituted with a group selected from the group q, or a naphthyl group which is optionally substituted with a group selected from the group q.

A compound represented by the formula (I) wherein
G is a —S—$R^{1g}$ group,
X is a —O—$R^{6x}$ group,
Z is a phenyl group which is optionally substituted with a group selected from the group q,
A is a hydrogen atom,
E is a —$R^1$ group,
$R^1$ is a C1-C10 alkyl group which is optionally substituted with a group selected from the group p, a phenyl group which is optionally substituted with a group selected from the group q, or a thienyl group which is optionally substituted with a group selected from the group q, $R^{1g}$ is a phenyl group which is optionally substituted with a group selected from the group q, or a naphthyl group which is optionally substituted with a group selected from the group q, and $R^{6x}$ is a phenyl group which is optionally substituted with a group selected from the group q, or a naphthyl group which is optionally substituted with a group selected from the group q.

A compound represented by the formula (I) wherein

G is a —S—$R^{1g}$ group,

X is a —O—$R^{6x}$ group,

Z is a phenyl group which is optionally substituted with a group selected from the group q, A is a hydrogen atom, E is a methyl group, an ethyl group, or a propyl group, $R^{1g}$ is a phenyl group which is optionally substituted with a group selected from the group q, or a naphthyl group which is optionally substituted with a group selected from the group q, and $R^{6x}$ is a phenyl group which is optionally substituted with a group selected from the group q, or a naphthyl group which is optionally substituted with a group selected from the group q.

A compound represented by the formula (I) wherein

G is a —O—$R^{1g}$ group,

X is a —O—$R^{6x}$ group,

Z is a phenyl group which is optionally substituted with a group selected from the group q, A is a hydrogen atom, E is a methyl group, ethyl group or propyl group, $R^{1g}$ is a C1-C10 alkyl group which is optionally substituted with a group selected from the group p, a phenyl group which is optionally substituted with a group selected from the group q, a naphthyl group which is optionally substituted with a group selected from the group q, or a thienyl group which is optionally substituted with a group selected from the group q, and $R^{6x}$ is a phenyl group which is optionally substituted with a group selected from the group q, or a naphthyl group which is optionally substituted with a group selected from the group q.

A compound represented by the formula (I) wherein

G is a —O—$R^{1g}$ group,

X is a —O—$R^{6x}$ group,

Z is a phenyl group which is optionally substituted with a group selected from the group q, A is a hydrogen atom, E is a —$R^1$ group, $R^1$ is a C1-C10 alkyl group which is optionally substituted with a group selected from the group p, a phenyl group which is optionally substituted with a group selected from the group q, or a thienyl group which is optionally substituted with a group selected from the group q, $R^{1g}$ is a C1-C10 alkyl group which is optionally substituted with a group selected from the group p, and $R^{6x}$ is a phenyl group which is optionally substituted with a group selected from the group q, or a naphthyl group which is optionally substituted with a group selected from the group q.

A compound represented by the formula (I) wherein

G is a —O—$R^{1g}$ group,

X is a —O—$R^{6x}$ group,

Z is a phenyl group which is optionally substituted with a group selected from the group q, A is a hydrogen atom, E is a methyl group, an ethyl group, or a propyl group, $R^{1g}$ is a C1-C10 alkyl group which is optionally substituted with a group selected from the group p, and $R^{6x}$ is a phenyl group which is optionally substituted with a group selected from the group q, or a naphthyl group which is optionally substituted with a group selected from the group q.

A compound represented by the formula (I) wherein

G is a —O—$R^{1g}$ group,

X is a —O—$R^{6x}$ group,

Z is a phenyl group which is optionally substituted with a group selected from the group q, A is a hydrogen atom, E is a —$R^1$ group, $R^1$ is a C1-C10 alkyl group which is optionally substituted with a group selected from the group p, a phenyl group which is optionally substituted with a group selected from the group q, or a thienyl group which is optionally substituted with a group selected from the group q, $R^{1g}$ is a phenyl group which is optionally substituted with a group selected from the group q, or a naphthyl group which is optionally substituted with a group selected from the group q, and $R^{6x}$ is a phenyl group which is optionally substituted with a group selected from the group q, or a naphthyl group which is optionally substituted with a group selected from the group q.

A compound represented by the formula (I) wherein

G is a —O—$R^{1g}$ group,

X is a —O—$R^{6x}$ group,

Z is a phenyl group which is optionally substituted with a group selected from the group q, A is a hydrogen atom, E is a methyl group, an ethyl group, or a propyl group, $R^{1g}$ is a phenyl group which is optionally substituted with a group selected from the group q, or a naphthyl group which is optionally substituted with a group selected from the group q, and $R^{6x}$ is a phenyl group which is optionally substituted with a group selected from the group q, or a naphthyl group which is optionally substituted with a group selected from the group q.

Then, processes for producing the compound of the present compound are described. The compound of the present invention can be produced by, for example, production processes as described below.

Production Process 1

Of the compounds of the present invention, a compound represented by the formula (Ia):

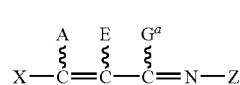

wherein $G^a$ represents a -$L^2$-$R^1$ group or a —N($R^2$)—$R^2$ group, and A, E, X, Z, $L^2$, $R^1$, $R^2$ and $R^3$ are as defined above (hereinafter referred to as the compound (Ia)) can be produced by reacting a compound represented by the formula (II):

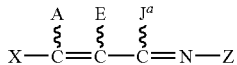
(II)

wherein $J^a$ represents a chlorine atom or a bromine atom, and A, E, X and Z are as defined above (hereinafter referred to as the compound (II)) with a compound represented by the formula (III):

$G^a$-H (III)

wherein $G^a$ is as defined above (hereinafter referred to as the compound (III)).

Although the compound (II) may be reacted with an excessive amount of the compound (III), 1 equivalent of the compound (II) is reacted with preferably 0.8 to 5 equivalents, more preferably 0.8 to 2 equivalents of the compound (III).

The reaction may be carried out in the presence of a base in the reaction system, if necessary.

Examples of the base include alkali metal alkoxides such as sodium methoxide and potassium tert-butoxide; nitrogen-containing compounds such as triethylamine and pyridine; carbonates such as potassium carbonate, sodium carbonate, sodium hydrogen carbonate, and potassium hydrogen carbonate; hydroxides such as sodium hydroxide and potassium hydroxide; and metal hydrides such as sodium hydride.

The amount of the base to be used is not particularly limited as long as the base exerts no adverse effect on the reaction, and it is preferably 0.8 to 5 equivalents, more preferably from 0.8 to 1.2 equivalents for 1 equivalent of the compound (III).

The reaction can be carried out using a suitable solvent. Examples of the solvent include aliphatic hydrocarbons such as hexane and petroleum ether; aromatic hydrocarbons such as benzene, toluene and xylene; esters such as ethyl acetate; ketones such as acetone; ethers such as diethyl ether and tetrahydrofuran; nitriles such as acetonitrile; acid amides such as dimethylformamide; and sulfoxide such as dimethylsulfoxide. These solvents may be used in mixture.

The temperature of the reaction is usually from −50 to 150° C., preferably from −20 to 120° C., and more preferably from −10 to 60° C. The reaction time is usually from 0.1 to 96 hours, and preferably from 0.1 to 24 hours.

After completion of the reaction, the compound (Ia) can be isolated by conventional post-treatment, for example, concentration of a reaction mixture, or pouring of a reaction mixture into water and then extraction with an organic solvent, followed by concentration. The obtained compound (Ia) can be purified by a conventional method such as distillation, reprecipitation, recrystallization or chromatography.

Production Process 2

Of the compounds of the present invention, a compound represented by the formula (Ib):

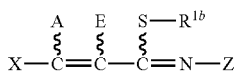
(Ib)

wherein $R^{1b}$ represents a C1-C20 chain hydrocarbon group which is optionally substituted with a group selected from the group b, and A, E, X and Z are as defined above (hereinafter referred to as the compound (Ib)) can be produced by reacting a compound represented by the formula (IV):

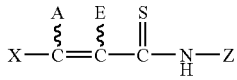
(IV)

wherein A, E, X and Z are as defined above (hereinafter referred to as the compound (IV)) with a compound represented by the formula (V):

$R^{1b}$-$J^{1b}$ (V)

wherein $J^{1b}$ represents a leaving group such as a chlorine atom, a bromine atom, an iodine atom, a —O—S(O)$_2$-$J^{2b}$ group, or a —S(O)$_2$-$J^{2b}$ group (wherein $J^{2b}$ represents a C1-C3 alkyl group which is optionally substituted with a halogen, such as a methyl group or a trifluoromethyl group, or a phenyl group which is optionally substituted with a C1-C3 alkyl group), and $R^{1b}$ is as defined above (hereinafter referred to as the compound (V)).

Although the compound (IV) may be reacted with an excessive amount of the compound (V), 1 equivalent of the compound (IV) is reacted with preferably 0.8 to 5 equivalents, more preferably 0.8 to 1.2 equivalents of the compound (V).

The reaction may be carried out in the presence of a base in the reaction system, if necessary.

Examples of the base include alkali metal alkoxides such as sodium methoxide and potassium tert-butoxide; nitrogen-containing compounds such as triethylamine and pyridine; carbonates such as potassium carbonate, sodium carbonate, sodium hydrogen carbonate, and potassium hydrogen carbonate; hydroxides such as sodium hydroxide and potassium hydroxide; and metal hydrides such as sodium hydride.

The amount of the base to be used is not particularly limited as long as the base exerts no adverse effect on the reaction, and it is preferably 0.8 to 5 equivalents, more preferably from 0.8 to 1.2 equivalents for 1 equivalent of the compound (IV).

The reaction can be carried out using a suitable solvent. Examples of the solvent include aliphatic hydrocarbons such as hexane and petroleum ether; aromatic hydrocarbons such as benzene, toluene and xylene; esters such as ethyl acetate; ketones such as acetone; ethers such as diethyl ether and tetrahydrofuran; nitriles such as acetonitrile; acid amides such as dimethylformamide; and sulfoxide such as dimethylsulfoxide. These solvents may be used in mixture, or may be used as a mixed solvent with water.

The temperature of the reaction is usually from −50 to 150° C., preferably from −20 to 120° C., and more preferably from −10 to 60° C. The reaction time is usually from 0.1 to 96 hours, and preferably from 0.1 to 24 hours.

After completion of the reaction, the compound (Ib) can be isolated by conventional post-treatment, for example, concentration of a reaction mixture, or pouring of a reaction mixture into water and then extraction with an organic solvent, followed by concentration. The obtained compound (Ib) can be purified by a conventional method such as distillation, reprecipitation, recrystallization or chromatography.

Production Process 3

Of the compounds of the present invention, a compound represented by the formula (Ic):

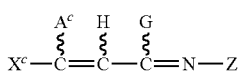
(Ic)

wherein $A^c$ represents a —$R^1$ group, $X^c$ represents a —S—$R^5$ group, and $R^1$, $R^5$, G and Z are as defined above (hereinafter referred to as the compound (Ic)) can be produced by reacting a compound represented by the formula (VI):

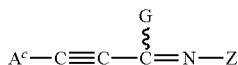 (VI)

wherein $A^c$, G and Z are as defined above (hereinafter referred to as the compound (VI)) with a compound represented by the formula (VII):

 (VII)

wherein $X^c$ is as defined above (hereinafter referred to as the compound (VII)).

Although the compound (VI) may be reacted with an excessive amount of the compound (VII), 1 equivalent of the compound (VI) is reacted with preferably 1 to 5 equivalents, more preferably 1 to 3 equivalents of the compound (VII).

The reaction may be carried out in the presence of a base or an acid in the reaction system, if necessary.

Examples of the base include alkali metal alkoxides such as sodium methoxide and potassium tert-butoxide; nitrogen-containing compounds such as triethylamine and pyridine; carbonates such as potassium carbonate, sodium carbonate, sodium hydrogen carbonate, and potassium hydrogen carbonate; hydroxides such as sodium hydroxide and potassium hydroxide; and metal hydrides such as sodium hydride.

The amount of the base to be used is not particularly limited as long as the base exerts no adverse effect on the reaction, and it is preferably 0.01 to 1 equivalents, more preferably from 0.01 to 0.2 equivalents for 1 equivalent of the compound (VII).

Examples of the acid include mineral acids such as hydrochloric acid, sulfuric acid and nitric acid; organic acids such as formic acid, acetic acid, propionic acid, trifluoroacetic acid, methanesulfonic acid, benzenesulfonic acid, and p-toluenesulfonic acid; acid addition salts of amines, such as triethylamine hydrochloride and pyridine hydrochloride; and Lewis acids such as aluminum chloride, zinc chloride, zinc iodide, titanium tetrachloride, cerium chloride, ytterbium triflate and a boron trifluoride-ether complex.

The amount of the acid to be used is not particularly limited as long as the acid exerts no adverse effect on the reaction, and it is preferably 0.01 to 1 equivalent, more preferably from 0.01 to 0.2 equivalents for 1 equivalent of the compound (VII).

The reaction can be carried out using a suitable solvent. Examples of the solvent include aliphatic hydrocarbons such as hexane and petroleum ether; aromatic hydrocarbons such as benzene, toluene, and xylene; esters such as ethyl acetate; ketones such as acetone; ethers such as diethyl ether and tetrahydrofuran; nitriles such as acetonitrile; acid amides such as dimethylformamide; and sulfoxide such as dimethylsulfoxide. These solvents may be used in mixture.

The temperature of the reaction is usually from –50 to 150° C., preferably from –20 to 120° C., and more preferably from –10 to 80° C. The reaction time is usually from 0.1 to 96 hours, and preferably from 0.1 to 24 hours.

After completion of the reaction, the compound (Ic) can be isolated by conventional post-treatment, for example, concentration of a reaction mixture, or pouring of a reaction mixture into water and then extraction with an organic solvent, followed by concentration. The obtained compound (Ic) can be purified by a conventional method such as distillation, reprecipitation, recrystallization or chromatography.

Production Process 4

Of the compounds of the present invention, a compound represented by the formula (Id):

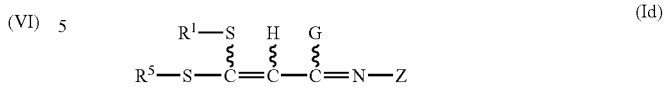 (Id)

wherein G, $R^1$, $R^5$ and Z are as defined above (hereinafter referred to as the compound (Id)) can be produced by reacting a compound represented by the formula (VIII):

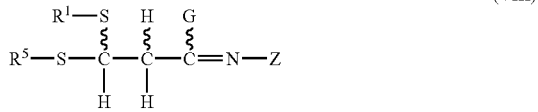 (VIII)

wherein G, $R^1$, $R^5$ and Z are as defined above (hereinafter referred to as the compound (VIII)) with N-chlorosuccinimide.

Although the compound (VIII) may be reacted with an excessive amount of N-chlorosuccinimide, 1 equivalent of the compound (VIII) is reacted with preferably 1 to 5 equivalents, more preferably 1 to 3 equivalents of N-chlorosuccinimide.

The reaction can be carried out using a suitable solvent. Examples of the solvent include ethers such as diethyl ether and tetrahydrofuran; and acid amides such as dimethylformamide. These solvents may be used in mixture.

The temperature of the reaction is usually from –50 to 150° C., preferably from –20 to 120° C., and more preferably from –10 to 80° C. The reaction time is usually from 0.1 to 96 hours, and preferably from 0.1 to 24 hours.

After completion of the reaction, the compound (Id) can be isolated by conventional post-treatment, for example, concentration of a reaction mixture, or pouring of a reaction mixture into water and then extraction with an organic solvent, followed by concentration. The obtained compound (Id) can be purified by a conventional method such as distillation, reprecipitation, recrystallization or chromatography.

Production Process 5

Of the compounds of the present invention, a compound represented by the formula (Ie) (hereinafter referred to as the compound (Ie)) can be produced by reacting a compound represented by the formula (XVII) (hereinafter referred to as the compound (XVII)) with a compound represented by the formula (XIX) (hereinafter referred to as the compound (XIX)) in the presence of a base, as shown in the following scheme:

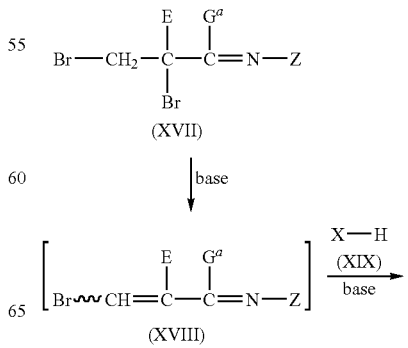

-continued

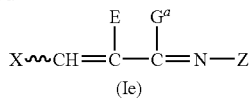

wherein E, $G^a$, X and Z are as defined above.

Examples of the base include alkali metal carbonates such as potassium carbonate and cesium carbonate; alkali metal hydrides such as sodium hydride; and nitrogen-containing organic compounds such as triethylamine and pyridine.

The amount of the base to be used is not particularly limited as long as the base exerts no adverse effect on the reaction, and it is preferably 2 to 5 equivalents for 1 equivalent of the compound (XIX).

The reaction can be carried out using a suitable solvent. Examples of the solvent include aliphatic hydrocarbons such as hexane and petroleum ether; aromatic hydrocarbons such as benzene, toluene and xylene; esters such as ethyl acetate; ketones such as acetone; ethers such as diethyl ether and tetrahydrofuran; nitriles such as acetonitrile; acid amides such as dimethylformamide; and sulfoxide such as dimethylsulfoxide. These solvents may be used in mixture.

The temperature of the reaction is usually from 0 to 150° C., and preferably from 50 to 100° C. The reaction time is usually from 0.1 to 96 hours, and preferably from 0.1 to 24 hours.

After completion of the reaction, the compound (Ie) can be isolated by conventional post-treatment, for example, concentration of a reaction mixture, or pouring of a reaction mixture into water and then extraction with an organic solvent, followed by concentration. The obtained compound (Ie) can be purified by a conventional method such as distillation, reprecipitation, recrystallization or chromatography.

The compound (XVII) is reacted with a base in a reaction system to be converted into a compound represented by the formula (XVIII) [wherein E, $G^a$ and Z are as defined above] (hereinafter referred to as the compound (XVIII)), which is reacted with a compound (XIX) in the presence of a base to give the compound (Ie).

Next, processes for producing the starting compounds used in production of the compounds of the present invention are shown.

The compound (II) can be produced by reacting a compound represented by the formula (IX):

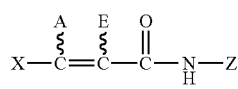

wherein A, E, X and Z are as defined above (hereinafter referred to as the compound (IX)) with a halogenating agent.

Examples of the halogenating agent used in the reaction include thionyl chloride, oxalyl chloride, phosphorous oxychloride, phosphorous pentachloride, phosphorous tribromide, carbon teterachloride, and carbon tetrabromide.

The amount of the halogenating agent to be used is not particularly limited. An excessive amount of the halogenating agent may be used as a solvent. Preferably, 0.8 to 3 equivalents of the halogenating agent is used for 1 equivalent of the compound (IX).

The reaction may be carried out in the presence of a catalyst in the reaction system, if necessary.

Examples of the catalyst include nitrogen-containing compounds such as triethylamine and pyridine; and acid amides such as dimethylformamide. The amount of the catalyst to be used is not particularly limited as long as the catalyst exerts no adverse effect on the reaction, and it is preferably 0.8 to 3 equivalents, more preferably 0.8 to 1.2 equivalents for 1 equivalent of the compound (IX).

The reaction can be carried out using a suitable solvent. Examples of the solvent include aliphatic hydrocarbons such as hexane and petroleum ether; aromatic hydrocarbons such as benzene, toluene and xylene; esters such as ethyl acetate; ketones such as acetone; ethers such as diethyl ether and tetrahydrofuran; nitriles such as acetonitrile; acid amides such as dimethylformamide; and sulfoxide such as dimethylsulfoxide. These solvents may be used in mixture.

The temperature of the reaction is usually from −50 to 150° C., preferably from −20 to 120° C., and more preferably from 10 to 100° C. The reaction time is usually from 0.1 to 96 hours, and preferably from 0.1 to 24 hours.

After completion of the reaction, although the obtained compound can be purified by a conventional method such as distillation, reprecipitation, recrystallization or chromatography, a reaction mixture may be used as it is in the next step.

The compound (III) is a known compound, or can be produced by a known method.

The compound (IV) can be produced by reacting the compound (IX) with a sulfurizing agent.

Examples of the sulfurizing agent used in the reaction include diphosphorus pentasulfide, Lawesson's reagent and $(Et_2Al)_2S$.

The amount of the sulfurizing agent to be used is not particularly limited. An excessive amount of the sulfurizing agent may be used. Preferably 0.8 to 3 equivalents of the sulfurizing agent is used for 1 equivalent of the compound (IX).

The reaction can be carried out using a suitable solvent. Examples of the solvent include aliphatic hydrocarbons such as hexane and petroleum ether; aromatic hydrocarbons such as benzene, toluene and xylene; esters such as ethyl acetate; ketones such as acetone; ethers such as diethyl ether and tetrahydrofuran; nitriles such as acetonitrile; and sulfoxide such as dimethylsulfoxide. These solvents may be used in mixture.

The temperature of the reaction is usually from −50 to 150° C., preferably from −20 to 120° C., and more preferably from 10 to 100° C. The reaction time is usually from 0.1 to 96 hours, and preferably from 0.1 to 24 hours.

After completion of the reaction, although the obtained compound can be purified by a conventional method such as distillation, reprecipitation, recrystallization or chromatography, a reaction mixture may be used as it is in the next step.

The compound (V) is a known compound, or can be produced by a known method.

The compound (VI) can be produced according to the method described in Chemistry Letters, 1261 (1989).

The compound (VII) is a known compound, or can be produced by a known method.

The compound (VIII) can be produced by reacting a compound represented by the formula (X):

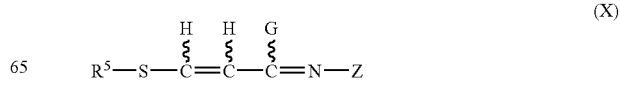

wherein G, $R^5$ and Z are as defined above (hereinafter referred to as the compound (X)) with a compound represented by the formula (XI):

 (XI)

wherein $R^1$ is as defined above (hereinafter referred to as the compound (XI)).

Although the compound (X) may be reacted with an excessive amount of the compound (XI), 1 equivalent of the compound (X) is reacted with preferably 0.8 to 5 equivalents, more preferably 0.8 to 1.2 equivalents of the compound (XI).

The reaction may be carried out in the presence of a base or an acid in the reaction system, if necessary.

Examples of the base include alkali metal alkoxides such as sodium methoxide and potassium tert-butoxide; nitrogen-containing compounds such as triethylamine and pyridine; carbonates such as potassium carbonate, sodium carbonate, sodium hydrogen carbonate and potassium hydrogen carbonate; hydroxides such as sodium hydroxide and potassium hydroxide; and metal hydrides such as sodium hydride. The amount of the base to be used is not particularly limited as long as the base exerts no adverse effect on the reaction, and it is preferably 0.01 to 1 equivalent, more preferably from 0.01 to 0.2 equivalents for 1 equivalent of the compound (X).

Examples of the acid include mineral acids such as hydrochloric acid, sulfuric acid and nitric acid; organic acids such as formic acid, acetic acid, propionic acid, trifluoroacetic acid, methanesulfonic acid, benzenesulfonic acid, and p-toluenesulfonic acid; acid addition salts of amines such as triethylamine hydrochloride and pyridine hydrochloride; and Lewis acids such as aluminum chloride, zinc chloride, zinc iodide, titanium tetrachloride, cerium chloride, ytterbium triflate and a boron trifluoride-ether complex. The amount of the acid to be used is not particularly limited as long as the acid exerts no adverse effect on the reaction, and it is preferably 0.01 to 1 equivalent, more preferably from 0.01 to 0.2 equivalents for 1 equivalent of the compound (X).

The reaction can be carried out using a suitable solvent. Examples of the solvent include aliphatic hydrocarbons such as hexane and petroleum ether; aromatic hydrocarbons such as benzene, toluene and xylene; esters such as ethyl acetate; ketones such as acetone; ethers such as diethyl ether and tetrahydrofuran; nitriles such as acetonitrile; acid amides such as dimethylformamide; and sulfoxide such as dimethylsulfoxide. These solvents may be used in mixture, or may be used as a mixed solvent with water.

The temperature of the reaction is usually from −50 to 150° C., preferably from −20 to 120° C., and more preferably from −10 to 80° C. The reaction time is usually from 0.1 to 96 hours, and preferably from 0.1 to 24 hours.

After completion of the reaction, the compound (VIII) can be isolated by conventional post-treatment, for example, concentration of a reaction mixture, or pouring of a reaction mixture into water and then extraction with an organic solvent, followed by concentration. The obtained compound (VIII) can be purified by a conventional method such as distillation, reprecipitation, recrystallization or chromatography.

The compound (X) can be produced according to the method described in WO 2007/063702 phamphlet.

The compound (IX) can be produced by reacting a compound represented by the formula (XII):

 (XII)

wherein A, E, X and $J^a$ are as defined above (hereinafter referred to as the compound (XII)) with a compound represented by the formula (XIII):

 (XIII)

wherein Z is as defined above (hereinafter referred to as the compound (XIII)).

Although the compound (XII) may be reacted with an excessive amount of the compound (XIII), 1 equivalent of the compound (XII) is reacted with preferably 1 to 5 equivalents, more preferably 1 to 3 equivalents of the compound (XIII).

The reaction may be carried out in the presence of a base in the reaction system, if necessary.

Examples of the base that can be used include nitrogen-containing compounds such as triethylamine and pyridine. The amount of the base to be used is not particularly limited as long as the base exerts no adverse effect on the reaction, and it is preferably 0.8 to 2 equivalents for 1 equivalent of the compound (XII).

The reaction can be carried out using a suitable solvent. Examples of the solvent include aliphatic hydrocarbons such as hexane and petroleum ether; aromatic hydrocarbons such as benzene, toluene and xylene; esters such as ethyl acetate; ketones such as acetone; ethers such as diethyl ether and tetrahydrofuran; and nitriles such as acetonitrile. These solvents may be used in mixture.

The temperature of the reaction is usually from −50 to 150° C., and preferably from −20 to 50° C. The reaction time is usually from 0.1 to 96 hours, and preferably from 0.1 to 24 hours.

After completion of the reaction, the compound (IX) can be isolated by conventional post-treatment, for example, concentration of a reaction mixture, or pouring of a reaction mixture into water and then extraction with an organic solvent, followed by concentration. The obtained compound (IX) can be purified by a conventional method such as distillation, reprecipitation, recrystallization or chromatography.

The compound (XIII) is a known compound and can be produced by a known method.

The compound (XII) can be produced by reacting a compound represented by the formula (XIV):

 (XIV)

wherein A, E and X are as defined above (hereinafter referred to as the compound (XIV)) with a halogenating agent.

Examples of the halogenating agent used in the reaction include thionyl chloride, oxalyl chloride, phosphorous oxychloride, phosphorous pentachloride, and phosphorous tribromide.

The amount of the halogenating agent to be used is not particularly limited. An excessive amount of the halogenating agent may be used as a solvent. Preferably 1 to 3 equivalents of the halogenating agent is used for 1 equivalent of the compound (XIV).

The reaction can be carried out using a suitable solvent. Examples of the solvent include aliphatic hydrocarbons such as hexane and petroleum ether; aromatic hydrocarbons such as benzene, toluene and xylene; esters such as ethyl acetate; ketones such as acetone; ethers such as diethyl ether and tetrahydrofuran; and nitriles such as acetonitrile. These solvents may be used in mixture.

The temperature of the reaction is usually from −20 to 150° C., and preferably from 0 to 120° C. The reaction time is usually from 0.1 to 96 hours, and preferably from 0.1 to 24 hours.

After completion of the reaction, although the compound (XII) can be isolated by conventional post-treatment such as concentration, a reaction mixture may be used as it is in the next step.

The compound (XIV) can be produced by reacting a compound represented by the formula (XV):

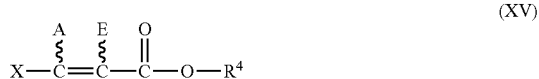

(XV)

wherein A, E, $R^4$ and X are as defined above (hereinafter referred to as the compound (XV)) with water in the presence of a base.

Examples of the base include alkali metal hydroxides such as lithium hydroxide, sodium hydroxide, and potassium hydroxide. The amount of the base to be used is not particularly limited as long as the base exerts no adverse effect on the reaction, and it is preferably 1 to 5 equivalents, more preferably from 1 to 2 equivalents for 1 equivalent of the compound (XV).

The reaction can be carried out in the presence of water using a suitable solvent. Examples of the solvent include ethers such as tetrahydrofuran; nitriles such as acetonitrile; and alcohols such as methanol, ethanol, and propanol. These solvents may be used in mixture.

The temperature of the reaction is usually from 0 to 150° C., and preferably from 20 to 80° C. The reaction time is usually from 0.1 to 96 hours, and preferably from 0.1 to 24 hours.

After completion of the reaction, the compound (XIV) can be isolated by a post-treatment operation, for example, by (i) adding acidic water (hydrochloric acid, etc.) to a reaction mixture and then collecting precipitated solids by filtration or (ii) adding acidic water (hydrochloric acid, etc.) to a reaction mixture, subjecting the mixture to extraction with an organic solvent, and then drying and concentrating an organic layer. The obtained compound (XIV) can be purified by a conventional method such as distillation, reprecipitation, recrystallization, or chromatography.

The compound (XV) can be produced by reacting a compound represented by the formula (XVI):

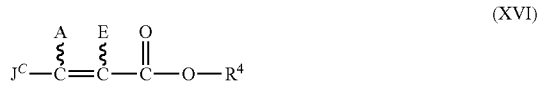

(XVI)

wherein $J^c$ represents $J^{1b}$ or a methoxy group, and E, $J^{1b}$ and $R^4$ are as defined above (hereinafter referred to as the compound (XVI)) with a compound (XVII):

(XVII)

in the presence of a base.

Examples of the base include alkali metal carbonates such as potassium carbonate and cesium carbonate; alkali metal hydrides such as sodium hydride; and nitrogen-containing organic compounds such as triethylamine and pyridine. The amount of the base to be used is not particularly limited as long as the base exerts no adverse effect on the reaction, and it is preferably 1 to 5 equivalents, more preferably from 1 to 2 equivalents for 1 equivalent of the compound (XVII).

The reaction can be carried out using a suitable solvent. Examples of the solvent include aliphatic hydrocarbons such as hexane and petroleum ether; aromatic hydrocarbons such as benzene, toluene and xylene; esters such as ethyl acetate; ketones such as acetone; ethers such as diethyl ether and tetrahydrofuran; nitriles such as acetonitrile; acid amides such as dimethylformamide; and sulfoxide such as dimethylsulfoxide. These solvents may be used in mixture.

The temperature of the reaction is usually from −20 to 150° C., and preferably from 0 to 100° C. The reaction time is usually from 0.1 to 96 hours, and preferably from 0.1 to 24 hours.

After completion of the reaction, the compound (XVI) can be isolated by conventional post-treatment, for example, concentration of a reaction mixture, or pouring of a reaction mixture into water and then extraction with an organic solvent, followed by concentration. The obtained compound (XVI) can be purified by a conventional method such as distillation, reprecipitation, recrystallization or chromatography.

Of the compounds (XVI), a compound in which $J^c$ is a methanesulfonyloxy group, a benzenesulfonyloxy group, a p-toluenesulfonyloxy group, or a methoxy group can be produced according to the method described in J. Am. Chem. Soc., 1979, 101, 7008.

Of the compounds (XVI), a compound in which $J^c$ is a bromine atom can be produced according to the method described in Org. Lett., 2007. 9, 3555.

Substituents on the compound of the present invention produced by the above described production processes 1 to 5 can be further converted into other desired substituents by a known procedure, such as substitution reaction, elimination reaction, oxidation reaction or reduction reaction.

The compound of the present invention may exist as various isomers including geometric isomers and stereoisomers. All isomers of the compound of the present invention and a mixture of the isomers are included in the scope of the present invention.

The compound of the present invention has an excellent controlling effect on pests including hygiene pests, animal parasitic pests and plant parasitic pests. A composition for pest control, that is, a pesticidal composition containing the compound of the present invention as an active ingredient is one aspect of the present invention.

The pesticidal composition of the present invention is usually formulated into forms which usual agrichemicals and animal drugs may take.

Examples of the form include an emulsifiable concentrate, a liquid formulation, a microemulsion, a flowable formulation, an oil solution, a wetting agent, a dust, a granule, a microgranule, a seed-coating agent, a smoking pesticide, a tablet, a microcapsule, a spray, an aerosol, a carbon dioxide gas formulation, a heating fumigant such as a mosquito coil, an electric mosquito mat or an electric mosquito liquid, an EW formulation, an ointment, a poison bait, a capsule, a pellet, an injectable, a resin formulation, and a shampoo formulation. The pesticidal composition of the present invention may further contain an emulsifier, a suspending agent, a spreading agent, a penetrating agent, a wetting agent, a thickener, or a stabilizer, if necessary.

The pesticidal composition of the present invention can be prepared by a known method. For example, the pesticidal composition agent can be prepared by dissolving or dispersing the compound of the present invention in a suitable liquid carrier, by mixing the compound of the present invention with a suitable solid carrier, or by adsorbing the compound of the present invention on a suitable solid carrier.

Examples of the liquid carrier include water, alcohols (e.g., methyl alcohol, ethyl alcohol, n-propyl alcohol, isopropyl alcohol, butyl alcohol, benzyl alcohol, ethylene glycol, etc.), ketones (e.g., acetone, methyl ethyl ketone, methyl isobutyl ketone, cyclohexanone etc.), ethers (e.g., tetrahydrofuran, ethylene glycol monomethyl ether, ethylene glycol dimethyl ether, diethylene glycol monomethyl ether, diethylene glycol monoethyl ether, propylene glycol monomethyl ether, etc.), aliphatic hydrocarbons (e.g., kerosine, kerosene, fuel oil, machine oil, etc.), aromatic hydrocarbons (e.g., toluene, xylene, solvent naphtha, methylnaphthalene, etc.), halogenated hydrocarbons (e.g., dichloromethane, chloroform, carbon tetrachloride, etc.), acid amides (e.g., N,N-dimethylformamide, N,N-dimethylacetamide, N-methylpyrrolidone, N-octylpyrrolidone, etc.), esters (e.g., ethyl acetate, butyl acetate, fatty acid glycerin ester, γ-butyrolactone, etc.), nitriles (e.g., acetonitrile, propionitrile, etc.), carbonates (e.g., propylene carbonate, etc.), and vegetable oils (e.g., rapeseed oil, cottonseed oil, corn oil, safflower oil, orange oil, etc.). These liquid carriers may be used alone, or two or more, preferably one to three of these liquid carriers may be mixed in appropriate proportions and then used.

Examples of the solid carrier (e.g., a diluent or a filler) include vegetable powders (e.g., soybean powder, tobacco powder, flour, wood powder, etc.), mineral powders (e.g., kaolin, bentonite, clay such as acid clay, talc such as talcum powder or agalmatolite powder, diatomaceous earth, silica such as mica powder, etc.), alumina, sulfur powder, activated carbon, calcium carbonate, potassium chloride, ammonium sulfate, sodium hydrogen carbonate, lactose, and urea. These solid carriers may be used alone, or two or more, preferably one to three of these solid carriers may be mixed in appropriate proportions and then used.

Examples of the gaseous carrier include fluorocarbon, butane gas, LPG (liquefied petroleum gas), dimethyl ether, and carbon dioxide gas. These gaseous carriers may be used alone, or two or more of these gaseous carriers may be mixed in appropriate proportions and then used. Alternatively, one or more of these gaseous carriers may be used in mixture with a suitable liquid carrier.

In the case where the compound of the present invention is formulated into an ointment, examples of a base material for the ointment include polyethylene glycol, pectin; esters of higher fatty acid and polyalcohol such as glyceryl monostearate ester; cellulose derivatives such as methylcellulose; sodium alginate, bentonite, higher alcohol; polyalcohol such as glycerin; petrolatum; white petrolatum; liquid paraffin; lard; vegetable oils; lanolin; anhydrous lanoiln; hydrogenated oils; and resin. These base materials may be used alone, or two or more, preferably one to three of these base materials may be used in mixture. Further, a surfactant as listed below may be added to the base material.

A surfactant may be used as an emulsifier, a spreading agent, a penetrating agent, a dispersant or the like in the above formulation.

Examples of the surfactant include soap; and nonionic and anionic surfactants such as polyoxyethylene alkyl aryl ether [NOIGEN (trade name), E A142 (trade name) manufactured by DAI-ICHI KOGYOU SEIYAKU CO., LTD.; NONAL (trade name) manufactured by TOHO CHEMICAL INDUSTRY CO., LTD.], alkyl sulfate [e.g. EMAL 10 (trade name) and EMAL 40 (trade name) manufactured by KAO CORPORATION], alkylbenzene sulfonate [e.g. NEOGEN (trade name) and NEOGEN T (trade name) manufactured by DAI-ICHI KOGYOU SEIYAKU CO., LTD.; NEIPELEX (trade name) manufactured by KAO CORPORATION], polyoxyethylene alkyl ether [e.g. NOIGEN ET-135 (trade name) manufactured by DAI-ICHI KOGYO SEIYAKU CO., LTD.], polyoxyethylene polyoxypropylene block polymer [e.g. NEWPOLE PE-64 (trade name) manufactured by SANYO CHEMICAL INDUSTRIES LTD.], polyalcohol ester [e.g. TWEEN 20 (trade name) and TWEEN 80 (trade name) manufactured by KAO CORPORATION], alkyl sulfosuccinate [e.g. SANMOLIN OT20 (trade name) manufactured by SANYO CHEMICAL INDUSTRIES LTD.; NEWKALGEN EX70 (trade name) manufactured by TAKEMOTO OIL & FAT CO., LTD.], alkyl naphthalenesulfonate [NEWKALGEN WG-1 (trade name) manufactured by TAKEMOTO OIL & FAT CO., LTD.], and alkenyl naphthalenesulfonate [SORPOL 5115 (trade name) manufactured by TOHO CHEMICAL INDUSTRY CO., LTD.]. These surfactants may be used alone, or two or more, preferably one to three of these surfactants may be mixed in appropriate proportions and then used.

Examples of a base material for the resin formulation include vinyl chloride polymers, and polyurethane. To the base material, if necessary, a plasticizer such as phthalate (e.g., dimethyl phthalate, dioctyl phthalate, etc.), adipate or stearic acid may be added. The resin formulation is prepared by kneading the compound of the present invention into the base material using a conventional kneader, followed by molding such as injection molding, extrusion molding or press molding. The resulting resin formulation may be formed into the shape of a plate, a film, a tape, a net, a string or the like via a further step of molding, cutting, or the like, if necessary. These resin formulations may be used, for example, the form of an animal collar, an animal ear tag, a sheet, a lead, or a horticultural post.

Examples of a base material of the poison bait include cereal powder, vegetable oil, sugar, and crystalline cellulose. To the base material, if necessary, an antioxidant such as dibutylhydroxytoluene or nordihydroguaiaretic acid, a preservative such as dehydroacetic acid, an agent for preventing children or pets from erroneously eating such as hot pepper powder, a pest-attractive perfume such as cheese perfume, onion perfume or peanut oil or the like may be added.

In addition, a sticking agent, a dispersant, a colorant, a stabilizer and the like, specifically, casein, gelatin, saccharides (e.g., starch, gum arabic, cellulose derivatives, alginic acid, etc.), lignin derivatives, bentonite, synthetic water-soluble polymers (e.g., polyvinyl alcohol, polyvinyl pyrrolidone, polyacrylic acid, etc.), PAP (acid isopropyl phosphate), BHT (2,6-di-tert-butyl-4-methylphenol), BHA (a mixture of 2-tert-butyl-4-methoxyphenol and 3-tert-butyl-4-methoxyphenol), other substances described in Code of Federal Regulation Title 40 §180, USA can be used as pharmaceutical auxiliary agents for preparing the pesticidal composition of the present invention.

A combination of the compound of the present invention and other pesticidal active ingredients can be formulated into a preparation, and then used, and examples of the other pesticidal active ingredients include an insecticide (e.g., pyrethroid insecticide, organic phosphorus insecticide, carbamate insecticide, neonicotinoid insecticide, nerve sodium channel blocker, insecticidal macrocyclic lactone, γ-amino butyric acid (GABA) antagonist, calcium channel activater, urea insecticide, insect hormone mimic, natural insecticide, etc.), an acaricide, a machine oil, a nematocide, a herbicide, a phytohormone agent, a plant growth regulator, a fungicide (e.g., copper fungicide, organic chlorine fungicide, organic sulfur fungicide, phenol fungicide, etc.), a synergist, an attractant, a repellent, a crop injury-reducing agent, a pigment, a fertilizer, an animal feed (e.g., feed for livestock such as cows, pigs and chickens, feed for pet animals such as dogs and cats, feed for cultured fish such as young yellowtail and sea bream, etc.), an animal drug (e.g., a drug for treatment or prevention of disease of livestock, pet animals and cultured fish), a nutritional supplement for animals, or the like.

The compound of the present invention can be used in combination with other active ingredients such as an insecticide (e.g., pyrethroid insecticide, organic phosphorus insecticide, carbamate insecticide, neonicotinoid insecticide, IGR agent, natural insecticide, etc.), an acaricide, a machine oil, a nematocide, a herbicide, a phytohormone agent, a plant growth regulator, a fungicide (e.g., copper fungicide, organic chlorine fungicide, organic sulfur fungicide, phenol fungicide, etc.), a synergist, an attractant, a repellent, a crop injury-reducing agent, a pigment, a fertilizer, an animal feed (e.g., feed for livestock such as cows, pigs and chickens, feed for pet animals such as dogs and cats, feed for cultured fish such as young yellowtail and sea bream, etc.), an animal drug (e.g., a drug for treatment or prevention of disease of livestock, pet animals and cultured fish), a nutritional supplement for animals, or the like.

The pesticidal composition of the present invention may comprise the compound of the present invention and other active ingredients.

The pesticidal composition of the present invention contains usually 0.1 to 80% by weight, preferably 1 to 20% by weight of the compound of the present invention. Specifically, when the pesticidal composition of the present invention is in the form of an emulsifiable concentrate, a liquid formulation or a wettable powder (e.g., a water dispersible granule), it contains usually 1 to 80% by weight, preferably 1 to 20% by weight of the compound of the present invention. When the pesticidal composition of the present invention is in the form of an oil solution or a dust, it contains usually 0.1 to 50% by weight, preferably 0.1 to 20% by weight of the compound of the present invention. When the pesticidal composition of the present invention is in the form of a granule, it contains usually 1 to 50% by weight, preferably 1 to 20% by weight of the compound of the present invention.

In the pesticidal composition of the present invention, active ingredients other than the compound of the present invention (e.g., insecticide, herbicide, acaricide, fungicide, etc.) amount to usually 0.1 to 80% by weight, preferably 1 to 20% by weight.

The content of additives other than the above active ingredients in the pesticidal composition of the present invention is usually 0.001 to 99.9% by weight, preferably 1 to 99% by weight, although it is different depending on the kind and content of the active ingredients, the form of the pesticidal composition and the like. Specifically, the content of a surfactant in the pesticidal composition of the present invention is usually 1 to 20% by weight, preferably 1 to 15% by weight. The content of a fluidizing aid in the pesticidal composition of the present invention is usually 1 to 20% by weight. The content of a carrier in the pesticidal composition of the present invention is usually 1 to 90% by weight, preferably 1 to 70% by weight.

When the pesticidal composition of the present invention is in the form of an emulsifiable concentrate or a wettable powder (e.g., a wate dispersible granule), it is preferably diluted with water by an appropriate concentration (e.g., 100 to 5,000 times) and then sprayed.

Active compounds of an insecticide, an acaricide, a nematocide, a fungicide, an herbicide, a phytohormone agent, a plant growth regulator, a synergist, and a crop injury-reducing agent which can be used in combination with the compound of the present invention are shown below.

Examples of active compounds of the insecticides include:
(1) Organic phosphorus compounds:
Acephate, Aluminium phosphide, butathiofos, cadusafos, chlorethoxyfos, chlorfenvinphos, chlorpyrifos, chlorpyrifos-methyl, cyanophos (CYAP), diazinon, DCIP (dichlorodiisopropyl ether), dichlofenthion (ECP), dichlorvos (DDVP), dimethoate, dimethylvinphos, disulfoton, EPN, ethion, ethoprophos, etrimfos, fenthion (MPP), fenitrothion (MEP), fosthiazate, formothion, hydrogen phosphide, isofenphos, isoxathion, malathion, mesulfenfos, methidathion (DMTP), monocrotophos, naled (BRP), oxydeprofos (ESP), parathion, phosalone, phosmet (PMP), pirimiphos-methyl, pyridafenthion, quinalphos, phenthoate (PAP), profenofos, propaphos, prothiofos, pyraclorfos, salithion, sulprofos, tebupirimfos, temephos, tetrachlorvinphos, terbufos, thiometon, trichlorphon (DEP), vamidothion, phorate, cadusafos, and the like;

(2) Carbamate compounds:
Alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb (MIPC), metolcarb, methomyl, methiocarb, NAC, oxamyl, pirimicarb, propoxur (PHC), XMC, thiodicarb, xylylcarb, aldicarb, and the like;

(3) Synthetic pyrethroid compounds:
Acrinathrin, allethrin, beta-cyfluthrin, bifenthrin, cycloprothrin, cyfluthrin, cyhalothrin, cypermethrin, empenthrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, metofluthrin, 2,3,5,6-tetrafluoro-4-methylbenzyl 2,2-dimethyl-3-(1-propenyl)cyclopropanecarboxylate, 2,3,5,6-tetrafluoro-4-(methoxymethyl)benzyl 2,2-dimethyl-3-(2-methyl-1-propenyl)cyclopropanecarboxylate, 2,3,5,6-tetrafluoro-4-(methoxymethyl)benzyl 2,2-dimethyl-3-(2-cyano-1-propenyl)cyclopropanecarboxylate, 2,3,5,6-tetrafluoro-4-(methoxymethyl)benzyl 2,2,3,3-tetramethylcyclopropanecarboxylate, and the like;

(4) Nereistoxin compounds:
Cartap, bensultap, thiocyclam, monosultap, bisultap, and the like;

(5) Neonicotinoid compounds:
Imidacloprid, nitenpyram, acetamiprid, thiamethoxam, thiacloprid, dinotefuran, clothianidin, and the like;

(6) Benzoylurea compounds:
Chlorfluazuron, bistrifluoron, diafenthiuron, diflubenzuron, fluazuron, flucycloxuron, flufenoxuron, hexaflumuron, lufenuron, novaluron, noviflumuron, teflubenzuron, triflumuron, triazuron, and the like;

(7) Phenylpyrazole compounds:
Acetoprole, ethiprole, fipronil, vaniliprole, pyriprole, pyrafluprole, and the like;

(8) Bt toxin insecticides:
Live spores derived from and crystal toxins produced from Bacillus thuringiesis and a mixture thereof;

(9) Hydrazine compounds:
Chromafenozide, halofenozide, methoxyfenozide, tebufenozide, and the like;

(10) Organic chlorine compounds:
Aldrin, dieldrin, dienochlor, endosulfan, methoxychlor, and the like;
(11) Natural insecticides:
Machine oil, nicotine-sulfate;
(12) Other insecticides:
Avermectin-B, bromopropylate, buprofezin, chlorphenapyr, cyromazine, D-D(1,3-Dichloropropene, emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, lepimectin, arsenic acid, benclothiaz, calcium cyanamide, calcium polysulfide, chlordane, chlordane, DDT, DSP, flufenerim, flonicamid, flurimfen, formetanate, metam-ammonium, metam-sodium, methyl bromide, potassium oleate, protrifenbute, spiromesifen, sulfur, metaflumizone, spirotetramat, pyrifluquinazone, spinetoram, chlorantraniliprole, tralopyril, any compound represented by the following formula (A):

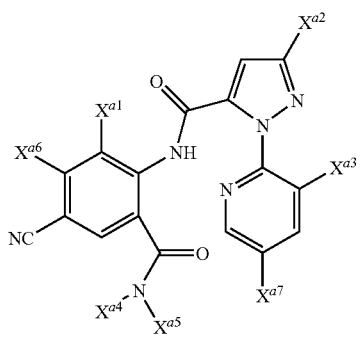

wherein $X^{a1}$ represents a methyl group, a chlorine atom, a bromine atom, or a fluorine atom; $X^{a2}$ represents a fluorine atom, a chlorine atom, a bromine atom, a C1-C4 haloalkyl group, or a C1-C4 haloalkoxy group; $X^{a3}$ represents a fluorine atom, a chlorine atom, or a bromine atom; $X^{a4}$ represents an optionally substituted C1-C4 alkyl group, an optionally substituted C3-C4 alkenyl group, an optionally substituted C3-C4 alkynyl group, an optionally substituted C3-C5 cycloalkylalkyl group, or a hydrogen atom; $X^{a5}$ represents a hydrogen atom or a methyl group; $X^{a6}$ represents a hydrogen atom, a fluorine atom, or a chlorine atom; and $X^{a7}$ represents a hydrogen atom, a fluorine atom, or a chlorine atom;
any compound represented by the following formula (B):

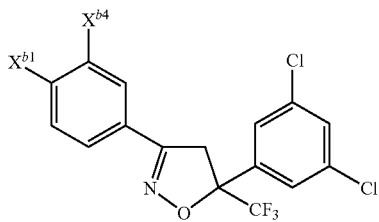

wherein $X^{b1}$ represents a $X^{b2}$—NH—C(=O) group, a $X^{b2}$—C(=O)—NH—CH_2 group, a $X^{b3}$—S(O) group, an optionally substituted pyrrol-1-yl group, an optionally substituted imidazol-1-yl group, an optionally substituted pyrazol-1-yl group, or an optionally substituted with 1,2,4-triazol-1-yl group; $X^{b2}$ represents an optionally substituted C1-C4 haloalkyl group such as a 2,2,2-trifluoroethyl group, or an optionally substituted C3-C6 cycloalkyl group such as a cyclopropyl group; $X^{b3}$ represents an optionally substituted C1-C4 alkyl group such as a methyl group; and $X^{b4}$ represents a hydrogen atom, a chlorine atom, a cyano group, or a methyl group; and
any compound represented by the following formula (C):

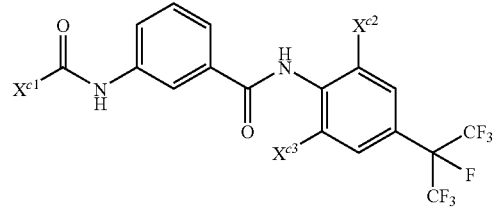

wherein $X^{c1}$ represents an optionally substituted C1-C4 alkyl group such as a 3,3,3-trifluoropropyl group, an optionally substituted C1-C4 alkoxy group such as a 2,2,2-trichloroethoxy group, an optionally substituted phenyl group such as a 4-cyanophenyl group, or an optionally substituted pyridyl group such as a 2-chloro-3-pyridyl group; $X^{c2}$ represents a methyl group or a trifluoromethylthio group; and $X^{c3}$ represents a methyl group or a halogen atom.

Examples of active ingredients of the acaricides include acequinocyl, amitraz, benzoximate, bifenaate, bromopropylate, chinomethionat, chlorobenzilate, CPCBS (chlorfenson), clofentezine, cyflumetofen, kelthane (dicofol), etoxazole, fenbutatin oxide, fenothiocarb, fenpyroximate, fluacrypyrim, fluproxyfen, hexythiazox, propargite (BPPS), polynactins, pyridaben, pyrimidifen, tebufenpyrad, tetradifon, spirodiclofen, spiromesifen, spirotetramat, amidoflumet, cyenopyrafen, and the like.

Examples of active ingredients of the nematicides include DCIP, fosthiazate, levamisol, methylsothiocyanate, morantel tartarate, imicyafos, and the like.

Examples of active ingredients of the fungicides include azole fungicidal compounds such as propiconazole, prothioconazole, triadimenol, prochloraz, penconazole, tebuconazole, flusilazole, diniconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanol, imazalil, and flutriafol;
cyclic amine fungicidal compouds such as fenpropimorph, tridemorph, and fenpropidin;
benzimidazole fungicidal compounds such as carbendezim, benomyl, thiabendazole, and thiophanate-methyl;
procymidone, cyprodinil, pyrimethanil, diethofencarb, thiuram, fluazinam, mancozeb, iprodione, vinclozolin, chlorothalonil, captan, mepanipyrim, fenpiclonil, fludioxonil, dichlofluanid, folpet, kresoxim-methyl, azoxystrobin, trifloxystrobin, fluoxastrobin, picoxystrobin, pyraclostrobin, dimoxystrobin, spiroxamine, quinoxyfen, fenhexamid, famoxadone, fenamidone, zoxamide, ethaboxam, amisulbrom, iprovalicarb, benthiavalicarb, cyazofamid, mandipropamid, boscalid, metrafenone, fluopiran, bixafen, cyflufenamid, and proquinazid.

Examples of active ingredients of the herbicides and the phytohormone agents include:

(1) Phenoxyfatty acid herbicidal compounds such as 2,4-PA, MCP, MCPB, phenothiol, mecoprop, fluoroxypyr, triclopyr, clomeprop, and naproanilide;
(2) Benzoic acid herbicidal compounds such as 2,3,6-TBA, dicamba, clopyralid, picloram, aminopyralid, quinclorac, and quinmerac;
(3) Urea herbicidal compounds such as diuron, linuron, chlortoluron, isoproturon, fluometuron, isouron, tebuthiuron, methabenzthiazuron, cumyluron, daimuron, and methyldaimuron;
(4) Triazine herbicidal compounds such as atrazine, ametoryn, cyanazine, simazine, propazine, simetryn, dimethametryn, prometryn, metribuzin, and triaziflam;
(5) Bipyridinium herbicidal compounds such as paraquat, and diquat;
(6) Hydroxybenzonitrile herbicidal compounds such as bromoxynil and ioxynil;
(7) Dinitroaniline herbicidal compounds such as pendimethalin, prodiamine, and trifluralin;
(8) Organic phosphorus herbicidal compounds such as amiprofos-methyl, butamifos, bensulide, piperophos, anilofos, glyphosate, glufosinate, and bialaphos;
(9) Carbamate herbicidal compounds such as di-allate, tri-allate, EPTC, butylate, benthiocarb, esprocarb, molinate, dimepiperate, swep, chlorpropham, phenmedipham, phenisopham, pyributicarb, and asulam;
(10) Acid amide herbicidal compounds such as propanil, propyzamide, bromobutide, and etobenzanid;
(11) Chloroacetanilide herbicidal compounds such as acetochlor, alachlor, butachlor, dimethenamid, propachlor, metazachlor, metolachlor, pretilachlor, thenylchlor, and pethoxamid;
(12) Diphenylether herbicidal compounds such as acifluorfen-sodium, bifenox, oxyfluorfen, lactofen, fomesafen, chlomethoxynil, and aclonifen;
(13) Cyclic imide herbicidal compounds such as oxadiazon, cinidon-ethyl, carfentrazone-ethyl, surfentrazone, flumiclorac-pentyl, flumioxazin, pyraflufen-ethyl, oxadiargyl, pentoxazone, fluthiacet-methyl, butafenacil, and benzfendizone;
(14) Pyrazole herbicidal compounds such as benzofenap, pyrazolate, pyrazoxyfen, topramezone, and pyrasulfotole;
(15) Triketone herbicidal compounds such as isoxaflutole, benzobicyclon, sulcotrione, mesotrione, tembotrione, and tefuryltrione;
(16) Aryloxyphenoxypropionic acid herbicidal compounds such as clodinafop-propargyl, cyhalofop-butyl, diclofop-methyl, fenoxaprop-ethyl, fluazifop-butyl, haloxyfop-methyl, and quizalofop-ethyl;
(17) Trioneoxime herbicidal compounds such as alloxydim-sodium, sethoxydim, butroxydim, clethodim, cloproxydim, cycloxydim, tepraloxydim, tralkoxydim, and profoxydim;
(18) Sulfonylurea herbicidal compounds such as chlorsulfuron, sulfometuron-methyl, metsulfuron-methyl, chlorimuron-ethyl, tribenuron-methyl, triasulfuron, bensulfuron-methyl, thifensulfuron-methyl, pyrazosulfuron-ethyl, primisulfuron-methyl, nicosulfuron, amidosulfuron, cinosulfuron, imazosulfuron, rimsulfuron, halosulfuron-methyl, prosulfuron, ethametsulfuron-methyl, triflusulfuron-methyl, flazasulfuron, cyclosulfamuron, flupyrsulfuron, sulfosulfuron, azimsulfuron, ethoxysulfuron, oxasulfuron, iodosulfuron-methyl-sodium, foramsulfuron, mesosulfuron-methyl, trifloxysulfuron, tritosulfuron, orthosulfamuron, flucetosulfuron, and 1-(2-chloro-6-propylimidazo[1,2-a]pyridazin-3-ylsulfonyl)-3-(4,6-dimethoxypyrimidin-2-yl)urea;
(19) Imidazolinone herbicidal compounds such as imazamethabenz-methyl, imazamethapyr, imazamox, imazapyr, imazaquin, and imazethapyr;
(20) Sulfonamide herbicidal compounds such as flumetsulam, metosulam, diclosulam, florasulam, cloransulam-methyl, penoxsulam, and pyroxsulam;
(21) Pyrimidinyloxybenzoic acid herbicidal compounds such as pyrithiobac-sodium, bispyribac-sodium, pyriminobac-methyl, pyribenzoxim, and pyriftalid; and
(22) Other herbicidal compounds such as bentazon, bromacil, terbacil, chlorthiamid, isoxaben, dinoseb, amitrole, cinmethylin, tridiphane, dalapon, diflufenzopyr-sodium, dithiopyr, thiazopyr, flucarbazone-sodium, propoxycarbazone-sodium, mefenacet, flufenacet, fentrazamide, cafenstrole, indanofan, oxaziclomefone, benfuresate, ACN, pyridate, chloridazon, norflurazon, flurtamone, diflufenican, picolinafen, beflubutamid, clomazone, amicarbazone, pinoxaden, and thiencarbazone-methyl.

Examples of active ingredients of the plant growth regulators include hymexazol, paclobutrazol, uniconazole-P, inabenfide, prohexadione-calcium, aviglycine, 1-naphthylacetamide, abscisic acid, indolebutyric acid, ethychlozate ethyl, ethephon, cloxyfonac, chlormequat, dichlorprop, gibberellin, prohydrojasmon, benzylaminopurine, forchlorfenuron, maleic hydrazide, calcium peroxide, mepiquat-chloride, and 4-CPA (4-chlorophenoxyacetic acid).

Examples of active compounds of the synergists include piperonyl butoxide, sesamex, sulfoxide, N-(2-ethylhexyl)-8,9,10-trinorborn-5-ene-2,3-dicarboxylmide (MGK 264), N-declyimidazole, WARF-antiresistant, TBPT, TPP, IBP, PSCP, methyl iodide ($CH_3I$), t-phenylbutenone, diethylmaleate, DMC, FDMC, ETP, and ETN.

Examples of active ingredients of the crop injury-reducing agents include benoxacor, cloquintocet-mexyl, cyometrinil, daimuron, dichlormid, fenchlorazole-ethyl, fenclorim, flurazole, fluxofenim, furilazole, mefenpyr-diethyl, MG191, oxabetrinil, allidochlor, isoxadifen-ethyl, cyprosulfamide, fluxofenim, and 1,8-naphthalic anhydride.

Examples of pests on which the compound of the present invention exhibits a controlling effect include arthropod pests such as harmful insects and harmful mites, and more specifically, the following pests.

Hemiptera:

Planthoppers (Delphacidae) such as small brown planthopper (*Laodelphax striatellus*), brown rice planthopper (*Nilaparvata lugens*), and white-backed rice planthopper (*Sogatella furcifera*); leafhoppers (Deltocephalidae) such as green rice leafhopper (*Nephotettix cincticeps*), green rice leafhopper (*Nephotettix virescens*), and tea green leafhopper (*Empoasca onukii*); aphids (Aphididae) such as cotton aphid (*Aphis gossypii*), green peach aphid (*Myzus persicae*), cabbage aphid (*Brevicoryne brassicae*), piraea aphid (*Aphis spiraecola*), potato aphid (*Macrosiphum euphorbiae*), foxglove aphid (*Aulacorthum solani*), oat bird-cherry aphid (*Rhopalosiphum padi*), tropical citrus aphid (*Toxoptera citricidus*), and mealy plum aphid (*Hyalopterus pruni*); stink bugs (Pentatomidae) such as green stink bug (*Nezara antennata*), bean bug (*Riptortus clavetus*), rice bug (*Leptocorisa chinensis*), white spotted spined bug (*Eysarcoris parvus*), and stink bug (*Halyomorpha mista*); whiteflies (Aleyrodidae) such as greenhouse whitefly (*Trialeurodes vaporariorum*), sweetpotato whitefly (*Bemisia tabaci*), silverleaf whitefly (*Bemisia argentifolii*), citrus whitefly (*Dialeurodes citri*), and citrus spiny white fly (*Aleurocanthus spiniferus*); scales (Coccidae)

such as Calfornia red scale (*Aonidiella aurantii*), San Jose scale (*Comstockaspis perniciosa*), citrus north scale (*Unaspis citri*), red wax scale (*Ceroplastes rubens*), cottonycushion scale (*Icerya purchasi*), Japanese mealybug (*Planococcus kraunhiae*), Cosmstock mealybug (*Pseudococcus longispinis*), and white peach scale (*Pseudaulacaspis pentagona*); lace bugs (Tingidae); cimices such as *Cimex lectularius*; psyllids (Psyllidae); etc.

Lepidoptera:

Pyralid moths (Pyralidae) such as rice stem borer (*Chilo suppressalis*), yellow rice borer (*Tryporyza incertulas*), rice leafroller (*Cnaphalocrocis medinalis*), cotton leafroller (*Notarcha derogata*), Indian meal moth (*Plodia interpunctella*), oriental corn borer (*Ostrinia furnacalis*), cabbage webworm (*Hellula undalis*), and bluegrass webworm (*Pediasia teterrellus*); owlet moths (Noctuidae) such as common cutworm (*Spodoptera litura*), beet armyworm (*Spodoptera exigua*), armyworm (*Pseudaletia separata*), cabbage armyworm (*Mamestra brassicae*), black cutworm (*Agrotis ipsilon*), beet semi-looper (*Plasia nigrisigna*), *Thoricoplusia* spp., *Heliothis* spp., and *Helicoverpa* spp.; white butterflies (Pieridae) such as common white (*Pieris rapae*); tortricid moths (Tortricidae) such as *Adoxophyes* spp., oriental fruit moth (*Grapholita molesta*), soybean pod borer (*Leguminivora glycinivorella*), azuki bean podworm (*Matsumuraeses azukivora*), summer fruit tortrix (*Adoxophyes orana fasciata*), smaller tea tortrix (*Adoxophyes* honmai.), oriental tea tortrix (*Homona magnanima*), apple tortrix (*Archips fuscocupreanus*), and codling moth (*Cydia pomonella*); leafblotch miners (Gracillariidae) such as tea leafroller (*Caloptilia theivora*), and apple leafminer (*Phyllonorycter ringoneella*); Carposimidae such as peach fruit moth (*Carposina niponensis*); lyonetiid moths (Lyonetiidae) such as *Lyonetia* spp.; tussock moths (Lymantriidae) such as *Lymantria* spp., and *Euproctis* spp.; yponomeutid moths (Yponomeutidae) such as diamondback (*Plutella xylostella*); gelechiid moths (Gelechiidae) such as pink bollworm (*Pectinophora gossypiella*), and potato tubeworm (*Phthorimaea operculella*); tiger moths and allies (Arctiidae) such as fall webworm (*Hyphantria cunea*); tineid moths (Tineidae) such as casemaking clothes moth (*Tinea translucens*), and webbing clothes moth (*Tineola bisselliella*); etc.

Thysanoptera:

Thrips (Thripidae) such as yellow citrus thrips (*Frankliniella occidentalis*), melon thrips (*Thrips palmi*), yellow tea thrips (*Scirtothrips dorsalis*), onion thrips (*Thrips tabaci*), flower thrips (*Frankliniella intonsa*), etc.

Diptera:

Culices such as common mosquito (*Culex pipiens pallens*), *Cluex tritaeniorhynchus*, and *Cluex quinquefasciatus*; *Aedes* spp. such as yellow fever mosquito (*Aedes aegypti*), and Asian tiger mosquito (*Aedes albopictus*); *Anopheles* spp. such as *Anopheles sinensis*; chironomids (Chironomidae); house flies (Muscidae) such as *Musca domestica*, and *Muscina stabulans*; blow flies (Calliphoridae); flesh flies (Sarcophagidae); little house flies (Fanniidae); anthomyiid flies (Anthomyiidae) such as seedcorn fly (*Delia platura*), and onion fly (*Delia antiqua*); leafminer flies (Agromyzidae) such as rice leafminer (*Agromyza oryzae*), little rice leafminer (*Hydrellia griseola*), tomato leafminer (*Liriomyza sativae*), legume leafminer (*Liriomyza trifolii*), and garden pea leafminer (*Chromatomyia horticola*); gout flies (Chloropidae) such as rice stem maggot (*Chlorops oryzae*); fruit flies (Tephritidae) such as melon fly (*Dacus cucurbitae*), and Mediteranean fruit fly (*Ceratitis capitata*); Drosophilidae; humpbacked flies (Phoridae) such as *Megaselia spiracularis*; moth flies (Psychodidae) such as *Clogmia albipunctata*; Simuliidae; Tabanidae such as horsefly (*Tabanus trigonus*); stable flies, etc.

Coleoptera:

Corn root worms (*Diabrotica* spp.) such as Western corn root worm (*Diabrotica virgifera virgifera*), and Sourthern corn root worm (*Diabrotica undecimpunctata howardi*); scarabs (Scarabaeidae) such as cupreous chafer (*Anomala cuprea*), soybean beetle (*Anomala rufocuprea*), and Japanese beetle (*Popillia japonica*); weevils such as maize weevil (*Sitophilus zeamais*), rice water weevil (*Lissorhoptrus oryzophilus*), azuki bean weevil (*Callosobruchus chinensis*), rice curculio (*Echinocnemus squameus*), boll weevil (*Anthonomus grandis*), and hunting billbug (*Sphenophorus venatus*); darkling beetles (Tenebrionidae) such as yellow mealworm (*Tenebrio molitor*), and red flour beetle (*Tribolium castaneum*); leaf beetles (Chrysomelidae) such as rice leaf beetle (*Oulema oryzae*), cucurbit leaf beetle (*Aulacophora femoralis*), striped flea beetle (*Phyllotreta striolata*), and Colorado potato beetle (*Leptinotarsa decemlineata*); dermestid beetles (Dermestidae) such as varied carper beetle (*Anthrenus verbasci*), and hide beetle (*Dermestes maculates*); deathwatch beetles (Anobiidae) such as cigarette beetle (*Lasioderma serricorne*); *Epilachna* such as Twenty-eight-spotted ladybird (*Epilachna vigintioctopunctata*); bark beetles (Scolytidae) such as powder-post beetle (*Lyctus brunneus*), and pine shoot beetle (*Tomicus piniperda*); false powder-post beetles (Bostrychidae); spider beetles (Ptimidae); longhorn beetles (Cerambycidae) such as white-spotted longicorn beetle (*Anoplophora malasiaca*); click beetles (*Agriotes* spp.); *Paederus fuscipens*, etc.

Orthoptera:

Asiatic locust (*Locusta migratoria*), African mole cricket (*Gryllotalpa africana*), rice grasshopper (*Oxya yezoensis*), rice grasshopper (*Oxya japonica*), Gryllidae, etc.

Shiphonaptera:

Cat flea (*Ctenocephalides felis*), dog flea (*Ctenocephalides canis*), human flea (*Pulex irritans*), oriental rat flea (*Xenopsylla cheopis*), etc.

Anoplura:

Human body louse (*Pediculus humanus corporis*), crab louse (*Phthirus pubis*), short-nosed cattle louse (*Haematopinus eurysternus*), sheep louse (*Dalmalinia ovis*), hog louse (*Haematopinus suis*), etc.

Hymenoptera:

Ants (Formicidae) such as pharaoh ant (*Monomorium pharaosis*), negro ant (*Formica fusca japonica*), black house ant (*Ochetellus glaber*), *Pristomyrmex pungens*, *Pheidole noda*, leaf-cutting ant (*Acromyrmex* spp.), and fire ant (*Solenopsis* spp.); hornets (Vespidae); bethylid wasps (Betylidae); sawflies (Tenthredimidae) such as cabbage sawfly (*Athalia rosae*), and *Athalia japonica*, etc.

Blattodea:

German cockroach (*Blattella germanica*), smokybrown cockroach (*Periplaneta fuliginosa*), American cockroach (*Periplaneta americana*), *Periplaneta brunnea*, oriental cockroach (*Blatta orientalis*);

Isoptera:

Termites such as Japanese subterranean termite (*Reticulitermes speratus*), Formosan subterranean termite (*Coptotermes formosanus*), western drywood termite (*Incisitermes minor*), Daikoku drywood termite (*Cryptotermes domesticus*), *Odontotermes formosanus*, *Neotermes koshunensis*, *Glyptotermes satsumesis*, *Glyptotermes nakajimai*, *Glyptotermes fuscus*, *Glyptotermes kodamai*, *Glyptotermes kushimensis*, Japanese dampwood termite (*Hodotermopsis japonica*), *Coptotermes guangzhoensis*, *Reticulitermes*

*miyatakei*, eastern subterranean termite (*Reticulitermes flavipes amamianus*), *Reticulitermes* sp., *Nasutitermes takasagoesis*, *Pericapritermes nitobei*, *Sinocapritermes mushae*, *Reticuliterumes flavipes*, *Reticulitermes hesperus*, *Reticulitermes virginicus*, *Reticulitermes tibialis*, *Heterotermes aureus*, and *Zootermopsis nevadensis*, etc.

Acarina:

Spider mites (Tetranychidae) such as two-spotted spider mite (*Tetranychus urticae*), Kanzawa spider mite (*Tetranychus kanzawai*), citrus red mite (*Panonychus citri*), European red mite (*Panonychus ulmi*), and *Oligonychus* spp.; eriophyid mites (Eriophyidae) such as pink citrus rust mite (*Aculops pelekassi*), *Phyllocoptruta citri*, tomato rust mite (*Aculops lycopersici*), purple tea mite (*Calacarus carinatus*), pink tea rust mite (*Acaphylla theavagran*), *Eriophyes chibaensis*, and apple rust mite (*Aculus schlechtendali*); tarosonemid mites (Tarsonemidae) such as broad mite (*Polyphagotarsonemus latus*); false spider mites (Tenuipalpidae) such as *Brevipalpus phoenicis*; Tuckerellidae; ticks (Ixodidae) such as *Haemaphysalis longicornis, Haemaphysalis flava, Dermacentor taiwanicus*, American dog tick (*Dermacentor variabilis*), *Ixodes ovatus, Ixodes persulcatus*, black legged tick (*Ixodes scapularis*), lone star tick (*Amblyomma americanum*), *Boophilus microplus*, and *Rhipicephalus sanguineus*; Psoroptidae such as ear mite (*Otodectes cynotis*); itch mites (Sarcoptidae) such as *Sarcoptes scabiei*; folicle mites (Demodicidae) such as dog folicle mite (*Demodex canis*); acarid mites (Acaridae) such as mold mite (*Tyrophagus putrescentiae*), and *Tyrophagus similis*; house dust mites (Pyroglyphidae) such as *Dermatophagoides farinae*, and *Dermatophagoides ptrenyssnus*; cheyletide mites (Cheyletidae) such as *Cheyletus eruditus, Cheyletus malaccensis,* and *Cheyletus moorei*; parasitoid mites (Dermanyssidae) such as tropical rat mite (*Ornithonyssus bacoti*), northern fowl mite (*Ornithonyssus sylviarum*), and poultry red mite (*Dermanyssus gallinae*); chiggers (Trombiculidae) such as *Leptotrombidium akamushi*; spiders (Araneae) such as Japanese foliage spider (*Chiracanthium japonicum*), redback spider (*Latrodectus hasseltii*), etc.

Chilopoda: house centipede (*Thereuonema hilgendorfi*), *Scolopendra subspinipes*, etc.;

Diplopoda: garden millipede (*Oxides gracilis*), *Nedyopus tambanus*, etc.;

Isopoda: common pill bug (*Armadillidium vulgare*), etc.;

Gastropoda: *Limax marginates, Limax flavus*, etc.

Nematoda:

Rice white-tip nematode (*Aphelenchoides besseyi*), strawberry bud nematode (*Nothotylenchus acris*), southern root-knot nematode (*Meloidogyne incognita*), northern root-knot nematode (*Meloidogyne hapla*), Javanese root-knot nematode (*Meloidogyne javanica*), soybean cyst nematode (*Heterodera glycines*), potato cyst nematode (*Globodera rostochiensis*), coffee root-lesion nematode (*Pratylenchus coffeae*), California root-lesion nematode (*Pratylenchus neglectus*), etc.

The compound of the present invention can be used as an insecticide for crop lands such as cultivated lands, paddy fields, lawns and orchards, or non-crop lands. The compound of the present invention can control pests in crop lands and the like where "crop plants" listed below are cultivated without causing adverse effects on the "crop plants", in some cases.

Specific examples of the "crop plant" are listed below.

Agricultural crops: corn, rice, wheat, barley, rye, oat, sorghum, cotton, soybean, peanut, sarrazin, sugar beet, rapeseed, sunflower, sugar cane, tobacco, etc.;

Vegetables: Solanaceae vegetables (eggplant, tomato, green pepper, hot pepper, potato etc.), Cucurbitaceae vegetables (cucumber, pumpkin, zucchini, watermelon, melon etc.), Cruciferae vegetables (Japanese radish, turnip, horseradish, kohlrabi, Chinese cabbage, cabbage, brown mustard, broccoli, cauliflower etc.), Compositae vegetables (burdock, garland chrysanthemum, artichoke, lettuce etc.), Liliaceae vegetables (Welsh onion, onion, garlic, asparagus etc.), Umbelliferae vegetables (carrot, parsley, celery, parsnip etc.), Chenopodiaceae vegetables (spinach, Swiss chard etc.), Labiatae vegetables (Japanese basil, mint, basil etc.), strawberry, sweat potato, yam, aroid, etc.;

Fruit trees: pomaceous fruits (apple, common pear, Japanese pear, Chinese quince, quince etc.), stone fleshy fruits (peach, plum, nectarine, Japanese plum, cherry, apricot, prune etc.), citrus plants (Satsuma mandarin, orange, lemon, lime, grapefruit etc.), nuts (chestnut, walnut, hazel nut, almond, pistachio, cashew nut, macadamia nut etc.), berry fruits (blueberry, cranberry, blackberry, raspberry etc.), grape, persimmon, olive, loquat, banana, coffee, date, coconut palm, oil palm, etc.;

Trees other than fruit trees: tea, mulberry, street trees (ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew, elm, horse-chestnut etc.), sweet viburnum, *Podocarpus macrophyllus*, Japanese cedar, Japanese cypress, croton, spindle tree, Chainese howthorn, etc.

Lawn: zoysia (Japanese lawn grass, mascarene grass, etc.), Bermuda grass (*Cynodon dactylon*, etc.), bent grass (creeping bent grass, *Agrostis stolonifera, Agrostis tenuis*, etc.), bluegrass (Kentucky bluegrass, rough bluegrass, etc.), fescue (tall fescue, chewing fescue, creeping fescue, etc.), ryegrass (darnel, perennial ryegrass, etc.), cocksfoot, timothy grass, etc.;

Oil crops: oil palm, Barbados nut, etc.;

Others: flowers (rose, carnation, chrysanthemum, Eustoma grandiflorum Shinners (prairie gentian), gypsophila, gerbera, pot marigold, salvia, petunia, verbena, tulip, aster, gentian, lily, pansy, cyclamen, orchid, lily of the valley, lavender, stock, ornamental kale, primula, poinsttia, gladiolus, cattleya, daisy, verbena, cymbidium, begonia, etc.), foliage plant; etc.

The above-described crop plants include crop plants having resistance to an HPPD inhibitor such as isoxaflutole, an ALS inhibitor such as imazethapyr or thifensulfuron-methyl, an EPSP synthesizing enzyme inhibitor such as glyphosate, a glutamine synthesizing enzyme inhibitor such as glufosinate, an acetyl CoA carboxylase inhibitor such as sethoxydim, a PPO inhibitor such as flumioxazin, or an herbicide such as bromoxynil, dicamba or 2,4-D, which resistance has been imparted by a classical breeding method or a genetic engineering technique.

Examples of the crop plant having the resistance imparted by a classical breeding method include rape, whieat, sunflower, rice and corn having resistance to imidazolinone herbicides such as imazethapyr, which are commercially available under the trade name of Clearfield (registered trademark); soybean having resistance to sulfonylurea ALS inhibitor herbicides such as thifensulfuron-methyl, which is commercially available under the trade name of STS soybean; and crop plants having resistance to acetyl CoA carboxylase inhibitors such as trione oxime herbicides and aryloxyphenoxypropionic acid herbicides, an example of which is SR corn. For example, a crop plant to which resistance to an acetyl CoA carboxylase inhibitor has been imparted is found in Proc. Natl. Acad. Sci. USA, 1990, vol. 87, p. 7175-7179. In addition, a mutant acetyl CoA carboxylase which is resistant to an acetyl CoA carboxylase inhibitor is described in Weed Science, vol. 53, p. 728-746, 2005. When a gene encoding the mutant acetyl CoA carboxylase is introduced into a crop plant by a genetic engineering technique or when a mutation related to impartation of the acetyl CoA carboxylase resistance is introduced into a gene encoding acetyl CoA carboxylase of a crop plant, a crop plant resistant to an acetyl CoA carboxylase inhibitor can be produced. Further, nucleic acids for introduction of a base substitution mutation can be introduced into the cells of a crop plant by chimeraplasty (see, Gura T. 1999, Repairing the Genome's Spelling Mistakes, Science 285: 316-318) to induce a site-directed amino acid substitution mutation in the gene which is targeted by an acetyl CoA carboxylase inhibitor/herbicide of the crop plant, and thereby a crop plant resistant to an acetyl CoA carboxylase inhibitor/herbicide can be produced.

Examples of the crop plant having the resistance imparted by a genetic engineering technique include corn, soybean, cotton, rape and sugar beet cultivars which are resistant to glyphosate, which are commercially available under the trade names of RoundupReady™ (registered trademark), AgrisureGT, and the like. Other examples of the crop plant having the resistance imparted by a genetic engineering technique include corn, soybean, cotton and rape cultivars which are resistant to glufosinate, which are commercially available under the trade name of LibertyLink™ and the like. In addition, a genetically engineered cotton cultivar having resisitance to bromoxynil is commarcially available under the trade name of BXN.

The above-described crop plants include genetically engineered plants which have one or more insecticidal pest-resistance genes imparted by a genetic engineering technique and produce one or more selective toxins.

Examples of insecticidal toxins produced by such genetically engineered plants include insecticidal proteins derived from Bacillus cereus and Bacillus popilliae; δ-endotoxins derived from Bacillus thuringiensis, such as Cry1Ab, Cry1Ac, Cry1F, Cry1Fa2, Cry2Ab, Cry3A, Cry3Bb1 and Cry9C; insecticidal proteins derived from Bacillus thuringiensis, such as VIP 1, VIP 2, VIP 3 and VIP 3A; insecticidal proteins derived from nematodes; toxins produced by animals such as scorpion toxins, spider toxins, bee toxins and insect-specific nerve toxins; fungal toxins; plant lectin; agglutinin; protease inhibitors such as trypsin inhibitors, serine protease inhibitors, patatin, cystatin, and papain inhibitors; ribosome-inactivating proteins (RIP) such as ricin, corn-RIP, abrin, saporin, and briodin; steroid metabolizing enzymes such as 3-hydroxysteroid oxidase, ecdysteroid-UDP-glucosyltransferase, and cholesterol oxidase; ecdysone inhibitors; HMG-CoA reductase; ion channel inhibitors such as sodium channel inhibitors and calcium channel inhibitors; juvenile hormone esterase; diuretic hormone receptors; stilbene synthase; bibenzyl synthase; chitinase; and glucanase.

The toxins produced by such genetically engineered plants also include hybrid toxins of the above-described insecticidal proteins, and toxins in which a part of amino acids constituting an insecticidal protein is deleted or modified. The hybrid toxin is made by combining different domains of the insecticidal proteins by a genetic engineering technique. An example of the toxin in which a part of amino acids constituting an insecticidal protein is deleted includes Cry1Ab in which a part of amino acids is deleted. An example of the toxin in which a part of amino acids constituting an insecticidal protein is modified includes a toxin in which one or more of amino acids of a naturally occurring toxin are substituted.

The insecticidal toxin and the genetically engineered crop plant having the ability to produce the insecticidal toxin are described, for example, in EP-A-0 374 753, WO 93/07278, WO 95/34656, EP-A-0 427 529, EP-A-451878, WO 03/052073, and the like.

The genetically engineered crop plant having the ability to produce the insecticidal toxin particularly has resistance to attack by a coleopteran pest, dipteran pest or a lepidopteran pest.

The genetically engineered plants which produce selective toxins are already known, and some of them are commercially available. Examples of such genetically engineered plants include YieldGard™ (a corn cultivar expressing Cry1Ab toxin), YieldGard Rootworm™ (a corn cultivar expressing Cry3Bb1 toxin), YieldGard Plus™ (a corn cultivar expressing Cry1Ab and Cry3Bb1 toxins), Herculex I™ (a corn cultivar expressing Cry1Fa2 toxin and phosphinothricin N-acetyltransferase (PAT) for imparting resistance to glupho-sinate), NuCOTN33B™ (a cotton cultivar expressing Cry1Ac toxin), Bollgard I™ (a cotton cultivar expressing Cry1Ac toxin), Bollgard II™ (a cotton cultivar expressing Cry1Ac and Cry2Ab toxins), VIPCOT™ (a cotton cultivar expressing VIP toxin), NewLeaf™ (a potato cultivar expressing Cry3A toxin), NatureGard Agrisure GT Advantage™ (GA21 glyphosate-resistance character), Agrisure CB Advantage™ (Bt11 corn borer (CB) character), Protecta™, and the like.

The above-described crop plants include crop plants having ability to produce anti-pathogen substances imparted by a genetic engineering technique.

Examples of the anti-pathogen substance includes PR proteins (PRPs described in EP-A-0 392 225); ion channel inhibitors such as sodium channel inhibitors, and calcium channel inhibitors (e.g. KP1, KP4, KP6 toxins etc. produced by viruses); stilbene synthase; bibenzyl synthase; chitinase; glucanase; substances produced by microorganisms such as peptide antibiotics, heterocycle-containing antibiotics, and protein factors involved in plant disease-resistance (described in WO 03/000906); and the like. Such anti-pathogen substances and genetically engineered plants which produce the anti-pathogen substances are described in EP-A-0 392 225, WO 05/33818, EP-A-0 353 191, and the like.

The above-described crop plants include crop plants having beneficial characters such as a modified oil component and an enhanced amino acid content which has been imparted by a genetic engineering technique. Examples of such crop palnts include VISTIVE™ (low linolenic soybean which has a reduced content of linolenic acid), and high-lysine (high-oil) corn (corn which has an increased content of lysine or oil).

Furthermore, the above-described crop plants include stacked plants which have a combination of two or more of beneficial characters such as the above-described classical harbicide-resistant character, or a herbicide-resistace gene, an insecticidal pest-resistance gene, an anti-pathogen substance-producing gene, a modified oil component, and an enhanced amino acid content.

When the compound of the present invention is used for the herbicide-resistant crop plant as described above, the plant is treated with sequentially or a mixture of the compound of the present invention and the herbicide (e.g., glyphosate or a salt thereof, glufosinate or a salt thereof, dicamba or a salt thereof, imazethapyr or a salt thereof, isoxaflutole, etc.) to which the plant is resistant, and thereby comprehensive weed control can be attained.

The compound of the present invention can be used in the field of livestock disease therapy and livestock industry for exterminating organisms parasitizing the inside and/or outside of the body of vertebrates such as human being, cow, sheep, goat, pig, poulty, dog, cat and fish.

Examples of such parasitic organisms include ticks (Ixodes spp.) (e.g. Ixodes scapularis), Boophilus spp. (e.g. Boophilus microplus), Amblyomma spp., Hyalomma spp., Rhipicephalus spp. (e.g. Rhipicephalus sanguineus), Haemaphysalis spp. (e.g. Haemaphysalis longicornis), dermacentor spp., Ornithodoros spp. (e.g. Ornithodoros moubata), parasitoid mites (Dermahyssus gallinae), northern fowl mite (Ornithonyssus sylviarum), itch mites (Sarcoptes spp.) (e.g Sarcoptes scabiei), Psoroptes spp., Chorioptes spp., folicle mites (Demodex spp.), chiggers (Eutrombicula spp.), Aedes spp. (e.g. Asian tiger mosquito (Aedes albopictus)), Anopheles spp., Culex spp., Culicodes spp., Musca spp., Hypoderma spp., Gasterophilus spp., Haematobia spp., Tabanus spp., Simulium spp., Triatoma spp., lice (Phthiraptera) (e.g. Damalinia spp., Linognathus spp., Haematopinus spp.), fleas (Ctenocephalides spp.) (e.g. cat flea (Ctenocephalides felis), Xenosylla spp.), pharaoh ants (Monomorium pharaonis), and Nematoda [for example, trichostrongyle (e.g. Nippostrongylus brasiliensis, Trichostrongylus axei, and Trichostrongylus colubriformis), trichina (e.g. Trichinella spiralis), Haemonchus contortus, Nematodirus (e.g. Nematodirus battus), Ostertagia circumcincta, Cooperia spp., Hymenolepis nana, and the like.

A method of controlling a pest which comprises applying the compound of the present invention to the pest or a place where the pest inhabits is also one aspect of the present inventions.

For the method of controlling a pest of the present invention, while the compound of the present invention may be used as it is, the compound of the present invention is usually formulated into the form of the pesticidal composition of the present invention as described above and then applied to a pest or a place where the pest inhabits.

Examples of a place where a pest inhabits include a paddy field, a dry field, a cultivated field, a tea field, a fruit orchard, a non-cultivated field, a house, a raising sesdling tray, a nursery box, nursery soil, a nursery mat, a water cluture medium in a hydroponic farm, and the like.

The method of controlling a pest of the present invention allows a pest to contact with or ingest the compound of the present invention by applying the compound of the present invention to a pest or a place where the pest inhabits. In the method of controlling a pest of the present invention, the compound of the present invention can be applied by the same method as an application method for conventional pesticides.

Examples of such an application method include spray treatment, soil treatment, seed treatment and water cluture medium treatment.

The spray treatment generally comprises treating the plant surface or a pest itself with an active ingredient (in the case of present invention, the compound of the present invention) to exert a controlling effect on a pest, and includes foliage spraying and truck spraying.

The soil treatment generally comprises adding an active ingredient to culture soil or irrigation liquid so as to allow the active ingredient to permeate from the root part or the like of a plant to inside of the plant, thereby the plant is protected from damage by a pest. Examples of the soil treatment include planting hole treatment (planting hole spraying, soil incorporation after planting hole treatment), plant foot treatment (plant foot spraying, soil incorporation at plant foot, plant foot drenching, plant foot treatment at a later seeding raising stage), planting furrow treatment (planting furrow spraying, soil incorporation after planting furrow treatment), planting row treatment (planting row spraying, soil incorporation after planting row treatment, planting row spraying at a growing stage), planting row treatment at the time of sowing (planting row spraying at the time of sowing, soil incorporation after planting row treatment at the time of sowing), broadcast treatment (overall soil surface spraying, soil incorporation after broadcast treatment), other soil spraying treatment (foliar spraying of a granule at a growth stage, spraying under trunks or around main stems, soil surface spraying, soil surface incorporation, sowing hole spraying, furrow surface spraying, and spraying between plants), other drenching treatment (soil drenching, drenching at a raising seedling stage, chemical injection treatment, plant foot drenching, chemical drip irrigation, chemigation), nursery box treatment (nursery box surface spraying, drenching of nursery box), nursery tray treatment (nursery tray spraying, nursery tray irrigation), nursery bed treatment (nursery bed surface spraying, drenching of nursery bed, lowland nursery bed surface spraying, seedling immersion), bed soil incorporation treatment (bed soil incorporation, presowing bed soil incorporation), and other treatments (ridging incorporation, plowing and fertilizing, surface soil incorporation, soil incorporation under canopy edge, planting position treatment, flower cluster treatment with a granule, paste fertilizer incorporation).

The seed treatment generally comprises treating the seeds, seed potatoes or bulbs of a crop plant to be protected, or the vicinity thereof with an active ingredient to exert a controlling effect on a pest. Examples of the seed treatment include spraying, smearing, immersion, impregnation, application, film coating and pellet coating.

The water culture medium treatment generally comprises adding an active ingredient to a water culture medium so as to allow the active ingredient to permeate from the root part or the like of a crop plant to inside of the plant, thereby the plant is protected from damage by a pest. Examples of the water culture medium treatment include water culture medium incorporation, and water culture medium interfusion.

The application amount of the compound of the present invention in the above-described application method can be widely changed depending on an application timing, an application place, a formulation form and the like. The compound of the present invention is usually applied in an amount of 0.3 to 3,000 g, preferably 50 to 3,000 g per 1 hectare. The compound of the present invention can be diluted with water so that the concentration of the compound of the present invention can be 0.1 to 1,000 ppm, preferably 10 to 500 ppm at the time of application, and then used.

The water dilution of the compound of the present invention may be applied directly to a plant to be protected from a pest, or to soil where the plant is grown.

When the compound of the present invention is formulated into a resin formulation, it can be processed into the form of a sheet or a string, and then used for pest control by winding it around a crop plant, disposing it in the vicinity of a crop plant, laying it on the soil surface at the plant foot, or the like.

Further, in the method of controlling a pest of the present invention, the pesticidal composition of the present invention can be administered to the inside (inside of body) or outside (the body surface) of the above-described vertebrates to exterminate organisms parasitizing the vertebrates systemically or non-systemically. Examples of an administration method to the inside include oral administration, anal administration, transplantation, and subcutaneous, intramuscular and intravenous administrations by injection. Examples of an administration method to the outside include percutaneous administration. In addition, sanitary insect pests generated in excrements of livestock can be exterminated by allowing the amninals to ingest the pesticidal composition of the present invention.

In the method of controlling a pest of the present invention, when the pesticidal composition of the present invention is administered to vertebrates, the administration amount can be different depending on an administration method and the like, and it is usually 0.1 to 2,000 mg, preferably 0.5 to 1,000 mg of the compound of the present invention per 1 kg body weight of the animals.

When the compound of the present invention is used for control of epidemic, the application amount is usually 0.001 to 10 mg/m$^3$ for application to space, and 0.001 to 100 mg/m$^2$ for application to a plane. When the compound of the present invention is formulated into an emulsifiable concentrate, a wettable powder or a flowable formulation, the formulation is usually applied after dilution with water so as to contain usually 0.001 to 10,000 ppm of the compound of the present invention. When the compound of the present invention is formulated into an oil solution, an aerosol formulation, a smoking pesticide or a poison bait, the formulation is usually applied as it is.

EXAMPLES

Hereinafter, the present invention is described in more detail by reference to Production Examples, Reference Production Examples, Formulation Examples and Test Examples to which the present invention is not limited.

In Production Examples and Reference Production Examples, check of reaction and operation of column chromatography were performed by analysis using TLC (thin layer chromatography) or the like. TLC was conducted by using Kieselgel 60F254 (70 to 230 mesh) manufactured by MERCK & CO., LTD., and a UV detector was employed. Column chromatography was conducted using silica gel 60 (spherical shape, particle size of 63 to 210 nm) manufactured by KANTO CHEMICAL CO., LTD., Fluorisil (100 to 200 mesh) manufactured by WAKO PURE CHEMICAL INDUSTRIES LTD, or the like. Medium pressure preparative high performance liquid chromatography was conducted by using Ultrapack (filler: silica gel) manufactured by YAMAZEN CO. NMR spectra were measured with a JEOL AL-400 (400 MHz)-type spectrometer or the like, using tetramethylsilane as an internal standard (the measurement temperature was 25° C. unless otherwise noted).

In Production Examples and Reference Production Examples, abbreviations and terms have meanings as described below.

s: singlet, br: broad, brs: broad singlet, brm: broad multiplet, d: doublet, t: triplet, q: quartet, quint: quintet, m: multiplet, Me: methyl group, Et: ethyl group, nPr: propyl group, iPr: isopropyl group, cPr: cyclopropyl group, Bu: butyl group, iBu: isobutyl group, sBu: sec-butyl group, tBu: tert-butyl group, Hex: hexyl group, Ph: phenyl group, THF: tetrahydrofuran, DMF: dimethylformamide, room temperature: about 15 to 25° C.

Next, examples of the compound of the present invention are shown. Compounds represented by the formuula (Iα) and the formuula (Iβ) shown below are specific examples of the compound of the present invention.

Compounds represented by the formula (Iα):

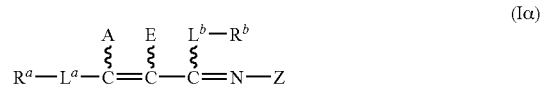

wherein $L^a$, $R^a$, A, E, $L^b$, $R^b$ and Z are any one of 1 to 6837 combinations shown below, together with compound numbers. [Compound number; $L^a$; $R^a$; A; E; $L^b$; $R^b$; Z]=[1; S; MeO(CH$_2$)$_4$; H; Me; S; Ph; Ph]; [2; S; MeS(CH$_2$)$_4$; H; Me; S; Ph; Ph]; [3; S; O$_2$N(CH$_2$)$_4$; H; Me; S; Ph; Ph]; [4; S; NC(CH$_2$)$_4$; H; Me; S; Ph; Ph]; [5; S; ClCH$_2$(CH$_2$)$_2$; H; Me; S; Ph; Ph]; [6; S; CF$_3$(CH$_2$)$_3$; H; Me; S; Ph; Ph]; [7; S; Ac(CH$_2$)$_4$; H; Me; S; Ph; Ph]; [8; S; AcO(CH$_2$)$_4$; H; Me; S; Ph; Ph]; [9; S; PhO(CH$_2$)$_4$; H; Me; S; Ph; Ph]; [10; S; PhS(CH$_2$)$_4$; H; Me; S; Ph; Ph]; [11; S; PhCH$_2$; H; Me; S; Ph; Ph]; [12; S; 4-Me-PhCH$_2$; H; Me; S; Ph; Ph]; [13; S; 4-MeO-PhCH$_2$; H; Me; S; Ph; Ph]; [14; S; 4-Cl-PhCH$_2$; H; Me; S; Ph; Ph]; [15; S; 4-Ph-PhCH$_2$; H; Me; S; Ph; Ph]; [16; S; 1-Naphthylmethyl; H; Me; S; Ph; Ph]; [17; S; 2-Naphthylmethyl; H; Me; S; Ph; Ph]; [18; S; α-Methylbenzyl; H; Me; S; Ph; Ph]; [19; S; 2-Picolyl; H; Me; S; Ph; Ph]; [20; S; 5-Chloro-2-picolyl; H; Me; S; Ph; Ph]; [21; S; 2-Furylmethyl; H; Me; S; Ph; Ph]; [22; S; (5-Methylthiophen-2-yl)methyl; H; Me; S; Ph; Ph]; [23; S; Cyclohexylmethyl; H; Me; S; Ph; Ph]; [24; S; 1-Cyclohexylethyl; H; Me; S; Ph; Ph]; [25; S; CH$_2$ (CH$_2$)$_9$; H; Me; S; Ph; Ph]; [26; S; Allyl; H; Me; S; Ph; Ph]; [27; S; 3-Chloro-3-propenyl; H; Me; S; Ph; Ph]; [28; S; 3-Phenyl-3-propenyl; H; Me; S; Ph; Ph]; [29; S; 2-Methyl-2-butenyl; H; Me; S; Ph; Ph]; [30; S; Propargyl; H; Me; S; Ph; Ph]; [31; S; 2-Butynyl; H; Me; S; Ph; Ph]; [32; S; Cyclohexyl; H; Me; S; Ph; Ph]; [33; S; 4-Methylcyclohexyl; H; Me; S; Ph; Ph]; [34; S; 4-Chlorohexyl; H; Me; S; Ph; Ph]; [35; S; 4-Methoxycyclohexyl; H; Me; S; Ph; Ph]; [36; S; 2-Perhydronaphthyl; H; Me; S; Ph; Ph]; [37; S; 2-Indanyl; H; Me; S; Ph; Ph]; [38; S; 2-Cyclohexen-1-yl; H; Me; S; Ph; Ph]; [39; S; 3-Methyl-2-Cyclohexenyl; H; Me; S; Ph; Ph]; [40; S; 1,4-Cyclohexadien-1-yl; H; Me; S; Ph; Ph]; [41; S; 2,5-Cyclohexadien-1-yl; H; Me; S; Ph; Ph]; [42; S; Ph; H; Me; S; Ph; Ph]; [43; S; 2-F-Ph; H; Me; S; Ph; Ph]; [44; S; 3-F-Ph; H; Me; S; Ph; Ph]; [45; S; 4-F-Ph; H; Me; S; Ph; Ph]; [46; S; 2-Cl-Ph; H; Me; S; Ph; Ph]; [47; S; 3-Cl-Ph; H; Me; S; Ph; Ph]; [48; S; 4-Cl-Ph; H; Me; S; Ph; Ph]; [49; S; 2-Me-Ph; H; Me; S; Ph; Ph]; [50; S; 3-Me-Ph; H; Me; S; Ph; Ph]; [51; S; 4-Me-Ph; H; Me; S; Ph; Ph]; [52; S; 2-Et-Ph; H; Me; S; Ph; Ph]; [53; S; 3-Et-Ph; H; Me; S; Ph; Ph]; [54; S; 4-Et-Ph; H; Me; S; Ph; Ph]; [55; S; 2-iPr-Ph; H; Me; S; Ph; Ph]; [56; S; 3-iPr-Ph; H; Me; S; Ph; Ph]; [57; S; 4-iPr-Ph; H; Me; S; Ph; Ph]; [58; S; 2-Ph-Ph; H; Me; S; Ph; Ph]; [59; S; 3-Ph-Ph; H; Me; S; Ph; Ph]; [60; S; 4-Ph-Ph; H; Me; S; Ph; Ph]; [61; S; 2-CF$_3$-Ph; H; Me; S; Ph; Ph]; [62; S; 3-CF$_3$-Ph; H; Me; S; Ph; Ph]; [63; S; 4-CF$_3$-Ph; H; Me; S; Ph; Ph]; [64; S; 2-MeO-Ph; H; Me; S; Ph; Ph]; [65; S; 3-MeO-Ph; H; Me; S; Ph; Ph]; [66; S; 4-MeO-Ph; H; Me; S; Ph; Ph]; [67; S; 2-PhO-Ph; H; Me; S; Ph; Ph]; [68; S; 3-PhO-Ph; H; Me; S; Ph; Ph]; [69; S; 4-PhO-Ph; H; Me; S; Ph; Ph]; [70; S; 4-CF$_3$O-Ph; H; Me; S; Ph; Ph]; [71; S; 4-Ac-Ph; H; Me; S; Ph; Ph]; [72; S; 4-PhC(=O)-Ph; H; Me; S; Ph; Ph]; [73; S; 4-MeOC(=O)-Ph; H; Me; S; Ph; Ph]; [74; S; 4-PhOC(=O)-Ph; H; Me; S; Ph; Ph]; [75; S; 4-MeC(=O)O-Ph; H; Me; S; Ph; Ph]; [76; S; 4-PhC(=O)O-Ph; H; Me; S; Ph; Ph]; [77; S; 4-Me$_2$NC(=O)-Ph; H; Me; S; Ph; Ph]; [78; S; 4-O$_2$N-Ph; H; Me; S; Ph; Ph]; [79; S; 4-NC-Ph; H; Me; S; Ph; Ph]; [80; S; 2,3-Mee-Ph; H; Me; S; Ph; Ph]; [81; S; 2,4-Me$_2$-Ph; H; Me; S; Ph; Ph]; [82; S; 2,5-Me$_2$-Ph; H; Me; S; Ph; Ph]; [83; S; 2,6-Mee-Ph; H; Me; S; Ph; Ph]; [84; S;

3,4-Me₂-Ph; H; Me; S; Ph; Ph]; [85; S; 3,5-Me₂-Ph; H; Me; S; Ph; Ph]; [86; S; 2,3-F₂-Ph; H; Me; S; Ph; Ph]; [87; S; 2,4-F₂-Ph; H; Me; S; Ph; Ph]; [88; S; 2,5-F₂-Ph; H; Me; S; Ph; Ph]; [89; S; 2,6-F₂-Ph; H; Me; S; Ph; Ph]; [90; S; 3,4-F₂-Ph; H; Me; S; Ph; Ph]; [91; S; 3,5-F₂-Ph; H; Me; S; Ph; Ph]; [92; S; 2,3-Cl₂-Ph; H; Me; S; Ph; Ph]; [93; S; 2,4-Cl₂-Ph; H; Me; S; Ph; Ph]; [94; S; 2,5-Cl₂-Ph; H; Me; S; Ph; Ph]; [95; S; 2,6-Cl₂-Ph; H; Me; S; Ph; Ph]; [96; S; 3,4-Cl₂-Ph; H; Me; S; Ph; Ph]; [97; S; 3,5-Cl₂-Ph; H; Me; S; Ph; Ph]; [98; S; 2,4-(MeO)₂-Ph; H; Me; S; Ph; Ph]; [99; S; 2,6-(MeO)₂-Ph; H; Me; S; Ph; Ph]; [100; S; 3,4-(MeO)₂-Ph; H; Me; S; Ph; Ph]; [101; S; 1-Naphthyl; H; Me; S; Ph; Ph]; [102; S; 2-Naphthyl; H; Me; S; Ph; Ph]; [103; S; 5-Indanyl; H; Me; S; Ph; Ph]; [104; S; 5-Benzodioxolyl; H; Me; S; Ph; Ph]; [105; S; 2-Pyridyl; H; Me; S; Ph; Ph]; [106; S; 3-Pyridyl; H; Me; S; Ph; Ph]; [107; S; 4-Pyridyl; H; Me; S; Ph; Ph]; [108; S; 2-Pyrimidinyl; H; Me; S; Ph; Ph]; [109; S; 2-Pyrazinyl; H; Me; S; Ph; Ph]; [110; S; 2-Thienyl; H; Me; S; Ph; Ph]; [111; S; 3-Thienyl; H; Me; S; Ph; Ph]; [112; S; 2-Furyl; H; Me; S; Ph; Ph]; [113; S; 3-Furyl; H; Me; S; Ph; Ph]; [114; S; 1-Methyltetrazol-5-yl; H; Me; S; Ph; Ph]; [115; S; 2-Methyltetrazol-5-yl; H; Me; S; Ph; Ph]; [116; S; 2-Oxazolyl; H; Me; S; Ph; Ph]; [117; S; 2-Thiazolyl; H; Me; S; Ph; Ph]; [118; S; 1,3,4-Thiadiazol-2-yl; H; Me; S; Ph; Ph]; [119; S; 2-Benzothiazolyl; H; Me; S; Ph; Ph]; [120; S; 2-Quinolinyl; H; Me; S; Ph; Ph]; [121; S; PhCH₂; H; Et; S; Ph; Ph]; [122; S; Ph; H; Et; S; Ph; Ph]; [123; S; 3-F-Ph; H; Et; S; Ph; Ph]; [124; S; 4-F-Ph; H; Et; S; Ph; Ph]; [125; S; 4-Cl-Ph; H; Et; S; Ph; Ph]; [126; S; 4-Me-Ph; H; Et; S; Ph; Ph]; [127; S; 3,4-Me₂-Ph; H; Et; S; Ph; Ph]; [128; S; 2-Naphthyl; H; Et; S; Ph; Ph]; [129; S; 5-Indanyl; H; Et; S; Ph; Ph]; [130; S; 5-Benzodioxolyl; H; Et; S; Ph; Ph]; [131; S; PhCH₂; H; Pr; S; Ph; Ph]; [132; S; Ph; H; Pr; S; Ph; Ph]; [133; S; 3-F-Ph; H; Pr; S; Ph; Ph]; [134; S; 4-F-Ph; H; Pr; S; Ph; Ph]; [135; S; 4-Cl-Ph; H; Pr; S; Ph; Ph]; [136; S; 4-Me-Ph; H; Pr; S; Ph; Ph]; [137; S; 3,4-Me₂-Ph; H; Pr; S; Ph; Ph]; [138; S; 2-Naphthyl; H; Pr; S; Ph; Ph]; [139; S; 5-Indanyl; H; Pr; S; Ph; Ph]; [140; S; 5-Benzodioxolyl; H; Pr; S; Ph; Ph]; [141; S; PhCH₂; H; Bu; S; Ph; Ph]; [142; S; Ph; H; Bu; S; Ph; Ph]; [143; S; 3-F-Ph; H; Bu; S; Ph; Ph]; [144; S; 4-F-Ph; H; Bu; S; Ph; Ph]; [145; S; 4-Cl-Ph; H; Bu; S; Ph; Ph]; [146; S; 4-Me-Ph; H; Bu; S; Ph; Ph]; [147; S; 3,4-H; Bu; S; Ph; Ph]; [148; S; 2-Naphthyl; H; Bu; S; Ph; Ph]; [149; S; 5-Indanyl; H; Bu; S; Ph; Ph]; [150; S; 5-Benzodioxolyl; H; Bu; S; Ph; Ph]; [151; S; PhCH₂; H; Ph; S; Ph; Ph]; [152; S; Ph; H; Ph; S; Ph; Ph]; [153; S; 3-F-Ph; H; Ph; S; Ph; Ph]; [154; S; 4-F-Ph; H; Ph; S; Ph; Ph]; [155; S; 4-Cl-Ph; H; Ph; S; Ph; Ph]; [156; S; 4-Me-Ph; H; Ph; S; Ph; Ph]; [157; S; 3,4-Me₂-Ph; H; Ph; S; Ph; Ph]; [158; S; 2-Naphthyl; H; Ph; S; Ph; Ph]; [159; S; 5-Indanyl; H; Ph; S; Ph; Ph]; [160; S; 5-Benzodioxolyl; H; Ph; S; Ph; Ph]; [161; S; PhCH₂; H; OMe; S; Ph; Ph]; [162; S; Ph; H; OMe; S; Ph; Ph]; [163; S; 3-F-Ph; H; OMe; S; Ph; Ph]; [164; S; 4-F-Ph; H; OMe; S; Ph; Ph]; [165; S; 4-Cl-Ph; H; OMe; S; Ph; Ph]; [166; S; 4-Me-Ph; H; OMe; S; Ph; Ph]; [167; S; 3,4-Me₂-Ph; H; OMe; S; Ph; Ph]; [168; S; 2-Naphthyl; H; OMe; S; Ph; Ph]; [169; S; 5-Indanyl; H; OMe; S; Ph; Ph]; [170; S; 5-Benzodioxolyl; H; OMe; S; Ph; Ph]; [171; S; PhCH₂; H; OPh; S; Ph; Ph]; [172; S; Ph; H; OPh; S; Ph; Ph]; [173; S; 3-F-Ph; H; OPh; S; Ph; Ph]; [174; S; 4-F-Ph; H; OPh; S; Ph; Ph]; [175; S; 4-Cl-Ph; H; OPh; S; Ph; Ph]; [176; S; 4-Me-Ph; H; OPh; S; Ph; Ph]; [177; S; 3,4-Me₂-Ph; H; OPh; S; Ph; Ph]; [178; S; 2-Naphthyl; H; OPh; S; Ph; Ph]; [179; S; 5-Indanyl; H; OPh; S; Ph; Ph]; [180; S; 5-Benzodioxolyl; H; OPh; S; Ph; Ph]; [181; S; PhCH₂; H; SMe; S; Ph; Ph]; [182; S; Ph; H; SMe; S; Ph; Ph]; [183; S; 3-F-Ph; H; SMe; S; Ph; Ph]; [184; S; 4-F-Ph; H; SMe; S; Ph; Ph]; [185; S; 4-Cl-Ph; H; SMe; S; Ph; Ph]; [186; S; 4-Me-Ph; H; SMe; S; Ph; Ph]; [187; S; 3,4-Me₂-Ph; H; SMe; S; Ph; Ph]; [188; S; 2-Naphthyl; H; SMe; S; Ph; Ph]; [189; S; 5-Indanyl; H; SMe; S; Ph; Ph]; [190; S; 5-Benzodioxolyl; H; SMe; S; Ph; Ph]; [191; S; PhCH₂; H; SPh; S; Ph; Ph]; [192; S; Ph; H; SPh; S; Ph; Ph]; [193; S; 3-F-Ph; H; SPh; S; Ph; Ph]; [194; S; 4-F-Ph; H; SPh; S; Ph; Ph]; [195; S; 4-Cl-Ph; H; SPh; S; Ph; Ph]; [196; S; 4-Me-Ph; H; SPh; S; Ph; Ph]; [197; S; 3,4-Me₂-Ph; H; SPh; S; Ph; Ph]; [198; S; 2-Naphthyl; H; SPh; S; Ph; Ph]; [199; S; 5-Indanyl; H; SPh; S; Ph; Ph]; [200; S; 5-Benzodioxolyl; H; SPh; S; Ph; Ph]; [201; S; PhCH₂; H; F; S; Ph; Ph]; [202; S; Ph; H; F; S; Ph; Ph]; [203; S; 3-F-Ph; H; F; S; Ph; Ph]; [204; S; 4-F-Ph; H; F; S; Ph; Ph]; [205; S; 4-Cl-Ph; H; F; S; Ph; Ph]; [206; S; 4-Me-Ph; H; F; S; Ph; Ph]; [207; S; 3,4-Me₂-Ph; H; F; S; Ph; Ph]; [208; S; 2-Naphthyl; H; F; S; Ph; Ph]; [209; S; 5-Indanyl; H; F; S; Ph; Ph]; [210; S; 5-Benzodioxolyl; H; F; S; Ph; Ph]; [211; S; PhCH₂; H; CN; S; Ph; Ph]; [212; S; Ph; H; CN; S; Ph; Ph]; [213; S; 3-F-Ph; H; CN; S; Ph; Ph]; [214; S; 4-F-Ph; H; CN; S; Ph; Ph]; [215; S; 4-Cl-Ph; H; CN; S; Ph; Ph]; [216; S; 4-Me-Ph; H; CN; S; Ph; Ph]; [217; S; 3,4-Me₂-Ph; H; CN; S; Ph; Ph]; [218; S; 2-Naphthyl; H; CN; S; Ph; Ph]; [219; S; 5-Indanyl; H; CN; S; Ph; Ph]; [220; S; 5-Benzodioxolyl; H; CN; S; Ph; Ph]; [221; S; PhCH₂; H; NO₂; S; Ph; Ph]; [222; S; Ph; H; NO₂; S; Ph; Ph]; [223; S; 3-F-Ph; H; NO₂; S; Ph; Ph]; [224; S; 4-F-Ph; H; NO₂; S; Ph; Ph]; [225; S; 4-Cl-Ph; H; NO₂; S; Ph; Ph]; [226; S; 4-Me-Ph; H; NO₂; S; Ph; Ph]; [227; S; 3,4-Me₂-Ph; H; NO₂; S; Ph; Ph]; [228; S; 2-Naphthyl; H; NO₂; S; Ph; Ph]; [229; S; 5-Indanyl; H; NO₂; S; Ph; Ph]; [230; S; 5-Benzodioxolyl; H; NO₂; S; Ph; Ph]; [231; S; PhCH₂; H; 2-Thienyl; S; Ph; Ph]; [232; S; Ph; H; 2-Thienyl; S; Ph; Ph]; [233; S; 3-F-Ph; H; 2-Thienyl; S; Ph; Ph]; [234; S; 4-F-Ph; H; 2-Thienyl; S; Ph; Ph]; [235; S; 4-Cl-Ph; H; 2-Thienyl; S; Ph; Ph]; [236; S; 4-Me-Ph; H; 2-Thienyl; S; Ph; Ph]; [237; S; 3,4-Me₂-Ph; H; 2-Thienyl; S; Ph; Ph]; [238; S; 2-Naphthyl; H; 2-Thienyl; S; Ph; Ph]; [239; S; 5-Indanyl; H; 2-Thienyl; S; Ph; Ph]; [240; S; 5-Benzodioxolyl; H; 2-Thienyl; S; Ph; Ph]; [241; S; PhCH₂; H; 3-Thienyl; S; Ph; Ph]; [242; S; Ph; H; 3-Thienyl; S; Ph; Ph]; [243; S; 3-F-Ph; H; 3-Thienyl; S; Ph; Ph]; [244; S; 4-F-Ph; H; 3-Thienyl; S; Ph; Ph]; [245; S; 4-Cl-Ph; H; 3-Thienyl; S; Ph; Ph]; [246; S; 4-Me-Ph; H; 3-Thienyl; S; Ph; Ph]; [247; S; 3,4-Me₂-Ph; H; 3-Thienyl; S; Ph; Ph]; [248; S; 2-Naphthyl; H; 3-Thienyl; S; Ph; Ph]; [249; S; 5-Indanyl; H; 3-Thienyl; S; Ph; Ph]; [250; S; 5-Benzodioxolyl; H; 3-Thienyl; S; Ph; Ph]; [251; S; PhCH₂; H; 2-Furyl; S; Ph; Ph]; [252; S; Ph; H; 2-Furyl; S; Ph; Ph]; [253; S; 3-F-Ph; H; 2-Furyl; S; Ph; Ph]; [254; S; 4-F-Ph; H; 2-Furyl; S; Ph; Ph]; [255; S; 4-Cl-Ph; H; 2-Furyl; S; Ph; Ph]; [256; S; 4-Me-Ph; H; 2-Furyl; S; Ph; Ph]; [257; S; 3,4-Me₂-Ph; H; 2-Furyl; S; Ph; Ph]; [258; S; 2-Naphthyl; H; 2-Furyl; S; Ph; Ph]; [259; S; 5-Indanyl; H; 2-Furyl; S; Ph; Ph]; [260; S; 5-Benzodioxolyl; H; 2-Furyl; S; Ph; Ph]; [261; S; PhCH₂; H; Ac; S; Ph; Ph]; [262; S; Ph; H; Ac; S; Ph; Ph]; [263; S; 3-F-Ph; H; Ac; S; Ph; Ph]; [264; S; 4-F-Ph; H; Ac; S; Ph; Ph]; [265; S; 4-Cl-Ph; H; Ac; S; Ph; Ph]; [266; S; 4-Me-Ph; H; Ac; S; Ph; Ph]; [267; S; 3,4-Me₂-Ph; H; Ac; S; Ph; Ph]; [268; S; 2-Naphthyl; H; Ac; S; Ph; Ph]; [269; S; 5-Indanyl; H; Ac; S; Ph; Ph]; [270; S; 5-Benzodioxolyl; H; Ac; S; Ph; Ph]; [271; S; PhCH₂; H; COOMe; S; Ph; Ph]; [272; S; Ph; H; COOMe; S; Ph; Ph]; [273; S; 3-F-Ph; H; COOMe; S; Ph; Ph]; [274; S; 4-F-Ph; H; COOMe; S; Ph; Ph]; [275; S; 4-Cl-Ph; H; COOMe; S; Ph; Ph]; [276; S; 4-Me-Ph; H; COOMe; S; Ph; Ph]; [277; S; 3,4-Me₂-Ph; H; COOMe; S; Ph; Ph]; [278; S; 2-Naphthyl; H; COOMe; S; Ph; Ph]; [279; S; 5-Indanyl; H; COOMe; S; Ph; Ph]; [280; S; 5-Benzodioxolyl; H; COOMe; S; Ph; Ph]; [281; S; Ph; H; CF₃; S; Ph; Ph]; [282; S; Ph; H; iPr; S; Ph; Ph]; [283; S; Ph; H; iBu; S; Ph; Ph]; [284; S; Ph; H; Cyclopropyl; S; Ph; Ph]; [285; S; Ph; H; Cyclohexyl; S; Ph; Ph]; [286; S; Ph; H; 2-Perhydronaphthyl; S; Ph; Ph]; [287; S; Ph; H; Allyl; S; Ph; Ph]; [288; S; Ph; H; Propargyl; S; Ph; Ph]; [289; S; Ph; H; MeOCH₂; S; Ph; Ph]; [290; S; Ph; H; PhOCH₂; S; Ph; Ph]; [291; S; Ph; H; MeSCH₂; S; Ph; Ph]; [292; S; Ph; H; PhSCH₂; S; Ph; Ph]; [293; S; Ph; H; CF₃CH₂; S; Ph; Ph]; [294; S; Ph; H; PhCH₂; S; Ph; Ph]; [295; S; Ph; H; 4-F-Ph; S; Ph; Ph]; [296; S; Ph; H; 4-Cl-Ph; S; Ph; Ph]; [297; S; Ph; H; 4-Me-Ph; S; Ph; Ph]; [298; S; Ph; H; 2-Naphthyl; S; Ph; Ph]; [299; S; Ph; H; 5-Indanyl; S; Ph; Ph]; [300; S; Ph; H; 2-Pyridyl; S; Ph; Ph]; [301; S; Ph; H; 2-Thiazolyl; S; Ph; Ph]; [302; S; Ph; H; 2-Methyltetrazol-5-yl; S; Ph; Ph]; [303; S; Ph; H; 2-Oxazolyl; S; Ph; Ph]; [304; S; Ph; H; 2-Benzothiazolyl; S; Ph; Ph]; [305; S; Ph; H; 2-Benzofuranyl; S; Ph; Ph]; [306; S; Ph; H; 2-Benzothienyl; S; Ph; Ph]; [307; S; Ph; H; MeS(=O); S; Ph; Ph]; [308; S; Ph; H; MeS(=O)₂; S; Ph; Ph]; [309; S; Ph; H; PhS(=O); S; Ph; Ph]; [310; S; Ph; H; PhS(=O)₂; S; Ph; Ph]; [311; S; Ph; H; MeC(=O)S; S; Ph; Ph]; [312; S; Ph; H; MeC(=O)O; S; Ph; Ph]; [313; S; Ph; H; MeS(=O)₂O; S; Ph; Ph]; [314; S; Ph; H; PhC(=O); S; Ph; Ph]; [315; S; Ph; H; PhOC(=O); S; Ph; Ph]; [316; S; Ph; H; Me₂N; S; Ph; Ph]; [317; S; Ph; H; (Ph)(Me)N; S; Ph; Ph]; [318; S; Ph; H; (Me)(MeO)N; S; Ph; Ph]; [319; S; Ph; H; (Me)(Me₂N)N; S; Ph; Ph]; [320; S; Ph; H; (Me)(MeOOC)N; S; Ph; Ph]; [321; S; MeO(CH₂)₄; Me; H; S; Ph; Ph]; [322; S; MeS(CH₂)₄; Me; H; S; Ph; Ph]; [323; S; O₂N(CH₂)₄; Me; H; S; Ph; Ph]; [324; S; NC(CH₂)₄; Me; H; S; Ph; Ph]; [325; S; ClCH₂(CH₂)₃; Me; H; S; Ph; Ph]; [326; S; CF₃(CH₂)₃; Me; H; S; Ph; Ph]; [327; S; Ac(CH₂)₄; Me; H; S; Ph; Ph]; [328; S; AcO(CH₂)₄; Me; H; S; Ph; Ph]; [329; S; PhO(CH₂)₄; Me; H; S; Ph; Ph]; [330; S; PhS(CH₂)₄; Me; H; S; Ph; Ph]; [331; S; PhCH₂; Me; H; S; Ph; Ph]; [332; S; 4-Me-PhCH₂; Me; H; S; Ph; Ph]; [333; S; 4-MeO-PhCH₂; Me; H; S; Ph; Ph]; [334; S; 4-Cl-PhCH₂; Me; H; S; Ph; Ph]; [335; S; 4-Ph-PhCH₂; Me; H; S; Ph; Ph]; [336; S; 1-Naphthylmethyl; Me; H; S; Ph; Ph]; [337; S; 2-Naphthylmethyl; Me; H; S; Ph; Ph]; [338; S; α-Methylbenzyl; Me; H; S; Ph; Ph]; [339; S; 2-Picolyl; Me; H; S; Ph; Ph]; [340; S; 5-Chloro-2-picolyl; Me; H; S; Ph; Ph]; [341; S; 2-Furylmethyl; Me; H; S; Ph; Ph]; [342; S; 2-Thieylmethyl; Me; H; S; Ph; Ph]; [343; S; Cyclohexylmethyl; Me; H; S; Ph; Ph]; [344; S; 1-Cyclohexylethyl; Me; H; S; Ph; Ph]; [345; S; CH₃(CH₂)₉; Me; H; S; Ph; Ph]; [346; S; Allyl; Me; H; S; Ph; Ph]; [347; S; 3-Chloro-3-propenyl; Me; H; S; Ph; Ph]; [348; S; 3-Phenyl-3-propenyl; Me; H; S; Ph; Ph]; [349; S; 2-Methyl-2-butenyl; Me; H; S; Ph; Ph]; [350; S; Propargyl; Me; H; S; Ph; Ph]; [351; S; 2-Butynyl; Me; H; S; Ph; Ph]; [352; S; Cyclohexyl; Me; H; S; Ph; Ph]; [353; S; 4-Methylcyclohexyl; Me; H; S; Ph; Ph]; [354; S; 4-Chlorohexyl; Me; H; S; Ph; Ph]; [355; S; 4-Methoxycyclohexyl; Me; H; S; Ph; Ph]; [356; S; 2-Perhydronaphthyl; Me; H; S; Ph; Ph]; [357; S; 2-Indanyl; Me; H; S; Ph; Ph]; [358; S; 2-Cyclohexen-1-yl; Me; H; S; Ph; Ph]; [359; S; 3-Methyl-2-Cyclohexenyl; Me; H; S; Ph; Ph]; [360; S; 1,4-Cyclohexadien-1-yl; Me; H; S; Ph; Ph]; [361; S; 2,5-Cyclohexadien-1-yl; Me; H; S; Ph; Ph]; [362; S; Ph; Me; H; S; Ph; Ph]; [363; S; 2-F-Ph; Me; H; S; Ph; Ph]; [364; S; 3-F-Ph; Me; H; S; Ph; Ph]; [365; S; 4-F-Ph; Me; H; S; Ph; Ph]; [366; S; 2-Cl-Ph; Me; H; S; Ph; Ph]; [367; S; 3-Cl-Ph; Me; H; S; Ph; Ph]; [368; S; 4-Cl-Ph; Me; H; S; Ph; Ph]; [369; S; 2-Me-Ph; Me; H; S; Ph; Ph]; [370; S; 3-Me-Ph; Me; H; S; Ph; Ph]; [371; S; 4-Me-Ph; Me; H; S; Ph; Ph]; [372; S; 2-Et-Ph; Me; H; S; Ph; Ph]; [373; S; 3-Et-Ph; Me; H; S; Ph; Ph]; [374; S; 4-Et-Ph; Me; H; S; Ph; Ph]; [375; S; 2-iPr-Ph; Me; H; S; Ph; Ph]; [376; S; 3-iPr-Ph; Me; H; S; Ph; Ph]; [377; S; 4-iPr-Ph; Me; H; S; Ph; Ph]; [378; S; 2-Ph-Ph; Me; H; S; Ph; Ph]; [379; S; 3-Ph-Ph; Me; H; S; Ph; Ph]; [380; S; 4-Ph-Ph; Me; H; S; Ph; Ph]; [381; S; 2-CF₃-Ph; Me; H; S; Ph; Ph]; [382; S; 3-CF₃-Ph; Me; H; S; Ph; Ph]; [383; S; 4-CF₃-Ph; Me; H; S; Ph; Ph]; [384; S; 2-MeO-Ph; Me; H; S; Ph; Ph]; [385; S; 3-MeO-Ph; Me; H; S; Ph; Ph]; [386; S; 4-MeO-Ph; Me; H; S; Ph; Ph]; [387; S; 2-PhO-Ph; Me; H; S; Ph; Ph]; [388; S; 3-PhO-Ph; Me; H; S; Ph; Ph]; [389; S; 4-PhO-Ph; Me; H; S; Ph; Ph]; [390; S; 4-CF₃O-Ph; Me; H; S; Ph; Ph]; [391; S; 4-Ac-Ph; Me; H; S; Ph; Ph]; [392; S; 4-PhC(=O)-Ph; Me; H; S; Ph; Ph]; [393; S; 4-MeOC(=O)-Ph; Me; H; S; Ph; Ph]; [394; S; 4-PhOC(=O)-Ph; Me; H; S; Ph; Ph]; [395; S; 4-MeC(=O)O-Ph; Me; H; S; Ph; Ph]; [396; S; 4-PhC(=O)O-Ph; Me; H; S; Ph; Ph]; [397; S; 4-Me₂NC(=O)-Ph; Me; H; S; Ph; Ph]; [398; S; 4-O₂N-Ph; Me; H; S; Ph; Ph]; [399; S; 4-NC-Ph; Me; H; S; Ph; Ph]; [400; S; 2,3-Me₂-Ph; Me; H; S; Ph; Ph]; [401; S; 2,4-Mee-Ph; Me; H; S; Ph; Ph]; [402; S; 2,5-Mee-Ph; Me; H; S; Ph; Ph]; [403; S; 2,6-Me₂-Ph; Me; H; S; Ph; Ph]; [404; S; 3,4-Me₂-Ph; Me; H; S; Ph; Ph]; [405; S; 3,5-Me₂-Ph; Me; H; S; Ph; Ph]; [406; S; 2,3-F₂-Ph; Me; H; S; Ph; Ph]; [407; S; 2,4-F₂-Ph; Me; H; S; Ph; Ph]; [408; S; Ph; Me; H; S; Ph; Ph]; [409; S; 2,6-F₂-Ph; Me; H; S; Ph; Ph]; [410; S; 3,4-F₂-Ph; Me; H; S; Ph; Ph]; [411; S; Ph; Me; H; S; Ph; Ph]; [412; S; 2,3-Cl₂-Ph; Me; H; S; Ph; Ph]; [413; S; 2,4-Cl₂-Ph; Me; H; S; Ph; Ph]; [414; S; 2,5-Cl₂-Ph; Me; H; S; Ph; Ph]; [415; S; 2,6-Cl₂-Ph; Me; H; S; Ph; Ph]; [416; S; 3,4-Cl₂-Ph; Me; H; S; Ph; Ph]; [417; S; 3,5-Cl₂-Ph; Me; H; S; Ph; Ph]; [418; S; 2,4-(MeO)₂-Ph; Me; H; S; Ph; Ph]; [419; S; 2,6-(MeO)₂-Ph; Me; H; S; Ph; Ph]; [420; S; 3,4-(MeO)₂-Ph; Me; H; S; Ph; Ph]; [421; S; 1-Naphthyl; Me; H; S; Ph; Ph]; [422; S; 2-Naphthyl; Me; H; S; Ph; Ph]; [423; S; 5-Indanyl; Me; H; S; Ph; Ph]; [424; S; 5-Benzodioxolyl; Me; H; S; Ph; Ph]; [425; S; 2-Pyridyl; Me; H; S; Ph; Ph]; [426; S; 3-Pyridyl; Me; H; S; Ph; Ph]; [427; S; 4-Pyridyl; Me; H; S; Ph; Ph]; [428; S; 2-Pyrimidinyl; Me; H; S; Ph; Ph]; [429; S; 2-Pyrazinyl; Me; H; S; Ph; Ph]; [430; S; 2-Thienyl; Me; H; S; Ph; Ph]; [431; S; 3-Thienyl; Me; H; S; Ph; Ph]; [432; S; 2-Furyl; Me; H; S; Ph; Ph]; [433; S; 3-Furyl; Me; H; S; Ph; Ph]; [434; S; 1-Methyltetrazol-5-yl; Me; H; S; Ph; Ph]; [435; S; 2-Methyltetrazol-5-yl; Me; H; S; Ph; Ph]; [436; S; 2-Oxazolyl; Me; H; S; Ph; Ph]; [437; S; 2-Thiazolyl; Me; H; S; Ph; Ph]; [438; S; 1,3,4-Thiadiazol-2-yl; Me; H; S; Ph; Ph]; [439; S; 2-Benzothiazolyl; Me; H; S; Ph; Ph]; [440; S; 2-Quinolinyl; Me; H; S; Ph; Ph]; [441; S; PhCH₂; Et; H; S; Ph; Ph]; [442; S; Ph; Et; H; S; Ph; Ph]; [443; S; 3-F-Ph; Et; H; S; Ph; Ph]; [444; S; 4-F-Ph; Et; H; S; Ph; Ph]; [445; S; 4-Cl-Ph; Et; H; S; Ph; Ph]; [446; S; 4-Me-Ph; Et; H; S; Ph; Ph]; [447; S; 3,4-M₂-Ph; Et; H; S; Ph; Ph]; [448; S; 2-Naphthyl; Et; H; S; Ph; Ph]; [449; S; 5-Indanyl; Et; H; S; Ph; Ph]; [450; S; 5-Benzodioxolyl; Et; H; S; Ph; Ph]; [451; S; PhCH₂; Pr; H; S; Ph; Ph]; [452; S; Ph; Pr; H; S; Ph; Ph]; [453; S; 3-F-Ph; Pr; H; S; Ph; Ph]; [454; S; 4-F-Ph; Pr; H; S; Ph; Ph]; [455; S; 4-Cl-Ph; Pr; H; S; Ph; Ph]; [456; S; 4-Me-Ph; Pr; H; S; Ph; Ph]; [457; S; 3,4-Me₂-Ph; Pr; H; S; Ph; Ph]; [458; S; 2-Naphthyl; Pr; H; S; Ph; Ph]; [459; S; 5-Indanyl; Pr; H; S; Ph; Ph]; [460; S; 5-Benzodioxolyl; Pr; H; S; Ph; Ph]; [461; S; PhCH₂; Ph; H; S; Ph; Ph]; [462; S; Ph; Ph; H; S; Ph; Ph]; [463; S; 3-F-Ph; Ph; H; S; Ph; Ph]; [464; S; 4-F-Ph; Ph; H; S; Ph; Ph]; [465; S; 4-Cl-Ph; Ph; H; S; Ph; Ph]; [466; S; 4-Me-Ph; Ph; H; S; Ph; Ph]; [467; S; 3,4-Me₂-Ph; Ph; H; S; Ph; Ph]; [468; S; 2-Naphthyl; Ph; H; S; Ph; Ph]; [469; S; 5-Indanyl; Ph; H; S; Ph; Ph]; [470; S; 5-Benzodioxolyl; Ph; H; S; Ph; Ph]; [471; S; PhCH₂; OMe; H; S; Ph; Ph]; [472; S; Ph; OMe; H; S; Ph; Ph]; [473; S; 3-F-Ph; OMe; H; S; Ph; Ph]; [474; S; 4-F-Ph;

OMe; H; S; Ph; Ph]; [475; S; 4-Cl-Ph; OMe; H; S; Ph; Ph]; [476; S; 4-Me-Ph; OMe; H; S; Ph; Ph]; [477; S; 3,4-Me$_2$-Ph; OMe; H; S; Ph; Ph]; [478; S; 2-Naphthyl; OMe; H; S; Ph; Ph]; [479; S; 5-Indanyl; OMe; H; S; Ph; Ph]; [480; S; 5-Benzodioxolyl; OMe; H; S; Ph; Ph]; [481; S; PhCH$_2$; SMe; H; S; Ph; Ph]; [482; S; Ph; SMe; H; S; Ph; Ph]; [483; S; 3-F-Ph; SMe; H; S; Ph; Ph]; [484; S; 4-F-Ph; SMe; H; S; Ph; Ph]; [485; S; 4-Cl-Ph; SMe; H; S; Ph; Ph]; [486; S; 4-Me-Ph; SMe; H; S; Ph; Ph]; [487; S; 3,4-M$_2$-Ph; SMe; H; S; Ph; Ph]; [488; S; 2-Naphthyl; SMe; H; S; Ph; Ph]; [489; S; 5-Indanyl; SMe; H; S; Ph; Ph]; [490; S; 5-Benzodioxolyl; SMe; H; S; Ph; Ph]; [491; S; PhCH$_2$; OPh; H; S; Ph; Ph]; [492; S; Ph; OPh; H; S; Ph; Ph]; [493; S; 3-F-Ph; OPh; H; S; Ph; Ph]; [494; S; 4-F-Ph; OPh; H; S; Ph; Ph]; [495; S; 4-Cl-Ph; OPh; H; S; Ph; Ph]; [496; S; 4-Me-Ph; OPh; H; S; Ph; Ph]; [497; S; 3,4-Me$_2$-Ph; OPh; H; S; Ph; Ph]; [498; S; 2-Naphthyl; OPh; H; S; Ph; Ph]; [499; S; 5-Indanyl; OPh; H; S; Ph; Ph]; [500; S; 5-Benzodioxolyl; OPh; H; S; Ph; Ph]; [501; S; PhCH$_2$; SPh; H; S; Ph; Ph]; [502; S; Ph; SPh; H; S; Ph; Ph]; [503; S; 3-F-Ph; SPh; H; S; Ph; Ph]; [504; S; 4-F-Ph; SPh; H; S; Ph; Ph]; [505; S; 4-Cl-Ph; SPh; H; S; Ph; Ph]; [506; S; 4-Me-Ph; SPh; H; S; Ph; Ph]; [507; S; 3,4-Me$_2$-Ph; SPh; H; S; Ph; Ph]; [508; S; 2-Naphthyl; SPh; H; S; Ph; Ph]; [509; S; 5-Indanyl; SPh; H; S; Ph; Ph]; [510; S; 5-Benzodioxolyl; SPh; H; S; Ph; Ph]; [511; S; PhCH$_2$; CF$_3$; H; S; Ph; Ph]; [512; S; Ph; CF$_3$; H; S; Ph; Ph]; [513; S; 3-F-Ph; CF$_3$; H; S; Ph; Ph]; [514; S; 4-F-Ph; CF$_3$; H; S; Ph; Ph]; [515; S; 4-Cl-Ph; CF$_3$; H; S; Ph; Ph]; [516; S; 4-Me-Ph; CF$_3$; H; S; Ph; Ph]; [517; S; 3,4-Me$_2$-Ph; CF$_3$; H; S; Ph; Ph]; [518; S; 2-Naphthyl; CF$_3$; H; S; Ph; Ph]; [519; S; 5-Indanyl; CF$_3$; H; S; Ph; Ph]; [520; S; 5-Benzodioxolyl; CF$_3$; H; S; Ph; Ph]; [521; S; PhCH$_2$; 2-Thienyl; H; S; Ph; Ph]; [522; S; Ph; 2-Thienyl; H; S; Ph; Ph]; [523; S; 3-F-Ph; 2-Thienyl; H; S; Ph; Ph]; [524; S; 4-F-Ph; 2-Thienyl; H; S; Ph; Ph]; [525; S; 4-Cl-Ph; 2-Thienyl; H; S; Ph; Ph]; [526; S; 4-Me-Ph; 2-Thienyl; H; S; Ph; Ph]; [527; S; 3,4-Me$_2$-Ph; 2-Thienyl; H; S; Ph; Ph]; [528; S; 2-Naphthyl; 2-Thienyl; H; S; Ph; Ph]; [529; S; 5-Indanyl; 2-Thienyl; H; S; Ph; Ph]; [530; S; 5-Benzodioxolyl; 2-Thienyl; H; S; Ph; Ph]; [531; S; PhCH$_2$; 3-Thienyl; H; S; Ph; Ph]; [532; S; Ph; 3-Thienyl; H; S; Ph; Ph]; [533; S; 3-F-Ph; 3-Thienyl; H; S; Ph; Ph]; [534; S; 4-F-Ph; 3-Thienyl; H; S; Ph; Ph]; [535; S; 4-Cl-Ph; 3-Thienyl; H; S; Ph; Ph]; [536; S; 4-Me-Ph; 3-Thienyl; H; S; Ph; Ph]; [537; S; 3,4-Me$_2$-Ph; 3-Thienyl; H; S; Ph; Ph]; [538; S; 2-Naphthyl; 3-Thienyl; H; S; Ph; Ph]; [539; S; 5-Indanyl; 3-Thienyl; H; S; Ph; Ph]; [540; S; 5-Benzodioxolyl; 3-Thienyl; H; S; Ph; Ph]; [541; S; PhCH$_2$; 2-Furyl; H; S; Ph; Ph]; [542; S; Ph; 2-Furyl; H; S; Ph; Ph]; [543; S; 3-F-Ph; 2-Furyl; H; S; Ph; Ph]; [544; S; 4-F-Ph; 2-Furyl; H; S; Ph; Ph]; [545; S; 4-Cl-Ph; 2-Furyl; H; S; Ph; Ph]; [546; S; 4-Me-Ph; 2-Furyl; H; S; Ph; Ph]; [547; S; 3,4-Me$_2$-Ph; 2-Furyl; H; S; Ph; Ph]; [548; S; 2-Naphthyl; 2-Furyl; H; S; Ph; Ph]; [549; S; 5-Indanyl; 2-Furyl; H; S; Ph; Ph]; [550; S; 5-Benzodioxolyl; 2-Furyl; H; S; Ph; Ph]; [551; S; PhCH$_2$; Ac; H; S; Ph; Ph]; [552; S; Ph; Ac; H; S; Ph; Ph]; [553; S; 3-F-Ph; Ac; H; S; Ph; Ph]; [554; S; 4-F-Ph; Ac; H; S; Ph; Ph]; [555; S; 4-Cl-Ph; Ac; H; S; Ph; Ph]; [556; S; 4-Me-Ph; Ac; H; S; Ph; Ph]; [557; S; 3,4-Me$_2$-Ph; Ac; H; S; Ph; Ph]; [558; S; 2-Naphthyl; Ac; H; S; Ph; Ph]; [559; S; 5-Indanyl; Ac; H; S; Ph; Ph]; [560; S; 5-Benzodioxolyl; Ac; H; S; Ph; Ph]; [561; S; Ph; F; H; S; Ph; Ph]; [562; S; Ph; iPr; H; S; Ph; Ph]; [563; S; Ph; iBu; H; S; Ph; Ph]; [564; S; Ph; Cyclopropyl; H; S; Ph; Ph]; [565; S; Ph; Cyclohexyl; H; S; Ph; Ph]; [566; S; Ph; 2-Perhydronaphthyl; H; S; Ph; Ph]; [567; S; Ph; Allyl; H; S; Ph; Ph]; [568; S; Ph; Propargyl; H; S; Ph; Ph]; [569; S; Ph; MeOCH$_2$; H; S; Ph; Ph]; [570; S; Ph; PhOCH$_2$; H; S; Ph; Ph]; [571; S; Ph; MeSCH$_2$; H; S; Ph; Ph]; [572; S; Ph; PhSCH$_2$; H; S; Ph; Ph]; [573; S; Ph; CF$_3$CH$_2$; H; S; Ph; Ph]; [574; S; Ph; PhCH$_2$; H; S; Ph; Ph]; [575; S; Ph; 4-F-Ph; H; S; Ph; Ph]; [576; S; Ph; 4-Cl-Ph; H; S; Ph; Ph]; [577; S; Ph; 4-Me-Ph; H; S; Ph; Ph]; [578; S; Ph; 2-Naphthyl; H; S; Ph; Ph]; [579; S; Ph; 5-Indanyl; H; S; Ph; Ph]; [580; S; Ph; 2-Pyridyl; H; S; Ph; Ph]; [581; S; Ph; 2-Thiazolyl; H; S; Ph; Ph]; [582; S; Ph; 2-Methyltetrazol-5-yl; H; S; Ph; Ph]; [583; S; Ph; 2-Oxazolyl; H; S; Ph; Ph]; [584; S; Ph; 2-Benzothiazolyl; H; S; Ph; Ph]; [585; S; Ph; 2-Benzofuranyl; H; S; Ph; Ph]; [586; S; Ph; 2-Benzothienyl; H; S; Ph; Ph]; [587; S; Ph; MeS(=O); H; S; Ph; Ph]; [588; S; Ph; MeS(=O)$_2$; H; S; Ph; Ph]; [589; S; Ph; PhS(=O); H; S; Ph; Ph]; [590; S; Ph; PhS(=O)$_2$; H; S; Ph; Ph]; [591; S; Ph; MeC(=O)S; H; S; Ph; Ph]; [592; S; Ph; MeC(=O)O; H; S; Ph; Ph]; [593; S; Ph; MeS(=O)$_2$O; H; S; Ph; Ph]; [594; S; Ph; PhC(=O); H; S; Ph; Ph]; [595; S; Ph; MeOC(=O); H; S; Ph; Ph]; [596; S; Ph; Me$_2$N; H; S; Ph; Ph]; [597; S; Ph; (Ph) (Me)N; H; S; Ph; Ph]; [598; S; Ph; (Me) (MeO)N; H; S; Ph; Ph]; [599; S; Ph; (Me) (Me$_2$N) N; H; S; Ph; Ph]; [600; S; Ph; (Me) (MeOC)N; H; S; Ph; Ph]; [601; S; PhCH$_2$; H; Me; S; Me; Ph]; [602; S; Ph; H; Me; S; Me; Ph]; [603; S; 3-F-Ph; H; Me; S; Me; Ph]; [604; S; 4-F-Ph; H; Me; S; Me; Ph]; [605; S; 4-Cl-Ph; H; Me; S; Me; Ph]; [606; S; 4-Me-Ph; H; Me; S; Me; Ph]; [607; S; 3,4-Me$_2$-Ph; H; Me; S; Me; Ph]; [608; S; 2-Naphthyl; H; Me; S; Me; Ph]; [609; S; 5-Indanyl; H; Me; S; Me; Ph]; [610; S; 5-Benzodioxolyl; H; Me; S; Me; Ph]; [611; S; PhCH$_2$; H; Me; S; Et; Ph]; [612; S; Ph; H; Me; S; Et; Ph]; [613; S; 3-F-Ph; H; Me; S; Et; Ph]; [614; S; 4-F-Ph; H; Me; S; Et; Ph]; [615; S; 4-Cl-Ph; H; Me; S; Et; Ph]; [616; S; 4-Me-Ph; H; Me; S; Et; Ph]; [617; S; 3,4-Me$_2$-Ph; H; Me; S; Et; Ph]; [618; S; 2-Naphthyl; H; Me; S; Et; Ph]; [619; S; 5-Indanyl; H; Me; S; Et; Ph]; [620; S; 5-Benzodioxolyl; H; Me; S; Et; Ph]; [621; S; PhCH$_2$; H; Me; S; Pr; Ph]; [622; S; Ph; H; Me; S; Pr; Ph]; [623; S; 3-F-Ph; H; Me; S; Pr; Ph]; [624; S; 4-F-Ph; H; Me; S; Pr; Ph]; [625; S; 4-Cl-Ph; H; Me; S; Pr; Ph]; [626; S; 4-Me-Ph; H; Me; S; Pr; Ph]; [627; S; 3,4-Me$_2$-Ph; H; Me; S; Pr; Ph]; [628; S; 2-Naphthyl; H; Me; S; Pr; Ph]; [629; S; 5-Indanyl; H; Me; S; Pr; Ph]; [630; S; 5-Benzodioxolyl; H; Me; S; Pr; Ph]; [631; S; PhCH$_2$; H; Me; S; Bu; Ph]; [632; S; Ph; H; Me; S; Bu; Ph]; [633; S; 3-F-Ph; H; Me; S; Bu; Ph]; [634; S; 4-F-Ph; H; Me; S; Bu; Ph]; [635; S; 4-Cl-Ph; H; Me; S; Bu; Ph]; [636; S; 4-Me-Ph; H; Me; S; Bu; Ph]; [637; S; 3,4-Me$_2$-Ph; H; Me; S; Bu; Ph]; [638; S; 2-Naphthyl; H; Me; S; Bu; Ph]; [639; S; 5-Indanyl; H; Me; S; Bu; Ph]; [640; S; 5-Benzodioxolyl; H; Me; S; Bu; Ph]; [641; S; PhCH$_2$; H; Me; S; CH$_3$(CH$_2$)$_4$; Ph]; [642; S; Ph; H; Me; S; CH$_3$(CH$_2$)$_4$; Ph]; [643; S; 3-F-Ph; H; Me; S; CH$_3$(CH$_2$)$_4$; Ph]; [644; S; 4-F-Ph; H; Me; S; CH$_3$(CH$_2$)$_4$; Ph]; [645; S; 4-Cl-Ph; H; Me; S; CH$_3$(CH$_2$)$_4$; Ph]; [646; S; 4-Me-Ph; H; Me; S; CH$_3$(CH$_2$)$_4$; Ph]; [647; S; 3,4-Me$_2$-Ph; H; Me; S; CH$_3$(CH$_2$)$_4$; Ph]; [648; S; 2-Naphthyl; H; Me; S; CH$_3$(CH$_2$)$_4$; Ph]; [649; S; 5-Indanyl; H; Me; S; CH$_3$(CH$_2$)$_4$; Ph]; [650; S; 5-Benzodioxolyl; H; Me; S; CH$_3$(CH$_2$)$_4$; Ph]; [651; S; PhCH$_2$; H; Me; S; CH$_3$(CH$_2$)$_5$; Ph]; [652; S; Ph; H; Me; S; CH$_3$(CH$_2$)$_5$; Ph]; [653; S; 3-F-Ph; H; Me; S; CH$_3$(CH$_2$)$_5$; Ph]; [654; S; 4-F-Ph; H; Me; S; CH$_3$(CH$_2$)$_5$; Ph]; [655; S; 4-Cl-Ph; H; Me; S; CH$_3$(CH$_2$)$_5$; Ph]; [656; S; 4-Me-Ph; H; Me; S; CH$_3$(CH$_2$)$_5$; Ph]; [657; S; 3,4-Me$_2$-Ph; H; Me; S; CH$_3$(CH$_2$)$_5$; Ph]; [658; S; 2-Naphthyl; H; Me; S; CH$_3$(CH$_2$)$_5$; Ph]; [659; S; 5-Indanyl; H; Me; S; CH$_3$(CH$_2$)$_5$; Ph]; [660; S; 5-Benzodioxolyl; H; Me; S; CH$_3$(CH$_2$)$_5$; Ph]; [661; S; PhCH$_2$; H; Me; S; CH$_3$(CH$_2$)$_6$; Ph]; [662; S; Ph; H; Me; S; CH$_3$(CH$_2$)$_6$; Ph]; [663; S; 3-F-Ph; H; Me; S; CH$_3$(CH$_2$)$_6$; Ph]; [664; S; 4-F-Ph; H; Me; S; CH$_3$(CH$_2$)$_6$; Ph]; [665; S; 4-Cl-Ph; H; Me; S; CH$_3$(CH$_2$)$_6$; Ph]; [666; S; 4-Me-Ph; H; Me;

S; CH₃(CH₂)₆; Ph]; [667; S; 3,4-Me₂-Ph; H; Me; S; CH₃(CH₂)₆; Ph]; [668; S; 2-Naphthyl; H; Me; S; CH₃(CH₂)₆; Ph]; [669; S; 5-Indanyl; H; Me; S; CH₃(CH₂)₆; Ph]; [670; S; 5-Benzodioxolyl; H; Me; S; CH₃(CH₂)₆; Ph]; [671; S; PhCH₂; H; Me; S; CH₃(CH₂)₇; Ph]; [672; S; Ph; H; Me; S; CH₃(CH₂)₇; Ph]; [673; S; 3-F-Ph; H; Me; S; CH₃(CH₂)₇; Ph]; [674; S; 4-F-Ph; H; Me; S; CH₃(CH₂)₇; Ph]; [675; S; 4-Cl-Ph; H; Me; S; CH₃(CH₂)₇; Ph]; [676; S; 4-Me-Ph; H; Me; S; CH₃(CH₂)₇; Ph]; [677; S; 3,4-Me₂-Ph; H; Me; S; CH₃(CH₂)₇; Ph]; [678; S; 2-Naphthyl; H; Me; S; CH₃(CH₂)₇; Ph]; [679; S; 5-Indanyl; H; Me; S; CH₃(CH₂)₇; Ph]; [680; S; 5-Benzodioxolyl; H; Me; S; CH₃(CH₂)₇; Ph]; [681; S; PhCH₂; H; Me; S; iPr; Ph]; [682; S; Ph; H; Me; S; iPr; Ph]; [683; S; 3-F-Ph; H; Me; S; iPr; Ph]; [684; S; 4-F-Ph; H; Me; S; iPr; Ph]; [685; S; 4-Cl-Ph; H; Me; S; iPr; Ph]; [686; S; 4-Me-Ph; H; Me; S; iPr; Ph]; [687; S; 3,4-Me₂-Ph; H; Me; S; iPr; Ph]; [688; S; 2-Naphthyl; H; Me; S; iPr; Ph]; [689; S; 5-Indanyl; H; Me; S; iPr; Ph]; [690; S; 5-Benzodioxolyl; H; Me; S; iPr; Ph]; [691; S; PhCH₂; H; Me; S; iBu; Ph]; [692; S; Ph; H; Me; S; iBu; Ph]; [693; S; 3-F-Ph; H; Me; S; iBu; Ph]; [694; S; 4-F-Ph; H; Me; S; iBu; Ph]; [695; S; 4-Cl-Ph; H; Me; S; iBu; Ph]; [696; S; 4-Me-Ph; H; Me; S; iBu; Ph]; [697; S; 3,4-Me₂-Ph; H; Me; S; iBu; Ph]; [698; S; 2-Naphthyl; H; Me; S; iBu; Ph]; [699; S; 5-Indanyl; H; Me; S; iBu; Ph]; [700; S; 5-Benzodioxolyl; H; Me; S; iBu; Ph]; [701; S; PhCH₂; H; Me; S; sec-Bu; Ph]; [702; S; Ph; H; Me; S; sec-Bu; Ph]; [703; S; 3-F-Ph; H; Me; S; sec-Bu; Ph]; [704; S; 4-F-Ph; H; Me; S; sec-Bu; Ph]; [705; S; 4-Cl-Ph; H; Me; S; sec-Bu; Ph]; [706; S; 4-Me-Ph; H; Me; S; sec-Bu; Ph]; [707; S; 3,4-Me₂-Ph; H; Me; S; sec-Bu; Ph]; [708; S; 2-Naphthyl; H; Me; S; sec-Bu; Ph]; [709; S; 5-Indanyl; H; Me; S; sec-Bu; Ph]; [710; S; 5-Benzodioxolyl; H; Me; S; sec-Bu; Ph]; [711; S; PhCH₂; H; Me; S; tBu; Ph]; [712; S; Ph; H; Me; S; tBu; Ph]; [713; S; 3-F-Ph; H; Me; S; tBu; Ph]; [714; S; 4-F-Ph; H; Me; S; tBu; Ph]; [715; S; 4-Cl-Ph; H; Me; S; tBu; Ph]; [716; S; 4-Me-Ph; H; Me; S; tBu; Ph]; [717; S; 3,4-Me₂-Ph; H; Me; S; tBu; Ph]; [718; S; 2-Naphthyl; H; Me; S; tBu; Ph]; [719; S; 5-Indanyl; H; Me; S; tBu; Ph]; [720; S; 5-Benzodioxolyl; H; Me; S; tBu; Ph]; [721; S; PhCH₂; H; Me; S; Isopentyl; Ph]; [722; S; Ph; H; Me; S; Isopentyl; Ph]; [723; S; 3-F-Ph; H; Me; S; Isopentyl; Ph]; [724; S; 4-F-Ph; H; Me; S; Isopentyl; Ph]; [725; S; 4-Cl-Ph; H; Me; S; Isopentyl; Ph]; [726; S; 4-Me-Ph; H; Me; S; Isopentyl; Ph]; [727; S; 3,4-Me₂-Ph; H; Me; S; Isopentyl; Ph]; [728; S; 2-Naphthyl; H; Me; S; Isopentyl; Ph]; [729; S; 5-Indanyl; H; Me; S; Isopentyl; Ph]; [730; S; 5-Benzodioxolyl; H; Me; S; Isopentyl; Ph]; [731; S; PhCH₂; H; Me; S; sec-Pentyl; Ph]; [732; S; Ph; H; Me; S; sec-Pentyl; Ph]; [733; S; 3-F-Ph; H; Me; S; sec-Pentyl; Ph]; [734; S; 4-F-Ph; H; Me; S; sec-Pentyl; Ph]; [735; S; 4-Cl-Ph; H; Me; S; sec-Penty; Ph]; [736; S; 4-Me-Ph; H; Me; S; sec-Pentyl; Ph]; [737; S; 3,4-Me₂-Ph; H; Me; S; sec-Pentyl; Ph]; [738; S; 2-Naphthyl; H; Me; S; sec-Pentyl; Ph]; [739; S; 5-Indanyl; H; Me; S; sec-Pentyl; Ph]; [740; S; 5-Benzodioxolyl; H; Me; S; sec-Pentyl; Ph]; [741; S; PhCH₂; H; Me; S; 1-Ethylpropyl; Ph]; [742; S; Ph; H; Me; S; 1-Ethylpropyl; Ph]; [743; S; 3-F-Ph; H; Me; S; 1-Ethylpropyl; Ph]; [744; S; 4-F-Ph; H; Me; S; 1-Ethylpropyl; Ph]; [745; S; 4-Cl-Ph; H; Me; S; 1-Ethylpropyl; Ph]; [746; S; 4-Me-Ph; H; Me; S; 1-Ethylpropyl; Ph]; [747; S; 3,4-Me₂-Ph; H; Me; S; 1-Ethylpropyl; Ph]; [748; S; 2-Naphthyl; H; Me; S; 1-Ethylpropyl; Ph]; [749; S; 5-Indanyl; H; Me; S; 1-Ethylpropyl; Ph]; [750; S; 5-Benzodioxolyl; H; Me; S; 1-Ethylpropyl; Ph]; [751; S; PhCH₂; H; Me; S; 2-Methylbutyl; Ph]; [752; S; Ph; H; Me; S; 2-Methylbutyl; Ph]; [753; S; 3-F-Ph; H; Me; S; 2-Methylbutyl; Ph]; [754; S; 4-F-Ph; H; Me; S; 2-Methylbutyl; Ph]; [755; S; 4-Cl-Ph; H; Me; S; 2-Methylbutyl; Ph]; [756; S; 4-Me-Ph; H; Me; S; 2-Methylbutyl; Ph]; [757; S; 3,4-Me₂-Ph; H; Me; S; 2-Methylbutyl; Ph]; [758; S; 2-Naphthyl; H; Me; S; 2-Methylbutyl; Ph]; [759; S; 5-Indanyl; H; Me; S; 2-Methylbutyl; Ph]; [760; S; 5-Benzodioxolyl; H; Me; S; 2-Ethylpropyl; Ph]; [761; S; PhCH₂; H; Me; S; 1-Methylpentyl; Ph]; [762; S; Ph; H; Me; S; 1-Methylpentyl; Ph]; [763; S; 3-F-Ph; H; Me; S; 1-Methylpentyl; Ph]; [764; S; 4-F-Ph; H; Me; S; 1-Methylpentyl; Ph]; [765; S; 4-Cl-Ph; H; Me; S; 1-Methylpentyl; Ph]; [766; S; 4-Me-Ph; H; Me; S; 1-Methylpentyl; Ph]; [767; S; 3,4-Me₂-Ph; H; Me; S; 1-Methylpentyl; Ph]; [768; S; 2-Naphthyl; H; Me; S; 1-Methylpentyl; Ph]; [769; S; 5-Indanyl; H; Me; S; 1-Methylpentyl; Ph]; [770; S; 5-Benzodioxolyl; H; Me; S; 1-Methylpentyl; Ph]; [771; S; PhCH₂; H; Me; S; 2-Methylpentyl; Ph]; [772; S; Ph; H; Me; S; 2-Methylpentyl; Ph]; [773; S; 3-F-Ph; H; Me; S; 2-Methylpentyl; Ph]; [774; S; 4-F-Ph; H; Me; S; 2-Methylpentyl; Ph]; [775; S; 4-Cl-Ph; H; Me; S; 2-Methylpentyl; Ph]; [776; S; 4-Me-Ph; H; Me; S; 2-Methylpentyl; Ph]; [777; S; 3,4-Me₂-Ph; H; Me; S; 2-Methylpentyl; Ph]; [778; S; 2-Naphthyl; H; Me; S; 2-Methylpentyl; Ph]; [779; S; 5-Indanyl; H; Me; S; 2-Methylpentyl; Ph]; [780; S; 5-Benzodioxolyl; H; Me; S; 2-Methylpentyl; Ph]; [781; S; PhCH₂; H; Me; S; Cyclopentyl; Ph]; [782; S; Ph; H; Me; S; Cyclopentyl; Ph]; [783; S; 3-F-Ph; H; Me; S; Cyclopentyl; Ph]; [784; S; 4-F-Ph; H; Me; S; Cyclopentyl; Ph]; [785; S; 4-Cl-Ph; H; Me; S; Cyclopentyl; Ph]; [786; S; 4-Me-Ph; H; Me; S; Cyclopentyl; Ph]; [787; S; 3,4-Me₂-Ph; H; Me; S; Cyclopentyl; Ph]; [788; S; 2-Naphthyl; H; Me; S; Cyclopentyl; Ph]; [789; S; 5-Indanyl; H; Me; S; Cyclopentyl; Ph]; [790; S; 5-Benzodioxolyl; H; Me; S; Cyclopentyl; Ph]; [791; S; PhCH₂; H; Me; S; Cyclohexyl; Ph]; [792; S; Ph; H; Me; S; Cyclohexyl; Ph]; [793; S; 3-F-Ph; H; Me; S; Cyclohexyl; Ph]; [794; S; 4-F-Ph; H; Me; S; Cyclohexyl; Ph]; [795; S; 4-Cl-Ph; H; Me; S; Cyclohexyl; Ph]; [796; S; 4-Me-Ph; H; Me; S; Cyclohexyl; Ph]; [797; S; 3,4-Me₂-Ph; H; Me; S; Cyclohexyl; Ph]; [798; S; 2-Naphthyl; H; Me; S; Cyclohexyl; Ph]; [799; S; 5-Indanyl; H; Me; S; Cyclohexyl; Ph]; [800; S; 5-Benzodioxolyl; H; Me; S; Cyclohexyl; Ph]; [801; S; PhCH₂; H; Me; S; 2-Perhydronaphthyl; Ph]; [802; S; Ph; H; Me; S; 2-Perhydronaphthyl; Ph]; [803; S; 3-F-Ph; H; Me; S; 2-Perhydronaphthyl; Ph]; [804; S; 4-F-Ph; H; Me; S; 2-Perhydronaphthyl; Ph]; [805; S; 4-Cl-Ph; H; Me; S; 2-Perhydronaphthyl; Ph]; [806; S; 4-Me-Ph; H; Me; S; 2-Perhydronaphthyl; Ph]; [807; S; 3,4-Me₂-Ph; H; Me; S; 2-Perhydronaphthyl; Ph]; [808; S; 2-Naphthyl; H; Me; S; 2-Perhydronaphthyl; Ph]; [809; S; 5-Indanyl; H; Me; S; 2-Perhydronaphthyl; Ph]; [810; S; 5-Benzodioxolyl; H; Me; S; 2-Perhydronaphthyl; Ph]; [811; S; PhCH₂; H; Me; S; Cyclopentylmethyl; Ph]; [812; S; Ph; H; Me; S; Cyclopentylmethyl; Ph]; [813; S; 3-F-Ph; H; Me; S; Cyclopentylmethyl; Ph]; [814; S; 4-F-Ph; H; Me; S; Cyclopentylmethyl; Ph]; [815; S; 4-Cl-Ph; H; Me; S; Cyclopentylmethyl; Ph]; [816; S; 4-Me-Ph; H; Me; S; Cyclopentylmethyl; Ph]; [817; S; 3,4-Me₂-Ph; H; Me; S; Cyclopentylmethyl; Ph]; [818; S; 2-Naphthyl; H; Me; S; Cyclopentylmethyl; Ph]; [819; S; 5-Indanyl; H; Me; S; Cyclopentylmethyl; Ph]; [820; S; 5-Benzodioxolyl; H; Me; S; Cyclopentylmethyl; Ph]; [821; S; PhCH₂; H; Me; S; Cyclohexylmethyl; Ph]; [822; S; Ph; H; Me; S; Cyclohexylmethyl; Ph]; [823; S; 3-F-Ph; H; Me; S; Cyclohexylmethyl; Ph]; [824; S; 4-F-Ph; H; Me; S; Cyclohexylmethyl; Ph]; [825; S; 4-Cl-Ph; H; Me; S; Cyclohexylmethyl; Ph]; [826; S; 4-Me-Ph; H; Me; S; Cyclohexylmethyl; Ph]; [827; S; 3,4-Me₂-Ph; H; Me; S; Cyclohexylmethyl; Ph]; [828; S; 2-Naphthyl; H; Me; S; Cyclohexylmethyl; Ph]; [829; S; 5-Indanyl; H; Me; S; Cyclohexylmethyl; Ph]; [830; S;

5-Benzodioxolyl; H; Me; S; Cyclohexylmethyl; Ph]; [831; S; PhCH$_2$; H; Me; S; 1-Cyclohexylethyl; Ph]; [832; S; Ph; H; Me; S; 1-Cyclohexylethyl; Ph]; [833; S; 3-F-Ph; H; Me; S; 1-Cyclohexylethyl; Ph]; [834; S; 4-F-Ph; H; Me; S; 1-Cyclohexylethyl; Ph]; [835; S; 4-Cl-Ph; H; Me; S; 1-Cyclohexylethyl; Ph]; [836; S; 4-Me-Ph; H; Me; S; 1-Cyclohexylethyl; Ph]; [837; S; 3,4-Me$_2$-Ph; H; Me; S; 1-Cyclohexylethyl; Ph]; [838; S; 2-Naphthyl; H; Me; S; 1-Cyclohexylethyl; Ph]; [839; S; 5-Indanyl; H; Me; S; 1-Cyclohexylethyl; Ph]; [840; S; 5-Benzodioxolyl; H; Me; S; 1-Cyclohexylethyl; Ph]; [841; S; PhCH$_2$; H; Me; S; PhCH$_2$; Ph]; [842; S; Ph; H; Me; S; PhCH$_2$; Ph]; [843; S; 3-F-Ph; H; Me; S; PhCH$_2$; Ph]; [844; S; 4-F-Ph; H; Me; S; PhCH$_2$; Ph]; [845; S; 4-Cl-Ph; H; Me; S; PhCH$_2$; Ph]; [846; S; 4-Me-Ph; H; Me; S; PhCH$_2$; Ph]; [847; S; 3,4-Me$_2$-Ph; H; Me; S; PhCH$_2$; Ph]; [848; S; 2-Naphthyl; H; Me; S; PhCH$_2$; Ph]; [849; S; 5-Indanyl; H; Me; S; PhCH$_2$; Ph]; [850; S; 5-Benzodioxolyl; H; Me; S; PhCH$_2$; Ph]; [851; S; PhCH$_2$; H; Me; S; 2-F-Ph; Ph]; [852; S; Ph; H; Me; S; 2-F-Ph; Ph]; [853; S; 3-F-Ph; H; Me; S; 2-F-Ph; Ph]; [854; S; 4-F-Ph; H; Me; S; 2-F-Ph; Ph]; [855; S; 4-Cl-Ph; H; Me; S; 2-F-Ph; Ph]; [856; S; 4-Me-Ph; H; Me; S; 2-F-Ph; Ph]; [857; S; 3,4-Me$_2$-Ph; H; Me; S; 2-F-Ph; Ph]; [858; S; 2-Naphthyl; H; Me; S; 2-F-Ph; Ph]; [859; S; 5-Indanyl; H; Me; S; 2-F-Ph; Ph]; [860; S; 5-Benzodioxolyl; H; Me; S; 2-F-Ph; Ph]; [861; S; PhCH$_2$; H; Me; S; 3-F-Ph; Ph]; [862; S; Ph; H; Me; S; 3-F-Ph; Ph]; [863; S; 3-F-Ph; H; Me; S; 3-F-Ph; Ph]; [864; S; 4-F-Ph; H; Me; S; 3-F-Ph; Ph]; [865; S; 4-Cl-Ph; H; Me; S; 3-F-Ph; Ph]; [866; S; 4-Me-Ph; H; Me; S; 3-F-Ph; Ph]; [867; S; 3,4-Me$_2$-Ph; H; Me; S; 3-F-Ph; Ph]; [868; S; 2-Naphthyl; H; Me; S; 3-F-Ph; Ph]; [869; S; 5-Indanyl; H; Me; S; 3-F-Ph; Ph]; [870; S; 5-Benzodioxolyl; H; Me; S; 3-F-Ph; Ph]; [871; S; PhCH$_2$; H; Me; S; 4-F-Ph; Ph]; [872; S; Ph; H; Me; S; 4-F-Ph; Ph]; [873; S; 3-F-Ph; H; Me; S; 4-F-Ph; Ph]; [874; S; 4-F-Ph; H; Me; S; 4-F-Ph; Ph]; [875; S; 4-Cl-Ph; H; Me; S; 4-F-Ph; Ph]; [876; S; 4-Me-Ph; H; Me; S; 4-F-Ph; Ph]; [877; S; 3,4-Me$_2$-Ph; H; Me; S; 4-F-Ph; Ph]; [878; S; 2-Naphthyl; H; Me; S; 4-F-Ph; Ph]; [879; S; 5-Indanyl; H; Me; S; 4-F-Ph; Ph]; [880; S; 5-Benzodioxolyl; H; Me; S; 4-F-Ph; Ph]; [881; S; PhCH$_2$; H; Me; S; 2-Cl-Ph; Ph]; [882; S; Ph; H; Me; S; 2-Cl-Ph; Ph]; [883; S; 3-F-Ph; H; Me; S; 2-Cl-Ph; Ph]; [884; S; 4-F-Ph; H; Me; S; 2-Cl-Ph; Ph]; [885; S; 4-Cl-Ph; H; Me; S; 2-Cl-Ph; Ph]; [886; S; 4-Me-Ph; H; Me; S; 2-Cl-Ph; Ph]; [887; S; 3,4-Me$_2$-Ph; H; Me; S; 2-Cl-Ph; Ph]; [888; S; 2-Naphthyl; H; Me; S; 2-Cl-Ph; Ph]; [889; S; 5-Indanyl; H; Me; S; 2-Cl-Ph; Ph]; [890; S; 5-Benzodioxolyl; H; Me; S; 2-Cl-Ph; Ph]; [891; S; PhCH$_2$; H; Me; S; 3-Cl-Ph; Ph]; [892; S; Ph; H; Me; S; 3-Cl-Ph; Ph]; [893; S; 3-F-Ph; H; Me; S; 3-Cl-Ph; Ph]; [894; S; 4-F-Ph; H; Me; S; 3-Cl-Ph; Ph]; [895; S; 4-Cl-Ph; H; Me; S; 3-Cl-Ph; Ph]; [896; S; 4-Me-Ph; H; Me; S; 3-Cl-Ph; Ph]; [897; S; 3,4-Me$_2$-Ph; H; Me; S; 3-Cl-Ph; Ph]; [898; S; 2-Naphthyl; H; Me; S; 3-Cl-Ph; Ph]; [899; S; 5-Indanyl; H; Me; S; 3-Cl-Ph; Ph]; [900; S; 5-Benzodioxolyl; H; Me; S; 3-Cl-Ph; Ph]; [901; S; PhCH$_2$; H; Me; S; 4-Cl-Ph; Ph]; [902; S; Ph; H; Me; S; 4-Cl-Ph; Ph]; [903; S; 3-F-Ph; H; Me; S; 4-Cl-Ph; Ph]; [904; S; 4-F-Ph; H; Me; S; 4-Cl-Ph; Ph]; [905; S; 4-Cl-Ph; H; Me; S; 4-Cl-Ph; Ph]; [906; S; 4-Me-Ph; H; Me; S; 4-Cl-Ph; Ph]; [907; S; 3,4-Me$_2$-Ph; H; Me; S; 4-Cl-Ph; Ph]; [908; S; 2-Naphthyl; H; Me; S; 4-Cl-Ph; Ph]; [909; S; 5-Indanyl; H; Me; S; 4-Cl-Ph; Ph]; [910; S; 5-Benzodioxolyl; H; Me; S; 4-Cl-Ph; Ph]; [911; S; PhCH$_2$; H; Me; S; 2-Me-Ph; Ph]; [912; S; Ph; H; Me; S; 2-Me-Ph; Ph]; [913; S; 3-F-Ph; H; Me; S; 2-Me-Ph; Ph]; [914; S; 4-F-Ph; H; Me; S; 2-Me-Ph; Ph]; [915; S; 4-Cl-Ph; H; Me; S; 2-Me-Ph; Ph]; [916; S; 4-Me-Ph; H; Me; S; 2-Me-Ph; Ph]; [917; S; 3,4-Me$_2$-Ph; H; Me; S; 2-Me-Ph; Ph]; [918; S; 2-Naphthyl; H; Me; S; 2-Me-Ph; Ph]; [919; S; 5-Indanyl; H; Me; S; 2-Me-Ph; Ph]; [920; S; 5-Benzodioxolyl; H; Me; S; 2-Me-Ph; Ph]; [921; S; PhCH$_2$; H; Me; S; 3-Me-Ph; Ph]; [922; S; Ph; H; Me; S; 3-Me-Ph; Ph]; [923; S; 3-F-Ph; H; Me; S; 3-Me-Ph; Ph]; [924; S; 4-F-Ph; H; Me; S; 3-Me-Ph; Ph]; [925; S; 4-Cl-Ph; H; Me; S; 3-Me-Ph; Ph]; [926; S; 4-Me-Ph; H; Me; S; 3-Me-Ph; Ph]; [927; S; 3,4-Me$_2$-Ph; H; Me; S; 3-Me-Ph; Ph]; [928; S; 2-Naphthyl; H; Me; S; 3-Me-Ph; Ph]; [929; S; 5-Indanyl; H; Me; S; 3-Me-Ph; Ph]; [930; S; 5-Benzodioxolyl; H; Me; S; 3-Me-Ph; Ph]; [931; S; PhCH$_2$; H; Me; S; 4-Me-Ph; Ph]; [932; S; Ph; H; Me; S; 4-Me-Ph; Ph]; [933; S; 3-F-Ph; H; Me; S; 4-Me-Ph; Ph]; [934; S; 4-F-Ph; H; Me; S; 4-Me-Ph; Ph]; [935; S; 4-Cl-Ph; H; Me; S; 4-Me-Ph; Ph]; [936; S; 4-Me-Ph; H; Me; S; 4-Me-Ph; Ph]; [937; S; 3,4-Me$_2$-Ph; H; Me; S; 4-Me-Ph; Ph]; [938; S; 2-Naphthyl; H; Me; S; 4-Me-Ph; Ph]; [939; S; 5-Indanyl; H; Me; S; 4-Me-Ph; Ph]; [940; S; 5-Benzodioxolyl; H; Me; S; 4-Me-Ph; Ph]; [941; S; PhCH$_2$; H; Me; S; 4-iPr-Ph; Ph]; [942; S; Ph; H; Me; S; 4-iPr-Ph; Ph]; [943; S; 3-F-Ph; H; Me; S; 4-iPr-Ph; Ph]; [944; S; 4-F-Ph; H; Me; S; 4-iPr-Ph; Ph]; [945; S; 4-Cl-Ph; H; Me; S; 4-iPr-Ph; Ph]; [946; S; 4-Me-Ph; H; Me; S; 4-iPr-Ph; Ph]; [947; S; 3,4-Me$_2$-Ph; H; Me; S; 4-iPr-Ph; Ph]; [948; S; 2-Naphthyl; H; Me; S; 4-iPr-Ph; Ph]; [949; S; 5-Indanyl; H; Me; S; 4-iPr-Ph; Ph]; [950; S; 5-Benzodioxolyl; H; Me; S; 4-iPr-Ph; Ph]; [951; S; PhCH$_2$; H; Me; S; 4-CF$_3$-Ph; Ph]; [952; S; Ph; H; Me; S; 4-CF$_3$-Ph; Ph]; [953; S; 3-F-Ph; H; Me; S; 4-CF$_3$-Ph; Ph]; [954; S; 4-F-Ph; H; Me; S; 4-CF$_3$-Ph; Ph]; [955; S; 4-Cl-Ph; H; Me; S; 4-CF$_3$-Ph; Ph]; [956; S; 4-Me-Ph; H; Me; S; 4-CF$_3$-Ph; Ph]; [957; S; 3,4-Me$_2$-Ph; H; Me; S; 4-CF$_3$-Ph; Ph]; [958; S; 2-Naphthyl; H; Me; S; 4-CF$_3$-Ph; Ph]; [959; S; 5-Indanyl; H; Me; S; 4-CF$_3$-Ph; Ph]; [960; S; 5-Benzodioxolyl; H; Me; S; 4-CF$_3$-Ph; Ph]; [961; S; PhCH$_2$; H; Me; S; 1-Naphthyl; Ph]; [962; S; Ph; H; Me; S; 1-Naphthyl; Ph]; [963; S; 3-F-Ph; H; Me; S; 1-Naphthyl; Ph]; [964; S; 4-F-Ph; H; Me; S; 1-Naphthyl; Ph]; [965; S; 4-Cl-Ph; H; Me; S; 1-Naphthyl; Ph]; [966; S; 4-Me-Ph; H; Me; S; 1-Naphthyl; Ph]; [967; S; 3,4-Me$_2$-Ph; H; Me; S; 1-Naphthyl; Ph]; [968; S; 2-Naphthyl; H; Me; S; 1-Naphthyl; Ph]; [969; S; 5-Indanyl; H; Me; S; 1-Naphthyl; Ph]; [970; S; 5-Benzodioxolyl; H; Me; S; 1-Naphthyl; Ph]; [971; S; PhCH$_2$; H; Me; S; 2-Naphthyl; Ph]; [972; S; Ph; H; Me; S; 2-Naphthyl; Ph]; [973; S; 3-F-Ph; H; Me; S; 2-Naphthyl; Ph]; [974; S; 4-F-Ph; H; Me; S; 2-Naphthyl; Ph]; [975; S; 4-Cl-Ph; H; Me; S; 2-Naphthyl; Ph]; [976; S; 4-Me-Ph; H; Me; S; 2-Naphthyl; Ph]; [977; S; 3,4-Me$_2$-Ph; H; Me; S; 2-Naphthyl; Ph]; [978; S; 2-Naphthyl; H; Me; S; 2-Naphthyl; Ph]; [979; S; 5-Indanyl; H; Me; S; 2-Naphthyl; Ph]; [980; S; 5-Benzodioxolyl; H; Me; S; 2-Naphthyl; Ph]; [981; S; PhCH$_2$; H; Me; S; 2-Indanyl; Ph]; [982; S; Ph; H; Me; S; 2-Indanyl; Ph]; [983; S; 3-F-Ph; H; Me; S; 2-Indanyl; Ph]; [984; S; 4-F-Ph; H; Me; S; 2-Indanyl; Ph]; [985; S; 4-Cl-Ph; H; Me; S; 2-Indanyl; Ph]; [986; S; 4-Me-Ph; H; Me; S; 2-Indanyl; Ph]; [987; S; 3,4-Me$_2$-Ph; H; Me; S; 2-Indanyl; Ph]; [988; S; 2-Naphthyl; H; Me; S; 2-Indanyl; Ph]; [989; S; 5-Indanyl; H; Me; S; 2-Indanyl; Ph]; [990; S; 5-Benzodioxolyl; H; Me; S; 2-Indanyl; Ph]; [991; S; PhCH$_2$; H; Me; S; 5-Indanyl; Ph]; [992; S; Ph; H; Me; S; 5-Indanyl; Ph]; [993; S; 3-F-Ph; H; Me; S; 5-Indanyl; Ph]; [994; S; 4-F-Ph; H; Me; S; 5-Indanyl; Ph]; [995; S; 4-Cl-Ph; H; Me; S; 5-Indanyl; Ph]; [996; S; 4-Me-Ph; H; Me; S; 5-Indanyl; Ph]; [997; S; 3,4-Me$_2$-Ph; H; Me; S; 5-Indanyl; Ph]; [998; S; 2-Naphthyl; H; Me; S; 5-Indanyl; Ph]; [999; S; 5-Indanyl; H; Me; S; 5-Indanyl; Ph]; [1000; S; 5-Benzodioxolyl; H; Me; S; 5-Indanyl; Ph];

[1001; S; Ph; H; Me; S; 3-Methylpentyl; Ph]; [1002; S; 4-F-Ph; H; Me; S; 3-Methylpentyl; Ph]; [1003; S; Ph; H; Me; S; 4-Methylpentyl; Ph]; [1004; S; 4-F-Ph; H; Me; S; 4-Methylpentyl; Ph]; [1005; S; Ph; H; Me; S; 1-Ethylbutyl; Ph]; [1006; S; 4-F-Ph; H; Me; S; 1-Ethylbutyl; Ph]; [1007; S; Ph; H; Me; S; 2-Ethylbutyl; Ph]; [1008; S; 4-F-Ph; H; Me; S; 2-Ethylbutyl; Ph]; [1009; S; Ph; H; Me; S; 3-Methylpentyl; Ph]; [1010; S; 4-F-Ph; H; Me; S; 3-Methylpentyl; Ph]; [1013; S; Ph; H; Me; S; 2-Methylpentyl; Ph]; [1014; S; 4-F-Ph; H; Me; S; 2-Methylpentyl; Ph]; [1015; S; Ph; H; Me; S; 1,1-Dimethylbutyl; Ph]; [1016; S; 4-F-Ph; H; Me; S; 1,1-Dimethylbutyl; Ph]; [1017; S; Ph; H; Me; S; 1,2-Dimethylbutyl; Ph]; [1018; S; 4-F-Ph; H; Me; S; 1,2-Dimethylbutyl; Ph]; [1019; S; Ph; H; Me; S; 1,3-Dimethylbutyl; Ph]; [1020; S; 4-F-Ph; H; Me; S; 1,3-Dimethylbutyl; Ph]; [1021; S; Ph; H; Me; S; 2,2-Dimethylbutyl; Ph]; [1022; S; 4-F-Ph; H; Me; S; 2,2-Dimethylbutyl; Ph]; [1023; S; Ph; H; Me; S; 2,3-Dimethylbutyl; Ph]; [1024; S; 4-F-Ph; H; Me; S; 2,3-Dimethylbutyl; Ph]; [1025; S; Ph; H; Me; S; 3,3-Dimethylbutyl; Ph]; [1026; S; 4-F-Ph; H; Me; S; 3,3-Dimethylbutyl; Ph]; [1027; S; Ph; H; Me; S; 1-Ethyl-1-methylpropyl; Ph]; [1028; S; 4-F-Ph; H; Me; S; 1-Ethyl-1-methylpropyl; Ph]; [1029; S; Ph; H; Me; S; 1-Ethyl-2-methylpropyl; Ph]; [1030; S; 4-F-Ph; H; Me; S; 1-Ethyl-2-methylpropyl; Ph]; [1031; S; Ph; H; Me; S; 1-Methylhexyl; Ph]; [1032; S; 4-F-Ph; H; Me; S; 1-Methylhexyl; Ph]; [1033; S; Ph; H; Me; S; 2-Methylhexyl; Ph]; [1034; S; 4-F-Ph; H; Me; S; 2-Methylhexyl; Ph]; [1035; S; Ph; H; Me; S; 1,1-Dimethylpentyl; Ph]; [1036; S; 4-F-Ph; H; Me; S; 1,1-Dimethylpentyl; Ph]; [1037; S; Ph; H; Me; S; 1,2-Dimethylpentyl; Ph]; [1038; S; 4-F-Ph; H; Me; S; 1,2-Dimethylpentyl; Ph]; [1039; S; Ph; H; Me; S; 1-Ethylpentyl; Ph]; [1040; S; 4-F-Ph; H; Me; S; 1-Ethylpentyl; Ph]; [1041; S; Ph; H; Me; S; 2-Ethylpentyl; Ph]; [1042; S; 4-F-Ph; H; Me; S; 2-Ethylpentyl; Ph]; [1043; S; Ph; H; Me; S; $CH_3(CH_2)_8$; Ph]; [1044; S; 4-F-Ph; H; Me; S; $CH_3(CH_2)_8$; Ph]; [1045; S; Ph; H; Me; S; $CH_3(CH_2)_9$; Ph]; [1046; S; 4-F-Ph; H; Me; S; $CH_3(CH_2)_9$; Ph]; [1047; S; Ph; H; Me; S; Cyclopropyl; Ph]; [1048; S; 4-F-Ph; H; Me; S; Cyclopropyl; Ph]; [1049; S; Ph; H; Me; S; Cyclobutyl; Ph]; [1050; S; 4-F-Ph; H; Me; S; Cyclobutyl; Ph]; [1051; S; Ph; H; Me; S; Cycloheptyl; Ph]; [1052; S; 4-F-Ph; H; Me; S; Cycloheptyl; Ph]; [1053; S; Ph; H; Me; S; Cyclopropylmethyl; Ph]; [1054; S; 4-F-Ph; H; Me; S; Cyclopropylmethyl; Ph]; [1055; S; Ph; H; Me; S; Cyclobutylmethyl; Ph]; [1056; S; 4-F-Ph; H; Me; S; Cyclobutylmethyl; Ph]; [1057; S; Ph; H; Me; S; 1-Cyclopropylethyl; Ph]; [1058; S; 4-F-Ph; H; Me; S; 1-Cyclopropylethyl; Ph]; [1059; S; Ph; H; Me; S; 1-Cyclobutylethyl; Ph]; [1060; S; 4-F-Ph; H; Me; S; 1-Cyclobutylethyl; Ph]; [1061; S; Ph; H; Me; S; 1-Cyclopentylethyl; Ph]; [1062; S; 4-F-Ph; H; Me; S; 1-Cyclopentylethyl; Ph]; [1063; S; Ph; H; Me; S; α-Methylbenzyl; Ph]; [1064; S; 4-F-Ph; H; Me; S; a-Methylbenzyl; Ph]; [1065; S; Ph; H; Me; S; 2-Fluorobenzyl; Ph]; [1066; S; 4-F-Ph; H; Me; S; 2-Fluorobenzyl; Ph]; [1067; S; Ph; H; Me; S; 3-Fluorobenzyl; Ph]; [1068; S; 4-F-Ph; H; Me; S; 3-Fluorobenzyl; Ph]; [1069; S; Ph; H; Me; S; 4-Fluorobenzyl; Ph]; [1070; S; 4-F-Ph; H; Me; S; 4-Fluorobenzyl; Ph]; [1071; S; Ph; H; Me; S; 4-MeO-Ph; Ph]; [1072; S; 4-F-Ph; H; Me; S; 4-MeO-Ph; Ph]; [1073; S; Ph; H; Me; S; 4-PhO-Ph; Ph]; [1074; S; 4-F-Ph; H; Me; S; 4-PhO-Ph; Ph]; [1075; S; Ph; H; Me; S; 4-NC-Ph; Ph]; [1076; S; 4-F-Ph; H; Me; S; 4-NC-Ph; Ph]; [1077; S; Ph; H; Me; S; 4-$O_2$N-Ph; Ph]; [1078; S; 4-F-Ph; H; Me; S; 4-$O_2$N-Ph; Ph]; [1079; S; Ph; H; Me; S; 4-MeOC-Ph; Ph]; [1080; S; 4-F-Ph; H; Me; S; 4-MeOC-Ph; Ph]; [1081; S; Ph; H; Me; S; 4-$F_3$CO-Ph; Ph]; [1082; S; 4-F-Ph; H; Me; S; 4-$F_3$CO-Ph; Ph]; [1083; S; Ph; H; Me; S; 4-MeS-Ph; Ph]; [1084; S; 4-F-Ph; H; Me; S; 4-MeS-Ph; Ph]; [1085; S; Ph; H; Me; S; 4-Ph-Ph; Ph]; [1086; S; 4-F-Ph; H; Me; S; 4-Ph-Ph; Ph]; [1087; S; Ph; H; Me; S; 2-Pyridyl; Ph]; [1088; S; 4-F-Ph; H; Me; S; 2-Pyridyl; Ph]; [1089; S; Ph; H; Me; S; 2-Pyrimidinyl; Ph]; [1090; S; 4-F-Ph; H; Me; S; 2-Pyrimidinyl; Ph]; [1091; S; Ph; H; Me; S; 2-Thienyl; Ph]; [1092; S; 4-F-Ph; H; Me; S; 2-Thienyl; Ph]; [1093; S; Ph; H; Me; S; 3-Thienyl; Ph]; [1094; S; 4-F-Ph; H; Me; S; 3-Thienyl; Ph]; [1095; S; Ph; H; Me; S; 2-Furyl; Ph]; [1096; S; 4-F-Ph; H; Me; S; 2-Furyl; Ph]; [1097; S; Ph; H; Me; S; 3-Furyl; Ph]; [1098; S; 4-F-Ph; H; Me; S; 3-Furyl; Ph]; [1099; S; Ph; H; Me; S; 1-Methyltetrazol-5-yl; Ph]; [1100; S; 4-F-Ph; H; Me; S; 1-Methyltetrazol-5-yl; Ph]; [1101; S; Ph; H; Me; S; 2-Methyltetrazol-5-yl; Ph]; [1102; S; 4-F-Ph; H; Me; S; 2-Methyltetrazol-5-yl; Ph]; [1103; S; Ph; H; Me; S; 2-Oxazolyl; Ph]; [1104; S; 4-F-Ph; H; Me; S; 2-Oxazolyl; Ph]; [1105; S; Ph; H; Me; S; 2-Thiazolyl; Ph]; [1106; S; 4-F-Ph; H; Me; S; 2-Thiazolyl; Ph]; [1107; S; Ph; H; Me; S; 2-Benzothiazolyl; Ph]; [1108; S; 4-F-Ph; H; Me; S; 2-Benzothiazolyl; Ph]; [1109; S; Ph; H; Me; S; 2-Quinolinyl; Ph]; [1110; S; 4-F-Ph; H; Me; S; 2-Quinolinyl; Ph]; [1111; S; Ph; H; Me; S; 5-Benzodioxolyl; Ph]; [1112; S; 4-F-Ph; H; Me; S; 5-Benzodioxolyl; Ph]; [1113; S; Ph; H; Me; S; Allyl; Ph]; [1114; S; 4-F-Ph; H; Me; S; Allyl; Ph]; [1115; S; Ph; H; Me; S; Propargyl; Ph]; [1116; S; 4-F-Ph; H; Me; S; Propargyl; Ph]; [1117; S; Ph; H; Me; S; 2,4-Hexadien-1-yl; Ph]; [1118; S; 4-F-Ph; H; Me; S; 2,4-Hexadien-1-yl; Ph]; [1119; S; Ph; H; Me; S; 2-Cyclohexen-1-yl; Ph]; [1120; S; 4-F-Ph; H; Me; S; 2-Cyclohexen-1-yl; Ph]; [1121; S; Ph; Me; H; S; Bu; Ph]; [1122; S; Ph; Me; H; S; $CH_3(CH_2)_5$; Ph]; [1123; S; Ph; Me; H; S; Isopentyl; Ph]; [1124; S; Ph; Me; H; S; Cyclopentyl; Ph]; [1125; S; Ph; Me; H; S; Cyclohexyl; Ph]; [1126; S; Ph; Me; H; S; Cyclopentylmethyl; Ph]; [1127; S; Ph; Me; H; S; Cyclohexylmethyl; Ph]; [1128; S; Ph; Me; H; S; 1-Cyclohexylethyl; Ph]; [1129; S; Ph; Me; H; S; 2-Perhydronaphthyl; Ph]; [1130; S; Ph; Me; H; S; $PhCH_2$; Ph]; [1131; S; Ph; Me; H; S; 2-F-Ph; Ph]; [1132; S; Ph; Me; H; S; 3-F-Ph; Ph]; [1133; S; Ph; Me; H; S; 4-F-Ph; Ph]; [1134; S; Ph; Me; H; S; 3-Cl-Ph; Ph]; [1135; S; Ph; Me; H; S; 4-Cl-Ph; Ph]; [1136; S; Ph; Me; H; S; 3-Me-Ph; Ph]; [1137; S; Ph; Me; H; S; 4-Me-Ph; Ph]; [1138; S; Ph; Me; H; S; 4-iPr-Ph; Ph]; [1139; S; Ph; Me; H; S; 4-$CF_3$-Ph; Ph]; [1140; S; Ph; Me; H; S; 4-MeO-Ph; Ph]; [1141; S; Ph; Me; H; S; 4-MeS-Ph; Ph]; [1142; S; Ph; Me; H; S; 4-$F_3$CO-Ph; Ph]; [1143; S; Ph; Me; H; S; 4-PhO-Ph; Ph]; [1144; S; Ph; Me; H; S; 4-Ph-Ph; Ph]; [1145; S; Ph; Me; H; S; 4-NC-Ph; Ph]; [1146; S; Ph; Me; H; S; 4-$O_2$N-Ph; Ph]; [1147; S; Ph; Me; H; S; 4-MeOOC-Ph; Ph]; [1148; S; Ph; Me; H; S; 1-Naphthyl; Ph]; [1149; S; Ph; Me; H; S; 2-Naphthyl; Ph]; [1150; S; Ph; Me; H; S; 5-Indanyl; Ph]; [1151; S; Ph; Me; H; S; 2-Pyridyl; Ph]; [1152; S; Ph; Me; H; S; 2-Pyrimidinyl; Ph]; [1153; S; Ph; Me; H; S; 2-Thienyl; Ph]; [1154; S; Ph; Me; H; S; 3-Thienyl; Ph]; [1155; S; Ph; Me; H; S; 2-Furyl; Ph]; [1156; S; Ph; Me; H; S; 3-Furyl; Ph]; [1157; S; Ph; Me; H; S; 2-Thiazolyl; Ph]; [1158; S; Ph; Me; H; S; 2-Benzothiazolyl; Ph]; [1159; S; Ph; Me; H; S; 5-Benzodioxolyl; Ph]; [1160; S; Ph; Me; H; S; 2-Quinolinyl; Ph]; [1161; S; Ph; Ph; H; S; Bu; Ph]; [1162; S; Ph; Ph; H; S; $CH_3(CH_2)_5$; Ph]; [1163; S; Ph; Ph; H; S; Isopentyl; Ph]; [1164; S; Ph; Ph; H; S; Cyclopentyl; Ph]; [1165; S; Ph; Ph; H; S; Cyclohexyl; Ph]; [1166; S; Ph; Ph; H; S; Cyclopentylmethyl; Ph]; [1167; S; Ph; Ph; H; S; Cyclohexylmethyl; Ph]; [1168; S; Ph; Ph; H; S; 1-Cyclohexylethyl; Ph]; [1169; S; Ph; Ph; H; S; 2-Perhydronaphthyl; Ph]; [1170; S; Ph; Ph; H; S; $PhCH_2$; Ph]; [1171; S; Ph; Ph; H; S; 2-F-Ph; Ph]; [1172; S; Ph; Ph; H; S; 3-F-Ph; Ph]; [1173; S; Ph; Ph; H; S; 4-F-Ph; Ph]; [1174; S; Ph; Ph; H; S; 3-Cl-Ph; Ph]; [1175; S; Ph; Ph; H; S; 4-Cl-Ph; Ph]; [1176; S; Ph; Ph; H; S; 3-Me-Ph; Ph]; [1177; S; Ph; Ph; H; S; 4-Me-Ph; Ph]; [1178; S; Ph; Ph; H; S; 4-iPr-Ph; Ph]; [1179; S; Ph; Ph; H; S; 4-$CF_3$-Ph; Ph]; [1180; S; Ph; Ph; H; S; 4-MeO-Ph; Ph]; [1181; S; Ph; Ph; H; S; 4-MeS-Ph; Ph]; [1182; S; Ph; Ph; H; S; 4-$F_3$CO-Ph;

Ph]; [1183; S; Ph; Ph; H; S; 4-PhO-Ph; Ph]; [1184; S; Ph; Ph; H; S; 4-Ph-Ph; Ph]; [1185; S; Ph; Ph; H; S; 4-NC-Ph; Ph]; [1186; S; Ph; Ph; H; S; 4-O$_2$N-Ph; Ph]; [1187; S; Ph; Ph; H; S; 4-MeOOC-Ph; Ph]; [1188; S; Ph; Ph; H; S; 1-Naphthyl; Ph]; [1189; S; Ph; Ph; H; S; 2-Naphthyl; Ph]; [1190; S; Ph; Ph; H; S; 5-Indanyl; Ph]; [1191; S; Ph; Ph; H; S; 2-Pyridyl; Ph]; [1192; S; Ph; Ph; H; S; 2-Pyrimidinyl; Ph]; [1193; S; Ph; Ph; H; S; 2-Thienyl; Ph]; [1194; S; Ph; Ph; H; S; 3-Thienyl; Ph]; [1195; S; Ph; Ph; H; S; 2-Furyl; Ph]; [1196; S; Ph; Ph; H; S; 3-Furyl; Ph]; [1197; S; Ph; Ph; H; S; 2-Thiazolyl; Ph]; [1198; S; Ph; Ph; H; S; 2-Benzothiazolyl; Ph]; [1199; S; Ph; Ph; H; S; 5-Benzodioxolyl; Ph]; [1200; S; Ph; Ph; H; S; 2-Quinolinyl; Ph]; [1201; S; Ph; PhS; H; S; Bu; Ph]; [1202; S; Ph; PhS; H; S; CH$_3$(CH$_2$)$_5$; Ph]; [1203; S; Ph; PhS; H; S; Isopentyl; Ph]; [1204; S; Ph; PhS; H; S; Cyclopentyl; Ph]; [1205; S; Ph; PhS; H; S; Cyclohexyl; Ph]; [1206; S; Ph; PhS; H; S; Cyclopentylmethyl; Ph]; [1207; S; Ph; PhS; H; S; Cyclohexylmethyl; Ph]; [1208; S; Ph; PhS; H; S; 1-Cyclohexylethyl; Ph]; [1209; S; Ph; PhS; H; S; 2-Perhydronaphthyl; Ph]; [1210; S; Ph; PhS; H; S; PhCH$_2$; Ph]; [1211; S; Ph; PhS; H; S; 2-F-Ph; Ph]; [1212; S; Ph; PhS; H; S; 3-F-Ph; Ph]; [1213; S; Ph; PhS; H; S; 4-F-Ph; Ph]; [1214; S; Ph; PhS; H; S; 3-Cl-Ph; Ph]; [1215; S; Ph; PhS; H; S; 4-Cl-Ph; Ph]; [1216; S; Ph; PhS; H; S; 3-Me-Ph]; [1217; S; Ph; PhS; H; S; 4-Me-Ph; Ph]; [1218; S; Ph; PhS; H; S; 4-iPr-Ph; Ph]; [1219; S; Ph; PhS; H; S; 4-CF$_3$-Ph; Ph]; [1220; S; Ph; PhS; H; S; 4-MeO-Ph; Ph]; [1221; S; Ph; PhS; H; S; 4-MeS-Ph; Ph]; [1222; S; Ph; PhS; H; S; 4-F$_3$CO-Ph; Ph]; [1223; S; Ph; PhS; H; S; 4-PhO-Ph; Ph]; [1224; S; Ph; PhS; H; S; 4-Ph-Ph; Ph]; [1225; S; Ph; PhS; H; S; 4-NC-Ph; Ph]; [1226; S; Ph; PhS; H; S; 4-O$_2$N-Ph; Ph]; [1227; S; Ph; PhS; H; S; 4-MeOOC-Ph; Ph]; [1228; S; Ph; PhS; H; S; 1-Naphthyl; Ph]; [1229; S; Ph; PhS; H; S; 2-Naphthyl; Ph]; [1230; S; Ph; PhS; H; S; 5-Indanyl; Ph]; [1231; S; Ph; PhS; H; S; 2-Pyridyl; Ph]; [1232; S; Ph; PhS; H; S; 2-Pyrimidinyl; Ph]; [1233; S; Ph; PhS; H; S; 2-Thienyl; Ph]; [1234; S; Ph; PhS; H; S; 3-Thienyl; Ph]; [1235; S; Ph; PhS; H; S; 2-Furyl; Ph]; [1236; S; Ph; PhS; H; S; 3-Furyl; Ph]; [1237; S; Ph; PhS; H; S; 2-Thiazolyl; Ph]; [1238; S; Ph; PhS; H; S; 2-Benzothiazolyl; Ph]; [1239; S; Ph; PhS; H; S; 5-Benzodioxolyl; Ph]; [1240; S; Ph; PhS; H; S; 2-Quinolinyl; Ph]; [1241; S; Ph; H; Me; S; Ph; Cyclopropyl]; [1242; S; Ph; H; Me; S; Ph; Cyclobutyl]; [1243; S; Ph; H; Me; S; Ph; Cyclopentyl]; [1244; S; Ph; H; Me; S; Ph; Cyclohexyl]; [1245; S; Ph; H; Me; S; Ph; Cycloheptyl]; [1246; S; Ph; H; Me; S; Ph; 2-Cyclohexen-1-yl]; [1247; S; Ph; H; Me; S; Ph; 1-Perhydronaphthyl]; [1248; S; Ph; H; Me; S; Ph; 2-Perhydronaphthyl]; [1249; S; Ph; H; Me; S; Ph; 2-F-Ph]; [1250; S; Ph; H; Me; S; Ph; 3-F-Ph]; [1251; S; Ph; H; Me; S; Ph; 4-F-Ph]; [1252; S; Ph; H; Me; S; Ph; 2-Cl-Ph]; [1253; S; Ph; H; Me; S; Ph; 3-Cl-Ph]; [1254; S; Ph; H; Me; S; Ph; 4-Cl-Ph]; [1255; S; Ph; H; Me; S; Ph; 2-Me-Ph]; [1256; S; Ph; H; Me; S; Ph; 3-Me-Ph]; [1257; S; Ph; H; Me; S; Ph; 4-Me-Ph]; [1258; S; Ph; H; Me; S; Ph; 4-iPr-Ph]; [1259; S; Ph; H; Me; S; Ph; 4-CF$_3$-Ph]; [1260; S; Ph; H; Me; S; Ph; 4-MeO-Ph]; [1261; S; Ph; H; Me; S; Ph; 4-MeS-Ph]; [1262; S; Ph; H; Me; S; Ph; 4-F$_3$CO-Ph]; [1263; S; Ph; H; Me; S; Ph; 4-PhO-Ph]; [1264; S; Ph; H; Me; S; Ph; 4-Ph-Ph]; [1265; S; Ph; H; Me; S; Ph; 4-NC-Ph]; [1266; S; Ph; H; Me; S; Ph; 4-O$_2$N-Ph]; [1267; S; Ph; H; Me; S; Ph; 4-MeOOC-Ph]; [1268; S; Ph; H; Me; S; Ph; 1-Naphthyl]; [1269; S; Ph; H; Me; S; Ph; 2-Naphthyl]; [1270; S; Ph; H; Me; S; Ph; 5-Indanyl]; [1271; S; Ph; H; Me; S; Ph; 2-Pyridyl]; [1272; S; Ph; H; Me; S; Ph; 2-Pyrimidinyl]; [1273; S; Ph; H; Me; S; Ph; 2-Thienyl]; [1274; S; Ph; H; Me; S; Ph; 3-Thienyl]; [1275; S; Ph; H; Me; S; Ph; 2-Furyl]; [1276; S; Ph; H; Me; S; Ph; 3-Furyl]; [1277; S; Ph; H; Me; S; Ph; 2-Thiazolyl]; [1278; S; Ph; H; Me; S; Ph; 2-Benzothiazolyl]; [1279; S; Ph; H; Me; S; Ph; 5-Benzodioxolyl]; [1280; S; Ph; H; Me; S; Ph; 2-Quinolinyl]; [1281; S; Ph; H; Ph; S; Ph; Cyclopropyl]; [1282; S; Ph; H; Ph; S; Ph; Cyclobutyl]; [1283; S; Ph; H; Ph; S; Ph; Cyclopentyl]; [1284; S; Ph; H; Ph; S; Ph; Cyclohexyl]; [1285; S; Ph; H; Ph; S; Ph; Cycloheptyl]; [1286; S; Ph; H; Ph; S; Ph; 2-Cyclohexen-1-yl]; [1287; S; Ph; H; Ph; S; Ph; 1-Perhydronaphthyl]; [1288; S; Ph; H; Ph; S; Ph; 2-Perhydronaphthyl]; [1289; S; Ph; H; Ph; S; Ph; 2-F-Ph]; [1290; S; Ph; H; Ph; S; Ph; 3-F-Ph]; [1291; S; Ph; H; Ph; S; Ph; 4-F-Ph]; [1292; S; Ph; H; Ph; S; Ph; 2-Cl-Ph]; [1293; S; Ph; H; Ph; S; Ph; 3-Cl-Ph]; [1294; S; Ph; H; Ph; S; Ph; 4-Cl-Ph]; [1295; S; Ph; H; Ph; S; Ph; 2-Me-Ph]; [1296; S; Ph; H; Ph; S; Ph; 3-Me-Ph]; [1297; S; Ph; H; Ph; S; Ph; 4-Me-Ph]; [1298; S; Ph; H; Ph; S; Ph; 4-iPr-Ph]; [1299; S; Ph; H; Ph; S; Ph; 4-CF$_3$-Ph]; [1300; S; Ph; H; Ph; S; Ph; 4-MeO-Ph]; [1301; S; Ph; H; Ph; S; Ph; 4-MeS-Ph]; [1302; S; Ph; H; Ph; S; Ph; 4-F$_3$CO-Ph]; [1303; S; Ph; H; Ph; S; Ph; 4-PhO-Ph]; [1304; S; Ph; H; Ph; S; Ph; 4-Ph-Ph]; [1305; S; Ph; H; Ph; S; Ph; 4-NC-Ph]; [1306; S; Ph; H; Ph; S; Ph; 4-O$_2$N-Ph]; [1307; S; Ph; H; Ph; S; Ph; 4-MeOOC-Ph]; [1308; S; Ph; H; Ph; S; Ph; 1-Naphthyl]; [1309; S; Ph; H; Ph; S; Ph; 2-Naphthyl]; [1310; S; Ph; H; Ph; S; Ph; 5-Indanyl]; [1311; S; Ph; H; Ph; S; Ph; 2-Pyridyl]; [1312; S; Ph; H; Ph; S; Ph; 2-Pyrimidinyl]; [1313; S; Ph; H; Ph; S; Ph; 2-Thienyl]; [1314; S; Ph; H; Ph; S; Ph; 3-Thienyl]; [1315; S; Ph; H; Ph; S; Ph; 2-Furyl]; [1316; S; Ph; H; Ph; S; Ph; 3-Furyl]; [1317; S; Ph; H; Ph; S; Ph; 2-Thiazolyl]; [1318; S; Ph; H; Ph; S; Ph; 2-Benzothiazolyl]; [1319; S; Ph; H; Ph; S; Ph; 5-Benzodioxolyl]; [1320; S; Ph; H; Ph; S; Ph; 2-Quinolinyl]; [1321; S; Ph; Me; H; S; Ph; Cyclopropyl]; [1322; S; Ph; Me; H; S; Ph; Cyclobutyl]; [1323; S; Ph; Me; H; S; Ph; Cyclopentyl]; [1324; S; Ph; Me; H; S; Ph; Cyclohexyl]; [1325; S; Ph; Me; H; S; Ph; Cycloheptyl]; [1326; S; Ph; Me; H; S; Ph; 2-Cyclohexen-1-yl]; [1327; S; Ph; Me; H; S; Ph; 1-Perhydronaphthyl]; [1328; S; Ph; Me; H; S; Ph; 2-Perhydronaphthyl]; [1329; S; Ph; Me; H; S; Ph; 2-F-Ph]; [1330; S; Ph; Me; H; S; Ph; 3-F-Ph]; [1331; S; Ph; Me; H; S; Ph; 4-F-Ph]; [1332; S; Ph; Me; H; S; Ph; 2-Cl-Ph]; [1333; S; Ph; Me; H; S; Ph; 3-Cl-Ph]; [1334; S; Ph; Me; H; S; Ph; 4-Cl-Ph]; [1335; S; Ph; Me; H; S; Ph; 2-Me-Ph]; [1336; S; Ph; Me; H; S; Ph; 3-Me-Ph]; [1337; S; Ph; Me; H; S; Ph; 4-Me-Ph]; [1338; S; Ph; Me; H; S; Ph; 4-iPr-Ph]; [1339; S; Ph; Me; H; S; Ph; 4-CF$_3$-Ph]; [1340; S; Ph; Me; H; S; Ph; 4-MeO-Ph]; [1341; S; Ph; Me; H; S; Ph; 4-MeS-Ph]; [1342; S; Ph; Me; H; S; Ph; 4-F$_3$CO-Ph]; [1343; S; Ph; Me; H; S; Ph; 4-PhO-Ph]; [1344; S; Ph; Me; H; S; Ph; 4-Ph-Ph]; [1345; S; Ph; Me; H; S; Ph; 4-NC-Ph]; [1346; S; Ph; Me; H; S; Ph; 4-O$_2$N-Ph]; [1347; S; Ph; Me; H; S; Ph; 4-MeOOC-Ph]; [1348; S; Ph; Me; H; S; Ph; 1-Naphthyl]; [1349; S; Ph; Me; H; S; Ph; 2-Naphthyl]; [1350; S; Ph; Me; H; S; Ph; 5-Indanyl]; [1351; S; Ph; Me; H; S; Ph; 2-Pyridyl]; [1352; S; Ph; Me; H; S; Ph; 2-Pyrimidinyl]; [1353; S; Ph; Me; H; S; Ph; 2-Thienyl]; [1354; S; Ph; Me; H; S; Ph; 3-Thienyl]; [1355; S; Ph; Me; H; S; Ph; 2-Furyl]; [1356; S; Ph; Me; H; S; Ph; 3-Furyl]; [1357; S; Ph; Me; H; S; Ph; 2-Thiazolyl]; [1358; S; Ph; Me; H; S; Ph; 2-Benzothiazolyl]; [1359; S; Ph; Me; H; S; Ph; 5-Benzodioxolyl]; [1360; S; Ph; Me; H; S; Ph; 2-Quinolinyl]; [1361; S; Ph; Ph; H; S; Ph; Cyclopropyl]; [1362; S; Ph; Ph; H; S; Ph; Cyclobutyl]; [1363; S; Ph; Ph; H; S; Ph; Cyclopentyl]; [1364; S; Ph; Ph; H; S; Ph; Cyclohexyl]; [1365; S; Ph; Ph; H; S; Ph; Cycloheptyl]; [1366; S; Ph; Ph; H; S; Ph; 2-Cyclohexen-1-yl]; [1367; S; Ph; Ph; H; S; Ph; 1-Perhydronaphthyl]; [1368; S; Ph; Ph; H; S; Ph; 2-Perhydronaphthyl]; [1369; S; Ph; Ph; H; S; Ph; 2-F-Ph]; [1370; S; Ph; Ph; H; S; Ph; 3-F-Ph]; [1371; S; Ph; Ph; H; S; Ph; 4-F-Ph]; [1372; S; Ph; Ph; H; S; Ph; 2-Cl-Ph]; [1373; S; Ph; Ph; H; S; Ph; 3-Cl-Ph]; [1374; S; Ph; Ph; H; S; Ph; 4-Cl-Ph]; [1375; S; Ph; Ph; H; S; Ph; 2-Me-Ph]; [1376; S; Ph; Ph; H; S; Ph; 3-Me-Ph]; [1377; S; Ph; Ph; H; S; Ph; 4-Me-Ph]; [1378; S; Ph; Ph; H; S;

Ph; 4-iPr-Ph]; [1379; S; Ph; Ph; H; S; Ph; 4-CF₃-Ph]; [1380; S; Ph; Ph; H; S; Ph; 4-MeO-Ph]; [1381; S; Ph; Ph; H; S; Ph; 4-MeS-Ph]; [1382; S; Ph; Ph; H; S; Ph; 4-F₃CO-Ph]; [1383; S; Ph; Ph; H; S; Ph; 4-PhO-Ph]; [1384; S; Ph; Ph; H; S; Ph; 4-Ph-Ph]; [1385; S; Ph; Ph; H; S; Ph; 4-NC-Ph]; [1386; S; Ph; Ph; H; S; Ph; 4-O₂N-Ph]; [1387; S; Ph; Ph; H; S; Ph; 4-MeOOC-Ph]; [1388; S; Ph; Ph; H; S; Ph; 1-Naphthyl]; [1389; S; Ph; Ph; H; S; Ph; 2-Naphthyl]; [1390; S; Ph; Ph; H; S; Ph; 5-Indanyl]; [1391; S; Ph; Ph; H; S; Ph; 2-Pyridyl]; [1392; S; Ph; Ph; H; S; Ph; 2-Pyrimidinyl]; [1393; S; Ph; Ph; H; S; Ph; 2-Thienyl]; [1394; S; Ph; Ph; H; S; Ph; 3-Thienyl]; [1395; S; Ph; Ph; H; S; Ph; 2-Furyl]; [1396; S; Ph; Ph; H; S; Ph; 3-Furyl]; [1397; S; Ph; Ph; H; S; Ph; 2-Thiazolyl]; [1398; S; Ph; Ph; H; S; Ph; 2-Benzothiazolyl]; [1399; S; Ph; Ph; H; S; Ph; 5-Benzodioxolyl]; [1400; S; Ph; Ph; H; S; Ph; 2-Quinolinyl]; [1401; S; 4-F-Ph; H; Me; S; Ph; Cyclopropyl]; [1402; S; 4-F-Ph; H; Me; S; Ph; Cyclobutyl]; [1403; S; 4-F-Ph; H; Me; S; Ph; Cyclopentyl]; [1404; S; 4-F-Ph; H; Me; S; Ph; Cyclohexyl]; [1405; S; 4-F-Ph; H; Me; S; Ph; Cycloheptyl]; [1406; S; 4-F-Ph; H; Me; S; Ph; 2-Cyclohexen-1-yl]; [1407; S; 4-F-Ph; H; Me; S; Ph; 1-Perhydronaphthyl]; [1408; S; 4-F-Ph; H; Me; S; Ph; 2-Perhydronaphthyl]; [1409; S; 4-F-Ph; H; Me; S; Ph; 2-F-Ph]; [1410; S; 4-F-Ph; H; Me; S; Ph; 3-F-Ph]; [1411; S; 4-F-Ph; H; Me; S; Ph; 4-F-Ph]; [1412; S; 4-F-Ph; H; Me; S; Ph; 2-Cl-Ph]; [1413; S; 4-F-Ph; H; Me; S; Ph; 3-Cl-Ph]; [1414; S; 4-F-Ph; H; Me; S; Ph; 4-Cl-Ph]; [1415; S; 4-F-Ph; H; Me; S; Ph; 2-Me-Ph]; [1416; S; 4-F-Ph; H; Me; S; Ph; 3-Me-Ph]; [1417; S; 4-F-Ph; H; Me; S; Ph; 4-Me-Ph]; [1418; S; 4-F-Ph; H; Me; S; Ph; 4-iPr-Ph]; [1419; S; 4-F-Ph; H; Me; S; Ph; 4-CF₃-Ph]; [1420; S; 4-F-Ph; H; Me; S; Ph; 4-MeO-Ph]; [1421; S; 4-F-Ph; H; Me; S; Ph; 4-MeS-Ph]; [1422; S; 4-F-Ph; H; Me; S; Ph; 4-F₃CO-Ph]; [1423; S; 4-F-Ph; H; Me; S; Ph; 4-PhO-Ph]; [1424; S; 4-F-Ph; H; Me; S; Ph; 4-Ph-Ph]; [1425; S; 4-F-Ph; H; Me; S; Ph; 4-NC-Ph]; [1426; S; 4-F-Ph; H; Me; S; Ph; 4-O₂N-Ph]; [1427; S; 4-F-Ph; H; Me; S; Ph; 4-MeOOC-Ph]; [1428; S; 4-F-Ph; H; Me; S; Ph; 1-Naphthyl]; [1429; S; 4-F-Ph; H; Me; S; Ph; 2-Naphthyl]; [1430; S; 4-F-Ph; H; Me; S; Ph; 5-Indanyl]; [1431; S; 4-F-Ph; H; Me; S; Ph; 2-Pyridyl]; [1432; S; 4-F-Ph; H; Me; S; Ph; 2-Pyrimidinyl]; [1433; S; 4-F-Ph; H; Me; S; Ph; 2-Thienyl]; [1434; S; 4-F-Ph; H; Me; S; Ph; 3-Thienyl]; [1435; S; 4-F-Ph; H; Me; S; Ph; 2-Furyl]; [1436; S; 4-F-Ph; H; Me; S; Ph; 3-Furyl]; [1437; S; 4-F-Ph; H; Me; S; Ph; 2-Thiazolyl]; [1438; S; 4-F-Ph; H; Me; S; Ph; 2-Benzothiazolyl]; [1439; S; 4-F-Ph; H; Me; S; Ph; 5-Benzodioxolyl]; [1440; S; 4-F-Ph; H; Me; S; Ph; 2-Quinolinyl]; [1441; S; 3-F-Ph; H; Me; S; Ph; 2-F-Ph]; [1442; S; 3-F-Ph; H; Me; S; Ph; 3-F-Ph]; [1443; S; 3-F-Ph; H; Me; S; Ph; 4-F-Ph]; [1444; S; 3-F-Ph; H; Me; S; Ph; 4-Cl-Ph]; [1445; S; 3-F-Ph; H; Me; S; Ph; 3-Me-Ph]; [1446; S; 3-F-Ph; H; Me; S; Ph; 4-Me-Ph]; [1447; S; 3-F-Ph; H; Me; S; Ph; 4-iPr-Ph]; [1448; S; 3-F-Ph; H; Me; S; Ph; 4-Ph-Ph]; [1449; S; 3-F-Ph; H; Me; S; Ph; 2-Naphthyl]; [1450; S; 3-F-Ph; H; Me; S; Ph; 5-Indanyl]; [1451; S; 3-Cl-Ph; H; Me; S; Ph; 2-F-Ph]; [1452; S; 3-Cl-Ph; H; Me; S; Ph; 3-F-Ph]; [1453; S; 3-Cl-Ph; H; Me; S; Ph; 4-F-Ph]; [1454; S; 3-Cl-Ph; H; Me; S; Ph; 4-Cl-Ph]; [1455; S; 3-Cl-Ph; H; Me; S; Ph; 3-Me-Ph]; [1456; S; 3-Cl-Ph; H; Me; S; Ph; 4-Me-Ph]; [1457; S; 3-Cl-Ph; H; Me; S; Ph; 4-iPr-Ph]; [1458; S; 3-Cl-Ph; H; Me; S; Ph; 4-Ph-Ph]; [1459; S; 3-Cl-Ph; H; Me; S; Ph; 2-Naphthyl]; [1460; S; 3-Cl-Ph; H; Me; S; Ph; 5-Indanyl]; [1461; S; 4-Cl-Ph; H; Me; S; Ph; 2-F-Ph]; [1462; S; 4-Cl-Ph; H; Me; S; Ph; 3-F-Ph]; [1463; S; 4-Cl-Ph; H; Me; S; Ph; 4-F-Ph]; [1464; S; 4-Cl-Ph; H; Me; S; Ph; 4-Cl-Ph]; [1465; S; 4-Cl-Ph; H; Me; S; Ph; 3-Me-Ph]; [1466; S; 4-Cl-Ph; H; Me; S; Ph; 4-Me-Ph]; [1467; S; 4-Cl-Ph; H; Me; S; Ph; 4-iPr-Ph]; [1468; S; 4-Cl-Ph; H; Me; S; Ph; 4-Ph-Ph]; [1469; S; 4-Cl-Ph; H; Me; S; Ph; 2-Naphthyl]; [1470; S; 4-Cl-Ph; H; Me; S; Ph; 5-Indanyl]; [1471; S; 3-Me-Ph; H; Me; S; Ph; 2-F-Ph]; [1472; S; 3-Me-Ph; H; Me; S; Ph; 3-F-Ph]; [1473; S; 3-Me-Ph; H; Me; S; Ph; 4-F-Ph]; [1474; S; 3-Me-Ph; H; Me; S; Ph; 4-Cl-Ph]; [1475; S; 3-Me-Ph; H; Me; S; Ph; 3-Me-Ph]; [1476; S; 3-Me-Ph; H; Me; S; Ph; 4-Me-Ph]; [1477; S; 3-Me-Ph; H; Me; S; Ph; 4-iPr-Ph]; [1478; S; 3-Me-Ph; H; Me; S; Ph; 4-Ph-Ph]; [1479; S; 3-Me-Ph; H; Me; S; Ph; 2-Naphthyl]; [1480; S; 3-Me-Ph; H; Me; S; Ph; 5-Indanyl]; [1481; S; 4-Me-Ph; H; Me; S; Ph; 2-F-Ph]; [1482; S; 4-Me-Ph; H; Me; S; Ph; 3-F-Ph]; [1483; S; 4-Me-Ph; H; Me; S; Ph; 4-F-Ph]; [1484; S; 4-Me-Ph; H; Me; S; Ph; 4-Cl-Ph]; [1485; S; 4-Me-Ph; H; Me; S; Ph; 3-Me-Ph]; [1486; S; 4-Me-Ph; H; Me; S; Ph; 4-Me-Ph]; [1487; S; 4-Me-Ph; H; Me; S; Ph; 4-iPr-Ph]; [1488; S; 4-Me-Ph; H; Me; S; Ph; 4-Ph-Ph]; [1489; S; 4-Me-Ph; H; Me; S; Ph; 2-Naphthyl]; [1490; S; 4-Me-Ph; H; Me; S; Ph; 5-Indanyl]; [1491; S; 4-iPr-Ph; H; Me; S; Ph; 2-F-Ph]; [1492; S; 4-iPr-Ph; H; Me; S; Ph; 3-F-Ph]; [1493; S; 4-iPr-Ph; H; Me; S; Ph; 4-F-Ph]; [1494; S; 4-iPr-Ph; H; Me; S; Ph; 4-Cl-Ph]; [1495; S; 4-iPr-Ph; H; Me; S; Ph; 3-Me-Ph]; [1496; S; 4-iPr-Ph; H; Me; S; Ph; 4-Me-Ph]; [1497; S; 4-iPr-Ph; H; Me; S; Ph; 4-iPr-Ph]; [1498; S; 4-iPr-Ph; H; Me; S; Ph; 4-Ph-Ph]; [1499; S; 4-iPr-Ph; H; Me; S; Ph; 2-Naphthyl]; [1500; S; 4-iPr-Ph; H; Me; S; Ph; 5-Indanyl]; [1501; S; 5-Indanyl; H; Me; S; Ph; 2-F-Ph]; [1502; S; 5-Indanyl; H; Me; S; Ph; 3-F-Ph]; [1503; S; 5-Indanyl; H; Me; S; Ph; 4-F-Ph]; [1504; S; 5-Indanyl; H; Me; S; Ph; 4-Cl-Ph]; [1505; S; 5-Indanyl; H; Me; S; Ph; 3-Me-Ph]; [1506; S; 5-Indanyl; H; Me; S; Ph; 4-Me-Ph]; [1507; S; 5-Indanyl; H; Me; S; Ph; 4-iPr-Ph]; [1508; S; 5-Indanyl; H; Me; S; Ph; 4-Ph-Ph]; [1509; S; 5-Indanyl; H; Me; S; Ph; 2-Naphthyl]; [1510; S; 5-Indanyl; H; Me; S; Ph; 5-Indanyl]; [1511; S; 2-Naphthyl; H; Me; S; Ph; 2-F-Ph]; [1512; S; 2-Naphthyl; H; Me; S; Ph; 3-F-Ph]; [1513; S; 2-Naphthyl; H; Me; S; Ph; 4-F-Ph]; [1514; S; 2-Naphthyl; H; Me; S; Ph; 4-Cl-Ph]; [1515; S; 2-Naphthyl; H; Me; S; Ph; 3-Me-Ph]; [1516; S; 2-Naphthyl; H; Me; S; Ph; 4-Me-Ph]; [1517; S; 2-Naphthyl; H; Me; S; Ph; 4-iPr-Ph]; [1518; S; 2-Naphthyl; H; Me; S; Ph; 4-Ph-Ph]; [1519; S; 2-Naphthyl; H; Me; S; Ph; 2-Naphthyl]; [1520; S; 2-Naphthyl; H; Me; S; Ph; 5-Indanyl]; [1521; S; 5-Benzodioxolyl; H; Me; S; Ph; 2-F-Ph]; [1522; S; 5-Benzodioxolyl; H; Me; S; Ph; 3-F-Ph]; [1523; S; 5-Benzodioxolyl; H; Me; S; Ph; 4-F-Ph]; [1524; S; 5-Benzodioxolyl; H; Me; S; Ph; 4-Cl-Ph]; [1525; S; 5-Benzodioxolyl; H; Me; S; Ph; 3-Me-Ph]; [1526; S; 5-Benzodioxolyl; H; Me; S; Ph; 4-Me-Ph]; [1527; S; 5-Benzodioxolyl; H; Me; S; Ph; 4-iPr-Ph]; [1528; S; 5-Benzodioxolyl; H; Me; S; Ph; 4-Ph-Ph]; [1529; S; 5-Benzodioxolyl; H; Me; S; Ph; 2-Naphthyl]; [1530; S; 5-Benzodioxolyl; H; Me; S; Ph; 5-Indanyl]; [1531; S; 3-F-Ph; Me; H; S; Ph; 2-F-Ph]; [1532; S; 3-F-Ph; Me; H; S; Ph; 3-F-Ph]; [1533; S; 3-F-Ph; Me; H; S; Ph; 4-F-Ph]; [1534; S; 3-F-Ph; Me; H; S; Ph; 4-Cl-Ph]; [1535; S; 3-F-Ph; Me; H; S; Ph; 3-Me-Ph]; [1536; S; 3-F-Ph; Me; H; S; Ph; 4-Me-Ph]; [1537; S; 3-F-Ph; Me; H; S; Ph; 4-iPr-Ph]; [1538; S; 3-F-Ph; Me; H; S; Ph; 4-Ph-Ph]; [1539; S; 3-F-Ph; Me; H; S; Ph; 2-Naphthyl]; [1540; S; 3-F-Ph; Me; H; S; Ph; 5-Indanyl]; [1541; S; 4-F-Ph; Me; H; S; Ph; 2-F-Ph]; [1542; S; 4-F-Ph; Me; H; S; Ph; 3-F-Ph]; [1543; S; 4-F-Ph; Me; H; S; Ph; 4-F-Ph]; [1544; S; 4-F-Ph; Me; H; S; Ph; 4-Cl-Ph]; [1545; S; 4-F-Ph; Me; H; S; Ph; 3-Me-Ph]; [1546; S; 4-F-Ph; Me; H; S; Ph; 4-Me-Ph]; [1547; S; 4-F-Ph; Me; H; S; Ph; 4-iPr-Ph]; [1548; S; 4-F-Ph; Me; H; S; Ph; 4-Ph-Ph]; [1549; S; 4-F-Ph; Me; H; S; Ph; 2-Naphthyl]; [1550; S; 4-F-Ph; Me; H; S; Ph; 5-Indanyl]; [1551; S; 3-Cl-Ph; Me; H; S; Ph; 2-F-Ph]; [1552; S; 3-Cl-Ph; Me; H; S; Ph; 3-F-Ph]; [1553; S; 3-Cl-Ph; Me; H; S; Ph; 4-F-Ph]; [1554; S; 3-Cl-Ph; Me; H; S; Ph; 4-Cl-Ph]; [1555; S; 3-Cl-Ph; Me; H; S; Ph; 3-Me-Ph]; [1556; S; 3-Cl-Ph; Me; H; S; Ph; 4-Me-Ph]; [1557; S; 3-Cl-Ph; Me; H; S; Ph; 4-iPr-Ph]; [1558; S; 3-Cl-Ph; Me; H; S; Ph; 4-Ph-Ph]; [1559;

S; 3-Cl-Ph; Me; H; S; Ph; 2-Naphthyl]; [1560; S; 3-Cl-Ph; Me; H; S; Ph; 5-Indanyl]; [1561; S; 4-Cl-Ph; Me; H; S; Ph; 2-F-Ph]; [1562; S; 4-Cl-Ph; Me; H; S; Ph; 3-F-Ph]; [1563; S; 4-Cl-Ph; Me; H; S; Ph; 4-F-Ph]; [1564; S; 4-Cl-Ph; Me; H; S; Ph; 4-Cl-Ph]; [1565; S; 4-Cl-Ph; Me; H; S; Ph; 3-Me-Ph]; [1566; S; 4-Cl-Ph; Me; H; S; Ph; 4-Me-Ph]; [1567; S; 4-Cl-Ph; Me; H; S; Ph; 4-iPr-Ph]; [1568; S; 4-Cl-Ph; Me; H; S; Ph; 4-Ph-Ph]; [1569; S; 4-Cl-Ph; Me; H; S; Ph; 2-Naphthyl]; [1570; S; 4-Cl-Ph; Me; H; S; Ph; 5-Indanyl]; [1571; S; 3-Me-Ph; Me; H; S; Ph; 2-F-Ph]; [1572; S; 3-Me-Ph; Me; H; S; Ph; 3-F-Ph]; [1573; S; 3-Me-Ph; Me; H; S; Ph; 4-F-Ph]; [1574; S; 3-Me-Ph; Me; H; S; Ph; 4-Cl-Ph]; [1575; S; 3-Me-Ph; Me; H; S; Ph; 3-Me-Ph]; [1576; S; 3-Me-Ph; Me; H; S; Ph; 4-Me-Ph]; [1577; S; 3-Me-Ph; Me; H; S; Ph; 4-iPr-Ph]; [1578; S; 3-Me-Ph; Me; H; S; Ph; 4-Ph-Ph]; [1579; S; 3-Me-Ph; Me; H; S; Ph; 2-Naphthyl]; [1580; S; 3-Me-Ph; Me; H; S; Ph; 5-Indanyl]; [1581; S; 4-Me-Ph; Me; H; S; Ph; 2-F-Ph]; [1582; S; 4-Me-Ph; Me; H; S; Ph; 3-F-Ph]; [1583; S; 4-Me-Ph; Me; H; S; Ph; 4-F-Ph]; [1584; S; 4-Me-Ph; Me; H; S; Ph; 4-Cl-Ph]; [1585; S; 4-Me-Ph; Me; H; S; Ph; 3-Me-Ph]; [1586; S; 4-Me-Ph; Me; H; S; Ph; 4-Me-Ph]; [1587; S; 4-Me-Ph; Me; H; S; Ph; 4-iPr-Ph]; [1588; S; 4-Me-Ph; Me; H; S; Ph; 4-Ph-Ph]; [1589; S; 4-Me-Ph; Me; H; S; Ph; 2-Naphthyl]; [1590; S; 4-Me-Ph; Me; H; S; Ph; 5-Indanyl]; [1591; S; 4-iPr-Ph; Me; H; S; Ph; 2-F-Ph]; [1592; S; 4-iPr-Ph; Me; H; S; Ph; 3-F-Ph]; [1593; S; 4-iPr-Ph; Me; H; S; Ph; 4-F-Ph]; [1594; S; 4-iPr-Ph; Me; H; S; Ph; 4-Cl-Ph]; [1595; S; 4-iPr-Ph; Me; H; S; Ph; 3-Me-Ph]; [1596; S; 4-iPr-Ph; Me; H; S; Ph; 4-Me-Ph]; [1597; S; 4-iPr-Ph; Me; H; S; Ph; 4-iPr-Ph]; [1598; S; 4-iPr-Ph; Me; H; S; Ph; 4-Ph-Ph]; [1599; S; 4-iPr-Ph; Me; H; S; Ph; 2-Naphthyl]; [1600; S; 4-iPr-Ph; Me; H; S; Ph; 5-Indanyl]; [1601; S; 5-Indanyl; Me; H; S; Ph; 2-F-Ph]; [1602; S; 5-Indanyl; Me; H; S; Ph; 3-F-Ph]; [1603; S; 5-Indanyl; Me; H; S; Ph; 4-F-Ph]; [1604; S; 5-Indanyl; Me; H; S; Ph; 4-Cl-Ph]; [1605; S; 5-Indanyl; Me; H; S; Ph; 3-Me-Ph]; [1606; S; 5-Indanyl; Me; H; S; Ph; 4-Me-Ph]; [1607; S; 5-Indanyl; Me; H; S; Ph; 4-iPr-Ph]; [1608; S; 5-Indanyl; Me; H; S; Ph; 4-Ph-Ph]; [1609; S; 5-Indanyl; Me; H; S; Ph; 2-Naphthyl]; [1610; S; 5-Indanyl; Me; H; S; Ph; 5-Indanyl]; [1611; S; 2-Naphthyl; Me; H; S; Ph; 2-F-Ph]; [1612; S; 2-Naphthyl; Me; H; S; Ph; 3-F-Ph]; [1613; S; 2-Naphthyl; Me; H; S; Ph; 4-F-Ph]; [1614; S; 2-Naphthyl; Me; H; S; Ph; 4-Cl-Ph]; [1615; S; 2-Naphthyl; Me; H; S; Ph; 3-Me-Ph]; [1616; S; 2-Naphthyl; Me; H; S; Ph; 4-Me-Ph]; [1617; S; 2-Naphthyl; Me; H; S; Ph; 4-iPr-Ph]; [1618; S; 2-Naphthyl; Me; H; S; Ph; 4-Ph-Ph]; [1619; S; 2-Naphthyl; Me; H; S; Ph; 2-Naphthyl]; [1620; S; 2-Naphthyl; Me; H; S; Ph; 5-Indanyl]; [1621; S; 5-Benzodioxolyl; Me; H; S; Ph; 2-F-Ph]; [1622; S; 5-Benzodioxolyl; Me; H; S; Ph; 3-F-Ph]; [1623; S; 5-Benzodioxolyl; Me; H; S; Ph; 4-F-Ph]; [1624; S; 5-Benzodioxolyl; Me; H; S; Ph; 4-Cl-Ph]; [1625; S; 5-Benzodioxolyl; Me; H; S; Ph; 3-Me-Ph]; [1626; S; 5-Benzodioxolyl; Me; H; S; Ph; 4-Me-Ph]; [1627; S; 5-Benzodioxolyl; Me; H; S; Ph; 4-iPr-Ph]; [1628; S; 5-Benzodioxolyl; Me; H; S; Ph; 4-Ph-Ph]; [1629; S; 5-Benzodioxolyl; Me; H; S; Ph; 2-Naphthyl]; [1630; S; 5-Benzodioxolyl; Me; H; S; Ph; 5-Indanyl]; [1631; S; Ph; H; Me; S; Cyclohexylmethyl; 2-F-Ph]; [1632; S; Ph; H; Me; S; Cyclohexylmethyl; 3-F-Ph]; [1633; S; Ph; H; Me; S; Cyclohexylmethyl; 4-F-Ph]; [1634; S; Ph; H; Me; S; Cyclohexylmethyl; 4-Cl-Ph]; [1635; S; Ph; H; Me; S; Cyclohexylmethyl; 3-Me-Ph]; [1636; S; Ph; H; Me; S; Cyclohexylmethyl; 4-Me-Ph]; [1637; S; Ph; H; Me; S; Cyclohexylmethyl; 4-iPr-Ph]; [1638; S; Ph; H; Me; S; Cyclohexylmethyl; 4-Ph-Ph]; [1639; S; Ph; H; Me; S; Cyclohexylmethyl; 2-Naphthyl]; [1640; S; Ph; H; Me; S; Cyclohexylmethyl; 5-Indanyl]; [1641; S; Ph; H; Me; S; 2-Perhydronaphthyl; 2-F-Ph]; [1642; S; Ph; H; Me; S; 2-Perhydronaphthyl; 3-F-Ph]; [1643; S; Ph; H; Me; S; 2-Perhydronaphthyl; 4-F-Ph]; [1644; S; Ph; H; Me; S; 2-Perhydronaphthyl; 4-Cl-Ph]; [1645; S; Ph; H; Me; S; 2-Perhydronaphthyl; 3-Me-Ph]; [1646; S; Ph; H; Me; S; 2-Perhydronaphthyl; 4-Me-Ph]; [1647; S; Ph; H; Me; S; 2-Perhydronaphthyl; 4-iPr-Ph]; [1648; S; Ph; H; Me; S; 2-Perhydronaphthyl; 4-Ph-Ph]; [1649; S; Ph; H; Me; S; 2-Perhydronaphthyl; 2-Naphthyl]; [1650; S; Ph; H; Me; S; 2-Perhydronaphthyl; 5-Indanyl]; [1651; S; Ph; H; Me; S; PhCH$_2$; 2-F-Ph]; [1652; S; Ph; H; Me; S; PhCH$_2$; 3-F-Ph]; [1653; S; Ph; H; Me; S; PhCH$_2$; 4-F-Ph]; [1654; S; Ph; H; Me; S; PhCH$_2$; 4-Cl-Ph]; [1655; S; Ph; H; Me; S; PhCH$_2$; 3-Me-Ph]; [1656; S; Ph; H; Me; S; PhCH$_2$; 4-Me-Ph]; [1657; S; Ph; H; Me; S; PhCH$_2$; 4-iPr-Ph]; [1658; S; Ph; H; Me; S; PhCH$_2$; 4-Ph-Ph]; [1659; S; Ph; H; Me; S; PhCH$_2$; 2-Naphthyl]; [1660; S; Ph; H; Me; S; PhCH$_2$; 5-Indanyl]; [1661; S; Ph; H; Me; S; 4-F-Ph; 2-F-Ph]; [1662; S; Ph; H; Me; S; 4-F-Ph; 3-F-Ph]; [1663; S; Ph; H; Me; S; 4-F-Ph; 4-F-Ph]; [1664; S; Ph; H; Me; S; 4-F-Ph; 4-Cl-Ph]; [1665; S; Ph; H; Me; S; 4-F-Ph; 3-Me-Ph]; [1666; S; Ph; H; Me; S; 4-F-Ph; 4-Me-Ph]; [1667; S; Ph; H; Me; S; 4-F-Ph; 4-iPr-Ph]; [1668; S; Ph; H; Me; S; 4-F-Ph; 4-Ph-Ph]; [1669; S; Ph; H; Me; S; 4-F-Ph; 2-Naphthyl]; [1670; S; Ph; H; Me; S; 4-F-Ph; 5-Indanyl]; [1671; S; Ph; H; Me; S; 4-Me-Ph; 2-F-Ph]; [1672; S; Ph; H; Me; S; 4-Me-Ph; 3-F-Ph]; [1673; S; Ph; H; Me; S; 4-Me-Ph; 4-F-Ph]; [1674; S; Ph; H; Me; S; 4-Me-Ph; 4-Cl-Ph]; [1675; S; Ph; H; Me; S; 4-Me-Ph; 3-Me-Ph]; [1676; S; Ph; H; Me; S; 4-Me-Ph; 4-Me-Ph]; [1677; S; Ph; H; Me; S; 4-Me-Ph; 4-iPr-Ph]; [1678; S; Ph; H; Me; S; 4-Me-Ph; 4-Ph-Ph]; [1679; S; Ph; H; Me; S; 4-Me-Ph; 2-Naphthyl]; [1680; S; Ph; H; Me; S; 4-Me-Ph; 5-Indanyl]; [1681; S; Ph; H; Me; S; 4-Cl-Ph; 2-F-Ph]; [1682; S; Ph; H; Me; S; 4-Cl-Ph; 3-F-Ph]; [1683; S; Ph; H; Me; S; 4-Cl-Ph; 4-F-Ph]; [1684; S; Ph; H; Me; S; 4-Cl-Ph; 4-Cl-Ph]; [1685; S; Ph; H; Me; S; 4-Cl-Ph; 3-Me-Ph]; [1686; S; Ph; H; Me; S; 4-Cl-Ph; 4-Me-Ph]; [1687; S; Ph; H; Me; S; 4-Cl-Ph; 4-iPr-Ph]; [1688; S; Ph; H; Me; S; 4-Cl-Ph; 4-Ph-Ph]; [1689; S; Ph; H; Me; S; 4-Cl-Ph; 2-Naphthyl]; [1690; S; Ph; H; Me; S; 4-Cl-Ph; 5-Indanyl]; [1691; S; Ph; H; Me; S; 5-Indanyl; 2-F-Ph]; [1692; S; Ph; H; Me; S; 5-Indanyl; 3-F-Ph]; [1693; S; Ph; H; Me; S; 5-Indanyl; 4-F-Ph]; [1694; S; Ph; H; Me; S; 5-Indanyl; 4-Cl-Ph]; [1695; S; Ph; H; Me; S; 5-Indanyl; 3-Me-Ph]; [1696; S; Ph; H; Me; S; 5-Indanyl; 4-Me-Ph]; [1697; S; Ph; H; Me; S; 5-Indanyl; 4-iPr-Ph]; [1698; S; Ph; H; Me; S; 5-Indanyl; 4-Ph-Ph]; [1699; S; Ph; H; Me; S; 5-Indanyl; 2-Naphthyl]; [1700; S; Ph; H; Me; S; 5-Indanyl; 5-Indanyl]; [1701; S; Ph; H; Me; S; 2-Naphthyl; 2-F-Ph]; [1702; S; Ph; H; Me; S; 2-Naphthyl; 3-F-Ph]; [1703; S; Ph; H; Me; S; 2-Naphthyl; 4-F-Ph]; [1704; S; Ph; H; Me; S; 2-Naphthyl; 4-Cl-Ph]; [1705; S; Ph; H; Me; S; 2-Naphthyl; 3-Me-Ph]; [1706; S; Ph; H; Me; S; 2-Naphthyl; 4-Me-Ph]; [1707; S; Ph; H; Me; S; 2-Naphthyl; 4-iPr-Ph]; [1708; S; Ph; H; Me; S; 2-Naphthyl; 4-Ph-Ph]; [1709; S; Ph; H; Me; S; 2-Naphthyl; 2-Naphthyl]; [1710; S; Ph; H; Me; S; 2-Naphthyl; 5-Indanyl]; [1711; S; 4-F-Ph; H; Me; S; Bu; 2-F-Ph]; [1712; S; 4-F-Ph; H; Me; S; Bu; 3-F-Ph]; [1713; S; 4-F-Ph; H; Me; S; Bu; 4-F-Ph]; [1714; S; 4-F-Ph; H; Me; S; Bu; 4-Cl-Ph]; [1715; S; 4-F-Ph; H; Me; S; Bu; 3-Me-Ph]; [1716; S; 4-F-Ph; H; Me; S; Bu; 4-Me-Ph]; [1717; S; 4-F-Ph; H; Me; S; Bu; 4-iPr-Ph]; [1718; S; 4-F-Ph; H; Me; S; Bu; 4-Ph-Ph]; [1719; S; 4-F-Ph; H; Me; S; Bu; 2-Naphthyl]; [1720; S; 4-F-Ph; H; Me; S; Bu; 5-Indanyl]; [1721; S; 4-F-Ph; H; Me; S; Cyclohexylmethyl; 2-F-Ph]; [1722; S; 4-F-Ph; H; Me; S; Cyclohexylmethyl; 3-F-Ph]; [1723; S; 4-F-Ph; H; Me; S; Cyclohexylmethyl; 4-F-Ph]; [1724; S; 4-F-Ph; H; Me; S; Cyclohexylmethyl; 4-Cl-Ph]; [1725; S; 4-F-Ph; H; Me; S; Cyclohexylmethyl; 3-Me-Ph]; [1726; S; 4-F-Ph; H; Me; S; Cyclohexylmethyl; 4-Me-Ph]; [1727; S; 4-F-Ph; H; Me; S; Cyclohexylmethyl; 4-iPr-Ph]; [1728; S; 4-F-Ph; H; Me; S;

Cyclohexylmethyl; 4-Ph-Ph]; [1729; S; 4-F-Ph; H; Me; S; Cyclohexylmethyl; 2-Naphthyl]; [1730; S; 4-F-Ph; H; Me; S; Cyclohexylmethyl; 5-Indanyl]; [1731; S; 4-F-Ph; H; Me; S; 2-Perhydronaphthyl; 2-F-Ph]; [1732; S; 4-F-Ph; H; Me; S; 2-Perhydronaphthyl; 3-F-Ph]; [1733; S; 4-F-Ph; H; Me; S; 2-Perhydronaphthyl; 4-F-Ph]; [1734; S; 4-F-Ph; H; Me; S; 2-Perhydronaphthyl; 4-Cl-Ph]; [1735; S; 4-F-Ph; H; Me; S; 2-Perhydronaphthyl; 3-Me-Ph]; [1736; S; 4-F-Ph; H; Me; S; 2-Perhydronaphthyl; 4-Me-Ph]; [1737; S; 4-F-Ph; H; Me; S; 2-Perhydronaphthyl; 4-iPr-Ph]; [1738; S; 4-F-Ph; H; Me; S; 2-Perhydronaphthyl; 4-Ph-Ph]; [1739; S; 4-F-Ph; H; Me; S; 2-Perhydronaphthyl; 2-Naphthyl]; [1740; S; 4-F-Ph; H; Me; S; 2-Perhydronaphthyl; 5-Indanyl]; [1741; S; 4-F-Ph; H; Me; S; PhCH$_2$; 2-F-Ph]; [1742; S; 4-F-Ph; H; Me; S; PhCH$_2$; 3-F-Ph]; [1743; S; 4-F-Ph; H; Me; S; PhCH$_2$; 4-F-Ph]; [1744; S; 4-F-Ph; H; Me; S; PhCH$_2$; 4-Cl-Ph]; [1745; S; 4-F-Ph; H; Me; S; PhCH$_2$; 3-Me-Ph]; [1746; S; 4-F-Ph; H; Me; S; PhCH$_2$; 4-Me-Ph]; [1747; S; 4-F-Ph; H; Me; S; PhCH$_2$; 4-iPr-Ph]; [1748; S; 4-F-Ph; H; Me; S; PhCH$_2$; 4-Ph-Ph]; [1749; S; 4-F-Ph; H; Me; S; PhCH$_2$; 2-Naphthyl]; [1750; S; 4-F-Ph; H; Me; S; PhCH$_2$; 5-Indanyl]; [1751; S; 4-F-Ph; H; Me; S; 4-F-Ph; 2-F-Ph]; [1752; S; 4-F-Ph; H; Me; S; 4-F-Ph; 3-F-Ph]; [1753; S; 4-F-Ph; H; Me; S; 4-F-Ph; 4-F-Ph]; [1754; S; 4-F-Ph; H; Me; S; 4-F-Ph; 4-Cl-Ph]; [1755; S; 4-F-Ph; H; Me; S; 4-F-Ph; 3-Me-Ph]; [1756; S; 4-F-Ph; H; Me; S; 4-F-Ph; 4-Me-Ph]; [1757; S; 4-F-Ph; H; Me; S; 4-F-Ph; 4-iPr-Ph]; [1758; S; 4-F-Ph; H; Me; S; 4-F-Ph; 4-Ph-Ph]; [1759; S; 4-F-Ph; H; Me; S; 4-F-Ph; 2-Naphthyl]; [1760; S; 4-F-Ph; H; Me; S; 4-F-Ph; 5-Indanyl]; [1761; S; 4-F-Ph; H; Me; S; 4-Me-Ph; 2-F-Ph]; [1762; S; 4-F-Ph; H; Me; S; 4-Me-Ph; 3-F-Ph]; [1763; S; 4-F-Ph; H; Me; S; 4-Me-Ph; 4-F-Ph]; [1764; S; 4-F-Ph; H; Me; S; 4-Me-Ph; 4-Cl-Ph]; [1765; S; 4-F-Ph; H; Me; S; 4-Me-Ph; 3-Me-Ph]; [1766; S; 4-F-Ph; H; Me; S; 4-Me-Ph; 4-Me-Ph]; [1767; S; 4-F-Ph; H; Me; S; 4-Me-Ph; 4-iPr-Ph]; [1768; S; 4-F-Ph; H; Me; S; 4-Me-Ph; 4-Ph-Ph]; [1769; S; 4-F-Ph; H; Me; S; 4-Me-Ph; 2-Naphthyl]; [1770; S; 4-F-Ph; H; Me; S; 4-Me-Ph; 5-Indanyl]; [1771; S; 4-F-Ph; H; Me; S; 4-iPr-Ph; 2-F-Ph]; [1772; S; 4-F-Ph; H; Me; S; 4-iPr-Ph; 3-F-Ph]; [1773; S; 4-F-Ph; H; Me; S; 4-iPr-Ph; 4-F-Ph]; [1774; S; 4-F-Ph; H; Me; S; 4-iPr-Ph; 4-Cl-Ph]; [1775; S; 4-F-Ph; H; Me; S; 4-iPr-Ph; 3-Me-Ph]; [1776; S; 4-F-Ph; H; Me; S; 4-iPr-Ph; 4-Me-Ph]; [1777; S; 4-F-Ph; H; Me; S; 4-iPr-Ph; 4-iPr-Ph]; [1778; S; 4-F-Ph; H; Me; S; 4-iPr-Ph; 4-Ph-Ph]; [1779; S; 4-F-Ph; H; Me; S; 4-iPr-Ph; 2-Naphthyl]; [1780; S; 4-F-Ph; H; Me; S; 4-iPr-Ph; 5-Indanyl]; [1781; S; 4-F-Ph; H; Me; S; 2-Naphthyl; 2-F-Ph]; [1782; S; 4-F-Ph; H; Me; S; 2-Naphthyl; 3-F-Ph]; [1783; S; 4-F-Ph; H; Me; S; 2-Naphthyl; 4-F-Ph]; [1784; S; 4-F-Ph; H; Me; S; 2-Naphthyl; 4-Cl-Ph]; [1785; S; 4-F-Ph; H; Me; S; 2-Naphthyl; 3-Me-Ph]; [1786; S; 4-F-Ph; H; Me; S; 2-Naphthyl; 4-Me-Ph]; [1787; S; 4-F-Ph; H; Me; S; 2-Naphthyl; 4-iPr-Ph]; [1788; S; 4-F-Ph; H; Me; S; 2-Naphthyl; 4-Ph-Ph]; [1789; S; 4-F-Ph; H; Me; S; 2-Naphthyl; 2-Naphthyl]; [1790; S; 4-F-Ph; H; Me; S; 2-Naphthyl; 5-Indanyl]; [1791; S; 4-F-Ph; H; Me; S; 5-Indanyl; 2-F-Ph]; [1792; S; 4-F-Ph; H; Me; S; 5-Indanyl; 3-F-Ph]; [1793; S; 4-F-Ph; H; Me; S; 5-Indanyl; 4-F-Ph]; [1794; S; 4-F-Ph; H; Me; S; 5-Indanyl; 4-Cl-Ph]; [1795; S; 4-F-Ph; H; Me; S; 5-Indanyl; 3-Me-Ph]; [1796; S; 4-F-Ph; H; Me; S; 5-Indanyl; 4-Me-Ph]; [1797; S; 4-F-Ph; H; Me; S; 5-Indanyl; 4-iPr-Ph]; [1798; S; 4-F-Ph; H; Me; S; 5-Indanyl; 4-Ph-Ph]; [1799; S; 4-F-Ph; H; Me; S; 5-Indanyl; 2-Naphthyl]; [1800; S; 4-F-Ph; H; Me; S; 5-Indanyl; 5-Indanyl]; [1801; S; 4-Cl-Ph; H; Me; S; Bu; 2-F-Ph]; [1802; S; 4-Cl-Ph; H; Me; S; Bu; 3-F-Ph]; [1803; S; 4-Cl-Ph; H; Me; S; Bu; 4-F-Ph]; [1804; S; 4-Cl-Ph; H; Me; S; Bu; 4-Cl-Ph]; [1805; S; 4-Cl-Ph; H; Me; S; Bu; 3-Me-Ph]; [1806; S; 4-Cl-Ph; H; Me; S; Bu; 4-Me-Ph]; [1807; S; 4-Cl-Ph; H; Me; S; Bu; 4-iPr-Ph]; [1808; S; 4-Cl-Ph; H; Me; S; Bu; 4-Ph-Ph]; [1809; S; 4-Cl-Ph; H; Me; S; Bu; 2-Naphthyl]; [1810; S; 4-Cl-Ph; H; Me; S; Bu; 5-Indanyl]; [1811; S; 4-Cl-Ph; H; Me; S; Cyclohexylmethyl; 2-F-Ph]; [1812; S; 4-Cl-Ph; H; Me; S; Cyclohexylmethyl; 3-F-Ph]; [1813; S; 4-Cl-Ph; H; Me; S; Cyclohexylmethyl; 4-F-Ph]; [1814; S; 4-Cl-Ph; H; Me; S; Cyclohexylmethyl; 4-Cl-Ph]; [1815; S; 4-Cl-Ph; H; Me; S; Cyclohexylmethyl; 3-Me-Ph]; [1816; S; 4-Cl-Ph; H; Me; S; Cyclohexylmethyl; 4-Me-Ph]; [1817; S; 4-Cl-Ph; H; Me; S; Cyclohexylmethyl; 4-iPr-Ph]; [1818; S; 4-Cl-Ph; H; Me; S; Cyclohexylmethyl; 4-Ph-Ph]; [1819; S; 4-Cl-Ph; H; Me; S; Cyclohexylmethyl; 2-Naphthyl]; [1820; S; 4-Cl-Ph; H; Me; S; Cyclohexylmethyl; 5-Indanyl]; [1821; S; 4-Cl-Ph; H; Me; S; 2-Perhydronaphthyl; 2-F-Ph]; [1822; S; 4-Cl-Ph; H; Me; S; 2-Perhydronaphthyl; 3-F-Ph]; [1823; S; 4-Cl-Ph; H; Me; S; 2-Perhydronaphthyl; 4-F-Ph]; [1824; S; 4-Cl-Ph; H; Me; S; 2-Perhydronaphthyl; 4-Cl-Ph]; [1825; S; 4-Cl-Ph; H; Me; S; 2-Perhydronaphthyl; 3-Me-Ph]; [1826; S; 4-Cl-Ph; H; Me; S; 2-Perhydronaphthyl; 4-Me-Ph]; [1827; S; 4-Cl-Ph; H; Me; S; 2-Perhydronaphthyl; 4-iPr-Ph]; [1828; S; 4-Cl-Ph; H; Me; S; 2-Perhydronaphthyl; 4-Ph-Ph]; [1829; S; 4-Cl-Ph; H; Me; S; 2-Perhydronaphthyl; 2-Naphthyl]; [1830; S; 4-Cl-Ph; H; Me; S; 2-Perhydronaphthyl; 5-Indanyl]; [1831; S; 4-Cl-Ph; H; Me; S; PhCH$_2$; 2-F-Ph]; [1832; S; 4-Cl-Ph; H; Me; S; PhCH$_2$; 3-F-Ph]; [1833; S; 4-Cl-Ph; H; Me; S; PhCH$_2$; 4-F-Ph]; [1834; S; 4-Cl-Ph; H; Me; S; PhCH$_2$; 4-Cl-Ph]; [1835; S; 4-Cl-Ph; H; Me; S; PhCH$_2$; 3-Me-Ph]; [1836; S; 4-Cl-Ph; H; Me; S; PhCH$_2$; 4-Me-Ph]; [1837; S; 4-Cl-Ph; H; Me; S; PhCH$_2$; 4-iPr-Ph]; [1838; S; 4-Cl-Ph; H; Me; S; PhCH$_2$; 4-Ph-Ph]; [1839; S; 4-Cl-Ph; H; Me; S; PhCH$_2$; 2-Naphthyl]; [1840; S; 4-Cl-Ph; H; Me; S; PhCH$_2$; 5-Indanyl]; [1841; S; 4-Cl-Ph; H; Me; S; 4-F-Ph; 2-F-Ph]; [1842; S; 4-Cl-Ph; H; Me; S; 4-F-Ph; 3-F-Ph]; [1843; S; 4-Cl-Ph; H; Me; S; 4-F-Ph; 4-F-Ph]; [1844; S; 4-Cl-Ph; H; Me; S; 4-F-Ph; 4-Cl-Ph]; [1845; S; 4-Cl-Ph; H; Me; S; 4-F-Ph; 3-Me-Ph]; [1846; S; 4-Cl-Ph; H; Me; S; 4-F-Ph; 4-Me-Ph]; [1847; S; 4-Cl-Ph; H; Me; S; 4-F-Ph; 4-iPr-Ph]; [1848; S; 4-Cl-Ph; H; Me; S; 4-F-Ph; 4-Ph-Ph]; [1849; S; 4-Cl-Ph; H; Me; S; 4-F-Ph; 2-Naphthyl]; [1850; S; 4-Cl-Ph; H; Me; S; 4-F-Ph; 5-Indanyl]; [1851; S; 4-Cl-Ph; H; Me; S; 4-Me-Ph; 2-F-Ph]; [1852; S; 4-Cl-Ph; H; Me; S; 4-Me-Ph; 3-F-Ph]; [1853; S; 4-Cl-Ph; H; Me; S; 4-Me-Ph; 4-F-Ph]; [1854; S; 4-Cl-Ph; H; Me; S; 4-Me-Ph; 4-Cl-Ph]; [1855; S; 4-Cl-Ph; H; Me; S; 4-Me-Ph; 3-Me-Ph]; [1856; S; 4-Cl-Ph; H; Me; S; 4-Me-Ph; 4-Me-Ph]; [1857; S; 4-Cl-Ph; H; Me; S; 4-Me-Ph; 4-iPr-Ph]; [1858; S; 4-Cl-Ph; H; Me; S; 4-Me-Ph; 4-Ph-Ph]; [1859; S; 4-Cl-Ph; H; Me; S; 4-Me-Ph; 2-Naphthyl]; [1860; S; 4-Cl-Ph; H; Me; S; 4-Me-Ph; 5-Indanyl]; [1861; S; 4-Cl-Ph; H; Me; S; 2-Naphthyl; 2-F-Ph]; [1862; S; 4-Cl-Ph; H; Me; S; 2-Naphthyl; 3-F-Ph]; [1863; S; 4-Cl-Ph; H; Me; S; 2-Naphthyl; 4-F-Ph]; [1864; S; 4-Cl-Ph; H; Me; S; 2-Naphthyl; 4-Cl-Ph]; [1865; S; 4-Cl-Ph; H; Me; S; 2-Naphthyl; 3-Me-Ph]; [1866; S; 4-Cl-Ph; H; Me; S; 2-Naphthyl; 4-Me-Ph]; [1867; S; 4-Cl-Ph; H; Me; S; 2-Naphthyl; 4-iPr-Ph]; [1868; S; 4-Cl-Ph; H; Me; S; 2-Naphthyl; 4-Ph-Ph]; [1869; S; 4-Cl-Ph; H; Me; S; 2-Naphthyl; 2-Naphthyl]; [1870; S; 4-Cl-Ph; H; Me; S; 2-Naphthyl; 5-Indanyl]; [1871; S; 4-Cl-Ph; H; Me; S; 5-Indanyl; 2-F-Ph]; [1872; S; 4-Cl-Ph; H; Me; S; 5-Indanyl; 3-F-Ph]; [1873; S; 4-Cl-Ph; H; Me; S; 5-Indanyl; 4-F-Ph]; [1874; S; 4-Cl-Ph; H; Me; S; 5-Indanyl; 4-Cl-Ph]; [1875; S; 4-Cl-Ph; H; Me; S; 5-Indanyl; 3-Me-Ph]; [1876; S; 4-Cl-Ph; H; Me; S; 5-Indanyl; 4-Me-Ph]; [1877; S; 4-Cl-Ph; H; Me; S; 5-Indanyl; 4-iPr-Ph]; [1878; S; 4-Cl-Ph; H; Me; S; 5-Indanyl; 4-Ph-Ph]; [1879; S; 4-Cl-Ph; H; Me; S; 5-Indanyl; 2-Naphthyl]; [1880; S; 4-Cl-Ph; H; Me; S; 5-Indanyl; 5-Indanyl]; [1881; S; 4-Me-Ph; H; Me; S; Bu; 2-F-Ph]; [1882; S; 4-Me-Ph; H; Me; S; Bu; 3-F-Ph]; [1883; S; 4-Me-Ph; H; Me; S; Bu; 4-F-Ph]; [1884; S;

4-Me-Ph; H; Me; S; Bu; 4-Cl-Ph]; [1885; S; 4-Me-Ph; H; Me; S; Bu; 3-Me-Ph]; [1886; S; 4-Me-Ph; H; Me; S; Bu; 4-Me-Ph]; [1887; S; 4-Me-Ph; H; Me; S; Bu; 4-iPr-Ph]; [1888; S; 4-Me-Ph; H; Me; S; Bu; 4-Ph-Ph]; [1889; S; 4-Me-Ph; H; Me; S; Bu; 2-Naphthyl]; [1890; S; 4-Me-Ph; H; Me; S; Bu; 5-Indanyl]; [1891; S; 4-Me-Ph; H; Me; S; Cyclohexylmethyl; 2-F-Ph]; [1892; S; 4-Me-Ph; H; Me; S; Cyclohexylmethyl; 3-F-Ph]; [1893; S; 4-Me-Ph; H; Me; S; Cyclohexylmethyl; 4-F-Ph]; [1894; S; 4-Me-Ph; H; Me; S; Cyclohexylmethyl; 4-Cl-Ph]; [1895; S; 4-Me-Ph; H; Me; S; Cyclohexylmethyl; 3-Me-Ph]; [1896; S; 4-Me-Ph; H; Me; S; Cyclohexylmethyl; 4-Me-Ph]; [1897; S; 4-Me-Ph; H; Me; S; Cyclohexylmethyl; 4-iPr-Ph]; [1898; S; 4-Me-Ph; H; Me; S; Cyclohexylmethyl; 4-Ph-Ph]; [1899; S; 4-Me-Ph; H; Me; S; Cyclohexylmethyl; 2-Naphthyl]; [1900; S; 4-Me-Ph; H; Me; S; Cyclohexylmethyl; 5-Indanyl]; [1901; S; 4-Me-Ph; H; Me; S; 2-Perhydronaphthyl; 2-F-Ph]; [1902; S; 4-Me-Ph; H; Me; S; 2-Perhydronaphthyl; 3-F-Ph]; [1903; S; 4-Me-Ph; H; Me; S; 2-Perhydronaphthyl; 4-F-Ph]; [1904; S; 4-Me-Ph; H; Me; S; 2-Perhydronaphthyl; 4-Cl-Ph]; [1905; S; 4-Me-Ph; H; Me; S; 2-Perhydronaphthyl; 3-Me-Ph]; [1906; S; 4-Me-Ph; H; Me; S; 2-Perhydronaphthyl; 4-Me-Ph]; [1907; S; 4-Me-Ph; H; Me; S; 2-Perhydronaphthyl; 4-iPr-Ph]; [1908; S; 4-Me-Ph; H; Me; S; 2-Perhydronaphthyl; 4-Ph-Ph]; [1909; S; 4-Me-Ph; H; Me; S; 2-Perhydronaphthyl; 2-Naphthyl]; [1910; S; 4-Me-Ph; H; Me; S; 2-Perhydronaphthyl; 5-Indanyl]; [1911; S; 4-Me-Ph; H; Me; S; PhCH$_2$; 2-F-Ph]; [1912; S; 4-Me-Ph; H; Me; S; PhCH$_2$; 3-F-Ph]; [1913; S; 4-Me-Ph; H; Me; S; PhCH$_2$; 4-F-Ph]; [1914; S; 4-Me-Ph; H; Me; S; PhCH$_2$; 4-Cl-Ph]; [1915; S; 4-Me-Ph; H; Me; S; PhCH$_2$; 3-Me-Ph]; [1916; S; 4-Me-Ph; H; Me; S; PhCH$_2$; 4-Me-Ph]; [1917; S; 4-Me-Ph; H; Me; S; PhCH$_2$; 4-iPr-Ph]; [1918; S; 4-Me-Ph; H; Me; S; PhCH$_2$; 4-Ph-Ph]; [1919; S; 4-Me-Ph; H; Me; S; PhCH$_2$; 2-Naphthyl]; [1920; S; 4-Me-Ph; H; Me; S; PhCH$_2$; 5-Indanyl]; [1921; S; 4-Me-Ph; H; Me; S; 4-F-Ph; 2-F-Ph]; [1922; S; 4-Me-Ph; H; Me; S; 4-F-Ph; 3-F-Ph]; [1923; S; 4-Me-Ph; H; Me; S; 4-F-Ph; 4-F-Ph]; [1924; S; 4-Me-Ph; H; Me; S; 4-F-Ph; 4-Cl-Ph]; [1925; S; 4-Me-Ph; H; Me; S; 4-F-Ph; 3-Me-Ph]; [1926; S; 4-Me-Ph; H; Me; S; 4-F-Ph; 4-Me-Ph]; [1927; S; 4-Me-Ph; H; Me; S; 4-F-Ph; 4-iPr-Ph]; [1928; S; 4-Me-Ph; H; Me; S; 4-F-Ph; 4-Ph-Ph]; [1929; S; 4-Me-Ph; H; Me; S; 4-F-Ph; 2-Naphthyl]; [1930; S; 4-Me-Ph; H; Me; S; 4-F-Ph; 5-Indanyl]; [1931; S; 4-Me-Ph; H; Me; S; 4-Me-Ph; 2-F-Ph]; [1932; S; 4-Me-Ph; H; Me; S; 4-Me-Ph; 3-F-Ph]; [1933; S; 4-Me-Ph; H; Me; S; 4-Me-Ph; 4-F-Ph]; [1934; S; 4-Me-Ph; H; Me; S; 4-Me-Ph; 4-Cl-Ph]; [1935; S; 4-Me-Ph; H; Me; S; 4-Me-Ph; 3-Me-Ph]; [1936; S; 4-Me-Ph; H; Me; S; 4-Me-Ph; 4-Me-Ph]; [1937; S; 4-Me-Ph; H; Me; S; 4-Me-Ph; 4-iPr-Ph]; [1938; S; 4-Me-Ph; H; Me; S; 4-Me-Ph; 4-Ph-Ph]; [1939; S; 4-Me-Ph; H; Me; S; 4-Me-Ph; 2-Naphthyl]; [1940; S; 4-Me-Ph; H; Me; S; 4-Me-Ph; 5-Indanyl]; [1941; S; 4-Me-Ph; H; Me; S; 2-Naphthyl; 2-F-Ph]; [1942; S; 4-Me-Ph; H; Me; S; 2-Naphthyl; 3-F-Ph]; [1943; S; 4-Me-Ph; H; Me; S; 2-Naphthyl; 4-F-Ph]; [1944; S; 4-Me-Ph; H; Me; S; 2-Naphthyl; 4-Cl-Ph]; [1945; S; 4-Me-Ph; H; Me; S; 2-Naphthyl; 3-Me-Ph]; [1946; S; 4-Me-Ph; H; Me; S; 2-Naphthyl; 4-Me-Ph]; [1947; S; 4-Me-Ph; H; Me; S; 2-Naphthyl; 4-iPr-Ph]; [1948; S; 4-Me-Ph; H; Me; S; 2-Naphthyl; 4-Ph-Ph]; [1949; S; 4-Me-Ph; H; Me; S; 2-Naphthyl; 2-Naphthyl]; [1950; S; 4-Me-Ph; H; Me; S; 2-Naphthyl; 5-Indanyl]; [1951; S; 4-Me-Ph; H; Me; S; 5-Indanyl; 2-F-Ph]; [1952; S; 4-Me-Ph; H; Me; S; 5-Indanyl; 3-F-Ph]; [1953; S; 4-Me-Ph; H; Me; S; 5-Indanyl; 4-F-Ph]; [1954; S; 4-Me-Ph; H; Me; S; 5-Indanyl; 4-Cl-Ph]; [1955; S; 4-Me-Ph; H; Me; S; 5-Indanyl; 3-Me-Ph]; [1956; S; 4-Me-Ph; H; Me; S; 5-Indanyl; 4-Me-Ph]; [1957; S; 4-Me-Ph; H; Me; S; 5-Indanyl; 4-iPr-Ph]; [1958; S; 4-Me-Ph; H; Me; S; 5-Indanyl; 4-Ph-Ph]; [1959; S; 4-Me-Ph; H; Me; S; 5-Indanyl; 2-Naphthyl]; [1960; S; 4-Me-Ph; H; Me; S; 5-Indanyl; 5-Indanyl]; [1961; S; 4-CF$_3$-Ph; H; Me; S; Bu; 2-F-Ph]; [1962; S; 4-CF$_3$-Ph; H; Me; S; Bu; 3-F-Ph]; [1963; S; 4-CF$_3$-Ph; H; Me; S; Bu; 4-F-Ph]; [1964; S; 4-CF$_3$-Ph; H; Me; S; Bu; 4-Cl-Ph]; [1965; S; 4-CF$_3$-Ph; H; Me; S; Bu; 3-Me-Ph]; [1966; S; 4-CF$_3$-Ph; H; Me; S; Bu; 4-Me-Ph]; [1967; S; 4-CF$_3$-Ph; H; Me; S; Bu; 4-iPr-Ph]; [1968; S; 4-CF$_3$-Ph; H; Me; S; Bu; 4-Ph-Ph]; [1969; S; 4-CF$_3$-Ph; H; Me; S; Bu; 2-Naphthyl]; [1970; S; 4-CF$_3$-Ph; H; Me; S; Bu; 5-Indanyl]; [1971; S; 4-CF$_3$-Ph; H; Me; S; Cyclohexylmethyl; 2-F-Ph]; [1972; S; 4-CF$_3$-Ph; H; Me; S; Cyclohexylmethyl; 3-F-Ph]; [1973; S; 4-CF$_3$-Ph; H; Me; S; Cyclohexylmethyl; 4-F-Ph]; [1974; S; 4-CF$_3$-Ph; H; Me; S; Cyclohexylmethyl; 4-Cl-Ph]; [1975; S; 4-CF$_3$-Ph; H; Me; S; Cyclohexylmethyl; 3-Me-Ph]; [1976; S; 4-CF$_3$-Ph; H; Me; S; Cyclohexylmethyl; 4-Me-Ph]; [1977; S; 4-CF$_3$-Ph; H; Me; S; Cyclohexylmethyl; 4-iPr-Ph]; [1978; S; 4-CF$_3$-Ph; H; Me; S; Cyclohexylmethyl; 4-Ph-Ph]; [1979; S; 4-CF$_3$-Ph; H; Me; S; Cyclohexylmethyl; 2-Naphthyl]; [1980; S; 4-CF$_3$-Ph; H; Me; S; Cyclohexylmethyl; 5-Indanyl]; [1981; S; 4-CF$_3$-Ph; H; Me; S; 2-Perhydronaphthyl; 2-F-Ph]; [1982; S; 4-CF$_3$-Ph; H; Me; S; 2-Perhydronaphthyl; 3-F-Ph]; [1983; S; 4-CF$_3$-Ph; H; Me; S; 2-Perhydronaphthyl; 4-F-Ph]; [1984; S; 4-CF$_3$-Ph; H; Me; S; 2-Perhydronaphthyl; 4-Cl-Ph]; [1985; S; 4-CF$_3$-Ph; H; Me; S; 2-Perhydronaphthyl; 3-Me-Ph]; [1986; S; 4-CF$_3$-Ph; H; Me; S; 2-Perhydronaphthyl; 4-Me-Ph]; [1987; S; 4-CF$_3$-Ph; H; Me; S; 2-Perhydronaphthyl; 4-iPr-Ph]; [1988; S; 4-CF$_3$-Ph; H; Me; S; 2-Perhydronaphthyl; 4-Ph-Ph]; [1989; S; 4-CF$_3$-Ph; H; Me; S; 2-Perhydronaphthyl; 2-Naphthyl]; [1990; S; 4-CF$_3$-Ph; H; Me; S; 2-Perhydronaphthyl; 5-Indanyl]; [1991; S; 4-CF$_3$-Ph; H; Me; S; PhCH$_2$; 2-F-Ph]; [1992; S; 4-CF$_3$-Ph; H; Me; S; PhCH$_2$; 3-F-Ph]; [1993; S; 4-CF$_3$-Ph; H; Me; S; PhCH$_2$; 4-F-Ph]; [1994; S; 4-CF$_3$-Ph; H; Me; S; PhCH$_2$; 4-Cl-Ph]; [1995; S; 4-CF$_3$-Ph; H; Me; S; PhCH$_2$; 3-Me-Ph]; [1996; S; 4-CF$_3$-Ph; H; Me; S; PhCH$_2$; 4-Me-Ph]; [1997; S; 4-CF$_3$-Ph; H; Me; S; PhCH$_2$; 4-iPr-Ph]; [1998; S; 4-CF$_3$-Ph; H; Me; S; PhCH$_2$; 4-Ph-Ph]; [1999; S; 4-CF$_3$-Ph; H; Me; S; PhCH$_2$; 2-Naphthyl]; [2000; S; 4-CF$_3$-Ph; H; Me; S; PhCH$_2$; 5-Indanyl]; [2001; S; 4-CF$_3$-Ph; H; Me; S; 4-F-Ph; 2-F-Ph]; [2002; S; 4-CF$_3$-Ph; H; Me; S; 4-F-Ph; 3-F-Ph]; [2003; S; 4-CF$_3$-Ph; H; Me; S; 4-F-Ph; 4-F-Ph]; [2004; S; 4-CF$_3$-Ph; H; Me; S; 4-F-Ph; 4-Cl-Ph]; [2005; S; 4-CF$_3$-Ph; H; Me; S; 4-F-Ph; 3-Me-Ph]; [2006; S; 4-CF$_3$-Ph; H; Me; S; 4-F-Ph; 4-Me-Ph]; [2007; S; 4-CF$_3$-Ph; H; Me; S; 4-F-Ph; 4-iPr-Ph]; [2008; S; 4-CF$_3$-Ph; H; Me; S; 4-F-Ph; 4-Ph-Ph]; [2009; S; 4-CF$_3$-Ph; H; Me; S; 4-F-Ph; 2-Naphthyl]; [2010; S; 4-CF$_3$-Ph; H; Me; S; 4-F-Ph; 5-Indanyl]; [2011; S; 4-CF$_3$-Ph; H; Me; S; 4-Me-Ph; 2-F-Ph]; [2012; S; 4-CF$_3$-Ph; H; Me; S; 4-Me-Ph; 3-F-Ph]; [2013; S; 4-CF$_3$-Ph; H; Me; S; 4-Me-Ph; 4-F-Ph]; [2014; S; 4-CF$_3$-Ph; H; Me; S; 4-Me-Ph; 4-Cl-Ph]; [2015; S; 4-CF$_3$-Ph; H; Me; S; 4-Me-Ph; 3-Me-Ph]; [2016; S; 4-CF$_3$-Ph; H; Me; S; 4-Me-Ph; 4-Me-Ph]; [2017; S; 4-CF$_3$-Ph; H; Me; S; 4-Me-Ph; 4-iPr-Ph]; [2018; S; 4-CF$_3$-Ph; H; Me; S; 4-Me-Ph; 4-Ph-Ph]; [2019; S; 4-CF$_3$-Ph; H; Me; S; 4-Me-Ph; 2-Naphthyl]; [2020; S; 4-CF$_3$-Ph; H; Me; S; 4-Me-Ph; 5-Indanyl]; [2021; S; 4-CF$_3$-Ph; H; Me; S; 2-Naphthyl; 2-F-Ph]; [2022; S; 4-CF$_3$-Ph; H; Me; S; 2-Naphthyl; 3-F-Ph]; [2023; S; 4-CF$_3$-Ph; H; Me; S; 2-Naphthyl; 4-F-Ph]; [2024; S; 4-CF$_3$-Ph; H; Me; S; 2-Naphthyl; 4-Cl-Ph]; [2025; S; 4-CF$_3$-Ph; H; Me; S; 2-Naphthyl; 3-Me-Ph]; [2026; S; 4-CF$_3$-Ph; H; Me; S; 2-Naphthyl; 4-Me-Ph]; [2027; S; 4-CF$_3$-Ph; H; Me; S; 2-Naphthyl; 4-iPr-Ph]; [2028; S; 4-CF$_3$-Ph; H; Me; S; 2-Naphthyl; 4-Ph-Ph]; [2029; S; 4-CF$_3$-Ph; H; Me; S; 2-Naphthyl; 2-Naphthyl]; [2030; S; 4-CF$_3$-Ph; H; Me; S; 2-Naphthyl; 5-Indanyl]; [2031; S; 4-CF$_3$-Ph; H; Me; S; 5-Indanyl; 2-F-Ph]; [2032; S; 4-CF$_3$-Ph; H; Me; S; 5-Indanyl; 3-F-Ph]; [2033; S; 4-CF$_3$-Ph; H; Me; S;

5-Indanyl; 4-F-Ph]; [2034; S; 4-CF₃-Ph; H; Me; S; 5-Indanyl; 4-Cl-Ph]; [2035; S; 4-CF₃-Ph; H; Me; S; 5-Indanyl; 3-Me-Ph]; [2036; S; 4-CF₃-Ph; H; Me; S; 5-Indanyl; 4-Me-Ph]; [2037; S; 4-CF₃-Ph; H; Me; S; 5-Indanyl; 4-iPr-Ph]; [2038; S; 4-CF₃-Ph; H; Me; S; 5-Indanyl; 4-Ph-Ph]; [2039; S; 4-CF₃-Ph; H; Me; S; 5-Indanyl; 2-Naphthyl]; [2040; S; 4-CF₃-Ph; H; Me; S; 5-Indanyl; 5-Indanyl]; [2041; S; 4-F-Ph; Me; H; S; Cyclohexylmethyl; 2-F-Ph]; [2042; S; 4-F-Ph; Me; H; S; Cyclohexylmethyl; 3-F-Ph]; [2043; S; 4-F-Ph; Me; H; S; Cyclohexylmethyl; 4-F-Ph]; [2044; S; 4-F-Ph; Me; H; S; Cyclohexylmethyl; 4-Cl-Ph]; [2045; S; 4-F-Ph; Me; H; S; Cyclohexylmethyl; 3-Me-Ph]; [2046; S; 4-F-Ph; Me; H; S; Cyclohexylmethyl; 4-Me-Ph]; [2047; S; 4-F-Ph; Me; H; S; Cyclohexylmethyl; 4-iPr-Ph]; [2048; S; 4-F-Ph; Me; H; S; Cyclohexylmethyl; 4-Ph-Ph]; [2049; S; 4-F-Ph; Me; H; S; Cyclohexylmethyl; 2-Naphthyl]; [2050; S; 4-F-Ph; Me; H; S; Cyclohexylmethyl; 5-Indanyl]; [2051; S; 4-F-Ph; Me; H; S; 4-F-Ph; 2-F-Ph]; [2052; S; 4-F-Ph; Me; H; S; 4-F-Ph; 3-F-Ph]; [2053; S; 4-F-Ph; Me; H; S; 4-F-Ph; 4-F-Ph]; [2054; S; 4-F-Ph; Me; H; S; 4-F-Ph; 4-Cl-Ph]; [2055; S; 4-F-Ph; Me; H; S; 4-F-Ph; 3-Me-Ph]; [2056; S; 4-F-Ph; Me; H; S; 4-F-Ph; 4-Me-Ph]; [2057; S; 4-F-Ph; Me; H; S; 4-F-Ph; 4-iPr-Ph]; [2058; S; 4-F-Ph; Me; H; S; 4-F-Ph; 4-Ph-Ph]; [2059; S; 4-F-Ph; Me; H; S; 4-F-Ph; 2-Naphthyl]; [2060; S; 4-F-Ph; Me; H; S; 4-F-Ph; 5-Indanyl]; [2061; S; Ph; Me; Me; S; Ph; Ph]; [2062; S; Ph; Ph; Me; S; Ph; Ph]; [2063; S; Ph; Me; Ph; S; Ph; Ph]; [2064; S; Ph; Ph; Ph; S; Ph; Ph]; [2065; S; Ph; MeS; Me; S; Ph; Ph]; [2066; S; Ph; Me; MeS; S; Ph; Ph]; [2067; S; Ph; CF₃; Me; S; Ph; Ph]; [2068; S; Ph; Me; Me; S; Cyclohexylmethyl; Ph]; [2069; S; Ph; Ph; Me; S; Cyclohexylmethyl; Ph]; [2070; S; Ph; Me; Ph; S; Cyclohexylmethyl; Ph]; [2071; S; Ph; Ph; Ph; S; Cyclohexylmethyl; Ph]; [2072; S; Ph; MeS; Me; S; Cyclohexylmethyl; Ph]; [2073; S; Ph; Me; MeS; S; Cyclohexylmethyl; Ph]; [2074; S; Ph; CF₃; Me; S; Cyclohexylmethyl; Ph]; [2075; S; PhCH₂; PhCH₂S; Me; S; Ph; Ph]; [2076; S; PhCH₂; PhCH₂S; Ac; S; Cyclohexylmethyl; Ph]; [2077; S; PhCH₂; PhCH₂S; Me; S; Cyclohexylmethyl; Ph]; [2078; S; PhCH₂; PhCH₂S; Ac; S; Ph; Ph]; [2079; S; PhCH₂; PhCH₂S; COOMe; S; Ph; Ph]; [2080; S; PhCH₂; PhCH₂S; MeS; S; Ph; Ph]; [2081; O; PhCH₂; H; Me; S; Ph; Ph]; [2082; O; 4-Me-PhCH₂; H; Me; S; Ph; Ph]; [2083; O; 4-MeO-PhCH₂; H; Me; S; Ph; Ph]; [2084; O; 4-Cl-PhCH₂; H; Me; S; Ph; Ph]; [2085; O; 4-Ph-PhCH₂; H; Me; S; Ph; Ph]; [2086; O; 1-Naphthylmethyl; H; Me; S; Ph; Ph]; [2087; O; 2-Naphthylmethyl; H; Me; S; Ph; Ph]; [2088; O; α-Methylbenzyl; H; Me; S; Ph; Ph]; [2089; O; Cyclohexylmethyl; H; Me; S; Ph; Ph]; [2090; O; Ph; H; Me; S; Ph; Ph]; [2091; O; 2-F-Ph; H; Me; S; Ph; Ph]; [2092; O; 3-F-Ph; H; Me; S; Ph; Ph]; [2093; O; 4-F-Ph; H; Me; S; Ph; Ph]; [2094; O; 2-Cl-Ph; H; Me; S; Ph; Ph]; [2095; O; 3-Cl-Ph; H; Me; S; Ph; Ph]; [2096; O; 4-Cl-Ph; H; Me; S; Ph; Ph]; [2097; O; 2-Me-Ph; H; Me; S; Ph; Ph]; [2098; O; 3-Me-Ph; H; Me; S; Ph; Ph]; [2099; O; 4-Me-Ph; H; Me; S; Ph; Ph]; [2100; O; 2-Et-Ph; H; Me; S; Ph; Ph]; [2101; O; 3-Et-Ph; H; Me; S; Ph; Ph]; [2102; O; 4-Et-Ph; H; Me; S; Ph; Ph]; [2103; O; 2-iPr-Ph; H; Me; S; Ph; Ph]; [2104; O; 3-iPr-Ph; H; Me; S; Ph; Ph]; [2105; O; 4-iPr-Ph; H; Me; S; Ph; Ph]; [2106; O; 2-Ph-Ph; H; Me; S; Ph; Ph]; [2107; O; 3-Ph-Ph; H; Me; S; Ph; Ph]; [2108; O; 4-Ph-Ph; H; Me; S; Ph; Ph]; [2109; O; 2-CF₃-Ph; H; Me; S; Ph; Ph]; [2110; O; 3-CF₃-Ph; H; Me; S; Ph; Ph]; [2111; O; 4-CF₃-Ph; H; Me; S; Ph; Ph]; [2112; O; 2-MeO-Ph; H; Me; S; Ph; Ph]; [2113; O; 3-MeO-Ph; H; Me; S; Ph; Ph]; [2114; O; 4-MeO-Ph; H; Me; S; Ph; Ph]; [2115; O; 2,3-Me₂-Ph; H; Me; S; Ph; Ph]; [2116; O; 2,4-Me₂-Ph; H; Me; S; Ph; Ph]; [2117; O; 2,5-Me₂-Ph; H; Me; S; Ph; Ph]; [2118; O; 2,6-Me₂-Ph; Me; S; Ph; Ph]; [2119; O; 3,4-Me₂-Ph; H; Me; S; Ph; Ph]; [2120; O; 3,5-Me₂-Ph; H; Me; S; Ph; Ph]; [2121; O; 2,3-F₂-Ph; H; Me; S; Ph; Ph]; [2122; O; 2,4-F₂-Ph; H; Me; S; Ph; Ph]; [2123; O; 2,5-F₂-Ph; H; Me; S; Ph; Ph]; [2124; O; 2,6-F₂-Ph; H; Me; S; Ph; Ph]; [2125; O; 3,4-F₂-Ph; H; Me; S; Ph; Ph]; [2126; O; 3,5-F₂-Ph; H; Me; S; Ph; Ph]; [2127; O; 2,3-Cl₂-Ph; H; Me; S; Ph; Ph]; [2128; O; 2,4-Cl₂-Ph; H; Me; S; Ph; Ph]; [2129; O; 2,5-Cl₂-Ph; H; Me; S; Ph; Ph]; [2130; O; 2,6-Cl₂-Ph; H; Me; S; Ph; Ph]; [2131; O; 3,4-Cl₂-Ph; H; Me; S; Ph; Ph]; [2132; O; 3,5-Cl₂-Ph; H; Me; S; Ph; Ph]; [2133; O; 4-O₂N-Ph; H; Me; S; Ph; Ph]; [2134; O; 4-NC-Ph; H; Me; S; Ph; Ph]; [2135; O; 4-PhO-Ph; H; Me; S; Ph; Ph]; [2136; O; 4-CF₃O-Ph; H; Me; S; Ph; Ph]; [2137; O; 1-Naphthyl; H; Me; S; Ph; Ph]; [2138; O; 2-Naphthyl; H; Me; S; Ph; Ph]; [2139; O; 5-Indanyl; H; Me; S; Ph; Ph]; [2140; O; 5-Benzodioxolyl; H; Me; S; Ph; Ph]; [2141; O; PhCH₂; H; Et; S; Ph; Ph]; [2142; O; Ph; H; Et; S; Ph; Ph]; [2143; O; 3-F-Ph; H; Et; S; Ph; Ph]; [2144; O; 4-F-Ph; H; Et; S; Ph; Ph]; [2145; O; 4-Cl-Ph; H; Et; S; Ph; Ph]; [2146; O; 4-Me-Ph; H; Et; S; Ph; Ph]; [2147; O; 3,4-Me₂-Ph; H; Et; S; Ph; Ph]; [2148; O; 2-Naphthyl; H; Et; S; Ph; Ph]; [2149; O; 5-Indanyl; H; Et; S; Ph; Ph]; [2150; O; 5-Benzodioxolyl; H; Et; S; Ph; Ph]; [2151; O; PhCH₂; H; Pr; S; Ph; Ph]; [2152; O; Ph; H; Pr; S; Ph; Ph]; [2153; O; 3-F-Ph; H; Pr; S; Ph; Ph]; [2154; O; 4-F-Ph; H; Pr; S; Ph; Ph]; [2155; O; 4-Cl-Ph; H; Pr; S; Ph; Ph]; [2156; O; 4-Me-Ph; H; Pr; S; Ph; Ph]; [2157; O; 3,4-Me₂-Ph; H; Pr; S; Ph; Ph]; [2158; O; 2-Naphthyl; H; Pr; S; Ph; Ph]; [2159; O; 5-Indanyl; H; Pr; S; Ph; Ph]; [2160; O; 5-Benzodioxolyl; H; Pr; S; Ph; Ph]; [2161; O; PhCH₂; H; Ph; S; Ph; Ph]; [2162; O; Ph; H; Ph; S; Ph; Ph]; [2163; O; 3-F-Ph; H; Ph; S; Ph; Ph]; [2164; O; 4-F-Ph; H; Ph; S; Ph; Ph]; [2165; O; 4-Cl-Ph; H; Ph; S; Ph; Ph]; [2166; O; 4-Me-Ph; H; Ph; S; Ph; Ph]; [2167; O; 3,4-Me₂-Ph; H; Ph; S; Ph; Ph]; [2168; O; 2-Naphthyl; H; Ph; S; Ph; Ph]; [2169; O; 5-Indanyl; H; Ph; S; Ph; Ph]; [2170; O; 5-Benzodioxolyl; H; Ph; S; Ph; Ph]; [2171; O; PhCH₂; H; OPh; S; Ph; Ph]; [2172; O; Ph; H; OPh; S; Ph; Ph]; [2173; O; 3-F-Ph; H; OPh; S; Ph; Ph]; [2174; O; 4-F-Ph; H; OPh; S; Ph; Ph]; [2175; O; 4-Cl-Ph; H; OPh; S; Ph; Ph]; [2176; O; 4-Me-Ph; H; OPh; S; Ph; Ph]; [2177; O; 3,4-Me₂-Ph; H; OPh; S; Ph; Ph]; [2178; O; 2-Naphthyl; H; OPh; S; Ph; Ph]; [2179; O; 5-Indanyl; H; OPh; S; Ph; Ph]; [2180; O; 5-Benzodioxolyl; H; OPh; S; Ph; Ph]; [2181; O; PhCH₂; H; SMe; S; Ph; Ph]; [2182; O; Ph; H; SMe; S; Ph; Ph]; [2183; O; 3-F-Ph; H; SMe; S; Ph; Ph]; [2184; O; 4-F-Ph; H; SMe; S; Ph; Ph]; [2185; O; 4-Cl-Ph; H; SMe; S; Ph; Ph]; [2186; O; 4-Me-Ph; H; SMe; S; Ph; Ph]; [2187; O; 3,4-Me₂-Ph; H; SMe; S; Ph; Ph]; [2188; O; 2-Naphthyl; H; SMe; S; Ph; Ph]; [2189; O; 5-Indanyl; H; SMe; S; Ph; Ph]; [2190; O; 5-Benzodioxolyl; H; SMe; S; Ph; Ph]; [2191; O; PhCH₂; H; SPh; S; Ph; Ph]; [2192; O; Ph; H; SPh; S; Ph; Ph]; [2193; O; 3-F-Ph; H; SPh; S; Ph; Ph]; [2194; O; 4-F-Ph; H; SPh; S; Ph; Ph]; [2195; O; 4-Cl-Ph; H; SPh; S; Ph; Ph]; [2196; O; 4-Me-Ph; H; SPh; S; Ph; Ph]; [2197; O; 3,4-Me₂-Ph; H; SPh; S; Ph; Ph]; [2198; O; 2-Naphthyl; H; SPh; S; Ph; Ph]; [2199; O; 5-Indanyl; H; SPh; S; Ph; Ph]; [2200; O; 5-Benzodioxolyl; H; SPh; S; Ph; Ph]; [2201; O; PhCH₂; Me; H; S; Ph; Ph]; [2202; O; 4-Me-PhCH₂; Me; H; S; Ph; Ph]; [2203; O; 4-MeO-PhCH₂; Me; H; S; Ph; Ph]; [2204; O; 4-Cl-PhCH₂; Me; H; S; Ph; Ph]; [2205; O; 4-Ph-PhCH₂; Me; H; S; Ph; Ph]; [2206; O; 1-Naphthylmethyl; Me; H; S; Ph; Ph]; [2207; O; 2-Naphthylmethyl; Me; H; S; Ph; Ph]; [2208; O; α-Methylbenzyl; Me; H; S; Ph; Ph]; [2209; O; Cyclohexylmethyl; Me; H; S; Ph; Ph]; [2210; O; Ph; Me; H; S; Ph; Ph]; [2211; O; 2-F-Ph; Me; H; S; Ph; Ph]; [2212; O; 3-F-Ph; Me; H; S; Ph; Ph]; [2213; O; 4-F-Ph; Me; H; S; Ph; Ph]; [2214; O; 2-Cl-Ph; Me; H; S; Ph; Ph]; [2215; O; 3-Cl-Ph; Me; H; S; Ph; Ph]; [2216; O; 4-Cl-Ph; Me; H; S; Ph; Ph]; [2217; O; 2-Me-Ph; Me; H; S; Ph; Ph]; [2218; O; 3-Me-Ph; Me; H; S; Ph; Ph]; [2219; O; 4-Me-Ph; Me; H; S; Ph; Ph]; [2220; O; 2-Et-Ph; Me; H; S; Ph; Ph]; [2221; O; 3-Et-Ph; Me; H; S; Ph; Ph]; [2222; O; 4-Et-Ph; Me;

H; S; Ph; Ph]; [2223; O; 2-iPr-Ph; Me; H; S; Ph; Ph]; [2224; O; 3-iPr-Ph; Me; H; S; Ph; Ph]; [2225; O; 4-iPr-Ph; Me; H; S; Ph; Ph]; [2226; O; 2-Ph-Ph; Me; H; S; Ph; Ph]; [2227; O; 3-Ph-Ph; Me; H; S; Ph; Ph]; [2228; O; 4-Ph-Ph; Me; H; S; Ph; Ph]; [2229; O; 2-CF$_3$-Ph; Me; H; S; Ph; Ph]; [2230; O; 3-CF$_3$-Ph; Me; H; S; Ph; Ph]; [2231; O; 4-CF$_3$-Ph; Me; H; S; Ph; Ph]; [2232; O; 2-MeO-Ph; Me; H; S; Ph; Ph]; [2233; O; 3-MeO-Ph; Me; H; S; Ph; Ph]; [2234; O; 4-MeO-Ph; Me; H; S; Ph; Ph]; [2235; O; 2,3-Me$_2$-Ph; Me; H; S; Ph; Ph]; [2236; O; 2,4-Me$_2$-Ph; Me; H; S; Ph; Ph]; [2237; O; 2,5-Me$_2$-Ph; Me; H; S; Ph; Ph]; [2238; O; 2,6-Me$_2$-Ph; Me; H; S; Ph; Ph]; [2239; O; 3,4-Me$_2$-Ph; Me; H; S; Ph; Ph]; [2240; O; 3,5-Me$_2$-Ph; Me; H; S; Ph; Ph]; [2241; O; 2,3-F$_2$-Ph; Me; H; S; Ph; Ph]; [2242; O; 2,4-F$_2$-Ph; Me; H; S; Ph; Ph]; [2243; O; 2,5-F$_2$-Ph; Me; H; S; Ph; Ph]; [2244; O; 2,6-F$_2$-Ph; Me; H; S; Ph; Ph]; [2245; O; 3,4-F$_2$-Ph; Me; H; S; Ph; Ph]; [2246; O; 3,5-F$_2$-Ph; Me; H; S; Ph; Ph]; [2247; O; 2,3-Cl$_2$-Ph; Me; H; S; Ph; Ph]; [2248; O; 2,4-Cl$_2$-Ph; Me; H; S; Ph; Ph]; [2249; O; 2,5-Cl$_2$-Ph; Me; H; S; Ph; Ph]; [2250; O; 2,6-Cl$_2$-Ph; Me; H; S; Ph; Ph]; [2251; O; 3,4-Cl$_2$-Ph; Me; H; S; Ph; Ph]; [2252; O; 3,5-Cl$_2$-Ph; Me; H; S; Ph; Ph]; [2253; O; 4-O$_2$N-Ph; Me; H; S; Ph; Ph]; [2254; O; 4-NC-Ph; Me; H; S; Ph; Ph]; [2255; O; 4-PhO-Ph; Me; H; S; Ph; Ph]; [2256; O; 4-CF$_3$O-Ph; Me; H; S; Ph; Ph]; [2257; O; 1-Naphthyl; Me; H; S; Ph; Ph]; [2258; O; 2-Naphthyl; Me; H; S; Ph; Ph]; [2259; O; 5-Indanyl; Me; H; S; Ph; Ph]; [2260; O; 5-Benzodioxolyl; Me; H; S; Ph; Ph]; [2261; O; PhCH$_2$; Et; H; S; Ph; Ph]; [2262; O; Ph; Et; H; S; Ph; Ph]; [2263; O; 3-F-Ph; Et; H; S; Ph; Ph]; [2264; O; 4-F-Ph; Et; H; S; Ph; Ph]; [2265; O; 4-Cl-Ph; Et; H; S; Ph; Ph]; [2266; O; 4-Me-Ph; Et; H; S; Ph; Ph]; [2267; O; 3,4-Me$_2$-Ph; Et; H; S; Ph; Ph]; [2268; O; 2-Naphthyl; Et; H; S; Ph; Ph]; [2269; O; 5-Indanyl; Et; H; S; Ph; Ph]; [2270; O; 5-Benzodioxolyl; Et; H; S; Ph; Ph]; [2271; O; PhCH$_2$; Ph; H; S; Ph; Ph]; [2272; O; Ph; Ph; H; S; Ph; Ph]; [2273; O; 3-F-Ph; Ph; H; S; Ph; Ph]; [2274; O; 4-F-Ph; Ph; H; S; Ph; Ph]; [2275; O; 4-Cl-Ph; Ph; H; S; Ph; Ph]; [2276; O; 4-Me-Ph; Ph; H; S; Ph; Ph]; [2277; O; 3,4-Me$_2$-Ph; Ph; H; S; Ph; Ph]; [2278; O; 2-Naphthyl; Ph; H; S; Ph; Ph]; [2279; O; 5-Indanyl; Ph; H; S; Ph; Ph]; [2280; O; 5-Benzodioxolyl; Ph; H; S; Ph; Ph]; [2301; O; PhCH$_2$; Et; H; S; Ph; Ph]; [2302; O; Ph; Et; H; S; Ph; Ph]; [2303; O; 3-F-Ph; Et; H; S; Ph; Ph]; [2304; O; 4-F-Ph; Et; H; S; Ph; Ph]; [2305; O; 4-Cl-Ph; Et; H; S; Ph; Ph]; [2306; O; 4-Me-Ph; Et; H; S; Ph; Ph]; [2307; O; 3,4-Me$_2$-Ph; Et; H; S; Ph; Ph]; [2308; O; 2-Naphthyl; Et; H; S; Ph; Ph]; [2309; O; 5-Indanyl; Et; H; S; Ph; Ph]; [2310; O; 5-Benzodioxolyl; Et; H; S; Ph; Ph]; [2311; O; PhCH$_2$; Ph; H; S; Ph; Ph]; [2312; O; Ph; Ph; H; S; Ph; Ph]; [2313; O; 3-F-Ph; Ph; H; S; Ph; Ph]; [2314; O; 4-F-Ph; Ph; H; S; Ph; Ph]; [2315; O; 4-Cl-Ph; Ph; H; S; Ph; Ph]; [2316; O; 4-Me-Ph; Ph; H; S; Ph; Ph]; [2317; O; 3,4-Me$_2$-Ph; Ph; H; S; Ph; Ph]; [2318; O; 2-Naphthyl; Ph; H; S; Ph; Ph]; [2319; O; 5-Indanyl; Ph; H; S; Ph; Ph]; [2320; O; 5-Benzodioxolyl; Ph; H; S; Ph; Ph]; [2321; O; Ph; H; Me; S; Bu; Ph]; [2322; O; Ph; H; Me; S; CH$_2$(CH$_2$)$_5$; Ph]; [2323; O; Ph; H; Me; S; Isopentyl; Ph]; [2324; O; Ph; H; Me; S; Cyclopentyl; Ph]; [2325; O; Ph; H; Me; S; Cyclohexyl; Ph]; [2326; O; Ph; H; Me; S; Cyclopentylmethyl; Ph]; [2327; O; Ph; H; Me; S; Cyclohexylmethyl; Ph]; [2328; O; Ph; H; Me; S; 1-Cyclohexylethyl; Ph]; [2329; O; Ph; H; Me; S; 2-Perhydronaphthyl; Ph]; [2330; O; Ph; H; Me; S; PhCH$_2$; Ph]; [2331; O; Ph; H; Me; S; 2-F-Ph; Ph]; [2332; O; Ph; H; Me; S; 3-F-Ph; Ph]; [2333; O; Ph; H; Me; S; 4-F-Ph; Ph]; [2334; O; Ph; H; Me; S; 3-Cl-Ph; Ph]; [2335; O; Ph; H; Me; S; 4-Cl-Ph; Ph]; [2336; O; Ph; H; Me; S; 3-Me-Ph; Ph]; [2337; O; Ph; H; Me; S; 4-Me-Ph; Ph]; [2338; O; Ph; H; Me; S; 4-iPr-Ph; Ph]; [2339; O; Ph; H; Me; S; 4-CF$_3$-Ph; Ph]; [2340; O; Ph; H; Me; S; 4-MeO-Ph; Ph]; [2341; O; Ph; H; Me; S; 4-MeS-Ph; Ph]; [2342; O; Ph; H; Me; S; 4-F$_3$CO-Ph; Ph]; [2343; O; Ph; H; Me; S; 4-PhO-Ph; Ph]; [2344; O; Ph; H; Me; S; 4-Ph-Ph; Ph]; [2345; O; Ph; H; Me; S; 4-NC-Ph; Ph]; [2346; O; Ph; H; Me; S; 4-O$_2$N-Ph; Ph]; [2347; O; Ph; H; Me; S; 4-MeOOC-Ph; Ph]; [2348; O; Ph; H; Me; S; 1-Naphthyl; Ph]; [2349; O; Ph; H; Me; S; 2-Naphthyl; Ph]; [2350; O; Ph; H; Me; S; 5-Indanyl; Ph]; [2351; O; Ph; H; Me; S; 2-Pyridyl; Ph]; [2352; O; Ph; H; Me; S; 2-Pyrimidinyl; Ph]; [2353; O; Ph; H; Me; S; 2-Thienyl; Ph]; [2354; O; Ph; H; Me; S; 3-Thienyl; Ph]; [2355; O; Ph; H; Me; S; 2-Furyl; Ph]; [2356; O; Ph; H; Me; S; 3-Furyl; Ph]; [2357; O; Ph; H; Me; S; 2-Thiazolyl; Ph]; [2358; O; Ph; H; Me; S; 2-Benzothiazolyl; Ph]; [2359; O; Ph; H; Me; S; 5-Benzodioxolyl; Ph]; [2360; O; Ph; H; Me; S; 2-Quinolinyl; Ph]; [2361; O; Ph; H; Ph; S; Bu; Ph]; [2362; O; Ph; H; Ph; S; CH$_3$(CH$_2$)$_5$; Ph]; [2363; O; Ph; H; Ph; S; Isopentyl; Ph]; [2364; O; Ph; H; Ph; S; Cyclopentyl; Ph]; [2365; O; Ph; H; Ph; S; Cyclohexyl; Ph]; [2366; O; Ph; H; Ph; S; Cyclopentylmethyl; Ph]; [2367; O; Ph; H; Ph; S; Cyclohexylmethyl; Ph]; [2368; O; Ph; H; Ph; S; 1-Cyclohexylethyl; Ph]; [2369; O; Ph; H; Ph; S; 2-Perhydronaphthyl; Ph]; [2370; O; Ph; H; Ph; S; PhCH$_2$; Ph]; [2371; O; Ph; H; Ph; S; 2-F-Ph; Ph]; [2372; O; Ph; H; Ph; S; 3-F-Ph; Ph]; [2373; O; Ph; H; Ph; S; 4-F-Ph; Ph]; [2374; O; Ph; H; Ph; S; 3-Cl-Ph; Ph]; [2375; O; Ph; H; Ph; S; 4-Cl-Ph; Ph]; [2376; O; Ph; H; Ph; S; 3-Me-Ph; Ph]; [2377; O; Ph; H; Ph; S; 4-Me-Ph; Ph]; [2378; O; Ph; H; Ph; S; 4-iPr-Ph; Ph]; [2379; O; Ph; H; Ph; S; 4-CF$_3$-Ph; Ph]; [2380; O; Ph; H; Ph; S; 4-MeO-Ph; Ph]; [2381; O; Ph; H; Ph; S; 4-MeS-Ph; Ph]; [2382; O; Ph; H; Ph; S; 4-F$_3$CO-Ph; Ph]; [2383; O; Ph; H; Ph; S; 4-PhO-Ph; Ph]; [2384; O; Ph; H; Ph; S; 4-Ph-Ph; Ph]; [2385; O; Ph; H; Ph; S; 4-NC-Ph; Ph]; [2386; O; Ph; H; Ph; S; 4-O$_2$N-Ph; Ph]; [2387; O; Ph; H; Ph; S; 4-MeOOC-Ph; Ph]; [2388; O; Ph; H; Ph; S; 1-Naphthyl; Ph]; [2389; O; Ph; H; Ph; S; 2-Naphthyl; Ph]; [2390; O; Ph; H; Ph; S; 5-Indanyl; Ph]; [2391; O; Ph; H; Ph; S; 2-Pyridyl; Ph]; [2392; O; Ph; H; Ph; S; 2-Pyrimidinyl; Ph]; [2393; O; Ph; H; Ph; S; 2-Thienyl; Ph]; [2394; O; Ph; H; Ph; S; 3-Thienyl; Ph]; [2395; O; Ph; H; Ph; S; 2-Furyl; Ph]; [2396; O; Ph; H; Ph; S; 3-Furyl; Ph]; [2397; O; Ph; H; Ph; S; 2-Thiazolyl; Ph]; [2398; O; Ph; H; Ph; S; 2-Benzothiazolyl; Ph]; [2399; O; Ph; H; Ph; S; 5-Benzodioxolyl; Ph]; [2400; O; Ph; H; Ph; S; 2-Quinolinyl; Ph]; [2401; O; Ph; Me; H; S; Bu; Ph]; [2402; O; Ph; Me; H; S; CH$_3$(CH$_2$)$_5$; Ph]; [2403; O; Ph; Me; H; S; Isopentyl; Ph]; [2404; O; Ph; Me; H; S; Cyclopentyl; Ph]; [2405; O; Ph; Me; H; S; Cyclohexyl; Ph]; [2406; O; Ph; Me; H; S; Cyclopentylmethyl; Ph]; [2407; O; Ph; Me; H; S; Cyclohexylmethyl; Ph]; [2408; O; Ph; Me; H; S; 1-Cyclohexylethyl; Ph]; [2409; O; Ph; Me; H; S; 2-Perhydronaphthyl; Ph]; [2410; O; Ph; Me; H; S; PhCH$_2$; Ph]; [2411; O; Ph; Me; H; S; 2-F-Ph; Ph]; [2412; O; Ph; Me; H; S; 3-F-Ph; Ph]; [2413; O; Ph; Me; H; S; 4-F-Ph; Ph]; [2414; O; Ph; Me; H; S; 3-Cl-Ph; Ph]; [2415; O; Ph; Me; H; S; 4-Cl-Ph; Ph]; [2416; O; Ph; Me; H; S; 3-Me-Ph; Ph]; [2417; O; Ph; Me; H; S; 4-Me-Ph; Ph]; [2418; O; Ph; Me; H; S; 4-iPr-Ph; Ph]; [2419; O; Ph; Me; H; S; 4-CF$_3$-Ph; Ph]; [2420; O; Ph; Me; H; S; 4-MeO-Ph; Ph]; [2421; O; Ph; Me; H; S; 4-MeS-Ph; Ph]; [2422; O; Ph; Me; H; S; 4-F$_3$CO-Ph; Ph]; [2423; O; Ph; Me; H; S; 4-PhO-Ph; Ph]; [2424; O; Ph; Me; H; S; 4-Ph-Ph; Ph]; [2425; O; Ph; Me; H; S; 4-NC-Ph; Ph]; [2426; O; Ph; Me; H; S; 4-O$_2$N-Ph; Ph]; [2427; O; Ph; Me; H; S; 4-MeOOC-Ph; Ph]; [2428; O; Ph; Me; H; S; 1-Naphthyl; Ph]; [2429; O; Ph; Me; H; S; 2-Naphthyl; Ph]; [2430; O; Ph; Me; H; S; 5-Indanyl; Ph]; [2431; O; Ph; Me; H; S; 2-Pyridyl; Ph]; [2432; O; Ph; Me; H; S; 2-Pyrimidinyl; Ph]; [2433; O; Ph; Me; H; S; 2-Thienyl; Ph]; [2434; O; Ph; Me; H; S; 3-Thienyl; Ph]; [2435; O; Ph; Me; H; S; 2-Furyl; Ph]; [2436; O; Ph; Me; H; S; 3-Furyl; Ph]; [2437; O; Ph; Me; H; S; 2-Thiazolyl; Ph]; [2438; O; Ph; Me; H; S; 2-Benzothiazolyl; Ph]; [2439; O; Ph; Me; H; S; 5-Benzodioxolyl; Ph]; [2440; O; Ph; Me; H; S; 2-Quinolinyl; Ph];

[2441; O; Ph; Ph; H; S; Bu; Ph]; [2442; O; Ph; Ph; H; S; CH₃(CH₂)₅; Ph]; [2443; O; Ph; Ph; H; S; Isopentyl; Ph]; [2444; O; Ph; Ph; H; S; Cyclopentyl; Ph]; [2445; O; Ph; Ph; H; S; Cyclohexyl; Ph]; [2446; O; Ph; Ph; H; S; Cyclopentylmethyl; Ph]; [2447; O; Ph; Ph; H; S; Cyclohexylmethyl; Ph]; [2448; O; Ph; Ph; H; S; 1-Cyclohexylethyl; Ph]; [2449; O; Ph; Ph; H; S; 2-Perhydronaphthyl; Ph]; [2450; O; Ph; Ph; H; S; PhCH₂; Ph]; [2451; O; Ph; Ph; H; S; 2-F-Ph; Ph]; [2452; O; Ph; Ph; H; S; 3-F-Ph; Ph]; [2453; O; Ph; Ph; H; S; 4-F-Ph; Ph]; [2454; O; Ph; Ph; H; S; 3-Cl-Ph; Ph]; [2455; O; Ph; Ph; H; S; 4-Cl-Ph; Ph]; [2456; O; Ph; Ph; H; S; 3-Me-Ph; Ph]; [2457; O; Ph; Ph; H; S; 4-Me-Ph; Ph]; [2458; O; Ph; Ph; H; S; 4-iPr-Ph; Ph]; [2459; O; Ph; Ph; H; S; 4-CF₃-Ph; Ph]; [2460; O; Ph; Ph; H; S; 4-MeO-Ph; Ph]; [2461; O; Ph; Ph; H; S; 4-MeS-Ph; Ph]; [2462; O; Ph; Ph; H; S; 4-F₃CO-Ph; Ph]; [2463; O; Ph; Ph; H; S; 4-PhO-Ph; Ph]; [2464; O; Ph; Ph; H; S; 4-Ph-Ph; Ph]; [2465; O; Ph; Ph; H; S; 4-NC-Ph; Ph]; [2466; O; Ph; Ph; H; S; 4-O₂N-Ph; Ph]; [2467; O; Ph; Ph; H; S; 4-MeOOC-Ph; Ph]; [2468; O; Ph; Ph; H; S; 1-Naphthyl; Ph]; [2469; O; Ph; Ph; H; S; 2-Naphthyl; Ph]; [2470; O; Ph; Ph; H; S; 5-Indanyl; Ph]; [2471; O; Ph; Ph; H; S; 2-Pyridyl; Ph]; [2472; O; Ph; Ph; H; S; 2-Pyrimidinyl; Ph]; [2473; O; Ph; Ph; H; S; 2-Thienyl; Ph]; [2474; O; Ph; Ph; H; S; 3-Thienyl; Ph]; [2475; O; Ph; Ph; H; S; 2-Furyl; Ph]; [2476; O; Ph; Ph; H; S; 3-Furyl; Ph]; [2477; O; Ph; Ph; H; S; 2-Thiazolyl; Ph]; [2478; O; Ph; Ph; H; S; 2-Benzothiazolyl; Ph]; [2479; O; Ph; Ph; H; S; 5-Benzodioxolyl; Ph]; [2480; O; Ph; Ph; H; S; 2-Quinolinyl; Ph]; [2481; O; Ph; H; Me; S; Ph; 2-F-Ph]; [2482; O; Ph; H; Me; S; Ph; 3-F-Ph]; [2483; O; Ph; H; Me; S; Ph; 4-F-Ph]; [2484; O; Ph; H; Me; S; Ph; 2-Cl-Ph]; [2485; O; Ph; H; Me; S; Ph; 3-Cl-Ph]; [2486; O; Ph; H; Me; S; Ph; 4-Cl-Ph]; [2487; O; Ph; H; Me; S; Ph; 2-Me-Ph]; [2488; O; Ph; H; Me; S; Ph; 3-Me-Ph]; [2489; O; Ph; H; Me; S; Ph; 4-Me-Ph]; [2490; O; Ph; H; Me; S; Ph; 4-iPr-Ph]; [2491; O; Ph; H; Me; S; Ph; 4-CF₃-Ph]; [2492; O; Ph; H; Me; S; Ph; 4-Ph-Ph]; [2493; O; Ph; H; Me; S; Ph; 1-Naphthyl]; [2494; O; Ph; H; Me; S; Ph; 2-Naphthyl]; [2495; O; Ph; H; Me; S; Ph; 5-Indanyl]; [2496; O; Ph; H; Me; S; Ph; 2-Pyridyl]; [2497; O; Ph; H; Me; S; Ph; 2-Thienyl]; [2498; O; Ph; H; Me; S; Ph; 2-Furyl]; [2499; O; Ph; H; Me; S; Ph; 2-Benzothiazolyl]; [2500; O; Ph; H; Me; S; Ph; 5-Benzodioxolyl]; [2501; O; Ph; H; Ph; S; Ph; 2-F-Ph]; [2502; O; Ph; H; Ph; S; Ph; 3-F-Ph]; [2503; O; Ph; H; Ph; S; Ph; 4-F-Ph]; [2504; O; Ph; H; Ph; S; Ph; 2-Cl-Ph]; [2505; O; Ph; H; Ph; S; Ph; 3-Cl-Ph]; [2506; O; Ph; H; Ph; S; Ph; 4-Cl-Ph]; [2507; O; Ph; H; Ph; S; Ph; 2-Me-Ph]; [2508; O; Ph; H; Ph; S; Ph; 3-Me-Ph]; [2509; O; Ph; H; Ph; S; Ph; 4-Me-Ph]; [2510; O; Ph; H; Ph; S; Ph; 4-iPr-Ph]; [2511; O; Ph; H; Ph; S; Ph; 4-CF₃-Ph]; [2512; O; Ph; H; Ph; S; Ph; 4-Ph-Ph]; [2513; O; Ph; H; Ph; S; Ph; 1-Naphthyl]; [2514; O; Ph; H; Ph; S; Ph; 2-Naphthyl]; [2515; O; Ph; H; Ph; S; Ph; 5-Indanyl]; [2516; O; Ph; H; Ph; S; Ph; 2-Pyridyl]; [2517; O; Ph; H; Ph; S; Ph; 2-Thienyl]; [2518; O; Ph; H; Ph; S; Ph; 2-Furyl]; [2519; O; Ph; H; Ph; S; Ph; 2-Benzothiazolyl]; [2520; O; Ph; H; Ph; S; Ph; 5-Benzodioxolyl]; [2521; O; Ph; Me; H; S; Ph; 2-F-Ph]; [2522; O; Ph; Me; H; S; Ph; 3-F-Ph]; [2523; O; Ph; Me; H; S; Ph; 4-F-Ph]; [2524; O; Ph; Me; H; S; Ph; 2-Cl-Ph]; [2525; O; Ph; Me; H; S; Ph; 3-Cl-Ph]; [2526; O; Ph; Me; H; S; Ph; 4-Cl-Ph]; [2527; O; Ph; Me; H; S; Ph; 2-Me-Ph]; [2528; O; Ph; Me; H; S; Ph; 3-Me-Ph]; [2529; O; Ph; Me; H; S; Ph; 4-Me-Ph]; [2530; O; Ph; Me; H; S; Ph; 4-iPr-Ph]; [2531; O; Ph; Me; H; S; Ph; 4-CF₃-Ph]; [2532; O; Ph; Me; H; S; Ph; 4-Ph-Ph]; [2533; O; Ph; Me; H; S; Ph; 1-Naphthyl]; [2534; O; Ph; Me; H; S; Ph; 2-Naphthyl]; [2535; O; Ph; Me; H; S; Ph; 5-Indanyl]; [2536; O; Ph; Me; H; S; Ph; 2-Pyridyl]; [2537; O; Ph; Me; H; S; Ph; 2-Thienyl]; [2538; O; Ph; Me; H; S; Ph; 2-Furyl]; [2539; O; Ph; Me; H; S; Ph; 2-Benzothiazolyl]; [2540; O; Ph; Me; H; S; Ph; 5-Benzodioxolyl]; [2541; O; Ph; Ph; H; S; Ph; 2-F-Ph]; [2542; O; Ph; Ph; H; S; Ph; 3-F-Ph]; [2543; O; Ph; Ph; H; S; Ph; 4-F-Ph]; [2544; O; Ph; Ph; H; S; Ph; 2-Cl-Ph]; [2545; O; Ph; Ph; H; S; Ph; 3-Cl-Ph]; [2546; O; Ph; Ph; H; S; Ph; 4-Cl-Ph]; [2547; O; Ph; Ph; H; S; Ph; 2-Me-Ph]; [2548; O; Ph; Ph; H; S; Ph; 3-Me-Ph]; [2549; O; Ph; Ph; H; S; Ph; 4-Me-Ph]; [2550; O; Ph; Ph; H; S; Ph; 4-iPr-Ph]; [2551; O; Ph; Ph; H; S; Ph; 4-CF₃-Ph]; [2552; O; Ph; Ph; H; S; Ph; 4-Ph-Ph]; [2553; O; Ph; Ph; H; S; Ph; 1-Naphthyl]; [2554; O; Ph; Ph; H; S; Ph; 2-Naphthyl]; [2555; O; Ph; Ph; H; S; Ph; 5-Indanyl]; [2556; O; Ph; Ph; H; S; Ph; 2-Pyridyl]; [2557; O; Ph; Ph; H; S; Ph; 2-Thienyl]; [2558; O; Ph; Ph; H; S; Ph; 2-Furyl]; [2559; O; Ph; Ph; H; S; Ph; 2-Benzothiazolyl]; [2560; O; Ph; Ph; H; S; Ph; 5-Benzodioxolyl]; [2561; O; 3-F-Ph; H; Me; S; Ph; 2-F-Ph]; [2562; O; 3-F-Ph; H; Me; S; Ph; 3-F-Ph]; [2563; O; 3-F-Ph; H; Me; S; Ph; 4-F-Ph]; [2564; O; 3-F-Ph; H; Me; S; Ph; 4-Cl-Ph]; [2565; O; 3-F-Ph; H; Me; S; Ph; 3-Me-Ph]; [2566; O; 3-F-Ph; H; Me; S; Ph; 4-Me-Ph]; [2567; O; 3-F-Ph; H; Me; S; Ph; 4-iPr-Ph]; [2568; O; 3-F-Ph; H; Me; S; Ph; 4-Ph-Ph]; [2569; O; 3-F-Ph; H; Me; S; Ph; 2-Naphthyl]; [2570; O; 3-F-Ph; H; Me; S; Ph; 5-Indanyl]; [2571; O; 4-F-Ph; H; Me; S; Ph; 2-F-Ph]; [2572; O; 4-F-Ph; H; Me; S; Ph; 3-F-Ph]; [2573; O; 4-F-Ph; H; Me; S; Ph; 4-F-Ph]; [2574; O; 4-F-Ph; H; Me; S; Ph; 4-Cl-Ph]; [2575; O; 4-F-Ph; H; Me; S; Ph; 3-Me-Ph]; [2576; O; 4-F-Ph; H; Me; S; Ph; 4-Me-Ph]; [2577; O; 4-F-Ph; H; Me; S; Ph; 4-iPr-Ph]; [2578; O; 4-F-Ph; H; Me; S; Ph; 4-Ph-Ph]; [2579; O; 4-F-Ph; H; Me; S; Ph; 2-Naphthyl]; [2580; O; 4-F-Ph; H; Me; S; Ph; 5-Indanyl]; [2581; O; 3-Cl-Ph; H; Me; S; Ph; 2-F-Ph]; [2582; O; 3-Cl-Ph; H; Me; S; Ph; 3-F-Ph]; [2583; O; 3-Cl-Ph; H; Me; S; Ph; 4-F-Ph]; [2584; O; 3-Cl-Ph; H; Me; S; Ph; 4-Cl-Ph]; [2585; O; 3-Cl-Ph; H; Me; S; Ph; 3-Me-Ph]; [2586; O; 3-Cl-Ph; H; Me; S; Ph; 4-Me-Ph]; [2587; O; 3-Cl-Ph; H; Me; S; Ph; 4-iPr-Ph]; [2588; O; 3-Cl-Ph; H; Me; S; Ph; 4-Ph-Ph]; [2589; O; 3-Cl-Ph; H; Me; S; Ph; 2-Naphthyl]; [2590; O; 3-Cl-Ph; H; Me; S; Ph; 5-Indanyl]; [2591; O; 4-Cl-Ph; H; Me; S; Ph; 2-F-Ph]; [2592; O; 4-Cl-Ph; H; Me; S; Ph; 3-F-Ph]; [2593; O; 4-Cl-Ph; H; Me; S; Ph; 4-F-Ph]; [2594; O; 4-Cl-Ph; H; Me; S; Ph; 4-Cl-Ph]; [2595; O; 4-Cl-Ph; H; Me; S; Ph; 3-Me-Ph]; [2596; O; 4-Cl-Ph; H; Me; S; Ph; 4-Me-Ph]; [2597; O; 4-Cl-Ph; H; Me; S; Ph; 4-iPr-Ph]; [2598; O; 4-Cl-Ph; H; Me; S; Ph; 4-Ph-Ph]; [2599; O; 4-Cl-Ph; H; Me; S; Ph; 2-Naphthyl]; [2600; O; 4-Cl-Ph; H; Me; S; Ph; 5-Indanyl]; [2601; O; 3-Me-Ph; H; Me; S; Ph; 2-F-Ph]; [2602; O; 3-Me-Ph; H; Me; S; Ph; 3-F-Ph]; [2603; O; 3-Me-Ph; H; Me; S; Ph; 4-F-Ph]; [2604; O; 3-Me-Ph; H; Me; S; Ph; 4-Cl-Ph]; [2605; O; 3-Me-Ph; H; Me; S; Ph; 3-Me-Ph]; [2606; O; 3-Me-Ph; H; Me; S; Ph; 4-Me-Ph]; [2607; O; 3-Me-Ph; H; Me; S; Ph; 4-iPr-Ph]; [2608; O; 3-Me-Ph; H; Me; S; Ph; 4-Ph-Ph]; [2609; O; 3-Me-Ph; H; Me; S; Ph; 2-Naphthyl]; [2610; O; 3-Me-Ph; H; Me; S; Ph; 5-Indanyl]; [2611; O; 4-Me-Ph; H; Me; S; Ph; 2-F-Ph]; [2612; O; 4-Me-Ph; H; Me; S; Ph; 3-F-Ph]; [2613; O; 4-Me-Ph; H; Me; S; Ph; 4-F-Ph]; [2614; O; 4-Me-Ph; H; Me; S; Ph; 4-Cl-Ph]; [2615; O; 4-Me-Ph; H; Me; S; Ph; 3-Me-Ph]; [2616; O; 4-Me-Ph; H; Me; S; Ph; 4-Me-Ph]; [2617; O; 4-Me-Ph; H; Me; S; Ph; 4-iPr-Ph]; [2618; O; 4-Me-Ph; H; Me; S; Ph; 4-Ph-Ph]; [2619; O; 4-Me-Ph; H; Me; S; Ph; 2-Naphthyl]; [2620; O; 4-Me-Ph; H; Me; S; Ph; 5-Indanyl]; [2621; O; 4-iPr-Ph; H; Me; S; Ph; 2-F-Ph]; [2622; O; 4-iPr-Ph; H; Me; S; Ph; 3-F-Ph]; [2623; O; 4-iPr-Ph; H; Me; S; Ph; 4-F-Ph]; [2624; O; 4-iPr-Ph; H; Me; S; Ph; 4-Cl-Ph]; [2625; O; 4-iPr-Ph; H; Me; S; Ph; 3-Me-Ph]; [2626; O; 4-iPr-Ph; H; Me; S; Ph; 4-Me-Ph]; [2627; O; 4-iPr-Ph; H; Me; S; Ph; 4-iPr-Ph]; [2628; O; 4-iPr-Ph; H; Me; S; Ph; 4-Ph-Ph]; [2629; O; 4-iPr-Ph; H; Me; S; Ph; 2-Naphthyl]; [2630; O; 4-iPr-Ph; H; Me; S; Ph; 5-Indanyl]; [2631; O; 5-Indanyl; H; Me; S; Ph; 2-F-Ph]; [2632; O; 5-Indanyl; H; Me; S; Ph; 3-F-Ph]; [2633; O; 5-Indanyl; H; Me; S; Ph; 4-F-Ph]; [2634; O; 5-Indanyl; H; Me; S; Ph; 4-Cl-Ph]; [2635; O; 5-Indanyl; H; Me; S; Ph; 3-Me-Ph]; [2636; O; 5-Indanyl; H; Me; S; Ph; 4-Me-Ph]; [2637; O; 5-Indanyl; H; Me; S; Ph; 4-iPr-Ph]; [2638; O; 5-Indanyl; H; Me; S; Ph; 4-Ph-Ph]; [2639; O; 5-Indanyl; H; Me; S; Ph; 2-Naphthyl]; [2640; O; 5-Indanyl; H; Me; S; Ph; 5-Indanyl]; [2641; O; 5-Benzodioxolyl; H; Me; S; Ph; 2-F-Ph]; [2642; O; 5-Benzodioxolyl; H; Me; S; Ph; 3-F-Ph]; [2643; O; 5-Benzodioxolyl; H; Me; S; Ph; 4-F-Ph]; [2644; O; 5-Benzodioxolyl; H; Me; S; Ph; 4-Cl-Ph]; [2645; O; 5-Benzodioxolyl; H; Me; S; Ph; 3-Me-Ph]; [2646; O; 5-Benzodioxolyl; H; Me; S; Ph; 4-Me-Ph]; [2647; O; 5-Benzodioxolyl; H; Me; S; Ph; 4-iPr-Ph]; [2648; O; 5-Benzodioxolyl; H; Me; S; Ph; 4-Ph-Ph]; [2649; O; 5-Benzodioxolyl; H; Me; S; Ph; 2-Naphthyl]; [2650; O; 5-Benzodioxolyl; H; Me; S; Ph; 5-Indanyl]; [2651; O; 3-F-Ph; Me; H; S; Ph; 2-F-Ph]; [2652; O; 3-F-Ph; Me; H; S; Ph; 3-F-Ph]; [2653; O; 3-F-Ph; Me; H; S; Ph; 4-F-Ph]; [2654; O; 3-F-Ph; Me; H; S; Ph; 4-Cl-Ph]; [2655; O; 3-F-Ph; Me; H; S; Ph; 3-Me-Ph]; [2656; O; 3-F-Ph; Me; H; S; Ph; 4-Me-Ph]; [2657; O; 3-F-Ph; Me; H; S; Ph; 4-iPr-Ph]; [2658; O; 3-F-Ph; Me; H; S; Ph; 4-Ph-Ph]; [2659; O; 3-F-Ph; Me; H; S; Ph; 2-Naphthyl]; [2660; O; 3-F-Ph; Me; H; S; Ph; 5-Indanyl]; [2661; O; 4-F-Ph; Me; H; S; Ph; 2-F-Ph]; [2662; O; 4-F-Ph; Me; H; S; Ph; 3-F-Ph]; [2663; O; 4-F-Ph; Me; H; S; Ph; 4-F-Ph]; [2664; O; 4-F-Ph; Me; H; S; Ph; 4-Cl-Ph]; [2665; O; 4-F-Ph; Me; H; S; Ph; 3-Me-Ph]; [2666; O; 4-F-Ph; Me; H; S; Ph; 4-Me-Ph]; [2667; O; 4-F-Ph; Me; H; S; Ph; 4-iPr-Ph]; [2668; O; 4-F-Ph; Me; H; S; Ph; 4-Ph-Ph]; [2669; O; 4-F-Ph; Me; H; S; Ph; 2-Naphthyl]; [2670; O; 4-F-Ph; Me; H; S; Ph; 5-Indanyl]; [2671; O; 3-Cl-Ph; Me; H; S; Ph; 2-F-Ph]; [2672; O; 3-Cl-Ph; Me; H; S; Ph; 3-F-Ph]; [2673; O; 3-Cl-Ph; Me; H; S; Ph; 4-F-Ph]; [2674; O; 3-Cl-Ph; Me; H; S; Ph; 4-Cl-Ph]; [2675; O; 3-Cl-Ph; Me; H; S; Ph; 3-Me-Ph]; [2676; O; 3-Cl-Ph; Me; H; S; Ph; 4-Me-Ph]; [2677; O; 3-Cl-Ph; Me; H; S; Ph; 4-iPr-Ph]; [2678; O; 3-Cl-Ph; Me; H; S; Ph; 4-Ph-Ph]; [2679; O; 3-Cl-Ph; Me; H; S; Ph; 2-Naphthyl]; [2680; O; 3-Cl-Ph; Me; H; S; Ph; 5-Indanyl]; [2681; O; 4-Cl-Ph; Me; H; S; Ph; 2-F-Ph]; [2682; O; 4-Cl-Ph; Me; H; S; Ph; 3-F-Ph]; [2683; O; 4-Cl-Ph; Me; H; S; Ph; 4-F-Ph]; [2684; O; 4-Cl-Ph; Me; H; S; Ph; 4-Cl-Ph]; [2685; O; 4-Cl-Ph; Me; H; S; Ph; 3-Me-Ph]; [2686; O; 4-Cl-Ph; Me; H; S; Ph; 4-Me-Ph]; [2687; O; 4-Cl-Ph; Me; H; S; Ph; 4-iPr-Ph]; [2688; O; 4-Cl-Ph; Me; H; S; Ph; 4-Ph-Ph]; [2689; O; 4-Cl-Ph; Me; H; S; Ph; 2-Naphthyl]; [2690; O; 4-Cl-Ph; Me; H; S; Ph; 5-Indanyl]; [2691; O; 4-Me-Ph; Me; H; S; Ph; 2-F-Ph]; [2692; O; 4-Me-Ph; Me; H; S; Ph; 3-F-Ph]; [2693; O; 4-Me-Ph; Me; H; S; Ph; 4-F-Ph]; [2694; O; 4-Me-Ph; Me; H; S; Ph; 4-Cl-Ph]; [2695; O; 4-Me-Ph; Me; H; S; Ph; 3-Me-Ph]; [2696; O; 4-Me-Ph; Me; H; S; Ph; 4-Me-Ph]; [2697; O; 4-Me-Ph; Me; H; S; Ph; 4-iPr-Ph]; [2698; O; 4-Me-Ph; Me; H; S; Ph; 4-Ph-Ph]; [2699; O; 4-Me-Ph; Me; H; S; Ph; 2-Naphthyl]; [2700; O; 4-Me-Ph; Me; H; S; Ph; 5-Indanyl]; [2701; O; 5-Indanyl; Me; H; S; Ph; 2-F-Ph]; [2702; O; 5-Indanyl; Me; H; S; Ph; 3-F-Ph]; [2703; O; 5-Indanyl; Me; H; S; Ph; 4-F-Ph]; [2704; O; 5-Indanyl; Me; H; S; Ph; 4-Cl-Ph]; [2705; O; 5-Indanyl; Me; H; S; Ph; 3-Me-Ph]; [2706; O; 5-Indanyl; Me; H; S; Ph; 4-Me-Ph]; [2707; O; 5-Indanyl; Me; H; S; Ph; 4-iPr-Ph]; [2708; O; 5-Indanyl; Me; H; S; Ph; 4-Ph-Ph]; [2709; O; 5-Indanyl; Me; H; S; Ph; 2-Naphthyl]; [2710; O; 5-Indanyl; Me; H; S; Ph; 5-Indanyl]; [2711; O; 5-Benzodioxolyl; Me; H; S; Ph; 2-F-Ph]; [2712; O; 5-Benzodioxolyl; Me; H; S; Ph; 3-F-Ph]; [2713; O; 5-Benzodioxolyl; Me; H; S; Ph; 4-F-Ph]; [2714; O; 5-Benzodioxolyl; Me; H; S; Ph; 4-Cl-Ph]; [2715; O; 5-Benzodioxolyl; Me; H; S; Ph; 3-Me-Ph]; [2716; O; 5-Benzodioxolyl; Me; H; S; Ph; 4-Me-Ph]; [2717; O; 5-Benzodioxolyl; Me; H; S; Ph; 4-iPr-Ph]; [2718; O; 5-Benzodioxolyl; Me; H; S; Ph; 4-Ph-Ph]; [2719; O; 5-Benzodioxolyl; Me; H; S; Ph; 2-Naphthyl]; [2720; O; 5-Benzodioxolyl; Me; H; S; Ph; 5-Indanyl]; [2721; O; Ph; H; Me; S; Cyclohexylmethyl; 2-F-Ph]; [2722; O; Ph; H; Me; S; Cyclohexylmethyl; 3-F-Ph]; [2723; O; Ph; H; Me; S; Cyclohexylmethyl; 4-F-Ph]; [2724; O; Ph; H; Me; S; Cyclohexylmethyl; 4-Cl-Ph]; [2725; O; Ph; H; Me; S; Cyclohexylmethyl; 3-Me-Ph]; [2726; O; Ph; H; Me; S; Cyclohexylmethyl; 4-Me-Ph]; [2727; O; Ph; H; Me; S; Cyclohexylmethyl; 4-iPr-Ph]; [2728; O; Ph; H; Me; S; Cyclohexylmethyl; 4-Ph-Ph]; [2729; O; Ph; H; Me; S; Cyclohexylmethyl; 2-Naphthyl]; [2730; O; Ph; H; Me; S; Cyclohexylmethyl; 5-Indanyl]; [2731; O; Ph; H; Me; S; 2-Perhydronaphthyl; 2-F-Ph]; [2732; O; Ph; H; Me; S; 2-Perhydronaphthyl; 3-F-Ph]; [2733; O; Ph; H; Me; S; 2-Perhydronaphthyl; 4-F-Ph]; [2734; O; Ph; H; Me; S; 2-Perhydronaphthyl; 4-Cl-Ph]; [2735; O; Ph; H; Me; S; 2-Perhydronaphthyl; 3-Me-Ph]; [2736; O; Ph; H; Me; S; 2-Perhydronaphthyl; 4-Me-Ph]; [2737; O; Ph; H; Me; S; 2-Perhydronaphthyl; 4-iPr-Ph]; [2738; O; Ph; H; Me; S; 2-Perhydronaphthyl; 4-Ph-Ph]; [2739; O; Ph; H; Me; S; 2-Perhydronaphthyl; 2-Naphthyl]; [2740; O; Ph; H; Me; S; 2-Perhydronaphthyl; 5-Indanyl]; [2741; O; Ph; H; Me; S; 4-F-Ph; 2-F-Ph]; [2742; O; Ph; H; Me; S; 4-F-Ph; 3-F-Ph]; [2743; O; Ph; H; Me; S; 4-F-Ph; 4-F-Ph]; [2744; O; Ph; H; Me; S; 4-F-Ph; 4-Cl-Ph]; [2745; O; Ph; H; Me; S; 4-F-Ph; 3-Me-Ph]; [2746; O; Ph; H; Me; S; 4-F-Ph; 4-Me-Ph]; [2747; O; Ph; H; Me; S; 4-F-Ph; 4-iPr-Ph]; [2748; O; Ph; H; Me; S; 4-F-Ph; 4-Ph-Ph]; [2749; O; Ph; H; Me; S; 4-F-Ph; 2-Naphthyl]; [2750; O; Ph; H; Me; S; 4-F-Ph; 5-Indanyl]; [2751; O; Ph; H; Me; S; 2-Naphthyl; 2-F-Ph]; [2752; O; Ph; H; Me; S; 2-Naphthyl; 3-F-Ph]; [2753; O; Ph; H; Me; S; 2-Naphthyl; 4-F-Ph]; [2754; O; Ph; H; Me; S; 2-Naphthyl; 4-Cl-Ph]; [2755; O; Ph; H; Me; S; 2-Naphthyl; 3-Me-Ph]; [2756; O; Ph; H; Me; S; 2-Naphthyl; 4-Me-Ph]; [2757; O; Ph; H; Me; S; 2-Naphthyl; 4-iPr-Ph]; [2758; O; Ph; H; Me; S; 2-Naphthyl; 4-Ph-Ph]; [2759; O; Ph; H; Me; S; 2-Naphthyl; 2-Naphthyl]; [2760; O; Ph; H; Me; S; 2-Naphthyl; 5-Indanyl]; [2761; O; 4-F-Ph; H; Me; S; Cyclohexylmethyl; 4-F-Ph]; [2762; O; 4-F-Ph; H; Me; S; Cyclohexylmethyl; 4-Cl-Ph]; [2763; O; 4-F-Ph; H; Me; S; Cyclohexylmethyl; 4-Me-Ph]; [2764; O; 4-F-Ph; H; Me; S; Cyclohexylmethyl; 4-Ph-Ph]; [2765; O; 4-F-Ph; H; Me; S; Cyclohexylmethyl; 2-Naphthyl]; [2766; O; 4-Cl-Ph; H; Me; S; Cyclohexylmethyl; 4-F-Ph]; [2767; O; 4-Cl-Ph; H; Me; S; Cyclohexylmethyl; 4-Cl-Ph]; [2768; O; 4-Cl-Ph; H; Me; S; Cyclohexylmethyl; 4-Me-Ph]; [2769; O; 4-Cl-Ph; H; Me; S; Cyclohexylmethyl; 4-Ph-Ph]; [2770; O; 4-Cl-Ph; H; Me; S; Cyclohexylmethyl; 2-Naphthyl]; [2771; O; 4-Me-Ph; H; Me; S; Cyclohexylmethyl; 4-F-Ph]; [2772; O; 4-Me-Ph; H; Me; S; Cyclohexylmethyl; 4-Cl-Ph]; [2773; O; 4-Me-Ph; H; Me; S; Cyclohexylmethyl; 4-Me-Ph]; [2774; O; 4-Me-Ph; H; Me; S; Cyclohexylmethyl; 4-Ph-Ph]; [2775; O; 4-Me-Ph; H; Me; S; Cyclohexylmethyl; 2-Naphthyl]; [2776; O; 2-Naphthyl; H; Me; S; Cyclohexylmethyl; 4-F-Ph]; [2777; O; 2-Naphthyl; H; Me; S; Cyclohexylmethyl; 4-Cl-Ph]; [2778; O; 2-Naphthyl; H; Me; S; Cyclohexylmethyl; 4-Me-Ph]; [2779; O; 2-Naphthyl; H; Me; S; Cyclohexylmethyl; 4-Ph-Ph]; [2780; O; 2-Naphthyl; H; Me; S; Cyclohexylmethyl; 2-Naphthyl]; [2781; O; 5-Indanyl; H; Me; S; Cyclohexylmethyl; 4-F-Ph]; [2782; O; 5-Indanyl; H; Me; S; Cyclohexylmethyl; 4-Cl-Ph]; [2783; O; 5-Indanyl; H; Me; S; Cyclohexylmethyl; 4-Me-Ph]; [2784; O; 5-Indanyl; H; Me; S; Cyclohexylmethyl; 4-Ph-Ph]; [2785; O; 5-Indanyl; H; Me; S; Cyclohexylmethyl; 2-Naphthyl]; [2786; O; 5-Benzodioxolyl; H; Me; S; Cyclohexylmethyl; 4-F-Ph]; [2787; O; 5-Benzodioxolyl; H; Me; S; Cyclohexylmethyl; 4-Cl-Ph]; [2788; O; 5-Benzodioxolyl; H; Me; S; Cyclohexylmethyl; 4-Me-Ph]; [2789; O; 5-Benzodioxolyl; H; Me; S; Cyclohexylmethyl; 4-Ph-Ph]; [2790; O; 5-Benzodioxolyl; H; Me; S; Cyclohexylmethyl; 2-Naphthyl];

[2791; O; 4-F-Ph; H; Me; S; 2-Perhydronaphthyl; 4-F-Ph]; [2792; O; 4-F-Ph; H; Me; S; 2-Perhydronaphthyl; 4-Cl-Ph]; [2793; O; 4-F-Ph; H; Me; S; 2-Perhydronaphthyl; 4-Me-Ph]; [2794; O; 4-F-Ph; H; Me; S; 2-Perhydronaphthyl; 4-Ph-Ph]; [2795; O; 4-F-Ph; H; Me; S; 2-Perhydronaphthyl; 2-Naphthyl]; [2796; O; 4-Cl-Ph; H; Me; S; 2-Perhydronaphthyl; 4-F-Ph]; [2797; O; 4-Cl-Ph; H; Me; S; 2-Perhydronaphthyl; 4-Cl-Ph]; [2798; O; 4-Cl-Ph; H; Me; S; 2-Perhydronaphthyl; 4-Me-Ph]; [2799; O; 4-Cl-Ph; H; Me; S; 2-Perhydronaphthyl; 4-Ph-Ph]; [2800; O; 4-Cl-Ph; H; Me; S; 2-Perhydronaphthyl; 2-Naphthyl]; [2801; O; 4-Me-Ph; H; Me; S; 2-Perhydronaphthyl; 4-F-Ph]; [2802; O; 4-Me-Ph; H; Me; S; 2-Perhydronaphthyl; 4-Cl-Ph]; [2803; O; 4-Me-Ph; H; Me; S; 2-Perhydronaphthyl; 4-Me-Ph]; [2804; O; 4-Me-Ph; H; Me; S; 2-Perhydronaphthyl; 4-Ph-Ph]; [2805; O; 4-Me-Ph; H; Me; S; 2-Perhydronaphthyl; 2-Naphthyl]; [2806; O; 2-Naphthyl; H; Me; S; 2-Perhydronaphthyl; 4-F-Ph]; [2807; O; 2-Naphthyl; H; Me; S; 2-Perhydronaphthyl; 4-Cl-Ph]; [2808; O; 2-Naphthyl; H; Me; S; 2-Perhydronaphthyl; 4-Me-Ph]; [2809; O; 2-Naphthyl; H; Me; S; 2-Perhydronaphthyl; 4-Ph-Ph]; [2810; O; 2-Naphthyl; H; Me; S; 2-Perhydronaphthyl; 2-Naphthyl]; [2811; O; 5-Indanyl; H; Me; S; 2-Perhydronaphthyl; 4-F-Ph]; [2812; O; 5-Indanyl; H; Me; S; 2-Perhydronaphthyl; 4-Cl-Ph]; [2813; O; 5-Indanyl; H; Me; S; 2-Perhydronaphthyl; 4-Me-Ph]; [2814; O; 5-Indanyl; H; Me; S; 2-Perhydronaphthyl; 4-Ph-Ph]; [2815; O; 5-Indanyl; H; Me; S; 2-Perhydronaphthyl; 2-Naphthyl]; [2816; O; 5-Benzodioxolyl; H; Me; S; 2-Perhydronaphthyl; 4-F-Ph]; [2817; O; 5-Benzodioxolyl; H; Me; S; 2-Perhydronaphthyl; 4-Cl-Ph]; [2818; O; 5-Benzodioxolyl; H; Me; S; 2-Perhydronaphthyl; 4-Me-Ph]; [2819; O; 5-Benzodioxolyl; H; Me; S; 2-Perhydronaphthyl; 4-Ph-Ph]; [2820; O; 5-Benzodioxolyl; H; Me; S; 2-Perhydronaphthyl; 2-Naphthyl]; [2821; O; 4-F-Ph; H; Me; S; PhCH$_2$; 4-F-Ph]; [2822; O; 4-F-Ph; H; Me; S; PhCH$_2$; 4-Cl-Ph]; [2823; O; 4-F-Ph; H; Me; S; PhCH$_2$; 4-Me-Ph]; [2824; O; 4-F-Ph; H; Me; S; PhCH$_2$; 4-Ph-Ph]; [2825; O; 4-F-Ph; H; Me; S; PhCH$_2$; 2-Naphthyl]; [2826; O; 4-Cl-Ph; H; Me; S; PhCH$_2$; 4-F-Ph]; [2827; O; 4-Cl-Ph; H; Me; S; PhCH$_2$; 4-Cl-Ph]; [2828; O; 4-Cl-Ph; H; Me; S; PhCH$_2$; 4-Me-Ph]; [2829; O; 4-Cl-Ph; H; Me; S; PhCH$_2$; 4-Ph-Ph]; [2830; O; 4-Cl-Ph; H; Me; S; PhCH$_2$; 2-Naphthyl]; [2831; O; 4-Me-Ph; H; Me; S; PhCH$_2$; 4-F-Ph]; [2832; O; 4-Me-Ph; H; Me; S; PhCH$_2$; 4-Cl-Ph]; [2833; O; 4-Me-Ph; H; Me; S; PhCH$_2$; 4-Me-Ph]; [2834; O; 4-Me-Ph; H; Me; S; PhCH$_2$; 4-Ph-Ph]; [2835; O; 4-Me-Ph; H; Me; S; PhCH$_2$; 2-Naphthyl]; [2836; O; 2-Naphthyl; H; Me; S; PhCH$_2$; 4-F-Ph]; [2837; O; 2-Naphthyl; H; Me; S; PhCH$_2$; 4-Cl-Ph]; [2838; O; 2-Naphthyl; H; Me; S; PhCH$_2$; 4-Me-Ph]; [2839; O; 2-Naphthyl; H; Me; S; PhCH$_2$; 4-Ph-Ph]; [2840; O; 2-Naphthyl; H; Me; S; PhCH$_2$; 2-Naphthyl]; [2841; O; 5-Indanyl; H; Me; S; PhCH$_2$; 4-F-Ph]; [2842; O; 5-Indanyl; H; Me; S; PhCH$_2$; 4-Cl-Ph]; [2843; O; 5-Indanyl; H; Me; S; PhCH$_2$; 4-Me-Ph]; [2844; O; 5-Indanyl; H; Me; S; PhCH$_2$; 4-Ph-Ph]; [2845; O; 5-Indanyl; H; Me; S; PhCH$_2$; 2-Naphthyl]; [2846; O; 5-Benzodioxolyl; H; Me; S; PhCH$_2$; 4-F-Ph]; [2847; O; 5-Benzodioxolyl; H; Me; S; PhCH$_2$; 4-Cl-Ph]; [2848; O; 5-Benzodioxolyl; H; Me; S; PhCH$_2$; 4-Me-Ph]; [2849; O; 5-Benzodioxolyl; H; Me; S; PhCH$_2$; 4-Ph-Ph]; [2850; O; 5-Benzodioxolyl; H; Me; S; PhCH$_2$; 2-Naphthyl]; [2851; O; 4-F-Ph; H; Me; S; 4-F-Ph; 4-F-Ph]; [2852; O; 4-F-Ph; H; Me; S; 4-F-Ph; 4-Cl-Ph]; [2853; O; 4-F-Ph; H; Me; S; 4-F-Ph; 4-Me-Ph]; [2854; O; 4-F-Ph; H; Me; S; 4-F-Ph; 4-Ph-Ph]; [2855; O; 4-F-Ph; H; Me; S; 4-F-Ph; 2-Naphthyl]; [2856; O; 4-Cl-Ph; H; Me; S; 4-F-Ph; 4-F-Ph]; [2857; O; 4-Cl-Ph; H; Me; S; 4-F-Ph; 4-Cl-Ph]; [2858; O; 4-Cl-Ph; H; Me; S; 4-F-Ph; 4-Me-Ph]; [2859; O; 4-Cl-Ph; H; Me; S; 4-F-Ph; 4-Ph-Ph]; [2860; O; 4-Cl-Ph; H; Me; S; 4-F-Ph; 2-Naphthyl]; [2861; O; 4-Me-Ph; H; Me; S; 4-F-Ph; 4-F-Ph]; [2862; O; 4-Me-Ph; H; Me; S; 4-F-Ph; 4-Cl-Ph]; [2863; O; 4-Me-Ph; H; Me; S; 4-F-Ph; 4-Me-Ph]; [2864; O; 4-Me-Ph; H; Me; S; 4-F-Ph; 4-Ph-Ph]; [2865; O; 4-Me-Ph; H; Me; S; 4-F-Ph; 2-Naphthyl]; [2866; O; 2-Naphthyl; H; Me; S; 4-F-Ph; 4-F-Ph]; [2867; O; 2-Naphthyl; H; Me; S; 4-F-Ph; 4-Cl-Ph]; [2868; O; 2-Naphthyl; H; Me; S; 4-F-Ph; 4-Me-Ph]; [2869; O; 2-Naphthyl; H; Me; S; 4-F-Ph; 4-Ph-Ph]; [2870; O; 2-Naphthyl; H; Me; S; 4-F-Ph; 2-Naphthyl]; [2871; O; 5-Indanyl; H; Me; S; 4-F-Ph; 4-F-Ph]; [2872; O; 5-Indanyl; H; Me; S; 4-F-Ph; 4-Cl-Ph]; [2873; O; 5-Indanyl; H; Me; S; 4-F-Ph; 4-Me-Ph]; [2874; O; 5-Indanyl; H; Me; S; 4-F-Ph; 4-Ph-Ph]; [2875; O; 5-Indanyl; H; Me; S; 4-F-Ph; 2-Naphthyl]; [2876; O; 5-Benzodioxolyl; H; Me; S; 4-F-Ph; 4-F-Ph]; [2877; O; 5-Benzodioxolyl; H; Me; S; 4-F-Ph; 4-Cl-Ph]; [2878; O; 5-Benzodioxolyl; H; Me; S; 4-F-Ph; 4-Me-Ph]; [2879; O; 5-Benzodioxolyl; H; Me; S; 4-F-Ph; 4-Ph-Ph]; [2880; O; 5-Benzodioxolyl; H; Me; S; 4-F-Ph; 2-Naphthyl]; [2881; O; 4-F-Ph; H; Me; S; 4-Cl-Ph; 4-F-Ph]; [2882; O; 4-F-Ph; H; Me; S; 4-Cl-Ph; 4-Cl-Ph]; [2883; O; 4-F-Ph; H; Me; S; 4-Cl-Ph; 4-Me-Ph]; [2884; O; 4-F-Ph; H; Me; S; 4-Cl-Ph; 4-Ph-Ph]; [2885; O; 4-F-Ph; H; Me; S; 4-Cl-Ph; 2-Naphthyl]; [2886; O; 4-Cl-Ph; H; Me; S; 4-Cl-Ph; 4-F-Ph]; [2887; O; 4-Cl-Ph; H; Me; S; 4-Cl-Ph; 4-Cl-Ph]; [2888; O; 4-Cl-Ph; H; Me; S; 4-Cl-Ph; 4-Me-Ph]; [2889; O; 4-Cl-Ph; H; Me; S; 4-Cl-Ph; 4-Ph-Ph]; [2890; O; 4-Cl-Ph; H; Me; S; 4-Cl-Ph; 2-Naphthyl]; [2891; O; 4-Me-Ph; H; Me; S; 4-Cl-Ph; 4-F-Ph]; [2892; O; 4-Me-Ph; H; Me; S; 4-Cl-Ph; 4-Cl-Ph]; [2893; O; 4-Me-Ph; H; Me; S; 4-Cl-Ph; 4-Me-Ph]; [2894; O; 4-Me-Ph; H; Me; S; 4-Cl-Ph; 4-Ph-Ph]; [2895; O; 4-Me-Ph; H; Me; S; 4-Cl-Ph; 2-Naphthyl]; [2896; O; 2-Naphthyl; H; Me; S; 4-Cl-Ph; 4-F-Ph]; [2897; O; 2-Naphthyl; H; Me; S; 4-Cl-Ph; 4-Cl-Ph]; [2898; O; 2-Naphthyl; H; Me; S; 4-Cl-Ph; 4-Me-Ph]; [2899; O; 2-Naphthyl; H; Me; S; 4-Cl-Ph; 4-Ph-Ph]; [2900; O; 2-Naphthyl; H; Me; S; 4-Cl-Ph; 2-Naphthyl]; [2901; O; 5-Indanyl; H; Me; S; 4-Cl-Ph; 4-F-Ph]; [2902; O; 5-Indanyl; H; Me; S; 4-Cl-Ph; 4-Cl-Ph]; [2903; O; 5-Indanyl; H; Me; S; 4-Cl-Ph; 4-Me-Ph]; [2904; O; 5-Indanyl; H; Me; S; 4-Cl-Ph; 4-Ph-Ph]; [2905; O; 5-Indanyl; H; Me; S; 4-Cl-Ph; 2-Naphthyl]; [2906; O; 5-Benzodioxolyl; H; Me; S; 4-Cl-Ph; 4-F-Ph]; [2907; O; 5-Benzodioxolyl; H; Me; S; 4-Cl-Ph; 4-Cl-Ph]; [2908; O; 5-Benzodioxolyl; H; Me; S; 4-Cl-Ph; 4-Me-Ph]; [2909; O; 5-Benzodioxolyl; H; Me; S; 4-Cl-Ph; 4-Ph-Ph]; [2910; O; 5-Benzodioxolyl; H; Me; S; 4-Cl-Ph; 2-Naphthyl]; [2911; O; 4-F-Ph; H; Me; S; 4-Me-Ph; 4-F-Ph]; [2912; O; 4-F-Ph; H; Me; S; 4-Me-Ph; 4-Cl-Ph]; [2913; O; 4-F-Ph; H; Me; S; 4-Me-Ph; 4-Me-Ph]; [2914; O; 4-F-Ph; H; Me; S; 4-Me-Ph; 4-Ph-Ph]; [2915; O; 4-F-Ph; H; Me; S; 4-Me-Ph; 2-Naphthyl]; [2916; O; 4-Cl-Ph; H; Me; S; 4-Me-Ph; 4-F-Ph]; [2917; O; 4-Cl-Ph; H; Me; S; 4-Me-Ph; 4-Cl-Ph]; [2918; O; 4-Cl-Ph; H; Me; S; 4-Me-Ph; 4-Me-Ph]; [2919; O; 4-Cl-Ph; H; Me; S; 4-Me-Ph; 4-Ph-Ph]; [2920; O; 4-Cl-Ph; H; Me; S; 4-Me-Ph; 2-Naphthyl]; [2921; O; 4-Me-Ph; H; Me; S; 4-Me-Ph; 4-F-Ph]; [2922; O; 4-Me-Ph; H; Me; S; 4-Me-Ph; 4-Cl-Ph]; [2923; O; 4-Me-Ph; H; Me; S; 4-Me-Ph; 4-Me-Ph]; [2924; O; 4-Me-Ph; H; Me; S; 4-Me-Ph; 4-Ph-Ph]; [2925; O; 4-Me-Ph; H; Me; S; 4-Me-Ph; 2-Naphthyl]; [2926; O; 2-Naphthyl; H; Me; S; 4-Me-Ph; 4-F-Ph]; [2927; O; 2-Naphthyl; H; Me; S; 4-Me-Ph; 4-Cl-Ph]; [2928; O; 2-Naphthyl; H; Me; S; 4-Me-Ph; 4-Me-Ph]; [2929; O; 2-Naphthyl; H; Me; S; 4-Me-Ph; 4-Ph-Ph]; [2930; O; 2-Naphthyl; H; Me; S; 4-Me-Ph; 2-Naphthyl]; [2931; O; 5-Indanyl; H; Me; S; 4-Me-Ph; 4-F-Ph]; [2932; O; 5-Indanyl; H; Me; S; 4-Me-Ph; 4-Cl-Ph]; [2933; O; 5-Indanyl; H; Me; S; 4-Me-Ph; 4-Me-Ph]; [2934; O; 5-Indanyl; H; Me; S; 4-Me-Ph; 4-Ph-Ph]; [2935; O; 5-Indanyl; H; Me; S; 4-Me-Ph; 2-Naphthyl]; [2936; O; 5-Benzodioxolyl; H; Me; S; 4-Me- Ph; 4-F-Ph]; [2937; O; 5-Benzodioxolyl; H; Me; S; 4-Me-Ph; 4-Cl-Ph]; [2938; O; 5-Benzodioxolyl; H; Me; S; 4-Me-Ph; 4-Me-Ph]; [2939; O; 5-Benzodioxolyl; H; Me; S; 4-Me-Ph; 4-Ph-Ph]; [2940; O; 5-Benzodioxolyl; H; Me; S; 4-Me-Ph; 2-Naphthyl]; [2941; O; 4-F-Ph; H; Me; S; 2-Naphthyl; 4-F-Ph]; [2942; O; 4-F-Ph; H; Me; S; 2-Naphthyl; 4-Cl-Ph]; [2943; O; 4-F-Ph; H; Me; S; 2-Naphthyl; 4-Me-Ph]; [2944; O; 4-F-Ph; H; Me; S; 2-Naphthyl; 4-Ph-Ph]; [2945; O; 4-F-Ph; H; Me; S; 2-Naphthyl; 2-Naphthyl]; [2946; O; 4-Cl-Ph; H; Me; S; 2-Naphthyl; 4-F-Ph]; [2947; O; 4-Cl-Ph; H; Me; S; 2-Naphthyl; 4-Cl-Ph]; [2948; O; 4-Cl-Ph; H; Me; S; 2-Naphthyl; 4-Me-Ph]; [2949; O; 4-Cl-Ph; H; Me; S; 2-Naphthyl; 4-Ph-Ph]; [2950; O; 4-Cl-Ph; H; Me; S; 2-Naphthyl; 2-Naphthyl]; [2951; O; 4-Me-Ph; H; Me; S; 2-Naphthyl; 4-F-Ph]; [2952; O; 4-Me-Ph; H; Me; S; 2-Naphthyl; 4-Cl-Ph]; [2953; O; 4-Me-Ph; H; Me; S; 2-Naphthyl; 4-Me-Ph]; [2954; O; 4-Me-Ph; H; Me; S; 2-Naphthyl; 4-Ph-Ph]; [2955; O; 4-Me-Ph; H; Me; S; 2-Naphthyl; 2-Naphthyl]; [2956; O; 2-Naphthyl; H; Me; S; 2-Naphthyl; 4-F-Ph]; [2957; O; 2-Naphthyl; H; Me; S; 2-Naphthyl; 4-Cl-Ph]; [2958; O; 2-Naphthyl; H; Me; S; 2-Naphthyl; 4-Me-Ph]; [2959; O; 2-Naphthyl; H; Me; S; 2-Naphthyl; 4-Ph-Ph]; [2960; O; 2-Naphthyl; H; Me; S; 2-Naphthyl; 2-Naphthyl]; [2961; O; 5-Indanyl; H; Me; S; 2-Naphthyl; 4-F-Ph]; [2962; O; 5-Indanyl; H; Me; S; 2-Naphthyl; 4-Cl-Ph]; [2963; O; 5-Indanyl; H; Me; S; 2-Naphthyl; 4-Me-Ph]; [2964; O; 5-Indanyl; H; Me; S; 2-Naphthyl; 4-Ph-Ph]; [2965; O; 5-Indanyl; H; Me; S; 2-Naphthyl; 2-Naphthyl]; [2966; O; 5-Benzodioxolyl; H; Me; S; 2-Naphthyl; 4-F-Ph]; [2967; O; 5-Benzodioxolyl; H; Me; S; 2-Naphthyl; 4-Cl-Ph]; [2968; O; 5-Benzodioxolyl; H; Me; S; 2-Naphthyl; 4-Me-Ph]; [2969; O; 5-Benzodioxolyl; H; Me; S; 2-Naphthyl; 4-Ph-Ph]; [2970; O; 5-Benzodioxolyl; H; Me; S; 2-Naphthyl; 2-Naphthyl]; [2971; O; 4-F-Ph; H; Me; S; 5-Indanyl; 4-F-Ph]; [2972; O; 4-F-Ph; H; Me; S; 5-Indanyl; 4-Cl-Ph]; [2973; O; 4-F-Ph; H; Me; S; 5-Indanyl; 4-Me-Ph]; [2974; O; 4-F-Ph; H; Me; S; 5-Indanyl; 4-Ph-Ph]; [2975; O; 4-F-Ph; H; Me; S; 5-Indanyl; 2-Naphthyl]; [2976; O; 4-Cl-Ph; H; Me; S; 5-Indanyl; 4-F-Ph]; [2977; O; 4-Cl-Ph; H; Me; S; 5-Indanyl; 4-Cl-Ph]; [2978; O; 4-Cl-Ph; H; Me; S; 5-Indanyl; 4-Me-Ph]; [2979; O; 4-Cl-Ph; H; Me; S; 5-Indanyl; 4-Ph-Ph]; [2980; O; 4-Cl-Ph; H; Me; S; 5-Indanyl; 2-Naphthyl]; [2981; O; 4-Me-Ph; H; Me; S; 5-Indanyl; 4-F-Ph]; [2982; O; 4-Me-Ph; H; Me; S; 5-Indanyl; 4-Cl-Ph]; [2983; O; 4-Me-Ph; H; Me; S; 5-Indanyl; 4-Me-Ph]; [2984; O; 4-Me-Ph; H; Me; S; 5-Indanyl; 4-Ph-Ph]; [2985; O; 4-Me-Ph; H; Me; S; 5-Indanyl; 2-Naphthyl]; [2986; O; Ph; Me; Me; S; Ph; Ph]; [2987; O; Ph; Ph; Me; S; Ph; Ph]; [2988; O; Ph; Me; Ph; S; Ph; Ph]; [2989; O; Ph; Ph; Ph; S; Ph; Ph]; [2990; O; Ph; CF$_3$; Me; S; Ph; Ph]; [2991; O; Ph; Me; Me; S; Cyclohexylmethyl; Ph]; [2992; O; Ph; Ph; Me; S; Cyclohexylmethyl; Ph]; [2993; O; Ph; Me; Ph; S; Cyclohexylmethyl; Ph]; [2994; O; Ph; Ph; Ph; S; Cyclohexylmethyl; Ph]; [2995; O; Ph; CF$_3$; Me; S; Cyclohexylmethyl; Ph]; [2996; O; 4-F-Ph; Me; Me; S; Ph; 4-F-Ph]; [2997; O; 4-F-Ph; Ph; Me; S; Ph; 4-F-Ph]; [2998; O; 4-F-Ph; Me; Ph; S; Ph; 4-F-Ph]; [2999; O; 4-F-Ph; Ph; Ph; S; Ph; 4-F-Ph]; [3000; O; 4-F-Ph; CF$_3$; Me; S; Ph; 4-F-Ph]; [3001; S; Ph; H; Me; O; Ph; Ph]; [3002; S; 3-F-Ph; H; Me; O; Ph; Ph]; [3003; S; 4-F-Ph; H; Me; O; Ph; Ph]; [3004; S; 3-Cl-Ph; H; Me; O; Ph; Ph]; [3005; S; 4-Cl-Ph; H; Me; O; Ph; Ph]; [3006; S; 3-Me-Ph; H; Me; O; Ph; Ph]; [3007; S; 4-Me-Ph; H; Me; O; Ph; Ph]; [3008; S; 2-Naphthyl; H; Me; O; Ph; Ph]; [3009; S; 5-Indanyl; H; Me; O; Ph; Ph]; [3010; S; 5-Benzodioxolyl; H; Me; O; Ph; Ph]; [3011; S; Ph; H; Ph; O; Ph; Ph]; [3012; S; 3-F-Ph; H; Ph; O; Ph; Ph]; [3013; S; 4-F-Ph; H; Ph; O; Ph; Ph]; [3014; S; 3-Cl-Ph; H; Ph; O; Ph; Ph]; [3015; S; 4-Cl-Ph; H; Ph; O; Ph; Ph]; [3016; S; 3-Me-Ph; H; Ph; O; Ph; Ph]; [3017; S; 4-Me-Ph; H; Ph; O; Ph; Ph]; [3018; S; 2-Naphthyl; H; Ph; O; Ph; Ph]; [3019; S; 5-Indanyl; H; Ph; O; Ph; Ph]; [3020; S; 5-Benzodioxolyl; H; Ph; O; Ph; Ph]; [3021; S; Ph; Me; H; O; Ph; Ph]; [3022; S; 3-F-Ph; Me; H; O; Ph; Ph]; [3023; S; 4-F-Ph; Me; H; O; Ph; Ph]; [3024; S; 3-Cl-Ph; Me; H; O; Ph; Ph]; [3025; S; 4-Cl-Ph; Me; H; O; Ph; Ph]; [3026; S; 3-Me-Ph; Me; H; O; Ph; Ph]; [3027; S; 4-Me-Ph; Me; H; O; Ph; Ph]; [3028; S; 2-Naphthyl; Me; H; O; Ph; Ph]; [3029; S; 5-Indanyl; Me; H; O; Ph; Ph]; [3030; S; 5-Benzodioxolyl; Me; H; O; Ph; Ph]; [3031; S; Ph; Ph; H; O; Ph; Ph]; [3032; S; 3-F-Ph; Ph; H; O; Ph; Ph]; [3033; S; 4-F-Ph; Ph; H; O; Ph; Ph]; [3034; S; 3-Cl-Ph; Ph; H; O; Ph; Ph]; [3035; S; 4-Cl-Ph; Ph; H; O; Ph; Ph]; [3036; S; 3-Me-Ph; Ph; H; O; Ph; Ph]; [3037; S; 4-Me-Ph; Ph; H; O; Ph; Ph]; [3038; S; 2-Naphthyl; Ph; H; O; Ph; Ph]; [3039; S; 5-Indanyl; Ph; H; O; Ph; Ph]; [3040; S; 5-Benzodioxolyl; Ph; H; O; Ph; Ph]; [3041; S; Ph; H; Me; O; Bu; Ph]; [3042; S; Ph; H; Me; O; Isopentyl; Ph]; [3043; S; Ph; H; Me; O; Cyclohexyl; Ph]; [3044; S; Ph; H; Me; O; Cyclohexylmethyl; Ph]; [3045; S; Ph; H; Me; O; 2-Perhydronaphthyl; Ph]; [3046; S; Ph; H; Me; O; PhCH$_2$; Ph]; [3047; S; Ph; H; Me; O; 4-F-Ph; Ph]; [3048; S; Ph; H; Me; O; 4-Cl-Ph; Ph]; [3049; S; Ph; H; Me; O; 4-Me-Ph; Ph]; [3050; S; Ph; H; Me; O; 2-Naphthyl; Ph]; [3051; S; Ph; H; Ph; O; Bu; Ph]; [3052; S; Ph; H; Ph; O; Isopentyl; Ph]; [3053; S; Ph; H; Ph; O; Cyclohexyl; Ph]; [3054; S; Ph; H; Ph; O; Cyclohexylmethyl; Ph]; [3055; S; Ph; H; Ph; O; 2-Perhydronaphthyl; Ph]; [3056; S; Ph; H; Ph; O; PhCH$_2$; Ph]; [3057; S; Ph; H; Ph; O; 4-F-Ph; Ph]; [3058; S; Ph; H; Ph; O; 4-Cl-Ph; Ph]; [3059; S; Ph; H; Ph; O; 4-Me-Ph; Ph]; [3060; S; Ph; H; Ph; O; 2-Naphthyl; Ph]; [3061; S; Ph; Me; H; O; Bu; Ph]; [3062; S; Ph; Me; H; O; Isopentyl; Ph]; [3063; S; Ph; Me; H; O; Cyclohexyl; Ph]; [3064; S; Ph; Me; H; O; Cyclohexylmethyl; Ph]; [3065; S; Ph; Me; H; O; 2-Perhydronaphthyl; Ph]; [3066; S; Ph; Me; H; O; PhCH$_2$; Ph]; [3067; S; Ph; Me; H; O; 4-F-Ph; Ph]; [3068; S; Ph; Me; H; O; 4-Cl-Ph; Ph]; [3069; S; Ph; Me; H; O; 4-Me-Ph; Ph]; [3070; S; Ph; Me; H; O; 2-Naphthyl; Ph]; [3071; S; Ph; Ph; H; O; Bu; Ph]; [3072; S; Ph; Ph; H; O; Isopentyl; Ph]; [3073; S; Ph; Ph; H; O; Cyclohexyl; Ph]; [3074; S; Ph; Ph; H; O; Cyclohexylmethyl; Ph]; [3075; S; Ph; Ph; H; O; 2-Perhydronaphthyl; Ph]; [3076; S; Ph; Ph; H; O; PhCH$_2$; Ph]; [3077; S; Ph; Ph; H; O; 4-F-Ph; Ph]; [3078; S; Ph; Ph; H; O; 4-Cl-Ph; Ph]; [3079; S; Ph; Ph; H; O; 4-Me-Ph; Ph]; [3080; S; Ph; Ph; H; O; 2-Naphthyl; Ph]; [3081; S; Ph; H; Me; O; Ph; 2-F-Ph]; [3082; S; Ph; H; Me; O; Ph; 3-F-Ph]; [3083; S; Ph; H; Me; O; Ph; 4-F-Ph]; [3084; S; Ph; H; Me; O; Ph; 4-Cl-Ph]; [3085; S; Ph; H; Me; O; Ph; 3-Me-Ph]; [3086; S; Ph; H; Me; O; Ph; 4-Me-Ph]; [3087; S; Ph; H; Me; O; Ph; 4-iPr-Ph]; [3088; S; Ph; H; Me; O; Ph; 4-Ph-Ph]; [3089; S; Ph; H; Me; O; Ph; 2-Naphthyl]; [3090; S; Ph; H; Me; O; Ph; 5-Indanyl]; [3091; S; Ph; H; Ph; O; Ph; 2-F-Ph]; [3092; S; Ph; H; Ph; O; Ph; 3-F-Ph]; [3093; S; Ph; H; Ph; O; Ph; 4-F-Ph]; [3094; S; Ph; H; Ph; O; Ph; 4-Cl-Ph]; [3095; S; Ph; H; Ph; O; Ph; 3-Me-Ph]; [3096; S; Ph; H; Ph; O; Ph; 4-Me-Ph]; [3097; S; Ph; H; Ph; O; Ph; 4-iPr-Ph]; [3098; S; Ph; H; Ph; O; Ph; 4-Ph-Ph]; [3099; S; Ph; H; Ph; O; Ph; 2-Naphthyl]; [3100; S; Ph; H; Ph; O; Ph; 5-Indanyl]; [3101; S; Ph; Me; H; O; Ph; 2-F-Ph]; [3102; S; Ph; Me; H; O; Ph; 3-F-Ph]; [3103; S; Ph; Me; H; O; Ph; 4-F-Ph]; [3104; S; Ph; Me; H; O; Ph; 4-Cl-Ph]; [3105; S; Ph; Me; H; O; Ph; 3-Me-Ph]; [3106; S; Ph; Me; H; O; Ph; 4-Me-Ph]; [3107; S; Ph; Me; H; O; Ph; 4-iPr-Ph]; [3108; S; Ph; Me; H; O; Ph; 4-Ph-Ph]; [3109; S; Ph; Me; H; O; Ph; 2-Naphthyl]; [3110; S; Ph; Me; H; O; Ph; 5-Indanyl]; [3111; S; Ph; Ph; H; O; Ph; 2-F-Ph]; [3112; S; Ph; Ph; H; O; Ph; 3-F-Ph]; [3113; S; Ph; Ph; H; O; Ph; 4-F-Ph]; [3114; S; Ph; Ph; H; O; Ph; 4-Cl-Ph]; [3115; S; Ph; Ph; H; O; Ph; 3-Me-Ph]; [3116; S; Ph; Ph; H; O; Ph; 4-Me-Ph]; [3117; S; Ph; Ph; H; O; Ph; 4-iPr-Ph]; [3118; S; Ph; Ph; H; O; Ph; 4-Ph-Ph]; [3119; S; Ph; Ph; H; O; Ph; 2-Naphthyl]; [3120; S;

Ph; Ph; H; O; Ph; 5-Indanyl]; [3121; S; 4-F-Ph; H; Me; O; Ph; 2-F-Ph]; [3122; S; 4-F-Ph; H; Me; O; Ph; 3-F-Ph]; [3123; S; 4-F-Ph; H; Me; O; Ph; 4-F-Ph]; [3124; S; 4-F-Ph; H; Me; O; Ph; 4-Cl-Ph]; [3125; S; 4-F-Ph; H; Me; O; Ph; 3-Me-Ph]; [3126; S; 4-F-Ph; H; Me; O; Ph; 4-Me-Ph]; [3127; S; 4-F-Ph; H; Me; O; Ph; 4-iPr-Ph]; [3128; S; 4-F-Ph; H; Me; O; Ph; 4-Ph-Ph]; [3129; S; 4-F-Ph; H; Me; O; Ph; 2-Naphthyl]; [3130; S; 4-F-Ph; H; Me; O; Ph; 5-Indanyl]; [3131; S; 4-Cl-Ph; H; Me; O; Ph; 2-F-Ph]; [3132; S; 4-Cl-Ph; H; Me; O; Ph; 3-F-Ph]; [3133; S; 4-Cl-Ph; H; Me; O; Ph; 4-F-Ph]; [3134; S; 4-Cl-Ph; H; Me; O; Ph; 4-Cl-Ph]; [3135; S; 4-Cl-Ph; H; Me; O; Ph; 3-Me-Ph]; [3136; S; 4-Cl-Ph; H; Me; O; Ph; 4-Me-Ph]; [3137; S; 4-Cl-Ph; H; Me; O; Ph; 4-iPr-Ph]; [3138; S; 4-Cl-Ph; H; Me; O; Ph; 4-Ph-Ph]; [3139; S; 4-Cl-Ph; H; Me; O; Ph; 2-Naphthyl]; [3140; S; 4-Cl-Ph; H; Me; O; Ph; 5-Indanyl]; [3141; S; 4-Me-Ph; H; Me; O; Ph; 2-F-Ph]; [3142; S; 4-Me-Ph; H; Me; O; Ph; 3-F-Ph]; [3143; S; 4-Me-Ph; H; Me; O; Ph; 4-F-Ph]; [3144; S; 4-Me-Ph; H; Me; O; Ph; 4-Cl-Ph]; [3145; S; 4-Me-Ph; H; Me; O; Ph; 3-Me-Ph]; [3146; S; 4-Me-Ph; H; Me; O; Ph; 4-Me-Ph]; [3147; S; 4-Me-Ph; H; Me; O; Ph; 4-iPr-Ph]; [3148; S; 4-Me-Ph; H; Me; O; Ph; 4-Ph-Ph]; [3149; S; 4-Me-Ph; H; Me; O; Ph; 2-Naphthyl]; [3150; S; 4-Me-Ph; H; Me; O; Ph; 5-Indanyl]; [3151; S; 5-Indanyl; H; Me; O; Ph; 2-F-Ph]; [3152; S; 5-Indanyl; H; Me; O; Ph; 3-F-Ph]; [3153; S; 5-Indanyl; H; Me; O; Ph; 4-F-Ph]; [3154; S; 5-Indanyl; H; Me; O; Ph; 4-Cl-Ph]; [3155; S; 5-Indanyl; H; Me; O; Ph; 3-Me-Ph]; [3156; S; 5-Indanyl; H; Me; O; Ph; 4-Me-Ph]; [3157; S; 5-Indanyl; H; Me; O; Ph; 4-iPr-Ph]; [3158; S; 5-Indanyl; H; Me; O; Ph; 4-Ph-Ph]; [3159; S; 5-Indanyl; H; Me; O; Ph; 2-Naphthyl]; [3160; S; 5-Indanyl; H; Me; O; Ph; 5-Indanyl]; [3161; S; 2-Naphthyl; H; Me; O; Ph; 2-F-Ph]; [3162; S; 2-Naphthyl; H; Me; O; Ph; 3-F-Ph]; [3163; S; 2-Naphthyl; H; Me; O; Ph; 4-F-Ph]; [3164; S; 2-Naphthyl; H; Me; O; Ph; 4-Cl-Ph]; [3165; S; 2-Naphthyl; H; Me; O; Ph; 3-Me-Ph]; [3166; S; 2-Naphthyl; H; Me; O; Ph; 4-Me-Ph]; [3167; S; 2-Naphthyl; H; Me; O; Ph; 4-iPr-Ph]; [3168; S; 2-Naphthyl; H; Me; O; Ph; 4-Ph-Ph]; [3169; S; 2-Naphthyl; H; Me; O; Ph; 2-Naphthyl]; [3170; S; 2-Naphthyl; H; Me; O; Ph; 5-Indanyl]; [3171; S; 5-Benzodioxolyl; H; Me; O; Ph; 2-F-Ph]; [3172; S; 5-Benzodioxolyl; H; Me; O; Ph; 3-F-Ph]; [3173; S; 5-Benzodioxolyl; H; Me; O; Ph; 4-F-Ph]; [3174; S; 5-Benzodioxolyl; H; Me; O; Ph; 4-Cl-Ph]; [3175; S; 5-Benzodioxolyl; H; Me; O; Ph; 3-Me-Ph]; [3176; S; 5-Benzodioxolyl; H; Me; O; Ph; 4-Me-Ph]; [3177; S; 5-Benzodioxolyl; H; Me; O; Ph; 4-iPr-Ph]; [3178; S; 5-Benzodioxolyl; H; Me; O; Ph; 4-Ph-Ph]; [3179; S; 5-Benzodioxolyl; H; Me; O; Ph; 2-Naphthyl]; [3180; S; 5-Benzodioxolyl; H; Me; O; Ph; 5-Indanyl]; [3181; S; Ph; H; Me; O; Cyclohexylmethyl; 2-F-Ph]; [3182; S; Ph; H; Me; O; Cyclohexylmethyl; 3-F-Ph]; [3183; S; Ph; H; Me; O; Cyclohexylmethyl; 4-F-Ph]; [3184; S; Ph; H; Me; O; Cyclohexylmethyl; 4-Cl-Ph]; [3185; S; Ph; H; Me; O; Cyclohexylmethyl; 3-Me-Ph]; [3186; S; Ph; H; Me; O; Cyclohexylmethyl; 4-Me-Ph]; [3187; S; Ph; H; Me; O; Cyclohexylmethyl; 4-iPr-Ph]; [3188; S; Ph; H; Me; O; Cyclohexylmethyl; 4-Ph-Ph]; [3189; S; Ph; H; Me; O; Cyclohexylmethyl; 2-Naphthyl]; [3190; S; Ph; H; Me; O; Cyclohexylmethyl; 5-Indanyl]; [3191; S; Ph; H; Me; O; 2-Perhydronaphthyl; 2-F-Ph]; [3192; S; Ph; H; Me; O; 2-Perhydronaphthyl; 3-F-Ph]; [3193; S; Ph; H; Me; O; 2-Perhydronaphthyl; 4-F-Ph]; [3194; S; Ph; H; Me; O; 2-Perhydronaphthyl; 4-Cl-Ph]; [3195; S; Ph; H; Me; O; 2-Perhydronaphthyl; 3-Me-Ph]; [3196; S; Ph; H; Me; O; 2-Perhydronaphthyl; 4-Me-Ph]; [3197; S; Ph; H; Me; O; 2-Perhydronaphthyl; 4-iPr-Ph]; [3198; S; Ph; H; Me; O; 2-Perhydronaphthyl; 4-Ph-Ph]; [3199; S; Ph; H; Me; O; 2-Perhydronaphthyl; 2-Naphthyl]; [3200; S; Ph; H; Me; O; 2-Perhydronaphthyl; 5-Indanyl]; [3201; S; Ph; H; Me; O; 4-F-Ph; 2-F-Ph]; [3202; S; Ph; H; Me; O; 4-F-Ph; 3-F-Ph]; [3203; S; Ph; H; Me; O; 4-F-Ph; 4-F-Ph]; [3204; S; Ph; H; Me; O; 4-F-Ph; 4-Cl-Ph]; [3205; S; Ph; H; Me; O; 4-F-Ph; 3-Me-Ph]; [3206; S; Ph; H; Me; O; 4-F-Ph; 4-Me-Ph]; [3207; S; Ph; H; Me; O; 4-F-Ph; 4-iPr-Ph]; [3208; S; Ph; H; Me; O; 4-F-Ph; 4-Ph-Ph]; [3209; S; Ph; H; Me; O; 4-F-Ph; 2-Naphthyl]; [3210; S; Ph; H; Me; O; 4-F-Ph; 5-Indanyl]; [3211; S; Ph; H; Me; O; 2-Naphthyl; 2-F-Ph]; [3212; S; Ph; H; Me; O; 2-Naphthyl; 3-F-Ph]; [3213; S; Ph; H; Me; O; 2-Naphthyl; 4-F-Ph]; [3214; S; Ph; H; Me; O; 2-Naphthyl; 4-Cl-Ph]; [3215; S; Ph; H; Me; O; 2-Naphthyl; 3-Me-Ph]; [3216; S; Ph; H; Me; O; 2-Naphthyl; 4-Me-Ph]; [3217; S; Ph; H; Me; O; 2-Naphthyl; 4-iPr-Ph]; [3218; S; Ph; H; Me; O; 2-Naphthyl; 4-Ph-Ph]; [3219; S; Ph; H; Me; O; 2-Naphthyl; 2-Naphthyl]; [3220; S; Ph; H; Me; O; 2-Naphthyl; 5-Indanyl]; [3221; S; 4-F-Ph; H; Me; O; Cyclohexylmethyl; 4-F-Ph]; [3222; S; 4-F-Ph; H; Me; O; Cyclohexylmethyl; 4-Cl-Ph]; [3223; S; 4-F-Ph; H; Me; O; Cyclohexylmethyl; 4-Me-Ph]; [3224; S; 4-F-Ph; H; Me; O; Cyclohexylmethyl; 4-Ph-Ph]; [3225; S; 4-F-Ph; H; Me; O; Cyclohexylmethyl; 2-Naphthyl]; [3226; S; 4-Me-Ph; H; Me; O; Cyclohexylmethyl; 4-F-Ph]; [3227; S; 4-Me-Ph; H; Me; O; Cyclohexylmethyl; 4-Cl-Ph]; [3228; S; 4-Me-Ph; H; Me; O; Cyclohexylmethyl; 4-Me-Ph]; [3229; S; 4-Me-Ph; H; Me; O; Cyclohexylmethyl; 4-Ph-Ph]; [3230; S; 4-Me-Ph; H; Me; O; Cyclohexylmethyl; 2-Naphthyl]; [3231; S; 2-Naphthyl; H; Me; O; Cyclohexylmethyl; 4-F-Ph]; [3232; S; 2-Naphthyl; H; Me; O; Cyclohexylmethyl; 4-Cl-Ph]; [3233; S; 2-Naphthyl; H; Me; O; Cyclohexylmethyl; 4-Me-Ph]; [3234; S; 2-Naphthyl; H; Me; O; Cyclohexylmethyl; 4-Ph-Ph]; [3235; S; 2-Naphthyl; H; Me; O; Cyclohexylmethyl; 2-Naphthyl]; [3236; S; 5-Benzodioxolyl; H; Me; O; Cyclohexylmethyl; 4-F-Ph]; [3237; S; 5-Benzodioxolyl; H; Me; O; Cyclohexylmethyl; 4-Cl-Ph]; [3238; S; 5-Benzodioxolyl; H; Me; O; Cyclohexylmethyl; 4-Me-Ph]; [3239; S; 5-Benzodioxolyl; H; Me; O; Cyclohexylmethyl; 4-Ph-Ph]; [3240; S; 5-Benzodioxolyl; H; Me; O; Cyclohexylmethyl; 2-Naphthyl]; [3241; S; 4-F-Ph; H; Me; O; 2-Perhydronaphthyl; 2-F-Ph]; [3242; S; 4-F-Ph; H; Me; O; 2-Perhydronaphthyl; 3-F-Ph]; [3243; S; 4-F-Ph; H; Me; O; 2-Perhydronaphthyl; 4-F-Ph]; [3244; S; 4-F-Ph; H; Me; O; 2-Perhydronaphthyl; 4-Cl-Ph]; [3245; S; 4-F-Ph; H; Me; O; 2-Perhydronaphthyl; 3-Me-Ph]; [3246; S; 4-Me-Ph; H; Me; O; 2-Perhydronaphthyl; 4-Me-Ph]; [3247; S; 4-Me-Ph; H; Me; O; 2-Perhydronaphthyl; 4-iPr-Ph]; [3248; S; 4-Me-Ph; H; Me; O; 2-Perhydronaphthyl; 4-Ph-Ph]; [3249; S; 4-Me-Ph; H; Me; O; 2-Perhydronaphthyl; 2-Naphthyl]; [3250; S; 4-Me-Ph; H; Me; O; 2-Perhydronaphthyl; 5-Indanyl]; [3251; S; 2-Naphthyl; H; Me; O; 2-Perhydronaphthyl; 2-F-Ph]; [3252; S; 2-Naphthyl; H; Me; O; 2-Perhydronaphthyl; 3-F-Ph]; [3253; S; 2-Naphthyl; H; Me; O; 2-Perhydronaphthyl; 4-F-Ph]; [3254; S; 2-Naphthyl; H; Me; O; 2-Perhydronaphthyl; 4-Cl-Ph]; [3255; S; 2-Naphthyl; H; Me; O; 2-Perhydronaphthyl; 3-Me-Ph]; [3256; S; 5-Benzodioxolyl; H; Me; O; 2-Perhydronaphthyl; 4-Me-Ph]; [3257; S; 5-Benzodioxolyl; H; Me; O; 2-Perhydronaphthyl; 4-iPr-Ph]; [3258; S; 5-Benzodioxolyl; H; Me; O; 2-Perhydronaphthyl; 4-Ph-Ph]; [3259; S; 5-Benzodioxolyl; H; Me; O; 2-Perhydronaphthyl; 2-Naphthyl]; [3260; S; 5-Benzodioxolyl; H; Me; O; 2-Perhydronaphthyl; 5-Indanyl]; [3261; S; 4-F-Ph; H; Me; O; PhCH$_2$; 4-F-Ph]; [3262; S; 4-F-Ph; H; Me; O; PhCH$_2$; 4-Cl-Ph]; [3263; S; 4-F-Ph; H; Me; O; PhCH$_2$; 4-Me-Ph]; [3264; S; 4-F-Ph; H; Me; O; PhCH$_2$; 4-Ph-Ph]; [3265; S; 4-F-Ph; H; Me; O; PhCH$_2$; 2-Naphthyl]; [3266; S; 4-Me-Ph; H; Me; O; PhCH$_2$; 4-F-Ph]; [3267; S; 4-Me-Ph; H; Me; O; PhCH$_2$; 4-Cl-Ph]; [3268; S; 4-Me-Ph; H; Me; O; PhCH$_2$; 4-Me-Ph]; [3269; S; 4-Me-Ph; H; Me; O; PhCH$_2$; 4-Ph-Ph]; [3270; S; 4-Me-Ph; H; Me; O; PhCH$_2$; 2-Naphthyl]; [3271; S; 2-Naphthyl; H; Me; O; PhCH$_2$; 4-F-Ph]; [3272; S; 2-Naphthyl; H; Me; O; PhCH$_2$; 4-Cl-Ph]; [3273; S; 2-Naphthyl; H; Me; O; PhCH$_2$; 4-Me-Ph]; [3274; S; 2-Naphthyl; H; Me; O; PhCH$_2$; 4-Ph-Ph]; [3275; S; 2-Naphthyl; H; Me; O; PhCH$_2$; 2-Naphthyl]; [3276; S; 5-Benzodioxolyl; H; Me; O; PhCH$_2$; 4-F-Ph]; [3277; S; 5-Benzodioxolyl; H; Me; O; PhCH$_2$; 4-Cl-Ph]; [3278; S; 5-Benzodioxolyl; H; Me; O; PhCH$_2$; 4-Me-Ph]; [3279; S; 5-Benzodioxolyl; H; Me; O; PhCH$_2$; 4-Ph-Ph]; [3280; S; 5-Benzodioxolyl; H; Me; O; PhCH$_2$; 2-Naphthyl]; [3281; S; 4-F-Ph; H; Me; O; 3-F-Ph; 2-F-Ph]; [3282; S; 4-F-Ph; H; Me; O; 3-F-Ph; 3-F-Ph]; [3283; S; 4-F-Ph; H; Me; O; 3-F-Ph; 4-F-Ph]; [3284; S; 4-F-Ph; H; Me; O; 3-F-Ph; 4-Cl-Ph]; [3285; S; 4-F-Ph; H; Me; O; 3-F-Ph; 3-Me-Ph]; [3286; S; 4-Me-Ph; H; Me; O; 3-F-Ph; 4-Me-Ph]; [3287; S; 4-Me-Ph; H; Me; O; 3-F-Ph; 4-iPr-Ph]; [3288; S; 4-Me-Ph; H; Me; O; 3-F-Ph; 4-Ph-Ph]; [3289; S; 4-Me-Ph; H; Me; O; 3-F-Ph; 2-Naphthyl]; [3290; S; 4-Me-Ph; H; Me; O; 3-F-Ph; 5-Indanyl]; [3291; S; 2-Naphthyl; H; Me; O; 3-F-Ph; 2-F-Ph]; [3292; S; 2-Naphthyl; H; Me; O; 3-F-Ph; 3-F-Ph]; [3293; S; 2-Naphthyl; H; Me; O; 3-F-Ph; 4-F-Ph]; [3294; S; 2-Naphthyl; H; Me; O; 3-F-Ph; 4-Cl-Ph]; [3295; S; 2-Naphthyl; H; Me; O; 3-F-Ph; 3-Me-Ph]; [3296; S; 5-Benzodioxolyl; H; Me; O; 3-F-Ph; 4-Me-Ph]; [3297; S; 5-Benzodioxolyl; H; Me; O; 3-F-Ph; 4-iPr-Ph]; [3298; S; 5-Benzodioxolyl; H; Me; O; 3-F-Ph; 4-Ph-Ph]; [3299; S; 5-Benzodioxolyl; H; Me; O; 3-F-Ph; 2-Naphthyl]; [3300; S; 5-Benzodioxolyl; H; Me; O; 3-F-Ph; 5-Indanyl]; [3301; S; 4-F-Ph; H; Me; O; 4-F-Ph; 4-F-Ph]; [3302; S; 4-F-Ph; H; Me; O; 4-F-Ph; 4-Cl-Ph]; [3303; S; 4-F-Ph; H; Me; O; 4-F-Ph; 4-Me-Ph]; [3304; S; 4-F-Ph; H; Me; O; 4-F-Ph; 4-Ph-Ph]; [3305; S; 4-F-Ph; H; Me; O; 4-F-Ph; 2-Naphthyl]; [3306; S; 4-Me-Ph; H; Me; O; 4-F-Ph; 4-F-Ph]; [3307; S; 4-Me-Ph; H; Me; O; 4-F-Ph; 4-Cl-Ph]; [3308; S; 4-Me-Ph; H; Me; O; 4-F-Ph; 4-Me-Ph]; [3309; S; 4-Me-Ph; H; Me; O; 4-F-Ph; 4-Ph-Ph]; [3310; S; 4-Me-Ph; H; Me; O; 4-F-Ph; 2-Naphthyl]; [3311; S; 2-Naphthyl; H; Me; O; 4-F-Ph; 4-F-Ph]; [3312; S; 2-Naphthyl; H; Me; O; 4-F-Ph; 4-Cl-Ph]; [3313; S; 2-Naphthyl; H; Me; O; 4-F-Ph; 4-Me-Ph]; [3314; S; 2-Naphthyl; H; Me; O; 4-F-Ph; 4-Ph-Ph]; [3315; S; 2-Naphthyl; H; Me; O; 4-F-Ph; 2-Naphthyl]; [3316; S; 5-Benzodioxolyl; H; Me; O; 4-F-Ph; 4-F-Ph]; [3317; S; 5-Benzodioxolyl; H; Me; O; 4-F-Ph; 4-Cl-Ph]; [3318; S; 5-Benzodioxolyl; H; Me; O; 4-F-Ph; 4-Me-Ph]; [3319; S; 5-Benzodioxolyl; H; Me; O; 4-F-Ph; 4-Ph-Ph]; [3320; S; 5-Benzodioxolyl; H; Me; O; 4-F-Ph; 2-Naphthyl]; [3321; S; 4-F-Ph; H; Me; O; 4-Cl-Ph; 2-F-Ph]; [3322; S; 4-F-Ph; H; Me; O; 4-Cl-Ph; 3-F-Ph]; [3323; S; 4-F-Ph; H; Me; O; 4-Cl-Ph; 4-F-Ph]; [3324; S; 4-F-Ph; H; Me; O; 4-Cl-Ph; 4-Cl-Ph]; [3325; S; 4-F-Ph; H; Me; O; 4-Cl-Ph; 3-Me-Ph]; [3326; S; 4-Me-Ph; H; Me; O; 4-Cl-Ph; 4-Me-Ph]; [3327; S; 4-Me-Ph; H; Me; O; 4-Cl-Ph; 4-iPr-Ph]; [3328; S; 4-Me-Ph; H; Me; O; 4-Cl-Ph; 4-Ph-Ph]; [3329; S; 4-Me-Ph; H; Me; O; 4-Cl-Ph; 2-Naphthyl]; [3330; S; 4-Me-Ph; H; Me; O; 4-Cl-Ph; 5-Indanyl]; [3331; S; 2-Naphthyl; H; Me; O; 4-Cl-Ph; 2-F-Ph]; [3332; S; 2-Naphthyl; H; Me; O; 4-Cl-Ph; 3-F-Ph]; [3333; S; 2-Naphthyl; H; Me; O; 4-Cl-Ph; 4-F-Ph]; [3334; S; 2-Naphthyl; H; Me; O; 4-Cl-Ph; 4-Cl-Ph]; [3335; S; 2-Naphthyl; H; Me; O; 4-Cl-Ph; 3-Me-Ph]; [3336; S; 5-Benzodioxolyl; H; Me; O; 4-Cl-Ph; 4-Me-Ph]; [3337; S; 5-Benzodioxolyl; H; Me; O; 4-Cl-Ph; 4-iPr-Ph]; [3338; S; 5-Benzodioxolyl; H; Me; O; 4-Cl-Ph; 4-Ph-Ph]; [3339; S; 5-Benzodioxolyl; H; Me; O; 4-Cl-Ph; 2-Naphthyl]; [3340; S; 5-Benzodioxolyl; H; Me; O; 4-Cl-Ph; 5-Indanyl]; [3341; S; 4-F-Ph; H; Me; O; 4-Me-Ph; 4-F-Ph]; [3342; S; 4-F-Ph; H; Me; O; 4-Me-Ph; 4-Cl-Ph]; [3343; S; 4-F-Ph; H; Me; O; 4-Me-Ph; 4-Me-Ph]; [3344; S; 4-F-Ph; H; Me; O; 4-Me-Ph; 4-Ph-Ph]; [3345; S; 4-F-Ph; H; Me; O; 4-Me-Ph; 2-Naphthyl]; [3346; S; 4-Me-Ph; H; Me; O; 4-Me-Ph; 4-F-Ph]; [3347; S; 4-Me-Ph; H; Me; O; 4-Me-Ph; 4-Cl-Ph]; [3348; S; 4-Me-Ph; H; Me; O; 4-Me-Ph; 4-Me-Ph]; [3349; S; 4-Me-Ph; H; Me; O; 4-Me-Ph; 4-Ph-Ph]; [3350; S; 4-Me-Ph; H; Me; O; 4-Me-Ph; 2-Naphthyl]; [3351; S; 2-Naphthyl; H; Me; O; 4-Me-Ph; 4-F-Ph]; [3352; S; 2-Naphthyl; H; Me; O; 4-Me-Ph; 4-Cl-Ph]; [3353; S; 2-Naphthyl; H; Me; O; 4-Me-Ph; 4-Me-Ph]; [3354; S; 2-Naphthyl; H; Me; O; 4-Me-Ph; 4-Ph-Ph]; [3355; S; 2-Naphthyl; H; Me; O; 4-Me-Ph; 2-Naphthyl]; [3356; S; 5-Benzodioxolyl; H; Me; O; 4-Me-Ph; 4-F-Ph]; [3357; S; 5-Benzodioxolyl; H; Me; O; 4-Me-Ph; 4-Cl-Ph]; [3358; S; 5-Benzodioxolyl; H; Me; O; 4-Me-Ph; 4-Me-Ph]; [3359; S; 5-Benzodioxolyl; H; Me; O; 4-Me-Ph; 4-Ph-Ph]; [3360; S; 5-Benzodioxolyl; H; Me; O; 4-Me-Ph; 2-Naphthyl]; [3361; S; 4-F-Ph; H; Me; O; 2-Naphthyl; 2-F-Ph]; [3362; S; 4-F-Ph; H; Me; O; 2-Naphthyl; 3-F-Ph]; [3363; S; 4-F-Ph; H; Me; O; 2-Naphthyl; 4-F-Ph]; [3364; S; 4-F-Ph; H; Me; O; 2-Naphthyl; 4-Cl-Ph]; [3365; S; 4-F-Ph; H; Me; O; 2-Naphthyl; 3-Me-Ph]; [3366; S; 4-Me-Ph; H; Me; O; 2-Naphthyl; 4-Me-Ph]; [3367; S; 4-Me-Ph; H; Me; O; 2-Naphthyl; 4-iPr-Ph]; [3368; S; 4-Me-Ph; H; Me; O; 2-Naphthyl; 4-Ph-Ph]; [3369; S; 4-Me-Ph; H; Me; O; 2-Naphthyl; 2-Naphthyl]; [3370; S; 4-Me-Ph; H; Me; O; 2-Naphthyl; 5-Indanyl]; [3371; S; 2-Naphthyl; H; Me; O; 2-Naphthyl; 2-F-Ph]; [3372; S; 2-Naphthyl; H; Me; O; 2-Naphthyl; 3-F-Ph]; [3373; S; 2-Naphthyl; H; Me; O; 2-Naphthyl; 4-F-Ph]; [3374; S; 2-Naphthyl; H; Me; O; 2-Naphthyl; 4-Cl-Ph]; [3375; S; 2-Naphthyl; H; Me; O; 2-Naphthyl; 3-Me-Ph]; [3376; S; 5-Benzodioxolyl; H; Me; O; 2-Naphthyl; 4-Me-Ph]; [3377; S; 5-Benzodioxolyl; H; Me; O; 2-Naphthyl; 4-iPr-Ph]; [3378; S; 5-Benzodioxolyl; H; Me; O; 2-Naphthyl; 4-Ph-Ph]; [3379; S; 5-Benzodioxolyl; H; Me; O; 2-Naphthyl; 2-Naphthyl]; [3380; S; 5-Benzodioxolyl; H; Me; O; 2-Naphthyl; 5-Indanyl]; [3381; S; Ph; Me; Me; O; Ph; Ph]; [3382; S; Ph; Ph; Me; O; Ph; Ph]; [3383; S; Ph; Me; Ph; O; Ph; Ph]; [3384; S; Ph; Ph; Ph; O; Ph; Ph]; [3385; S; Ph; CF$_3$; Me; O; Ph; Ph]; [3386; S; Ph; Me; Me; O; Cyclohexylmethyl; Ph]; [3387; S; Ph; Ph; Me; O; Cyclohexylmethyl; Ph]; [3388; S; Ph; Me; Ph; O; Cyclohexylmethyl; Ph]; [3389; S; Ph; Ph; Ph; O; Cyclohexylmethyl; Ph]; [3390; S; Ph; CF$_3$; Me; O; Cyclohexylmethyl; Ph]; [3391; S; 4-F-Ph; Me; Me; O; Ph; 4-F-Ph]; [3392; S; 4-F-Ph; Ph; Me; O; Ph; 4-F-Ph]; [3393; S; 4-F-Ph; Me; Ph; O; Ph; 4-F-Ph]; [3394; S; 4-F-Ph; Ph; Ph; O; Ph; 4-F-Ph]; [3395; S; 4-F-Ph; CF$_3$; Me; O; Ph; 4-F-Ph]; [3396; S; Ph; Me; Me; O; Ph; 4-Me-Ph]; [3397; S; Ph; Ph; Me; O; Ph; 4-Me-Ph]; [3398; S; Ph; Me; Ph; O; Ph; 4-Me-Ph]; [3399; S; Ph; Ph; Ph; O; Ph; 4-Me-Ph]; [3400; S; Ph; CF$_3$; Me; O; Ph; 4-Me-Ph]; [3401; O; Ph; H; Me; O; Ph; Ph]; [3402; O; 3-F-Ph; H; Me; O; Ph; Ph]; [3403; O; 4-F-Ph; H; Me; O; Ph; Ph]; [3404; O; 3-Cl-Ph; H; Me; O; Ph; Ph]; [3405; O; 4-Cl-Ph; H; Me; O; Ph; Ph]; [3406; O; 3-Me-Ph; H; Me; O; Ph; Ph]; [3407; O; 4-Me-Ph; H; Me; O; Ph; Ph]; [3408; O; 2-Naphthyl; H; Me; O; Ph; Ph]; [3409; O; 5-Indanyl; H; Me; O; Ph; Ph]; [3410; O; 5-Benzodioxolyl; H; Me; O; Ph; Ph]; [3411; O; Ph; H; Ph; O; Ph; Ph]; [3412; O; 3-F-Ph; H; Ph; O; Ph; Ph]; [3413; O; 4-F-Ph; H; Ph; O; Ph; Ph]; [3414; O; 3-Cl-Ph; H; Ph; O; Ph; Ph]; [3415; O; 4-Cl-Ph; H; Ph; O; Ph; Ph]; [3416; O; 3-Me-Ph; H; Ph; O; Ph; Ph]; [3417; O; 4-Me-Ph; H; Ph; O; Ph; Ph]; [3418; O; 2-Naphthyl; H; Ph; O; Ph; Ph]; [3419; O; 5-Indanyl; H; Ph; O; Ph; Ph]; [3420; O; 5-Benzodioxolyl; H; Ph; O; Ph; Ph]; [3421; O; Ph; Me; H; O; Ph; Ph]; [3422; O; 3-F-Ph; Me; H; O; Ph; Ph]; [3423; O; 4-F-Ph; Me; H; O; Ph; Ph]; [3424; O; 3-Cl-Ph; Me; H; O; Ph; Ph]; [3425; O; 4-Cl-Ph; Me; H; O; Ph; Ph]; [3426; O; 3-Me-Ph; Me; H; O; Ph; Ph]; [3427; O; 4-Me-Ph; Me; H; O; Ph; Ph]; [3428; O; 2-Naphthyl; Me; H; O; Ph; Ph]; [3429; O; 5-Indanyl; Me; H; O; Ph; Ph]; [3430; O; 5-Benzodioxolyl; Me; H; O; Ph; Ph]; [3431; O; Ph; Ph; H; O; Ph; Ph]; [3432; O; 3-F-Ph;

Ph; H; O; Ph; Ph]; [3433; O; 4-F-Ph; Ph; H; O; Ph; Ph]; [3434; O; 3-Cl-Ph; Ph; H; O; Ph; Ph]; [3435; O; 4-Cl-Ph; Ph; H; O; Ph; Ph]; [3436; O; 3-Me-Ph; Ph; H; O; Ph; Ph]; [3437; O; 4-Me-Ph; Ph; H; O; Ph; Ph]; [3438; O; 2-Naphthyl; Ph; H; O; Ph; Ph]; [3439; O; 5-Indanyl; Ph; H; O; Ph; Ph]; [3440; O; 5-Benzodioxolyl; Ph; H; O; Ph; Ph]; [3441; O; Ph; H; Me; O; Bu; Ph]; [3442; O; Ph; H; Me; O; Isopentyl; Ph]; [3443; O; Ph; H; Me; O; Cyclohexyl; Ph]; [3444; O; Ph; H; Me; O; Cyclohexylmethyl; Ph]; [3445; O; Ph; H; Me; O; 2-Perhydronaphthyl; Ph]; [3446; O; Ph; H; Me; O; PhCH$_2$; Ph]; [3447; O; Ph; H; Me; O; 4-F-Ph; Ph]; [3448; O; Ph; H; Me; O; 4-Cl-Ph; Ph]; [3449; O; Ph; H; Me; O; 4-Me-Ph; Ph]; [3450; O; Ph; H; Me; O; 2-Naphthyl; Ph]; [3451; O; Ph; H; Ph; O; Bu; Ph]; [3452; O; Ph; H; Ph; O; Isopentyl; Ph]; [3453; O; Ph; H; Ph; O; Cyclohexyl; Ph]; [3454; O; Ph; H; Ph; O; Cyclohexylmethyl; Ph]; [3455; O; Ph; H; Ph; O; 2-Perhydronaphthyl; Ph]; [3456; O; Ph; H; Ph; O; PhCH$_2$; Ph]; [3457; O; Ph; H; Ph; O; 4-F-Ph; Ph]; [3458; O; Ph; H; Ph; O; 4-Cl-Ph; Ph]; [3459; O; Ph; H; Ph; O; 4-Me-Ph; Ph]; [3460; O; Ph; H; Ph; O; 2-Naphthyl; Ph]; [3461; O; Ph; Me; H; O; Bu; Ph]; [3462; O; Ph; Me; H; O; Isopentyl; Ph]; [3463; O; Ph; Me; H; O; Cyclohexyl; Ph]; [3464; O; Ph; Me; H; O; Cyclohexylmethyl; Ph]; [3465; O; Ph; Me; H; O; 2-Perhydronaphthyl; Ph]; [3466; O; Ph; Me; H; O; PhCH$_2$; Ph]; [3467; O; Ph; Me; H; O; 4-F-Ph; Ph]; [3468; O; Ph; Me; H; O; 4-Cl-Ph; Ph]; [3469; O; Ph; Me; H; O; 4-Me-Ph; Ph]; [3470; O; Ph; Me; H; O; 2-Naphthyl; Ph]; [3471; O; Ph; Ph; H; O; Bu; Ph]; [3472; O; Ph; Ph; H; O; Isopentyl; Ph]; [3473; O; Ph; Ph; H; O; Cyclohexyl; Ph]; [3474; O; Ph; Ph; H; O; Cyclohexylmethyl; Ph]; [3475; O; Ph; Ph; H; O; 2-Perhydronaphthyl; Ph]; [3476; O; Ph; Ph; H; O; PhCH$_2$; Ph]; [3477; O; Ph; Ph; H; O; 4-F-Ph; Ph]; [3478; O; Ph; Ph; H; O; 4-Cl-Ph; Ph]; [3479; O; Ph; Ph; H; O; 4-Me-Ph; Ph]; [3480; O; Ph; Ph; H; O; 2-Naphthyl; Ph]; [3481; O; Ph; H; Me; O; Ph; 2-F-Ph]; [3482; O; Ph; H; Me; O; Ph; 3-F-Ph]; [3483; O; Ph; H; Me; O; Ph; 4-F-Ph]; [3484; O; Ph; H; Me; O; Ph; 4-Cl-Ph]; [3485; O; Ph; H; Me; O; Ph; 3-Me-Ph]; [3486; O; Ph; H; Me; O; Ph; 4-Me-Ph]; [3487; O; Ph; H; Me; O; Ph; 4-iPr-Ph]; [3488; O; Ph; H; Me; O; Ph; 4-Ph-Ph]; [3489; O; Ph; H; Me; O; Ph; 2-Naphthyl]; [3490; O; Ph; H; Me; O; Ph; 5-Indanyl]; [3491; O; Ph; H; Ph; O; Ph; 2-F-Ph]; [3492; O; Ph; H; Ph; O; Ph; 3-F-Ph]; [3493; O; Ph; H; Ph; O; Ph; 4-F-Ph]; [3494; O; Ph; H; Ph; O; Ph; 4-Cl-Ph]; [3495; O; Ph; H; Ph; O; Ph; 3-Me-Ph]; [3496; O; Ph; H; Ph; O; Ph; 4-Me-Ph]; [3497; O; Ph; H; Ph; O; Ph; 4-iPr-Ph]; [3498; O; Ph; H; Ph; O; Ph; 4-Ph-Ph]; [3499; O; Ph; H; Ph; O; Ph; 2-Naphthyl]; [3500; O; Ph; H; Ph; O; Ph; 5-Indanyl]; [3501; O; Ph; Me; H; O; Ph; 2-F-Ph]; [3502; O; Ph; Me; H; O; Ph; 3-F-Ph]; [3503; O; Ph; Me; H; O; Ph; 4-F-Ph]; [3504; O; Ph; Me; H; O; Ph; 4-Cl-Ph]; [3505; O; Ph; Me; H; O; Ph; 3-Me-Ph]; [3506; O; Ph; Me; H; O; Ph; 4-Me-Ph]; [3507; O; Ph; Me; H; O; Ph; 4-iPr-Ph]; [3508; O; Ph; Me; H; O; Ph; 4-Ph-Ph]; [3509; O; Ph; Me; H; O; Ph; 2-Naphthyl]; [3510; O; Ph; Me; H; O; Ph; 5-Indanyl]; [3511; O; Ph; Ph; H; O; Ph; 2-F-Ph]; [3512; O; Ph; Ph; H; O; Ph; 3-F-Ph]; [3513; O; Ph; Ph; H; O; Ph; 4-F-Ph]; [3514; O; Ph; Ph; H; O; Ph; 4-Cl-Ph]; [3515; O; Ph; Ph; H; O; Ph; 3-Me-Ph]; [3516; O; Ph; Ph; H; O; Ph; 4-Me-Ph]; [3517; O; Ph; Ph; H; O; Ph; 4-iPr-Ph]; [3518; O; Ph; Ph; H; O; Ph; 4-Ph-Ph]; [3519; O; Ph; Ph; H; O; Ph; 2-Naphthyl]; [3520; O; Ph; Ph; H; O; Ph; 5-Indanyl]; [3521; O; 4-F-Ph; H; Me; O; Ph; 2-F-Ph]; [3522; O; 4-F-Ph; H; Me; O; Ph; 3-F-Ph]; [3523; O; 4-F-Ph; H; Me; O; Ph; 4-F-Ph]; [3524; O; 4-F-Ph; H; Me; O; Ph; 4-Cl-Ph]; [3525; O; 4-F-Ph; H; Me; O; Ph; 3-Me-Ph]; [3526; O; 4-F-Ph; H; Me; O; Ph; 4-Me-Ph]; [3527; O; 4-F-Ph; H; Me; O; Ph; 4-iPr-Ph]; [3528; O; 4-F-Ph; H; Me; O; Ph; 4-Ph-Ph]; [3529; O; 4-F-Ph; H; Me; O; Ph; 2-Naphthyl]; [3530; O; 4-F-Ph; H; Me; O; Ph; 5-Indanyl]; [3531; O; 4-Cl-Ph; H; Me; O; Ph; 2-F-Ph]; [3532; O; 4-Cl-Ph; H; Me; O; Ph; 3-F-Ph]; [3533; O; 4-Cl-Ph; H; Me; O; Ph; 4-F-Ph]; [3534; O; 4-Cl-Ph; H; Me; O; Ph; 4-Cl-Ph]; [3535; O; 4-Cl-Ph; H; Me; O; Ph; 3-Me-Ph]; [3536; O; 4-Cl-Ph; H; Me; O; Ph; 4-Me-Ph]; [3537; O; 4-Cl-Ph; H; Me; O; Ph; 4-iPr-Ph]; [3538; O; 4-Cl-Ph; H; Me; O; Ph; 4-Ph-Ph]; [3539; O; 4-Cl-Ph; H; Me; O; Ph; 2-Naphthyl]; [3540; O; 4-Cl-Ph; H; Me; O; Ph; 5-Indanyl]; [3541; O; 4-Me-Ph; H; Me; O; Ph; 2-F-Ph]; [3542; O; 4-Me-Ph; H; Me; O; Ph; 3-F-Ph]; [3543; O; 4-Me-Ph; H; Me; O; Ph; 4-F-Ph]; [3544; O; 4-Me-Ph; H; Me; O; Ph; 4-Cl-Ph]; [3545; O; 4-Me-Ph; H; Me; O; Ph; 3-Me-Ph]; [3546; O; 4-Me-Ph; H; Me; O; Ph; 4-Me-Ph]; [3547; O; 4-Me-Ph; H; Me; O; Ph; 4-iPr-Ph]; [3548; O; 4-Me-Ph; H; Me; O; Ph; 4-Ph-Ph]; [3549; O; 4-Me-Ph; H; Me; O; Ph; 2-Naphthyl]; [3550; O; 4-Me-Ph; H; Me; O; Ph; 5-Indanyl]; [3551; O; 5-Indanyl; H; Me; O; Ph; 2-F-Ph]; [3552; O; 5-Indanyl; H; Me; O; Ph; 3-F-Ph]; [3553; O; 5-Indanyl; H; Me; O; Ph; 4-F-Ph]; [3554; O; 5-Indanyl; H; Me; O; Ph; 4-Cl-Ph]; [3555; O; 5-Indanyl; H; Me; O; Ph; 3-Me-Ph]; [3556; O; 5-Indanyl; H; Me; O; Ph; 4-Me-Ph]; [3557; O; 5-Indanyl; H; Me; O; Ph; 4-iPr-Ph]; [3558; O; 5-Indanyl; H; Me; O; Ph; 4-Ph-Ph]; [3559; O; 5-Indanyl; H; Me; O; Ph; 2-Naphthyl]; [3560; O; 5-Indanyl; H; Me; O; Ph; 5-Indanyl]; [3561; O; 2-Naphthyl; H; Me; O; Ph; 2-F-Ph]; [3562; O; 2-Naphthyl; H; Me; O; Ph; 3-F-Ph]; [3563; O; 2-Naphthyl; H; Me; O; Ph; 4-F-Ph]; [3564; O; 2-Naphthyl; H; Me; O; Ph; 4-Cl-Ph]; [3565; O; 2-Naphthyl; H; Me; O; Ph; 3-Me-Ph]; [3566; O; 2-Naphthyl; H; Me; O; Ph; 4-Me-Ph]; [3567; O; 2-Naphthyl; H; Me; O; Ph; 4-iPr-Ph]; [3568; O; 2-Naphthyl; H; Me; O; Ph; 4-Ph-Ph]; [3569; O; 2-Naphthyl; H; Me; O; Ph; 2-Naphthyl]; [3570; O; 2-Naphthyl; H; Me; O; Ph; 5-Indanyl]; [3571; O; 5-Benzodioxolyl; H; Me; O; Ph; 2-F-Ph]; [3572; O; 5-Benzodioxolyl; H; Me; O; Ph; 3-F-Ph]; [3573; O; 5-Benzodioxolyl; H; Me; O; Ph; 4-F-Ph]; [3574; O; 5-Benzodioxolyl; H; Me; O; Ph; 4-Cl-Ph]; [3575; O; 5-Benzodioxolyl; H; Me; O; Ph; 3-Me-Ph]; [3576; O; 5-Benzodioxolyl; H; Me; O; Ph; 4-Me-Ph]; [3577; O; 5-Benzodioxolyl; H; Me; O; Ph; 4-iPr-Ph]; [3578; O; 5-Benzodioxolyl; H; Me; O; Ph; 4-Ph-Ph]; [3579; O; 5-Benzodioxolyl; H; Me; O; Ph; 2-Naphthyl]; [3580; O; 5-Benzodioxolyl; H; Me; O; Ph; 5-Indanyl]; [3581; O; Ph; H; Me; O; Cyclohexylmethyl; 2-F-Ph]; [3582; O; Ph; H; Me; O; Cyclohexylmethyl; 3-F-Ph]; [3583; O; Ph; H; Me; O; Cyclohexylmethyl; 4-F-Ph]; [3584; O; Ph; H; Me; O; Cyclohexylmethyl; 4-Cl-Ph]; [3585; O; Ph; H; Me; O; Cyclohexylmethyl; 3-Me-Ph]; [3586; O; Ph; H; Me; O; Cyclohexylmethyl; 4-Me-Ph]; [3587; O; Ph; H; Me; O; Cyclohexylmethyl; 4-iPr-Ph]; [3588; O; Ph; H; Me; O; Cyclohexylmethyl; 4-Ph-Ph]; [3589; O; Ph; H; Me; O; Cyclohexylmethyl; 2-Naphthyl]; [3590; O; Ph; H; Me; O; Cyclohexylmethyl; 5-Indanyl]; [3591; O; Ph; H; Me; O; 2-Perhydronaphthyl; 2-F-Ph]; [3592; O; Ph; H; Me; O; 2-Perhydronaphthyl; 3-F-Ph]; [3593; O; Ph; H; Me; O; 2-Perhydronaphthyl; 4-F-Ph]; [3594; O; Ph; H; Me; O; 2-Perhydronaphthyl; 4-Cl-Ph]; [3595; O; Ph; H; Me; O; 2-Perhydronaphthyl; 3-Me-Ph]; [3596; O; Ph; H; Me; O; 2-Perhydronaphthyl; 4-Me-Ph]; [3597; O; Ph; H; Me; O; 2-Perhydronaphthyl; 4-iPr-Ph]; [3598; O; Ph; H; Me; O; 2-Perhydronaphthyl; 4-Ph-Ph]; [3599; O; Ph; H; Me; O; 2-Perhydronaphthyl; 2-Naphthyl]; [3600; O; Ph; H; Me; O; 2-Perhydronaphthyl; 5-Indanyl]; [3601; O; Ph; H; Me; O; 4-F-Ph; 2-F-Ph]; [3602; O; Ph; H; Me; O; 4-F-Ph; 3-F-Ph]; [3603; O; Ph; H; Me; O; 4-F-Ph; 4-F-Ph]; [3604; O; Ph; H; Me; O; 4-F-Ph; 4-Cl-Ph]; [3605; O; Ph; H; Me; O; 4-F-Ph; 3-Me-Ph]; [3606; O; Ph; H; Me; O; 4-F-Ph; 4-Me-Ph]; [3607; O; Ph; H; Me; O; 4-F-Ph; 4-iPr-Ph]; [3608; O; 4-F-Ph; 4-Ph-Ph]; [3609; O; Ph; H; Me; O; 4-F-Ph; 2-Naphthyl]; [3610; O; Ph; H; Me; O; 4-F-Ph; 5-Indanyl]; [3611; O; Ph; H; Me; O; 2-Naphthyl; 2-F-Ph]; [3612; O; Ph; H; Me; O;

2-Naphthyl; 3-F-Ph]; [3613; O; Ph; H; Me; O; 2-Naphthyl; 4-F-Ph]; [3614; O; Ph; H; Me; O; 2-Naphthyl; 4-Cl-Ph]; [3615; O; Ph; H; Me; O; 2-Naphthyl; 3-Me-Ph]; [3616; O; Ph; H; Me; O; 2-Naphthyl; 4-Me-Ph]; [3617; O; Ph; H; Me; O; 2-Naphthyl; 4-iPr-Ph]; [3618; O; Ph; H; Me; O; 2-Naphthyl; 4-Ph-Ph]; [3619; O; Ph; H; Me; O; 2-Naphthyl; 2-Naphthyl]; [3620; O; Ph; H; Me; O; 2-Naphthyl; 5-Indanyl]; [3621; O; 4-F-Ph; H; Me; O; Cyclohexylmethyl; 4-F-Ph]; [3622; O; 4-F-Ph; H; Me; O; Cyclohexylmethyl; 4-Cl-Ph]; [3623; O; 4-F-Ph; H; Me; O; Cyclohexylmethyl; 4-Me-Ph]; [3624; O; 4-F-Ph; H; Me; O; Cyclohexylmethyl; 4-Ph-Ph]; [3625; O; 4-F-Ph; H; Me; O; Cyclohexylmethyl; 2-Naphthyl]; [3626; O; 4-Me-Ph; H; Me; O; Cyclohexylmethyl; 4-F-Ph]; [3627; O; 4-Me-Ph; H; Me; O; Cyclohexylmethyl; 4-Cl-Ph]; [3628; O; 4-Me-Ph; H; Me; O; Cyclohexylmethyl; 4-Me-Ph]; [3629; O; 4-Me-Ph; H; Me; O; Cyclohexylmethyl; 4-Ph-Ph]; [3630; O; 4-Me-Ph; H; Me; O; Cyclohexylmethyl; 2-Naphthyl]; [3631; O; 2-Naphthyl; H; Me; O; Cyclohexylmethyl; 4-F-Ph]; [3632; O; 2-Naphthyl; H; Me; O; Cyclohexylmethyl; 4-Cl-Ph]; [3633; O; 2-Naphthyl; H; Me; O; Cyclohexylmethyl; 4-Me-Ph]; [3634; O; 2-Naphthyl; H; Me; O; Cyclohexylmethyl; 4-Ph-Ph]; [3635; O; 2-Naphthyl; H; Me; O; Cyclohexylmethyl; 2-Naphthyl]; [3636; O; 5-Benzodioxolyl; H; Me; O; Cyclohexylmethyl; 4-F-Ph]; [3637; O; 5-Benzodioxolyl; H; Me; O; Cyclohexylmethyl; 4-Cl-Ph]; [3638; O; 5-Benzodioxolyl; H; Me; O; Cyclohexylmethyl; 4-Me-Ph]; [3639; O; 5-Benzodioxolyl; H; Me; O; Cyclohexylmethyl; 4-Ph-Ph]; [3640; O; 5-Benzodioxolyl; H; Me; O; Cyclohexylmethyl; 2-Naphthyl]; [3641; O; 4-F-Ph; H; Me; O; 2-Perhydronaphthyl; 2-F-Ph]; [3642; O; 4-F-Ph; H; Me; O; 2-Perhydronaphthyl; 3-F-Ph]; [3643; O; 4-F-Ph; H; Me; O; 2-Perhydronaphthyl; 4-F-Ph]; [3644; O; 4-F-Ph; H; Me; O; 2-Perhydronaphthyl; 4-Cl-Ph]; [3645; O; 4-F-Ph; H; Me; O; 2-Perhydronaphthyl; 3-Me-Ph]; [3646; O; 4-Me-Ph; H; Me; O; 2-Perhydronaphthyl; 4-Me-Ph]; [3647; O; 4-Me-Ph; H; Me; O; 2-Perhydronaphthyl; 4-iPr-Ph]; [3648; O; 4-Me-Ph; H; Me; O; 2-Perhydronaphthyl; 4-Ph-Ph]; [3649; O; 4-Me-Ph; H; Me; O; 2-Perhydronaphthyl; 2-Naphthyl]; [3650; O; 4-Me-Ph; H; Me; O; 2-Perhydronaphthyl; 5-Indanyl]; [3651; O; 2-Naphthyl; H; Me; O; 2-Perhydronaphthyl; 2-F-Ph]; [3652; O; 2-Naphthyl; H; Me; O; 2-Perhydronaphthyl; 3-F-Ph]; [3653; O; 2-Naphthyl; H; Me; O; 2-Perhydronaphthyl; 4-F-Ph]; [3654; O; 2-Naphthyl; H; Me; O; 2-Perhydronaphthyl; 4-Cl-Ph]; [3655; O; 2-Naphthyl; H; Me; O; 2-Perhydronaphthyl; 3-Me-Ph]; [3656; O; 5-Benzodioxolyl; H; Me; O; 2-Perhydronaphthyl; 4-Me-Ph]; [3657; O; 5-Benzodioxolyl; H; Me; O; 2-Perhydronaphthyl; 4-iPr-Ph]; [3658; O; 5-Benzodioxolyl; H; Me; O; 2-Perhydronaphthyl; 4-Ph-Ph]; [3659; O; 5-Benzodioxolyl; H; Me; O; 2-Perhydronaphthyl; 2-Naphthyl]; [3660; O; 5-Benzodioxolyl; H; Me; O; 2-Perhydronaphthyl; 5-Indanyl]; [3661; O; 4-F-Ph; H; Me; O; PhCH$_2$; 4-F-Ph]; [3662; O; 4-F-Ph; H; Me; O; PhCH$_2$; 4-Cl-Ph]; [3663; O; 4-F-Ph; H; Me; O; PhCH$_2$; 4-Me-Ph]; [3664; O; 4-F-Ph; H; Me; O; PhCH$_2$; 4-Ph-Ph]; [3665; O; 4-F-Ph; H; Me; O; PhCH$_2$; 2-Naphthyl]; [3666; O; 4-Me-Ph; H; Me; O; PhCH$_2$; 4-F-Ph]; [3667; O; 4-Me-Ph; H; Me; O; PhCH$_2$; 4-Cl-Ph]; [3668; O; 4-Me-Ph; H; Me; O; PhCH$_2$; 4-Me-Ph]; [3669; O; 4-Me-Ph; H; Me; O; PhCH$_2$; 4-Ph-Ph]; [3670; O; 4-Me-Ph; H; Me; O; PhCH$_2$; 2-Naphthyl]; [3671; O; 2-Naphthyl; H; Me; O; PhCH$_2$; 4-F-Ph]; [3672; O; 2-Naphthyl; H; Me; O; PhCH$_2$; 4-Cl-Ph]; [3673; O; 2-Naphthyl; H; Me; O; PhCH$_2$; 4-Me-Ph]; [3674; O; 2-Naphthyl; H; Me; O; PhCH$_2$; 4-Ph-Ph]; [3675; O; 2-Naphthyl; H; Me; O; PhCH$_2$; 2-Naphthyl]; [3676; O; 5-Benzodioxolyl; H; Me; O; PhCH$_2$; 4-F-Ph]; [3677; O; 5-Benzodioxolyl; H; Me; O; PhCH$_2$; 4-Cl-Ph]; [3678; O; 5-Benzodioxolyl; H; Me; O; PhCH$_2$; 4-Me-Ph]; [3679; O; 5-Benzodioxolyl; H; Me; O; PhCH$_2$; 4-Ph-Ph]; [3680; O; 5-Benzodioxolyl; H; Me; O; PhCH$_2$; 2-Naphthyl]; [3681; O; 4-F-Ph; H; Me; O; 3-F-Ph; 2-F-Ph]; [3682; O; 4-F-Ph; H; Me; O; 3-F-Ph; 3-F-Ph]; [3683; O; 4-F-Ph; H; Me; O; 3-F-Ph; 4-F-Ph]; [3684; O; 4-F-Ph; H; Me; O; 3-F-Ph; 4-Cl-Ph]; [3685; O; 4-F-Ph; H; Me; O; 3-F-Ph; 3-Me-Ph]; [3686; O; 4-Me-Ph; H; Me; O; 3-F-Ph; 4-Me-Ph]; [3687; O; 4-Me-Ph; H; Me; O; 3-F-Ph; 4-iPr-Ph]; [3688; O; 4-Me-Ph; H; Me; O; 3-F-Ph; 4-Ph-Ph]; [3689; O; 4-Me-Ph; H; Me; O; 3-F-Ph; 2-Naphthyl]; [3690; O; 4-Me-Ph; H; Me; O; 3-F-Ph; 5-Indanyl]; [3691; O; 2-Naphthyl; H; Me; O; 3-F-Ph; 2-F-Ph]; [3692; O; 2-Naphthyl; H; Me; O; 3-F-Ph; 3-F-Ph]; [3693; O; 2-Naphthyl; H; Me; O; 3-F-Ph; 4-F-Ph]; [3694; O; 2-Naphthyl; H; Me; O; 3-F-Ph; 4-Cl-Ph]; [3695; O; 2-Naphthyl; H; Me; O; 3-F-Ph; 3-Me-Ph]; [3696; O; 5-Benzodioxolyl; H; Me; O; 3-F-Ph; 4-Me-Ph]; [3697; O; 5-Benzodioxolyl; H; Me; O; 3-F-Ph; 4-iPr-Ph]; [3698; O; 5-Benzodioxolyl; H; Me; O; 3-F-Ph; 4-Ph-Ph]; [3699; O; 5-Benzodioxolyl; H; Me; O; 3-F-Ph; 2-Naphthyl]; [3700; O; 5-Benzodioxolyl; H; Me; O; 3-F-Ph; 5-Indanyl]; [3701; O; 4-F-Ph; H; Me; O; 4-F-Ph; 4-F-Ph]; [3702; O; 4-F-Ph; H; Me; O; 4-F-Ph; 4-Cl-Ph]; [3703; O; 4-F-Ph; H; Me; O; 4-F-Ph; 4-Me-Ph]; [3704; O; 4-F-Ph; H; Me; O; 4-F-Ph; 4-Ph-Ph]; [3705; O; 4-F-Ph; H; Me; O; 4-F-Ph; 2-Naphthyl]; [3706; O; 4-Me-Ph; H; Me; O; 4-F-Ph; 4-F-Ph]; [3707; O; 4-Me-Ph; H; Me; O; 4-F-Ph; 4-Cl-Ph]; [3708; O; 4-Me-Ph; H; Me; O; 4-F-Ph; 4-Me-Ph]; [3709; O; 4-Me-Ph; H; Me; O; 4-F-Ph; 4-Ph-Ph]; [3710; O; 4-Me-Ph; H; Me; O; 4-F-Ph; 2-Naphthyl]; [3711; O; 2-Naphthyl; H; Me; O; 4-F-Ph; 4-F-Ph]; [3712; O; 2-Naphthyl; H; Me; O; 4-F-Ph; 4-Cl-Ph]; [3713; O; 2-Naphthyl; H; Me; O; 4-F-Ph; 4-Me-Ph]; [3714; O; 2-Naphthyl; H; Me; O; 4-F-Ph; 4-Ph-Ph]; [3715; O; 2-Naphthyl; H; Me; O; 4-F-Ph; 2-Naphthyl]; [3716; O; 5-Benzodioxolyl; H; Me; O; 4-F-Ph; 4-F-Ph]; [3717; O; 5-Benzodioxolyl; H; Me; O; 4-F-Ph; 4-Cl-Ph]; [3718; O; 5-Benzodioxolyl; H; Me; O; 4-F-Ph; 4-Me-Ph]; [3719; O; 5-Benzodioxolyl; H; Me; O; 4-F-Ph; 4-Ph-Ph]; [3720; O; 5-Benzodioxolyl; H; Me; O; 4-F-Ph; 2-Naphthyl]; [3721; O; 4-F-Ph; H; Me; O; 4-Cl-Ph; 2-F-Ph]; [3722; O; 4-F-Ph; H; Me; O; 4-Cl-Ph; 3-F-Ph]; [3723; O; 4-F-Ph; H; Me; O; 4-Cl-Ph; 4-F-Ph]; [3724; O; 4-F-Ph; H; Me; O; 4-Cl-Ph; 4-Cl-Ph]; [3725; O; 4-F-Ph; H; Me; O; 4-Cl-Ph; 3-Me-Ph]; [3726; O; 4-Me-Ph; H; Me; O; 4-Cl-Ph; 4-Me-Ph]; [3727; O; 4-Me-Ph; H; Me; O; 4-Cl-Ph; 4-iPr-Ph]; [3728; O; 4-Me-Ph; H; Me; O; 4-Cl-Ph; 4-Ph-Ph]; [3729; O; 4-Me-Ph; H; Me; O; 4-Cl-Ph; 2-Naphthyl]; [3730; O; 4-Me-Ph; H; Me; O; 4-Cl-Ph; 5-Indanyl]; [3731; O; 2-Naphthyl; H; Me; O; 4-Cl-Ph; 2-F-Ph]; [3732; O; 2-Naphthyl; H; Me; O; 4-Cl-Ph; 3-F-Ph]; [3733; O; 2-Naphthyl; H; Me; O; 4-Cl-Ph; 4-F-Ph]; [3734; O; 2-Naphthyl; H; Me; O; 4-Cl-Ph; 4-Cl-Ph]; [3735; O; 2-Naphthyl; H; Me; O; 4-Cl-Ph; 3-Me-Ph]; [3736; O; 5-Benzodioxolyl; H; Me; O; 4-Cl-Ph; 4-Me-Ph]; [3737; O; 5-Benzodioxolyl; H; Me; O; 4-Cl-Ph; 4-iPr-Ph]; [3738; O; 5-Benzodioxolyl; H; Me; O; 4-Cl-Ph; 4-Ph-Ph]; [3739; O; 5-Benzodioxolyl; H; Me; O; 4-Cl-Ph; 2-Naphthyl]; [3740; O; 5-Benzodioxolyl; H; Me; O; 4-Cl-Ph; 5-Indanyl]; [3741; O; 4-F-Ph; H; Me; O; 4-Me-Ph; 4-F-Ph]; [3742; O; 4-F-Ph; H; Me; O; 4-Me-Ph; 4-Cl-Ph]; [3743; O; 4-F-Ph; H; Me; O; 4-Me-Ph; 4-Me-Ph]; [3744; O; 4-F-Ph; H; Me; O; 4-Me-Ph; 4-Ph-Ph]; [3745; O; 4-F-Ph; H; Me; O; 4-Me-Ph; 2-Naphthyl]; [3746; O; 4-Me-Ph; H; Me; O; 4-Me-Ph; 4-F-Ph]; [3747; O; 4-Me-Ph; H; Me; O; 4-Me-Ph; 4-Cl-Ph]; [3748; O; 4-Me-Ph; H; Me; O; 4-Me-Ph; 4-Me-Ph]; [3749; O; 4-Me-Ph; H; Me; O; 4-Me-Ph; 4-Ph-Ph]; [3750; O; 4-Me-Ph; H; Me; O; 4-Me-Ph; 2-Naphthyl]; [3751; O; 2-Naphthyl; H; Me; O; 4-Me-Ph; 4-F-Ph]; [3752; O; 2-Naphthyl; H; Me; O; 4-Me-Ph; 4-Cl-Ph]; [3753; O; 2-Naphthyl; H; Me; O; 4-Me-Ph; 4-Me-Ph]; [3754; O; 2-Naphthyl; H; Me; O; 4-Me-Ph;

4-Ph-Ph]; [3755; O; 2-Naphthyl; H; Me; O; 4-Me-Ph; 2-Naphthyl]; [3756; O; 5-Benzodioxolyl; H; Me; O; 4-Me-Ph; 4-F-Ph]; [3757; O; 5-Benzodioxolyl; H; Me; O; 4-Me-Ph; 4-Cl-Ph]; [3758; O; 5-Benzodioxolyl; H; Me; O; 4-Me-Ph; 4-Me-Ph]; [3759; O; 5-Benzodioxolyl; H; Me; O; 4-Me-Ph; 4-Ph-Ph]; [3760; O; 5-Benzodioxolyl; H; Me; O; 4-Me-Ph; 2-Naphthyl]; [3761; O; 4-F-Ph; H; Me; O; 2-Naphthyl; 2-F-Ph]; [3762; O; 4-F-Ph; H; Me; O; 2-Naphthyl; 3-F-Ph]; [3763; O; 4-F-Ph; H; Me; O; 2-Naphthyl; 4-F-Ph]; [3764; O; 4-F-Ph; H; Me; O; 2-Naphthyl; 4-Cl-Ph]; [3765; O; 4-F-Ph; H; Me; O; 2-Naphthyl; 3-Me-Ph]; [3766; O; 4-Me-Ph; H; Me; O; 2-Naphthyl; 4-Me-Ph]; [3767; O; 4-Me-Ph; H; Me; O; 2-Naphthyl; 4-iPr-Ph]; [3768; O; 4-Me-Ph; H; Me; O; 2-Naphthyl; 4-Ph-Ph]; [3769; O; 4-Me-Ph; H; Me; O; 2-Naphthyl; 2-Naphthyl]; [3770; O; 4-Me-Ph; H; Me; O; 2-Naphthyl; 5-Indanyl]; [3771; O; 2-Naphthyl; H; Me; O; 2-Naphthyl; 2-F-Ph]; [3772; O; 2-Naphthyl; H; Me; O; 2-Naphthyl; 3-F-Ph]; [3773; O; 2-Naphthyl; H; Me; O; 2-Naphthyl; 4-F-Ph]; [3774; O; 2-Naphthyl; H; Me; O; 2-Naphthyl; 4-Cl-Ph]; [3775; O; 2-Naphthyl; H; Me; O; 2-Naphthyl; 3-Me-Ph]; [3776; O; 5-Benzodioxolyl; H; Me; O; 2-Naphthyl; 4-Me-Ph]; [3777; O; 5-Benzodioxolyl; H; Me; O; 2-Naphthyl; 4-iPr-Ph]; [3778; O; 5-Benzodioxolyl; H; Me; O; 2-Naphthyl; 4-Ph-Ph]; [3779; O; 5-Benzodioxolyl; H; Me; O; 2-Naphthyl; 2-Naphthyl]; [3780; O; 5-Benzodioxolyl; H; Me; O; 2-Naphthyl; 5-Indanyl]; [3781; O; Ph; Me; Me; O; Ph; Ph]; [3782; O; Ph; Ph; Me; O; Ph; Ph]; [3783; O; Ph; Me; Ph; O; Ph; Ph]; [3784; O; Ph; Ph; Ph; O; Ph; Ph]; [3785; O; Ph; CF$_3$; Me; O; Ph; Ph]; [3786; O; Ph; Me; Me; O; Cyclohexylmethyl; Ph]; [3787; O; Ph; Ph; Me; O; Cyclohexylmethyl; Ph]; [3788; O; Ph; Me; Ph; O; Cyclohexylmethyl; Ph]; [3789; O; Ph; Ph; Ph; O; Cyclohexylmethyl; Ph]; [3790; O; Ph; CF$_3$; Me; O; Cyclohexylmethyl; Ph]; [3791; O; 4-F-Ph; Me; Me; O; Ph; 4-F-Ph]; [3792; O; 4-F-Ph; Ph; Me; O; Ph; 4-F-Ph]; [3793; O; 4-F-Ph; Me; Ph; O; Ph; 4-F-Ph]; [3794; O; 4-F-Ph; Ph; Ph; O; Ph; 4-F-Ph]; [3795; O; 4-F-Ph; CF$_3$; Me; O; Ph; 4-F-Ph]; [3796; O; Ph; Me; Me; O; Ph; 4-Me-Ph]; [3797; O; Ph; Ph; Me; O; Ph; 4-Me-Ph]; [3798; O; Ph; Me; Ph; O; Ph; 4-Me-Ph]; [3799; O; Ph; Ph; Ph; O; Ph; 4-Me-Ph]; [3800; O; Ph; CF$_3$; Me; O; Ph; 4-Me-Ph]; [3801; S; Ph; H; Me; SO$_2$; Ph; Ph]; [3802; S; 4-F-Ph; H; Me; SO$_2$; Ph; Ph]; [3803; S; 4-Me-Ph; H; Me; SO$_2$; Ph; Ph]; [3804; S; 2-Naphthyl; H; Me; SO$_2$; Ph; Ph]; [3805; S; 5-Benzodioxolyl; H; Me; SO$_2$; Ph; Ph]; [3806; S; Ph; H; Ph; SO$_2$; Ph; Ph]; [3807; S; 4-F-Ph; H; Ph; SO$_2$; Ph; Ph]; [3808; S; 4-Me-Ph; H; Ph; SO$_2$; Ph; Ph]; [3809; S; 2-Naphthyl; H; Ph; SO$_2$; Ph; Ph]; [3810; S; 5-Benzodioxolyl; H; Ph; SO$_2$; Ph; Ph]; [3811; S; Ph; H; Me; SO$_2$; Cyclohexylmethyl; Ph]; [3812; S; 4-F-Ph; H; Me; SO$_2$; 4-F-Ph; Ph]; [3813; S; 4-Me-Ph; H; Me; SO$_2$; 4-Me-Ph; Ph]; [3814; S; 2-Naphthyl; H; Me; SO$_2$; 2-Naphthyl; Ph]; [3815; S; 5-Benzodioxolyl; H; Me; SO$_2$; 5-Indanyl; Ph]; [3816; S; Ph; H; Me; SO$_2$; Ph; Cyclohexyl]; [3817; S; Ph; H; Me; SO$_2$; Ph; 4-F-Ph]; [3818; S; Ph; H; Me; SO$_2$; Ph; 4-Me-Ph]; [3819; S; Ph; H; Me; SO$_2$; Ph; 2-Naphthyl]; [3820; S; Ph; H; Me; SO$_2$; Ph; 5-Benzodioxolyl]; [3821; O; Ph; H; Me; SO$_2$; Ph; Ph]; [3822; O; 4-F-Ph; H; Me; SO$_2$; Ph; Ph]; [3823; O; 4-Me-Ph; H; Me; SO$_2$; Ph; Ph]; [3824; O; 2-Naphthyl; H; Me; SO$_2$; Ph; Ph]; [3825; O; 5-Benzodioxolyl; H; Me; SO$_2$; Ph; Ph]; [3826; O; Ph; H; Ph; SO$_2$; Ph; Ph]; [3827; O; 4-F-Ph; H; Ph; SO$_2$; Ph; Ph]; [3828; O; 4-Me-Ph; H; Ph; SO$_2$; Ph; Ph]; [3829; O; 2-Naphthyl; H; Ph; SO$_2$; Ph; Ph]; [3830; O; 5-Benzodioxolyl; H; Ph; SO$_2$; Ph; Ph]; [3831; O; Ph; H; Me; SO$_2$; Cyclohexylmethyl; Ph]; [3832; O; 4-F-Ph; H; Me; SO$_2$; 4-F-Ph; Ph]; [3833; O; 4-Me-Ph; H; Me; SO$_2$; 4-Me-Ph; Ph]; [3834; O; 2-Naphthyl; H; Me; SO$_2$; 2-Naphthyl; Ph]; [3835; O; 5-Benzodioxolyl; H; Me; SO$_2$; 5-Indanyl; Ph]; [3836; O; Ph; H; Me; SO$_2$; Ph; Cyclohexyl]; [3837; O; Ph; H; Me; SO$_2$; Ph; 4-F-Ph]; [3838; O; Ph; H; Me; SO$_2$; Ph; 4-Me-Ph]; [3839; O; Ph; H; Me; SO$_2$; Ph; 2-Naphthyl]; [3840; O; Ph; H; Me; SO$_2$; Ph; 5-Benzodioxolyl]; [3900; S; Ph; H; Me; S; 1,1,3,3-Tetramethylbutyl; Ph]; [3901; S; Ph; H; Me; S; 2-Ethylhexyl; Ph]; [3902; S; Ph; H; Me; S; 1-ethyl-3-Methylbutyl; Ph]; [3903; S; Ph; H; Me; S; 3-Methyl-1-propylbutyl; Ph]; [3904; S; Hex; H; Me; S; Hex; Ph]; [3905; S; Ph; H; Me; S; 3,5-Dimethylcyclohexyl; Ph]; [3906; S; Ph; H; Me; S; 1-Perhydronaphthyl; Ph]; [3907; O; 3,4-(MeO)$_2$-Ph; H; Me; S; Ph; Ph]; [3908; O; 2-F-Ph; H; Et; S; Ph; Ph]; [3909; O; 2-Cl-Ph; H; Et; S; Ph; Ph]; [3910; O; 3-Cl-Ph; H; Et; S; Ph; Ph]; [3911; O; 2-Me-Ph; H; Et; S; Ph; Ph]; [3912; O; 3-Me-Ph; H; Et; S; Ph; Ph]; [3913; O; 3-MeO-Ph; H; Et; S; Ph; Ph]; [3914; O; 4-MeO-Ph; H; Et; S; Ph; Ph]; [3915; O; 3,4-F$_2$-Ph; H; Et; S; Ph; Ph]; [3916; O; 3,4-Cl$_2$-Ph; H; Et; S; Ph; Ph]; [3917; O; 3,4-(MeO)$_2$-Ph; H; Et; S; Ph; Ph]; [3918; O; 2-F-Ph; H; Pr; S; Ph; Ph]; [3919; O; 2-Cl-Ph; H; Pr; S; Ph; Ph]; [3920; O; 3-Cl-Ph; H; Pr; S; Ph; Ph]; [3921; O; 2-Me-Ph; H; Pr; S; Ph; Ph]; [3922; O; 3-Me-Ph; H; Pr; S; Ph; Ph]; [3923; O; 3-MeO-Ph; H; Pr; S; Ph; Ph]; [3924; O; 4-MeO-Ph; H; Pr; S; Ph; Ph]; [3925; O; 3,4-F$_2$-Ph; H; Pr; S; Ph; Ph]; [3926; O; 3,4-Cl$_2$-Ph; H; Pr; S; Ph; Ph]; [3927; O; 3,4-(MeO)$_2$-Ph; H; Pr; S; Ph; Ph]; [3928; O; 2-F-Ph; H; Ph; S; Ph; Ph]; [3929; O; 2-Cl-Ph; H; Ph; S; Ph; Ph]; [3930; O; 3-Cl-Ph; H; Ph; S; Ph; Ph]; [3931; O; 2-Me-Ph; H; Ph; S; Ph; Ph]; [3932; O; 3-Me-Ph; H; Ph; S; Ph; Ph]; [3933; O; 3-MeO-Ph; H; Ph; S; Ph; Ph]; [3934; O; 4-MeO-Ph; H; Ph; S; Ph; Ph]; [3935; O; 3,4-F$_2$-Ph; H; Ph; S; Ph; Ph]; [3936; O; 3,4-Cl$_2$-Ph; H; Ph; S; Ph; Ph]; [3937; O; 3,4-(MeO)$_2$-Ph; H; Ph; S; Ph; Ph]; [3938; O; 2-F-Ph; H; SMe; S; Ph; Ph]; [3939; O; 2-Cl-Ph; H; SMe; S; Ph; Ph]; [3940; O; 3-Cl-Ph; H; SMe; S; Ph; Ph]; [3941; O; 2-Me-Ph; H; SMe; S; Ph; Ph]; [3942; O; 3-Me-Ph; H; SMe; S; Ph; Ph]; [3943; O; 3-MeO-Ph; H; SMe; S; Ph; Ph]; [3944; O; 4-MeO-Ph; H; SMe; S; Ph; Ph]; [3945; O; 3,4-F$_2$-Ph; H; SMe; S; Ph; Ph]; [3946; O; 3,4-Cl$_2$-Ph; H; SMe; S; Ph; Ph]; [3947; O; 3,4-(MeO)$_2$-Ph; H; SMe; S; Ph; Ph]; [3948; O; 2-F-Ph; H; SPh; S; Ph; Ph]; [3949; O; 2-Cl-Ph; H; SPh; S; Ph; Ph]; [3950; O; 3-Cl-Ph; H; SPh; S; Ph; Ph]; [3951; O; 2-Me-Ph; H; SPh; S; Ph; Ph]; [3952; O; 3-Me-Ph; H; SPh; S; Ph; Ph]; [3953; O; 3-MeO-Ph; H; SPh; S; Ph; Ph]; [3954; O; 4-MeO-Ph; H; SPh; S; Ph; Ph]; [3955; O; 3,4-F$_2$-Ph; H; SPh; S; Ph; Ph]; [3956; O; 3,4-Cl$_2$-Ph; H; SPh; S; Ph; Ph]; [3957; O; 3,4-(MeO)$_2$-Ph; H; SPh; S; Ph; Ph]; [3958; O; Ph; H; 2-Thienyl; S; Ph; Ph]; [3959; O; 2-F-Ph; H; 2-Thienyl; S; Ph; Ph]; [3960; O; 3-F-Ph; H; 2-Thienyl; S; Ph; Ph]; [3961; O; 4-F-Ph; H; 2-Thienyl; S; Ph; Ph]; [3962; O; 2-Cl-Ph; H; 2-Thienyl; S; Ph; Ph]; [3963; O; 3-Cl-Ph; H; 2-Thienyl; S; Ph; Ph]; [3964; O; 4-Cl-Ph; H; 2-Thienyl; S; Ph; Ph]; [3965; O; 2-Me-Ph; H; 2-Thienyl; S; Ph; Ph]; [3966; O; 3-Me-Ph; H; 2-Thienyl; S; Ph; Ph]; [3967; O; 4-Me-Ph; H; 2-Thienyl; S; Ph; Ph]; [3968; O; 3-MeO-Ph; H; 2-Thienyl; S; Ph; Ph]; [3969; O; 4-MeO-Ph; H; 2-Thienyl; S; Ph; Ph]; [3970; O; 3,4-Me$_2$-Ph; H; 2-Thienyl; S; Ph; Ph]; [3971; O; 3,4-F$_2$-Ph; H; 2-Thienyl; S; Ph; Ph]; [3972; O; 3,4-Cl$_2$-Ph; H; 2-Thienyl; S; Ph; Ph]; [3973; O; 3,4-(MeO)$_2$-Ph; H; 2-Thienyl; S; Ph; Ph]; [3974; O; 5-Indanyl; H; 2-Thienyl; S; Ph; Ph]; [3975; O; 5-Benzodioxolyl; H; 2-Thienyl; S; Ph; Ph]; [3976; O; Ph; H; iPr; S; Ph; Ph]; [3977; O; Ph; H; iBu; S; Ph; Ph]; [3978; O; Ph; H; cPr; S; Ph; Ph]; [3979; O; Ph; H; cyclohexyl; S; Ph; Ph]; [3980; O; Ph; H; cPrCH$_2$; S; Ph; Ph]; [3981; O; Ph; H; PhCH$_2$; S; Ph; Ph]; [3982; O; Ph; H; MeSCH$_2$; S; Ph; Ph]; [3983; O; Ph; H; CF$_3$; S; Ph; Ph]; [3984; O; Ph; H; 3-Thienyl; S; Ph; Ph]; [3985; O; Ph; H; 2-Furyl; S; Ph; Ph]; [3986; O; Ph; H; 2-Pyridyl; S; Ph; Ph]; [3987; O; Ph; H; 2-Thiazolyl; S; Ph; Ph]; [3988; O; Ph; H; F; S; Ph; Ph]; [3989; O; Ph; H; Me; S; Me; Ph]; [3990; O; Ph; H; Me; S; Et; Ph]; [3991; O; Ph; H; Me; S; Pr; Ph]; [3992; O; Ph; H; Me; S; CH$_3$(CH$_2$)$_4$; Ph];

[3993; O; Ph; H; Me; S; CH₃(CH₂)₆; Ph]; [3994; O; Ph; H; Me; S; CH₃(CH₂)₇; Ph]; [3995; O; Ph; H; Me; S; iPr; Ph]; [3996; O; Ph; H; Me; S; sBu; Ph]; [3997; O; Ph; H; Me; S; iBu; Ph]; [3998; O; Ph; H; Me; S; tBu; Ph]; [3999; O; Ph; H; Me; S; 1-Methylbutyl; Ph]; [4000; O; Ph; H; Me; S; 2-Methylbutyl; Ph]; [4001; O; Ph; H; Me; S; 1-Ethylpropyl; Ph]; [4002; O; Ph; H; Me; S; 1,1-Dimethylpropyl; Ph]; [4003; O; Ph; H; Me; S; 1,2-Dimethylpropyl; Ph]; [4004; O; Ph; H; Me; S; 1-Methylpentyl; Ph]; [4005; O; Ph; H; Me; S; 2-Methylpentyl; Ph]; [4006; O; Ph; H; Me; S; 3-Methylpentyl; Ph]; [4007; O; Ph; H; Me; S; 4-Methylpentyl; Ph]; [4008; O; Ph; H; Me; S; 1-Ethylbutyl; Ph]; [4009; O; Ph; H; Me; S; 2-Ethylbutyl; Ph]; [4010; O; Ph; H; Me; S; 1,1-Dimethylbutyl; Ph]; [4011; O; Ph; H; Me; S; 1,2-Dimethylbutyl; Ph]; [4012; O; Ph; H; Me; S; 1,3-Dimethylbutyl; Ph]; [4013; O; Ph; H; Me; S; 3,3-Dimethylbutyl; Ph]; [4014; O; Ph; H; Me; S; 1-Ethyl-1-methylbutyl; Ph]; [4015; O; Ph; H; Me; S; 1-Methylhexyl; Ph]; [4016; O; Ph; H; Me; S; 2-Methylhexyl; Ph]; [4017; O; Ph; H; Me; S; 1-Ethylpentyl; Ph]; [4018; O; Ph; H; Me; S; 2-Ethylpentyl; Ph]; [4019; O; Ph; H; Me; S; 1-Ethyl-3-methylbutyl; Ph]; [4020; O; Ph; H; Me; S; 1-Propylbutyl; Ph]; [4021; O; Ph; H; Me; S; 1-Methylheptyl; Ph]; [4022; O; Ph; H; Me; S; 2-Methylheptyl; Ph]; [4023; O; Ph; H; Me; S; 1-Ethylhexyl; Ph]; [4024; O; Ph; H; Me; S; 2-Ethylhexyl; Ph]; [4025; O; Ph; H; Me; S; 1-Propylpentyl; Ph]; [4026; O; Ph; H; Me; S; 1-Propyl-3-methylbutyl; Ph]; [4027; O; Ph; H; Me; S; 1,1,3,3-Tetramethylbutyl; Ph]; [4028; O; Ph; H; Me; S; cPr; Ph]; [4029; O; Ph; H; Me; S; Cyclobutyl; Ph]; [4030; O; Ph; H; Me; S; Cycloheptyl; Ph]; [4031; O; Ph; H; Me; S; 1-Perhydronaphthyl; Ph]; [4032; O; Ph; H; Me; S; cPrCH₂; Ph]; [4033; O; Ph; H; Me; S; cyclobutylmethyl; Ph]; [4034; O; Ph; H; Me; S; 2-Cl-Ph; Ph]; [4035; O; Ph; H; Me; S; 2-Me-Ph; Ph]; [4036; O; Ph; H; Me; S; 3,4-F₂-Ph; Ph]; [4037; O; Ph; H; Me; S; 3,4-Cl₂-Ph; Ph]; [4038; O; Ph; H; Me; S; 3,4-Me₂-Ph; Ph]; [4039; O; Ph; H; Et; S; Bu; Ph]; [4040; O; Ph; H; Et; S; CH₃(CH₂)₄; Ph]; [4041; O; Ph; H; Et; S; CH₃(CH₂)₅; Ph]; [4042; O; Ph; H; Et; S; sBu; Ph]; [4043; O; Ph; H; Et; S; iBu; Ph]; [4044; O; Ph; H; Et; S; 1-Methylbutyl; Ph]; [4045; O; Ph; H; Et; S; 2-Methylbutyl; Ph]; [4046; O; Ph; H; Et; S; 1-Ethylpropyl; Ph]; [4047; O; Ph; H; Et; S; 1,2-Dimethylpropyl; Ph]; [4048; O; Ph; H; Et; S; 1-Methylpentyl; Ph]; [4049; O; Ph; H; Et; S; 2-Methylpentyl; Ph]; [4050; O; Ph; H; Et; S; 1-Ethylbutyl; Ph]; [4051; O; Ph; H; Et; S; 2-Ethylbutyl; Ph]; [4052; O; Ph; H; Et; S; 1,3-Dimethylbutyl; Ph]; [4053; O; Ph; H; Et; S; 1-Ethyl-1-methylbutyl; Ph]; [4054; O; Ph; H; Et; S; 1-Methylhexyl; Ph]; [4055; O; Ph; H; Et; S; 2-Methylhexyl; Ph]; [4056; O; Ph; H; Et; S; 1-Ethylpentyl; Ph]; [4057; O; Ph; H; Et; S; 1-Ethyl-3-methylbutyl; Ph]; [4058; O; Ph; H; Et; S; 1-Propylbutyl; Ph]; [4059; O; Ph; H; Et; S; 1-Propylpentyl; Ph]; [4060; O; Ph; H; Et; S; 1-Propyl-3-methylbutyl; Ph]; [4061; O; Ph; H; Et; S; Cyclopentyl; Ph]; [4062; O; Ph; H; Et; S; Cyclohexyl; Ph]; [4063; O; Ph; H; Et; S; 2-Perhydronaphthyl; Ph]; [4064; O; Ph; H; Et; S; cyclopentylmethyl; Ph]; [4065; O; Ph; H; Et; S; cyclohexylmethyl; Ph]; [4066; O; Ph; H; Et; S; cyclopentylethyl; Ph]; [4067; O; Ph; H; Et; S; cyclohexylethyl; Ph]; [4068; O; Ph; H; Et; S; PhCH₂; Ph]; [4069; O; Ph; H; Et; S; 2-F-Ph; Ph]; [4070; O; Ph; H; Et; S; 3-F-Ph; Ph]; [4071; O; Ph; H; Et; S; 4-F-Ph; Ph]; [4072; O; Ph; H; Et; S; 2-Cl-Ph; Ph]; [4073; O; Ph; H; Et; S; 3-Cl-Ph; Ph]; [4074; O; Ph; H; Et; S; 4-Cl-Ph; Ph]; [4075; O; Ph; H; Et; S; 2-Me-Ph; Ph]; [4076; O; Ph; H; Et; S; 3-Me-Ph; Ph]; [4077; O; Ph; H; Et; S; 4-Me-Ph; Ph]; [4078; O; Ph; H; Et; S; 4-iPr-Ph; Ph]; [4079; O; Ph; H; Et; S; 4-CF₃-Ph; Ph]; [4080; O; Ph; H; Et; S; 4-MeO-Ph; Ph]; [4081; O; Ph; H; Et; S; 4-MeS-Ph; Ph]; [4082; O; Ph; H; Et; S; 4-F3CO-Ph; Ph]; [4083; O; Ph; H; Et; S; 4-PhO-Ph; Ph]; [4084; O; Ph; H; Et; S; 3,4-F₂-Ph; Ph]; [4085; O; Ph; H; Et; S; 3,4-Cl₂-Ph; Ph]; [4086; O; Ph; H; Et; S; 3,4-M₂-Ph; Ph]; [4087; O; Ph; H; Et; S; 1-Naphthyl; Ph]; [4088; O; Ph; H; Et; S; 2-Naphthyl; Ph]; [4089; O; Ph; H; Et; S; 5-Indanyl; Ph]; [4090; O; Ph; H; Et; S; 2-Thienyl; Ph]; [4091; O; Ph; H; Pr; S; Bu; Ph]; [4092; O; Ph; H; Pr; S; CH₃(CH₂)₄; Ph]; [4093; O; Ph; H; Pr; S; CH₃(CH₂)₅; Ph]; [4094; O; Ph; H; Pr; S; 1-Methylbutyl; Ph]; [4095; O; Ph; H; Pr; S; 2-Methylbutyl; Ph]; [4096; O; Ph; H; Pr; S; 1,2-Dimethylpropyl; Ph]; [4097; O; Ph; H; Pr; S; 1-Methylpentyl; Ph]; [4098; O; Ph; H; Pr; S; 2-Methylpentyl; Ph]; [4099; O; Ph; H; Pr; S; 1-Ethylbutyl; Ph]; [4100; O; Ph; H; Pr; S; 2-Ethylbutyl; Ph]; [4101; O; Ph; H; Pr; S; 1,3-Dimethylbutyl; Ph]; [4102; O; Ph; H; Pr; S; 1-Ethyl-1-methylbutyl; Ph]; [4103; O; Ph; H; Pr; S; 1-Ethylpentyl; Ph]; [4104; O; Ph; H; Pr; S; 1-Ethyl-3-methylbutyl; Ph]; [4105; O; Ph; H; Pr; S; 1-Propylbutyl; Ph]; [4106; O; Ph; H; Pr; S; 1-Propylpentyl; Ph]; [4107; O; Ph; H; Pr; S; 1-Propyl-3-methylbutyl; Ph]; [4108; O; Ph; H; Pr; S; Cyclopentyl; Ph]; [4109; O; Ph; H; Pr; S; Cyclohexyl; Ph]; [4110; O; Ph; H; Pr; S; 2-Perhydronaphthyl; Ph]; [4111; O; Ph; H; Pr; S; cyclopentylmethyl; Ph]; [4112; O; Ph; H; Pr; S; cyclohexylmethyl; Ph]; [4113; O; Ph; H; Pr; S; cyclopentylethyl; Ph]; [4114; O; Ph; H; Pr; S; cyclohexylethyl; Ph]; [4115; O; Ph; H; Pr; S; PhCH₂; Ph]; [4116; O; Ph; H; Pr; S; 2-F-Ph; Ph]; [4117; O; Ph; H; Pr; S; 3-F-Ph; Ph]; [4118; O; Ph; H; Pr; S; 4-F-Ph; Ph]; [4119; O; Ph; H; Pr; S; 2-Cl-Ph; Ph]; [4120; O; Ph; H; Pr; S; 3-Cl-Ph; Ph]; [4121; O; Ph; H; Pr; S; 4-Cl-Ph; Ph]; [4122; O; Ph; H; Pr; S; 2-Me-Ph; Ph]; [4123; O; Ph; H; Pr; S; 3-Me-Ph; Ph]; [4124; O; Ph; H; Pr; S; 4-Me-Ph; Ph]; [4125; O; Ph; H; Pr; S; 4-CF₃-Ph; Ph]; [4126; O; Ph; H; Pr; S; 4-MeO-Ph; Ph]; [4127; O; Ph; H; Pr; S; 4-MeS-Ph; Ph]; [4128; O; Ph; H; Pr; S; 4-F3CO-Ph; Ph]; [4129; O; Ph; H; Pr; S; 3,4-F₂-Ph; Ph]; [4130; O; Ph; H; Pr; S; 3,4-Cl₂-Ph; Ph]; [4131; O; Ph; H; Pr; S; 3,4-Me₂-Ph; Ph]; [4132; O; Ph; H; Pr; S; 2-Naphthyl; Ph]; [4133; O; Ph; H; Ph; S; CH₃(CH₂)₄; Ph]; [4134; O; Ph; H; Ph; S; 1-Methylbutyl; Ph]; [4135; O; Ph; H; Ph; S; 2-Methylbutyl; Ph]; [4136; O; Ph; H; Ph; S; 1,2-Dimethylpropyl; Ph]; [4137; O; Ph; H; Ph; S; 1-Methylpentyl; Ph]; [4138; O; Ph; H; Ph; S; 2-Methylpentyl; Ph]; [4139; O; Ph; H; Ph; S; 1,3-Dimethylbutyl; Ph]; [4140; O; Ph; H; Ph; S; 1-Ethyl-1-methylbutyl; Ph]; [4141; O; Ph; H; Ph; S; 1-Ethyl-3-methylbutyl; Ph]; [4142; O; Ph; H; Ph; S; 1-Propylbutyl; Ph]; [4143; O; Ph; H; Ph; S; 1-Propyl-3-methylbutyl; Ph]; [4144; O; Ph; H; Ph; S; 2-Cl-Ph; Ph]; [4145; O; Ph; H; Ph; S; 2-Me-Ph; Ph]; [4146; O; Ph; H; Ph; S; 3,4-F₂-Ph; Ph]; [4147; O; Ph; H; Ph; S; 3,4-Cl₂-Ph; Ph]; [4148; O; Ph; H; Ph; S; 3,4-Me₂-Ph; Ph]; [4149; O; Ph; H; SMe; S; Bu; Ph]; [4150; O; Ph; H; SMe; S; CH₃(CH₂)₄; Ph]; [4151; O; Ph; H; SMe; S; CH₃(CH₂)₅; Ph]; [4152; O; Ph; H; SMe; S; 1-Methylbutyl; Ph]; [4153; O; Ph; H; SMe; S; 2-Methylbutyl; Ph]; [4154; O; Ph; H; SMe; S; 1,2-Dimethylpropyl; Ph]; [4155; O; Ph; H; SMe; S; 1-Methylpentyl; Ph]; [4156; O; Ph; H; SMe; S; 2-Methylpentyl; Ph]; [4157; O; Ph; H; SMe; S; 1-Ethylbutyl; Ph]; [4158; O; Ph; H; SMe; S; 2-Ethylbutyl; Ph]; [4159; O; Ph; H; SMe; S; 1,3-Dimethylbutyl; Ph]; [4160; O; Ph; H; SMe; S; 1-Ethyl-1-methylbutyl; Ph]; [4161; O; Ph; H; SMe; S; 1-Ethylpentyl; Ph]; [4162; O; Ph; H; SMe; S; 1-Ethyl-3-methylbutyl; Ph]; [4163; O; Ph; H; SMe; S; 1-Propylbutyl; Ph]; [4164; O; Ph; H; SMe; S; 1-Propylpentyl; Ph]; [4165; O; Ph; H; SMe; S; 1-Propyl-3-methylbutyl; Ph]; [4166; O; Ph; H; SMe; S; Cyclopentyl; Ph]; [4167; O; Ph; H; SMe; S; Cyclohexyl; Ph]; [4168; O; Ph; H; SMe; S; 2-Perhydronaphthyl; Ph]; [4169; 0; Ph; H; SMe; S; cyclopentylmethyl; Ph]; [4170; O; Ph; H; SMe; S; cyclohexylmethyl; Ph]; [4171; O; Ph; H; SMe; S; cyclopentylethyl; Ph]; [4172; O; Ph; H; SMe; S; cyclohexylethyl; Ph]; [4173; O; Ph; H; SMe; S; 2-F-Ph; Ph]; [4174; O; Ph; H; SMe; S; 3-F-Ph; Ph]; [4175; O; Ph; H; SMe; S; 4-F-Ph; Ph]; [4176; O; Ph; H; SMe; S; 2-Cl-Ph; Ph]; [4177; O; Ph; H;

SMe; S; 3-Cl-Ph; Ph]; [4178; O; Ph; H; SMe; S; 4-Cl-Ph; Ph]; [4179; O; Ph; H; SMe; S; 2-Me-Ph; Ph]; [4180; O; Ph; H; SMe; S; 3-Me-Ph; Ph]; [4181; O; Ph; H; SMe; S; 4-Me-Ph; Ph]; [4182; O; Ph; H; SMe; S; 4-CF$_3$-Ph; Ph]; [4183; O; Ph; H; SMe; S; 4-MeO-Ph; Ph]; [4184; O; Ph; H; SMe; S; 4-MeS-Ph; Ph]; [4185; O; Ph; H; SMe; S; 4-F3CO-Ph; Ph]; [4186; O; Ph; H; SMe; S; 3,4-F$_2$-Ph; Ph]; [4187; O; Ph; H; SMe; S; 3,4-Cl$_2$-Ph; Ph]; [4188; O; Ph; H; SMe; S; 3,4-Me$_2$-Ph; Ph]; [4189; O; Ph; H; SMe; S; 2-Naphthyl; Ph]; [4190; 0; Ph; H; SMe; S; 5-Indanyl; Ph]; [4191; O; Ph; H; 2-Thienyl; S; Bu; Ph]; [4192; O; Ph; H; 2-Thienyl; S; CH$_2$(CH$_2$)$_4$; Ph]; [4193; O; Ph; H; 2-Thienyl; S; CH$_2$(CH$_2$)$_5$; Ph]; [4194; O; Ph; H; 2-Thienyl; S; 1-Methylbutyl; Ph]; [4195; O; Ph; H; 2-Thienyl; S; 2-Methylbutyl; Ph]; [4196; O; Ph; H; 2-Thienyl; S; 1,2-Dimethylpropyl; Ph]; [4197; O; Ph; H; 2-Thienyl; S; 1-Methylpentyl; Ph]; [4198; O; Ph; H; 2-Thienyl; S; 2-Methylpentyl; Ph]; [4199; O; Ph; H; 2-Thienyl; S; 1-Ethylbutyl; Ph]; [4200; O; Ph; H; 2-Thienyl; S; 2-Ethylbutyl; Ph]; [4201; O; Ph; H; 2-Thienyl; S; 1,3-Dimethylbutyl; Ph]; [4202; O; Ph; H; 2-Thienyl; S; 1-Ethyl-1-methylbutyl; Ph]; [4203; O; Ph; H; 2-Thienyl; S; 1-Ethylpentyl; Ph]; [4204; O; Ph; H; 2-Thienyl; S; 1-Ethyl-3-methylbutyl; Ph]; [4205; O; Ph; H; 2-Thienyl; S; 1-Propylbutyl; Ph]; [4206; O; Ph; H; 2-Thienyl; S; 1-Propylpentyl; Ph]; [4207; O; Ph; H; 2-Thienyl; S; 1-Propyl-3-methylbutyl; Ph]; [4208; O; Ph; H; 2-Thienyl; S; Cyclopentyl; Ph]; [4209; O; Ph; H; 2-Thienyl; S; Cyclohexyl; Ph]; [4210; O; Ph; H; 2-Thienyl; S; 2-Perhydronaphthyl; Ph]; [4211; O; Ph; H; 2-Thienyl; S; cyclopentylmethyl; Ph]; [4212; O; Ph; H; 2-Thienyl; S; cyclohexylmethyl; Ph]; [4213; O; Ph; H; 2-Thienyl; S; cyclopentylethyl; Ph]; [4214; O; Ph; H; 2-Thienyl; S; cyclohexylethyl; Ph]; [4215; O; Ph; H; 2-Thienyl; S; 2-F-Ph; Ph]; [4216; O; Ph; H; 2-Thienyl; S; 3-F-Ph; Ph]; [4217; O; Ph; H; 2-Thienyl; S; 4-F-Ph; Ph]; [4218; O; Ph; H; 2-Thienyl; S; 2-Cl-Ph; Ph]; [4219; O; Ph; H; 2-Thienyl; S; 3-Cl-Ph; Ph]; [4220; O; Ph; H; 2-Thienyl; S; 4-Cl-Ph; Ph]; [4221; O; Ph; H; 2-Thienyl; S; 2-Me-Ph; Ph]; [4222; O; Ph; H; 2-Thienyl; S; 3-Me-Ph; Ph]; [4223; O; Ph; H; 2-Thienyl; S; 4-Me-Ph; Ph]; [4224; O; Ph; H; 2-Thienyl; S; 4-CF$_3$-Ph; Ph]; [4225; O; Ph; H; 2-Thienyl; S; 4-MeO-Ph; Ph]; [4226; O; Ph; H; 2-Thienyl; S; 4-MeS-Ph; Ph]; [4227; O; Ph; H; 2-Thienyl; S; 4-F3CO-Ph; Ph]; [4228; O; Ph; H; 2-Thienyl; S; 3,4-F$_2$-Ph; Ph]; [4229; O; Ph; H; 2-Thienyl; S; 3,4-Cl$_2$-Ph; Ph]; [4230; O; Ph; H; 2-Thienyl; S; 3,4-Me$_2$-Ph; Ph]; [4231; O; Ph; H; 2-Thienyl; S; 2-Naphthyl; Ph]; [4232; O; Ph; H; 2-Thienyl; S; 5-Indanyl; Ph]; [4233; O; Ph; H; Me; S; Ph; 4-Et-Ph]; [4234; O; Ph; H; Me; S; Ph; 4-MeO-Ph]; [4235; O; Ph; H; Me; S; Ph; 4-CF$_3$O-Ph]; [4236; O; Ph; H; Me; S; Ph; 2,3-F$_2$-Ph]; [4237; O; Ph; H; Me; S; Ph; 2,4-F$_2$-Ph]; [4238; O; Ph; H; Me; S; Ph; 2,5-F$_2$-Ph]; [4239; O; Ph; H; Me; S; Ph; 2,6-F$_2$-Ph]; [4240; O; Ph; H; Me; S; Ph; 3,4-F$_2$-Ph]; [4241; O; Ph; H; Me; S; Ph; 3,5-F$_2$-Ph]; [4242; O; Ph; H; Me; S; Ph; 2,3-Cl$_2$-Ph]; [4243; O; Ph; H; Me; S; Ph; 2,4-Cl$_2$-Ph]; [4244; O; Ph; H; Me; S; Ph; 2,5-Cl$_2$-Ph]; [4245; O; Ph; H; Me; S; Ph; 2,6-Cl$_2$-Ph]; [4246; O; Ph; H; Me; S; Ph; 3,4-Cl$_2$-Ph]; [4247; O; Ph; H; Me; S; Ph; 3,5-Cl$_2$-Ph]; [4248; O; Ph; H; Me; S; Ph; 2,3-Me$_2$-Ph]; [4249; O; Ph; H; Me; S; Ph; 2,4-Me$_2$-Ph]; [4250; O; Ph; H; Me; S; Ph; 2,5-Me$_2$-Ph]; [4251; O; Ph; H; Me; S; Ph; 2,6-Me$_2$-Ph]; [4252; O; Ph; H; Me; S; Ph; 3,4-Me$_2$-Ph]; [4253; O; Ph; H; Me; S; Ph; 3,5-Me$_2$-Ph]; [4254; O; Ph; H; Me; S; Ph; 4-Br-Ph]; [4255; O; Ph; H; Me; S; Ph; 2-Me-4-Ph-Ph]; [4256; O; Ph; H; Me; S; Ph; 3-Me-4-Ph-Ph]; [4257; O; Ph; H; Me; S; Ph; 4-(2-Me-Ph)-Ph]; [4258; O; Ph; H; Me; S; Ph; 4-(3-Me-Ph)-Ph]; [4259; O; Ph; H; Me; S; Ph; 4-(4-Me-Ph)-Ph]; [4260; O; Ph; H; Et; S; Ph; 2-F-Ph]; [4261; O; Ph; H; Et; S; Ph; 3-F-Ph]; [4262; O; Ph; H; Et; S; Ph; 4-F-Ph]; [4263; O; Ph; H; Et; S; Ph; 2-Cl-Ph]; [4264; O; Ph; H; Et; S; Ph; 3-Cl-Ph]; [4265; O; Ph; H; Et; S; Ph; 4-Cl-Ph]; [4266; O; Ph; H; Et; S; Ph; 2-Me-Ph]; [4267; O; Ph; H; Et; S; Ph; 3-Me-Ph]; [4268; O; Ph; H; Et; S; Ph; 4-Me-Ph]; [4269; O; Ph; H; Et; S; Ph; 4-Et-Ph]; [4270; O; Ph; H; Et; S; Ph; 4-iPr-Ph]; [4271; O; Ph; H; Et; S; Ph; 4-CF$_3$-Ph]; [4272; O; Ph; H; Et; S; Ph; 4-MeO-Ph]; [4273; O; Ph; H; Et; S; Ph; 4-CF$_3$O-Ph]; [4274; O; Ph; H; Et; S; Ph; 2,3-F$_2$-Ph]; [4275; O; Ph; H; Et; S; Ph; 2,4-F$_2$-Ph]; [4276; O; Ph; H; Et; S; Ph; 2,5-F$_2$-Ph]; [4277; O; Ph; H; Et; S; Ph; 2,6-F$_2$-Ph]; [4278; O; Ph; H; Et; S; Ph; 3,4-F$_2$-Ph]; [4279; O; Ph; H; Et; S; Ph; 3,5-F$_2$-Ph]; [4280; O; Ph; H; Et; S; Ph; 2,3-Cl$_2$-Ph]; [4281; O; Ph; H; Et; S; Ph; 2,4-Cl$_2$-Ph]; [4282; O; Ph; H; Et; S; Ph; 2,5-Cl$_2$-Ph]; [4283; O; Ph; H; Et; S; Ph; 2,6-Cl$_2$-Ph]; [4284; O; Ph; H; Et; S; Ph; 3,4-Cl$_2$-Ph]; [4285; O; Ph; H; Et; S; Ph; 3,5-Cl$_2$-Ph]; [4286; O; Ph; H; Et; S; Ph; 2,3-Me$_2$-Ph]; [4287; O; Ph; H; Et; S; Ph; 2,4-Me$_2$-Ph]; [4288; O; Ph; H; Et; S; Ph; 2,5-Me$_2$-Ph]; [4289; O; Ph; H; Et; S; Ph; 2,6-Me$_2$-Ph]; [4290; O; Ph; H; Et; S; Ph; 3,4-Me$_2$-Ph]; [4291; O; Ph; H; Et; S; Ph; 3,5-Me$_2$-Ph]; [4292; O; Ph; H; Et; S; Ph; 2-Naphthyl]; [4293; O; Ph; H; Et; S; Ph; 5-Indanyl]; [4294; O; Ph; H; Pr; S; Ph; 2-F-Ph]; [4295; O; Ph; H; Pr; S; Ph; 3-F-Ph]; [4296; O; Ph; H; Pr; S; Ph; 4-F-Ph]; [4297; O; Ph; H; Pr; S; Ph; 2-Cl-Ph]; [4298; O; Ph; H; Pr; S; Ph; 3-Cl-Ph]; [4299; O; Ph; H; Pr; S; Ph; 4-Cl-Ph]; [4300; O; Ph; H; Pr; S; Ph; 2-Me-Ph]; [4301; O; Ph; H; Pr; S; Ph; 3-Me-Ph]; [4302; O; Ph; H; Pr; S; Ph; 4-Me-Ph]; [4303; O; Ph; H; Pr; S; Ph; 4-Et-Ph]; [4304; O; Ph; H; Pr; S; Ph; 3,4-Me$_2$-Ph]; [4305; O; Ph; H; Pr; S; Ph; 5-Indanyl]; [4306; O; Ph; H; Ph; S; Ph; 3,4-Me$_2$-Ph]; [4307; O; Ph; H; SMe; S; Ph; 2-F-Ph]; [4308; O; Ph; H; SMe; S; Ph; 3-F-Ph]; [4309; O; Ph; H; SMe; S; Ph; 4-F-Ph]; [4310; O; Ph; H; SMe; S; Ph; 2-Cl-Ph]; [4311; O; Ph; H; SMe; S; Ph; 3-Cl-Ph]; [4312; O; Ph; H; SMe; S; Ph; 4-Cl-Ph]; [4313; O; Ph; H; SMe; S; Ph; 2-Me-Ph]; [4314; O; Ph; H; SMe; S; Ph; 3-Me-Ph]; [4315; O; Ph; H; SMe; S; Ph; 4-Me-Ph]; [4316; O; Ph; H; SMe; S; Ph; 4-Et-Ph]; [4317; O; Ph; H; SMe; S; Ph; 4-iPr-Ph]; [4318; O; Ph; H; SMe; S; Ph; 3,4-Me$_2$-Ph]; [4319; O; Ph; H; SMe; S; Ph; 5-Indanyl]; [4320; O; Ph; H; 2-Thienyl; S; Ph; 4-F-Ph]; [4321; O; Ph; H; 2-Thienyl; S; Ph; 4-Cl-Ph]; [4322; O; Ph; H; 2-Thienyl; S; Ph; 3-Me-Ph]; [4323; O; Ph; H; 2-Thienyl; S; Ph; 4-Me-Ph]; [4324; O; Ph; H; 2-Thienyl; S; Ph; 3,4-Me$_2$-Ph]; [4325; O; Ph; H; 2-Thienyl; S; Ph; 5-Indanyl]; [4326; O; 3-F-Ph; H; Me; S; Ph; 4-Et-Ph]; [4327; O; 3-F-Ph; H; Me; S; Ph; 3,4-Me$_2$-Ph]; [4328; O; 4-F-Ph; H; Me; S; Ph; 4-Et-Ph]; [4329; O; 4-F-Ph; H; Me; S; Ph; 3,4-Me$_2$-Ph]; [4330; O; 4-Cl-Ph; H; Me; S; Ph; 4-Et-Ph]; [4331; O; 4-Cl-Ph; H; Me; S; Ph; 3,4-Me$_2$-Ph]; [4332; O; 3-Me-Ph; H; Me; S; Ph; 4-Et-Ph]; [4333; O; 3-Me-Ph; H; Me; S; Ph; 3,4-Me$_2$-Ph]; [4334; O; 4-Me-Ph; H; Me; S; Ph; 4-Et-Ph]; [4335; O; 4-Me-Ph; H; Me; S; Ph; 3,4-Me$_2$-Ph]; [4336; O; 5-Benzodioxolyl; H; Me; S; Ph; 4-Et-Ph]; [4337; O; 5-Benzodioxolyl; H; Me; S; Ph; 3,4-Me$_2$-Ph]; [4338; O; 4-F-Ph; H; Et; S; Ph; 4-F-Ph]; [4339; O; 4-F-Ph; H; Et; S; Ph; 4-Cl-Ph]; [4340; O; 4-F-Ph; H; Et; S; Ph; 3-Me-Ph]; [4341; O; 4-F-Ph; H; Et; S; Ph; 4-Me-Ph]; [4342; O; 4-F-Ph; H; Et; S; Ph; 4-Et-Ph]; [4343; O; 4-F-Ph; H; Et; S; Ph; 4-iPr-Ph]; [4344; O; 4-F-Ph; H; Et; S; Ph; 3,4-Me$_2$-Ph]; [4345; O; 4-F-Ph; H; Et; S; Ph; 5-Indanyl]; [4346; O; 4-Cl-Ph; H; Et; S; Ph; 4-F-Ph]; [4347; O; 4-Cl-Ph; H; Et; S; Ph; 4-Cl-Ph]; [4348; O; 4-Cl-Ph; H; Et; S; Ph; 3-Me-Ph]; [4349; O; 4-Cl-Ph; H; Et; S; Ph; 4-Me-Ph]; [4350; O; 4-Cl-Ph; H; Et; S; Ph; 4-Et-Ph]; [4351; O; 4-Cl-Ph; H; Et; S; Ph; 4-iPr-Ph]; [4352; O; 4-Cl-Ph; H; Et; S; Ph; 3,4-Me$_2$-Ph]; [4353; O; 4-Cl-Ph; H; Et; S; Ph; 5-Indanyl]; [4354; O; 4-Me-Ph; H; Et; S; Ph; 4-F-Ph]; [4355; O; 4-Me-Ph; H; Et; S; Ph; 4-Cl-Ph]; [4356; O; 4-Me-Ph; H; Et; S; Ph; 3-Me-Ph]; [4357; O; 4-Me-Ph; H; Et; S; Ph; 4-Me-Ph]; [4358; O; 4-Me-Ph; H; Et; S; Ph; 4-Et-Ph]; [4359; O; 4-Me-Ph; H; Et; S; Ph; 4-iPr-Ph]; [4360; O; 4-Me-Ph; H; Et; S; Ph; 3,4-Me$_2$-Ph]; [4361; O; 4-Me-Ph; H; Et; S; Ph; 5-Indanyl];

[4362; O; 4-MeO-Ph; H; Et; S; Ph; 4-F-Ph]; [4363; O; 4-MeO-Ph; H; Et; S; Ph; 4-Cl-Ph]; [4364; O; 4-MeO-Ph; H; Et; S; Ph; 3-Me-Ph]; [4365; O; 4-MeO-Ph; H; Et; S; Ph; 4-Me-Ph]; [4366; O; 4-MeO-Ph; H; Et; S; Ph; 4-Et-Ph]; [4367; O; 4-MeO-Ph; H; Et; S; Ph; 4-iPr-Ph]; [4368; O; 4-MeO-Ph; H; Et; S; Ph; 3,4-Me$_2$-Ph]; [4369; O; 4-MeO-Ph; H; Et; S; Ph; 5-Indanyl]; [4370; O; 5-Benzodioxolyl; H; Et; S; Ph; 4-F-Ph]; [4371; O; 5-Benzodioxolyl; H; Et; S; Ph; 4-Cl-Ph]; [4372; O; 5-Benzodioxolyl; H; Et; S; Ph; 3-Me-Ph]; [4373; O; 5-Benzodioxolyl; H; Et; S; Ph; 4-Me-Ph]; [4374; O; 5-Benzodioxolyl; H; Et; S; Ph; 4-Et-Ph]; [4375; O; 5-Benzodioxolyl; H; Et; S; Ph; 4-iPr-Ph]; [4376; O; 5-Benzodioxolyl; H; Et; S; Ph; 3,4-Me$_2$-Ph]; [4377; O; 5-Benzodioxolyl; H; Et; S; Ph; 5-Indanyl]; [4378; O; 4-F-Ph; H; Pr; S; Ph; 4-F-Ph]; [4379; O; 4-F-Ph; H; Pr; S; Ph; 4-Cl-Ph]; [4380; O; 4-F-Ph; H; Pr; S; Ph; 3-Me-Ph]; [4381; O; 4-F-Ph; H; Pr; S; Ph; 4-Me-Ph]; [4382; O; 4-F-Ph; H; Pr; S; Ph; 4-Et-Ph]; [4383; O; 4-F-Ph; H; Pr; S; Ph; 4-iPr-Ph]; [4384; O; 4-F-Ph; H; Pr; S; Ph; 3,4-Me$_2$-Ph]; [4385; O; 4-F-Ph; H; Pr; S; Ph; 5-Indanyl]; [4386; O; 4-Cl-Ph; H; Pr; S; Ph; 4-F-Ph]; [4387; 0; 4-Cl-Ph; H; Pr; S; Ph; 4-Cl-Ph]; [4388; O; 4-Cl-Ph; H; Pr; S; Ph; 3-Me-Ph]; [4389; O; 4-Cl-Ph; H; Pr; S; Ph; 4-Me-Ph]; [4390; O; 4-Cl-Ph; H; Pr; S; Ph; 4-Et-Ph]; [4391; O; 4-Cl-Ph; H; Pr; S; Ph; 4-iPr-Ph]; [4392; O; 4-Cl-Ph; H; Pr; S; Ph; 3,4-Me$_2$-Ph]; [4393; O; 4-Cl-Ph; H; Pr; S; Ph; 5-Indanyl]; [4394; O; 4-Me-Ph; H; Pr; S; Ph; 4-F-Ph]; [4395; 0; 4-Me-Ph; H; Pr; S; Ph; 4-Cl-Ph]; [4396; O; 4-Me-Ph; H; Pr; S; Ph; 3-Me-Ph]; [4397; O; 4-Me-Ph; H; Pr; S; Ph; 4-Me-Ph]; [4398; O; 4-F-Ph; H; Pr; S; Ph; 4-Et-Ph]; [4399; O; 4-Me-Ph; H; Pr; S; Ph; 4-iPr-Ph]; [4400; O; 4-Me-Ph; H; Pr; S; Ph; 3,4-Me$_2$-Ph]; [4401; O; 4-Me-Ph; H; Pr; S; Ph; 5-Indanyl]; [4402; O; 4-MeO-Ph; H; Pr; S; Ph; 4-F-Ph]; [4403; O; 4-MeO-Ph; H; Pr; S; Ph; 4-Cl-Ph]; [4404; O; 4-MeO-Ph; H; Pr; S; Ph; 3-Me-Ph]; [4405; O; 4-MeO-Ph; H; Pr; S; Ph; 4-Me-Ph]; [4406; O; 4-MeO-Ph; H; Pr; S; Ph; 4-Et-Ph]; [4407; O; 4-MeO-Ph; H; Pr; S; Ph; 4-iPr-Ph]; [4408; O; 4-MeO-Ph; H; Pr; S; Ph; 3,4-Me$_2$-Ph]; [4409; O; 4-MeO-Ph; H; Pr; S; Ph; 5-Indanyl]; [4410; O; 5-Benzodioxolyl; H; Pr; S; Ph; 4-F-Ph]; [4411; O; 5-Benzodioxolyl; H; Pr; S; Ph; 4-Cl-Ph]; [4412; O; 5-Benzodioxolyl; H; Pr; S; Ph; 3-Me-Ph]; [4413; O; 5-Benzodioxolyl; H; Pr; S; Ph; 4-Me-Ph]; [4414; O; 5-Benzodioxolyl; H; Pr; S; Ph; 4-Et-Ph]; [4415; O; 5-Benzodioxolyl; H; Pr; S; Ph; 4-iPr-Ph]; [4416; O; 5-Benzodioxolyl; H; Pr; S; Ph; 3,4-Me$_2$-Ph]; [4417; O; 5-Benzodioxolyl; H; Pr; S; Ph; 5-Indanyl]; [4418; O; 4-F-Ph; H; Ph; S; Ph; 4-F-Ph]; [4419; O; 4-F-Ph; H; Ph; S; Ph; 4-Cl-Ph]; [4420; O; 4-F-Ph; H; Ph; S; Ph; 3-Me-Ph]; [4421; O; 4-F-Ph; H; Ph; S; Ph; 4-Me-Ph]; [4422; O; 4-F-Ph; H; Ph; S; Ph; 4-Et-Ph]; [4423; O; 4-F-Ph; H; Ph; S; Ph; 4-iPr-Ph]; [4424; O; 4-F-Ph; H; Ph; S; Ph; 3,4-Me$_2$-Ph]; [4425; O; 4-F-Ph; H; Ph; S; Ph; 5-Indanyl]; [4426; O; 4-Cl-Ph; H; Ph; S; Ph; 4-F-Ph]; [4427; O; 4-Cl-Ph; H; Ph; S; Ph; 4-Cl-Ph]; [4428; O; 4-Cl-Ph; H; Ph; S; Ph; 3-Me-Ph]; [4429; O; 4-Cl-Ph; H; Ph; S; Ph; 4-Me-Ph]; [4430; O; 4-Cl-Ph; H; Ph; S; Ph; 4-Et-Ph]; [4431; O; 4-Cl-Ph; H; Ph; S; Ph; 4-iPr-Ph]; [4432; O; 4-Cl-Ph; H; Ph; S; Ph; 3,4-Me$_2$-Ph]; [4433; O; 4-Cl-Ph; H; Ph; S; Ph; 5-Indanyl]; [4434; O; 4-Me-Ph; H; Ph; S; Ph; 4-F-Ph]; [4435; O; 4-Me-Ph; H; Ph; S; Ph; 4-Cl-Ph]; [4436; O; 4-Me-Ph; H; Ph; S; Ph; 3-Me-Ph]; [4437; O; 4-Me-Ph; H; Ph; S; Ph; 4-Me-Ph]; [4438; O; 4-F-Ph; H; Ph; S; Ph; 4-Et-Ph]; [4439; O; 4-Me-Ph; H; Ph; S; Ph; 4-iPr-Ph]; [4440; O; 4-Me-Ph; H; Ph; S; Ph; 3,4-Me$_2$-Ph]; [4441; O; 4-Me-Ph; H; Ph; S; Ph; 5-Indanyl]; [4442; O; 4-MeO-Ph; H; Ph; S; Ph; 4-F-Ph]; [4443; O; 4-MeO-Ph; H; Ph; S; Ph; 4-Cl-Ph]; [4444; O; 4-MeO-Ph; H; Ph; S; Ph; 3-Me-Ph]; [4445; O; 4-MeO-Ph; H; Ph; S; Ph; 4-Me-Ph]; [4446; O; 4-MeO-Ph; H; Ph; S; Ph; 4-Et-Ph]; [4447; O; 4-MeO-Ph; H; Ph; S; Ph; 4-iPr-Ph]; [4448; O; 4-MeO-Ph; H; Ph; S; Ph; 3,4-Me$_2$-Ph]; [4449; O; 4-MeO-Ph; H; Ph; S; Ph; 5-Indanyl]; [4450; O; 5-Benzodioxolyl; H; Ph; S; Ph; 4-F-Ph]; [4451; O; 5-Benzodioxolyl; H; Ph; S; Ph; 4-Cl-Ph]; [4452; O; 5-Benzodioxolyl; H; Ph; S; Ph; 3-Me-Ph]; [4453; O; 5-Benzodioxolyl; H; Ph; S; Ph; 4-Me-Ph]; [4454; O; 5-Benzodioxolyl; H; Ph; S; Ph; 4-Et-Ph]; [4455; O; 5-Benzodioxolyl; H; Ph; S; Ph; 4-iPr-Ph]; [4456; O; 5-Benzodioxolyl; H; Ph; S; Ph; 3,4-Me$_2$-Ph]; [4457; O; 5-Benzodioxolyl; H; Ph; S; Ph; 5-Indanyl]; [4458; O; 4-F-Ph; H; SMe; S; Ph; 4-F-Ph]; [4459; 0; 4-F-Ph; H; SMe; S; Ph; 4-Cl-Ph]; [4460; O; 4-F-Ph; H; SMe; S; Ph; 3-Me-Ph]; [4461; O; 4-F-Ph; H; SMe; S; Ph; 4-Me-Ph]; [4462; O; 4-F-Ph; H; SMe; S; Ph; 4-Et-Ph]; [4463; O; 4-F-Ph; H; SMe; S; Ph; 4-iPr-Ph]; [4464; O; 4-F-Ph; H; SMe; S; Ph; 3,4-Me$_2$-Ph]; [4465; O; 4-F-Ph; H; SMe; S; Ph; 5-Indanyl]; [4466; O; 4-Cl-Ph; H; SMe; S; Ph; 4-F-Ph]; [4467; 0; 4-Cl-Ph; H; SMe; S; Ph; 4-Cl-Ph]; [4468; O; 4-Cl-Ph; H; SMe; S; Ph; 3-Me-Ph]; [4469; O; 4-Cl-Ph; H; SMe; S; Ph; 4-Me-Ph]; [4470; O; 4-Cl-Ph; H; SMe; S; Ph; 4-Et-Ph]; [4471; 0; 4-Cl-Ph; H; SMe; S; Ph; 4-iPr-Ph]; [4472; O; 4-Cl-Ph; H; SMe; S; Ph; 3,4-Me$_2$-Ph]; [4473; O; 4-Cl-Ph; H; SMe; S; Ph; 5-Indanyl]; [4474; O; 4-Me-Ph; H; SMe; S; Ph; 4-F-Ph]; [4475; O; 4-Me-Ph; H; SMe; S; Ph; 4-Cl-Ph]; [4476; O; 4-Me-Ph; H; SMe; S; Ph; 3-Me-Ph]; [4477; O; 4-Me-Ph; H; SMe; S; Ph; 4-Me-Ph]; [4478; O; 4-F-Ph; H; SMe; S; Ph; 4-Et-Ph]; [4479; O; 4-Me-Ph; H; SMe; S; Ph; 4-iPr-Ph]; [4480; O; 4-Me-Ph; H; SMe; S; Ph; 3,4-Me$_2$-Ph]; [4481; O; 4-Me-Ph; H; SMe; S; Ph; 5-Indanyl]; [4482; O; 4-MeO-Ph; H; SMe; S; Ph; 4-F-Ph]; [4483; O; 4-MeO-Ph; H; SMe; S; Ph; 4-Cl-Ph]; [4484; O; 4-MeO-Ph; H; SMe; S; Ph; 3-Me-Ph]; [4485; O; 4-MeO-Ph; H; SMe; S; Ph; 4-Me-Ph]; [4486; O; 4-MeO-Ph; H; SMe; S; Ph; 4-Et-Ph]; [4487; O; 4-MeO-Ph; H; SMe; S; Ph; 4-iPr-Ph]; [4488; O; 4-MeO-Ph; H; SMe; S; Ph; 3,4-Me$_2$-Ph]; [4489; O; 4-MeO-Ph; H; SMe; S; Ph; 5-Indanyl]; [4490; O; 5-Benzodioxolyl; H; SMe; S; Ph; 4-F-Ph]; [4491; O; 5-Benzodioxolyl; H; SMe; S; Ph; 4-Cl-Ph]; [4492; O; 5-Benzodioxolyl; H; SMe; S; Ph; 3-Me-Ph]; [4493; O; 5-Benzodioxolyl; H; SMe; S; Ph; 4-Me-Ph]; [4494; O; 5-Benzodioxolyl; H; SMe; S; Ph; 4-Et-Ph]; [4495; O; 5-Benzodioxolyl; H; SMe; S; Ph; 4-iPr-Ph]; [4496; O; 5-Benzodioxolyl; H; SMe; S; Ph; 3,4-Me$_2$-Ph]; [4497; O; 5-Benzodioxolyl; H; SMe; S; Ph; 5-Indanyl]; [4498; O; 4-F-Ph; H; 2-Thienyl; S; Ph; 4-F-Ph]; [4499; O; 4-F-Ph; H; 2-Thienyl; S; Ph; 4-Cl-Ph]; [4500; O; 4-F-Ph; H; 2-Thienyl; S; Ph; 3-Me-Ph]; [4501; O; 4-F-Ph; H; 2-Thienyl; S; Ph; 4-Me-Ph]; [4502; O; 4-F-Ph; H; 2-Thienyl; S; Ph; 4-Et-Ph]; [4503; O; 4-F-Ph; H; 2-Thienyl; S; Ph; 4-iPr-Ph]; [4504; O; 4-F-Ph; H; 2-Thienyl; S; Ph; 3,4-Me$_2$-Ph]; [4505; O; 4-F-Ph; H; 2-Thienyl; S; Ph; 5-Indanyl]; [4506; O; 4-Cl-Ph; H; 2-Thienyl; S; Ph; 4-F-Ph]; [4507; O; 4-Cl-Ph; H; 2-Thienyl; S; Ph; 4-Cl-Ph]; [4508; O; 4-Cl-Ph; H; 2-Thienyl; S; Ph; 3-Me-Ph]; [4509; O; 4-Cl-Ph; H; 2-Thienyl; S; Ph; 4-Me-Ph]; [4510; O; 4-Cl-Ph; H; 2-Thienyl; S; Ph; 4-Et-Ph]; [4511; O; 4-Cl-Ph; H; 2-Thienyl; S; Ph; 4-iPr-Ph]; [4512; O; 4-Cl-Ph; H; 2-Thienyl; S; Ph; 3,4-Me$_2$-Ph]; [4513; O; 4-Cl-Ph; H; 2-Thienyl; S; Ph; 5-Indanyl]; [4514; O; 4-Me-Ph; H; 2-Thienyl; S; Ph; 4-F-Ph]; [4515; O; 4-Me-Ph; H; 2-Thienyl; S; Ph; 4-Cl-Ph]; [4516; O; 4-Me-Ph; H; 2-Thienyl; S; Ph; 3-Me-Ph]; [4517; O; 4-Me-Ph; H; 2-Thienyl; S; Ph; 4-Me-Ph]; [4518; O; 4-F-Ph; H; 2-Thienyl; S; Ph; 4-Et-Ph]; [4519; O; 4-Me-Ph; H; 2-Thienyl; S; Ph; 4-iPr-Ph]; [4520; O; 4-Me-Ph; H; 2-Thienyl; S; Ph; 3,4-Me$_2$-Ph]; [4521; O; 4-Me-Ph; H; 2-Thienyl; S; Ph; 5-Indanyl]; [4522; O; 4-MeO-Ph; H; 2-Thienyl; S; Ph; 4-F-Ph]; [4523; O; 4-MeO-Ph; H; 2-Thienyl; S; Ph; 4-Cl-Ph]; [4524; O; 4-MeO-Ph; H; 2-Thienyl; S; Ph; 3-Me-Ph]; [4525; O; 4-MeO-Ph; H; 2-Thienyl; S; Ph; 4-Me-Ph]; [4526; O; 4-MeO-Ph; H; 2-Thienyl; S; Ph; 4-Et-Ph]; [4527; O; 4-MeO-Ph; H; 2-Thienyl; S; Ph; 4-iPr-Ph];

[4528; O; 4-MeO-Ph; H; 2-Thienyl; S; Ph; 3,4-Me₂-Ph]; [4529; O; 4-MeO-Ph; H; 2-Thienyl; S; Ph; 5-Indanyl]; [4530; O; 5-Benzodioxolyl; H; 2-Thienyl; S; Ph; 4-F-Ph]; [4531; O; 5-Benzodioxolyl; H; 2-Thienyl; S; Ph; 4-Cl-Ph]; [4532; O; 5-Benzodioxolyl; H; 2-Thienyl; S; Ph; 3-Me-Ph]; [4533; O; 5-Benzodioxolyl; H; 2-Thienyl; S; Ph; 4-Me-Ph]; [4534; O; 5-Benzodioxolyl; H; 2-Thienyl; S; Ph; 4-Et-Ph]; [4535; O; 5-Benzodioxolyl; H; 2-Thienyl; S; Ph; 4-iPr-Ph]; [4536; O; 5-Benzodioxolyl; H; 2-Thienyl; S; Ph; 3,4-Me₂-Ph]; [4537; O; 5-Benzodioxolyl; H; 2-Thienyl; S; Ph; 5-Indanyl]; [4538; O; Ph; H; Me; S; Cyclohexyl; 2-F-Ph]; [4539; O; Ph; H; Me; S; Cyclohexyl; 3-F-Ph]; [4540; O; Ph; H; Me; S; Cyclohexyl; 4-F-Ph]; [4541; O; Ph; H; Me; S; Cyclohexyl; 4-Cl-Ph]; [4542; O; Ph; H; Me; S; Cyclohexyl; 3-Me-Ph]; [4543; O; Ph; H; Me; S; Cyclohexyl; 4-Me-Ph]; [4544; O; Ph; H; Me; S; Cyclohexyl; 4-iPr-Ph]; [4545; O; Ph; H; Me; S; Cyclohexyl; 3,4-Me₂-Ph]; [4546; O; Ph; H; Me; S; Cyclohexyl; 2-Naphthyl]; [4547; O; Ph; H; Me; S; Cyclohexyl; 5-Indanyl]; [4548; O; Ph; H; Me; S; Cyclohexylmethyl; 3,4-Me₂-Ph]; [4549; O; Ph; H; Me; S; 2-Perhydronaphthyl; 3,4-Me₂-Ph]; [4550; O; Ph; H; Me; S; 4-F-Ph; 3,4-Me₂-Ph]; [4551; O; Ph; H; Me; S; 3-Cl-Ph; 4-F-Ph]; [4552; O; Ph; H; Me; S; 3-Cl-Ph; 4-Cl-Ph]; [4553; O; Ph; H; Me; S; 3-Cl-Ph; 3-Me-Ph]; [4554; O; Ph; H; Me; S; 3-Cl-Ph; 4-Me-Ph]; [4555; O; Ph; H; Me; S; 3-Cl-Ph; 3,4-Me₂-Ph]; [4556; O; Ph; H; Me; S; 3-Cl-Ph; 5-Indanyl]; [4557; O; Ph; H; Me; S; 4-Cl-Ph; 4-F-Ph]; [4558; O; Ph; H; Me; S; 4-Cl-Ph; 4-Cl-Ph]; [4559; O; Ph; H; Me; S; 4-Me-Ph; 4-F-Ph]; [4560; O; Ph; H; Me; S; 4-Me-Ph; 4-Cl-Ph]; [4561; O; Ph; H; Me; S; 4-Me-Ph; 3-Me-Ph]; [4562; 0; Ph; H; Me; S; 4-Me-Ph; 4-Me-Ph]; [4563; O; Ph; H; Me; S; 4-Me-Ph; 3,4-Me₂-Ph]; [4564; O; Ph; H; Me; S; 4-Me-Ph; 5-Indanyl]; [4565; O; Ph; H; Me; S; 2-Naphthyl; 3,4-Me₂-Ph]; [4566; O; Ph; H; Et; S; Cyclohexyl; 4-F-Ph]; [4567; O; Ph; H; Et; S; Cyclohexyl; 4-Cl-Ph]; [4568; O; Ph; H; Et; S; Cyclohexyl; 3-Me-Ph]; [4569; O; Ph; H; Et; S; Cyclohexyl; 4-Me-Ph]; [4570; O; Ph; H; Et; S; Cyclohexyl; 3,4-Me₂-Ph]; [4571; O; Ph; H; Et; S; Cyclohexyl; 5-Indanyl]; [4572; O; Ph; H; Et; S; Cyclohexylmethyl; 4-F-Ph]; [4573; O; Ph; H; Et; S; Cyclohexylmethyl; 4-Cl-Ph]; [4574; O; Ph; H; Et; S; Cyclohexylmethyl; 3-Me-Ph]; [4575; O; Ph; H; Et; S; Cyclohexylmethyl; 4-Me-Ph]; [4576; O; Ph; H; Et; S; Cyclohexylmethyl; 4-Ph-Ph]; [4577; O; Ph; H; Et; S; Cyclohexylmethyl; 3,4-Me₂-Ph]; [4578; O; Ph; H; Et; S; Cyclohexylmethyl; 5-Indanyl]; [4579; O; Ph; H; Et; S; 4-F-Ph; 4-F-Ph]; [4580; O; Ph; H; Et; S; 4-F-Ph; 4-Cl-Ph]; [4581; O; Ph; H; Et; S; 4-F-Ph; 3-Me-Ph]; [4582; O; Ph; H; Et; S; 4-F-Ph; 4-Me-Ph]; [4583; O; Ph; H; Et; S; 4-F-Ph; 3,4-Me₂-Ph]; [4584; O; Ph; H; Et; S; 4-F-Ph; 5-Indanyl]; [4585; O; Ph; H; Et; S; 3-Cl-Ph; 4-F-Ph]; [4586; O; Ph; H; Et; S; 3-Cl-Ph; 4-Cl-Ph]; [4587; O; Ph; H; Et; S; 3-Cl-Ph; 3-Me-Ph]; [4588; O; Ph; H; Et; S; 3-Cl-Ph; 4-Me-Ph]; [4589; O; Ph; H; Et; S; 3-Cl-Ph; 3,4-Me₂-Ph]; [4590; O; Ph; H; Et; S; 3-Cl-Ph; 5-Indanyl]; [4591; O; Ph; H; Et; S; 4-Cl-Ph; 4-F-Ph]; [4592; O; Ph; H; Et; S; 4-Cl-Ph; 4-Cl-Ph]; [4593; O; Ph; H; Et; S; 3-Cl-Ph; 3-Me-Ph]; [4594; O; Ph; H; Et; S; 4-Cl-Ph; 4-Me-Ph]; [4595; O; Ph; H; Et; S; 4-Cl-Ph; 3,4-Me₂-Ph]; [4596; O; Ph; H; Et; S; 4-Cl-Ph; 5-Indanyl]; [4597; O; Ph; H; Et; S; 4-Me-Ph; 4-F-Ph]; [4598; O; Ph; H; Et; S; 4-Me-Ph; 4-Cl-Ph]; [4599; O; Ph; H; Et; S; 4-Me-Ph; 3-Me-Ph]; [4600; O; Ph; H; Et; S; 4-Me-Ph; 4-Me-Ph]; [4601; O; Ph; H; Et; S; 4-Me-Ph; 3,4-Me₂-Ph]; [4602; O; Ph; H; Et; S; 4-Me-Ph; 5-Indanyl]; [4603; O; Ph; H; Et; S; 2-Naphthyl; 4-F-Ph]; [4604; O; Ph; H; Et; S; 2-Naphthyl; 4-Cl-Ph]; [4605; O; Ph; H; Et; S; 2-Naphthyl; 3-Me-Ph]; [4606; O; Ph; H; Et; S; 2-Naphthyl; 4-Me-Ph]; [4607; O; Ph; H; Et; S; 2-Naphthyl; 3,4-Me₂-Ph]; [4608; O; Ph; H; Et; S; 2-Naphthyl; 5-Indanyl]; [4609; O; Ph; H; Pr; S; Cyclohexyl; 4-F-Ph]; [4610; O; Ph; H; Pr; S; Cyclohexyl; 4-Cl-Ph]; [4611; O; Ph; H; Pr; S; Cyclohexyl; 3-Me-Ph]; [4612; O; Ph; H; Pr; S; Cyclohexyl; 4-Me-Ph]; [4613; O; Ph; H; Pr; S; Cyclohexyl; 3,4-Me₂-Ph]; [4614; O; Ph; H; Pr; S; Cyclohexyl; 5-Indanyl]; [4615; O; Ph; H; Pr; S; Cyclohexylmethyl; 4-F-Ph]; [4616; O; Ph; H; Pr; S; Cyclohexylmethyl; 4-Cl-Ph]; [4617; O; Ph; H; Pr; S; Cyclohexylmethyl; 3-Me-Ph]; [4618; O; Ph; H; Pr; S; Cyclohexylmethyl; 4-Me-Ph]; [4619; O; Ph; H; Pr; S; Cyclohexylmethyl; 4-Ph-Ph]; [4620; O; Ph; H; Pr; S; Cyclohexylmethyl; Ph]; [4621; O; Ph; H; Pr; S; Cyclohexylmethyl; 5-Indanyl]; [4622; O; Ph; H; Pr; S; 4-F-Ph; 4-F-Ph]; [4623; O; Ph; H; Pr; S; 4-F-Ph; 4-Cl-Ph]; [4624; O; Ph; H; Pr; S; 4-F-Ph; 3-Me-Ph]; [4625; O; Ph; H; Pr; S; 4-F-Ph; 4-Me-Ph]; [4626; O; Ph; H; Pr; S; 4-F-Ph; 3,4-Me₂-Ph]; [4627; O; Ph; H; Pr; S; 4-F-Ph; 5-Indanyl]; [4628; O; Ph; H; Pr; S; 3-Cl-Ph; 4-F-Ph]; [4629; O; Ph; H; Pr; S; 3-Cl-Ph; 4-Cl-Ph]; [4630; O; Ph; H; Pr; S; 3-Cl-Ph; 3-Me-Ph]; [4631; O; Ph; H; Pr; S; 3-Cl-Ph; 4-Me-Ph]; [4632; O; Ph; H; Pr; S; 3-Cl-Ph; 3,4-Me₂-Ph]; [4633; O; Ph; H; Pr; S; 3-Cl-Ph; 5-Indanyl]; [4634; O; Ph; H; Pr; S; 4-Cl-Ph; 4-F-Ph]; [4635; O; Ph; H; Pr; S; 4-Cl-Ph; 4-Cl-Ph]; [4636; O; Ph; H; Pr; S; 3-Cl-Ph; 3-Me-Ph]; [4637; O; Ph; H; Pr; S; 4-Cl-Ph; 4-Me-Ph]; [4638; O; Ph; H; Pr; S; 4-Cl-Ph; 3,4-Me₂-Ph]; [4639; O; Ph; H; Pr; S; 4-Cl-Ph; 5-Indanyl]; [4640; O; Ph; H; Pr; S; 4-Me-Ph; 4-F-Ph]; [4641; O; Ph; H; Pr; S; 4-Me-Ph; 4-Cl-Ph]; [4642; O; Ph; H; Pr; S; 4-Me-Ph; 3-Me-Ph]; [4643; O; Ph; H; Pr; S; 4-Me-Ph; 4-Me-Ph]; [4644; O; Ph; H; Pr; S; 4-Me-Ph; 3,4-Me₂-Ph]; [4645; O; Ph; H; Pr; S; 4-Me-Ph; 5-Indanyl]; [4646; O; Ph; H; Pr; S; 2-Naphthyl; 4-F-Ph]; [4647; 0; Ph; H; Pr; S; 2-Naphthyl; 4-Cl-Ph]; [4648; O; Ph; H; Pr; S; 2-Naphthyl; 3-Me-Ph]; [4649; O; Ph; H; Pr; S; 2-Naphthyl; 4-Me-Ph]; [4650; O; Ph; H; Pr; S; 2-Naphthyl; 3,4-Me₂-Ph]; [4651; O; Ph; H; Pr; S; 2-Naphthyl; 5-Indanyl]; [4652; O; Ph; H; Ph; S; Cyclohexyl; 4-F-Ph]; [4653; O; Ph; H; Ph; S; Cyclohexyl; 4-Cl-Ph]; [4654; O; Ph; H; Ph; S; Cyclohexyl; 3-Me-Ph]; [4655; O; Ph; H; Ph; S; Cyclohexyl; 4-Me-Ph]; [4656; O; Ph; H; Ph; S; Cyclohexyl; 3,4-Me₂-Ph]; [4657; O; Ph; H; Ph; S; Cyclohexyl; 5-Indanyl]; [4658; O; Ph; H; Ph; S; Cyclohexylmethyl; 4-F-Ph]; [4659; O; Ph; H; Ph; S; Cyclohexylmethyl; 4-Cl-Ph]; [4660; O; Ph; H; Ph; S; Cyclohexylmethyl; 3-Me-Ph]; [4661; O; Ph; H; Ph; S; Cyclohexylmethyl; 4-Me-Ph]; [4662; O; Ph; H; Ph; S; Cyclohexylmethyl; 4-Ph-Ph]; [4663; O; Ph; H; Ph; S; Cyclohexylmethyl; 3,4-Me₂-Ph]; [4664; O; Ph; H; Ph; S; Cyclohexylmethyl; 5-Indanyl]; [4665; O; Ph; H; Ph; S; 4-F-Ph; 4-F-Ph]; [4666; O; Ph; H; Ph; S; 4-F-Ph; 4-Cl-Ph]; [4667; O; Ph; H; Ph; S; 4-F-Ph; 3-Me-Ph]; [4668; O; Ph; H; Ph; S; 4-F-Ph; 4-Me-Ph]; [4669; O; Ph; H; Ph; S; 4-F-Ph; 3,4-Me₂-Ph]; [4670; O; Ph; H; Ph; S; 4-F-Ph; 5-Indanyl]; [4671; O; Ph; H; Ph; S; 3-Cl-Ph; 4-F-Ph]; [4672; O; Ph; H; Ph; S; 3-Cl-Ph; 4-Cl-Ph]; [4673; O; Ph; H; Ph; S; 3-Cl-Ph; 3-Me-Ph]; [4674; O; Ph; H; Ph; S; 3-Cl-Ph; 4-Me-Ph]; [4675; O; Ph; H; Ph; S; 3-Cl-Ph; 3,4-Me₂-Ph]; [4676; O; Ph; H; Ph; S; 3-Cl-Ph; 5-Indanyl]; [4677; O; Ph; H; Ph; S; 4-Cl-Ph; 4-F-Ph]; [4678; O; Ph; H; Ph; S; 4-Cl-Ph; 4-Cl-Ph]; [4679; O; Ph; H; Ph; S; 3-Cl-Ph; 3-Me-Ph]; [4680; O; Ph; H; Ph; S; 4-Cl-Ph; 4-Me-Ph]; [4681; O; Ph; H; Ph; S; 4-Cl-Ph; 3,4-Me₂-Ph]; [4682; O; Ph; H; Ph; S; 4-Cl-Ph; 5-Indanyl]; [4683; O; Ph; H; Ph; S; 4-Me-Ph; 4-F-Ph]; [4684; O; Ph; H; Ph; S; 4-Me-Ph; 4-Cl-Ph]; [4685; O; Ph; H; Ph; S; 4-Me-Ph; 3-Me-Ph]; [4686; O; Ph; H; Ph; S; 4-Me-Ph; 4-Me-Ph]; [4687; O; Ph; H; Ph; S; 4-Me-Ph; 3,4-Me₂-Ph]; [4688; O; Ph; H; Ph; S; 4-Me-Ph; 5-Indanyl]; [4689; O; Ph; H; Ph; S; 2-Naphthyl; 4-F-Ph]; [4690; O; Ph; H; Ph; S; 2-Naphthyl; 4-Cl-Ph]; [4691; O; Ph; H; Ph; S; 2-Naphthyl; 3-Me-Ph]; [4692; O; Ph; H; Ph; S; 2-Naphthyl; 4-Me-Ph]; [4693; O; Ph; H; Ph; S; 2-Naphthyl; 3,4-Me₂-Ph]; [4694; O; Ph; H; Ph; S; 2-Naphthyl; 5-Indanyl]; [4695; O; Ph; H; SMe; S; Cyclohexyl; 4-F-Ph]; [4696; O; Ph; H; SMe; S; Cyclohexyl; 4-Cl-Ph]; [4697;

O; Ph; H; SMe; S; Cyclohexyl; 3-Me-Ph]; [4698; O; Ph; H; SMe; S; Cyclohexyl; 4-Me-Ph]; [4699; O; Ph; H; SMe; S; Cyclohexyl; 3,4-Me$_2$-Ph]; [4700; O; Ph; H; SMe; S; Cyclohexyl; 5-Indanyl]; [4701; O; Ph; H; SMe; S; Cyclohexylmethyl; 4-F-Ph]; [4702; O; Ph; H; SMe; S; Cyclohexylmethyl; 4-Cl-Ph]; [4703; O; Ph; H; SMe; S; Cyclohexylmethyl; 3-Me-Ph]; [4704; O; Ph; H; SMe; S; Cyclohexylmethyl; 4-Me-Ph]; [4705; O; Ph; H; SMe; S; Cyclohexylmethyl; 4-Ph-Ph]; [4706; O; Ph; H; SMe; S; Cyclohexylmethyl; 3,4-Me$_2$-Ph]; [4707; O; Ph; H; SMe; S; Cyclohexylmethyl; 5-Indanyl]; [4708; O; Ph; H; SMe; S; 4-F-Ph; 4-F-Ph]; [4709; O; Ph; H; SMe; S; 4-F-Ph; 4-Cl-Ph]; [4710; O; Ph; H; SMe; S; 4-F-Ph; 3-Me-Ph]; [4711; O; Ph; H; SMe; S; 4-F-Ph; 4-Me-Ph]; [4712; O; Ph; H; SMe; S; 4-F-Ph; 3,4-Me$_2$-Ph]; [4713; O; Ph; H; SMe; S; 4-F-Ph; 5-Indanyl]; [4714; O; Ph; H; SMe; S; 3-Cl-Ph; 4-F-Ph]; [4715; O; Ph; H; SMe; S; 3-Cl-Ph; 4-Cl-Ph]; [4716; O; Ph; H; SMe; S; 3-Cl-Ph; 3-Me-Ph]; [4717; O; Ph; H; SMe; S; 3-Cl-Ph; 4-Me-Ph]; [4718; O; Ph; H; SMe; S; 3-Cl-Ph; 3,4-Me$_2$-Ph]; [4719; O; Ph; H; SMe; S; 3-Cl-Ph; 5-Indanyl]; [4720; O; Ph; H; SMe; S; 4-Cl-Ph; 4-F-Ph]; [4721; O; Ph; H; SMe; S; 4-Cl-Ph; 4-Cl-Ph]; [4722; O; Ph; H; SMe; S; 3-Cl-Ph; 3-Me-Ph]; [4723; O; Ph; H; SMe; S; 4-Cl-Ph; 4-Me-Ph]; [4724; O; Ph; H; SMe; S; 4-Cl-Ph; 3,4-Me$_2$-Ph]; [4725; O; Ph; H; SMe; S; 4-Cl-Ph; 5-Indanyl]; [4726; O; Ph; H; SMe; S; 4-Me-Ph; 4-F-Ph]; [4727; O; Ph; H; SMe; S; 4-Me-Ph; 4-Cl-Ph]; [4728; O; Ph; H; SMe; S; 4-Me-Ph; 3-Me-Ph]; [4729; O; Ph; H; SMe; S; 4-Me-Ph; 4-Me-Ph]; [4730; O; Ph; H; SMe; S; 4-Me-Ph; 3,4-Me$_2$-Ph]; [4731; O; Ph; H; SMe; S; 4-Me-Ph; 5-Indanyl]; [4732; O; Ph; H; SMe; S; 2-Naphthyl; 4-F-Ph]; [4733; O; Ph; H; SMe; S; 2-Naphthyl; 4-Cl-Ph]; [4734; O; Ph; H; SMe; S; 2-Naphthyl; 3-Me-Ph]; [4735; O; Ph; H; SMe; S; 2-Naphthyl; 4-Me-Ph]; [4736; O; Ph; H; SMe; S; 2-Naphthyl; 3,4-Me$_2$-Ph]; [4737; O; Ph; H; SMe; S; 2-Naphthyl; 5-Indanyl]; [4738; O; Ph; H; 2-Thienyl; S; Cyclohexyl; 4-F-Ph]; [4739; O; Ph; H; 2-Thienyl; S; Cyclohexyl; 4-Cl-Ph]; [4740; O; Ph; H; 2-Thienyl; S; Cyclohexyl; 3-Me-Ph]; [4741; O; Ph; H; 2-Thienyl; S; Cyclohexyl; 4-Me-Ph]; [4742; O; Ph; H; 2-Thienyl; S; Cyclohexyl; 3,4-Me$_2$-Ph]; [4743; O; Ph; H; 2-Thienyl; S; Cyclohexyl; 5-Indanyl]; [4744; O; Ph; H; 2-Thienyl; S; Cyclohexylmethyl; 4-F-Ph]; [4745; O; Ph; H; 2-Thienyl; S; Cyclohexylmethyl; 4-Cl-Ph]; [4746; O; Ph; H; 2-Thienyl; S; Cyclohexylmethyl; 3-Me-Ph]; [4747; O; Ph; H; 2-Thienyl; S; Cyclohexylmethyl; 4-Me-Ph]; [4748; O; Ph; H; 2-Thienyl; S; Cyclohexylmethyl; 4-Ph-Ph]; [4749; O; Ph; H; 2-Thienyl; S; Cyclohexylmethyl; 3,4-Me$_2$-Ph]; [4750; O; Ph; H; 2-Thienyl; S; Cyclohexylmethyl; 5-Indanyl]; [4751; O; Ph; H; 2-Thienyl; S; 4-F-Ph; 4-F-Ph]; [4752; O; Ph; H; 2-Thienyl; S; 4-F-Ph; 4-Cl-Ph]; [4753; O; Ph; H; 2-Thienyl; S; 4-F-Ph; 3-Me-Ph]; [4754; O; Ph; H; 2-Thienyl; S; 4-F-Ph; 4-Me-Ph]; [4755; O; Ph; H; 2-Thienyl; S; 4-F-Ph; 3,4-Me$_2$-Ph]; [4756; O; Ph; H; 2-Thienyl; S; 4-F-Ph; 5-Indanyl]; [4757; O; Ph; H; 2-Thienyl; S; 3-Cl-Ph; 4-F-Ph]; [4758; O; Ph; H; 2-Thienyl; S; 3-Cl-Ph; 4-Cl-Ph]; [4759; O; Ph; H; 2-Thienyl; S; 3-Cl-Ph; 3-Me-Ph]; [4760; O; Ph; H; 2-Thienyl; S; 3-Cl-Ph; 4-Me-Ph]; [4761; O; Ph; H; 2-Thienyl; S; 3-Cl-Ph; 3,4-Me$_2$-Ph]; [4762; O; Ph; H; 2-Thienyl; S; 3-Cl-Ph; 5-Indanyl]; [4763; O; Ph; H; 2-Thienyl; S; 4-Cl-Ph; 4-F-Ph]; [4764; O; Ph; H; 2-Thienyl; S; 4-Cl-Ph; 4-Cl-Ph]; [4765; O; Ph; H; 2-Thienyl; S; 3-Cl-Ph; 3-Me-Ph]; [4766; O; Ph; H; 2-Thienyl; S; 4-Cl-Ph; 4-Me-Ph]; [4767; O; Ph; H; 2-Thienyl; S; 4-Cl-Ph; 3,4-Me$_2$-Ph]; [4768; O; Ph; H; 2-Thienyl; S; 4-Cl-Ph; 5-Indanyl]; [4769; O; Ph; H; 2-Thienyl; S; 4-Me-Ph; 4-F-Ph]; [4770; O; Ph; H; 2-Thienyl; S; 4-Me-Ph; 4-Cl-Ph]; [4771; O; Ph; H; 2-Thienyl; S; 4-Me-Ph; 3-Me-Ph]; [4772; O; Ph; H; 2-Thienyl; S; 4-Me-Ph; 4-Me-Ph]; [4773; O; Ph; H; 2-Thienyl; S; 4-Me-Ph; 3,4-Me$_2$-Ph]; [4774; O; Ph; H; 2-Thienyl; S; 4-Me-Ph; 5-Indanyl]; [4775; O; Ph; H; 2-Thienyl; S; 2-Naphthyl; 4-F-Ph]; [4776; O; Ph; H; 2-Thienyl; S; 2-Naphthyl; 4-Cl-Ph]; [4777; O; Ph; H; 2-Thienyl; S; 2-Naphthyl; 3-Me-Ph]; [4778; O; Ph; H; 2-Thienyl; S; 2-Naphthyl; 4-Me-Ph]; [4779; O; Ph; H; 2-Thienyl; S; 2-Naphthyl; 3,4-Me$_2$-Ph]; [4780; O; Ph; H; 2-Thienyl; S; 2-Naphthyl; 5-Indanyl]; [4781; O; 4-F-Ph; H; Me; S; Cyclohexylmethyl; 3,4-Me$_2$-Ph]; [4782; O; 4-F-Ph; H; Me; S; Cyclohexylmethyl; 5-Indanyl]; [4783; O; 4-Cl-Ph; H; Me; S; Cyclohexylmethyl; 3,4-Me$_2$-Ph]; [4784; O; 4-Cl-Ph; H; Me; S; Cyclohexylmethyl; 5-Indanyl]; [4785; O; 4-Me-Ph; H; Me; S; Cyclohexylmethyl; 3,4-Me$_2$-Ph]; [4786; O; 4-Me-Ph; H; Me; S; Cyclohexylmethyl; 5-Indanyl]; [4787; O; 5-Benzodioxolyl; H; Me; S; Cyclohexylmethyl; 3,4-Me$_2$-Ph]; [4788; O; 5-Benzodioxolyl; H; Me; S; Cyclohexylmethyl; 5-Indanyl]; [4789; O; 4-F-Ph; H; Me; S; 4-F-Ph; 3,4-Me$_2$-Ph]; [4790; O; 4-F-Ph; H; Me; S; 4-F-Ph; 5-Indanyl]; [4791; O; 4-Cl-Ph; H; Me; S; 4-F-Ph; 3,4-Me$_2$-Ph]; [4792; O; 4-Cl-Ph; H; Me; S; 4-F-Ph; 5-Indanyl]; [4793; O; 4-Me-Ph; H; Me; S; 4-F-Ph; 3,4-Me$_2$-Ph]; [4794; O; 4-Me-Ph; H; Me; S; 4-F-Ph; 5-Indanyl]; [4795; O; 5-Benzodioxolyl; H; Me; S; 4-F-Ph; 3,4-Me$_2$-Ph]; [4796; O; 5-Benzodioxolyl; H; Me; S; 4-F-Ph; 5-Indanyl]; [4797; O; 4-F-Ph; H; Me; S; 4-Cl-Ph; Ph]; [4798; O; 4-F-Ph; H; Me; S; 4-Cl-Ph; 5-Indanyl]; [4799; O; 4-Cl-Ph; H; Me; S; 4-Cl-Ph; 3,4-Me$_2$-Ph]; [4800; O; 4-F-Ph; H; Me; S; 4-Cl-Ph; 5-Indanyl]; [4801; O; 4-Me-Ph; H; Me; S; 4-Cl-Ph; 3,4-Me$_2$-Ph]; [4802; O; 4-Me-Ph; H; Me; S; 4-Cl-Ph; 5-Indanyl]; [4803; O; 5-Benzodioxolyl; H; Me; S; 4-Cl-Ph; 3,4-Me$_2$-Ph]; [4804; O; 5-Benzodioxolyl; H; Me; S; 4-Cl-Ph; 5-Indanyl]; [4805; O; 4-F-Ph; H; Me; S; 4-Me-Ph; 3,4-Me$_2$-Ph]; [4806; O; 4-F-Ph; H; Me; S; 4-Me-Ph; 5-Indanyl]; [4807; O; 4-Cl-Ph; H; Me; S; 4-Me-Ph; 3,4-Me$_2$-Ph]; [4808; O; 4-Cl-Ph; H; Me; S; 4-Me-Ph; 5-Indanyl]; [4809; O; 4-Me-Ph; H; Me; S; 4-Me-Ph; 3,4-Me$_2$-Ph]; [4810; O; 4-Me-Ph; H; Me; S; 4-Me-Ph; 5-Indanyl]; [4811; O; 5-Benzodioxolyl; H; Me; S; 4-Me-Ph; 3,4-Me$_2$-Ph]; [4812; O; 5-Benzodioxolyl; H; Me; S; 4-Me-Ph; 5-Indanyl]; [4813; O; 4-F-Ph; H; Et; S; Cyclohexyl; 4-F-Ph]; [4814; O; 4-F-Ph; H; Et; S; Cyclohexyl; 4-Cl-Ph]; [4815; O; 4-F-Ph; H; Et; S; Cyclohexyl; 4-Me-Ph]; [4816; O; 4-F-Ph; H; Et; S; Cyclohexyl; 3,4-Me$_2$-Ph]; [4817; O; 4-F-Ph; H; Et; S; Cyclohexyl; 5-Indanyl]; [4818; O; 4-Cl-Ph; H; Et; S; Cyclohexyl; 4-F-Ph]; [4819; O; 4-Cl-Ph; H; Et; S; Cyclohexyl; 4-Cl-Ph]; [4820; O; 4-Cl-Ph; H; Et; S; Cyclohexyl; 4-Me-Ph]; [4821; O; 4-Cl-Ph; H; Et; S; Cyclohexyl; 3,4-Me$_2$-Ph]; [4822; O; 4-Cl-Ph; H; Et; S; Cyclohexyl; 5-Indanyl]; [4823; O; 4-Me-Ph; H; Et; S; Cyclohexyl; 4-F-Ph]; [4824; O; 4-Me-Ph; H; Et; S; Cyclohexyl; 4-Cl-Ph]; [4825; O; 4-Me-Ph; H; Et; S; Cyclohexyl; 4-Me-Ph]; [4826; O; 4-Me-Ph; H; Et; S; Cyclohexyl; 3,4-Me$_2$-Ph]; [4827; O; 4-Me-Ph; H; Et; S; Cyclohexyl; 5-Indanyl]; [4828; O; 5-Benzodioxolyl; H; Et; S; Cyclohexyl; 4-F-Ph]; [4829; O; 5-Benzodioxolyl; H; Et; S; Cyclohexyl; 4-Cl-Ph]; [4830; O; 5-Benzodioxolyl; H; Et; S; Cyclohexyl; 4-Me-Ph]; [4831; O; 5-Benzodioxolyl; H; Et; S; Cyclohexyl; 3,4-Me$_2$-Ph]; [4832; O; 5-Benzodioxolyl; H; Et; S; Cyclohexyl; 5-Indanyl]; [4833; O; 4-F-Ph; H; Et; S; Cyclohexylmethyl; 4-F-Ph]; [4834; O; 4-F-Ph; H; Et; S; Cyclohexylmethyl; 4-Cl-Ph]; [4835; O; 4-F-Ph; H; Et; S; Cyclohexylmethyl; 4-Me-Ph]; [4836; O; 4-F-Ph; H; Et; S; Cyclohexylmethyl; 3,4-Me$_2$-Ph]; [4837; O; 4-F-Ph; H; Et; S; Cyclohexylmethyl; 5-Indanyl]; [4838; O; 4-Cl-Ph; H; Et; S; Cyclohexylmethyl; 4-F-Ph]; [4839; O; 4-Cl-Ph; H; Et; S; Cyclohexylmethyl; 4-Cl-Ph]; [4840; O; 4-Cl-Ph; H; Et; S; Cyclohexylmethyl; 4-Me-Ph]; [4841; O; 4-Cl-Ph; H; Et; S; Cyclohexylmethyl; 3,4-Me$_2$-Ph]; [4842; O; 4-Cl-Ph; H; Et; S; Cyclohexylmethyl; 5-Indanyl]; [4843; O; 4-Me-Ph; H; Et; S; Cyclohexylmethyl; 4-F-Ph]; [4844; O; 4-Me-Ph; H; Et; S; Cyclohexylmethyl; 4-Cl-Ph]; [4845; O; 4-Me-Ph; H; Et; S;

Cyclohexylmethyl; 4-Me-Ph]; [4846; O; 4-Me-Ph; H; Et; S; Cyclohexylmethyl; 3,4-Me$_2$-Ph]; [4847; O; 4-Me-Ph; H; Et; S; Cyclohexylmethyl; 5-Indanyl]; [4848; O; 5-Benzodioxolyl; H; Et; S; Cyclohexylmethyl; 4-F-Ph]; [4849; O; 5-Benzodioxolyl; H; Et; S; Cyclohexylmethyl; 4-Cl-Ph]; [4850; O; 5-Benzodioxolyl; H; Et; S; Cyclohexylmethyl; 4-Me-Ph]; [4851; 0; 5-Benzodioxolyl; H; Et; S; Cyclohexylmethyl; 3,4-Me$_2$-Ph]; [4852; O; 5-Benzodioxolyl; H; Et; S; Cyclohexylmethyl; 5-Indanyl]; [4853; O; 4-F-Ph; H; Et; S; 4-F-Ph; 4-F-Ph]; [4854; O; 4-F-Ph; H; Et; S; 4-F-Ph; 4-Cl-Ph]; [4855; O; 4-F-Ph; H; Et; S; 4-F-Ph; 4-Me-Ph]; [4856; O; 4-F-Ph; H; Et; S; 4-F-Ph; 3,4-Me$_2$-Ph]; [4857; O; 4-F-Ph; H; Et; S; 4-F-Ph; 5-Indanyl]; [4858; O; 4-Cl-Ph; H; Et; S; 4-F-Ph; 4-F-Ph]; [4859; O; 4-Cl-Ph; H; Et; S; 4-F-Ph; 4-Cl-Ph]; [4860; O; 4-Cl-Ph; H; Et; S; 4-F-Ph; 4-Me-Ph]; [4861; O; 4-Cl-Ph; H; Et; S; 4-F-Ph; 3,4-Me$_2$-Ph]; [4862; O; 4-Cl-Ph; H; Et; S; 4-F-Ph; 5-Indanyl]; [4863; O; 4-Me-Ph; H; Et; S; 4-F-Ph; 4-F-Ph]; [4864; O; 4-Me-Ph; H; Et; S; 4-F-Ph; 4-Cl-Ph]; [4865; O; 4-Me-Ph; H; Et; S; 4-F-Ph; 4-Me-Ph]; [4866; O; 4-Me-Ph; H; Et; S; 4-F-Ph; 3,4-Me$_2$-Ph]; [4867; O; 4-Me-Ph; H; Et; S; 4-F-Ph; 5-Indanyl]; [4868; O; 5-Benzodioxolyl; H; Et; S; 4-F-Ph; 4-F-Ph]; [4869; O; 5-Benzodioxolyl; H; Et; S; 4-F-Ph; 4-Cl-Ph]; [4870; O; 5-Benzodioxolyl; H; Et; S; 4-F-Ph; 4-Me-Ph]; [4871; O; 5-Benzodioxolyl; H; Et; S; 4-F-Ph; 3,4-Me$_2$-Ph]; [4872; O; 5-Benzodioxolyl; H; Et; S; 4-F-Ph; 5-Indanyl]; [4873; O; 4-F-Ph; H; Et; S; 4-Cl-Ph; 4-F-Ph]; [4874; O; 4-F-Ph; H; Et; S; 4-Cl-Ph; 4-Cl-Ph]; [4875; O; 4-F-Ph; H; Et; S; 4-Cl-Ph; 4-Me-Ph]; [4876; O; 4-F-Ph; H; Et; S; 4-Cl-Ph; 3,4-Me$_2$-Ph]; [4877; O; 4-F-Ph; H; Et; S; 4-Cl-Ph; 5-Indanyl]; [4878; O; 4-Cl-Ph; H; Et; S; 4-Cl-Ph; 4-F-Ph]; [4879; O; 4-Cl-Ph; H; Et; S; 4-Cl-Ph; 4-Cl-Ph]; [4880; O; 4-Cl-Ph; H; Et; S; 4-Cl-Ph; 4-Me-Ph]; [4881; O; 4-Cl-Ph; H; Et; S; 4-Cl-Ph; 3,4-Me$_2$-Ph]; [4882; O; 4-F-Ph; H; Et; S; 4-Cl-Ph; 5-Indanyl]; [4883; O; 4-Me-Ph; H; Et; S; 4-Cl-Ph; 4-F-Ph]; [4884; O; 4-Me-Ph; H; Et; S; 4-Cl-Ph; 4-Cl-Ph]; [4885; O; 4-Me-Ph; H; Et; S; 4-Cl-Ph; 4-Me-Ph]; [4886; O; 4-Me-Ph; H; Et; S; 4-Cl-Ph; 3,4-Me$_2$-Ph]; [4887; O; 4-Me-Ph; H; Et; S; 4-Cl-Ph; 5-Indanyl]; [4888; O; 5-Benzodioxolyl; H; Et; S; 4-Cl-Ph; 4-F-Ph]; [4889; O; 5-Benzodioxolyl; H; Et; S; 4-Cl-Ph; 4-Cl-Ph]; [4890; O; 5-Benzodioxolyl; H; Et; S; 4-Cl-Ph; 4-Me-Ph]; [4891; O; 5-Benzodioxolyl; H; Et; S; 4-Cl-Ph; 3,4-Me$_2$-Ph]; [4892; O; 5-Benzodioxolyl; H; Et; S; 4-Cl-Ph; 5-Indanyl]; [4893; O; 4-F-Ph; H; Et; S; 4-Me-Ph; 4-F-Ph]; [4894; O; 4-F-Ph; H; Et; S; 4-Me-Ph; 4-Cl-Ph]; [4895; O; 4-F-Ph; H; Et; S; 4-Me-Ph; 4-Me-Ph]; [4896; O; 4-F-Ph; H; Et; S; 4-Me-Ph; 3,4-Me$_2$-Ph]; [4897; O; 4-F-Ph; H; Et; S; 4-Me-Ph; 5-Indanyl]; [4898; O; 4-Cl-Ph; H; Et; S; 4-Me-Ph; 4-F-Ph]; [4899; O; 4-Cl-Ph; H; Et; S; 4-Me-Ph; 4-Cl-Ph]; [4900; O; 4-Cl-Ph; H; Et; S; 4-Me-Ph; 4-Me-Ph]; [4901; O; 4-Cl-Ph; H; Et; S; 4-Me-Ph; 3,4-Me$_2$-Ph]; [4902; O; 4-Cl-Ph; H; Et; S; 4-Me-Ph; 5-Indanyl]; [4903; O; 4-Me-Ph; H; Et; S; 4-Me-Ph; 4-F-Ph]; [4904; O; 4-Me-Ph; H; Et; S; 4-Me-Ph; 4-Cl-Ph]; [4905; O; 4-Me-Ph; H; Et; S; 4-Me-Ph; 4-Me-Ph]; [4906; O; 4-Me-Ph; H; Et; S; 4-Me-Ph; 3,4-Me$_2$-Ph]; [4907; O; 4-Me-Ph; H; Et; S; 4-Me-Ph; 5-Indanyl]; [4908; O; 5-Benzodioxolyl; H; Et; S; 4-Me-Ph; 4-F-Ph]; [4909; O; 5-Benzodioxolyl; H; Et; S; 4-Me-Ph; 4-Cl-Ph]; [4910; O; 5-Benzodioxolyl; H; Et; S; 4-Me-Ph; 4-Me-Ph]; [4911; O; 5-Benzodioxolyl; H; Et; S; 4-Me-Ph; 3,4-Me$_2$-Ph]; [4912; O; 5-Benzodioxolyl; H; Et; S; 4-Me-Ph; 5-Indanyl]; [4913; O; 4-F-Ph; H; Pr; S; Cyclohexyl; 4-F-Ph]; [4914; O; 4-F-Ph; H; Pr; S; Cyclohexyl; 4-Cl-Ph]; [4915; O; 4-F-Ph; H; Pr; S; Cyclohexyl; 4-Me-Ph]; [4916; O; 4-F-Ph; H; Pr; S; Cyclohexyl; 3,4-Me$_2$-Ph]; [4917; O; 4-F-Ph; H; Pr; S; Cyclohexyl; 5-Indanyl]; [4918; O; 4-Cl-Ph; H; Pr; S; Cyclohexyl; 4-F-Ph]; [4919; O; 4-Cl-Ph; H; Pr; S; Cyclohexyl; 4-Cl-Ph]; [4920; O; 4-Cl-Ph; H; Pr; S; Cyclohexyl; 4-Me-Ph]; [4921; O; 4-Cl-Ph; H; Pr; S; Cyclohexyl; 3,4-Me$_2$-Ph]; [4922; O; 4-Cl-Ph; H; Pr; S; Cyclohexyl; 5-Indanyl]; [4923; O; 4-Me-Ph; H; Pr; S; Cyclohexyl; 4-F-Ph]; [4924; O; 4-Me-Ph; H; Pr; S; Cyclohexyl; 4-Cl-Ph]; [4925; O; 4-Me-Ph; H; Pr; S; Cyclohexyl; 4-Me-Ph]; [4926; O; 4-Me-Ph; H; Pr; S; Cyclohexyl; 3,4-Me$_2$-Ph]; [4927; O; 4-Me-Ph; H; Pr; S; Cyclohexyl; 5-Indanyl]; [4928; O; 5-Benzodioxolyl; H; Pr; S; Cyclohexyl; 4-F-Ph]; [4929; O; 5-Benzodioxolyl; H; Pr; S; Cyclohexyl; 4-Cl-Ph]; [4930; O; 5-Benzodioxolyl; H; Pr; S; Cyclohexyl; 4-Me-Ph]; [4931; O; 5-Benzodioxolyl; H; Pr; S; Cyclohexyl; 3,4-Me$_2$-Ph]; [4932; O; 5-Benzodioxolyl; H; Pr; S; Cyclohexyl; 5-Indanyl]; [4933; O; 4-F-Ph; H; Pr; S; Cyclohexylmethyl; 4-F-Ph]; [4934; O; 4-F-Ph; H; Pr; S; Cyclohexylmethyl; 4-Cl-Ph]; [4935; O; 4-F-Ph; H; Pr; S; Cyclohexylmethyl; 4-Me-Ph]; [4936; O; 4-F-Ph; H; Pr; S; Cyclohexylmethyl; 3,4-Me$_2$-Ph]; [4937; O; 4-F-Ph; H; Pr; S; Cyclohexylmethyl; 5-Indanyl]; [4938; O; 4-Cl-Ph; H; Pr; S; Cyclohexylmethyl; 4-F-Ph]; [4939; O; 4-Cl-Ph; H; Pr; S; Cyclohexylmethyl; 4-Cl-Ph]; [4940; O; 4-Cl-Ph; H; Pr; S; Cyclohexylmethyl; 4-Me-Ph]; [4941; O; 4-Cl-Ph; H; Pr; S; Cyclohexylmethyl; 3,4-Me$_2$-Ph]; [4942; O; 4-Cl-Ph; H; Pr; S; Cyclohexylmethyl; 5-Indanyl]; [4943; O; 4-Me-Ph; H; Pr; S; Cyclohexylmethyl; 4-F-Ph]; [4944; O; 4-Me-Ph; H; Pr; S; Cyclohexylmethyl; 4-Cl-Ph]; [4945; O; 4-Me-Ph; H; Pr; S; Cyclohexylmethyl; 4-Me-Ph]; [4946; O; 4-Me-Ph; H; Pr; S; Cyclohexylmethyl; 3,4-Me$_2$-Ph]; [4947; O; 4-Me-Ph; H; Pr; S; Cyclohexylmethyl; 5-Indanyl]; [4948; O; 5-Benzodioxolyl; H; Pr; S; Cyclohexylmethyl; 4-F-Ph]; [4949; O; 5-Benzodioxolyl; H; Pr; S; Cyclohexylmethyl; 4-Cl-Ph]; [4950; O; 5-Benzodioxolyl; H; Pr; S; Cyclohexylmethyl; 4-Me-Ph]; [4951; O; 5-Benzodioxolyl; H; Pr; S; Cyclohexylmethyl; 3,4-Me$_2$-Ph]; [4952; O; 5-Benzodioxolyl; H; Pr; S; Cyclohexylmethyl; 5-Indanyl]; [4953; O; 4-F-Ph; H; Pr; S; 4-F-Ph; 4-F-Ph]; [4954; O; 4-F-Ph; H; Pr; S; 4-F-Ph; 4-Cl-Ph]; [4955; O; 4-F-Ph; H; Pr; S; 4-F-Ph; 4-Me-Ph]; [4956; O; 4-F-Ph; H; Pr; S; 4-F-Ph; 3,4-Me$_2$-Ph]; [4957; O; 4-F-Ph; H; Pr; S; 4-F-Ph; 5-Indanyl]; [4958; O; 4-Cl-Ph; H; Pr; S; 4-F-Ph; 4-F-Ph]; [4959; O; 4-Cl-Ph; H; Pr; S; 4-F-Ph; 4-Cl-Ph]; [4960; O; 4-Cl-Ph; H; Pr; S; 4-F-Ph; 4-Me-Ph]; [4961; O; 4-Cl-Ph; H; Pr; S; 4-F-Ph; 3,4-Me$_2$-Ph]; [4962; O; 4-Cl-Ph; H; Pr; S; 4-F-Ph; 5-Indanyl]; [4963; O; 4-Me-Ph; H; Pr; S; 4-F-Ph; 4-F-Ph]; [4964; O; 4-Me-Ph; H; Pr; S; 4-F-Ph; 4-Cl-Ph]; [4965; O; 4-Me-Ph; H; Pr; S; 4-F-Ph; 4-Me-Ph]; [4966; O; 4-Me-Ph; H; Pr; S; 4-F-Ph; 3,4-Me$_2$-Ph]; [4967; O; 4-Me-Ph; H; Pr; S; 4-F-Ph; 5-Indanyl]; [4968; O; 5-Benzodioxolyl; H; Pr; S; 4-F-Ph; 4-F-Ph]; [4969; O; 5-Benzodioxolyl; H; Pr; S; 4-F-Ph; 4-Cl-Ph]; [4970; O; 5-Benzodioxolyl; H; Pr; S; 4-F-Ph; 4-Me-Ph]; [4971; O; 5-Benzodioxolyl; H; Pr; S; 4-F-Ph; 3,4-Me$_2$-Ph]; [4972; O; 5-Benzodioxolyl; H; Pr; S; 4-F-Ph; 5-Indanyl]; [4973; O; 4-F-Ph; H; Pr; S; 4-Cl-Ph; 4-F-Ph]; [4974; O; 4-F-Ph; H; Pr; S; 4-Cl-Ph; 4-Cl-Ph]; [4975; O; 4-F-Ph; H; Pr; S; 4-Cl-Ph; 4-Me-Ph]; [4976; O; 4-F-Ph; H; Pr; S; 4-Cl-Ph; 3,4-Me$_2$-Ph]; [4977; O; 4-F-Ph; H; Pr; S; 4-Cl-Ph; 5-Indanyl]; [4978; O; 4-Cl-Ph; H; Pr; S; 4-Cl-Ph; 4-F-Ph]; [4979; O; 4-Cl-Ph; H; Pr; S; 4-Cl-Ph; 4-Cl-Ph]; [4980; O; 4-Cl-Ph; H; Pr; S; 4-Cl-Ph; 4-Me-Ph]; [4981; O; 4-Cl-Ph; H; Pr; S; 4-Cl-Ph; 3,4-Me$_2$-Ph]; [4982; O; 4-F-Ph; H; Pr; S; 4-Cl-Ph; 5-Indanyl]; [4983; O; 4-Me-Ph; H; Pr; S; 4-Cl-Ph; 4-F-Ph]; [4984; O; 4-Me-Ph; H; Pr; S; 4-Cl-Ph; 4-Cl-Ph]; [4985; O; 4-Me-Ph; H; Pr; S; 4-Cl-Ph; 4-Me-Ph]; [4986; O; 4-Me-Ph; H; Pr; S; 4-Cl-Ph; 3,4-Me$_2$-Ph]; [4987; O; 4-Me-Ph; H; Pr; S; 4-Cl-Ph; 5-Indanyl]; [4988; O; 5-Benzodioxolyl; H; Pr; S; 4-Cl-Ph; 4-F-Ph]; [4989; O; 5-Benzodioxolyl; H; Pr; S; 4-Cl-Ph; 4-Cl-Ph]; [4990; O; 5-Benzodioxolyl; H; Pr; S; 4-Cl-Ph; 4-Me-Ph]; [4991; O; 5-Benzodioxolyl; H; Pr; S; 4-Cl-Ph; 3,4-Me$_2$-Ph]; [4992; O; 5-Benzodioxolyl; H; Pr; S; 4-Cl-Ph; 5-Indanyl]; [4993; O; 4-F-Ph; H; Pr; S; 4-Me-Ph;

4-F-Ph]; [4994; O; 4-F-Ph; H; Pr; S; 4-Me-Ph; 4-Cl-Ph]; [4995; O; 4-F-Ph; H; Pr; S; 4-Me-Ph; 4-Me-Ph]; [4996; O; 4-F-Ph; H; Pr; S; 4-Me-Ph; 3,4-Me$_2$-Ph]; [4997; O; 4-F-Ph; H; Pr; S; 4-Me-Ph; 5-Indanyl]; [4998; O; 4-Cl-Ph; H; Pr; S; 4-Me-Ph; 4-F-Ph]; [4999; O; 4-Cl-Ph; H; Pr; S; 4-Me-Ph; 4-Cl-Ph]; [5000; O; 4-Cl-Ph; H; Pr; S; 4-Me-Ph; 4-Me-Ph]; [5001; O; 4-Cl-Ph; H; Pr; S; 4-Me-Ph; 3,4-Me$_2$-Ph]; [5002; O; 4-Cl-Ph; H; Pr; S; 4-Me-Ph; 5-Indanyl]; [5003; O; 4-Me-Ph; H; Pr; S; 4-Me-Ph; 4-F-Ph]; [5004; O; 4-Me-Ph; H; Pr; S; 4-Me-Ph; 4-Cl-Ph]; [5005; O; 4-Me-Ph; H; Pr; S; 4-Me-Ph; 4-Me-Ph]; [5006; O; 4-Me-Ph; H; Pr; S; 4-Me-Ph; 3,4-Me$_2$-Ph]; [5007; O; 4-Me-Ph; H; Pr; S; 4-Me-Ph; 5-Indanyl]; [5008; O; 5-Benzodioxolyl; H; Pr; S; 4-Me-Ph; 4-F-Ph]; [5009; O; 5-Benzodioxolyl; H; Pr; S; 4-Me-Ph; 4-Cl-Ph]; [5010; O; 5-Benzodioxolyl; H; Pr; S; 4-Me-Ph; 4-Me-Ph]; [5011; O; 5-Benzodioxolyl; H; Pr; S; 4-Me-Ph; 3,4-Me$_2$-Ph]; [5012; O; 5-Benzodioxolyl; H; Pr; S; 4-Me-Ph; 5-Indanyl]; [5013; O; 4-F-Ph; H; Ph; S; Cyclohexyl; 4-F-Ph]; [5014; O; 4-F-Ph; H; Ph; S; Cyclohexyl; 4-Cl-Ph]; [5015; O; 4-F-Ph; H; Ph; S; Cyclohexyl; 4-Me-Ph]; [5016; O; 4-F-Ph; H; Ph; S; Cyclohexyl; 3,4-Me$_2$-Ph]; [5017; O; 4-F-Ph; H; Ph; S; Cyclohexyl; 5-Indanyl]; [5018; O; 4-Cl-Ph; H; Ph; S; Cyclohexyl; 4-F-Ph]; [5019; O; 4-Cl-Ph; H; Ph; S; Cyclohexyl; 4-Cl-Ph]; [5020; O; 4-Cl-Ph; H; Ph; S; Cyclohexyl; 4-Me-Ph]; [5021; O; 4-Cl-Ph; H; Ph; S; Cyclohexyl; 3,4-Me$_2$-Ph]; [5022; O; 4-Cl-Ph; H; Ph; S; Cyclohexyl; 5-Indanyl]; [5023; O; 4-Me-Ph; H; Ph; S; Cyclohexyl; 4-F-Ph]; [5024; O; 4-Me-Ph; H; Ph; S; Cyclohexyl; 4-Cl-Ph]; [5025; O; 4-Me-Ph; H; Ph; S; Cyclohexyl; 4-Me-Ph]; [5026; O; 4-Me-Ph; H; Ph; S; Cyclohexyl; 3,4-Me$_2$-Ph]; [5027; O; 4-Me-Ph; H; Ph; S; Cyclohexyl; 5-Indanyl]; [5028; O; 5-Benzodioxolyl; H; Ph; S; Cyclohexyl; 4-F-Ph]; [5029; O; 5-Benzodioxolyl; H; Ph; S; Cyclohexyl; 4-Cl-Ph]; [5030; O; 5-Benzodioxolyl; H; Ph; S; Cyclohexyl; 4-Me-Ph]; [5031; O; 5-Benzodioxolyl; H; Ph; S; Cyclohexyl; 3,4-Me$_2$-Ph]; [5032; O; 5-Benzodioxolyl; H; Ph; S; Cyclohexyl; 5-Indanyl]; [5033; O; 4-F-Ph; H; Ph; S; Cyclohexylmethyl; 4-F-Ph]; [5034; O; 4-F-Ph; H; Ph; S; Cyclohexylmethyl; 4-Cl-Ph]; [5035; O; 4-F-Ph; H; Ph; S; Cyclohexylmethyl; 4-Me-Ph]; [5036; O; 4-F-Ph; H; Ph; S; Cyclohexylmethyl; 3,4-Me$_2$-Ph]; [5037; O; 4-F-Ph; H; Ph; S; Cyclohexylmethyl; 5-Indanyl]; [5038; O; 4-Cl-Ph; H; Ph; S; Cyclohexylmethyl; 4-F-Ph]; [5039; O; 4-Cl-Ph; H; Ph; S; Cyclohexylmethyl; 4-Cl-Ph]; [5040; O; 4-Cl-Ph; H; Ph; S; Cyclohexylmethyl; 4-Me-Ph]; [5041; O; 4-Cl-Ph; H; Ph; S; Cyclohexylmethyl; 3,4-Me$_2$-Ph]; [5042; O; 4-Cl-Ph; H; Ph; S; Cyclohexylmethyl; 5-Indanyl]; [5043; O; 4-Me-Ph; H; Ph; S; Cyclohexylmethyl; 4-F-Ph]; [5044; O; 4-Me-Ph; H; Ph; S; Cyclohexylmethyl; 4-Cl-Ph]; [5045; O; 4-Me-Ph; H; Ph; S; Cyclohexylmethyl; 4-Me-Ph]; [5046; O; 4-Me-Ph; H; Ph; S; Cyclohexylmethyl; 3,4-Me$_2$-Ph]; [5047; O; 4-Me-Ph; H; Ph; S; Cyclohexylmethyl; 5-Indanyl]; [5048; O; 5-Benzodioxolyl; H; Ph; S; Cyclohexylmethyl; 4-F-Ph]; [5049; O; 5-Benzodioxolyl; H; Ph; S; Cyclohexylmethyl; 4-Cl-Ph]; [5050; O; 5-Benzodioxolyl; H; Ph; S; Cyclohexylmethyl; 4-Me-Ph]; [5051; O; 5-Benzodioxolyl; H; Ph; S; Cyclohexylmethyl; 3,4-Me$_2$-Ph]; [5052; O; 5-Benzodioxolyl; H; Ph; S; Cyclohexylmethyl; 5-Indanyl]; [5053; O; 4-F-Ph; H; Ph; S; 4-F-Ph; 4-F-Ph]; [5054; O; 4-F-Ph; H; Ph; S; 4-F-Ph; 4-Cl-Ph]; [5055; O; 4-F-Ph; H; Ph; S; 4-F-Ph; 4-Me-Ph]; [5056; O; 4-F-Ph; H; Ph; S; 4-F-Ph; 3,4-Me$_2$-Ph]; [5057; O; 4-F-Ph; H; Ph; S; 4--F -Ph; 5-Indanyl]; [5058; O; 4-Cl-Ph; H; Ph; S; 4-F-Ph; 4-F-Ph]; [5059; O; 4-Cl-Ph; H; Ph; S; 4-F-Ph; 4-Cl-Ph]; [5060; O; 4-Cl-Ph; H; Ph; S; 4-F-Ph; 4-Me-Ph]; [5061; O; 4-Cl-Ph; H; Ph; S; 4-F-Ph; 3,4-Me$_2$-Ph]; [5062; O; 4-Cl-Ph; H; Ph; S; 4-F-Ph; 5-Indanyl]; [5063; O; 4-Me-Ph; H; Ph; S; 4-F-Ph; 4-F -Ph]; [5064; O; 4-Me-Ph; H; Ph; S; 4-F-Ph; 4-Cl-Ph]; [5065; O; 4-Me-Ph; H; Ph; S; 4-F-Ph; 4-Me-Ph]; [5066; O; 4-Me-Ph; H; Ph; S; 4-F-Ph; 3,4-Me$_2$-Ph]; [5067; O; 4-Me-Ph; H; Ph; S; 4-F-Ph; 5-Indanyl]; [5068; O; 5-Benzodioxolyl; H; Ph; S; 4-F-Ph; 4-F-Ph]; [5069; O; 5-Benzodioxolyl; H; Ph; S; 4-F-Ph; 4-Cl-Ph]; [5070; O; 5-Benzodioxolyl; H; Ph; S; 4-F-Ph; 4-Me-Ph]; [5071; O; 5-Benzodioxolyl; H; Ph; S; 4-F-Ph; 3,4-Me$_2$-Ph]; [5072; O; 5-Benzodioxolyl; H; Ph; S; 4-F-Ph; 5-Indanyl]; [5073; O; 4-F-Ph; H; Ph; S; 4-Cl-Ph; 4-F-Ph]; [5074; O; 4-F-Ph; H; Ph; S; 4-Cl-Ph; 4-Cl-Ph]; [5075; O; 4-F-Ph; H; Ph; S; 4-Cl-Ph; 4-Me-Ph]; [5076; O; 4-F-Ph; H; Ph; S; 4-Cl-Ph; 3,4-Me$_2$-Ph]; [5077; O; 4-F-Ph; H; Ph; S; 4-Cl-Ph; 5-Indanyl]; [5078; O; 4-Cl-Ph; H; Ph; S; 4-Cl-Ph; 4-F-Ph]; [5079; O; 4-Cl-Ph; H; Ph; S; 4-Cl-Ph; 4-Cl-Ph]; [5080; 0; 4-Cl-Ph; H; Ph; S; 4-Cl-Ph; 4-Me-Ph]; [5081; O; 4-Cl-Ph; H; Ph; S; 4-Cl-Ph; 3,4-Me$_2$-Ph]; [5082; O; 4-F-Ph; H; Ph; S; 4-Cl-Ph; 5-Indanyl]; [5083; O; 4-Me-Ph; H; Ph; S; 4-Cl-Ph; 4-F-Ph]; [5084; O; 4-Me-Ph; H; Ph; S; 4-Cl-Ph; 4-Cl-Ph]; [5085; O; 4-Me-Ph; H; Ph; S; 4-Cl-Ph; 4-Me-Ph]; [5086; O; 4-Me-Ph; H; Ph; S; 4-Cl-Ph; 3,4-Me$_2$-Ph]; [5087; O; 4-Me-Ph; H; Ph; S; 4-Cl-Ph; 5-Indanyl]; [5088; O; 5-Benzodioxolyl; H; Ph; S; 4-Cl-Ph; 4-F-Ph]; [5089; O; 5-Benzodioxolyl; H; Ph; S; 4-Cl-Ph; 4-Cl-Ph]; [5090; O; 5-Benzodioxolyl; H; Ph; S; 4-Cl-Ph; 4-Me-Ph]; [5091; O; 5-Benzodioxolyl; H; Ph; S; 4-Cl-Ph; 3,4-Me$_2$-Ph]; [5092; O; 5-Benzodioxolyl; H; Ph; S; 4-Cl-Ph; 5-Indanyl]; [5093; O; 4-F-Ph; H; Ph; S; 4-Me-Ph; 4-F-Ph]; [5094; O; 4-F-Ph; H; Ph; S; 4-Me-Ph; 4-Cl-Ph]; [5095; O; 4-F-Ph; H; Ph; S; 4-Me-Ph; 4-Me-Ph]; [5096; O; 4-F-Ph; H; Ph; S; 4-Me-Ph; 3,4-Me$_2$-Ph]; [5097; O; 4-F-Ph; H; Ph; S; 4-Me-Ph; 5-Indanyl]; [5098; O; 4-Cl-Ph; H; Ph; S; 4-Me-Ph; 4-F-Ph]; [5099; O; 4-Cl-Ph; H; Ph; S; 4-Me-Ph; 4-Cl-Ph]; [5100; O; 4-Cl-Ph; H; Ph; S; 4-Me-Ph; 4-Me-Ph]; [5101; O; 4-Cl-Ph; H; Ph; S; 4-Me-Ph; 3,4-Me$_2$-Ph]; [5102; O; 4-Cl-Ph; H; Ph; S; 4-Me-Ph; 5-Indanyl]; [5103; O; 4-Me-Ph; H; Ph; S; 4-Me-Ph; 4-F-Ph]; [5104; O; 4-Me-Ph; H; Ph; S; 4-Me-Ph; 4-Cl-Ph]; [5105; O; 4-Me-Ph; H; Ph; S; 4-Me-Ph; 4-Me -Ph]; [5106; O; 4-Me-Ph; H; Ph; S; 4-Me-Ph; 3,4-Me$_2$-Ph]; [5107; O; 4-Me-Ph; H; Ph; S; 4-Me-Ph; 5-Indanyl]; [5108; O; 5-Benzodioxolyl; H; Ph; S; 4-Me-Ph; 4-F-Ph]; [5109; O; 5-Benzodioxolyl; H; Ph; S; 4-Me-Ph; 4-Cl-Ph]; [5110; O; 5-Benzodioxolyl; H; Ph; S; 4-Me-Ph; 4-Me-Ph]; [5111; O; 5-Benzodioxolyl; H; Ph; S; 4-Me-Ph; 3,4-Me$_2$-Ph]; [5112; O; 5-Benzodioxolyl; H; Ph; S; 4-Me-Ph; 5-Indanyl]; [5113; O; 4-F-Ph; H; SMe; S; Cyclohexyl; 4-F-Ph]; [5114; O; 4-F-Ph; H; SMe; S; Cyclohexyl; 4-Cl-Ph]; [5115; O; 4-F-Ph; H; SMe; S; Cyclohexyl; 4-Me-Ph]; [5116; O; 4-F-Ph; H; SMe; S; Cyclohexyl; 3,4-Me$_2$-Ph]; [5117; O; 4-F-Ph; H; SMe; S; Cyclohexyl; 5-Indanyl]; [5118; O; 4-Cl-Ph; H; SMe; S; Cyclohexyl; 4-F-Ph]; [5119; O; 4-Cl-Ph; H; SMe; S; Cyclohexyl; 4-Cl-Ph]; [5120; O; 4-Cl-Ph; H; SMe; S; Cyclohexyl; 4-Me-Ph]; [5121; O; 4-Cl-Ph; H; SMe; S; Cyclohexyl; 3,4-Me$_2$-Ph]; [5122; O; 4-Cl-Ph; H; SMe; S; Cyclohexyl; 5-Indanyl]; [5123; O; 4-Me-Ph; H; SMe; S; Cyclohexyl; 4-F-Ph]; [5124; O; 4-Me-Ph; H; SMe; S; Cyclohexyl; 4-Cl-Ph]; [5125; O; 4-Me-Ph; H; SMe; S; Cyclohexyl; 4-Me-Ph]; [5126; O; 4-Me-Ph; H; SMe; S; Cyclohexyl; 3,4-Me$_2$-Ph]; [5127; O; 4-Me-Ph; H; SMe; S; Cyclohexyl; 5-Indanyl]; [5128; O; 5-Benzodioxolyl; H; SMe; S; Cyclohexyl; 4-F-Ph]; [5129; O; 5-Benzodioxolyl; H; SMe; S; Cyclohexyl; 4-Cl-Ph]; [5130; O; 5-Benzodioxolyl; H; SMe; S; Cyclohexyl; 4-Me-Ph]; [5131; O; 5-Benzodioxolyl; H; SMe; S; Cyclohexyl; 3,4-Me$_2$-Ph]; [5132; O; 5-Benzodioxolyl; H; SMe; S; Cyclohexyl; 5-Indanyl]; [5133; O; 4-F-Ph; H; SMe; S; Cyclohexylmethyl; 4-F-Ph]; [5134; O; 4-F-Ph; H; SMe; S; Cyclohexylmethyl; 4-Cl-Ph]; [5135; O; 4-F-Ph; H; SMe; S; Cyclohexylmethyl; 4-Me-Ph]; [5136; O; 4-F-Ph; H; SMe; S; Cyclohexylmethyl; 3,4-Me$_2$-Ph]; [5137; O; 4-F-Ph; H; SMe; S; Cyclohexylmethyl; 5-Indanyl]; [5138; O; 4-Cl-Ph; H; SMe; S; Cyclohexylmethyl; 4-F-Ph]; [5139; O; 4-Cl-Ph; H;

SMe; S; Cyclohexylmethyl; 4-Cl-Ph]; [5140; O; 4-Cl-Ph; H; SMe; S; Cyclohexylmethyl; 4-Me-Ph]; [5141; O; 4-Cl-Ph; H; SMe; S; Cyclohexylmethyl; 3,4-Me$_2$-Ph]; [5142; O; 4-Cl-Ph; H; SMe; S; Cyclohexylmethyl; 5-Indanyl]; [5143; O; 4-Me-Ph; H; SMe; S; Cyclohexylmethyl; 4-F-Ph]; [5144; O; 4-Me-Ph; H; SMe; S; Cyclohexylmethyl; 4-Cl-Ph]; [5145; O; 4-Me-Ph; H; SMe; S; Cyclohexylmethyl; 4-Me-Ph]; [5146; O; 4-Me-Ph; H; SMe; S; Cyclohexylmethyl; 3,4-Me$_2$-Ph]; [5147; O; 4-Me-Ph; H; SMe; S; Cyclohexylmethyl; 5-Indanyl]; [5148; O; 5-Benzodioxolyl; H; SMe; S; Cyclohexylmethyl; 4-F-Ph]; [5149; O; 5-Benzodioxolyl; H; SMe; S; Cyclohexylmethyl; 4-Cl-Ph]; [5150; O; 5-Benzodioxolyl; H; SMe; S; Cyclohexylmethyl; 4-Me-Ph]; [5151; O; 5-Benzodioxolyl; H; SMe; S; Cyclohexylmethyl; 3,4-Me$_2$-Ph]; [5152; O; 5-Benzodioxolyl; H; SMe; S; Cyclohexylmethyl; 5-Indanyl]; [5153; O; 4-F-Ph; H; SMe; S; 4-F-Ph; 4-F-Ph]; [5154; O; 4-F-Ph; H; SMe; S; 4-F-Ph; 4-Cl-Ph]; [5155; O; 4-F-Ph; H; SMe; S; 4-F-Ph; 4-Me-Ph]; [5156; O; 4-F-Ph; H; SMe; S; 4-F-Ph; 3,4-Me$_2$-Ph]; [5157; O; 4-F -Ph; H; SMe; S; 4-F-Ph; 5-Indanyl]; [5158; O; 4-Cl-Ph; H; SMe; S; 4-F-Ph; 4-F-Ph]; [5159; O; 4-Cl-Ph; H; SMe; S; 4-F-Ph; 4-Cl-Ph]; [5160; O; 4-Cl-Ph; H; SMe; S; 4-F-Ph; 4-Me-Ph]; [5161; O; 4-Cl-Ph; H; SMe; S; 4-F-Ph; 3,4-Me$_2$-Ph]; [5162; O; 4-Cl-Ph; H; SMe; S; 4-F-Ph; 5-Indanyl]; [5163; O; 4-Me-Ph; H; SMe; S; 4-F-Ph; 4-F-Ph]; [5164; O; 4-Me-Ph; H; SMe; S; 4-F-Ph; 4-Cl-Ph]; [5165; O; 4-Me-Ph; H; SMe; S; 4-F-Ph; 4-Me-Ph]; [5166; O; 4-Me-Ph; H; SMe; S; 4-F-Ph; 3,4-Me$_2$-Ph]; [5167; O; 4-Me-Ph; H; SMe; S; 4-F-Ph; 5-Indanyl]; [5168; O; 5-Benzodioxolyl; H; SMe; S; 4-F-Ph; 4-F-Ph]; [5169; O; 5-Benzodioxolyl; H; SMe; S; 4-F-Ph; 4-Cl-Ph]; [5170; O; 5-Benzodioxolyl; H; SMe; S; 4-F-Ph; 4-Me-Ph]; [5171; O; 5-Benzodioxolyl; H; SMe; S; 4-F-Ph; 3,4-Me$_2$-Ph]; [5172; O; 5-Benzodioxolyl; H; SMe; S; 4-F-Ph; 5-Indanyl]; [5173; O; 4-F-Ph; H; SMe; S; 4-Cl-Ph; 4-F-Ph]; [5174; O; 4-F-Ph; H; SMe; S; 4-Cl-Ph; 4-Cl-Ph]; [5175; O; 4-F-Ph; H; SMe; S; 4-Cl-Ph; 4-Me-Ph]; [5176; O; 4-F-Ph; H; SMe; S; 4-Cl-Ph; 3,4-Me$_2$-Ph]; [5177; O; 4-F-Ph; H; SMe; S; 4-Cl-Ph; 5-Indanyl]; [5178; O; 4-Cl-Ph; H; SMe; S; 4-Cl-Ph; 4-F-Ph]; [5179; O; 4-Cl-Ph; H; SMe; S; 4-Cl-Ph; 4-Cl-Ph]; [5180; O; 4-Cl-Ph; H; SMe; S; 4-Cl-Ph; 4-Me-Ph]; [5181; O; 4-Cl-Ph; H; SMe; S; 4-Cl-Ph; 3,4-Me$_2$-Ph]; [5182; O; 4-F-Ph; H; SMe; S; 4-Cl-Ph; 5-Indanyl]; [5183; O; 4-Me-Ph; H; SMe; S; 4-Cl-Ph; 4-F-Ph]; [5184; O; 4-Me-Ph; H; SMe; S; 4-Cl-Ph; 4-Cl-Ph]; [5185; O; 4-Me-Ph; H; SMe; S; 4-Cl-Ph; 4-Me-Ph]; [5186; O; 4-Me-Ph; H; SMe; S; 4-Cl-Ph; 3,4-Me$_2$-Ph]; [5187; O; 4-Me-Ph; H; SMe; S; 4-Cl-Ph; 5-Indanyl]; [5188; O; 5-Benzodioxolyl; H; SMe; S; 4-Cl-Ph; 4-F-Ph]; [5189; O; 5-Benzodioxolyl; H; SMe; S; 4-Cl-Ph; 4-Cl-Ph]; [5190; O; 5-Benzodioxolyl; H; SMe; S; 4-Cl-Ph; 4-Me-Ph]; [5191; O; 5-Benzodioxolyl; H; SMe; S; 4-Cl-Ph; 3,4-Me$_2$-Ph]; [5192; O; 5-Benzodioxolyl; H; SMe; S; 4-Cl-Ph; 5-Indanyl]; [5193; O; 4-F-Ph; H; SMe; S; 4-Me-Ph; 4-F-Ph]; [5194; O; 4-F-Ph; H; SMe; S; 4-Me-Ph; 4-Cl-Ph]; [5195; O; 4-F-Ph; H; SMe; S; 4-Me-Ph; 4-Me-Ph]; [5196; O; 4-F-Ph; H; SMe; S; 4-Me-Ph; 3,4-Me$_2$-Ph]; [5197; O; 4-F-Ph; H; SMe; S; 4-Me-Ph; 5-Indanyl]; [5198; O; 4-Cl-Ph; H; SMe; S; 4-Me-Ph; 4-F-Ph]; [5199; O; 4-Cl-Ph; H; SMe; S; 4-Me-Ph; 4-Cl-Ph]; [5200; O; 4-Cl-Ph; H; SMe; S; 4-Me-Ph; 4-Me-Ph]; [5201; O; 4-Cl-Ph; H; SMe; S; 4-Me-Ph; 3,4-Me$_2$-Ph]; [5202; O; 4-Cl-Ph; H; SMe; S; 4-Me-Ph; 5-Indanyl]; [5203; O; 4-Me-Ph; H; SMe; S; 4-Me-Ph; 4-F-Ph]; [5204; O; 4-Me-Ph; H; SMe; S; 4-Me-Ph; 4-Cl-Ph]; [5205; O; 4-Me-Ph; H; SMe; S; 4-Me-Ph; 4-Me-Ph]; [5206; O; 4-Me-Ph; H; SMe; S; 4-Me-Ph; 3,4-Me$_2$-Ph]; [5207; O; 4-Me-Ph; H; SMe; S; 4-Me-Ph; 5-Indanyl]; [5208; O; 5-Benzodioxolyl; H; SMe; S; 4-Me-Ph; 4-F-Ph]; [5209; O; 5-Benzodioxolyl; H; SMe; S; 4-Me-Ph; 4-Cl-Ph]; [5210; O; 5-Benzodioxolyl; H; SMe; S; 4-Me-Ph; 4-Me-Ph]; [5211; O; 5-Benzodioxolyl; H; SMe; S; 4-Me-Ph; 3,4-Me$_2$-Ph]; [5212; O; 5-Benzodioxolyl; H; SMe; S; 4-Me-Ph; 5-Indanyl]; [5213; O; 4-F-Ph; H; 2-Thienyl; S; Cyclohexyl; 4-F-Ph]; [5214; O; 4-F-Ph; H; 2-Thienyl; S; Cyclohexyl; 4-Cl-Ph]; [5215; O; 4-F-Ph; H; 2-Thienyl; S; Cyclohexyl; 4-Me-Ph]; [5216; O; 4-F-Ph; H; 2-Thienyl; S; Cyclohexyl; 3,4-Me$_2$-Ph]; [5217; O; 4-F-Ph; H; 2-Thienyl; S; Cyclohexyl; 5-Indanyl]; [5218; O; 4-Cl-Ph; H; 2-Thienyl; S; Cyclohexyl; 4-F-Ph]; [5219; O; 4-Cl-Ph; H; 2-Thienyl; S; Cyclohexyl; 4-Cl-Ph]; [5220; O; 4-Cl-Ph; H; 2-Thienyl; S; Cyclohexyl; 4-Me-Ph]; [5221; O; 4-Cl-Ph; H; 2-Thienyl; S; Cyclohexyl; 3,4-Me$_2$-Ph]; [5222; O; 4-Cl-Ph; H; 2-Thienyl; S; Cyclohexyl; 5-Indanyl]; [5223; O; 4-Me-Ph; H; 2-Thienyl; S; Cyclohexyl; 4-F-Ph]; [5224; O; 4-Me-Ph; H; 2-Thienyl; S; Cyclohexyl; 4-Cl-Ph]; [5225; O; 4-Me-Ph; H; 2-Thienyl; S; Cyclohexyl; 4-Me-Ph]; [5226; O; 4-Me-Ph; H; 2-Thienyl; S; Cyclohexyl; 3,4-Me$_2$-Ph]; [5227; O; 4-Me-Ph; H; 2-Thienyl; S; Cyclohexyl; 5-Indanyl]; [5228; O; 5-Benzodioxolyl; H; 2-Thienyl; S; Cyclohexyl; 4-F-Ph]; [5229; O; 5-Benzodioxolyl; H; 2-Thienyl; S; Cyclohexyl; 4-Cl-Ph]; [5230; O; 5-Benzodioxolyl; H; 2-Thienyl; S; Cyclohexyl; 4-Me-Ph]; [5231; O; 5-Benzodioxolyl; H; 2-Thienyl; S; Cyclohexyl; 3,4-Me$_2$-Ph]; [5232; O; 5-Benzodioxolyl; H; 2-Thienyl; S; Cyclohexyl; 5-Indanyl]; [5233; O; 4-F-Ph; H; 2-Thienyl; S; Cyclohexylmethyl; 4-F-Ph]; [5234; O; 4-F-Ph; H; 2-Thienyl; S; Cyclohexylmethyl; 4-Cl-Ph]; [5235; O; 4-F-Ph; H; 2-Thienyl; S; Cyclohexylmethyl; 4-Me-Ph]; [5236; O; 4-F-Ph; H; 2-Thienyl; S; Cyclohexylmethyl; 3,4-Me$_2$-Ph]; [5237; O; 4-F-Ph; H; 2-Thienyl; S; Cyclohexylmethyl; 5-Indanyl]; [5238; O; 4-Cl-Ph; H; 2-Thienyl; S; Cyclohexylmethyl; 4-F-Ph]; [5239; O; 4-Cl-Ph; H; 2-Thienyl; S; Cyclohexylmethyl; 4-Cl-Ph]; [5240; O; 4-Cl-Ph; H; 2-Thienyl; S; Cyclohexylmethyl; 4-Me-Ph]; [5241; O; 4-Cl-Ph; H; 2-Thienyl; S; Cyclohexylmethyl; 3,4-Me$_2$-Ph]; [5242; O; 4-Cl-Ph; H; 2-Thienyl; S; Cyclohexylmethyl; 5-Indanyl]; [5243; O; 4-Me-Ph; H; 2-Thienyl; S; Cyclohexylmethyl; 4-F-Ph]; [5244; O; 4-Me-Ph; H; 2-Thienyl; S; Cyclohexylmethyl; 4-Cl-Ph]; [5245; O; 4-Me-Ph; H; 2-Thienyl; S; Cyclohexylmethyl; 4-Me-Ph]; [5246; O; 4-Me-Ph; H; 2-Thienyl; S; Cyclohexylmethyl; 3,4-Me$_2$-Ph]; [5247; O; 4-Me-Ph; H; 2-Thienyl; S; Cyclohexylmethyl; 5-Indanyl]; [5248; O; 5-Benzodioxolyl; H; 2-Thienyl; S; Cyclohexylmethyl; 4-F-Ph]; [5249; O; 5-Benzodioxolyl; H; 2-Thienyl; S; Cyclohexylmethyl; 4-Cl-Ph]; [5250; O; 5-Benzodioxolyl; H; 2-Thienyl; S; Cyclohexylmethyl; 4-Me-Ph]; [5251; O; 5-Benzodioxolyl; H; 2-Thienyl; S; Cyclohexylmethyl; 3,4-Me$_2$-Ph]; [5252; O; 5-Benzodioxolyl; H; 2-Thienyl; S; Cyclohexylmethyl; 5-Indanyl]; [5253; O; 4-F-Ph; H; 2-Thienyl; S; 4-F-Ph; 4-F-Ph]; [5254; O; 4-F-Ph; H; 2-Thienyl; S; 4-F-Ph; 4-Cl-Ph]; [5255; O; 4-F-Ph; H; 2-Thienyl; S; 4-F-Ph; 4-Me-Ph]; [5256; O; 4-F-Ph; H; 2-Thienyl; S; 4-F-Ph; 3,4-Me$_2$-Ph]; [5257; O; 4-F-Ph; H; 2-Thienyl; S; 4-F-Ph; 5-Indanyl]; [5258; O; 4-Cl-Ph; H; 2-Thienyl; S; 4-F-Ph; 4-F-Ph]; [5259; O; 4-Cl-Ph; H; 2-Thienyl; S; 4-F-Ph; 4-Cl-Ph]; [5260; O; 4-Cl-Ph; H; 2-Thienyl; S; 4-F-Ph; 4-Me-Ph]; [5261; O; 4-Cl-Ph; H; 2-Thienyl; S; 4-F-Ph; 3,4-Me$_2$-Ph]; [5262; O; 4-Cl-Ph; H; 2-Thienyl; S; 4-F-Ph; 5-Indanyl]; [5263; O; 4-Me-Ph; H; 2-Thienyl; S; 4-F-Ph; 4-F-Ph]; [5264; O; 4-Me-Ph; H; 2-Thienyl; S; 4-F-Ph; 4-Cl-Ph]; [5265; O; 4-Me-Ph; H; 2-Thienyl; S; 4-F-Ph; 4-Me-Ph]; [5266; O; 4-Me-Ph; H; 2-Thienyl; S; 4-F-Ph; 3,4-Me$_2$-Ph]; [5267; O; 4-Me-Ph; H; 2-Thienyl; S; 4-F-Ph; 5-Indanyl]; [5268; O; 5-Benzodioxolyl; H; 2-Thienyl; S; 4-F-Ph; 4-F-Ph]; [5269; O; 5-Benzodioxolyl; H; 2-Thienyl; S; 4-F-Ph; 4-Cl-Ph]; [5270; O; 5-Benzodioxolyl; H; 2-Thienyl; S; 4-F-Ph; 4-Me-Ph]; [5271; O; 5-Benzodioxolyl; H; 2-Thienyl; S; 4-F-Ph; 3,4-Me$_2$-Ph]; [5272; O; 5-Benzodioxolyl; H; 2-Thienyl; S; 4-F-Ph; 5-Indanyl]; [5273; O; 4-F-Ph; H; 2-Thienyl; S; 4-Cl-Ph; 4-F-Ph]; [5274; O; 4-F-Ph; H; 2-Thienyl; S; 4-Cl-Ph; 4-Cl-Ph]; [5275; O; 4-F-Ph; H; 2-Thienyl; S; 4-Cl-Ph; 4-Me-Ph]; [5276; O; 4-F-Ph; H; 2-Thienyl; S; 4-Cl-Ph; 3,4-Me$_2$-Ph]; [5277; O; 4-F-Ph; H; 2-Thienyl; S; 4-Cl-Ph; 5-Indanyl]; [5278; O; 4-Cl-Ph; H; 2-Thienyl; S; 4-Cl-Ph; 4-F -Ph]; [5279; O; 4-Cl-Ph; H; 2-Thienyl; S; 4-Cl-Ph; 4-Cl-Ph]; [5280; O; 4-Cl-Ph; H; 2-Thienyl; S; 4-Cl-Ph; 4-Me-Ph]; [5281; O; 4-Cl-Ph; H; 2-Thienyl; S; 4-Cl-Ph; 3,4-Me$_2$-Ph]; [5282; O; 4-F-Ph; H; 2-Thienyl; S; 4-Cl-Ph; 5-Indanyl]; [5283; O; 4-Me-Ph; H; 2-Thienyl; S; 4-Cl-Ph; 4-F -Ph]; [5284; O; 4-Me-Ph; H; 2-Thienyl; S; 4-Cl-Ph; 4-Cl-Ph]; [5285; O; 4-Me-Ph; H; 2-Thienyl; S; 4-Cl-Ph; 4-Me-Ph]; [5286; O; 4-Me-Ph; H; 2-Thienyl; S; 4-Cl-Ph; 3,4-Me$_2$-Ph]; [5287; O; 4-Me-Ph; H; 2-Thienyl; S; 4-Cl-Ph; 5-Indanyl]; [5288; O; 5-Benzodioxolyl; H; 2-Thienyl; S; 4-Cl-Ph; 4-F-Ph]; [5289; O; 5-Benzodioxolyl; H; 2-Thienyl; S; 4-Cl-Ph; 4-Cl-Ph]; [5290; O; 5-Benzodioxolyl; H; 2-Thienyl; S; 4-Cl-Ph; 4-Me-Ph]; [5291; O; 5-Benzodioxolyl; H; 2-Thienyl; S; 4-Cl-Ph; 3,4-Me$_2$-Ph]; [5292; O; 5-Benzodioxolyl; H; 2-Thienyl; S; 4-Cl-Ph; 5-Indanyl]; [5293; O; 4-F-Ph; H; 2-Thienyl; S; 4-Me-Ph; 4-F-Ph]; [5294; O; 4-F-Ph; H; 2-Thienyl; S; 4-Me-Ph; 4-Cl-Ph]; [5295; O; 4-F-Ph; H; 2-Thienyl; S; 4-Me-Ph; 4-Me-Ph]; [5296; O; 4-F-Ph; H; 2-Thienyl; S; 4-Me-Ph; 3,4-Me$_2$-Ph]; [5297; O; 4-F-Ph; H; 2-Thienyl; S; 4-Me-Ph; 5-Indanyl]; [5298; O; 4-Cl-Ph; H; 2-Thienyl; S; 4-Me-Ph; 4-F-Ph]; [5299; O; 4-Cl-Ph; H; 2-Thienyl; S; 4-Me-Ph; 4-Cl-Ph]; [5300; O; 4-Cl-Ph; H; 2-Thienyl; S; 4-Me-Ph; 4-Me-Ph]; [5301; O; 4-Cl-Ph; H; 2-Thienyl; S; 4-Me-Ph; 3,4-Me$_2$-Ph]; [5302; O; 4-Cl-Ph; H; 2-Thienyl; S; 4-Me-Ph; 5-Indanyl]; [5303; O; 4-Me-Ph; H; 2-Thienyl; S; 4-Me-Ph; 4-F -Ph]; [5304; O; 4-Me-Ph; H; 2-Thienyl; S; 4-Me-Ph; 4-Cl-Ph]; [5305; O; 4-Me-Ph; H; 2-Thienyl; S; 4-Me-Ph; 4-Me-Ph]; [5306; O; 4-Me-Ph; H; 2-Thienyl; S; 4-Me-Ph; 3,4-Me$_2$-Ph]; [5307; O; 4-Me-Ph; H; 2-Thienyl; S; 4-Me-Ph; 5-Indanyl]; [5308; O; 5-Benzodioxolyl; H; 2-Thienyl; S; 4-Me-Ph; 4-F-Ph]; [5309; O; 5-Benzodioxolyl; H; 2-Thienyl; S; 4-Me-Ph; 4-Cl-Ph];[5310; O; 5-Benzodioxolyl; H; 2-Thienyl; S; 4-Me-Ph; 4-Me-Ph]; [5311; O; 5-Benzodioxolyl; H; 2-Thienyl; S; 4-Me-Ph; 3,4-Me$_2$-Ph]; [5312; O; 5-Benzodioxolyl; H; 2-Thienyl; S; 4-Me-Ph; 5-Indanyl]; [5313; O; 2-F-Ph; H; Me; O; Ph; Ph]; [5314; O; 2-Cl-Ph; H; Me; O; Ph; Ph]; [5315; O; 2-Cl-Ph; H; Me; O; Ph; Ph]; [5316; O; 2-Et-Ph; H; Me; O; Ph; Ph]; [5317; O; 3-Et-Ph; H; Me; O; Ph; Ph]; [5318; O; 4-Et-Ph; H; Me; O; Ph; Ph]; [5319; O; 2-iPr-Ph; H; Me; O; Ph; Ph]; [5320; O; 3-iPr-Ph; H; Me; O; Ph; Ph]; [5321; O; 4-iPr-Ph; H; Me; O; Ph; Ph]; [5322; O; 2-CF$_3$-Ph; H; Me; O; Ph; Ph]; [5323; O; 3-CF$_3$-Ph; H; Me; O; Ph; Ph]; [5324; O; 4-CF$_3$-Ph; H; Me; O; Ph; Ph]; [5325; O; 4-Ph-Ph; H; Me; O; Ph; Ph]; [5326; O; 2-MeO-Ph; H; Me; O; Ph; Ph]; [5327; O; 3-MeO-Ph; H; Me; O; Ph; Ph]; [5328; O; 4-MeO-Ph; H; Me; O; Ph; Ph]; [5329; O; 2,3-Me$_2$-Ph; H; Me; O; Ph; Ph]; [5330; O; 2,4-Me$_2$-Ph; H; Me; O; Ph; Ph]; [5331; O; 2,5-Me$_2$-Ph; H; Me; O; Ph; Ph]; [5332; O; 2,6-Me$_2$-Ph; H; Me; O; Ph; Ph]; [5333; O; 3,4-Me$_2$-Ph; H; Me; O; Ph; Ph]; [5334; O; 3,5-Me$_2$-Ph; H; Me; O; Ph; Ph]; [5335; O; 2,3-F$_2$-Ph; H; Me; O; Ph; Ph]; [5336; O; 2,4-F$_2$-Ph; H; Me; O; Ph; Ph]; [5337; O; 2,5-F$_2$-Ph; H; Me; O; Ph; Ph]; [5338; O; 2,6-F$_2$-Ph; H; Me; O; Ph; Ph]; [5339; O; 3,4-F$_2$-Ph; H; Me; O; Ph; Ph]; [5340; O; 3,5-F$_2$-Ph; H; Me; O; Ph; Ph]; [5341; O; 2,3-Cl$_2$-Ph; H; Me; O; Ph; Ph]; [5342; O; 2,4-Cl$_2$-Ph; H; Me; O; Ph; Ph]; [5343; O; 2,5-Cl$_2$-Ph; H; Me; O; Ph; Ph]; [5344; O; 2,6-Cl$_2$-Ph; H; Me; O; Ph; Ph]; [5345; O; 3,4-Cl$_2$-Ph; H; Me; O; Ph; Ph]; [5346; O; 3,5-Cl$_2$-Ph; H; Me; O; Ph; Ph]; [5347; O; 3,4-(MeO)$_2$-Ph; H; Me; O; Ph; Ph]; [5348; O; 4-PhO-Ph; H; Me; O; Ph]; [5349; O; 4-CF$_3$O-Ph; H; Me; O; Ph; Ph]; [5350; O; Ph; H; Et; O; Ph; Ph]; [5351; O; 2-F-Ph; H; Et; O; Ph; Ph]; [5352; O; 3-F-Ph; H; Et; O; Ph; Ph]; [5353; O; 4-F-Ph; H; Et; O; Ph; Ph]; [5354; O; 2-Cl-Ph; H; Et; O; Ph; Ph]; [5355; O; 3-Cl-Ph; H; Et; O; Ph; Ph]; [5356; O; 4-Cl-Ph; H; Et; O; Ph; Ph]; [5357; O; 2-Me-Ph; H; Et; O; Ph; Ph]; [5358; O; 3-Me-Ph; H; Et; O; Ph; Ph]; [5359; O; 4-Me-Ph; H; Et; O; Ph; Ph]; [5360; O; 3-MeO-Ph; H; Et; O; Ph; Ph]; [5361; O; 4-MeO-Ph; H; Et; O; Ph; Ph]; [5362; O; 3,4-Me$_2$-Ph; H; Et; O; Ph; Ph]; [5363; O; 3,4-F$_2$-Ph; H; Et; O; Ph; Ph]; [5364; O; 3,4-Cl$_2$-Ph; H; Et; O; Ph; Ph]; [5365; O; 3,4-(MeO)$_2$-Ph; H; Et; O; Ph; Ph]; [5366; O; 2-Naphthyl; H; Et; O; Ph; Ph]; [5367; O; 5-Indanyl; H; Et; O; Ph; Ph]; [5368; O; 5-Benzodioxolyl; H; Et; O; Ph; Ph]; [5369; O; PhCH$_2$; H; Pr; O; Ph; Ph]; [5370; O; Ph; H; Pr; O; Ph; Ph]; [5371; O; 2-F-Ph; H; Pr; O; Ph; Ph]; [5372; O; 3-F-Ph; H; Pr; O; Ph; Ph]; [5373; O; 4-F-Ph; H; Pr; O; Ph; Ph]; [5374; O; 2-Cl-Ph; H; Pr; O; Ph; Ph]; [5375; O; 3-Cl-Ph; H; Pr; O; Ph; Ph]; [5376; O; 4-Cl-Ph; H; Pr; O; Ph; Ph]; [5377; O; 2-Me-Ph; H; Pr; O; Ph; Ph]; [5378; O; 3-Me-Ph; H; Pr; O; Ph; Ph]; [5379; O; 4-Me-Ph; H; Pr; O; Ph; Ph]; [5380; O; 3-MeO-Ph; H; Pr; O; Ph; Ph]; [5381; O; 4-MeO-Ph; H; Pr; O; Ph; Ph]; [5382; O; 3,4-Me$_2$-Ph; H; Pr; O; Ph; Ph]; [5383; O; 3,4-F$_2$-Ph; H; Pr; O; Ph; Ph]; [5384; O; 3,4-Cl$_2$-Ph; H; Pr; O; Ph; Ph]; [5385; O; 3,4-(MeO)$_2$-Ph; H; Pr; O; Ph; Ph]; [5386; O; 2-Naphthyl; H; Pr; O; Ph; Ph]; [5387; O; 5-Indanyl; H; Pr; O; Ph; Ph]; [5388; O; 5-Benzodioxolyl; H; Pr; O; Ph; Ph]; [5389; O; Ph; H; SMe; O; Ph; Ph]; [5390; O; 2-F-Ph; H; SMe; O; Ph; Ph]; [5391; O; 3-F-Ph; H; SMe; O; Ph; Ph]; [5392; O; 4-F-Ph; H; SMe; O; Ph; Ph]; [5393; O; 4-Cl-Ph; H; SMe; O; Ph; Ph]; [5394; O; 4-Me-Ph; H; SMe; O; Ph; Ph]; [5395; O; 3-MeO-Ph; H; SMe; O; Ph; Ph]; [5396; O; 4-MeO-Ph; H; SMe; O; Ph; Ph]; [5397; O; 3,4-Me$_2$-Ph; H; SMe; O; Ph; Ph]; [5398; O; 3,4-F$_2$-Ph; H; SMe; O; Ph; Ph]; [5399; O; 3,4-Cl$_2$-Ph; H; SMe; O; Ph; Ph]; [5400; O; 3,4-(MeO)$_2$-Ph; H; SMe; O; Ph; Ph]; [5401; O; 2-Naphthyl; H; SMe; O; Ph; Ph]; [5402; O; 5-Indanyl; H; SMe; O; Ph; Ph]; [5403; O; 5-Benzodioxolyl; H; SMe; O; Ph; Ph]; [5404; O; Ph; H; 2-Thienyl; O; Ph; Ph]; [5405; O; 4-F-Ph; H; 2-Thienyl; O; Ph; Ph]; [5406; O; 4-Cl-Ph; H; 2-Thienyl; O; Ph; Ph]; [5407; O; 4-Me-Ph; H; 2-Thienyl; O; Ph; Ph]; [5408; O; 4-MeO-Ph; H; 2-Thienyl; O; Ph; Ph]; [5409; O; 5-Benzodioxolyl; H; 2-Thienyl; O; Ph; Ph]; [5410; O; Ph; H; iPr; O; Ph; Ph]; [5411; O; Ph; H; iBu; O; Ph; Ph]; [5412; O; Ph; H; cPr; O; Ph; Ph]; [5413; O; Ph; H; cyclohexyl; O; Ph; Ph]; [5414; O; Ph; H; cPrCH$_2$; O; Ph; Ph]; [5415; O; Ph; H; PhCH$_2$; O; Ph; Ph]; [5416; O; Ph; H; MeSCH$_2$; O; Ph; Ph]; [5417; O; Ph; H; CF$_3$; O; Ph; Ph]; [5418; O; Ph; H; 3-Thienyl; O; Ph; Ph]; [5419; O; Ph; H; 2-Furyl; O; Ph; Ph]; [5420; O; Ph; H; 2-Pyridyl; O; Ph; Ph]; [5421; O; Ph; H; 2-Thiazolyl; O; Ph; Ph]; [5422; O; Ph; H; F; O; Ph; Ph]; [5423; O; Ph; H; Me; O; CH$_3$(CH$_2$)$_4$; Ph]; [5424; O; Ph; H; Me; O; CH$_3$(CH$_2$)$_5$; Ph]; [5425; O; Ph; H; Me; O; CH$_3$(CH$_2$)$_6$; Ph]; [5426; O; Ph; H; Me; O; CH$_3$(CH$_2$)$_7$; Ph]; [5427; O; Ph; H; Me; O; iPr; Ph]; [5428; O; Ph; H; Me; O; sBu; Ph]; [5429; O; Ph; H; Me; O; iBu; Ph]; [5430; O; Ph; H; Me; O; tBu; Ph]; [5431; O; Ph; H; Me; O; 1-Methylbutyl; Ph]; [5432; O; Ph; H; Me; O; 2-Methylbutyl; Ph]; [5433; O; Ph; H; Me; O; Isopentyl; Ph]; [5434; O; Ph; H; Me; O; 1-Ethylpropyl; Ph]; [5435; O; Ph; H; Me; O; 1,1-Dimethylpropyl; Ph]; [5436; O; Ph; H; Me; O; 1,2-Dimethylpropyl; Ph]; [5437; O; Ph; H; Me; O; 1-Methylpentyl; Ph]; [5438; O; Ph; H; Me; O; 2-Methylpentyl; Ph]; [5439; O; Ph; H; Me; O; 3-Methylpentyl; Ph]; [5440; O; Ph; H; Me; O; 4-Methylpentyl; Ph]; [5441; O; Ph; H; Me; O; 1-Ethylbutyl; Ph]; [5442; O; Ph; H; Me; O; 2-Ethylbutyl; Ph]; [5443; O; Ph; H; Me; O; 1,1-Dimethylbutyl; Ph]; [5444; O; Ph; H; Me; O; 1,2-Dimethylbutyl; Ph]; [5445; O; Ph; H; Me; O; 1,3-Dimethylbutyl; Ph]; [5446; O; Ph; H; Me; O; 3,3-Dimethylbutyl; Ph]; [5447; O; Ph; H; Me; O; 1-Ethyl-1-methylbutyl; Ph]; [5448; O; Ph; H; Me; O; 1-Methylhexyl; Ph]; [5449; O; Ph;

H; Me; O; 2-Methylhexyl; Ph]; [5450; O; Ph; H; Me; O; 1-Ethylpentyl; Ph]; [5451; O; Ph; H; Me; O; 2-Ethylpentyl; Ph]; [5452; O; Ph; H; Me; O; 1-Ethyl-3-methylbutyl; Ph]; [5453; O; Ph; H; Me; O; 1-Propylbutyl; Ph]; [5454; O; Ph; H; Me; O; 1-Methylheptyl; Ph]; [5455; O; Ph; H; Me; O; 2-Methylheptyl; Ph]; [5456; O; Ph; H; Me; O; 1-Ethylhexyl; Ph]; [5457; O; Ph; H; Me; O; 2-Ethylhexyl; Ph]; [5458; O; Ph; H; Me; O; 1-Propylpentyl; Ph]; [5459; O; Ph; H; Me; O; 1-Propyl-3-methylbutyl; Ph]; [5460; O; Ph; H; Me; O; 1,1,3,3-Tetramethylbutyl; Ph]; [5461; O; Ph; H; Me; O; cPr; Ph]; [5462; O; Ph; H; Me; O; Cyclobutyl; Ph]; [5463; O; Ph; H; Me; O; Cyclopentyl; Ph]; [5464; O; Ph; H; Me; O; Cycloheptyl; Ph]; [5465; O; Ph; H; Me; O; cPrCH$_2$; Ph]; [5466; O; Ph; H; Me; O; cyclobutylmethyl; Ph]; [5467; O; Ph; H; Me; O; Cyclopentylmethyl; Ph]; [5468; O; Ph; H; Me; O; Cyclopentylmethyl; Ph]; [5469; O; Ph; H; Me; O; 1-Cyclohexylethyl; Ph]; [5470; O; Ph; H; Me; O; 1-Perhydronaphthyl; Ph]; [5471; O; Ph; H; Me; O; 2-F-Ph; Ph]; [5472; O; Ph; H; Me; O; 3-F-Ph; Ph]; [5473; O; Ph; H; Me; O; 2-Cl-Ph; Ph]; [5474; O; Ph; H; Me; O; 3-Cl-Ph; Ph]; [5475; O; Ph; H; Me; O; 2-Me-Ph; Ph]; [5476; O; Ph; H; Me; O; 3-Me-Ph; Ph]; [5477; O; Ph; H; Me; O; 4-Et-Ph; Ph]; [5478; O; Ph; H; Me; O; 4-iPr-Ph; Ph]; [5479; O; Ph; H; Me; O; 4-CF$_3$-Ph; Ph]; [5480; O; Ph; H; Me; O; 4-MeO-Ph; Ph]; [5481; O; Ph; H; Me; O; 4-MeS-Ph; Ph]; [5482; O; Ph; H; Me; O; 4-F3CO-Ph; Ph]; [5483; O; Ph; H; Me; O; 4-PhO-Ph; Ph]; [5484; O; Ph; H; Me; O; 4-Ph-Ph; Ph]; [5485; O; Ph; H; Me; O; 4-NC-Ph; Ph]; [5486; O; Ph; H; Me; O; 4-O$_2$N-Ph; Ph]; [5487; O; Ph; H; Me; O; 4-MeOOC-Ph; Ph]; [5488; O; Ph; H; Me; O; 3,4-F$_2$-Ph; Ph]; [5489; O; Ph; H; Me; O; 3,4-Cl$_2$-Ph; Ph]; [5490; O; Ph; H; Me; O; 3,4-Me$_2$-Ph; Ph]; [5491; O; Ph; H; Me; O; 1-Naphthyl; Ph]; [5492; O; Ph; H; Me; O; 5-Indanyl; Ph]; [5493; O; Ph; H; Me; O; 5-Benzodioxolyl; Ph]; [5494; O; Ph; H; Et; O; Bu; Ph]; [5495; O; Ph; H; Et; O; CH$_3$(CH$_2$)$_4$; Ph]; [5496; O; Ph; H; Et; O; CH$_3$(CH$_2$)$_5$; Ph]; [5497; O; Ph; H; Et; O; sBu; Ph]; [5498; O; Ph; H; Et; O; iBu; Ph]; [5499; O; Ph; H; Et; O; 1-Methylbutyl; Ph]; [5500; O; Ph; H; Et; O; 2-Methylbutyl; Ph]; [5501; O; Ph; H; Et; O; 1-Ethylpropyl; Ph]; [5502; O; Ph; H; Et; O; 1,2-Dimethylpropyl; Ph]; [5503; O; Ph; H; Et; O; 1-Methylpentyl; Ph]; [5504; O; Ph; H; Et; O; 2-Methylpentyl; Ph]; [5505; O; Ph; H; Et; O; 1-Ethylbutyl; Ph]; [5506; O; Ph; H; Et; O; 2-Ethylbutyl; Ph]; [5507; O; Ph; H; Et; O; 1,3-Dimethylbutyl; Ph]; [5508; O; Ph; H; Et; O; 1-Ethyl-1-methylbutyl; Ph]; [5509; O; Ph; H; Et; O; 1-Methylhexyl; Ph]; [5510; O; Ph; H; Et; O; 2-Methylhexyl; Ph]; [5511; O; Ph; H; Et; O; 1-Ethylpentyl; Ph]; [5512; O; Ph; H; Et; O; 1-Ethyl-3-methylbutyl; Ph]; [5513; O; Ph; H; Et; O; 1-Propylbutyl; Ph]; [5514; O; Ph; H; Et; O; 1-Propylpentyl; Ph]; [5515; O; Ph; H; Et; O; 1-Propyl-3-methylbutyl; Ph]; [5516; O; Ph; H; Et; O; Cyclopentyl; Ph]; [5517; O; Ph; H; Et; O; Cyclohexyl; Ph]; [5518; O; Ph; H; Et; O; 2-Perhydronaphthyl; Ph]; [5519; O; Ph; H; Et; O; cyclopentylmethyl; Ph]; [5520; O; Ph; H; Et; O; cyclohexylmethyl; Ph]; [5521; O; Ph; H; Et; O; cyclopentylethyl; Ph]; [5522; O; Ph; H; Et; O; cyclohexylethyl; Ph]; [5523; O; Ph; H; Et; O; PhCH$_2$; Ph]; [5524; O; Ph; H; Et; O; 2-F-Ph; Ph]; [5525; O; Ph; H; Et; O; 3-F-Ph; Ph]; [5526; O; Ph; H; Et; O; 4-F-Ph; Ph]; [5527; O; Ph; H; Et; O; 2-Cl-Ph; Ph]; [5528; O; Ph; H; Et; O; 3-Cl-Ph; Ph]; [5529; O; Ph; H; Et; O; 4-Cl-Ph; Ph]; [5530; O; Ph; H; Et; O; 2-Me-Ph; Ph]; [5531; O; Ph; H; Et; O; 3-Me-Ph; Ph]; [5532; O; Ph; H; Et; O; 4-Me-Ph; Ph]; [5533; O; Ph; H; Et; O; 4-iPr-Ph; Ph]; [5534; O; Ph; H; Et; O; 4-CF$_3$-Ph; Ph]; [5535; O; Ph; H; Et; O; 4-MeO-Ph; Ph]; [5536; O; Ph; H; Et; O; 4-MeS-Ph; Ph]; [5537; O; Ph; H; Et; O; 4-F3CO-Ph; Ph]; [5538; O; Ph; H; Et; O; 4-PhO-Ph; Ph]; [5539; O; Ph; H; Et; O; 3,4-F$_2$-Ph; Ph]; [5540; O; Ph; H; Et; O; 3,4-Cl$_2$-Ph; Ph]; [5541; O; Ph; H; Et; O; 3,4-Me$_2$-Ph; Ph]; [5542; O; Ph; H; Et; O; 1-Naphthyl; Ph]; [5543; O; Ph; H; Et; O; 2-Naphthyl; Ph]; [5544; O; Ph; H; Et; O; 5-Indanyl; Ph]; [5545; O; Ph; H; Et; O; 2-Thienyl; Ph]; [5546; O; Ph; H; Pr; O; Bu; Ph]; [5547; O; Ph; H; Pr; O; CH$_3$(CH$_2$)$_4$; Ph]; [5548; O; Ph; H; Pr; O; CH$_3$(CH$_2$)$_5$; Ph]; [5549; O; Ph; H; Pr; O; 1-Methylbutyl; Ph]; [5550; O; Ph; H; Pr; O; 2-Methylbutyl; Ph]; [5551; O; Ph; H; Pr; O; 1,2-Dimethylpropyl; Ph]; [5552; O; Ph; H; Pr; O; 1-Methylpentyl; Ph]; [5553; O; Ph; H; Pr; O; 2-Methylpentyl; Ph]; [5554; O; Ph; H; Pr; O; 1-Ethylbutyl; Ph]; [5555; O; Ph; H; Pr; O; 2-Ethylbutyl; Ph]; [5556; O; Ph; H; Pr; O; 1,3-Dimethylbutyl; Ph]; [5557; O; Ph; H; Pr; O; 1-Ethyl-1-methylbutyl; Ph]; [5558; O; Ph; H; Pr; O; 1-Ethylpentyl; Ph]; [5559; O; Ph; H; Pr; O; 1-Ethyl-3-methylbutyl; Ph]; [5560; O; Ph; H; Pr; O; 1-Propylbutyl; Ph]; [5561; O; Ph; H; Pr; O; 1-Propylpentyl; Ph]; [5562; O; Ph; H; Pr; O; 1-Propyl-3-methylbutyl; Ph]; [5563; O; Ph; H; Pr; O; Cyclopentyl; Ph]; [5564; O; Ph; H; Pr; O; Cyclohexyl; Ph]; [5565; O; Ph; H; Pr; O; 2-Perhydronaphthyl; Ph]; [5566; O; Ph; H; Pr; O; cyclopentylmethyl; Ph]; [5567; O; Ph; H; Pr; O; cyclohexylmethyl; Ph]; [5568; O; Ph; H; Pr; O; cyclopentylethyl; Ph]; [5569; O; Ph; H; Pr; O; cyclohexylethyl; Ph]; [5570; O; Ph; H; Pr; O; PhCH$_2$; Ph]; [5571; O; Ph; H; Pr; O; 2-F-Ph; Ph]; [5572; O; Ph; H; Pr; O; 3-F-Ph; Ph]; [5573; O; Ph; H; Pr; O; 4-F-Ph; Ph]; [5574; O; Ph; H; Pr; O; 2-Cl-Ph; Ph]; [5575; O; Ph; H; Pr; O; 3-Cl-Ph; Ph]; [5576; O; Ph; H; Pr; O; 4-Cl-Ph; Ph]; [5577; O; Ph; H; Pr; O; 2-Me-Ph; Ph]; [5578; O; Ph; H; Pr; O; 3-Me-Ph; Ph]; [5579; O; Ph; H; Pr; O; 4-Me-Ph; Ph]; [5580; O; Ph; H; Pr; O; 4-CF$_3$-Ph; Ph]; [5581; O; Ph; H; Pr; O; 4-MeO-Ph; Ph]; [5582; O; Ph; H; Pr; O; 4-MeS-Ph; Ph]; [5583; O; Ph; H; Pr; O; 4-F3CO-Ph; Ph]; [5584; O; Ph; H; Pr; O; 3,4-F$_2$-Ph; Ph]; [5585; O; Ph; H; Pr; O; 3,4-Cl$_2$-Ph; Ph]; [5586; O; Ph; H; Pr; O; 3,4-Me$_2$-Ph; Ph]; [5587; O; Ph; H; Pr; O; 2-Naphthyl; Ph]; [5588; O; Ph; H; SMe; O; CH$_3$(CH$_2$)$_5$; Ph]; [5589; O; Ph; H; SMe; O; Cyclopentyl; Ph]; [5590; O; Ph; H; SMe; O; Cyclohexyl; Ph]; [5591; O; Ph; H; SMe; O; 2-Perhydronaphthyl; Ph]; [5592; O; Ph; H; SMe; O; cyclopentylmethyl; Ph]; [5593; O; Ph; H; SMe; O; cyclohexylmethyl; Ph]; [5594; O; Ph; H; SMe; O; cyclopentylethyl; Ph]; [5595; O; Ph; H; SMe; O; cyclohexylethyl; Ph]; [5596; O; Ph; H; SMe; O; 2-F-Ph; Ph]; [5597; O; Ph; H; SMe; O; 3-F-Ph; Ph]; [5598; O; Ph; H; SMe; O; 4-F-Ph; Ph]; [5599; O; Ph; H; SMe; O; 4-Cl-Ph; Ph]; [5600; O; Ph; H; SMe; O; 4-Me-Ph; Ph]; [5601; O; Ph; H; SMe; O; 2-Naphthyl; Ph]; [5602; O; Ph; H; SMe; O; 5-Indanyl; Ph]; [5603; O; Ph; H; 2-Thienyl; O; CH$_3$(CH$_2$)$_5$; Ph]; [5604; O; Ph; H; 2-Thienyl; O; Cyclopentyl; Ph]; [5605; O; Ph; H; 2-Thienyl; O; Cyclohexyl; Ph]; [5606; O; Ph; H; 2-Thienyl; O; 2-Perhydronaphthyl; Ph]; [5607; O; Ph; H; 2-Thienyl; O; cyclopentylmethyl; Ph]; [5608; O; Ph; H; 2-Thienyl; O; cyclohexylmethyl; Ph]; [5609; O; Ph; H; 2-Thienyl; O; cyclopentylethyl; Ph]; [5610; O; Ph; H; 2-Thienyl; O; cyclohexylethyl; Ph]; [5611; O; Ph; H; 2-Thienyl; O; 2-F-Ph; Ph]; [5612; O; Ph; H; 2-Thienyl; O; 3-F-Ph; Ph]; [5613; O; Ph; H; 2-Thienyl; O; 4-F-Ph; Ph]; [5614; O; Ph; H; 2-Thienyl; O; 4-Cl-Ph; Ph]; [5615; O; Ph; H; 2-Thienyl; O; 4-Me-Ph; Ph]; [5616; O; Ph; H; 2-Thienyl; O; 2-Naphthyl; Ph]; [5617; O; Ph; H; Me; O; Ph; 2-Cl-Ph]; [5618; O; Ph; H; Me; O; Ph; 3-Cl-Ph]; [5619; O; Ph; H; Me; O; Ph; 2-Me-Ph]; [5620; O; Ph; H; Me; O; Ph; 4-Et-Ph]; [5621; O; Ph; H; Me; O; Ph; 4-CF$_3$-Ph]; [5622; O; Ph; H; Me; O; Ph; 4-MeO-Ph]; [5623; O; Ph; H; Me; O; Ph; 4-CF$_3$O-Ph]; [5624; O; Ph; H; Me; O; Ph; 2,3-F$_2$-Ph]; [5625; O; Ph; H; Me; O; Ph; 2,4-F$_2$-Ph]; [5626; O; Ph; H; Me; O; Ph; 2,5-F$_2$-Ph]; [5627; O; Ph; H; Me; O; Ph; 2,6-F$_2$-Ph]; [5628; O; Ph; H; Me; O; Ph; 3,4-F$_2$-Ph]; [5629; O; Ph; H; Me; O; Ph; 3,5-F$_2$-Ph]; [5630; O; Ph; H; Me; O; Ph; 2,3-Cl$_2$-Ph]; [5631; O; Ph; H; Me; O; Ph; 2,4-Cl$_2$-Ph]; [5632; O; Ph; H; Me; O; Ph; 2,5-Cl$_2$-Ph]; [5633; O; Ph; H; Me; O; Ph; 2,6-Cl$_2$-Ph]; [5634; O; Ph; H; Me; O; Ph;

3,4-Cl₂-Ph]; [5635; O; Ph; H; Me; O; Ph; 3,5-Cl₂-Ph]; [5636; O; Ph; H; Me; O; Ph; 2,3-Me₂-Ph]; [5637; O; Ph; H; Me; O; Ph; 2,4-Me₂-Ph]; [5638; O; Ph; H; Me; O; Ph; 2,5-Me₂-Ph]; [5639; O; Ph; H; Me; O; Ph; 2,6-Me₂-Ph]; [5640; O; Ph; H; Me; O; Ph; 3,4-Me₂-Ph]; [5641; O; Ph; H; Me; O; Ph; 3,5-Me₂-Ph]; [5642; O; Ph; H; Me; O; Ph; 4-Br-Ph]; [5643; O; Ph; H; Me; O; Ph; 2-Me-4-Ph-Ph]; [5644; O; Ph; H; Me; O; Ph; 3-Me-4-Ph-Ph]; [5645; O; Ph; H; Me; O; Ph; 4-(2-Me-Ph)-Ph]; [5646; O; Ph; H; Me; O; Ph; 4-(3-Me-Ph)-Ph]; [5647; O; Ph; H; Me; O; Ph; 4-(4-Me-Ph)-Ph]; [5648; O; Ph; H; Me; O; Ph; 1-Naphthyl]; [5649; O; Ph; H; Et; O; Ph; 2-F-Ph]; [5650; O; Ph; H; Et; O; Ph; 3-F-Ph]; [5651; O; Ph; H; Et; O; Ph; 4-F-Ph]; [5652; O; Ph; H; Et; O; Ph; 2-Cl-Ph]; [5653; O; Ph; H; Et; O; Ph; 3-Cl-Ph]; [5654; O; Ph; H; Et; O; Ph; 4-Cl-Ph]; [5655; O; Ph; H; Et; O; Ph; 2-Me-Ph]; [5656; O; Ph; H; Et; O; Ph; 3-Me-Ph]; [5657; O; Ph; H; Et; O; Ph; 4-Me-Ph]; [5658; O; Ph; H; Et; O; Ph; 4-Et-Ph]; [5659; O; Ph; H; Et; O; Ph; 4-iPr-Ph]; [5660; O; Ph; H; Et; O; Ph; 4-CF₃-Ph]; [5661; O; Ph; H; Et; O; Ph; 4-MeO-Ph]; [5662; O; Ph; H; Et; O; Ph; 4-CF₃O-Ph]; [5663; O; Ph; H; Et; O; Ph; 2,3-F₂-Ph]; [5664; O; Ph; H; Et; O; Ph; 2,4-F₂-Ph]; [5665; O; Ph; H; Et; O; Ph; 2,5-F₂-Ph]; [5666; O; Ph; H; Et; O; Ph; 2,6-F₂-Ph]; [5667; O; Ph; H; Et; O; Ph; 3,4-F₂-Ph]; [5668; O; Ph; H; Et; O; Ph; 3,5-F₂-Ph]; [5669; O; Ph; H; Et; O; Ph; 2,3-Cl₂-Ph]; [5670; O; Ph; H; Et; O; Ph; 2,4-Cl₂-Ph]; [5671; O; Ph; H; Et; O; Ph; 2,5-Cl₂-Ph]; [5672; O; Ph; H; Et; O; Ph; 2,6-Cl₂-Ph]; [5673; O; Ph; H; Et; O; Ph; 3,4-Cl₂-Ph]; [5674; O; Ph; H; Et; O; Ph; 3,5-Cl₂-Ph]; [5675; O; Ph; H; Et; O; Ph; 2,3-Me₂-Ph]; [5676; O; Ph; H; Et; O; Ph; 2,4-Me₂-Ph]; [5677; O; Ph; H; Et; O; Ph; 2,5-Me₂-Ph]; [5678; O; Ph; H; Et; O; Ph; 2,6-Me₂-Ph]; [5679; O; Ph; H; Et; O; Ph; 3,4-Me₂-Ph]; [5680; O; Ph; H; Et; O; Ph; 3,5-Me₂-Ph]; [5681; O; Ph; H; Et; O; Ph; 2-Naphthyl]; [5682; O; Ph; H; Et; O; Ph; 5-Indanyl]; [5683; O; Ph; H; Pr; O; Ph; 2-F-Ph]; [5684; O; Ph; H; Pr; O; Ph; 3-F-Ph]; [5685; O; Ph; H; Pr; O; Ph; 4-F-Ph]; [5686; O; Ph; H; Pr; O; Ph; 2-Cl-Ph]; [5687; O; Ph; H; Pr; O; Ph; 3-Cl-Ph]; [5688; O; Ph; H; Pr; O; Ph; 4-Cl-Ph]; [5689; O; Ph; H; Pr; O; Ph; 2-Me-Ph]; [5690; O; Ph; H; Pr; O; Ph; 3-Me-Ph]; [5691; O; Ph; H; Pr; O; Ph; 4-Me-Ph]; [5692; O; Ph; H; Pr; O; Ph; 4-Et-Ph]; [5693; O; Ph; H; Pr; O; Ph; 3,4-Me₂-Ph]; [5694; O; Ph; H; Pr; O; Ph; 5-Indanyl]; [5695; O; Ph; H; Ph; O; Ph; 2-Cl-Ph]; [5696; O; Ph; H; Ph; O; Ph; 3-Cl-Ph]; [5697; O; Ph; H; Ph; O; Ph; 2-Me-Ph]; [5698; O; Ph; H; Ph; O; Ph; 4-CF₃-Ph]; [5699; O; Ph; H; Ph; O; Ph; 3,4-Me₂-Ph]; [5700; O; Ph; H; Ph; O; Ph; 1-Naphthyl]; [5701; O; Ph; H; SMe; O; Ph; 2-F-Ph]; [5702; O; Ph; H; SMe; O; Ph; 3-F-Ph]; [5703; O; Ph; H; SMe; O; Ph; 4-F-Ph]; [5704; O; Ph; H; SMe; O; Ph; 2-Cl-Ph]; [5705; O; Ph; H; SMe; O; Ph; 3-Cl-Ph]; [5706; O; Ph; H; SMe; O; Ph; 4-Cl-Ph]; [5707; O; Ph; H; SMe; O; Ph; 2-Me-Ph]; [5708; O; Ph; H; SMe; O; Ph; 3-Me-Ph]; [5709; O; Ph; H; SMe; O; Ph; 4-Me-Ph]; [5710; O; Ph; H; SMe; O; Ph; 4-Et-Ph]; [5711; O; Ph; H; SMe; O; Ph; 4-iPr-Ph]; [5712; O; Ph; H; SMe; O; Ph; 3,4-Me₂-Ph]; [5713; O; Ph; H; SMe; O; Ph; 5-Indanyl]; [5714; O; Ph; H; 2-Thienyl; O; Ph; 4-F-Ph]; [5715; O; Ph; H; 2-Thienyl; O; Ph; 4-Cl-Ph]; [5716; O; Ph; H; 2-Thienyl; O; Ph; 3-Me-Ph]; [5717; O; Ph; H; 2-Thienyl; O; Ph; 4-Me-Ph]; [5718; O; Ph; H; 2-Thienyl; O; Ph; 3,4-Me₂-Ph]; [5719; O; Ph; H; 2-Thienyl; O; Ph; 5-Indanyl]; [5720; O; 3-F-Ph; H; Me; O; Ph; 2-F-Ph]; [5721; O; 3-F-Ph; H; Me; O; Ph; 3-F-Ph]; [5722; O; 3-F-Ph; H; Me; O; Ph; 4-Cl-Ph]; [5724; O; 3-F-Ph; H; Me; O; Ph; 3-Me-Ph]; [5725; O; 3-F-Ph; H; Me; O; Ph; 4-Me-Ph]; [5726; O; 3-F-Ph; H; Me; O; Ph; 4-Et-Ph]; [5727; O; 3-F-Ph; H; Me; O; Ph; 4-iPr-Ph]; [5728; O; 3-F-Ph; H; Me; O; Ph; 4-Ph-Ph]; [5729; O; 3-F-Ph; H; Me; O; Ph; 3,4-Me₂-Ph]; [5730; O; 3-F-Ph; H; Me; O; Ph; 2-Naphthyl]; [5731; O; 3-F-Ph; H; Me; O; Ph; 5-Indanyl]; [5732; O; 4-F-Ph; H; Me; O; Ph; 4-Et-Ph]; [5733; O; 4-F-Ph; H; Me; O; Ph; 3,4-Me₂-Ph]; [5734; O; 3-Cl-Ph; H; Me; O; Ph; 2-F-Ph]; [5735; O; 3-Cl-Ph; H; Me; O; Ph; 3-F-Ph]; [5736; O; 3-Cl-Ph; H; Me; O; Ph; 4-F-Ph]; [5737; O; 3-Cl-Ph; H; Me; O; Ph; 4-Cl-Ph]; [5738; O; 3-Cl-Ph; H; Me; O; Ph; 3-Me-Ph]; [5739; O; 3-Cl-Ph; H; Me; O; Ph; 4-Me-Ph]; [5740; O; 3-Cl-Ph; H; Me; O; Ph; 4-iPr-Ph]; [5741; O; 3-Cl-Ph; H; Me; O; Ph; 4-Ph-Ph]; [5742; O; 3-Cl-Ph; H; Me; O; Ph; 2-Naphthyl]; [5743; O; 3-Cl-Ph; H; Me; O; Ph; 5-Indanyl]; [5744; O; 4-Cl-Ph; H; Me; O; Ph; 4-Et-Ph]; [5745; O; 4-Cl-Ph; H; Me; O; Ph; 3,4-Me₂-Ph]; [5746; O; 3-Me-Ph; H; Me; O; Ph; 2-F-Ph]; [5747; O; 3-Me-Ph; H; Me; O; Ph; 3-F-Ph]; [5748; O; 3-Me-Ph; H; Me; O; Ph; 4-F-Ph]; [5749; O; 3-Me-Ph; H; Me; O; Ph; 4-Cl-Ph]; [5750; O; 3-Me-Ph; H; Me; O; Ph; 3-Me-Ph]; [5751; O; 3-Me-Ph; H; Me; O; Ph; 4-Me-Ph]; [5752; O; 3-Me-Ph; H; Me; O; Ph; 4-Et-Ph]; [5753; O; 3-Me-Ph; H; Me; O; Ph; 4-iPr-Ph]; [5754; O; 3-Me-Ph; H; Me; O; Ph; 4-Ph-Ph]; [5755; O; 3-Me-Ph; H; Me; O; Ph; 3,4-Me₂-Ph]; [5756; O; 3-Me-Ph; H; Me; O; Ph; 2-Naphthyl]; [5757; O; 3-Me-Ph; H; Me; O; Ph; 5-Indanyl]; [5758; O; 4-Me-Ph; H; Me; O; Ph; 4-Et-Ph]; [5759; O; 4-Me-Ph; H; Me; O; Ph; 3,4-Me₂-Ph]; [5760; O; 4-iPr-Ph; H; Me; O; Ph; 2-F-Ph]; [5761; O; 4-iPr-Ph; H; Me; O; Ph; 3-F-Ph]; [5762; O; 4-iPr-Ph; H; Me; O; Ph; 4-F-Ph]; [5763; O; 4-iPr-Ph; H; Me; O; Ph; 4-Cl-Ph]; [5764; O; 4-iPr-Ph; H; Me; O; Ph; 3-Me-Ph]; [5765; O; 4-iPr-Ph; H; Me; O; Ph; 4-Me-Ph]; [5766; O; 4-iPr-Ph; H; Me; O; Ph; 4-iPr-Ph]; [5767; O; 4-iPr-Ph; H; Me; O; Ph; 4-Ph-Ph]; [5768; O; 4-iPr-Ph; H; Me; O; Ph; 2-Naphthyl]; [5769; O; 4-iPr-Ph; H; Me; O; Ph; 5-Indanyl]; [5770; O; 5-Benzodioxolyl; H; Me; O; Ph; 4-Et-Ph]; [5771; O; 5-Benzodioxolyl; H; Me; O; Ph; 3,4-Me₂-Ph]; [5772; O; 4-F-Ph; H; Et; O; Ph; 4-F-Ph]; [5773; O; 4-F-Ph; H; Et; O; Ph; 4-Cl-Ph]; [5774; O; 4-F-Ph; H; Et; O; Ph; 3-Me-Ph]; [5775; O; 4-F-Ph; H; Et; O; Ph; 4-Me-Ph]; [5776; O; 4-F-Ph; H; Et; O; Ph; 4-Et-Ph]; [5777; O; 4-F-Ph; H; Et; O; Ph; 4-iPr-Ph]; [5778; O; 4-F-Ph; H; Et; O; Ph; 3,4-Me₂-Ph]; [5779; O; 4-F-Ph; H; Et; O; Ph; 5-Indanyl]; [5780; O; 4-Cl-Ph; H; Et; O; Ph; 4-F-Ph]; [5781; O; 4-Cl-Ph; H; Et; O; Ph; 4-Cl-Ph]; [5782; O; 4-Cl-Ph; H; Et; O; Ph; 3-Me-Ph]; [5783; O; 4-Cl-Ph; H; Et; O; Ph; 4-Me-Ph]; [5784; O; 4-Cl-Ph; H; Et; O; Ph; 4-Et-Ph]; [5785; O; 4-Cl-Ph; H; Et; O; Ph; 4-iPr-Ph]; [5786; O; 4-Cl-Ph; H; Et; O; Ph; 3,4-Me₂-Ph]; [5787; O; 4-Cl-Ph; H; Et; O; Ph; 5-Indanyl]; [5788; O; 4-Me-Ph; H; Et; O; Ph; 4-F-Ph]; [5789; O; 4-Me-Ph; H; Et; O; Ph; 4-Cl-Ph]; [5790; O; 4-Me-Ph; H; Et; O; Ph; 3-Me-Ph]; [5791; O; 4-Me-Ph; H; Et; O; Ph; 4-Me-Ph]; [5792; O; 4-F-Ph; H; Et; O; Ph; 4-Et-Ph]; [5793; O; 4-Me-Ph; H; Et; O; Ph; 4-iPr-Ph]; [5794; O; 4-Me-Ph; H; Et; O; Ph; 3,4-Me₂-Ph]; [5795; O; 4-Me-Ph; H; Et; O; Ph; 5-Indanyl]; [5796; O; 4-MeO-Ph; H; Et; O; Ph; 4-F-Ph]; [5797; O; 4-MeO-Ph; H; Et; O; Ph; 4-Cl-Ph]; [5798; O; 4-MeO-Ph; H; Et; O; Ph; 3-Me-Ph]; [5799; O; 4-MeO-Ph; H; Et; O; Ph; 4-Me-Ph]; [5800; O; 4-MeO-Ph; H; Et; O; Ph; 4-Et-Ph]; [5801; O; 4-MeO-Ph; H; Et; O; Ph; 4-iPr-Ph]; [5802; O; 4-MeO-Ph; H; Et; O; Ph; 3,4-Me₂-Ph]; [5803; O; 4-MeO-Ph; H; Et; O; Ph; 5-Indanyl]; [5804; O; 5-Benzodioxolyl; H; Et; O; Ph; 4-F-Ph]; [5805; O; 5-Benzodioxolyl; H; Et; O; Ph; 4-Cl-Ph]; [5806; O; 5-Benzodioxolyl; H; Et; O; Ph; 3-Me-Ph]; [5807; O; 5-Benzodioxolyl; H; Et; O; Ph; 4-Me-Ph]; [5808; O; 5-Benzodioxolyl; H; Et; O; Ph; 4-Et-Ph]; [5809; O; 5-Benzodioxolyl; H; Et; O; Ph; 4-iPr-Ph]; [5810; O; 5-Benzodioxolyl; H; Et; O; Ph; 3,4-Me₂-Ph]; [5811; O; 5-Benzodioxolyl; H; Et; O; Ph; 5-Indanyl][; O; 4-F-Ph; H; Pr; O; Ph; 4-F-Ph]; [5812; O; 4-F-Ph; H; Pr; O; Ph; 4-Cl-Ph]; [5813; O; 4-F-Ph; H; Pr; O; Ph; 3-Me-Ph]; [5814; O; 4-F-Ph; H; Pr; O; Ph; 4-Me-Ph]; [5815; O; 4-F-Ph; H; Pr; O; Ph; 4-Et-Ph]; [5816; O; 4-F-Ph; H; Pr; O; Ph; 4-iPr-Ph]; [5817; O; 4-F-Ph; H; Pr; O; Ph; 3,4-Me₂-Ph]; [5818; O; 4-F-Ph; H; Pr; O; Ph; 5-Indanyl]; [5819; O; 4-Cl-Ph; H; Pr; O; Ph; 4-F-Ph];

[5820; O; 4-Cl-Ph; H; Pr; O; Ph; 4-Cl-Ph]; [5821; O; 4-Cl-Ph; H; Pr; O; Ph; 3-Me-Ph]; [5822; O; 4-Cl-Ph; H; Pr; O; Ph; 4-Me-Ph]; [5823; O; 4-Cl-Ph; H; Pr; O; Ph; 4-Et-Ph]; [5824; O; 4-Cl-Ph; H; Pr; O; Ph; 4-iPr-Ph]; [5825; O; 4-Cl-Ph; H; Pr; O; Ph; 3,4-Me$_2$-Ph]; [5826; O; 4-Cl-Ph; H; Pr; O; Ph; 5-Indanyl]; [5827; O; 4-Me-Ph; H; Pr; O; Ph; 4-F-Ph]; [5828; O; 4-Me-Ph; H; Pr; O; Ph; 4-Cl-Ph]; [5829; O; 4-Me-Ph; H; Pr; O; Ph; 3-Me-Ph]; [5830; O; 4-Me-Ph; H; Pr; O; Ph; 4-Me-Ph]; [5831; O; 4-F-Ph; H; Pr; O; Ph; 4-Et-Ph]; [5832; O; 4-Me-Ph; H; Pr; O; Ph; 4-iPr-Ph]; [5833; O; 4-Me-Ph; H; Pr; O; Ph; 3,4-Me$_2$-Ph]; [5834; O; 4-Me-Ph; H; Pr; O; Ph; 5-Indanyl]; [5835; O; 4-MeO-Ph; H; Pr; O; Ph; 4-F-Ph]; [5836; O; 4-MeO-Ph; H; Pr; O; Ph; 4-Cl-Ph]; [5837; O; 4-MeO-Ph; H; Pr; O; Ph; 3-Me-Ph]; [5838; O; 4-MeO-Ph; H; Pr; O; Ph; 4-Me-Ph]; [5839; O; 4-MeO-Ph; H; Pr; O; Ph; 4-Et-Ph]; [5840; O; 4-MeO-Ph; H; Pr; O; Ph; 4-iPr-Ph]; [5841; O; 4-MeO-Ph; H; Pr; O; Ph; 3,4-Me$_2$-Ph]; [5842; O; 4-MeO-Ph; H; Pr; O; Ph; 5-Indanyl]; [5843; O; 5-Benzodioxolyl; H; Pr; O; Ph; 4-F-Ph]; [5844; O; 5-Benzodioxolyl; H; Pr; O; Ph; 4-Cl-Ph]; [5845; O; 5-Benzodioxolyl; H; Pr; O; Ph; 3-Me-Ph]; [5846; O; 5-Benzodioxolyl; H; Pr; O; Ph; 4-Me-Ph]; [5847; O; 5-Benzodioxolyl; H; Pr; O; Ph; 4-Et-Ph]; [5848; O; 5-Benzodioxolyl; H; Pr; O; Ph; 4-iPr-Ph]; [5849; O; 5-Benzodioxolyl; H; Pr; O; Ph; 3,4-Me$_2$-Ph]; [5850; O; 5-Benzodioxolyl; H; Pr; O; Ph; 5-Indanyl]; [5851; O; 4-F-Ph; H; Ph; O; Ph; 4-F-Ph]; [5852; O; 4-F-Ph; H; Ph; O; Ph; 4-Cl-Ph]; [5853; O; 4-F-Ph; H; Ph; O; Ph; 3-Me-Ph]; [5854; O; 4-F-Ph; H; Ph; O; Ph; 4-Me-Ph]; [5855; O; 4-F-Ph; H; Ph; O; Ph; 4-Et-Ph]; [5856; O; 4-F-Ph; H; Ph; O; Ph; 4-iPr-Ph]; [5857; O; 4-F-Ph; H; Ph; O; Ph; 3,4-Me$_2$-Ph]; [5858; O; 4-F-Ph; H; Ph; O; Ph; 5-Indanyl]; [5859; O; 4-Cl-Ph; H; Ph; O; Ph; 4-F-Ph]; [5860; O; 4-Cl-Ph; H; Ph; O; Ph; 4-Cl-Ph]; [5861; O; 4-Cl-Ph; H; Ph; O; Ph; 3-Me-Ph]; [5862; O; 4-Cl-Ph; H; Ph; O; Ph; 4-Me-Ph]; [5863; O; 4-Cl-Ph; H; Ph; O; Ph; 4-Et-Ph]; [5864; O; 4-Cl-Ph; H; Ph; O; Ph; 4-iPr-Ph]; [5865; O; 4-Cl-Ph; H; Ph; O; Ph; 3,4-Me$_2$-Ph]; [5866; O; 4-Cl-Ph; H; Ph; O; Ph; 5-Indanyl]; [5867; O; 4-Me-Ph; H; Ph; O; Ph; 4-F-Ph]; [5868; O; 4-Me-Ph; H; Ph; O; Ph; 4-Cl-Ph]; [5869; O; 4-Me-Ph; H; Ph; O; Ph; 3-Me-Ph]; [5870; O; 4-Me-Ph; H; Ph; O; Ph; 4-Me-Ph]; [5871; O; 4-F-Ph; H; Ph; O; Ph; 4-Et-Ph]; [5872; O; 4-Me-Ph; H; Ph; O; Ph; 4-iPr-Ph]; [5873; O; 4-Me-Ph; H; Ph; O; Ph; 3,4-Me$_2$-Ph]; [5874; O; 4-Me-Ph; H; Ph; O; Ph; 5-Indanyl]; [5875; O; 4-MeO-Ph; H; Ph; O; Ph; 4-F-Ph]; [5876; O; 4-MeO-Ph; H; Ph; O; Ph; 4-Cl-Ph]; [5877; O; 4-MeO-Ph; H; Ph; O; Ph; 3-Me-Ph]; [5878; O; 4-MeO-Ph; H; Ph; O; Ph; 4-Me-Ph]; [5879; O; 4-MeO-Ph; H; Ph; O; Ph; 4-Et-Ph]; [5880; O; 4-MeO-Ph; H; Ph; O; Ph; 4-iPr-Ph]; [5881; O; 4-MeO-Ph; H; Ph; O; Ph; 3,4-Me$_2$-Ph]; [5882; O; 4-MeO-Ph; H; Ph; O; Ph; 5-Indanyl]; [5883; O; 5-Benzodioxolyl; H; Ph; O; Ph; 4-F-Ph]; [5884; O; 5-Benzodioxolyl; H; Ph; O; Ph; 4-Cl-Ph]; [5885; O; 5-Benzodioxolyl; H; Ph; O; Ph; 3-Me-Ph]; [5886; O; 5-Benzodioxolyl; H; Ph; O; Ph; 4-Me-Ph]; [5887; O; 5-Benzodioxolyl; H; Ph; O; Ph; 4-Et-Ph]; [5888; O; 5-Benzodioxolyl; H; Ph; O; Ph; 4-iPr-Ph]; [5889; O; 5-Benzodioxolyl; H; Ph; O; Ph; 3,4-Me$_2$-Ph]; [5890; O; 5-Benzodioxolyl; H; Ph; O; Ph; 5-Indanyl]; [5891; O; 4-F-Ph; H; SMe; O; Ph; 4-F-Ph]; [5892; O; 4-F-Ph; H; SMe; O; Ph; 4-Cl-Ph]; [5893; O; 4-F-Ph; H; SMe; O; Ph; 3-Me-Ph]; [5894; O; 4-F-Ph; H; SMe; O; Ph; 4-Me-Ph]; [5895; O; 4-F-Ph; H; SMe; O; Ph; 4-Et-Ph]; [5896; O; 4-F-Ph; H; SMe; O; Ph; 4-iPr-Ph]; [5897; O; 4-F-Ph; H; SMe; O; Ph; 3,4-Me$_2$-Ph]; [5898; O; 4-F-Ph; H; SMe; O; Ph; 5-Indanyl]; [5899; O; 4-Cl-Ph; H; SMe; O; Ph; 4-F-Ph]; [5900; O; 4-Cl-Ph; H; SMe; O; Ph; 4-Cl-Ph]; [5901; O; 4-Cl-Ph; H; SMe; O; Ph; 3-Me-Ph]; [5902; O; 4-Cl-Ph; H; SMe; O; Ph; 4-Me-Ph]; [5903; O; 4-Cl-Ph; H; SMe; O; Ph; 4-Et-Ph]; [5904; O; 4-Cl-Ph; H; SMe; O; Ph; 4-iPr-Ph]; [5905; O; 4-Cl-Ph; H; SMe; O; Ph; 3,4-Me$_2$-Ph]; [5906; O; 4-Cl-Ph; H; SMe; O; Ph; 5-Indanyl]; [5907; O; 4-Me-Ph; H; SMe; O; Ph; 4-F-Ph]; [5908; O; 4-Me-Ph; H; SMe; O; Ph; 4-Cl-Ph]; [5909; O; 4-Me-Ph; H; SMe; O; Ph; 3-Me-Ph]; [5910; O; 4-Me-Ph; H; SMe; O; Ph; 4-Me-Ph]; [5911; O; 4-F-Ph; H; SMe; O; Ph; 4-Et-Ph]; [5912; O; 4-Me-Ph; H; SMe; O; Ph; 4-iPr-Ph]; [5913; O; 4-Me-Ph; H; SMe; O; Ph; 3,4-Me$_2$-Ph]; [5914; O; 4-Me-Ph; H; SMe; O; Ph; 5-Indanyl]; [5915; O; 4-MeO-Ph; H; SMe; O; Ph; 4-F-Ph]; [5916; O; 4-MeO-Ph; H; SMe; O; Ph; 4-Cl-Ph]; [5917; O; 4-MeO-Ph; H; SMe; O; Ph; 3-Me-Ph]; [5918; O; 4-MeO-Ph; H; SMe; O; Ph; 4-Me-Ph]; [5919; O; 4-MeO-Ph; H; SMe; O; Ph; 4-Et-Ph]; [5920; O; 4-MeO-Ph; H; SMe; O; Ph; 4-iPr-Ph]; [5921; O; 4-MeO-Ph; H; SMe; O; Ph; 3,4-Me$_2$-Ph]; [5922; O; 4-MeO-Ph; H; SMe; O; Ph; 5-Indanyl]; [5923; O; 5-Benzodioxolyl; H; SMe; O; Ph; 4-F-Ph]; [5924; O; 5-Benzodioxolyl; H; SMe; O; Ph; 4-Cl-Ph]; [5925; O; 5-Benzodioxolyl; H; SMe; O; Ph; 3-Me-Ph]; [5926; O; 5-Benzodioxolyl; H; SMe; O; Ph; 4-Me-Ph]; [5927; O; 5-Benzodioxolyl; H; SMe; O; Ph; 4-Et-Ph]; [5928; O; 5-Benzodioxolyl; H; SMe; O; Ph; 4-iPr-Ph]; [5929; O; 5-Benzodioxolyl; H; SMe; O; Ph; 3,4-Me$_2$-Ph]; [5930; O; 5-Benzodioxolyl; H; SMe; O; Ph; 5-Indanyl]; [5931; O; 4-F-Ph; H; 2-Thienyl; O; Ph; 4-F-Ph]; [5932; O; 4-F-Ph; H; 2-Thienyl; O; Ph; 4-Cl-Ph]; [5933; O; 4-F-Ph; H; 2-Thienyl; O; Ph; 3-Me-Ph]; [5934; O; 4-F-Ph; H; 2-Thienyl; O; Ph; 4-Me-Ph]; [5935; O; 4-F-Ph; H; 2-Thienyl; O; Ph; 4-Et-Ph]; [5936; O; 4-F-Ph; H; 2-Thienyl; O; Ph; 4-iPr-Ph]; [5937; O; 4-F-Ph; H; 2-Thienyl; O; Ph; 3,4-Me$_2$-Ph]; [5938; O; 4-F-Ph; H; 2-Thienyl; O; Ph; 5-Indanyl]; [5939; O; 4-Cl-Ph; H; 2-Thienyl; O; Ph; 4-F-Ph]; [5940; O; 4-Cl-Ph; H; 2-Thienyl; O; Ph; 4-Cl-Ph]; [5941; O; 4-Cl-Ph; H; 2-Thienyl; O; Ph; 3-Me-Ph]; [5942; O; 4-Cl-Ph; H; 2-Thienyl; O; Ph; 4-Me-Ph]; [5943; O; 4-Cl-Ph; H; 2-Thienyl; O; Ph; 4-Et-Ph]; [5944; O; 4-Cl-Ph; H; 2-Thienyl; O; Ph; 4-iPr-Ph]; [5945; O; 4-Cl-Ph; H; 2-Thienyl; O; Ph; 3,4-Me$_2$-Ph]; [5946; O; 4-Cl-Ph; H; 2-Thienyl; O; Ph; 5-Indanyl]; [5947; O; 4-Me-Ph; H; 2-Thienyl; O; Ph; 4-F-Ph]; [5948; O; 4-Me-Ph; H; 2-Thienyl; O; Ph; 4-Cl-Ph]; [5949; O; 4-Me-Ph; H; 2-Thienyl; O; Ph; 3-Me-Ph]; [5950; O; 4-Me-Ph; H; 2-Thienyl; O; Ph; 4-Me-Ph]; [5951; O; 4-F-Ph; H; 2-Thienyl; O; Ph; 4-Et-Ph]; [5952; O; 4-Me-Ph; H; 2-Thienyl; O; Ph; 4-iPr-Ph]; [5953; O; 4-Me-Ph; H; 2-Thienyl; O; Ph; 3,4-Me$_2$-Ph]; [5954; O; 4-Me-Ph; H; 2-Thienyl; O; Ph; 5-Indanyl]; [5955; O; 4-MeO-Ph; H; 2-Thienyl; O; Ph; 4-F-Ph]; [5956; O; 4-MeO-Ph; H; 2-Thienyl; O; Ph; 4-Cl-Ph]; [5957; O; 4-MeO-Ph; H; 2-Thienyl; O; Ph; 3-Me-Ph]; [5958; O; 4-MeO-Ph; H; 2-Thienyl; O; Ph; 4-Me-Ph]; [5959; O; 4-MeO-Ph; H; 2-Thienyl; O; Ph; 4-Et-Ph]; [5960; O; 4-MeO-Ph; H; 2-Thienyl; O; Ph; 4-iPr-Ph]; [5961; O; 4-MeO-Ph; H; 2-Thienyl; O; Ph; 3,4-Me$_2$-Ph]; [5962; O; 4-MeO-Ph; H; 2-Thienyl; O; Ph; 5-Indanyl]; [5963; O; 5-Benzodioxolyl; H; 2-Thienyl; O; Ph; 4-F-Ph]; [5964; O; 5-Benzodioxolyl; H; 2-Thienyl; O; Ph; 4-Cl-Ph]; [5965; O; 5-Benzodioxolyl; H; 2-Thienyl; O; Ph; 3-Me-Ph]; [5966; O; 5-Benzodioxolyl; H; 2-Thienyl; O; Ph; 4-Me-Ph]; [5967; O; 5-Benzodioxolyl; H; 2-Thienyl; O; Ph; 4-Et-Ph]; [5968; O; 5-Benzodioxolyl; H; 2-Thienyl; O; Ph; 4-iPr-Ph]; [5969; O; 5-Benzodioxolyl; H; 2-Thienyl; O; Ph; 3,4-Me$_2$-Ph]; [5970; O; 5-Benzodioxolyl; H; 2-Thienyl; O; Ph; 5-Indanyl]; [5971; O; Ph; H; Me; O; Cyclohexyl; 2-F-Ph]; [5972; O; Ph; H; Me; O; Cyclohexyl; 3-F-Ph]; [5973; O; Ph; H; Me; O; Cyclohexyl; 4-F-Ph]; [5974; O; Ph; H; Me; O; Cyclohexyl; 4-Cl-Ph]; [5975; O; Ph; H; Me; O; Cyclohexyl; 3-Me-Ph]; [5976; O; Ph; H; Me; O; Cyclohexyl; 4-Me-Ph]; [5977; O; Ph; H; Me; O; Cyclohexyl; 4-iPr-Ph]; [5978; O; Ph; H; Me; O; Cyclohexyl; 3,4-Me$_2$-Ph]; [5979; O; Ph; H; Me; O; Cyclohexyl; 2-Naphthyl]; [5980; O; Ph; H; Me; O; Cyclohexyl; 5-Indanyl]; [5981; O; Ph; H; Me; O; Cyclohexylmethyl; 3,4-

Me₂-Ph]; [5982; O; Ph; H; Me; O; 2-Perhydronaphthyl; 3,4-Me₂-Ph]; [5983; O; Ph; H; Me; O; 4-F-Ph; 3,4-Me₂-Ph]; [5984; O; Ph; H; Me; O; 3-Cl-Ph; 4-F-Ph]; [5985; O; Ph; H; Me; O; 3-Cl-Ph; 4-Cl-Ph]; [5986; O; Ph; H; Me; O; 3-Cl-Ph; 3-Me-Ph]; [5987; O; Ph; H; Me; O; 3-Cl-Ph; 4-Me-Ph]; [5988; O; Ph; H; Me; O; 3-Cl-Ph; 3,4-Me₂-Ph]; [5989; O; Ph; H; Me; O; 3-Cl-Ph; 5-Indanyl]; [5990; O; Ph; H; Me; O; 4-Cl-Ph; 4-F-Ph]; [5991; O; Ph; H; Me; O; 4-Cl-Ph; 4-Cl-Ph]; [5992; O; Ph; H; Me; O; 4-Me-Ph; 4-F-Ph]; [5993; O; Ph; H; Me; O; 4-Me-Ph; 4-Cl-Ph]; [5994; O; Ph; H; Me; O; 4-Me-Ph; 3-Me-Ph]; [5995; O; Ph; H; Me; O; 4-Me-Ph; 4-Me-Ph]; [5996; O; Ph; H; Me; O; 4-Me-Ph; 3,4-Me₂-Ph]; [5997; O; Ph; H; Me; O; 4-Me-Ph; 5-Indanyl]; [5998; O; Ph; H; Me; O; 2-Naphthyl; 3,4-Me₂-Ph]; [5999; O; Ph; H; Et; O; Cyclohexyl; 4-F-Ph]; [6000; O; Ph; H; Et; O; Cyclohexyl; 4-Cl-Ph]; [6001; O; Ph; H; Et; O; Cyclohexyl; 3-Me-Ph]; [6002; O; Ph; H; Et; O; Cyclohexyl; 4-Me-Ph]; [6003; O; Ph; H; Et; O; Cyclohexyl; 3,4-Me₂-Ph]; [6004; O; Ph; H; Et; O; Cyclohexyl; 5-Indanyl]; [6005; O; Ph; H; Et; O; Cyclohexylmethyl; 4-F-Ph]; [6006; O; Ph; H; Et; O; Cyclohexylmethyl; 4-Cl-Ph]; [6007; O; Ph; H; Et; O; Cyclohexylmethyl; 3-Me-Ph]; [6008; O; Ph; H; Et; O; Cyclohexylmethyl; 4-Me-Ph]; [6009; O; Ph; H; Et; O; Cyclohexylmethyl; 4-Ph-Ph]; [6010; O; Ph; H; Et; O; Cyclohexylmethyl; 3,4-Me₂-Ph]; [6011; O; Ph; H; Et; O; Cyclohexylmethyl; 5-Indanyl]; [6012; O; Ph; H; Et; O; 4-F-Ph; 4-F-Ph]; [6013; O; Ph; H; Et; O; 4-F-Ph; 4-Cl-Ph]; [6014; O; Ph; H; Et; O; 4-F-Ph; 3-Me-Ph]; [6015; O; Ph; H; Et; O; 4-F-Ph; 4-Me-Ph]; [6016; O; Ph; H; Et; O; 4-F-Ph; 3,4-Me₂-Ph]; [6017; O; Ph; H; Et; O; 4-F-Ph; 5-Indanyl]; [6018; O; Ph; H; Et; O; 3-Cl-Ph; 4-F-Ph]; [6019; O; Ph; H; Et; O; 3-Cl-Ph; 4-Cl-Ph]; [6020; O; Ph; H; Et; O; 3-Cl-Ph; 3-Me-Ph]; [6021; O; Ph; H; Et; O; 3-Cl-Ph; 4-Me-Ph]; [6022; O; Ph; H; Et; O; 3-Cl-Ph; 3,4-Me₂-Ph]; [6023; O; Ph; H; Et; O; 3-Cl-Ph; 5-Indanyl]; [6024; O; Ph; H; Et; O; 4-Cl-Ph; 4-F-Ph]; [6025; O; Ph; H; Et; O; 4-Cl-Ph; 4-Cl-Ph]; [6026; O; Ph; H; Et; O; 3-Cl-Ph; 3-Me-Ph]; [6027; O; Ph; H; Et; O; 4-Cl-Ph; 4-Me-Ph]; [6028; O; Ph; H; Et; O; 4-Cl-Ph; 3,4-Me₂-Ph]; [6029; O; Ph; H; Et; O; 4-Cl-Ph; 5-Indanyl]; [6030; O; Ph; H; Et; O; 4-Me-Ph; 4-F-Ph]; [6031; O; Ph; H; Et; O; 4-Me-Ph; 4-Cl-Ph]; [6032; O; Ph; H; Et; O; 4-Me-Ph; 3-Me-Ph]; [6033; O; Ph; H; Et; O; 4-Me-Ph; 4-Me-Ph]; [6034; O; Ph; H; Et; O; 4-Me-Ph; 3,4-Me₂-Ph]; [6035; O; Ph; H; Et; O; 4-Me-Ph; 5-Indanyl]; [6036; O; Ph; H; Et; O; 2-Naphthyl; 4-F-Ph]; [6037; O; Ph; H; Et; O; 2-Naphthyl; 4-Cl-Ph]; [6038; O; Ph; H; Et; O; 2-Naphthyl; 3-Me-Ph]; [6039; O; Ph; H; Et; O; 2-Naphthyl; 4-Me-Ph]; [6040; O; Ph; H; Et; O; 2-Naphthyl; 3,4-Me₂-Ph]; [6041; O; Ph; H; Et; O; 2-Naphthyl; 5-Indanyl]; [6042; O; Ph; H; Pr; O; Cyclohexyl; 4-F-Ph]; [6043; O; Ph; H; Pr; O; Cyclohexyl; 4-Cl-Ph]; [6044; O; Ph; H; Pr; O; Cyclohexyl; 3-Me-Ph]; [6045; O; Ph; H; Pr; O; Cyclohexyl; 4-Me-Ph]; [6046; O; Ph; H; Pr; O; Cyclohexyl; 3,4-Me₂-Ph]; [6047; O; Ph; H; Pr; O; Cyclohexyl; 5-Indanyl]; [6048; O; Ph; H; Pr; O; Cyclohexylmethyl; 4-F-Ph]; [6049; O; Ph; H; Pr; O; Cyclohexylmethyl; 4-Cl-Ph]; [6050; O; Ph; H; Pr; O; Cyclohexylmethyl; 3-Me-Ph]; [6051; O; Ph; H; Pr; O; Cyclohexylmethyl; 4-Me-Ph]; [6052; O; Ph; H; Pr; O; Cyclohexylmethyl; 4-Ph-Ph]; [6053; O; Ph; H; Pr; O; Cyclohexylmethyl; 3,4-Me₂-Ph]; [6054; O; Ph; H; Pr; O; Cyclohexylmethyl; 5-Indanyl]; [6055; O; Ph; H; Pr; O; 4-F-Ph; 4-F-Ph]; [6056; O; Ph; H; Pr; O; 4-F-Ph; 4-Cl-Ph]; [6057; O; Ph; H; Pr; O; 4-F-Ph; 3-Me-Ph]; [6058; O; Ph; H; Pr; O; 4-F-Ph; 4-Me-Ph]; [6059; O; Ph; H; Pr; O; 4-F-Ph; 3,4-Me₂-Ph]; [6060; O; Ph; H; Pr; O; 4-F-Ph; 5-Indanyl]; [6061; O; Ph; H; Pr; O; 3-Cl-Ph; 4-F-Ph]; [6062; O; Ph; H; Pr; O; 3-Cl-Ph; 4-Cl-Ph]; [6063; O; Ph; H; Pr; O; 3-Cl-Ph; 3-Me-Ph]; [6064; O; Ph; H; Pr; O; 3-Cl-Ph; 4-Me-Ph]; [6065; O; Ph; H; Pr; O; 3-Cl-Ph; 3,4-Me₂-Ph]; [6066; O; Ph; H; Pr; O; 3-Cl-Ph; 5-Indanyl]; [6067; O; Ph; H; Pr; O; 4-Cl-Ph; 4-F-Ph]; [6068; O; Ph; H; Pr; O; 4-Cl-Ph; 4-Cl-Ph]; [6069; O; Ph; H; Pr; O; 3-Cl-Ph; 3-Me-Ph]; [6070; O; Ph; H; Pr; O; 4-Cl-Ph; 4-Me-Ph]; [6071; O; Ph; H; Pr; O; 4-Cl-Ph; 3,4-Me₂-Ph]; [6072; O; Ph; H; Pr; O; 4-Cl-Ph; 5-Indanyl]; [6073; O; Ph; H; Pr; O; 4-Me-Ph; 4-F-Ph]; [6074; O; Ph; H; Pr; O; 4-Me-Ph; 4-Cl-Ph]; [6075; O; Ph; H; Pr; O; 4-Me-Ph; 3-Me-Ph]; [6076; O; Ph; H; Pr; O; 4-Me-Ph; 4-Me-Ph]; [6077; O; Ph; H; Pr; O; 4-Me-Ph; 3,4-Me₂-Ph]; [6078; O; Ph; H; Pr; O; 4-Me-Ph; 5-Indanyl]; [6079; O; Ph; H; Pr; O; 2-Naphthyl; 4-F-Ph]; [6080; O; Ph; H; Pr; O; 2-Naphthyl; 4-Cl-Ph]; [6081; O; Ph; H; Pr; O; 2-Naphthyl; 3-Me-Ph]; [6082; O; Ph; H; Pr; O; 2-Naphthyl; 4-Me-Ph]; [6083; O; Ph; H; Pr; O; 2-Naphthyl; 3,4-Me₂-Ph]; [6084; O; Ph; H; Pr; O; 2-Naphthyl; 5-Indanyl]; [6085; O; Ph; H; Ph; O; Cyclohexyl; 4-F-Ph]; [6086; O; Ph; H; Ph; O; Cyclohexyl; 4-Cl-Ph]; [6087; O; Ph; H; Ph; O; Cyclohexyl; 3-Me-Ph]; [6088; O; Ph; H; Ph; O; Cyclohexyl; 4-Me-Ph]; [6089; O; Ph; H; Ph; O; Cyclohexyl; 3,4-Me₂-Ph]; [6090; O; Ph; H; Ph; O; Cyclohexyl; 5-Indanyl]; [6091; O; Ph; H; Ph; O; Cyclohexylmethyl; 4-F-Ph]; [6092; O; Ph; H; Ph; O; Cyclohexylmethyl; 4-Cl-Ph]; [6093; O; Ph; H; Ph; O; Cyclohexylmethyl; 3-Me-Ph]; [6094; O; Ph; H; Ph; O; Cyclohexylmethyl; 4-Me-Ph]; [6095; O; Ph; H; Ph; O; Cyclohexylmethyl; 4-Ph-Ph]; [6096; O; Ph; H; Ph; O; Cyclohexylmethyl; 3,4-Me₂-Ph]; [6097; O; Ph; H; Ph; O; Cyclohexylmethyl; 5-Indanyl]; [6098; O; Ph; H; Ph; O; 4-F-Ph; 4-F-Ph]; [6099; O; Ph; H; Ph; O; 4-F-Ph; 4-Cl-Ph]; [6100; O; Ph; H; Ph; O; 4-F-Ph; 3-Me-Ph]; [6101; O; Ph; H; Ph; O; 4-F-Ph; 4-Me-Ph]; [6102; O; Ph; H; Ph; O; 4-F-Ph; 3,4-Me₂-Ph]; [6103; O; Ph; H; Ph; O; 4-F-Ph; 5-Indanyl]; [6104; O; Ph; H; Ph; O; 3-Cl-Ph; 4-F-Ph]; [6105; O; Ph; H; Ph; O; 3-Cl-Ph; 4-Cl-Ph]; [6106; O; Ph; H; Ph; O; 3-Cl-Ph; 3-Me-Ph]; [6107; O; Ph; H; Ph; O; 3-Cl-Ph; 4-Me-Ph]; [6108; O; Ph; H; Ph; O; 3-Cl-Ph; 3,4-Me₂-Ph]; [6109; O; Ph; H; Ph; O; 3-Cl-Ph; 5-Indanyl]; [6110; O; Ph; H; Ph; O; 4-Cl-Ph; 4-F-Ph]; [6111; O; Ph; H; Ph; O; 4-Cl-Ph; 4-Cl-Ph]; [6112; O; Ph; H; Ph; O; 3-Cl-Ph; 3-Me-Ph]; [6113; O; Ph; H; Ph; O; 4-Cl-Ph; 4-Me-Ph]; [6114; O; Ph; H; Ph; O; 4-Cl-Ph; 3,4-Me₂-Ph]; [6115; O; Ph; H; Ph; O; 4-Cl-Ph; 5-Indanyl]; [6116; O; Ph; H; Ph; O; 4-Me-Ph; 4-F-Ph]; [6117; O; Ph; H; Ph; O; 4-Me-Ph; 4-Cl-Ph]; [6118; O; Ph; H; Ph; O; 4-Me-Ph; 3-Me-Ph]; [6119; O; Ph; H; Ph; O; 4-Me-Ph; 4-Me-Ph]; [6120; O; Ph; H; Ph; O; 4-Me-Ph; 3,4-Me₂-Ph]; [6121; O; Ph; H; Ph; O; 4-Me-Ph; 5-Indanyl]; [6122; O; Ph; H; Ph; O; 2-Naphthyl; 4-F-Ph]; [6123; O; Ph; H; Ph; O; 2-Naphthyl; 4-Cl-Ph]; [6124; O; Ph; H; Ph; O; 2-Naphthyl; 3-Me-Ph]; [6125; O; Ph; H; Ph; O; 2-Naphthyl; 4-Me-Ph]; [6126; O; Ph; H; Ph; O; 2-Naphthyl; 3,4-Me₂-Ph]; [6127; O; Ph; H; Ph; O; 2-Naphthyl; 5-Indanyl]; [6128; O; Ph; H; SMe; O; Cyclohexyl; 4-F-Ph]; [6129; O; Ph; H; SMe; O; Cyclohexyl; 4-Cl-Ph]; [6130; O; Ph; H; SMe; O; Cyclohexyl; 3-Me-Ph]; [6131; O; Ph; H; SMe; O; Cyclohexyl; 4-Me-Ph]; [6132; O; Ph; H; SMe; O; Cyclohexyl; 3,4-Me₂-Ph]; [6133; O; Ph; H; SMe; O; Cyclohexyl; 5-Indanyl]; [6134; O; Ph; H; SMe; O; Cyclohexylmethyl; 4-F-Ph]; [6135; O; Ph; H; SMe; O; Cyclohexylmethyl; 4-Cl-Ph]; [6136; O; Ph; H; SMe; O; Cyclohexylmethyl; 3-Me-Ph]; [6137; O; Ph; H; SMe; O; Cyclohexylmethyl; 4-Me-Ph]; [6138; O; Ph; H; SMe; O; Cyclohexylmethyl; 4-Ph-Ph]; [6139; O; Ph; H; SMe; O; Cyclohexylmethyl; 3,4-Me₂-Ph]; [6140; O; Ph; H; SMe; O; Cyclohexylmethyl; 5-Indanyl]; [6141; O; Ph; H; SMe; O; 4-F-Ph; 4-F-Ph]; [6142; O; Ph; H; SMe; O; 4-F-Ph; 4-Cl-Ph]; [6143; O; Ph; H; SMe; O; 4-F-Ph; 3-Me-Ph]; [6144; O; Ph; H; SMe; O; 4-F-Ph; 4-Me-Ph]; [6145; O; Ph; H; SMe; O; 4-F-Ph; 3,4-Me₂-Ph]; [6146; O; Ph; H; SMe; O; 4-F-Ph; 5-Indanyl]; [6147; O; Ph; H; SMe; O; 3-Cl-Ph; 4-F-Ph]; [6148; O; Ph; H; SMe; O; 3-Cl-Ph; 4-Cl-Ph]; [6149; O; Ph; H; SMe; O; 3-Cl-Ph; 3-Me-Ph]; [6150; O; Ph; H; SMe; O; 3-Cl-Ph;

4-Me-Ph]; [6151; O; Ph; H; SMe; O; 3-Cl-Ph; 3,4-Me₂-Ph]; [6152; O; Ph; H; SMe; O; 3-Cl-Ph; 5-Indanyl]; [6153; O; Ph; H; SMe; O; 4-Cl-Ph; 4-F-Ph]; [6154; O; Ph; H; SMe; O; 4-Cl-Ph; 4-Cl-Ph]; [6155; O; Ph; H; SMe; O; 3-Cl-Ph; 3-Me-Ph]; [6156; O; Ph; H; SMe; O; 4-Cl-Ph; 4-Me-Ph]; [6157; O; Ph; H; SMe; O; 4-Cl-Ph; 3,4-Me₂-Ph]; [6158; O; Ph; H; SMe; O; 4-Cl-Ph; 5-Indanyl]; [6159; O; Ph; H; SMe; O; 4-Me-Ph; 4-F-Ph]; [6160; O; Ph; H; SMe; O; 4-Me-Ph; 4-Cl-Ph]; [6161; O; Ph; H; SMe; O; 4-Me-Ph; 3-Me-Ph]; [6162; O; Ph; H; SMe; O; 4-Me-Ph; 4-Me-Ph]; [6163; O; Ph; H; SMe; O; 4-Me-Ph; 3,4-Me₂-Ph]; [6164; O; Ph; H; SMe; O; 4-Me-Ph; 5-Indanyl]; [6165; O; Ph; H; SMe; O; 2-Naphthyl; 4-F-Ph]; [6166; O; Ph; H; SMe; O; 2-Naphthyl; 4-Cl-Ph]; [6167; O; Ph; H; SMe; O; 2-Naphthyl; 3-Me-Ph]; [6168; O; Ph; H; SMe; O; 2-Naphthyl; 4-Me-Ph]; [6169; O; Ph; H; SMe; O; 2-Naphthyl; 3,4-Me₂-Ph]; [6170; O; Ph; H; SMe; O; 2-Naphthyl; 5-Indanyl]; [6171; O; Ph; H; 2-Thienyl; O; Cyclohexyl; 4-F-Ph]; [6172; O; Ph; H; 2-Thienyl; O; Cyclohexyl; 4-Cl-Ph]; [6173; O; Ph; H; 2-Thienyl; O; Cyclohexyl; 3-Me-Ph]; [6174; O; Ph; H; 2-Thienyl; O; Cyclohexyl; 4-Me-Ph]; [6175; O; Ph; H; 2-Thienyl; O; Cyclohexyl; 3,4-Me₂-Ph]; [6176; O; Ph; H; 2-Thienyl; O; Cyclohexyl; 5-Indanyl]; [6177; O; Ph; H; 2-Thienyl; O; Cyclohexylmethyl; 4-F-Ph]; [6178; O; Ph; H; 2-Thienyl; O; Cyclohexylmethyl; 4-Cl-Ph]; [6179; O; Ph; H; 2-Thienyl; O; Cyclohexylmethyl; 3-Me-Ph]; [6180; O; Ph; H; 2-Thienyl; O; Cyclohexylmethyl; 4-Me-Ph]; [6181; O; Ph; H; 2-Thienyl; O; Cyclohexylmethyl; 4-Ph-Ph]; [6182; O; Ph; H; 2-Thienyl; O; Cyclohexylmethyl; 3,4-Me₂-Ph]; [6183; O; Ph; H; 2-Thienyl; O; Cyclohexylmethyl; 5-Indanyl]; [6184; O; Ph; H; 2-Thienyl; O; 4-F-Ph; 4-F-Ph]; [6185; O; Ph; H; 2-Thienyl; O; 4-F-Ph; 4-Cl-Ph]; [6186; O; Ph; H; 2-Thienyl; O; 4-F-Ph; 3-Me-Ph]; [6187; O; Ph; H; 2-Thienyl; O; 4-F-Ph; 4-Me-Ph]; [6188; O; Ph; H; 2-Thienyl; O; 4-F-Ph; 3,4-Me₂-Ph]; [6189; O; Ph; H; 2-Thienyl; O; 4-F-Ph; 5-Indanyl]; [6190; O; Ph; H; 2-Thienyl; O; 3-Cl-Ph; 4-F-Ph]; [6191; O; Ph; H; 2-Thienyl; O; 3-Cl-Ph; 4-Cl-Ph]; [6192; O; Ph; H; 2-Thienyl; O; 3-Cl-Ph; 3-Me-Ph]; [6193; O; Ph; H; 2-Thienyl; O; 3-Cl-Ph; 4-Me-Ph]; [6194; O; Ph; H; 2-Thienyl; O; 3-Cl-Ph; 3,4-Me₂-Ph]; [6195; O; Ph; H; 2-Thienyl; O; 3-Cl-Ph; 5-Indanyl]; [6196; O; Ph; H; 2-Thienyl; O; 4-Cl-Ph; 4-F-Ph]; [6197; O; Ph; H; 2-Thienyl; O; 4-Cl-Ph; 4-Cl-Ph]; [6198; O; Ph; H; 2-Thienyl; O; 3-Cl-Ph; 3-Me-Ph]; [6199; O; Ph; H; 2-Thienyl; O; 4-Cl-Ph; 4-Me-Ph]; [6200; O; Ph; H; 2-Thienyl; O; 4-Cl-Ph; 3,4-Me₂-Ph]; [6201; O; Ph; H; 2-Thienyl; O; 4-Cl-Ph; 5-Indanyl]; [6202; O; Ph; H; 2-Thienyl; O; 4-Me-Ph; 4-F-Ph]; [6203; O; Ph; H; 2-Thienyl; O; 4-Me-Ph; 4-Cl-Ph]; [6204; O; Ph; H; 2-Thienyl; O; 4-Me-Ph; 3-Me-Ph]; [6205; O; Ph; H; 2-Thienyl; O; 4-Me-Ph; 4-Me-Ph]; [6206; O; Ph; H; 2-Thienyl; O; 4-Me-Ph; 3,4-Me₂-Ph]; [6207; O; Ph; H; 2-Thienyl; O; 4-Me-Ph; 5-Indanyl]; [6208; O; Ph; H; 2-Thienyl; O; 2-Naphthyl; 4-F-Ph]; [6209; O; Ph; H; 2-Thienyl; O; 2-Naphthyl; 4-Cl-Ph]; [6210; O; Ph; H; 2-Thienyl; O; 2-Naphthyl; 3-Me-Ph]; [6211; O; Ph; H; 2-Thienyl; O; 2-Naphthyl; 4-Me-Ph]; [6212; O; Ph; H; 2-Thienyl; O; 2-Naphthyl; 3,4-Me₂-Ph]; [6213; O; Ph; H; 2-Thienyl; O; 2-Naphthyl; 5-Indanyl]; [6214; O; 4-F-Ph; H; Me; O; Cyclohexylmethyl; 3,4-Me₂-Ph]; [6215; O; 4-F-Ph; H; Me; O; Cyclohexylmethyl; 5-Indanyl]; [6216; O; 4-Cl-Ph; H; Me; O; Cyclohexylmethyl; 4-F-Ph]; [6217; O; 4-Cl-Ph; H; Me; O; Cyclohexylmethyl; 4-Cl-Ph]; [6218; O; 4-Cl-Ph; H; Me; O; Cyclohexylmethyl; 4-Me-Ph]; [6219; O; 4-Cl-Ph; H; Me; O; Cyclohexylmethyl; 4-Ph-Ph]; [6220; O; 4-Cl-Ph; H; Me; O; Cyclohexylmethyl; 3,4-Me₂-Ph]; [6221; O; 4-Cl-Ph; H; Me; O; Cyclohexylmethyl; 2-Naphthyl]; [6222; O; 4-Cl-Ph; H; Me; O; Cyclohexylmethyl; 5-Indanyl]; [6223; O; 4-Me-Ph; H; Me; O; Cyclohexylmethyl; 3,4-Me₂-Ph]; [6224; O; 4-Me-Ph; H; Me; O; Cyclohexylmethyl; 5-Indanyl]; [6225; O; 5-Benzodioxolyl; H; Me; O; Cyclohexylmethyl; 4-F-Ph]; [6226; O; 5-Benzodioxolyl; H; Me; O; Cyclohexylmethyl; 4-Cl-Ph]; [6227; O; 5-Benzodioxolyl; H; Me; O; Cyclohexylmethyl; 4-Me-Ph]; [6228; O; 5-Benzodioxolyl; H; Me; O; Cyclohexylmethyl; 4-Ph-Ph]; [6229; O; 5-Benzodioxolyl; H; Me; O; Cyclohexylmethyl; 3,4-Me₂-Ph]; [6230; O; 5-Benzodioxolyl; H; Me; O; Cyclohexylmethyl; 2-Naphthyl]; [6231; O; 5-Benzodioxolyl; H; Me; O; Cyclohexylmethyl; 5-Indanyl]; [6232; O; 5-Indanyl; H; Me; O; 2-Perhydronaphthyl; 4-F-Ph]; [6233; O; 5-Indanyl; H; Me; O; 2-Perhydronaphthyl; 4-Cl-Ph]; [6234; O; 5-Indanyl; H; Me; O; 2-Perhydronaphthyl; 4-Me-Ph]; [6235; O; 5-Indanyl; H; Me; O; 2-Perhydronaphthyl; 4-Ph-Ph]; [6236; O; 5-Indanyl; H; Me; O; 2-Perhydronaphthyl; 2-Naphthyl]; [6237; O; 4-Cl-Ph; H; Me; O; PhCH₂; 4-F-Ph]; [6238; O; 4-Cl-Ph; H; Me; O; PhCH₂; 4-Cl-Ph]; [6239; O; 4-Cl-Ph; H; Me; O; PhCH₂; 4-Me₂-Ph]; [6240; O; 4-Cl-Ph; H; Me; O; PhCH₂; 4-Ph-Ph]; [6241; O; 4-Cl-Ph; H; Me; O; PhCH₂; 2-Naphthyl]; [6242; O; 5-Indanyl; H; Me; O; PhCH₂; 4-F-Ph]; [6243; O; 5-Indanyl; H; Me; O; PhCH₂; 4-Cl-Ph]; [6244; O; 5-Indanyl; H; Me; O; PhCH₂; 4-Me-Ph]; [6245; O; 5-Indanyl; H; Me; O; PhCH₂; 4-Ph-Ph]; [6246; O; 5-Indanyl; H; Me; O; PhCH₂; 2-Naphthyl]; [6247; O; 4-F-Ph; H; Me; O; 4-F-Ph; 3,4-Me₂-Ph]; [6248; O; 4-F-Ph; H; Me; O; 4-F-Ph; 5-Indanyl]; [6249; O; 4-Cl-Ph; H; Me; O; 4-F-Ph; 4-Me-Ph]; [6250; O; 4-Cl-Ph; H; Me; O; 4-F-Ph; 4-Cl-Ph]; [6251; O; 4-Cl-Ph; H; Me; O; 4-F-Ph; 4-Me-Ph]; [6252; O; 4-Cl-Ph; H; Me; O; 4-F-Ph; 4-Ph-Ph]; [6253; O; 4-Cl-Ph; H; Me; O; 4-F-Ph; 3,4-Me₂-Ph]; [6254; O; 4-Cl-Ph; H; Me; O; 4-F-Ph; 2-Naphthyl]; [6255; O; 4-Cl-Ph; H; Me; O; 4-F-Ph; 5-Indanyl]; [6256; O; 4-Me-Ph; H; Me; O; 4-F-Ph; 3,4-Me₂-Ph]; [6257; O; 4-Me-Ph; H; Me; O; 4-F-Ph; 5-Indanyl]; [6258; O; 5-Indanyl; H; Me; O; 4-F-Ph; 4-F-Ph]; [6259; O; 5-Indanyl; H; Me; O; 4-F-Ph; 4-Cl-Ph]; [6260; O; 5-Indanyl; H; Me; O; 4-F-Ph; 4-Me-Ph]; [6261; O; 5-Indanyl; H; Me; O; 4-F-Ph; 4-Ph-Ph]; [6262; O; 5-Indanyl; H; Me; O; 4-F-Ph; 2-Naphthyl]; [6263; O; 4-F-Ph; H; Me; O; 4-Cl-Ph; 3,4-Me₂-Ph]; [6264; O; 4-Cl-Ph; H; Me; O; 4-Cl-Ph; 4-F-Ph]; [6265; O; 4-Cl-Ph; H; Me; O; 4-Cl-Ph; 4-Cl-Ph]; [6266; O; 4-Cl-Ph; H; Me; O; 4-Cl-Ph; 4-Me-Ph]; [6267; O; 4-Cl-Ph; H; Me; O; 4-Cl-Ph; 4-Ph-Ph]; [6268; O; 4-Cl-Ph; H; Me; O; 4-Cl-Ph; 3,4-Me₂-Ph]; [6269; O; 4-Cl-Ph; H; Me; O; 4-Cl-Ph; 2-Naphthyl]; [6270; O; 4-F-Ph; H; Me; O; 4-Cl-Ph; 5-Indanyl]; [6271; O; 4-Me-Ph; H; Me; O; 4-Cl-Ph; 4-F-Ph]; [6272; O; 4-Me-Ph; H; Me; O; 4-Cl-Ph; 4-Cl-Ph]; [6273; O; 4-Me-Ph; H; Me; O; 4-Cl-Ph; 4-Me-Ph]; [6274; O; 4-Me-Ph; H; Me; O; 4-Cl-Ph; 4-Ph-Ph]; [6275; O; 4-Me-Ph; H; Me; O; 4-Cl-Ph; 3,4-Me₂-Ph]; [6276; O; 4-Me-Ph; H; Me; O; 4-Cl-Ph; 2-Naphthyl]; [6277; O; 4-Me-Ph; H; Me; O; 4-Cl-Ph; 5-Indanyl]; [6278; O; 5-Indanyl; H; Me; O; 4-Cl-Ph; 4-F-Ph]; [6279; O; 5-Indanyl; H; Me; O; 4-Cl-Ph; 4-Cl-Ph]; [6280; O; 5-Indanyl; H; Me; O; 4-Cl-Ph; 4-Me-Ph]; [6281; O; 5-Indanyl; H; Me; O; 4-Cl-Ph; 4-Ph-Ph]; [6282; O; 5-Indanyl; H; Me; O; 4-Cl-Ph; 2-Naphthyl]; [6283; O; 5-Benzodioxolyl; H; Me; O; 4-Cl-Ph; 4-F-Ph]; [6284; O; 5-Benzodioxolyl; H; Me; O; 4-Cl-Ph; 4-Cl-Ph]; [6285; O; 5-Benzodioxolyl; H; Me; O; 4-Cl-Ph; 3,4-Me₂-Ph]; [6286; O; 4-F-Ph; H; Me; O; 4-Me-Ph; 3,4-Me₂-Ph]; [6287; O; 4-F-Ph; H; Me; O; 4-Me-Ph; 5-Indanyl]; [6288; O; 4-Cl-Ph; H; Me; O; 4-Me-Ph; 4-F-Ph]; [6289; O; 4-Cl-Ph; H; Me; O; 4-Me-Ph; 4-Cl-Ph]; [6290; O; 4-Cl-Ph; H; Me; O; 4-Me-Ph; 4-Me-Ph]; [6291; O; 4-Cl-Ph; H; Me; O; 4-Me-Ph; 4-Ph-Ph]; [6292; O; 4-Cl-Ph; H; Me; O; 4-Me-Ph; 3,4-Me₂-Ph]; [6293; O; 4-Cl-Ph; H; Me; O; 4-Me-Ph; 2-Naphthyl]; [6294; O; 4-Cl-Ph; H; Me; O; 4-Me-Ph; 5-Indanyl]; [6295; O; 4-Me-Ph; H; Me; O; 4-Me-Ph; 3,4-Me₂-Ph]; [6296; O; 4-Me-Ph; H; Me; O; 4-Me-Ph; 5-Indanyl]; [6297; O; 5-Indanyl; H; Me; O; 4-Me-Ph; 4-F-Ph]; [6298; O; 5-Indanyl; H; Me; O;

4-Me-Ph; 4-Cl-Ph]; [6299; O; 5-Indanyl; H; Me; O; 4-Me-Ph; 4-Me-Ph]; [6300; O; 5-Indanyl; H; Me; O; 4-Me-Ph; 4-Ph-Ph]; [6301; O; 5-Indanyl; H; Me; O; 4-Me-Ph; 2-Naphthyl]; [6302; O; 5-Benzodioxolyl; H; Me; O; 4-Me-Ph; 3,4-Me$_2$-Ph]; [6303; O; 5-Benzodioxolyl; H; Me; O; 4-Me-Ph; 5-Indanyl]; [6304; O; 4-F-Ph; H; Me; O; 2-Naphthyl; 4-Me-Ph]; [6305; O; 4-F-Ph; H; Me; O; 2-Naphthyl; 2-Naphthyl]; [6306; O; 4-Cl-Ph; H; Me; O; 2-Naphthyl; 4-F-Ph]; [6307; O; 4-Cl-Ph; H; Me; O; 2-Naphthyl; 4-Cl-Ph]; [6308; O; 4-Cl-Ph; H; Me; O; 2-Naphthyl; 4-Me-Ph]; [6309; O; 4-Cl-Ph; H; Me; O; 2-Naphthyl; 4-Ph-Ph]; [6310; O; 4-Cl-Ph; H; Me; O; 2-Naphthyl; 2-Naphthyl]; [6311; O; 4-Me-Ph; H; Me; O; 2-Naphthyl; 4-F-Ph]; [6312; O; 4-Me-Ph; H; Me; O; 2-Naphthyl; 4-Cl-Ph]; [6313; O; 2-Naphthyl; H; Me; O; 2-Naphthyl; 4-Me-Ph]; [6314; O; 2-Naphthyl; H; Me; O; 2-Naphthyl; 4-Ph-Ph]; [6315; O; 2-Naphthyl; H; Me; O; 2-Naphthyl; 2-Naphthyl]; [6316; O; 5-Indanyl; H; Me; O; 2-Naphthyl; 4-F-Ph]; [6317; O; 5-Indanyl; H; Me; O; 2-Naphthyl; 4-Cl-Ph]; [6318; O; 5-Indanyl; H; Me; O; 2-Naphthyl; 4-Me-Ph]; [6319; O; 5-Indanyl; H; Me; O; 2-Naphthyl; 4-Ph-Ph]; [6320; O; 5-Indanyl; H; Me; O; 2-Naphthyl; 2-Naphthyl]; [6321; O; 5-Benzodioxolyl; H; Me; O; 2-Naphthyl; 4-F-Ph]; [6322; O; 5-Benzodioxolyl; H; Me; O; 2-Naphthyl; 4-Cl-Ph]; [6323; O; 4-F-Ph; H; Me; O; 5-Indanyl; 4-F-Ph]; [6324; O; 4-F-Ph; H; Me; O; 5-Indanyl; 4-Cl-Ph]; [6325; O; 4-F-Ph; H; Me; O; 5-Indanyl; 4-Me-Ph]; [6326; O; 4-F-Ph; H; Me; O; 5-Indanyl; 4-Ph-Ph]; [6327; O; 4-F-Ph; H; Me; O; 5-Indanyl; 2-Naphthyl]; [6328; O; 4-Cl-Ph; H; Me; O; 5-Indanyl; 4-F-Ph]; [6329; O; 4-Cl-Ph; H; Me; O; 5-Indanyl; 4-Cl-Ph]; [6330; O; 4-Cl-Ph; H; Me; O; 5-Indanyl; 4-Me-Ph]; [6331; O; 4-Cl-Ph; H; Me; O; 5-Indanyl; 4-Ph-Ph]; [6332; O; 4-Cl-Ph; H; Me; O; 5-Indanyl; 2-Naphthyl]; [6333; O; 4-Me-Ph; H; Me; O; 5-Indanyl; 4-F-Ph]; [6334; O; 4-Me-Ph; H; Me; O; 5-Indanyl; 4-Cl-Ph]; [6335; O; 4-Me-Ph; H; Me; O; 5-Indanyl; 4-Me-Ph]; [6336; O; 4-Me-Ph; H; Me; O; 5-Indanyl; 4-Ph-Ph]; [6337; O; 4-Me-Ph; H; Me; O; 5-Indanyl; 2-Naphthyl]; [6338; O; 4-F-Ph; H; Et; O; Cyclohexyl; 4-F-Ph]; [6339; O; 4-F-Ph; H; Et; O; Cyclohexyl; 4-Cl-Ph]; [6340; O; 4-F-Ph; H; Et; O; Cyclohexyl; 4-Me-Ph]; [6341; O; 4-F-Ph; H; Et; O; Cyclohexyl; 3,4-Me$_2$-Ph]; [6342; O; 4-F-Ph; H; Et; O; Cyclohexyl; 5-Indanyl]; [6343; O; 4-Cl-Ph; H; Et; O; Cyclohexyl; 4-F-Ph]; [6344; O; 4-Cl-Ph; H; Et; O; Cyclohexyl; 4-Cl-Ph]; [6345; O; 4-Cl-Ph; H; Et; O; Cyclohexyl; 4-Me-Ph]; [6346; O; 4-Cl-Ph; H; Et; O; Cyclohexyl; 3,4-Me$_2$-Ph]; [6347; O; 4-Cl-Ph; H; Et; O; Cyclohexyl; 5-Indanyl]; [6348; O; 4-Me-Ph; H; Et; O; Cyclohexyl; 4-F-Ph]; [6349; O; 4-Me-Ph; H; Et; O; Cyclohexyl; 4-Cl-Ph]; [6350; O; 4-Me-Ph; H; Et; O; Cyclohexyl; 4-Me-Ph]; [6351; O; 4-Me-Ph; H; Et; O; Cyclohexyl; 3,4-Me$_2$-Ph]; [6352; O; 4-Me-Ph; H; Et; O; Cyclohexyl; 5-Indanyl]; [6353; O; 5-Benzodioxolyl; H; Et; O; Cyclohexyl; 4-F-Ph]; [6354; O; 5-Benzodioxolyl; H; Et; O; Cyclohexyl; 4-Cl-Ph]; [6355; O; 5-Benzodioxolyl; H; Et; O; Cyclohexyl; 4-Me-Ph]; [6356; O; 5-Benzodioxolyl; H; Et; O; Cyclohexyl; 3,4-Me$_2$-Ph]; [6357; O; 5-Benzodioxolyl; H; Et; O; Cyclohexyl; 5-Indanyl]; [6358; O; 4-F-Ph; H; Et; O; Cyclohexylmethyl; 4-F-Ph]; [6359; O; 4-F-Ph; H; Et; O; Cyclohexylmethyl; 4-Cl-Ph]; [6360; O; 4-F-Ph; H; Et; O; Cyclohexylmethyl; 4-Me-Ph]; [6361; O; 4-F-Ph; H; Et; O; Cyclohexylmethyl; 3,4-Me$_2$-Ph]; [6362; O; 4-F-Ph; H; Et; O; Cyclohexylmethyl; 5-Indanyl]; [6363; O; 4-Cl-Ph; H; Et; O; Cyclohexylmethyl; 4-F-Ph]; [6364; O; 4-Cl-Ph; H; Et; O; Cyclohexylmethyl; 4-Cl-Ph]; [6365; O; 4-Cl-Ph; H; Et; O; Cyclohexylmethyl; 4-Me-Ph]; [6366; O; 4-Cl-Ph; H; Et; O; Cyclohexylmethyl; 3,4-Me$_2$-Ph]; [6367; O; 4-Cl-Ph; H; Et; O; Cyclohexylmethyl; 5-Indanyl]; [6368; O; 4-Me-Ph; H; Et; O; Cyclohexylmethyl; 4-F-Ph]; [6369; O; 4-Me-Ph; H; Et; O; Cyclohexylmethyl; 4-Cl-Ph]; [6370; O; 4-Me-Ph; H; Et; O; Cyclohexylmethyl; 4-Me-Ph]; [6371; O; 4-Me-Ph; H; Et; O; Cyclohexylmethyl; 3,4-Me$_2$-Ph]; [6372; O; 4-Me-Ph; H; Et; O; Cyclohexylmethyl; 5-Indanyl]; [6373; O; 5-Benzodioxolyl; H; Et; O; Cyclohexylmethyl; 4-F-Ph]; [6374; O; 5-Benzodioxolyl; H; Et; O; Cyclohexylmethyl; 4-Cl-Ph]; [6375; O; 5-Benzodioxolyl; H; Et; O; Cyclohexylmethyl; 4-Me-Ph]; [6376; O; 5-Benzodioxolyl; H; Et; O; Cyclohexylmethyl; 3,4-Me$_2$-Ph]; [6377; O; 5-Benzodioxolyl; H; Et; O; Cyclohexylmethyl; 5-Indanyl]; [6378; O; 4-F-Ph; H; Et; O; 4-F-Ph; 4-F-Ph]; [6379; O; 4-F-Ph; H; Et; O; 4-F-Ph; 4-Cl-Ph]; [6380; O; 4-F-Ph; H; Et; O; 4-F-Ph; 4-Me-Ph]; [6381; O; 4-F-Ph; H; Et; O; 4-F-Ph; 3,4-Me$_2$-Ph]; [6382; O; 4-F-Ph; H; Et; O; 4-F-Ph; 5-Indanyl]; [6383; O; 4-Cl-Ph; H; Et; O; 4-F-Ph; 4-F-Ph]; [6384; O; 4-Cl-Ph; H; Et; O; 4-F-Ph; 4-Cl-Ph]; [6385; O; 4-Cl-Ph; H; Et; O; 4-F-Ph; 4-Me-Ph]; [6386; O; 4-Cl-Ph; H; Et; O; 4-F-Ph; 3,4-Me$_2$-Ph]; [6387; O; 4-Cl-Ph; H; Et; O; 4-F-Ph; 5-Indanyl]; [6388; O; 4-Me-Ph; H; Et; O; 4-F-Ph; 4-F-Ph]; [6389; O; 4-Me-Ph; H; Et; O; 4-F-Ph; 4-Cl-Ph]; [6390; O; 4-Me-Ph; H; Et; O; 4-F-Ph; 4-Me-Ph]; [6391; O; 4-Me-Ph; H; Et; O; 4-F-Ph; 3,4-Me$_2$-Ph]; [6392; O; 4-Me-Ph; H; Et; O; 4-F-Ph; 5-Indanyl]; [6393; O; 5-Benzodioxolyl; H; Et; O; 4-F-Ph; 4-F-Ph]; [6394; O; 5-Benzodioxolyl; H; Et; O; 4-F-Ph; 4-Cl-Ph]; [6395; O; 5-Benzodioxolyl; H; Et; O; 4-F-Ph; 4-Me-Ph]; [6396; O; 5-Benzodioxolyl; H; Et; O; 4-F-Ph; 3,4-Me$_2$-Ph]; [6397; O; 5-Benzodioxolyl; H; Et; O; 4-F-Ph; 5-Indanyl]; [6398; O; 4-F-Ph; H; Et; O; 4-Cl-Ph; 4-F-Ph]; [6399; O; 4-F-Ph; H; Et; O; 4-Cl-Ph; 4-Cl-Ph]; [6400; O; 4-F-Ph; H; Et; O; 4-Cl-Ph; 4-Me-Ph]; [6401; O; 4-F-Ph; H; Et; O; 4-Cl-Ph; 3,4-Me$_2$-Ph]; [6402; O; 4-F-Ph; H; Et; O; 4-Cl-Ph; 5-Indanyl]; [6403; O; 4-Cl-Ph; H; Et; O; 4-Cl-Ph; 4-F-Ph]; [6404; O; 4-Cl-Ph; H; Et; O; 4-Cl-Ph; 4-Cl-Ph]; [6405; O; 4-Cl-Ph; H; Et; O; 4-Cl-Ph; 4-Me-Ph]; [6406; O; 4-Cl-Ph; H; Et; O; 4-Cl-Ph; 3,4-Me$_2$-Ph]; [6407; O; 4-Cl-Ph; H; Et; O; 4-Cl-Ph; 5-Indanyl]; [6408; O; 4-Me-Ph; H; Et; O; 4-Cl-Ph; 4-F-Ph]; [6409; O; 4-Me-Ph; H; Et; O; 4-Cl-Ph; 4-Cl-Ph]; [6410; O; 4-Me-Ph; H; Et; O; 4-Cl-Ph; 4-Me-Ph]; [6411; O; 4-Me-Ph; H; Et; O; 4-Cl-Ph; 3,4-Me$_2$-Ph]; [6412; O; 4-Me-Ph; H; Et; O; 4-Cl-Ph; 5-Indanyl]; [6413; O; 5-Benzodioxolyl; H; Et; O; 4-Cl-Ph; 4-F-Ph]; [6414; O; 5-Benzodioxolyl; H; Et; O; 4-Cl-Ph; 4-Cl-Ph]; [6415; O; 5-Benzodioxolyl; H; Et; O; 4-Cl-Ph; 4-Me-Ph]; [6416; O; 5-Benzodioxolyl; H; Et; O; 4-Cl-Ph; 3,4-Me$_2$-Ph]; [6417; O; 5-Benzodioxolyl; H; Et; O; 4-Cl-Ph; 5-Indanyl]; [6418; O; 4-F-Ph; H; Et; O; 4-Me-Ph; 4-F-Ph]; [6419; O; 4-F-Ph; H; Et; O; 4-Me-Ph; 4-Cl-Ph]; [6420; O; 4-F-Ph; H; Et; O; 4-Me-Ph; 4-Me-Ph]; [6421; O; 4-F-Ph; H; Et; O; 4-Me-Ph; 3,4-Me$_2$-Ph]; [6422; O; 4-F-Ph; H; Et; O; 4-Me-Ph; 5-Indanyl]; [6423; O; 4-Cl-Ph; H; Et; O; 4-Me-Ph; 4-F-Ph]; [6424; O; 4-Cl-Ph; H; Et; O; 4-Me-Ph; 4-Cl-Ph]; [6425; O; 4-Cl-Ph; H; Et; O; 4-Me-Ph; 4-Me-Ph]; [6426; O; 4-Cl-Ph; H; Et; O; 4-Me-Ph; 3,4-Me$_2$-Ph]; [6427; O; 4-Cl-Ph; H; Et; O; 4-Me-Ph; 5-Indanyl]; [6428; O; 4-Me-Ph; H; Et; O; 4-Me-Ph; 4-F-Ph]; [6429; O; 4-Me-Ph; H; Et; O; 4-Me-Ph; 4-Cl-Ph]; [6430; O; 4-Me-Ph; H; Et; O; 4-Me-Ph; 4-Me-Ph]; [6431; O; 4-Me-Ph; H; Et; O; 4-Me-Ph; 3,4-Me$_2$-Ph]; [6432; O; 4-Me-Ph; H; Et; O; 4-Me-Ph; 5-Indanyl]; [6433; O; 5-Benzodioxolyl; H; Et; O; 4-Me-Ph; 4-F-Ph]; [6434; O; 5-Benzodioxolyl; H; Et; O; 4-Me-Ph; 4-Cl-Ph]; [6435; O; 5-Benzodioxolyl; H; Et; O; 4-Me-Ph; 4-Me-Ph]; [6436; O; 5-Benzodioxolyl; H; Et; O; 4-Me-Ph; 3,4-Me$_2$-Ph]; [6437; O; 5-Benzodioxolyl; H; Et; O; 4-Me-Ph; 5-Indanyl]; [6438; O; 4-F-Ph; H; Pr; O; Cyclohexyl; 4-F-Ph]; [6439; O; 4-F-Ph; H; Pr; O; Cyclohexyl; 4-Cl-Ph]; [6440; O; 4-F-Ph; H; Pr; O; Cyclohexyl; 4-Me-Ph]; [6441; O; 4-F-Ph; H; Pr; O; Cyclohexyl; 3,4-Me$_2$-Ph]; [6442; O; 4-F-Ph; H; Pr; O; Cyclohexyl; 5-Indanyl]; [6443; O; 4-Cl-Ph; H; Pr; O; Cyclohexyl; 4-F-Ph]; [6444; O; 4-Cl-Ph; H; Pr; O; Cyclohexyl; 4-Cl-Ph]; [6445; O; 4-Cl-Ph; H; Pr; O; Cyclohexyl; 4-Me-Ph]; [6446; O; 4-Cl-Ph; H; Pr; O; Cyclohexyl; 3,4-Me₂-Ph]; [6447; O; 4-Cl-Ph; H; Pr; O; Cyclohexyl; 5-Indanyl]; [6448; O; 4-Me-Ph; H; Pr; O; Cyclohexyl; 4-F-Ph]; [6449; O; 4-Me-Ph; H; Pr; O; Cyclohexyl; 4-Cl-Ph]; [6450; O; 4-Me-Ph; H; Pr; O; Cyclohexyl; 4-Me-Ph]; [6451; O; 4-Me-Ph; H; Pr; O; Cyclohexyl; 3,4-Me₂-Ph]; [6452; O; 4-Me-Ph; H; Pr; O; Cyclohexyl; 5-Indanyl]; [6453; O; 5-Benzodioxolyl; H; Pr; O; Cyclohexyl; 4-F-Ph]; [6454; O; 5-Benzodioxolyl; H; Pr; O; Cyclohexyl; 4-Cl-Ph]; [6455; O; 5-Benzodioxolyl; H; Pr; O; Cyclohexyl; 4-Me-Ph]; [6456; O; 5-Benzodioxolyl; H; Pr; O; Cyclohexyl; 3,4-Me₂-Ph]; [6457; O; 5-Benzodioxolyl; H; Pr; O; Cyclohexyl; 5-Indanyl]; [6458; O; 4-F-Ph; H; Pr; O; Cyclohexylmethyl; 4-F-Ph]; [6459; O; 4-F-Ph; H; Pr; O; Cyclohexylmethyl; 4-Cl-Ph]; [6460; O; 4-F-Ph; H; Pr; O; Cyclohexylmethyl; 4-Me-Ph]; [6461; O; 4-F-Ph; H; Pr; O; Cyclohexylmethyl; 3,4-Me₂-Ph]; [6462; O; 4-F-Ph; H; Pr; O; Cyclohexylmethyl; 5-Indanyl]; [6463; O; 4-Cl-Ph; H; Pr; O; Cyclohexylmethyl; 4-F-Ph]; [6464; O; 4-Cl-Ph; H; Pr; O; Cyclohexylmethyl; 4-Cl-Ph]; [6465; O; 4-Cl-Ph; H; Pr; O; Cyclohexylmethyl; 4-Me-Ph]; [6466; O; 4-Cl-Ph; H; Pr; O; Cyclohexylmethyl; 3,4-Me₂-Ph]; [6467; O; 4-Cl-Ph; H; Pr; O; Cyclohexylmethyl; 5-Indanyl]; [6468; O; 4-Me-Ph; H; Pr; O; Cyclohexylmethyl; 4-F-Ph]; [6469; O; 4-Me-Ph; H; Pr; O; Cyclohexylmethyl; 4-Cl-Ph]; [6470; O; 4-Me-Ph; H; Pr; O; Cyclohexylmethyl; 4-Me-Ph]; [6471; O; 4-Me-Ph; H; Pr; O; Cyclohexylmethyl; 3,4-Me₂-Ph]; [6472; O; 4-Me-Ph; H; Pr; O; Cyclohexylmethyl; 5-Indanyl]; [6473; O; 5-Benzodioxolyl; H; Pr; O; Cyclohexylmethyl; 4-F-Ph]; [6474; O; 5-Benzodioxolyl; H; Pr; O; Cyclohexylmethyl; 4-Cl-Ph]; [6475; O; 5-Benzodioxolyl; H; Pr; O; Cyclohexylmethyl; 4-Me-Ph]; [6476; O; 5-Benzodioxolyl; H; Pr; O; Cyclohexylmethyl; 3,4-Me₂-Ph]; [6477; O; 5-Benzodioxolyl; H; Pr; O; Cyclohexylmethyl; 5-Indanyl]; [6478; O; 4-F-Ph; H; Pr; O; 4-F-Ph; 4-F-Ph]; [6479; O; 4-F-Ph; H; Pr; O; 4-F-Ph; 4-Cl-Ph]; [6480; O; 4-F-Ph; H; Pr; O; 4-F-Ph; 4-Me-Ph]; [6481; O; 4-F-Ph; H; Pr; O; 4-F-Ph; 3,4-Me₂-Ph]; [6482; O; 4-F-Ph; H; Pr; O; 4-F-Ph; 5-Indanyl]; [6483; O; 4-Cl-Ph; H; Pr; O; 4-F-Ph; 4-F-Ph]; [6484; O; 4-Cl-Ph; H; Pr; O; 4-F-Ph; 4-Cl-Ph]; [6485; O; 4-Cl-Ph; H; Pr; O; 4-F-Ph; 4-Me-Ph]; [6486; O; 4-Cl-Ph; H; Pr; O; 4-F-Ph; 3,4-Me₂-Ph]; [6487; O; 4-Cl-Ph; H; Pr; O; 4-F-Ph; 5-Indanyl]; [6488; O; 4-Me-Ph; H; Pr; O; 4-F-Ph; 4-F-Ph]; [6489; O; 4-Me-Ph; H; Pr; O; 4-F-Ph; 4-Cl-Ph]; [6490; O; 4-Me-Ph; H; Pr; O; 4-F-Ph; 4-Me-Ph]; [6491; O; 4-Me-Ph; H; Pr; O; 4-F-Ph; 3,4-Me₂-Ph]; [6492; O; 4-Me-Ph; H; Pr; O; 4-F-Ph; 5-Indanyl]; [6493; O; 5-Benzodioxolyl; H; Pr; O; 4-F-Ph; 4-F-Ph]; [6494; O; 5-Benzodioxolyl; H; Pr; O; 4-F-Ph; 4-Cl-Ph]; [6495; O; 5-Benzodioxolyl; H; Pr; O; 4-F-Ph; 4-Me-Ph]; [6496; O; 5-Benzodioxolyl; H; Pr; O; 4-F-Ph; 3,4-Me₂-Ph]; [6497; O; 5-Benzodioxolyl; H; Pr; O; 4-F-Ph; 5-Indanyl]; [6498; O; 4-F-Ph; H; Pr; O; 4-Cl-Ph; 4-F-Ph]; [6499; O; 4-F-Ph; H; Pr; O; 4-Cl-Ph; 4-Cl-Ph]; [6500; O; 4-F-Ph; H; Pr; O; 4-Cl-Ph; 4-Me-Ph]; [6501; O; 4-F-Ph; H; Pr; O; 4-Cl-Ph; 3,4-Me₂-Ph]; [6502; O; 4-F-Ph; H; Pr; O; 4-Cl-Ph; 5-Indanyl]; [6503; O; 4-Cl-Ph; H; Pr; O; 4-Cl-Ph; 4-F-Ph]; [6504; O; 4-Cl-Ph; H; Pr; O; 4-Cl-Ph; 4-Cl-Ph]; [6505; O; 4-Cl-Ph; H; Pr; O; 4-Cl-Ph; 4-Me-Ph]; [6506; O; 4-Cl-Ph; H; Pr; O; 4-Cl-Ph; 3,4-Me₂-Ph]; [6507; O; 4-F-Ph; H; Pr; O; 4-Cl-Ph; 5-Indanyl]; [6508; O; 4-Me-Ph; H; Pr; O; 4-Cl-Ph; 4-F-Ph]; [6509; O; 4-Me-Ph; H; Pr; O; 4-Cl-Ph; 4-Cl-Ph]; [6510; O; 4-Me-Ph; H; Pr; O; 4-Cl-Ph; 4-Me-Ph]; [6511; O; 4-Me-Ph; H; Pr; O; 4-Cl-Ph; 3,4-Me₂-Ph]; [6512; O; 4-Me-Ph; H; Pr; O; 4-Cl-Ph; 5-Indanyl]; [6513; O; 5-Benzodioxolyl; H; Pr; O; 4-Cl-Ph; 4-F-Ph]; [6514; O; 5-Benzodioxolyl; H; Pr; O; 4-Cl-Ph; 4-Cl-Ph]; [6515; O; 5-Benzodioxolyl; H; Pr; O; 4-Cl-Ph; 4-Me-Ph]; [6516; O; 5-Benzodioxolyl; H; Pr; O; 4-Cl-Ph; 3,4-Me₂-Ph]; [6517; O; 5-Benzodioxolyl; H; Pr; O; 4-Cl-Ph; 5-Indanyl]; [6518; O; 4-F-Ph; H; Pr; O; 4-Me-Ph; 4-F-Ph]; [6519; O; 4-F-Ph; H; Pr; O; 4-Me-Ph; 4-Cl-Ph]; [6520; O; 4-F-Ph; H; Pr; O; 4-Me-Ph; 4-Me-Ph]; [6521; O; 4-F-Ph; H; Pr; O; 4-Me-Ph; 3,4-Me₂-Ph]; [6522; O; 4-F-Ph; H; Pr; O; 4-Me-Ph; 5-Indanyl]; [6523; O; 4-Cl-Ph; H; Pr; O; 4-Me-Ph; 4-F-Ph]; [6524; O; 4-Cl-Ph; H; Pr; O; 4-Me-Ph; 4-Cl-Ph]; [6525; O; 4-Cl-Ph; H; Pr; O; 4-Me-Ph; 4-Me-Ph]; [6526; O; 4-Cl-Ph; H; Pr; O; 4-Me-Ph; 3,4-Me₂-Ph]; [6527; O; 4-Cl-Ph; H; Pr; O; 4-Me-Ph; 5-Indanyl]; [6528; O; 4-Me-Ph; H; Pr; O; 4-Me-Ph; 4-F-Ph]; [6529; O; 4-Me-Ph; H; Pr; O; 4-Me-Ph; 4-Cl-Ph]; [6530; O; 4-Me-Ph; H; Pr; O; 4-Me-Ph; 4-Me-Ph]; [6531; O; 4-Me-Ph; H; Pr; O; 4-Me-Ph; 3,4-Me₂-Ph]; [6532; O; 4-Me-Ph; H; Pr; O; 4-Me-Ph; 5-Indanyl]; [6533; O; 5-Benzodioxolyl; H; Pr; O; 4-Me-Ph; 4-F-Ph]; [6534; O; 5-Benzodioxolyl; H; Pr; O; 4-Me-Ph; 4-Cl-Ph]; [6535; O; 5-Benzodioxolyl; H; Pr; O; 4-Me-Ph; 4-Me-Ph]; [6536; O; 5-Benzodioxolyl; H; Pr; O; 4-Me-Ph; 3,4-Me₂-Ph]; [6537; O; 5-Benzodioxolyl; H; Pr; O; 4-Me-Ph; 5-Indanyl]; [6538; O; 4-F-Ph; H; Ph; O; Cyclohexyl; 4-F-Ph]; [6539; O; 4-F-Ph; H; Ph; O; Cyclohexyl; 4-Cl-Ph]; [6540; O; 4-F-Ph; H; Ph; O; Cyclohexyl; 4-Me-Ph]; [6541; O; 4-F-Ph; H; Ph; O; Cyclohexyl; 3,4-Me₂-Ph]; [6542; O; 4-F-Ph; H; Ph; O; Cyclohexyl; 5-Indanyl]; [6543; O; 4-Cl-Ph; H; Ph; O; Cyclohexyl; 4-F-Ph]; [6544; O; 4-Cl-Ph; H; Ph; O; Cyclohexyl; 4-Cl-Ph]; [6545; O; 4-Cl-Ph; H; Ph; O; Cyclohexyl; 4-Me-Ph]; [6546; O; 4-Cl-Ph; H; Ph; O; Cyclohexyl; 3,4-Me₂-Ph]; [6547; O; 4-Cl-Ph; H; Ph; O; Cyclohexyl; 5-Indanyl]; [6548; O; 4-Me-Ph; H; Ph; O; Cyclohexyl; 4-F-Ph]; [6549; O; 4-Me-Ph; H; Ph; O; Cyclohexyl; 4-Cl-Ph]; [6550; O; 4-Me-Ph; H; Ph; O; Cyclohexyl; 4-Me-Ph]; [6551; O; 4-Me-Ph; H; Ph; O; Cyclohexyl; 3,4-Me₂-Ph]; [6552; O; 4-Me-Ph; H; Ph; O; Cyclohexyl; 5-Indanyl]; [6553; O; 5-Benzodioxolyl; H; Ph; O; Cyclohexyl; 4-F-Ph]; [6554; O; 5-Benzodioxolyl; H; Ph; O; Cyclohexyl; 4-Cl-Ph]; [6555; O; 5-Benzodioxolyl; H; Ph; O; Cyclohexyl; 4-Me-Ph]; [6556; O; 5-Benzodioxolyl; H; Ph; O; Cyclohexyl; 3,4-Me₂-Ph]; [6557; O; 5-Benzodioxolyl; H; Ph; O; Cyclohexyl; 5-Indanyl]; [6558; O; 4-F-Ph; H; Ph; O; Cyclohexylmethyl; 4-F-Ph]; [6559; O; 4-F-Ph; H; Ph; O; Cyclohexylmethyl; 4-Cl-Ph]; [6560; O; 4-F-Ph; H; Ph; O; Cyclohexylmethyl; 4-Me-Ph]; [6561; O; 4-F-Ph; H; Ph; O; Cyclohexylmethyl; 3,4-Me₂-Ph]; [6562; O; 4-F-Ph; H; Ph; O; Cyclohexylmethyl; 5-Indanyl]; [6563; O; 4-Cl-Ph; H; Ph; O; Cyclohexylmethyl; 4-F-Ph]; [6564; O; 4-Cl-Ph; H; Ph; O; Cyclohexylmethyl; 4-Cl-Ph]; [6565; O; 4-Cl-Ph; H; Ph; O; Cyclohexylmethyl; 4-Me-Ph]; [6566; O; 4-Cl-Ph; H; Ph; O; Cyclohexylmethyl; 3,4-Me₂-Ph]; [6567; O; 4-Cl-Ph; H; Ph; O; Cyclohexylmethyl; 5-Indanyl]; [6568; O; 4-Me-Ph; H; Ph; O; Cyclohexylmethyl; 4-F-Ph]; [6569; O; 4-Me-Ph; H; Ph; O; Cyclohexylmethyl; 4-Cl-Ph]; [6570; O; 4-Me-Ph; H; Ph; O; Cyclohexylmethyl; 4-Me-Ph]; [6571; O; 4-Me-Ph; H; Ph; O; Cyclohexylmethyl; 3,4-Me₂-Ph]; [6572; O; 4-Me-Ph; H; Ph; O; Cyclohexylmethyl; 5-Indanyl]; [6573; O; 5-Benzodioxolyl; H; Ph; O; Cyclohexylmethyl; 4-F-Ph]; [6574; O; 5-Benzodioxolyl; H; Ph; O; Cyclohexylmethyl; 4-Cl-Ph]; [6575; O; 5-Benzodioxolyl; H; Ph; O; Cyclohexylmethyl; 4-Me-Ph]; [6576; O; 5-Benzodioxolyl; H; Ph; O; Cyclohexylmethyl; 3,4-Me₂-Ph]; [6577; O; 5-Benzodioxolyl; H; Ph; O; Cyclohexylmethyl; 5-Indanyl]; [6578; O; 4-F-Ph; H; Ph; O; 4-F-Ph; 4-F-Ph]; [6579; O; 4-F-Ph; H; Ph; O; 4-F-Ph; 4-Cl-Ph]; [6580; O; 4-F-Ph; H; Ph; O; 4-F-Ph; 4-Me-Ph]; [6581; O; 4-F-Ph; H; Ph; O; 4-F-Ph; 3,4-Me₂-Ph]; [6582; O; 4-F-Ph; H; Ph; O; 4-F-Ph; 5-Indanyl]; [6583; O; 4-Cl-Ph; H; Ph; O; 4-F-Ph; 4-F-Ph]; [6584; O; 4-Cl-Ph; H; Ph; O; 4-F-Ph; 4-Cl-Ph]; [6585; O; 4-Cl-Ph; H; Ph; O; 4-F-Ph; 4-Me-Ph]; [6586; O; 4-Cl-Ph; H; Ph; O; 4-F-Ph; 3,4-Me₂-Ph]; [6587; O; 4-Cl-Ph; H; Ph; O; 4-F-Ph; 5-Indanyl]; [6588; O; 4-Me-Ph; H; Ph;

O; 4-F-Ph; 4-F-Ph]; [6589; O; 4-Me-Ph; H; Ph; O; 4-F-Ph; 4-Cl-Ph]; [6590; O; 4-Me-Ph; H; Ph; O; 4-F-Ph; 4-Me-Ph]; [6591; O; 4-Me-Ph; H; Ph; O; 4-F-Ph; 3,4-Me$_2$-Ph]; [6592; O; 4-Me-Ph; H; Ph; O; 4-F-Ph; 5-Indanyl]; [6593; O; 5-Benzodioxolyl; H; Ph; O; 4-F-Ph; 4-F-Ph]; [6594; O; 5-Benzodioxolyl; H; Ph; O; 4-F-Ph; 4-Cl-Ph]; [6595; O; 5-Benzodioxolyl; H; Ph; O; 4-F-Ph; 4-Me-Ph]; [6596; O; 5-Benzodioxolyl; H; Ph; O; 4-F-Ph; 3,4-Me$_2$-Ph]; [6597; O; 5-Benzodioxolyl; H; Ph; O; 4-F-Ph; 5-Indanyl]; [6598; O; 4-F-Ph; H; Ph; O; 4-Cl-Ph; 4-F-Ph]; [6599; O; 4-F-Ph; H; Ph; O; 4-Cl-Ph; 4-Cl-Ph]; [6600; O; 4-F-Ph; H; Ph; O; 4-Cl-Ph; 4-Me-Ph]; [6601; O; 4-F-Ph; H; Ph; O; 4-Cl-Ph; 3,4-Me$_2$-Ph]; [6602; O; 4-F-Ph; H; Ph; O; 4-Cl-Ph; 5-Indanyl]; [6603; O; 4-Cl-Ph; H; Ph; O; 4-Cl-Ph; 4-F-Ph]; [6604; O; 4-Cl-Ph; H; Ph; O; 4-Cl-Ph; 4-Cl-Ph]; [6605; O; 4-Cl-Ph; H; Ph; O; 4-Cl-Ph; 4-Me-Ph]; [6606; O; 4-Cl-Ph; H; Ph; O; 4-Cl-Ph; 3,4-Me$_2$-Ph]; [6607; O; 4-F-Ph; H; Ph; O; 4-Cl-Ph; 5-Indanyl]; [6608; O; 4-Me-Ph; H; Ph; O; 4-Cl-Ph; 4-F-Ph]; [6609; O; 4-Me-Ph; H; Ph; O; 4-Cl-Ph; 4-Cl-Ph]; [6610; O; 4-Me-Ph; H; Ph; O; 4-Cl-Ph; 4-Me-Ph]; [6611; O; 4-Me-Ph; H; Ph; O; 4-Cl-Ph; 3,4-Me$_2$-Ph]; [6612; O; 4-Me-Ph; H; Ph; O; 4-Cl-Ph; 5-Indanyl]; [6613; O; 5-Benzodioxolyl; H; Ph; O; 4-Cl-Ph; 4-F-Ph]; [6614; O; 5-Benzodioxolyl; H; Ph; O; 4-Cl-Ph; 4-Cl-Ph]; [6615; O; 5-Benzodioxolyl; H; Ph; O; 4-Cl-Ph; 4-Me-Ph]; [6616; O; 5-Benzodioxolyl; H; Ph; O; 4-Cl-Ph; 3,4-Me$_2$-Ph]; [6617; O; 5-Benzodioxolyl; H; Ph; O; 4-Cl-Ph; 5-Indanyl]; [6618; O; 4-F-Ph; H; Ph; O; 4-Me-Ph; 4-F-Ph]; [6619; O; 4-F-Ph; H; Ph; O; 4-Me-Ph; 4-Cl-Ph]; [6620; O; 4-F-Ph; H; Ph; O; 4-Me-Ph; 4-Me-Ph]; [6621; O; 4-F-Ph; H; Ph; O; 4-Me-Ph; 3,4-Me$_2$-Ph]; [6622; O; 4-F-Ph; H; Ph; O; 4-Me-Ph; 5-Indanyl]; [6623; O; 4-Cl-Ph; H; Ph; O; 4-Me-Ph; 4-F-Ph]; [6624; O; 4-Cl-Ph; H; Ph; O; 4-Me-Ph; 4-Cl-Ph]; [6625; O; 4-Cl-Ph; H; Ph; O; 4-Me-Ph; 4-Me-Ph]; [6626; O; 4-Cl-Ph; H; Ph; O; 4-Me-Ph; 3,4-Me$_2$-Ph]; [6627; O; 4-Cl-Ph; H; Ph; O; 4-Me-Ph; 5-Indanyl]; [6628; O; 4-Me-Ph; H; Ph; O; 4-Me-Ph; 4-F-Ph]; [6629; O; 4-Me-Ph; H; Ph; O; 4-Me-Ph; 4-Cl-Ph]; [6630; O; 4-Me-Ph; H; Ph; O; 4-Me-Ph; 4-Me-Ph]; [6631; O; 4-Me-Ph; H; Ph; O; 4-Me-Ph; 3,4-Me$_2$-Ph]; [6632; O; 4-Me-Ph; H; Ph; O; 4-Me-Ph; 5-Indanyl]; [6633; O; 5-Benzodioxolyl; H; Ph; O; 4-Me-Ph; 4-F-Ph]; [6634; O; 5-Benzodioxolyl; H; Ph; O; 4-Me-Ph; 4-Cl-Ph]; [6635; O; 5-Benzodioxolyl; H; Ph; O; 4-Me-Ph; 4-Me-Ph]; [6636; O; 5-Benzodioxolyl; H; Ph; O; 4-Me-Ph; 3,4-Me$_2$-Ph]; [6637; O; 5-Benzodioxolyl; H; Ph; O; 4-Me-Ph; 5-Indanyl]; [6638; O; 4-F-Ph; H; SMe; O; Cyclohexyl; 4-F-Ph]; [6639; O; 4-F-Ph; H; SMe; O; Cyclohexyl; 4-Cl-Ph]; [6640; O; 4-F-Ph; H; SMe; O; Cyclohexyl; 4-Me-Ph]; [6641; O; 4-F-Ph; H; SMe; O; Cyclohexyl; 3,4-Me$_2$-Ph]; [6642; O; 4-F-Ph; H; SMe; O; Cyclohexyl; 5-Indanyl]; [6643; O; 4-Cl-Ph; H; SMe; O; Cyclohexyl; 4-F-Ph]; [6644; O; 4-Cl-Ph; H; SMe; O; Cyclohexyl; 4-Cl-Ph]; [6645; O; 4-Cl-Ph; H; SMe; O; Cyclohexyl; 4-Me-Ph]; [6646; O; 4-Cl-Ph; H; SMe; O; Cyclohexyl; 3,4-Me$_2$-Ph]; [6647; O; 4-Cl-Ph; H; SMe; O; Cyclohexyl; 5-Indanyl]; [6648; O; 4-Me-Ph; H; SMe; O; Cyclohexyl; 4-F-Ph]; [6649; O; 4-Me-Ph; H; SMe; O; Cyclohexyl; 4-Cl-Ph]; [6650; O; 4-Me-Ph; H; SMe; O; Cyclohexyl; 4-Me-Ph]; [6651; O; 4-Me-Ph; H; SMe; O; Cyclohexyl; 3,4-Me$_2$-Ph]; [6652; O; 4-Me-Ph; H; SMe; O; Cyclohexyl; 5-Indanyl]; [6653; O; 5-Benzodioxolyl; H; SMe; O; Cyclohexyl; 4-F-Ph]; [6654; O; 5-Benzodioxolyl; H; SMe; O; Cyclohexyl; 4-Cl-Ph]; [6655; O; 5-Benzodioxolyl; H; SMe; O; Cyclohexyl; 4-Me-Ph]; [6656; O; 5-Benzodioxolyl; H; SMe; O; Cyclohexyl; 3,4-Me$_2$-Ph]; [6657; O; 5-Benzodioxolyl; H; SMe; O; Cyclohexyl; 5-Indanyl]; [6658; O; 4-F-Ph; H; SMe; O; Cyclohexylmethyl; 4-F-Ph]; [6659; O; 4-F-Ph; H; SMe; O; Cyclohexylmethyl; 4-Cl-Ph]; [6660; O; 4-F-Ph; H; SMe; O; Cyclohexylmethyl; 4-Me-Ph]; [6661; O; 4-F-Ph; H; SMe; O; Cyclohexylmethyl; 3,4-Me$_2$-Ph]; [6662; O; 4-F-Ph; H; SMe; O; Cyclohexylmethyl; 5-Indanyl]; [6663; O; 4-Cl-Ph; H; SMe; O; Cyclohexylmethyl; 4-F-Ph]; [6664; O; 4-Cl-Ph; H; SMe; O; Cyclohexylmethyl; 4-Cl-Ph]; [6665; O; 4-Cl-Ph; H; SMe; O; Cyclohexylmethyl; 4-Me-Ph]; [6666; O; 4-Cl-Ph; H; SMe; O; Cyclohexylmethyl; 3,4-Me$_2$-Ph]; [6667; O; 4-Cl-Ph; H; SMe; O; Cyclohexylmethyl; 5-Indanyl]; [6668; O; 4-Me-Ph; H; SMe; O; Cyclohexylmethyl; 4-F-Ph]; [6669; O; 4-Me-Ph; H; SMe; O; Cyclohexylmethyl; 4-Cl-Ph]; [6670; O; 4-Me-Ph; H; SMe; O; Cyclohexylmethyl; 4-Me-Ph]; [6671; O; 4-Me-Ph; H; SMe; O; Cyclohexylmethyl; 3,4-Me$_2$-Ph]; [6672; O; 4-Me-Ph; H; SMe; O; Cyclohexylmethyl; 5-Indanyl]; [6673; O; 5-Benzodioxolyl; H; SMe; O; Cyclohexylmethyl; 4-F-Ph]; [6674; O; 5-Benzodioxolyl; H; SMe; O; Cyclohexylmethyl; 4-Cl-Ph]; [6675; O; 5-Benzodioxolyl; H; SMe; O; Cyclohexylmethyl; 4-Me-Ph]; [6676; O; 5-Benzodioxolyl; H; SMe; O; Cyclohexylmethyl; 3,4-Me$_2$-Ph]; [6677; O; 5-Benzodioxolyl; H; SMe; O; Cyclohexylmethyl; 5-Indanyl]; [6678; O; 4-F-Ph; H; SMe; O; 4-F-Ph; 4-F-Ph]; [6679; O; 4-F-Ph; H; SMe; O; 4-F-Ph; 4-Cl-Ph]; [6680; O; 4-F-Ph; H; SMe; O; 4-F-Ph; 4-Me-Ph]; [6681; O; 4-F-Ph; H; SMe; O; 4-F-Ph; 3,4-Me$_2$-Ph]; [6682; O; 4-F-Ph; H; SMe; O; 4-F-Ph; 5-Indanyl]; [6683; O; 4-Cl-Ph; H; SMe; O; 4-F-Ph; 4-F-Ph]; [6684; O; 4-Cl-Ph; H; SMe; O; 4-F-Ph; 4-Cl-Ph]; [6685; O; 4-Cl-Ph; H; SMe; O; 4-F-Ph; 4-Me-Ph]; [6686; O; 4-Cl-Ph; H; SMe; O; 4-F-Ph; 3,4-Me$_2$-Ph]; [6687; O; 4-Cl-Ph; H; SMe; O; 4-F-Ph; 5-Indanyl]; [6688; O; 4-Me-Ph; H; SMe; O; 4-F-Ph; 4-F-Ph]; [6689; O; 4-Me-Ph; H; SMe; O; 4-F-Ph; 4-Cl-Ph]; [6690; O; 4-Me-Ph; H; SMe; O; 4-F-Ph; 4-Me-Ph]; [6691; O; 4-Me-Ph; H; SMe; O; 4-F-Ph; 3,4-Me$_2$-Ph]; [6692; O; 4-Me-Ph; H; SMe; O; 4-F-Ph; 5-Indanyl]; [6693; O; 5-Benzodioxolyl; H; SMe; O; 4-F-Ph; 4-F-Ph]; [6694; O; 5-Benzodioxolyl; H; SMe; O; 4-F-Ph; 4-Cl-Ph]; [6695; O; 5-Benzodioxolyl; H; SMe; O; 4-F-Ph; 4-Me-Ph]; [6696; O; 5-Benzodioxolyl; H; SMe; O; 4-F-Ph; 3,4-Me$_2$-Ph]; [6697; O; 5-Benzodioxolyl; H; SMe; O; 4-F-Ph; 5-Indanyl]; [6698; O; 4-F-Ph; H; SMe; O; 4-Cl-Ph; 4-F-Ph]; [6699; O; 4-F-Ph; H; SMe; O; 4-Cl-Ph; 4-Cl-Ph]; [6700; O; 4-F-Ph; H; SMe; O; 4-Cl-Ph; 4-Me-Ph]; [6701; O; 4-F-Ph; H; SMe; O; 4-Cl-Ph; 3,4-Me$_2$-Ph]; [6702; O; 4-F-Ph; H; SMe; O; 4-Cl-Ph; 5-Indanyl]; [6703; O; 4-Cl-Ph; H; SMe; O; 4-Cl-Ph; 4-F-Ph]; [6704; O; 4-Cl-Ph; H; SMe; O; 4-Cl-Ph; 4-Cl-Ph]; [6705; O; 4-Cl-Ph; H; SMe; O; 4-Cl-Ph; 4-Me-Ph]; [6706; O; 4-Cl-Ph; H; SMe; O; 4-Cl-Ph; 3,4-Me$_2$-Ph]; [6707; O; 4-F-Ph; H; SMe; O; 4-Cl-Ph; 5-Indanyl]; [6708; O; 4-Me-Ph; H; SMe; O; 4-Cl-Ph; 4-F-Ph]; [6709; O; 4-Me-Ph; H; SMe; O; 4-Cl-Ph; 4-Cl-Ph]; [6710; O; 4-Me-Ph; H; SMe; O; 4-Cl-Ph; 4-Me-Ph]; [6711; O; 4-Me-Ph; H; SMe; O; 4-Cl-Ph; 3,4-Me$_2$-Ph]; [6712; O; 4-Me-Ph; H; SMe; O; 4-Cl-Ph; 5-Indanyl]; [6713; O; 5-Benzodioxolyl; H; SMe; O; 4-Cl-Ph; 4-F-Ph]; [6714; O; 5-Benzodioxolyl; H; SMe; O; 4-Cl-Ph; 4-Cl-Ph]; [6715; O; 5-Benzodioxolyl; H; SMe; O; 4-Cl-Ph; 4-Me-Ph]; [6716; O; 5-Benzodioxolyl; H; SMe; O; 4-Cl-Ph; 3,4-Me$_2$-Ph]; [6717; O; 5-Benzodioxolyl; H; SMe; O; 4-Cl-Ph; 5-Indanyl]; [6718; O; 4-F-Ph; H; SMe; O; 4-Me-Ph; 4-F-Ph]; [6719; O; 4-F-Ph; H; SMe; O; 4-Me-Ph; 4-Cl-Ph]; [6720; O; 4-F-Ph; H; SMe; O; 4-Me-Ph; 4-Me-Ph]; [6721; O; 4-F-Ph; H; SMe; O; 4-Me-Ph; 3,4-Me$_2$-Ph]; [6722; O; 4-F-Ph; H; SMe; O; 4-Me-Ph; 5-Indanyl]; [6723; O; 4-Cl-Ph; H; SMe; O; 4-Me-Ph; 4-F-Ph]; [6724; O; 4-Cl-Ph; H; SMe; O; 4-Me-Ph; 4-Cl-Ph]; [6725; O; 4-Cl-Ph; H; SMe; O; 4-Me-Ph; 4-Me-Ph]; [6726; O; 4-Cl-Ph; H; SMe; O; 4-Me-Ph; 3,4-Me$_2$-Ph]; [6727; O; 4-Cl-Ph; H; SMe; O; 4-Me-Ph; 5-Indanyl]; [6728; O; 4-Me-Ph; H; SMe; O; 4-Me-Ph; 4-F-Ph]; [6729; O; 4-Me-Ph; H; SMe; O; 4-Me-Ph; 4-Cl-Ph]; [6730; O; 4-Me-Ph; H; SMe; O; 4-Me-Ph; 4-Me-Ph]; [6731; O; 4-Me-Ph; H; SMe; O; 4-Me-Ph; 3,4-Me$_2$-Ph]; [6732; O;

4-Me-Ph; H; SMe; O; 4-Me-Ph; 5-Indanyl]; [6733; O; 5-Benzodioxolyl; H; SMe; O; 4-Me-Ph; 4-F-Ph]; [6734; O; 5-Benzodioxolyl; H; SMe; O; 4-Me-Ph; 4-Cl-Ph]; [6735; O; 5-Benzodioxolyl; H; SMe; O; 4-Me-Ph; 4-Me-Ph]; [6736; O; 5-Benzodioxolyl; H; SMe; O; 4-Me-Ph; 3,4-Me$_2$-Ph]; [6737; O; 5-Benzodioxolyl; H; SMe; O; 4-Me-Ph; 5-Indanyl]; [6738; O; 4-F-Ph; H; 2-Thienyl; O; Cyclohexyl; 4-F-Ph]; [6739; O; 4-F-Ph; H; 2-Thienyl; O; Cyclohexyl; 4-Cl-Ph]; [6740; O; 4-F-Ph; H; 2-Thienyl; O; Cyclohexyl; 4-Me-Ph]; [6741; O; 4-F-Ph; H; 2-Thienyl; O; Cyclohexyl; 3,4-Me$_2$-Ph]; [6742; O; 4-F-Ph; H; 2-Thienyl; O; Cyclohexyl; 5-Indanyl]; [6743; O; 4-Cl-Ph; H; 2-Thienyl; O; Cyclohexyl; 4-F-Ph]; [6744; O; 4-Cl-Ph; H; 2-Thienyl; O; Cyclohexyl; 4-Cl-Ph]; [6745; O; 4-Cl-Ph; H; 2-Thienyl; O; Cyclohexyl; 4-Me-Ph]; [6746; O; 4-Cl-Ph; H; 2-Thienyl; O; Cyclohexyl; 3,4-Me$_2$-Ph]; [6747; O; 4-Cl-Ph; H; 2-Thienyl; O; Cyclohexyl; 5-Indanyl]; [6748; O; 4-Me-Ph; H; 2-Thienyl; O; Cyclohexyl; 4-F-Ph]; [6749; O; 4-Me-Ph; H; 2-Thienyl; O; Cyclohexyl; 4-Cl-Ph]; [6750; O; 4-Me-Ph; H; 2-Thienyl; O; Cyclohexyl; 4-Me-Ph]; [6751; O; 4-Me-Ph; H; 2-Thienyl; O; Cyclohexyl; 3,4-Me$_2$-Ph]; [6752; O; 4-Me-Ph; H; 2-Thienyl; O; Cyclohexyl; 5-Indanyl]; [6753; O; 5-Benzodioxolyl; H; 2-Thienyl; O; Cyclohexyl; 4-F-Ph]; [6754; O; 5-Benzodioxolyl; H; 2-Thienyl; O; Cyclohexyl; 4-Cl-Ph]; [6755; O; 5-Benzodioxolyl; H; 2-Thienyl; O; Cyclohexyl; 4-Me-Ph]; [6756; O; 5-Benzodioxolyl; H; 2-Thienyl; O; Cyclohexyl; 3,4-Me$_2$-Ph]; [6757; O; 5-Benzodioxolyl; H; 2-Thienyl; O; Cyclohexyl; 5-Indanyl]; [6758; O; 4-F-Ph; H; 2-Thienyl; O; Cyclohexylmethyl; 4-F-Ph]; [6759; O; 4-F-Ph; H; 2-Thienyl; O; Cyclohexylmethyl; 4-Cl-Ph]; [6760; O; 4-F-Ph; H; 2-Thienyl; O; Cyclohexylmethyl; 4-Me-Ph]; [6761; O; 4-F-Ph; H; 2-Thienyl; O; Cyclohexylmethyl; 3,4-Me$_2$-Ph]; [6762; O; 4-F-Ph; H; 2-Thienyl; O; Cyclohexylmethyl; 5-Indanyl]; [6763; O; 4-Cl-Ph; H; 2-Thienyl; O; Cyclohexylmethyl; 4-F-Ph]; [6764; O; 4-Cl-Ph; H; 2-Thienyl; O; Cyclohexylmethyl; 4-Cl-Ph]; [6765; O; 4-Cl-Ph; H; 2-Thienyl; O; Cyclohexylmethyl; 4-Me-Ph]; [6766; O; 4-Cl-Ph; H; 2-Thienyl; O; Cyclohexylmethyl; 3,4-Me$_2$-Ph]; [6767; O; 4-Cl-Ph; H; 2-Thienyl; O; Cyclohexylmethyl; 5-Indanyl]; [6768; O; 4-Me-Ph; H; 2-Thienyl; O; Cyclohexylmethyl; 4-F-Ph]; [6769; O; 4-Me-Ph; H; 2-Thienyl; O; Cyclohexylmethyl; 4-Cl-Ph]; [6770; O; 4-Me-Ph; H; 2-Thienyl; O; Cyclohexylmethyl; 4-Me-Ph]; [6771; O; 4-Me-Ph; H; 2-Thienyl; O; Cyclohexylmethyl; 3,4-Me$_2$-Ph]; [6772; O; 4-Me-Ph; H; 2-Thienyl; O; Cyclohexylmethyl; 5-Indanyl]; [6773; O; 5-Benzodioxolyl; H; 2-Thienyl; O; Cyclohexylmethyl; 4-F-Ph]; [6774; O; 5-Benzodioxolyl; H; 2-Thienyl; O; Cyclohexylmethyl; 4-Cl-Ph]; [6775; O; 5-Benzodioxolyl; H; 2-Thienyl; O; Cyclohexylmethyl; 4-Me-Ph]; [6776; O; 5-Benzodioxolyl; H; 2-Thienyl; O; Cyclohexylmethyl; 3,4-Me$_2$-Ph]; [6777; O; 5-Benzodioxolyl; H; 2-Thienyl; O; Cyclohexylmethyl; 5-Indanyl]; [6778; O; 4-F-Ph; H; 2-Thienyl; O; 4-F-Ph; 4-F-Ph]; [6779; O; 4-F-Ph; H; 2-Thienyl; O; 4-F-Ph; 4-Cl-Ph]; [6780; O; 4-F-Ph; H; 2-Thienyl; O; 4-F-Ph; 4-Me-Ph]; [6781; O; 4-F-Ph; H; 2-Thienyl; O; 4-F-Ph; 3,4-Me$_2$-Ph]; [6782; O; 4-F-Ph; H; 2-Thienyl; O; 4-F-Ph; 5-Indanyl]; [6783; O; 4-Cl-Ph; H; 2-Thienyl; O; 4-F-Ph; 4-F-Ph]; [6784; O; 4-Cl-Ph; H; 2-Thienyl; O; 4-F-Ph; 4-Cl-Ph]; [6785; O; 4-Cl-Ph; H; 2-Thienyl; O; 4-F-Ph; 4-Me-Ph]; [6786; O; 4-Cl-Ph; H; 2-Thienyl; O; 4-F-Ph; 3,4-Me$_2$-Ph]; [6787; O; 4-Cl-Ph; H; 2-Thienyl; O; 4-F-Ph; 5-Indanyl]; [6788; O; 4-Me-Ph; H; 2-Thienyl; O; 4-F-Ph; 4-F-Ph]; [6789; O; 4-Me-Ph; H; 2-Thienyl; O; 4-F-Ph; 4-Cl-Ph]; [6790; O; 4-Me-Ph; H; 2-Thienyl; O; 4-F-Ph; 4-Me-Ph]; [6791; O; 4-Me-Ph; H; 2-Thienyl; O; 4-F-Ph; 3,4-Me$_2$-Ph]; [6792; O; 4-Me-Ph; H; 2-Thienyl; O; 4-F-Ph; 5-Indanyl]; [6793; O; 5-Benzodioxolyl; H; 2-Thienyl; O; 4-F-Ph; 4-F-Ph]; [6794; O; 5-Benzodioxolyl; H; 2-Thienyl; O; 4-F-Ph; 4-Cl-Ph]; [6795; O; 5-Benzodioxolyl; H; 2-Thienyl; O; 4-F-Ph; 4-Me-Ph]; [6796; O; 5-Benzodioxolyl; H; 2-Thienyl; O; 4-F-Ph; 3,4-Me$_2$-Ph]; [6797; O; 5-Benzodioxolyl; H; 2-Thienyl; O; 4-F-Ph; 5-Indanyl]; [6798; O; 4-F-Ph; H; 2-Thienyl; O; 4-Cl-Ph; 4-F-Ph]; [6799; O; 4-F-Ph; H; 2-Thienyl; O; 4-Cl-Ph; 4-Cl-Ph]; [6800; O; 4-F-Ph; H; 2-Thienyl; O; 4-Cl-Ph; 4-Me-Ph]; [6801; O; 4-F-Ph; H; 2-Thienyl; O; 4-Cl-Ph; 3,4-Me$_2$-Ph]; [6802; O; 4-F-Ph; H; 2-Thienyl; O; 4-Cl-Ph; 5-Indanyl]; [6803; O; 4-Cl-Ph; H; 2-Thienyl; O; 4-Cl-Ph; 4-F-Ph]; [6804; O; 4-Cl-Ph; H; 2-Thienyl; O; 4-Cl-Ph; 4-Cl-Ph]; [6805; O; 4-Cl-Ph; H; 2-Thienyl; O; 4-Cl-Ph; 4-Me-Ph]; [6806; O; 4-Cl-Ph; H; 2-Thienyl; O; 4-Cl-Ph; 3,4-Me$_2$-Ph]; [6807; O; 4-F-Ph; H; 2-Thienyl; O; 4-Cl-Ph; 5-Indanyl]; [6808; O; 4-Me-Ph; H; 2-Thienyl; O; 4-Cl-Ph; 4-F-Ph]; [6809; O; 4-Me-Ph; H; 2-Thienyl; O; 4-Cl-Ph; 4-Cl-Ph]; [6810; O; 4-Me-Ph; H; 2-Thienyl; O; 4-Cl-Ph; 4-Me-Ph]; [6811; O; 4-Me-Ph; H; 2-Thienyl; O; 4-Cl-Ph; 3,4-Me$_2$-Ph]; [6812; O; 4-Me-Ph; H; 2-Thienyl; O; 4-Cl-Ph; 5-Indanyl]; [6813; O; 5-Benzodioxolyl; H; 2-Thienyl; O; 4-Cl-Ph; 4-F-Ph]; [6814; O; 5-Benzodioxolyl; H; 2-Thienyl; O; 4-Cl-Ph; 4-Cl-Ph]; [6815; O; 5-Benzodioxolyl; H; 2-Thienyl; O; 4-Cl-Ph; 4-Me-Ph]; [6816; O; 5-Benzodioxolyl; H; 2-Thienyl; O; 4-Cl-Ph; 3,4-Me$_2$-Ph]; [6817; O; 5-Benzodioxolyl; H; 2-Thienyl; O; 4-Cl-Ph; 5-Indanyl]; [6818; O; 4-F-Ph; H; 2-Thienyl; O; 4-Me-Ph; 4-F-Ph]; [6819; O; 4-F-Ph; H; 2-Thienyl; O; 4-Me-Ph; 4-Cl-Ph]; [6820; O; 4-F-Ph; H; 2-Thienyl; O; 4-Me-Ph; 4-Me-Ph]; [6821; O; 4-F-Ph; H; 2-Thienyl; O; 4-Me-Ph; 3,4-Me$_2$-Ph]; [6822; O; 4-F-Ph; H; 2-Thienyl; O; 4-Me-Ph; 5-Indanyl]; [6823; O; 4-Cl-Ph; H; 2-Thienyl; O; 4-Me-Ph; 4-F-Ph]; [6824; O; 4-Cl-Ph; H; 2-Thienyl; O; 4-Me-Ph; 4-Cl-Ph]; [6825; O; 4-Cl-Ph; H; 2-Thienyl; O; 4-Me-Ph; 4-Me-Ph]; [6826; O; 4-Cl-Ph; H; 2-Thienyl; O; 4-Me-Ph; 3,4-Me$_2$-Ph]; [6827; O; 4-Cl-Ph; H; 2-Thienyl; O; 4-Me-Ph; 5-Indanyl]; [6828; O; 4-Me-Ph; H; 2-Thienyl; O; 4-Me-Ph; 4-F-Ph]; [6829; O; 4-Me-Ph; H; 2-Thienyl; O; 4-Me-Ph; 4-Cl-Ph]; [6830; O; 4-Me-Ph; H; 2-Thienyl; O; 4-Me-Ph; 4-Me-Ph]; [6831; O; 4-Me-Ph; H; 2-Thienyl; O; 4-Me-Ph; 3,4-Me$_2$-Ph]; [6832; O; 4-Me-Ph; H; 2-Thienyl; O; 4-Me-Ph; 5-Indanyl]; [6833; O; 5-Benzodioxolyl; H; 2-Thienyl; O; 4-Me-Ph; 4-F-Ph]; [6834; O; 5-Benzodioxolyl; H; 2-Thienyl; O; 4-Me-Ph; 4-Cl-Ph]; [6835; O; 5-Benzodioxolyl; H; 2-Thienyl; O; 4-Me-Ph; 4-Me-Ph]; [6836; O; 5-Benzodioxolyl; H; 2-Thienyl; O; 4-Me-Ph; 3,4-Me$_2$-Ph]; [6837; O; 5-Benzodioxolyl; H; 2-Thienyl; O; 4-Me-Ph; 5-Indanyl]

Compounds represented by the formula (Iβ):

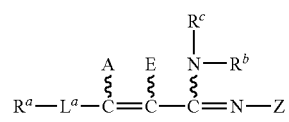

wherein $L^a$, $R^a$, A, E, $R^b$, $R^c$ and Z are any one of 10041 to 10080 combinations shown below, together with compound numbers.

[Compound number; $L^a$; $R^a$; A; E; $R^b$; $R^c$; Z]=[10041; S; Ph; H; Me; H; Ph; Ph]; [10042; S; 4-F-Ph; H; Me; H; Ph; Ph]; [10043; S; 4-Me-Ph; H; Me; H; Ph; Ph]; [10044; S; 2-Naphthyl; H; Me; H; Ph; Ph]; [10045; S; 5-Benzodioxolyl; H; Me; H; Ph; Ph]; [10046; S; Ph; H; Me; Me; Ph; Ph]; [10047; S; 4-F-Ph; H; Me; Me; Ph; Ph]; [10048; S; 4-Me-Ph; H; Me; Me; Ph; Ph]; [10049; S; 2-Naphthyl; H; Me; Me; Ph; Ph]; [10050; S; 5-Benzodioxolyl; H; Me; Me; Ph; Ph]; [10051; S; Ph; H; Me; Me; Cyclohexylmethyl; Ph];

[10052; S; Ph; H; Me; Me; 4-F-Ph; Ph]; [10053; S; Ph; H; Me; Me; 4-Me-Ph; Ph]; [10054; S; Ph; H; Me; Me; 2-Naphthyl; Ph]; [10055; S; Ph; H; Me; Me; 5-Indanyl; Ph]; [10056; S; Ph; H; Me; Me; Ph; Cyclohexyl]; [10057; S; Ph; H; Me; Me; Ph; 4-F-Ph]; [10058; S; Ph; H; Me; Me; Ph; 4-Me-Ph]; [10059; S; Ph; H; Me; Me; Ph; 2-Naphthyl]; [10060; S; Ph; H; Me; Me; Ph; 5-Benzodioxolyl]; [10061; O; Ph; H; Me; H; Ph; Ph]; [10062; O; 4-F-Ph; H; Me; H; Ph; Ph]; [10063; O; 4-Me-Ph; H; Me; H; Ph; Ph]; [10064; O; 2-Naphthyl; H; Me; H; Ph; Ph]; [10065; O; 5-Benzodioxolyl; H; Me; H; Ph; Ph]; [10066; O; Ph; H; Me; Me; Ph; Ph]; [10067; O; 4-F-Ph; H; Me; Me; Ph; Ph]; [10068; O; 4-Me-Ph; H; Me; Me; Ph; Ph]; [10069; O; 2-Naphthyl; H; Me; Me; Ph; Ph]; [10070; O; 5-Benzodioxolyl; H; Me; Me; Ph; Ph]; [10071; O; Ph; H; Me; Me; Cyclohexylmethyl; Ph]; [10072; 0; Ph; H; Me; Me; 4-F-Ph; Ph]; [10073; O; Ph; H; Me; Me; 4-Me-Ph; Ph]; [10074; O; Ph; H; Me; Me; 2-Naphthyl; Ph]; [10075; O; Ph; H; Me; Me; 5-Indanyl; Ph]; [10076; O; Ph; H; Me; Me; Ph; Cyclohexyl]; [10077; O; Ph; H; Me; Me; Ph; 4-F-Ph]; [10078; O; Ph; H; Me; Me; Ph; 4-Me-Ph]; [10079; O; Ph; H; Me; Me; Ph; 2-Naphthyl]; [10080; O; Ph; H; Me; Me; Ph; 5-Benzodioxolyl]

Next, Production Examples of the compound of the present invention are shown.

Production Example 1

To a suspension of 0.8 g (3 mmol) of (E)-2-methyl-N-phenyl-3-(phenylthio)-2-propenamide in toluene (4 ml) was added 0.62 g (3 mmol) of phosphorus pentachloride and the mixture was stirred at room temperature for 4 hours. After concentration of the mixture under vacuum, the residue was dissolved in 35 ml of N,N-dimethylformamide [DMF] and then 793 mg (6 mmol) of a benzenethiol sodium salt was added portionwise under ice cooling. The mixture was stirred at room temperature for 2 hours. After dilution with tert-butyl methyl ether, the mixture was washed sequentially with water (three times) and saturated NaCl solution, dried over anhydrous MgSO$_4$, and concentrated under vacuum. The residue was purified by silica gel column chromatography (hexane/ethyl acetate=20/1) to obtain 0.4 g of phenyl 2-methyl-N-phenyl-3-(phenylthio)-2-propenimidothioate (hereinafter referred to as the present compound 1).

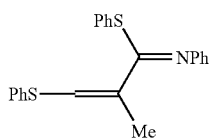

$^1$H-NMR (CDCl$_3$) δ: 1.56 (3H, s), 6.79 (1H, s), 6.81 (1H, s), 7.00-7.39 (15H, m).

Production Example 2

In the same manner as in Production Example 1 except that 2-(methylthio)-N-phenyl-3-(phenylthio)-2-propenamide was used as a material, the following phenyl 2-(methylthio)-N-phenyl-3-(phenylthio)-2-propenimidothioate (hereinafter referred to as the present compound 2) was obtained.

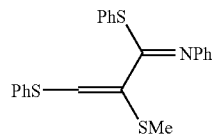

$^1$H-NMR (CDCl$_3$) δ: 2.25 (0.7H, s), 2.45 (2.3H, s), 6.76-7.71 (16H, m).

Production Example 3

In the same manner as in Production Example 1 except that 3-(4-fluorophenylthio)-2-(methylthio)-N-phenyl-2-propenamide was used as a material, the following phenyl 3-(4-fluorophenylthio)-2-(methylthio)-N-phenyl-2-propenimidothioate (hereinafter referred to as the present compound 3) was obtained.

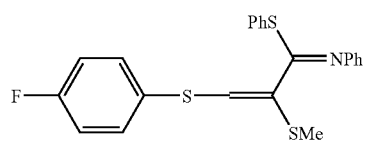

$^1$H-NMR (CDCl$_3$) δ: 2.22-2.49 (3H, m), 6.75-7.64 (15H, m).

Production Example 4

In the same manner as in Production Example 1 except that 3-(4-fluorophenylthio)-2-phenoxy-N-phenyl-2-propenamide was used as the starting material, the following phenyl 3-(4-fluorophenylthio)-2-phenoxy-N-phenyl-2-propenimidothioate (hereinafter referred to as the present compound 4) was obtained.

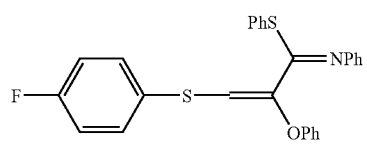

$^1$H-NMR (CDCl$_3$) δ: 6.60-6.73 (2H, m), 6.87-7.45 (18H, m).

Production Example 5

In the same manner as in Production Example 1 except that N-phenyl-3-(phenylthio)-2-(2-thienyl)-2-propenamide was used as a material, the following phenyl N-phenyl-3-(phenylthio)-2-(2-thienyl)-2-propenimidothioate (hereinafter referred to as the present compound 5) was obtained.

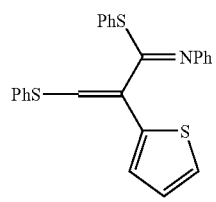

$^1$H-NMR (CDCl$_3$) δ: 6.87-7.62 (19H, m).

Production Example 6

In the same manner as in Production Example 1 except that 3-(4-fluorophenylthio)-N-phenyl-2-(2-thienyl)-2-propenamide was used as a material, the following phenyl 3-(4-fluorophenylthio)-N-phenyl-2-(2-thienyl)-2-propenimidothioate (hereinafter referred to as the present compound 6) was obtained.

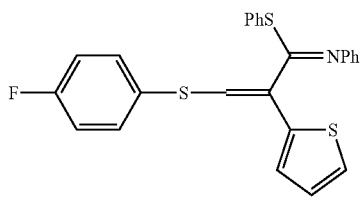

$^1$H-NMR (CDCl$_3$) δ: 6.77-7.50 (18H, m).

Production Example 7

In the same manner as in Production Example 1 except that N-phenyl-3-(phenylthio)-2-(3-thienyl)-2-propenamide was used as a material, the following phenyl N-phenyl-3-(phenylthio)-2-(3-thienyl)-2-propenimidothioate (hereinafter referred to as the present compound 7) was obtained.

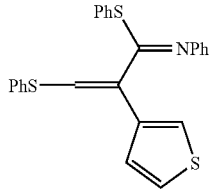

$^1$H-NMR (CDCl$_3$) δ: 6.46-7.61 (19H, m).

Production Example 8

In the same manner as in Production Example 1 except that 3-(4-fluorophenylthio)-N-phenyl-2-(3-thienyl)-2-propenamide was used as a material, the following phenyl 3-(4-fluorophenylthio)-N-phenyl-2-(3-thienyl)-2-propenimidothioate (hereinafter referred to as the present compound 8) was obtained.

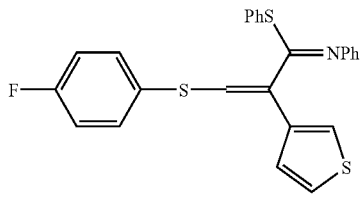

$^1$H-NMR (CDCl$_3$) δ: 6.46-7.60 (18H, m).

Production Example 9

In the same manner as in Production Example 1 except that 2,3-bis(phenylthio)-N-phenyl-2-propenamide was used as a material, the following phenyl 2,3-bis(phenylthio)-N-phenyl-2-propenimidothioate (hereinafter referred to as the present compound 9) was obtained.

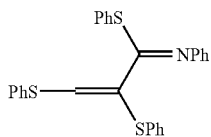

$^1$H-NMR (CDCl$_3$) δ: 6.80 (2H, d, J=7.3 Hz), 6.86 (1H, br s), 7.09 (1H, t, J=7.3 Hz), 7.19-7.42 (15H, m), 7.51 (2H, d, J=7.3 Hz).

Production Example 10

In the same manner as in Production Example 1 except that 3-(4-fluorophenylthio)-N-phenyl-2-(phenylthio)-2-propenamide was used as a material, the following phenyl 3-(4-fluorophenylthio)-N-phenyl-2-(phenylthio)-2-propenimidothioate (hereinafter referred to as the present compound 10) was obtained.

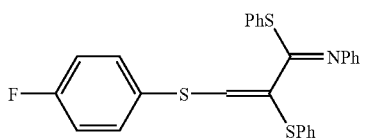

$^1$H-NMR (CDCl$_3$) δ: 6.72-7.56 (20H, m).

Production Example 11

In the same manner as in Production Example 1 except that 2-fluoro-N-phenyl-3-(phenylthio)-2-propenamide was used as a material, the following phenyl 2-fluoro-N-phenyl-3-(phenylthio)-2-propenimidothioate (hereinafter referred to as the present compound 11) was obtained.

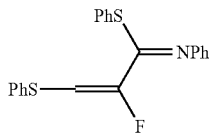

$^1$H-NMR (CDCl$_3$) δ: 6.84 (2H, d, J=7.5 Hz), 6.91 (1H, d, J=32.4 Hz), 7.08 (1H, t, J=7.5 Hz), 7.16-7.32 (12H, m).

Production Example 12

In the same manner as in Production Example 1 except that 2-fluoro-3-(4-fluorophenylthio)-N-phenyl-2-propenamide was used as a material, the following phenyl 2-fluoro-3-(4-- fluorophenylthio)-N-phenyl-2-propenimidothioate (hereinafter referred to as the present compound 12) was obtained.

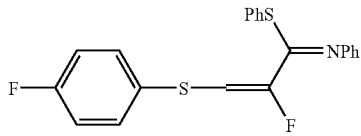

$^1$H-NMR (CDCl$_3$) δ: 6.75-7.36 (15H, m).

Production Example 13

In the same manner as in Production Example 1 except that 2,N-diphenyl-3-(phenylthio)-2-propenamide was used as a material, the following phenyl 2,N-diphenyl-3-(phenylthio)-2-propenimidothioate (hereinafter referred to as the present compound 13) was obtained.

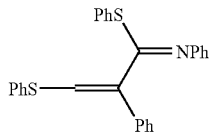

$^1$H-NMR (CDCl$_3$) δ: 6.67 (1H, s), 7.02-7.49 (20H, m).

Production Example 14

A mixture of 3.68 g (13 mmol) of 2-ethyl-N-phenyl-3-(phenylthio)-2-propenamide, 1.9 ml (26 mmol) of thionyl chloride, 10 mg of DMF, and 20 ml of toluene was refluxed for 1 hour. After concentration of the mixture under vacuum, the residue was dissolved in 35 ml of DMF and then 2.0 g (15.1 mmol) of a benzenethiol sodium salt was added portionwise under ice cooling and stirred at room temperature for 1 hour. After dilution with tert-butyl methyl ether, the mixture was washed sequentially with water (three times) and saturated NaCl solution, dried over anhydrous MgSO$_4$, and concentrated under vacuum. The residue was purified by silica gel column chromatography (hexane/ethyl acetate=20/1) to obtain 2.03 g of phenyl 2-ethyl-N-phenyl-3-(phenylthio)-2-propenimidothioate (hereinafter referred to as the present compound 14).

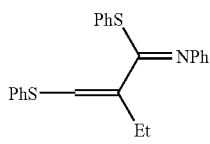

$^1$H-NMR (CDCl$_3$) δ: 1.17 (3H, t, J=7.1 Hz), 2.51-2.67 (2H, br m), 6.80 (2H, d, J=7.3 Hz), 7.00-7.33 (14H, m).

Production Example 15

In the same manner as in Production Example 14 except that N-phenyl-3-(phenylthio)-2-n-propyl-2-propenamide was used as a material, the following phenyl N-phenyl-3-(phenylthio)-2-n-propyl-2-propenimidothioate (hereinafter referred to as the present compound 15) was obtained.

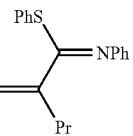

$^1$H-NMR (CDCl$_3$) δ: 0.99 (3H, t, J=7.2 Hz), 1.57-1.70 (2H, br), 2.49-2.61 (2H, br), 6.76-6.84 (2H, br), 7.00-7.38 (14H, br).

Production Example 16

In the same manner as in Production Example 14 except that 2-n-butyl-N-phenyl-3-(phenylthio)-2-propenamide was used as a material, the following phenyl 2-n-butyl-N-phenyl-3-(phenylthio)-2-propenimidothioate (hereinafter referred to as the present compound 16) was obtained.

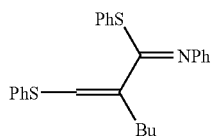

$^1$H-NMR (CDCl$_3$) δ: 0.96 (3H, t, J=7.2 Hz), 1.32-1.45 (2H, m), 1.51-1.63 (2H, m), 2.49-2.63 (2H, m), 6.76-6.83 (2H, m), 7.01-7.35 (14H, m).

Production Example 17

In the same manner as in Production Example 14 except that 2-n-butyl-3-(4-fluorophenylthio)-N-phenyl-2-propenamide was used as a material, the following phenyl 2-n-butyl-3-(4-fluorophenylthio)-N-phenyl-2-propenimidothioate (hereinafter referred to as the present compound 17) was obtained.

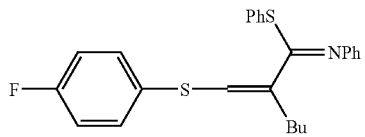

$^1$H-NMR (CDCl$_3$) δ: 0.96 (3H, t, J=7.4 Hz), 1.32-1.46 (2H, m), 1.49-1.63 (2H, m), 2.45-2.64 (2H, m), 6.73-6.82 (2H, m), 6.84-7.38 (13H, m).

Production Example 18

In the same manner as in Production Example 14 except that 2-phenoxy-N-phenyl-3-(phenylthio)-2-propenamide was used as a material, the following phenyl 2-phenoxy-N-phenyl-3-(phenylthio)-2-propenimidothioate (hereinafter referred to as the present compound 18) was obtained.

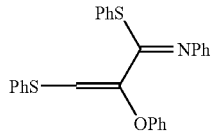

$^1$H-NMR (CDCl$_3$) δ: 6.67 (2H, d, J=7.7 Hz), 6.93-7.10 (4H, m), 7.16-7.38 (15H, m).

Production Example 19

In the same manner as in Production Example 14 except that N-phenyl-3-(phenylthio)-4,4,4-trifluoro-2-butenamide was used as a material, the following phenyl N-phenyl-3-(phenylthio)-4,4,4-trifluoro-2-butenimidothioate (hereinafter referred to as the present compound 19) was obtained.

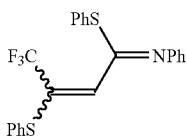

$^1$H-NMR (CDCl$_3$) δ: 6.70-6.73 (1H, m), 6.97-7.02 (2H, m), 7.18 (1H, t, J=7.4 Hz), 7.29-7.34 (3H, m), 7.36-7.43 (5H, m), 7.48-7.55 (4H, m).

Production Example 20

In the same manner as in Production Example 14 except that N-(4-methylphenyl)-3-(phenylthio)-4,4,4-trifluoro-2-butenamide was used as a material, the following phenyl N-(methylphenyl)-3-(phenylthio)-4,4,4-trifluoro-2-butenimidothioate (hereinafter referred to as the present compound 20) was obtained.

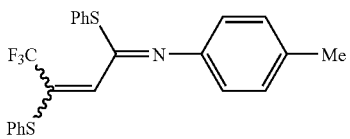

$^1$H-NMR (CDCl$_3$) δ: 2.36 (3H, s), 6.69-6.72 (1H, m), 6.90 (2H, d, J=8.2 Hz), 7.20 (2H, d, J=8.2 Hz), 7.28-7.34 (3H, m), 7.35-7.43 (3H, m), 7.47-7.55 (4H, m).

Production Example 21

A mixture of 0.5 g (1.85 mmol) of (E)-2-methyl-N-phenyl-3-(phenylthio)-2-propenamide, 0.4 ml of thionyl chloride, 5 mg of DMF, and 10 ml of toluene was refluxed for 1 hour and then concentrated. The residue was dissolved in 5 ml of DMF and cooled to 0° C. To a solution of 277 mg (2.23 mmol) of 2-methylthiophenol in 5 ml of DMF was added 90 mg of sodium hydride (60% in oil) under ice cooling and stirred for 5 minutes. The solution was added portionwise to the above-described DMF solution of the residue under ice cooling and stirred at room temperature for 1 hour. The reaction mixture was poured into water and extracted with tert-butyl methyl ether (three times). The combined organic layer was washed sequentially with water and a saturated NaCl solution, dried over anhydrous MgSO$_4$, and concentrated. The residue was purified by silica gel column chromatography (hexane/ethyl acetate=20/1) to obtain 573 mg of 2-methylphenyl 2-methyl-N-phenyl-3-(phenylthio)-2-propenimidothioate (hereinafter referred to as the present compound 21):

2-Methylphenyl 2-methyl-N-phenyl-3-(phenylthio)-2-propenimidothioate (hereinafter referred to as the present compound 21):

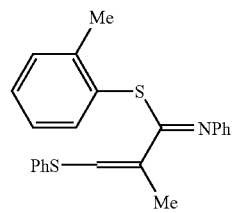

$^1$H-NMR (CDCl$_3$, 50° C.) δ: 2.05 (3H, s), 2.22 (3H, s), 6.77 (2H, d, J=7.5 Hz), 6.97-7.31 (13H, m).

Production Example 22

In the same manner as in Production Example 21 except that 3-methylthiophenol was used as a material, the following 3-methylphenyl 2-methyl-N-phenyl-3-(phenylthio)-2-propenimidothioate (hereinafter referred to as the present compound 22) was obtained.

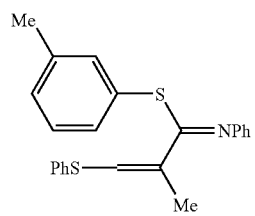

$^1$H-NMR (CDCl$_3$, 50° C.) δ 2.05 (3H, s), 2.23-2.34 (3H, m), 6.79 (2H, d, J=7.5 Hz), 6.88-7.39 (13H, m).

Production Example 23

In the same manner as in Production Example 21 except that 4-methylthiophenol was used as a material, the following 4-methylphenyl 2-methyl-N-phenyl-3-(phenylthio)-2-propenimidothioate (hereinafter referred to as the compound of the present invention 23) was obtained.

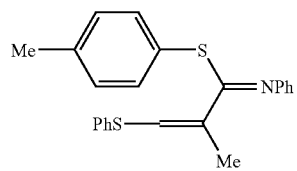

$^1$H-NMR (CDCl$_3$, 50° C.) δ: 2.03 (3H, s), 2.30 (2.4H, s), 2.33 (0.6H, s), 6.75-6.83 (2H, m), 6.98-7.30 (13H, m).

Production Example 24

In the same manner as in Production Example 21 except that 2-chlorothiophenol was used as a material, the following 2-chlorophenyl 2-methyl-N-phenyl-3-(phenylthio)-2-propenimidothioate (hereinafter referred to as the present compound 24) was obtained.

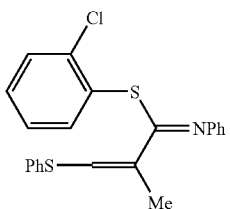

¹H-NMR (CDCl₃, 50° C.) δ: 2.08 (3H, s), 6.80 (2H, d, J=7.3 Hz), 7.00 (1H, t, J=7.3 Hz), 7.04-7.37 (12H, m).

Production Example 25

In the same manner as in Production Example 21 except that 3-chlorothiophenol was used as a material, the following 3-chlorophenyl 2-methyl-N-phenyl-3-(phenylthio)-2-propenimidothioate (hereinafter referred to as the present compound 25) was obtained.

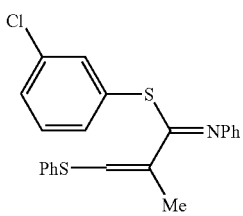

¹H-NMR (CDCl₃, 50° C.) δ: 1.99-2.13 (3H, br), 6.72-6.83 (2H, m), 6.94-7.45 (13H, m).

Production Example 26

In the same manner as in Production Example 21 except that 4-chlorothiophenol was used as a material, the following 4-chlorophenyl 2-methyl-N-phenyl-3-(phenylthio)-2-propenimidothioate (hereinafter referred to as the present compound 26) was obtained.

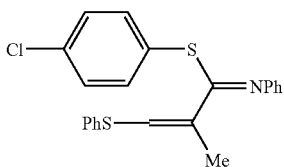

¹H-NMR (CDCl₃, 50° C.) δ: 2.06 (3H, s), 6.75 (1H, d, J=7.7 Hz), 6.77-6.81 (1H, m), 6.96-7.36 (13H, m).

Production Example 27

In the same manner as in Production Example 14 except that 2-methyl-N-(2-methylphenyl)-3-(phenylthio)-2-propenamide was used as a material, the following phenyl 2-methyl-N-(2-methylphenyl)-3-(phenylthio)-2-propenimidothioate (hereinafter referred to as the present compound 27) was obtained.

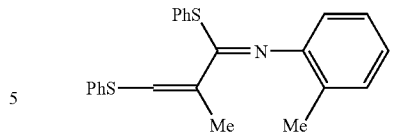

¹H-NMR (CDCl₃, 50° C.) δ: 2.08 (3H, s), 2.10 (3H, s), 6.68 (1H, d, J=7.6 Hz), 6.96 (1H, t, J=7.6 Hz), 7.05-7.13 (4H, m), 7.14-7.30 (9H, m).

Production Example 28

In the same manner as in Production Example 14 except that (E)-2-methyl-N-(3-methylphenyl)-3-(phenylthio)-2-propenamide was used as a material, the following phenyl 2-methyl-N-(3-methylphenyl)-3-(phenylthio)-2-propenimidothioate (hereinafter referred to as the present compound 28) was obtained.

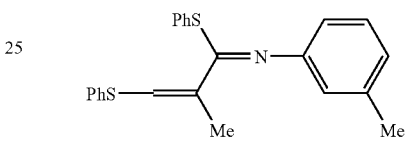

¹H-NMR (CDCl₃) 50° C.) δ: 2.05 (3H, s), 2.28 (3H, s), 6.56-6.63 (2H, m), 6.85 (1H, d, J=7.7 Hz), 7.07-7.34 (12H, m).

Production Example 29

In the same manner as in Production Example 14 except that 2-methyl-N-(4-methylphenyl)-3-(phenylthio)-2-propenamide was used as a material, the following phenyl 2-methyl-N-(4-methylphenyl)-3-(phenylthio)-2-propenimidothioate (hereinafter referred to as the present compound 29) was obtained.

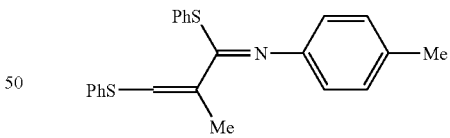

¹H-NMR (CDCl₃, 50° C.) δ: 2.06 (3H, s), 2.30 (3H, s), 6.72 (2H, d, J=8.0 Hz), 7.03-7.11 (4H, m), 7.13-7.28 (9H, m).

Production Example 30

In the same manner as in Production Example 14 except that (E)-N-(4-ethylphenyl)-2-methyl-3-(phenylthio)-2-propenamide was used as a material, the following phenyl N-(4-ethylphenyl)-2-methyl-3-(phenylthio)-2-propenimidothioate (hereinafter referred to as the present compound 30) was obtained.

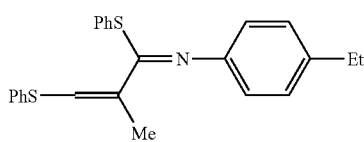

¹H-NMR (CDCl₃, 50° C.) δ: 1.21 (3H, t, J=7.6 Hz), 2.06 (3H, s), 2.60 (2H, q, J=7.6 Hz), 6.73 (2H, d, J=8.3 Hz), 7.05-7.33 (13H, m).

Production Example 31

In the same manner as in Production Example 14 except that (E)-N-(4-isopropylphenyl)-2-methyl-3-(phenylthio)-2-propenamide was used as a material, the following phenyl N-(4-isopropylphenyl)-2-methyl-3-(phenylthio)-2-propenimidothioate (hereinafter referred to as the present compound 31) was obtained.

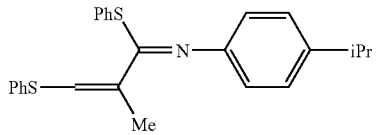

¹H-NMR (CDCl₃, 50° C.) δ: 1.23 (6H, d, J=7.0 Hz), 2.07 (3H, s), 2.85 (1H, sept, J=7.0 Hz), 6.73 (2H, d, J=8.5 Hz), 7.04-7.40 (13H, m).

Production Example 32

In the same manner as in Production Example 14 except that (E)-N-(5-indanyl)-2-methyl-3-(phenylthio)-2-propenamide was used as a material, the following phenyl N-(5-indanyl)-2-methyl-3-(phenylthio)-2-propenimidothioate (hereinafter referred to as the present compound 32) was obtained.

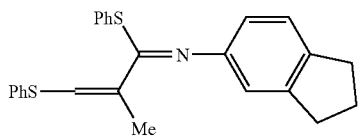

¹H-NMR (CDCl₃, 50° C.) δ: 1.99-2.12 (5H, m), 2.85 (4H, t, J=7.4 Hz), 6.59 (1H, d, J=7.7 Hz), 6.66 (1H, s), 7.04-7.12 (3H, m), 7.14-7.30 (9H, m).

Production Example 33

In the same manner as in Production Example 21 except that phenol was used as a material, the following phenyl 2-methyl-N-phenyl-3-(phenylthio)-2-propenimidate (hereinafter referred to as the present compound 33) was obtained.

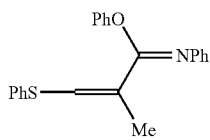

¹H-NMR (CDCl₃) δ: 2.16 (3H, br s), 6.69-7.49 (16H, br m).

Production Example 34

In the same manner as in Production Example 21 except that 3-methylphenol was used as a material, the following 3-methylphenyl 2-methyl-N-phenyl-3-(phenylthio)-2-propenimidate (hereinafter referred to as the present compound 34) was obtained.

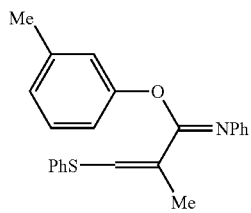

¹H-NMR (DMSO-D₆, 70° C.) δ: 2.01 (3H, s), 2.25 (3H, s), 6.70-7.39 (15H, m).

Production Example 35

In the same manner as in Production Example 21 except that 4-methylphenol was used as a material, the following 4-methylphenyl 2-methyl-N-phenyl-3-(phenylthio)-2-propenimidate (hereinafter referred to as the present compound 35) was obtained.

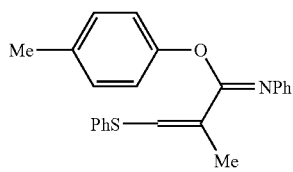

¹H-NMR (DMSO-D₆, 70° C.) δ: 1.99 (3H, s), 2.24 (3H, s), 6.82-6.91 (4H, m), 6.96-7.03 (2H, m), 7.07-7.14 (4H, m), 7.22 (2H, t, J=7.8 Hz), 7.27-7.33 (3H, m).

Production Example 36

In the same manner as in Production Example 21 except that 4-chlorophenol was used as a material, the following 4-chlorophenyl 2-methyl-N-phenyl-3-(phenylthio)-2-propenimidate (hereinafter referred to as the present compound 36) was obtained.

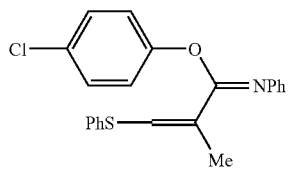

¹H-NMR (DMSO-D₆, 70° C.) δ: 2.00 (3H, s), 6.87 (2H, d, J=7.5 Hz), 6.97-7.10 (4H, m), 7.12-7.18 (2H, m), 7.23 (2H, t, J=7.8 Hz), 7.28-7.36 (5H, m).

Production Example 37

In the same manner as in Production Example 21 except that 4-fluorophenol was used as a material, the following 4-fluorophenyl 2-methyl-N-phenyl-3-(phenylthio)-2-propenimidate (hereinafter referred to as the present compound 37) was obtained.

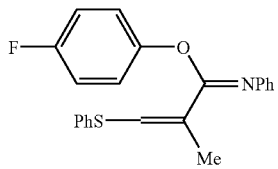

¹H-NMR (DMSO-D₆, 70° C.) δ: 1.98 (3H, s), 6.85 (2H, d, J=7.6 Hz), 6.96-7.18 (8H, m), 7.23 (2H, t, J=7.8 Hz), 7.27-7.36 (3H, m).

Production Example 38

In the same manner as in Production Example 21 except that (E)-2-methyl-N-(4-methylphenyl)-3-(phenylthio)-2-propenamide and phenol were used as materials, the following phenyl 2-methyl-N-(4-methylphenyl)-3-(phenylthio)-2-propenimidate (hereinafter referred to as the present compound 38) was obtained.

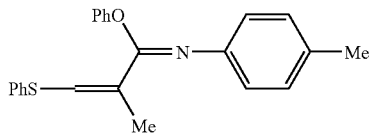

¹H-NMR (DMSO-D₆, 70° C.) δ: 2.02 (3H, s), 2.21 (3H, s), 6.83 (2H, d, J=7.3 Hz), 6.92-7.17 (8H, m), 7.23-7.39 (5H, m).

Production Example 39

In the same manner as in Production Example 21 except that (E)-N-(4-ethylphenyl)-2-methyl-3-(phenylthio)-2-propenamide and phenol were used as materials, the following phenyl N-(4-ethylphenyl)-2-methyl-3-(phenylthio)-2-propenimidate (hereinafter referred to as the present compound 39) was obtained.

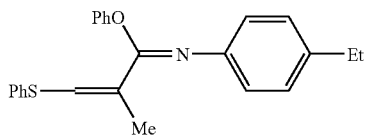

¹H-NMR (DMSO-D₆, 70° C.) δ: 1.13 (3H, t, J=7.6 Hz), 2.02 (3H, s), 2.52 (2H, q, J=7.6 Hz), 6.84 (2H, d, J=7.6 Hz), 6.91-7.14 (8H, m), 7.24-7.34 (5H, m).

Production Example 40

In the same manner as in Production Example 21 except that (E)-N-(4-isopropylphenyl)-2-methyl-3-(phenylthio)-2-propenamide and phenol were used as materials, the following phenyl N-(4-isopropylphenyl)-2-methyl-3-(phenylthio)-2-propenimidate (hereinafter referred to as the present compound 40) was obtained.

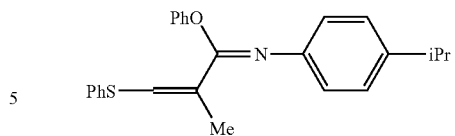

¹H-NMR (DMSO-D₆, 70° C.) δ: 1.14 (6H, d, J=6.8 Hz), 2.02 (3H, s), 2.80 (1H, t, J=6.8 Hz), 6.85 (2H, d, J=7.8 Hz), 6.93-7.15 (8H, m), 7.25-7.33 (5H, m).

Production Example 41

In the same manner as in Production Example 21 except that (E)-N-(5-indanyl)-2-methyl-3-(phenylthio)-2-propenamide and phenol were used as materials, the following phenyl N-(5-indanyl)-2-methyl-3-(phenylthio)-2-propenimidate (hereinafter referred to as the present compound 41) was obtained.

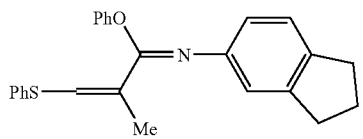

¹H-NMR (DMSO-D₆, 70° C.) δ: 1.96 (2H, quint, J=7.3 Hz), 2.02 (3H, s), 2.75 (2H, t, J=7.3 Hz), 2.76 (2H, t, J=7.3 Hz), 6.69 (1H, d, J=7.3 Hz), 6.79 (1H, s), 6.91-7.13 (7H, m), 7.25-7.33 (5H, m).

Production Example 42

To a solution of 201 mg of phenyl 3,N-diphenylpropynimidothioate in 5 ml of THF was added 0.08 ml of thiophenol and tert-butoxy potassium (a catalytic amount). The mixture was stirred at room temperature for 2 hours and then refluxed for 2 hours. The reaction mixture was concentrated under vacuum. The residue was purified by medium pressure preparative HPLC to obtain 269 mg of phenyl 3,N-diphenyl-3-(phenylthio)-2-propenimidothioate (hereinafter referred to as the present compound 42) as a yellow oil.

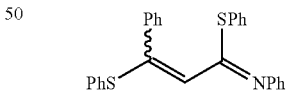

¹HNMR (CDCl₃) δ: 5.36 (0.23H, s), 6.11 (0.77H, s), 6.61-7.62 (20H, m).

Production Example 43

In the same manner as in Production Example 42 except that cyclohexylmercaptane was used as materials, the following cyclohexyl 3,N-diphenyl-3-(phenylthio)-2-propenimidothioate (hereinafter referred to as the present compound 43) was obtained.

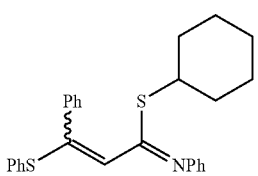

¹H-NMR (CDCl₃) δ: 1.26-2.15 (10H, m), 3.30-3.89 (1H, m), 6.36-7.35 (16H, m).

Production Example 44

To a suspension of 0.76 g (4.8 mmol) of N-phenyl-1-propynecarboxamide in toluene (15 mL) was added 1.0 g (4.8 mmol) of phosphorus pentachloride at room temperature and stirred for 4 hours. After removal of the solvent, the residue was dissolved in DMF (15 mL). To a solution of 1.2 mL (12 mmol) of thiophenol in DMF (15 mL) was added 0.31 g (7.1 mmol) of sodium hydride (60% in oil) under ice cooling and stirred for 0.5 hours. The mixture was added to the above-described DMF solution of the residue and stirred under ice cooling for 3 hours. After dilution with tert-butyl methyl ether (150 mL), the mixture was washed sequentially with water and a saturated NaCl solution, dried over anhydrous MgSO₄, and concentrated under vacuum. The residue was purified by silica gel column chromatography (hexane:ethyl acetate=20:1) to obtain 0.39 g of phenyl N-phenyl-3-(phenylthio)-2-butenimidothioate (hereinafter referred to as the present compound 44).

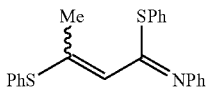

¹H-NMR (CDCl₃) δ: 2.35 (3H, s), 5.15 (1H, s), 6.92-7.50 (15H, m).

Production Example 45

To a solution of 0.50 g (1.1 mmol) of phenyl 3,3-bis(phenylthio)-N-(phenyl)propanimidothioate in toluene (5 mL) was added 0.16 g (1.2 mmol) of N-chlorosuccinimide under ice cooling and stirred at room temperature for 3 hours. After dilution with t-butyl methyl ether (50 mL), the mixture was washed with saturated NaCl solution, dried over MgSO₄, and concentrated under vacuum. The residue was purified by silica gel column chromatography (hexane:ethyl acetate=20:1) to obtain 38 mg of phenyl 3,3-bis(phenylthio)-N-phenyl-2-propenimidothioate (hereinafter referred to as the present compound 45).

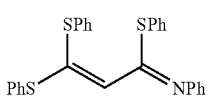

¹H-NMR (CDCl₃) δ: 6.57 (2H, d, J=7.2 Hz), 7.00-7.47 (19H, m).

Production Example 46

In the same manner as in Production Example 45 except that cyclohexylmercaptane was used as materials, the following cyclohexyl N-phenyl-3-(phenylthio)-2-butenimidothioate (hereinafter referred to as the present compound 46) was obtained.

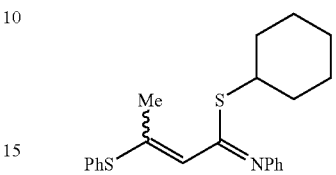

¹H-NMR (CDCl₃) δ: 1.19-2.34 (13H, m), 2.82 (0.36H, br), 3.75 (0.64H, br), 5.55 (0.64H, br s), 5.70 (0.36H, br s), 6.70-7.56 (10H, m).

Production Examples 47 to 48

A suspension of 1.0 g (3.71 mmol) of (E)-2-methyl-N-phenyl-3-(phenylthio)-2-propenamide, 0.81 ml of thionyl chloride, and 10 mg of DMF in 10 ml of toluene was refluxed for 1 hour and then concentrated under vacuum. The residue was dissolved in 5 ml of DMF and cooled in ice bath. To a solution of 241 mg of n-hexylthiol in 5 ml of DMF was added 90 mg of sodium hydride (60% in oil) under ice cooling and stirred for 5 minutes. The mixture was added portionwise to the above-described DMF solution of the residue under ice cooling and then stirred at room temperature for 1 hour. The reaction mixture was poured into water and extracted with tert-butyl methyl ether (three times). The combined organic layer was washed sequentially with water and a saturated NaCl solution, dried over anhydrous MgSO₄, and concentrated. The residue was purified by silica gel column chromatography (hexane/ethyl acetate=20/1) to obtain 82 mg of n-hexyl 2-methyl-N-phenyl-3-(phenylthio)-2-propenimidothioate (hereinafter referred to as the present compound 47) and 114 mg of n-hexyl 3-(hexylthio)-2-methyl-N-phenyl-2-propenimidothioate (hereinafter referred to as the present compound 48).

n-Hexyl 2-methyl-N-phenyl-3-(phenylthio)-2-propenimidothioate (hereinafter referred to as the present compound 47)

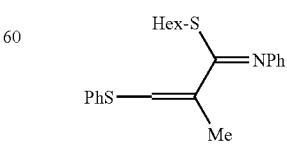

¹H-NMR (CDCl₃, 50° C.) δ: 0.87 (3H, t, J=6.8 Hz), 1.17-1.43 (6H, br m), 1.50-1.92 (5H, br m), 2.67-3.06 (2H, br m), 6.82 (2H, d, J=7.6 Hz), 7.04 (1H, t, J=7.6 Hz), 7.19-7.35 (8H, m).

n-Hexyl 3-(hexylthio)-2-methyl-N-phenyl-2-propenimidothioate (hereinafter referred to as the present compound 48)

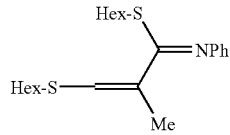

$^1$H-NMR (CDCl$_3$, 50° C.) δ: 0.87 (6H, t, J=6.9 Hz), 0.90 (6H, t, J=6.9 Hz), 1.18-1.44 (13H, m), 1.50-1.79 (6H, m), 2.64-2.93 (2H, br m), 2.73 (2H, t, J=7.2 Hz), 6.80 (2H, d, J=7.6 Hz), 7.00 (1H, t, J=7.6 Hz), 7.25 (2H, t, J=7.6 Hz), 7.25 (1H, s).

Production Example 49

In the same manner as in Production Example 14 except that (E)-3-(4-fluorophenylthio)-2-methyl-N-phenyl-2-propenamide was used as a material, the following phenyl 3-(4-fluorophenylthio)-2-methyl-N-phenyl-2-propenimidothioate (hereinafter referred to as the present compound 49) was obtained.

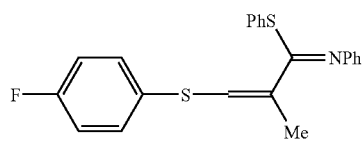

$^1$H-NMR (CDCl$_3$, 50° C.) δ: 2.05 (3H, s), 6.72-6.83 (2H, m), 6.85-7.39 (13H, m).

Production Example 50

In the same manner as in Production Example 21 except that (E)-3-(4-fluorophenylthio)-2-methyl-N-phenyl-2-propenamide and 4-methylthiophenol were used as materials, the following 4-methylphenyl 3-(4-fluorophenylthio)-2-methyl-N-phenyl-2-propenimidothioate (hereinafter referred to as the present compound 50) was obtained.

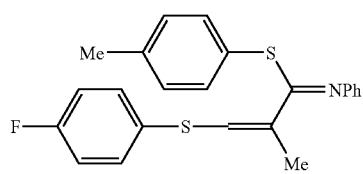

$^1$H-NMR (CDCl$_3$, 50° C.) δ: 2.02 (3H, s), 2.26-2.36 (3H, m), 6.71-6.82 (2H, m), 6.84-7.15 (8H, m), 7.17-7.29 (3H, m).

Production Example 51

In the same manner as in Production Example 14 except that (E)-3-(4-fluorophenylthio)-2-methyl-N-(4-methylphenyl)-2-propenamide was used as a material, the following phenyl 3-(4-fluorophenylthio)-2-methyl-N-(4-methylphenyl)-2-propenimidothioate (hereinafter referred to as the present compound 51) was obtained.

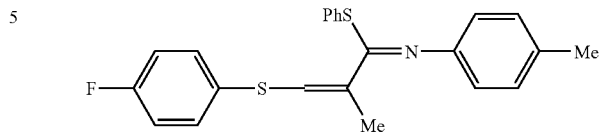

$^1$H-NMR (CDCl$_3$, 50° C.) δ: 2.05 (3H, s), 2.30 (3H, s), 6.64-6.76 (2H, m), 6.85-7.32 (12H, m).

Production Example 52

In the same manner as in Production Example 21 except that (E)-3-(4-fluorophenylthio)-2-methyl-N-(4-methylphenyl)-2-propenamide and 4-methylthiophenol were used as materials, the following 4-methylphenyl 3-(4-fluorophenylthio)-2-methyl-N-(4-methylphenyl)-2-propenimidothioate (hereinafter referred to as the present compound 52) was obtained.

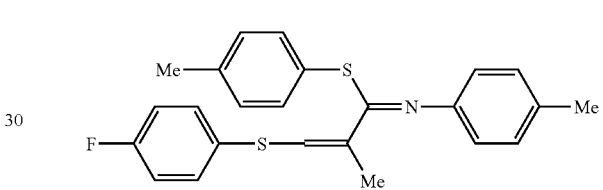

$^1$H-NMR (CDCl$_3$, 50° C.) δ: 2.01 (3H, s), 2.31 (3H, s), 2.32 (3H, s), 6.65-6.75 (2H, m), 6.86-7.19 (11H, m).

Production Example 53

In the same manner as in Production Example 14 except that (E)-3-(4-chlorophenylthio)-2-methyl-N-phenyl-2-propenamide was used as a material, the following phenyl 3-(4-chlorophenylthio)-2-methyl-N-phenyl-2-propenimidothioate (hereinafter referred to as the present compound 53) was obtained.

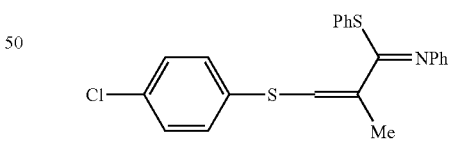

$^1$H-NMR (CDCl$_3$, 50° C.) δ: 2.05 (3H, s), 6.70-6.82 (2H, m), 6.93-7.51 (13H, m).

Production Example 54

In the same manner as in Production Example 21 except that (E)-3-(4-chlorophenylthio)-2-methyl-N-phenyl-2-propenamide and 4-methylthiophenol were used as materials, the following 4-methylphenyl 3-(4-chlorophenylthio)-2-methyl-N-phenyl-2-propenimidothioate (hereinafter referred to as the present compound 54) was obtained.

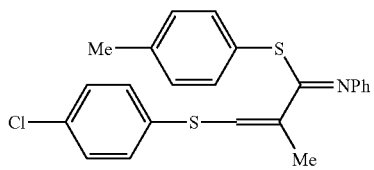

¹H-NMR (CDCl₃, 50° C.) δ: 2.03 (3H, s), 2.27-2.38 (3H, m), 6.71-6.83 (2H, m), 6.95-7.31 (12H, m).

Production Example 55

In the same manner as in Production Example 14 except that (E)-3-(4-chlorophenylthio)-2-methyl-N-(4-methylphenyl)-2-propenamide was used as a material, the following phenyl 3-(4-chlorophenylthio)-2-methyl-N-(4-methylphenyl)-2-propenimidothioate (hereinafter referred to as the present compound 55) was obtained.

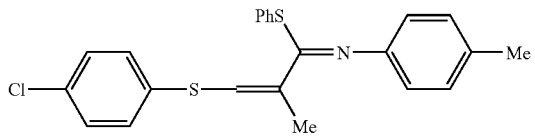

¹H-NMR (CDCl₃, 50° C.) δ: 2.06 (3H, s), 2.31 (3H, s), 6.65-6.75 (2H, m), 6.92-7.51 (12H, m).

Production Example 56

In the same manner as in Production Example 21 except that (E)-3-(4-chlorophenylthio)-2-methyl-N-(4-methylphenyl)-2-propenamide and 4-methylthiophenol were used as materials, the following 4-methylphenyl 3-(4-chlorophenylthio)-2-methyl-N-(4-methylphenyl)-2-propenimidothioate (hereinafter referred to as the present compound 56) was obtained.

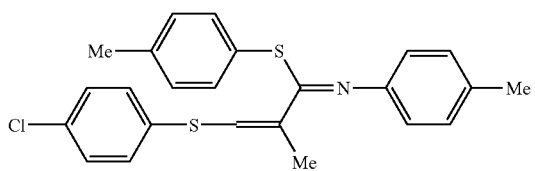

¹H-NMR (CDCl₃, 50° C.) δ: 2.03 (3H, s), 2.27-2.38 (6H, m), 6.65-6.76 (2H, m), 6.94-7.42 (11H, m).

Production Example 57

In the same manner as in Production Example 14 except that (E)-2-methyl-3-(4-methylphenylthio)-N-phenyl-2-propenamide was used as a material, the following phenyl 2-methyl-3-(4-methylphenylthio)-N-phenyl-2-propenimidothioate (hereinafter referred to as the present compound 57) was obtained.

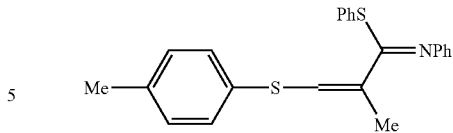

¹H-NMR (CDCl₃, 50° C.) δ: 2.04 (3H, s), 2.33 (3H, s), 6.78 (2H, d, J=7.3 Hz), 6.97-7.34 (13H, m).

Production Example 58

In the same manner as in Production Example 21 except that (E)-2-methyl-3-(4-methylphenylthio)-N-phenyl-2-propenamide and 4-methylthiophenol were used as materials, the following 4-methylphenyl 2-methyl-3-(4-methylphenylthio)-N-phenyl-2-propenimidothioate (hereinafter referred to as the present compound 58) was obtained.

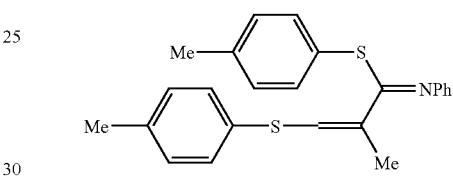

¹H-NMR (CDCl₃, 50° C.) δ: 2.01 (3H, s), 2.31 (3H, s), 2.33 (3H, s), 6.78 (2H, d, J=7.7 Hz), 6.98-7.12 (10H, m), 7.23 (2H, t, J=7.7 Hz).

Production Example 59

In the same manner as in Production Example 14 except that (E)-2-methyl-N-(4-methylphenyl)-3-(4-methylphenylthio)-2-propenamide was used as a material, the following phenyl 2-methyl-N-(4-methylphenyl)-3-(4-methylphenylthio)-2-propenimidothioate (hereinafter referred to as the present compound 59) was obtained.

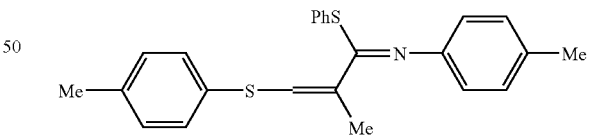

¹H-NMR (CDCl₃, 50° C.) δ: 2.04 (3H, s), 2.27-2.37 (6H, m), 6.68-6.75 (2H, m), 6.95-7.32 (12H, m).

Production Example 60

In the same manner as in Production Example 21 except that (E)-2-methyl-N-(4-methylphenyl)-3-(4-methylphenylthio)-2-propenamide and 4-methylthiophenol were used as materials, the following 4-methylphenyl 2-methyl-N-(4-methylphenyl)-3-(4-methylphenylthio)-2-propenimidothio ate (hereinafter referred to as the present compound 60) was obtained.

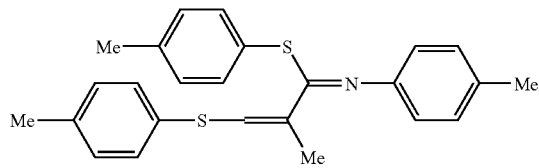

¹H-NMR (CDCl₃, 50° C.) δ: 2.00 (3H, s), 2.30 (3H, s), 2.31 (3H, s), 2.33 (3H, s), 6.71 (2H, d, J=8.3 Hz), 6.97-7.19 (11H, m).

Production Example 61

In the same manner as in Production Example 21 except that 2-methyl-N-(4-methylphenyl)-3-(phenylthio)-2-propenamide and 4-methylthiophenol were used as materials, the following 4-methylphenyl 2-methyl-N-(4-methylphenyl)-3-(phenylthio)-2-propenimidothioate (hereinafter referred to as the present compound 61) was obtained.

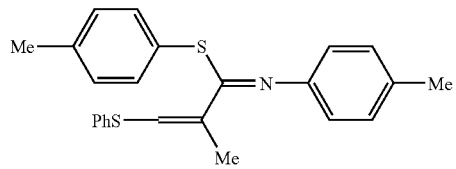

¹H-NMR (CDCl₃) δ: 2.01-2.11 (3H, br), 2.32 (3H, s), 2.33 (3H, s), 6.74 (2H, d, J=8.2 Hz), 7.00-7.30 (12H, m).

Production Example 62

In the same manner as in Production Example 21 except that 4-fluorothiophenol was used as a material, the following 4-fluorophenyl 2-methyl-N-phenyl-3-(phenylthio)-2-propenimidothioate (hereinafter referred to as the present compound 62) was obtained.

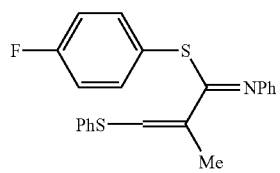

¹H-NMR (CDCl₃, 50° C.) δ: 1.97-2.11 (3H, br m), 6.75 (1H, d, J=7.7 Hz), 6.79 (1H, d, J=7.7 Hz), 6.84-7.37 (13H, m).

Production Example 63

In the same manner as in Production Example 21 except that 3,4-dichlorothiophenol was used as a material, the following 3,4-dichlorophenyl 2-methyl-N-phenyl-3-(phenylthio)-2-propenimidothioate (hereinafter referred to as the present compound 63) was obtained.

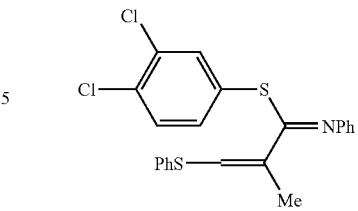

¹H-NMR (CDCl₃, 50° C.) δ: 2.00-2.14 (3H, br m), 6.70-7.50 (14H, m).

Production Example 64

In the same manner as in Production Example 21 except that 4-methoxythiophenol was used as a material, the following 4-methoxyphenyl 2-methyl-N-phenyl-3-(phenylthio)-2-propenimidothioate (hereinafter referred to as the present compound 64) was obtained.

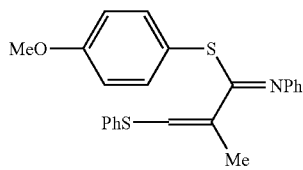

¹H-NMR (CDCl₃, 50° C.) δ: 1.90-2.12 (3H, m), 3.75-3.84 (3H, m), 6.69-6.87 (4H, m), 6.97-7.36 (11H, m).

Production Example 65

In the same manner as in Production Example 14 except that (E)-2-methyl-3-phenoxy-N-phenyl-2-propenamide was used as a material, the following phenyl 2-methyl-3-phenoxy-N-phenyl-2-propenimidothioate (hereinafter referred to as the present compound 65) was obtained.

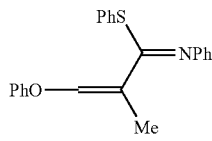

¹H-NMR (CDCl₃) δ: 2.06 (3H, br s), 6.71 (2H, d, J=8.0 Hz), 6.80 (2H, d, J=7.2 Hz), 7.01-7.11 (2H, m), 7.13-7.30 (9H, m), 7.55 (1H, br s).

Production Example 66

In the same manner as in Production Example 14 except that (E)-2-methyl-N-(4-methylphenyl)-3-phenoxy-2-propenamide was used as a material, the following phenyl 2-methyl-N-(4-methylphenyl)-3-phenoxy-2-propenimidothioate (hereinafter referred to as the present compound 66) was obtained.

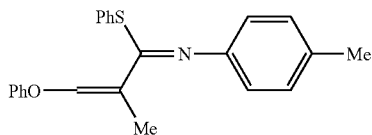

¹H-NMR (CDCl₃, 50° C.) δ: 2.02 (3H, br s), 2.30 (3H, s), 6.66-6.75 (4H, m), 7.00-7.10 (3H, m), 7.14-7.30 (7H, m), 7.45 (1H, br s).

Production Example 67

In the same manner as in Production Example 14 except that (E)-N-(5-indanyl)-2-methyl-3-phenoxy-2-propenamide was used as a material, the following phenyl N-(5-indanyl)-2-methyl-3-phenoxy-2-propenimidothioate (hereinafter referred to as the present compound 67) was obtained.

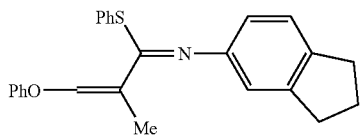

¹H-NMR (CDCl₃, 50° C.) δ: 2.04 (3H, br s), 2.05 (2H, quint, J=7.3 Hz), 2.85 (4H, t, J=7.3 Hz), 6.55-6.74 (3H, m), 7.02-7.12 (2H, m), 7.15-7.32 (8H, m), 7.39-7.49 (1H, br).

Production Example 68

In the same manner as in Production Example 21 except that (E)-2-methyl-3-phenoxy-N-phenyl-2-propenamide and phenol were used as materials, the following phenyl 2-methyl-3-phenoxy-N-phenyl-2-propenimidate (hereinafter referred to as the present compound 68) was obtained.

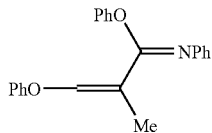

¹H-NMR (CDCl₃, 50° C.) δ: 2.03 (3H, br s), 6.77-7.00 (8H, m), 7.06 (1H, t, J=7.4 Hz), 7.11-7.38 (7H, m).

Production Example 69

In the same manner as in Production Example 21 except that (E)-2-methyl-N-(4-methylphenyl)-3-phenoxy-2-propenamide and phenol were used as materials, the following phenyl 2-methyl-N-(4-methylphenyl)-3-phenoxy-2-propenimidate (hereinafter referred to as the present compound 69) was obtained.

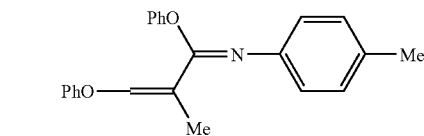

¹H-NMR (CDCl₃, 50° C.) δ: 2.03 (3H, br s), 2.23 (3H, s), 6.74-7.03 (9H, m), 7.05 (1H, t, J=7.4 Hz), 7.14-7.37 (5H, m).

Production Example 70

In the same manner as in Production Example 21 except that (E)-N-(5-indanyl)-2-methyl-3-phenoxy-2-propenamide and phenol was used as material, the following phenyl N-(5-indanyl)-2-methyl-3-phenoxy-2-propenimidate (hereinafter referred to as the present compound 70) was obtained.

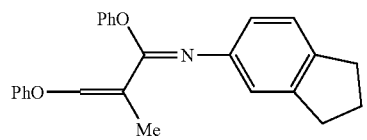

¹H-NMR (CDCl₃, 50° C.) δ: 1.92-2.10 (5H, m), 2.79 (4H, t, J=7.3 Hz), 6.65-7.08 (9H, m), 7.14-7.33 (5H, m).

Production Example 71

In the same manner as in Production Example 21 except that 1,1,3,3-tetramethylbutanethiol was used as a material, the following 1,1,3,3-tetramethylbutyl 2-methyl-N-phenyl-3-(phenylthio)-2-propenimidothioate (hereinafter referred to as the present compound 71) was obtained.

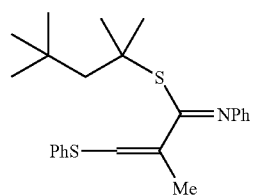

¹H-NMR (CDCl₃, 50° C.) δ: 1.03 (9H, br s), 1.58 (6H, br s), 1.70 (3H, br s), 1.93 (2H, br s), 6.79 (2H, d, J=8.5 Hz), 7.02 (1H, t, J=7.4 Hz), 7.18-7.31 (8H, m).

Production Example 72

In the same manner as in Production Example 21 except that cyclohexylmethylthiol was used as a material, the following cyclohexylmethyl 2-methyl-N-phenyl-3-(phenylthio)-2-propenimidothioate (hereinafter referred to as the present compound 72) was obtained.

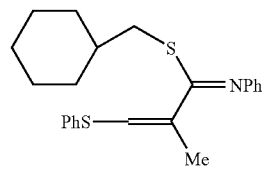

¹H-NMR (CDCl₃, 50° C.) δ: 0.84-1.30 (5H, m), 1.39-1.90 (9H, m), 2.81 (2H, br), 6.81 (2H, d, J=7.4 Hz), 7.03 (1H, t, J=7.4 Hz), 7.17-7.35 (8H, m).

Production Example 73

In the same manner as in Production Example 21 except that 3-methyl-1-propylbutanethiol was used as a material, the following 3-methyl-1-propylbutyl 2-methyl-N-phenyl-3-(phenylthio)-2-propenimidothioate (hereinafter referred to as the present compound 73) was obtained.

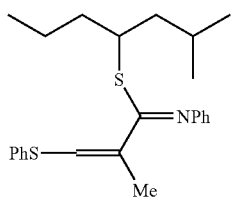

¹H-NMR (CDCl₃, 50° C.) δ: 0.69-0.97 (9H, m), 1.20-1.97 (10H, m), 3.62-3.72 (1H, m), 6.81 (2H, d, J=7.4 Hz), 7.03 (1H, t, J=7.4 Hz), 7.20-7.34 (8H, m).

Production Example 74

In the same manner as in Production Example 21 except that 2-ethylhexanethiol was used as a material, the following 2-ethylhexyl 2-methyl-N-phenyl-3-(phenylthio)-2-propenimidothioate (hereinafter referred to as the present compound 74) was obtained.

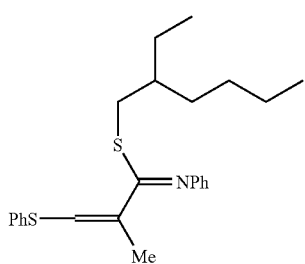

¹H-NMR (CDCl₃, 50° C.) δ: 0.72-0.95 (6H, m), 1.13-1.43 (8H, m), 1.52 (1H, br), 1.77 (3H, br), 2.92 (2H, br), 6.81 (2H, d, J=7.6 Hz), 7.03 (1H, t, J=7.6 Hz), 7.18-7.34 (8H, m).

Production Example 75

In the same manner as in Production Example 14 except that (E)-2-methyl-N-(3-methylphenyl)-3-phenoxy-2-propenamide was used as a material, the following phenyl 2-methyl-N-(3-methylphenyl)-3-phenoxy-2-propenimidothioate (hereinafter referred to as the present compound 75) was obtained.

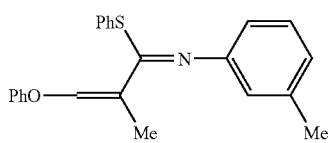

¹H-NMR (CDCl₃, 50° C.) δ: 2.02 (3H, br), 2.28 (3H, s), 6.59 (1H, s), 6.60 (1H, d, J=7.6 Hz), 6.73 (2H, d, J=7.8 Hz), 6.83 (1H, d, J=7.6 Hz), 7.06 (1H, t, J=7.3 Hz), 7.12 (1H, t, J=7.6 Hz), 7.15-7.29 (7H, m), 7.49 (1H, br).

Production Example 76

In the same manner as in Production Example 21 except that (E)-2-methyl-N-(3-methylphenyl)-3-phenoxy-2-propenamide and phenol were used as materials, the following phenyl 2-methyl-N-(3-methylphenyl)-3-phenoxy-2-propenimidate (hereinafter referred to as the present compound 76) was obtained.

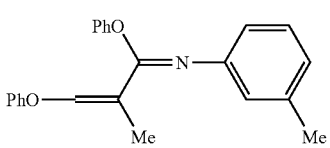

¹H-NMR (CDCl₃, 50° C.) δ: 2.02 (3H, br), 2.22 (3H, s), 6.70 (2H, d, J=9.8 Hz), 6.75 (1H, d, J=7.6 Hz), 6.80-6.99 (5H, m), 7.00-7.10 (2H, m), 7.15-7.36 (5H, m).

Production Example 77

In the same manner as in Production Example 14 except that (E)-N-(3,4-dimethylphenyl)-2-methyl-3-phenoxy-2-propenamide was used as a material, the following phenyl N-(3,4-dimethylphenyl)-2-methyl-3-phenoxy-2-propenimidothioate (hereinafter referred to as the present compound 77) was obtained.

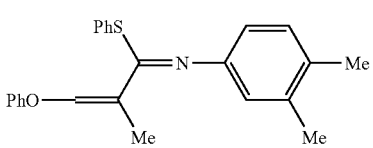

¹H-NMR (CDCl₃, 50° C.) δ: 2.01 (3H, br), 2.21 (6H, s), 6.54-6.61 (2H, m), 6.70 (2H, d, J=8.3 Hz), 6.98-7.08 (2H, m), 7.14-7.28 (7H, m), 7.43 (1H, br).

Production Example 78

In the same manner as in Production Example 21 except that (E)-N-(3,4-dimethylphenyl)-2-methyl-3-phenoxy-2-propenamide and phenol were used as materials, the following phenyl N-(3,4-dimethylphenyl)-2-methyl-3-phenoxy-2-propenimidate (hereinafter referred to as the present compound 78) was obtained.

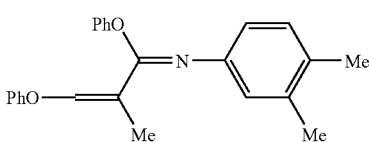

¹H-NMR (CDCl₃, 50° C.) δ: 2.02 (3H, br), 2.14 (6H, s), 6.64-7.10 (9H, br m), 7.16-7.31 (5H, br m).

Production Example 79

In the same manner as in Production Example 14 except that (E)-N-(4-fluorophenyl)-2-methyl-3-phenoxy-2-propenamide was used as a material, the following phenyl N-(4-fluorophenyl)-2-methyl-3-phenoxy-2-propenimidothioate (hereinafter referred to as the present compound 79) was obtained.

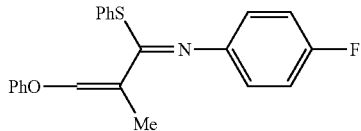

¹H-NMR (CDCl₃, 50° C.) δ: 1.93-2.18 (3H, br), 6.68-7.02 (5H, m), 7.04-7.31 (9H, m), 7.33-7.66 (1H, br m).

Production Example 80

In the same manner as in Production Example 21 except that (E)-N-(4-fluorophenyl)-2-methyl-3-phenoxy-2-propenamide and phenol were used as materials, the following phenyl N-(4-fluorophenyl)-2-methyl-3-phenoxy-2-propenimidate (hereinafter referred to as the present compound 80) was obtained.

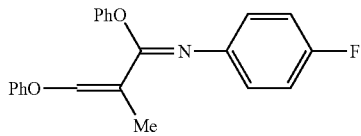

¹H-NMR (CDCl₃, 50° C.) δ: 1.84-2.19 (3H, br), 6.64-7.01 (10H, m), 7.07 (1H, t, J=7.4 Hz), 7.12-7.43 (4H, m).

Production Example 81

In the same manner as in Production Example 14 except that (E)-2-methyl-3-(4-methylphenyloxy)-N-phenyl-2-propenamide was used as a material, the following phenyl 2-methyl-3-(4-methylphenyloxy)-N-phenyl-2-propenimidothioate (hereinafter referred to as the present compound 81) was obtained.

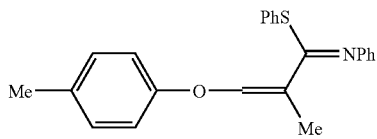

¹H-NMR (CDCl₃, 50° C.) δ: 1.94-2.11 (3H, br), 2.29 (3H, s), 6.63 (2H, d, J=8.3 Hz), 6.78 (2H, d, J=8.3 Hz), 6.96-7.08 (3H, m), 7.14-7.29 (7H, m), 7.49 (1H, br s).

Production Example 82

In the same manner as in Production Example 21 except that (E)-2-methyl-3-(4-methylphenyloxy)-N-phenyl-2-propenamide and phenol were used as materials, the following phenyl 2-methyl-3-(4-methylphenyloxy)-N-phenyl-2-propenimidate (hereinafter referred to as the present compound 82) was obtained.

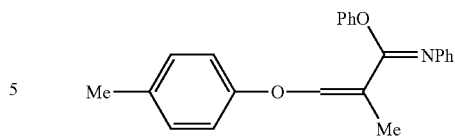

¹H-NMR (CDCl₃, 50° C.) δ: 2.02 (3H, br s), 2.28 (3H, s), 6.73 (2H, d, J=8.0 Hz), 6.81-6.99 (6H, m), 7.05 (2H, d, J=8.8 Hz), 7.11-7.23 (4H, m), 7.27 (1H, br s).

Production Examples 83 and 84

In the same manner as in Production Examples 47 and 48 except that (E)-N-(3-fluorophenyl)-2-methyl-3-phenoxy-2-propenamide was used as materials, the following phenyl N-(3-fluorophenyl)-2-methyl-3-phenoxy-2-propenimidothioate (hereinafter referred to as the present compound 83) and the following phenyl N-(3-fluorophenyl)-2-methyl-3-(phenylthio)-2-propenimidothioate (hereinafter referred to as the present compound 84) were obtained.

Phenyl N-(3-fluorophenyl)-2-methyl-3-phenoxy-2-propenimidothioate

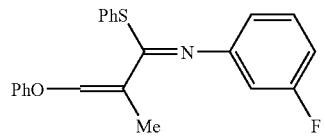

¹H-NMR (DMSO-D₆, 50° C.) δ: 2.01 (3H, br s), 6.71 (2H, d, J=8.5 Hz), 6.77-6.85 (1H, m), 6.95-7.19 (5H, m), 7.20-7.43 (7H, m).

Phenyl N-(3-fluorophenyl)-2-methyl-3-(phenylthio)-2-propenimidothioate

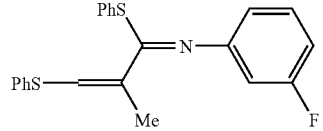

¹H-NMR (DMSO-D₆, 50° C.) δ: 1.97 (3H, br s), 6.61-6.70 (2H, m), 6.86 (1H, td, J=8.7, 2.4 Hz), 7.10 (2H, d, J=7.8 Hz), 7.20-7.44 (10H, m).

Production Examples 85 and 86

In the same manner as in Production Examples 47 and 48 except that (E)-N-(4-chlorophenyl)-2-methyl-3-phenoxy-2-propenamide was used as materials, the following phenyl N-(4-chlorophenyl)-2-methyl-3-phenoxy-2-propenimidothioate (hereinafter referred to as the present compound 85) and the following phenyl N-(4-chlorophenyl)-2-methyl-3-

(phenylthio)-2-propenimidothioate (hereinafter referred to as the present compound 86) were obtained.

Phenyl N-(4-chlorophenyl)-2-methyl-3-phenoxy-2-propenimidothioate

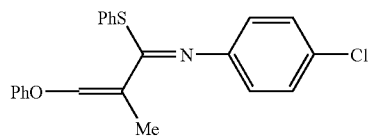

$^1$H-NMR (DMSO-D$_6$, 50° C.) δ: 2.02 (3H, br s), 6.84-7.20 (8H, m), 7.22-7.46 (7H, m).

Phenyl N-(4-chlorophenyl)-2-methyl-3-(phenylthio)-2-propenimidothioate

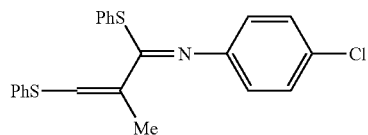

$^1$H-NMR (DMSO-D$_6$, 50° C.) δ: 1.98 (3H, br s), 6.84 (2H, d, J=8.1 Hz), 7.09 (2H, d, J=8.1 Hz), 7.18-7.43 (11H, m).

Production Examples 87 and 88

In the same manner as in Production Examples 47 and 48 except that (E)-N-(4-methoxyphenyl)-2-methyl-3-phenoxy-2-propenamide was used as a material, the following phenyl N-(4-methoxyphenyl)-2-methyl-3-phenoxy-2-propenimidothioate (hereinafter referred to as the present compound 87) and the following phenyl N-(4-methoxyphenyl)-2-methyl-3-(phenylthio)-2-propenimidothioate (hereinafter referred to as the present compound 88) were obtained.

Phenyl N-(4-methoxyphenyl)-2-methyl-3-phenoxy-2-propenimidothioate

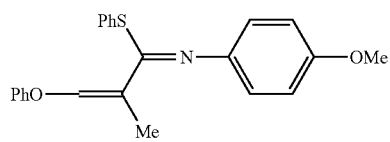

$^1$H-NMR (DMSO-D$_6$, 50° C.) δ: 1.94 (3H, br s), 3.73 (3H, s), 6.66-6.78 (2H, br m), 6.79 (2H, d, J=8.8 Hz), 6.88 (2H, d, J=8.8 Hz), 7.11 (1H, t, J=7.3 Hz), 7.21-7.38 (7H, m), 7.42 (1H, br s).

Phenyl N-(4-methoxyphenyl)-2-methyl-3-(phenylthio)-2-propenimidothioate

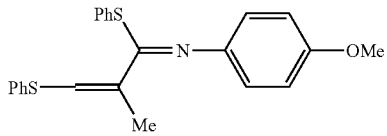

$^1$H-NMR (CDCl$_3$) δ: 2.10 (3H, s), 3.78 (3H, s), 6.75-6.87 (4H, m), 6.99-7.08 (2H, m), 7.15 (2H, d, J=7.5 Hz), 7.18-7.27 (6H, m), 7.31 (1H, br s).

Production Examples 89 and 90

In the same manner as in Production Examples 47 and 48 except that (E)-2-methyl-3-phenoxy-N-phenyl-2-propenamide and 2-methylthiophenol were used as materials, the following 2-methylphenyl 2-methyl-3-phenoxy-N-phenyl-2-propenimidothioate (hereinafter referred to as the present compound 89) and the following 2-methylphenyl 2-methyl-3-(2-methylphenylthio)-N-phenyl-2-propenimidothioate (hereinafter referred to as the present compound 90) were obtained.

2-Methylphenyl 2-methyl-3-phenoxy-N-phenyl-2-propenimidothioate

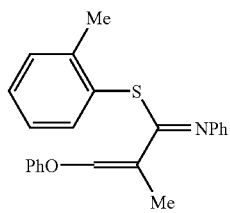

$^1$H-NMR (DMSO-D$_6$, 50° C.) δ: 1.92 (3H, br s), 2.25 (3H, br s), 6.72 (2H, d, J=7.6 Hz), 6.78 (2H, d, J=7.3 Hz), 7.04 (1H, t, J=7.3 Hz), 7.12 (1H, t, J=7.4 Hz), 7.14-7.19 (1H, m), 7.21-7.37 (8H, m).

2-Methylphenyl 2-methyl-3-(2-methylphenylthio)-N-phenyl-2-propenimidothioate

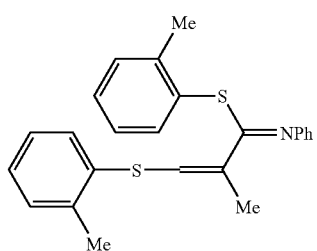

$^1$H-NMR (DMSO-D$_6$, 50° C.) δ: 1.99 (3H, br s), 2.17 (3H, br s), 2.24 (3H, s), 6.75-6.87 (3H, m), 6.97 (1H, br s), 7.05 (1H, t, J=7.4 Hz), 7.10-7.32 (9H, m).

Production Examples 91 and 92

In the same manner as in Production Examples 47 and 48 except that (E)-2-methyl-3-phenoxy-N-phenyl-2-propenamide and 3-methylthiophenol were used as materials, the following 3-methylphenyl 2-methyl-3-phenoxy-N-phenyl-2-propenimidothioate (hereinafter referred to as the present compound 91) and the following 3-methylphenyl 2-methyl-3-(3-methylphenylthio)-N-phenyl-2-propenimidothioate (hereinafter referred to as the present compound 92) were obtained.

3-Methylphenyl 2-methyl-3-phenoxy-N-phenyl-2-propenimidothioate

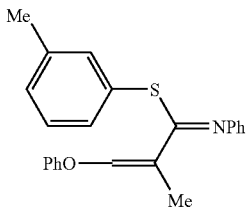

$^1$H-NMR (DMSO-D$_6$, 50° C.) δ: 1.92 (3H, br s), 2.26 (3H, br s), 6.75 (2H, d, J=8.0 Hz), 6.80 (2H, d, J=7.6 Hz), 7.01-7.16 (5H, m), 7.22 (1H, t, J=7.6 Hz), 7.26-7.35 (4H, m), 7.42 (1H, br s).

3-Methylphenyl 2-methyl-3-(3-methylphenylthio)-N-phenyl-2-propenimidothioate

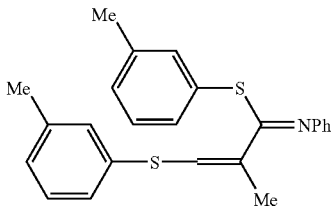

$^1$H-NMR (DMSO-D$_6$, 50° C.) δ: 1.97 (3H, br s), 2.24 (3H, s), 2.29 (3H, s), 6.80 (2H, d, J=7.3 Hz), 6.85 (1H, d, J=7.6 Hz), 7.00-7.15 (6H, m), 7.18-7.25 (3H, m), 7.29 (2H, t, J=7.8 Hz).

Production Examples 93 and 94

In the same manner as in Production Examples 47 and 48 except that (E)-2-methyl-3-phenoxy-N-phenyl-2-propenamide and 4-fluorothiophenol were used as materials, the following 4-fluorophenyl 2-methyl-3-phenoxy-N-phenyl-2-propenimidothioate (hereinafter referred to as the present compound 93) and the following 4-fluorophenyl 3-(4-fluorophenylthio)-2-methyl-N-phenyl-2-propenimidothioate (hereinafter referred to as the present compound 94) were obtained.

4-Fluorophenyl 2-methyl-3-phenoxy-N-phenyl-2-propenimidothioate

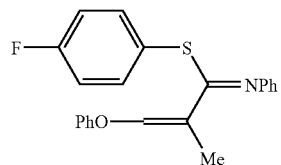

$^1$H-NMR (DMSO-D$_6$, 50° C.) δ: 1.76-2.07 (3H, br), 6.78 (2H, d, J=8.0 Hz), 6.87 (2H, d, J=7.5 Hz), 7.04 (1H, t, J=7.5 Hz), 7.10-7.19 (3H, m), 7.20-7.40 (6H, m), 7.47 (1H, br s).

4-Fluorophenyl 3-(4-fluorophenylthio)-2-methyl-N-phenyl-2-propenimidothioate

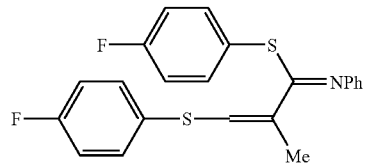

$^1$H-NMR (DMSO-D$_6$, 50° C.) δ: 1.93 (3H, br s), 6.79 (2H, d, J=7.7 Hz), 7.01-7.38 (12H, m).

Production Examples 95 and 96

In the same manner as in Production Examples 47 and 48 except that (E)-2-methyl-3-phenoxy-N-phenyl-2-propenamide and 4-chlorothiophenol were used as materials, the following 4-chlorophenyl 2-methyl-3-phenoxy-N-phenyl-2-propenimidothioate (hereinafter referred to as the present compound 95) and the following 4-chlorophenyl 3-(4-chlorophenylthio)-2-methyl-N-phenyl-2-propenimidothioate (hereinafter referred to as the present compound 96) were obtained.

4-Chlorophenyl 2-methyl-3-phenoxy-N-phenyl-2-propenimidothioate

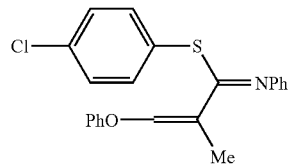

$^1$H-NMR (DMSO-D$_6$, 50° C.) δ: 1.92 (3H, br s), 6.79 (2H, d, J=8.0 Hz), 6.84 (2H, d, J=8.0 Hz), 7.05 (1H, t, J=7.4 Hz), 7.14 (1H, t, J=7.4 Hz), 7.23-7.40 (8H, m), 7.47 (1H, br s).

4-Chlorophenyl 3-(4-chlorophenylthio)-2-methyl-N-phenyl-2-propenimidothioate

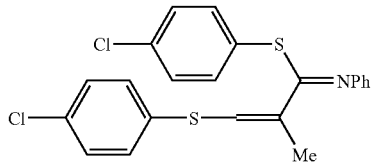

¹H-NMR (DMSO-D₆, 50° C.) δ: 1.98 (3H, br s), 6.81 (2H, d, J=8.3 Hz), 7.08 (1H, t, J=7.4 Hz), 7.14 (2H, d, J=8.5 Hz), 7.23-7.34 (4H, m), 7.36-7.45 (5H, m).

Production Examples 97 and 98

In the same manner as in Production Examples 47 and 48 except that (E)-2-methyl-3-phenoxy-N-phenyl-2-propenamide and cyclohexylmethanol were used as materials, the following cyclohexylmethyl 2-methyl-3-phenoxy-N-phenyl-2-propenimidate (hereinafter referred to as the present compound 97) and the following cyclohexylmethyl 3-(cyclohexylmethyl)-2-methyl-N-phenyl-2-propenimidate (hereinafter referred to as the present compound 98) were obtained.

Cyclohexylmethyl 2-methyl-3-phenoxy-N-phenyl-2-propenimidate

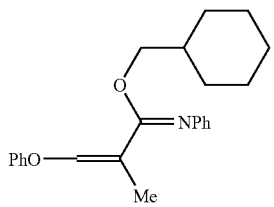

¹H-NMR (CDCl₃) δ: 1.00-1.12 (2H, m), 1.14-1.36 (3H, m), 1.65-1.89 (6H, m), 1.71 (3H, d, J=1.2 Hz), 4.01 (2H, d, J=6.3 Hz), 6.60 (2H, d, J=8.1 Hz), 6.71 (1H, br s), 6.82 (2H, d, J=8.4 Hz), 7.02 (2H, t, J=7.3 Hz), 7.21 (2H, dd, J=8.4, 7.3 Hz), 7.28 (2H, dd, J=8.1, 7.3 Hz).

Cyclohexylmethyl 3-(cyclohexylmethyl)-2-methyl-N-phenyl-2-propenimidate

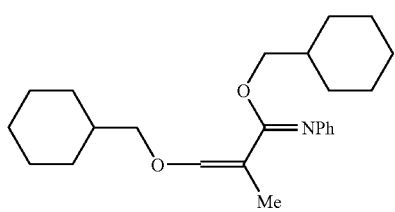

¹H-NMR (CDCl₃) δ: 0.77-0.91 (2H, m), 0.98-1.34 (10H, m), 1.37-1.49 (4H, m), 1.55-1.88 (11H, m), 3.50 (2H, d, J=6.6 Hz), 3.95 (2H, d, J=6.3 Hz), 6.45 (1H, br), 6.77 (2H, d, J=7.5 Hz), 6.94 (1H, t, J=7.5 Hz), 7.21 (2H, t, J=7.5 Hz).

Production Examples 99 and 100

To a solution of 1.0 g (2.51 mmol) of phenyl 2,3-dibromo-2-methylpropanimidate and 466 mg (3.02 mmol) of 3,4-dimethoxyphenol in 5 ml of DMF was added 2.05 g (6.29 mmol) of cesium carbonate and stirred at 70° C. for 5 hours. After cooling to room temperature, the reaction solution was poured into water and extracted with tert-butyl methyl ether. The organic layer was washed sequentially with water and a saturated NaCl, dried over anhydrous MgSO₄, and concentrated under vacuum. The residue was purified by silica gel column chromatography (hexane/ethyl acetate=5/1) to obtain 252 mg of phenyl 3-(3,4-dimethoxyphenyloxy)-2-methyl-N-phenyl-2-propenimidate (hereinafter referred to as the present compound 99) and 145 mg of 3,4-dimethoxyphenyl 3-(3,4-dimethoxyphenyloxy)-2-methyl-N-phenyl-2-propenimidate (hereinafter referred to as the present compound 100).

Phenyl 3-(3,4-dimethoxyphenyloxy)-2-methyl-N-phenyl-2-propenimidate

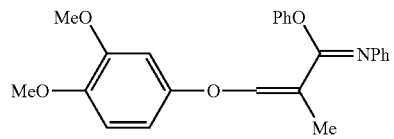

¹H-NMR (DMSO-D₆, 50° C.) δ: 1.84-1.98 (3H, br), 3.70 (3H, s), 3.70 (3H, s), 6.34-6.39 (1H, m), 6.57 (1H, d, J=2.9 Hz), 6.82-7.36 (12H, m).

3,4-Dimethoxyphenyl 3-(3,4-dimethoxyphenyloxy)-2-methyl-N-phenyl-2-propenimidate

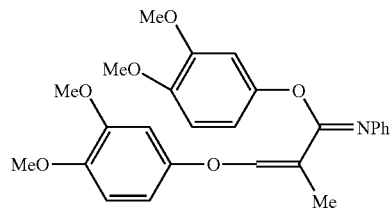

¹H-NMR (DMSO-D₆, 50° C.) δ: 1.88 (3H, br s), 3.68 (3H, s), 3.69 (3H, s), 3.70 (3H, s), 3.71 (3H, s), 6.40 (1H, d, J=7.8 Hz), 6.51 (1H, br s), 6.57 (1H, d, J=2.7 Hz), 6.66 (1H, br s), 6.80-6.90 (4H, m), 6.98 (1H, t, J=7.4 Hz), 7.17-7.29 (3H, m).

Production Examples 101 and 102

In the same manner as in Production Examples 99 and 100 except that 3,4-(methylenedioxy)phenol was used as a material, the following phenyl 2-methyl-3-(3,4-(methylenedioxy)phenyloxy)-N-phenyl-2-propenimidate (hereinafter referred to as the present compound 101) and the following 3,4-(methylenedioxy)phenyl 2-methyl-3-(3,4-(methylenedioxy)phenyloxy)-N-phenyl-2-propenimidate (hereinafter referred to as the present compound 102) were obtained.

Phenyl 2-methyl-3-(3,4-(methylenedioxy)phenyloxy)-N-phenyl-2-propenimidate

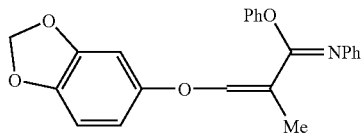

¹H-NMR (DMSO-D₆, 50° C.) δ: 1.89 (3H, br s), 5.99 (2H, s), 6.27-6.37 (1H, m), 6.54-6.61 (1H, m), 6.79 (1H, d, J=8.5 Hz), 6.83-7.40 (11H, m).

3,4-(Methylenedioxy)phenyl 2-methyl-3-(3,4-(methylenedioxy)phenyloxy)-N-phenyl-2-propenimidate

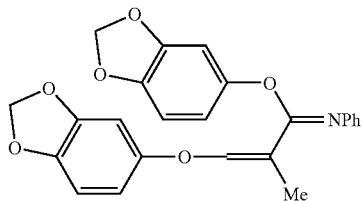

¹H-NMR (DMSO-D₆, 50° C.) δ: 1.82 (3H, br s), 5.96 (2H, s), 6.00 (2H, s), 6.34 (1H, d, J=7.3 Hz), 6.47 (1H, br), 6.58 (1H, br), 6.71 (1H, br), 6.76-6.89 (4H, m), 6.98 (1H, t, J=7.6 Hz), 7.14 (1H, br), 7.23 (2H, t, J=7.6 Hz).

Production Example 103

In the same manner as in Production Example 21 except that (E)-2-methyl-3-phenoxy-N-phenyl-2-propenamide and 4-methylthiophenol were used as materials, the following 4-methylphenyl 2-methyl-3-phenoxy-N-phenyl-2-propenimidothioate (hereinafter referred to as the present compound 103) was obtained.

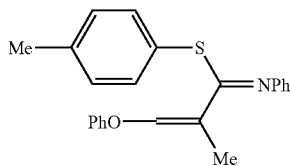

¹H-NMR (DMSO-D₆, 50° C.) δ: 1.89 (3H, br s), 2.29 (3H, s), 6.74 (2H, d, J=8.0 Hz), 6.80 (2H, d, J=8.5 Hz), 7.06 (1H, t, J=7.4 Hz), 7.12 (1H, t, J=7.5 Hz), 7.14-7.25 (4H, br m), 7.26-7.34 (4H, m), 7.36 (1H, br s).

Production Example 104

In the same manner as in Production Example 14 except that (E)-2-methyl-N-(2-methylphenyl)-3-phenoxy-2-propenamide wase used as materials, the following phenyl 2-methyl-N-(2-methylphenyl)-3-phenoxy-2-propenimidothioate (hereinafter referred to as the present compound 104) was obtained.

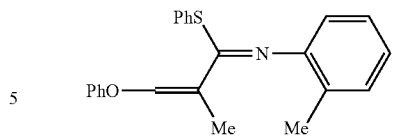

¹H-NMR (DMSO-D₆) δ: 1.94 (3H, br s), 2.07 (3H, s), 6.69 (1H, d, J=7.6 Hz), 6.74 (2H, d, J=8.0 Hz), 6.97 (1H, t, J=7.0 Hz), 7.08-7.18 (3H, m), 7.25-7.44 (8H, m).

Production Example 105

In the same manner as in Production Example 14 except that (E)-N-(4-ethylphenyl)-2-methyl-3-phenoxy-2-propenamide was used as a material, the following phenyl N-(4-ethylphenyl)-2-methyl-3-phenoxy-2-propenimidothioate (hereinafter referred to as the present compound 105) was obtained.

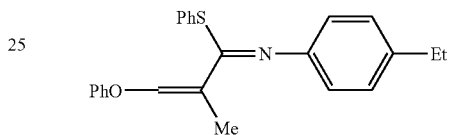

¹H-NMR (DMSO-D₆, 50° C.) δ: 1.18 (3H, t, J=7.6 Hz), 1.93 (3H, br s), 2.57 (2H, q, J=7.6 Hz), 6.73 (4H, d, J=8.0 Hz), 7.10 (1H, t, J=7.6 Hz), 7.13 (2H, d, J=8.0 Hz), 7.21-7.37 (7H, m), 7.42 (1H, br s).

Production Example 106

In the same manner as in Production Example 14 except that (E)-N-(4-isopropylphenyl)-2-methyl-3-phenoxy-2-propenamide was used as a material, the following phenyl N-(4-isopropylphenyl)-2-methyl-3-phenoxy-2-propenimidothioate (hereinafter referred to as the present compound 106) was obtained.

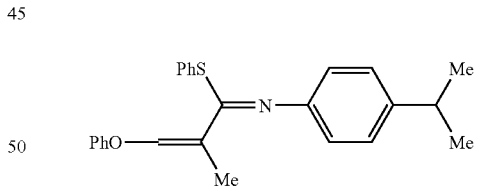

¹H-NMR (DMSO-D₆, 50° C.) δ: 1.19 (6H, d, J=7.1 Hz), 1.94 (3H, br s), 2.85 (1H, quint, J=7.1 Hz), 6.74 (4H, d, J=8.0 Hz), 7.11 (1H, t, J=7.4 Hz), 7.15 (2H, d, J=8.3 Hz), 7.20-7.36 (7H, m), 7.44 (1H, br s).

Production Example 107

In the same manner as in Production Example 14 except that (E)-2-methyl-3-(2-methylphenyloxy)-N-phenyl-2-propenamide was used as materials, the following phenyl 2-methyl-3-(2-methylphenyloxy)-N-phenyl-2-propenimidothioate (hereinafter referred to as the present compound 107) was obtained.

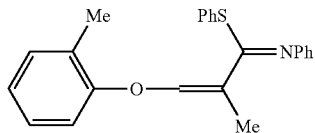

¹H-NMR (DMSO-D$_6$, 50° C.) δ: 1.95 (3H, br s), 2.13 (3H, s), 6.44 (1H, d, J=7.3 Hz), 6.80 (2H, d, J=7.3 Hz), 6.99-7.13 (3H, m), 7.21 (1H, d, J=7.3 Hz), 7.24-7.43 (8H, m).

Production Example 108

In the same manner as in Production Example 14 except that (E)-2-methyl-3-(3-methylphenyloxy)-N-phenyl-2-propenamide and thiophenol were used as materials, the following phenyl 2-methyl-3-(3-methylphenyloxy)-N-phenyl-2-propenimidothioate (hereinafter referred to as the present compound 108) was obtained.

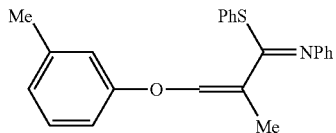

¹H-NMR (DMSO-D$_6$, 50° C.) δ: 1.92 (3H, br s), 2.26 (3H, s), 6.51 (1H, s), 6.56 (1H, d, J=8.0 Hz), 6.81 (2H, d, J=7.6 Hz), 6.93 (1H, d, J=7.6 Hz), 7.06 (1H, t, J=7.3 Hz), 7.18 (1H, t, J=8.0 Hz), 7.25-7.38 (8H, m).

Production Example 109

In the same manner as in Production Example 21 except that (E)-2-methyl-3-(3-methylphenyloxy)-N-phenyl-2-propenamide and 3-methylthiophenol were used as materials, the following 3-methylphenyl 2-methyl-3-(3-methylphenyloxy)-N-phenyl-2-propenimidothioate (hereinafter referred to as the present compound 109) was obtained.

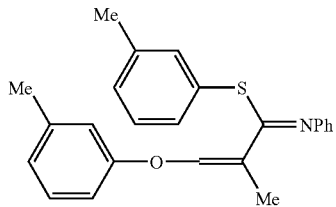

¹H-NMR (DMSO-D$_6$, 50° C.) δ: 1.92 (3H, br s), 2.25 (3H, s), 2.26 (3H, s), 6.56 (2H, s), 6.80 (2H, d, J=8.3 Hz), 6.93 (1H, d, J=7.6 Hz), 7.02-7.15 (4H, m), 7.15-7.25 (2H, m), 7.29 (2H, t, J=7.7 Hz), 7.42 (1H, s).

Production Example 110

In the same manner as in Production Example 14 except that (E)-2-methyl-N-(4-methylphenyl)-3-(3-methylphenyloxy)-2-propenamide was used as materials, the following phenyl 2-methyl-N-(4-methylphenyl)-3-(3-methylphenyloxy)-2-propenimidothioate (hereinafter referred to as the present compound 110) was obtained.

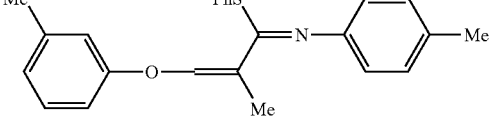

¹H-NMR (DMSO-D$_6$, 50° C.) δ: 1.92 (3H, br s), 2.25 (3H, s), 2.27 (3H, s), 6.49 (1H, s), 6.54 (1H, d, J=8.0 Hz), 6.72 (2H, d, J=8.2 Hz), 6.92 (1H, d, J=7.3 Hz), 7.11 (2H, d, J=8.2 Hz), 7.17 (1H, t, J=7.8 Hz), 7.22-7.42 (6H, m).

Production Example 111

In the same manner as in Production Example 21 except that (E)-2-methyl-N-(4-methylphenyl)-3-(3-methylphenyloxy)-2-propenamide and 3-methylthiophenol were used as materials, the following 3-methylphenyl 2-methyl-N-(4-methylphenyl)-3-(3-methylphenyloxy)-2-propenimidothioate (hereinafter referred to as the present compound III) was obtained.

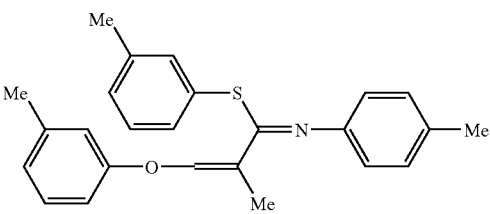

¹H-NMR (DMSO-D$_6$, 50° C.) δ: 1.92 (3H, br s), 2.25 (3H, s), 2.26 (3H, s), 2.27 (3H, s), 6.50-6.58 (2H, m), 6.70 (2H, d, J=8.0 Hz), 6.93 (1H, d, J=7.3 Hz), 7.04-7.14 (5H, m), 7.15-7.26 (2H, m), 7.39 (1H, s).

Production Example 112

In the same manner as in Production Example 14 except that (E)-N-(4-methoxyphenyl)-2-methyl-3-(3-methylphenyloxy)-2-propenamide was used as materials, the following phenyl N-(4-methoxyphenyl)-2-methyl-3-(3-methylphenyloxy)-2-propenimidothioate (hereinafter referred to as the present compound 112) was obtained.

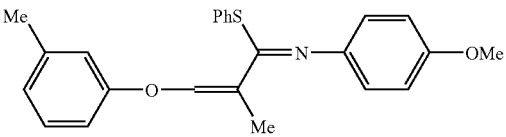

¹H-NMR (DMSO-D$_6$, 50° C.) δ: 1.95 (3H, br s), 2.26 (3H, s), 3.73 (3H, s), 6.49 (1H, s), 6.55 (1H, d, J=7.1 Hz), 6.79 (2H, d, J=8.8 Hz), 6.84-6.95 (3H, m), 7.17 (1H, t, J=7.9 Hz), 7.21-7.45 (6H, m).

Production Example 113

In the same manner as in Production Example 14 except that (E)-N-(4-methoxyphenyl)-2-methyl-3-(4-methylphenyloxy)-2-propenamide was used as materials, the following phenyl N-(4-methoxyphenyl)-2-methyl-3-(4-methylphenyloxy)-2-propenimidothioate (hereinafter referred to as the present compound 113) was obtained.

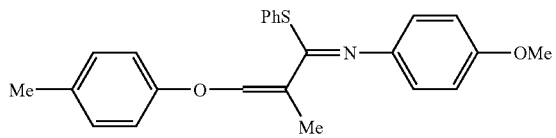

¹H-NMR (DMSO-D$_6$, 50° C.) δ: 1.93 (3H, br s), 2.25 (3H, s), 3.73 (3H, s), 6.61 (2H, d, J=6.3 Hz), 6.78 (2H, d, J=8.9 Hz), 6.88 (2H, d, J=8.9 Hz), 7.09 (2H, d, J=8.0 Hz), 7.19-7.43 (6H, m).

Production Example 114

In the same manner as in Production Example 14 except that (E)-3-(4-ethylphenyloxy)-2-methyl-N-phenyl-2-propenamide was used as materials, the following phenyl 3-(4-ethylphenyloxy)-2-methyl-N-phenyl-2-propenimidothioate (hereinafter referred to as the present compound 114) was obtained.

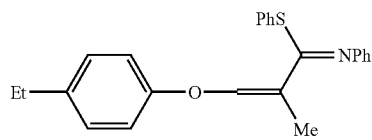

¹H-NMR (DMSO-D$_6$, 50° C.) δ: 1.15 (3H, t, J=7.7 Hz), 1.91 (3H, br s), 2.56 (2H, q, J=7.7 Hz), 6.65 (2H, d, J=8.5 Hz), 6.80 (2H, d, J=8.3 Hz), 7.05 (1H, t, J=7.4 Hz), 7.13 (2H, d, J=8.5 Hz), 7.23-7.45 (8H, m).

Production Example 115

In the same manner as in Production Example 14 except that (E)-3-(4-isopropylphenyloxy)-2-methyl-N-phenyl-2-propenamide was used as materials, the following phenyl 3-(4-isopropylphenyloxy)-2-methyl-N-phenyl-2-propenimidothioate (hereinafter referred to as the present compound 115) was obtained.

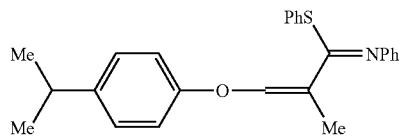

¹H-NMR (DMSO-D$_6$, 50° C.) δ: 1.17 (6H, d, J=7.1 Hz), 1.91 (3H, br s), 2.80-2.92 (1H, m), 6.67 (2H, d, J=8.7 Hz), 6.80 (2H, d, J=8.3 Hz), 7.05 (1H, t, J=7.3 Hz), 7.16 (2H, d, J=8.7 Hz), 7.21-7.48 (8H, m).

Production Example 116

In the same manner as in Production Example 14 except that (E)-3-(2-methoxyphenyloxy)-2-methyl-N-phenyl-2-propenamide was used as materials, the following phenyl 3-(2-methoxyphenyloxy)-2-methyl-N-phenyl-2-propenimidothioate (hereinafter referred to as the present compound 116) was obtained.

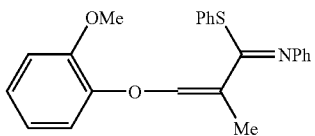

¹H-NMR (DMSO-D$_6$, 50° C.) δ: 1.92 (3H, br s), 3.75 (3H, s), 6.57 (1H, d, J=7.8 Hz), 6.75-6.80 (2H, m), 6.82-6.87 (1H, m), 7.01-7.13 (3H, m), 7.18-7.40 (8H, m).

Production Example 117

In the same manner as in Production Example 21 except that (E)-3-(2-methoxyphenyloxy)-2-methyl-N-phenyl-2-propenamide and 3-methylthiophenol were used as materials, the following 3-methylphenyl 3-(2-methoxyphenyloxy)-2-methyl-N-phenyl-2-propenimidothioate (hereinafter referred to as the present compound 117) was obtained.

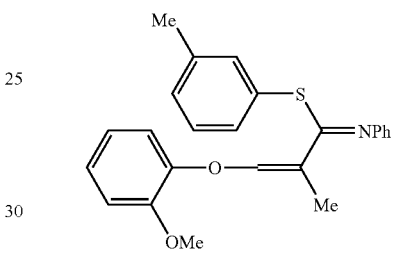

¹H-NMR (DMSO-D$_6$, 50° C.) δ: 1.92 (3H, br s), 2.23 (3H, s), 3.76 (3H, s), 6.56 (1H, d, J=7.6 Hz), 6.77 (2H, d, J=7.3 Hz), 6.82-6.87 (1H, m), 6.99-7.13 (6H, m), 7.19 (1H, t, J=7.4 Hz), 7.27 (2H, dd, J=8.2, 7.4 Hz), 7.32-7.40 (1H, br).

Production Example 118

In the same manner as in Production Example 14 except that (E)-3-(2-methoxyphenyloxy)-2-methyl-N-(4-methylphenyl)-2-propenamide was used as materials, the following phenyl 3-(2-methoxyphenyloxy)-2-methyl-N-(4-methylphenyl)-2-propenimidothioate (hereinafter referred to as the present compound 118) was obtained.

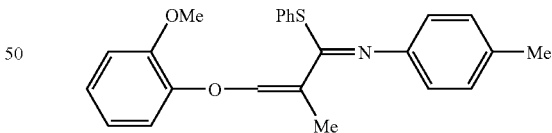

¹H-NMR (DMSO-D$_6$, 50° C.) δ: 1.92 (3H, br s), 2.26 (3H, s), 3.74 (3H, s), 6.50-6.58 (1H, br m), 6.69 (2H, d, J=8.0 Hz), 6.80-6.86 (1H, m), 7.04-7.13 (4H, m), 7.18-7.41 (6H, m).

Production Example 119

In the same manner as in Production Example 21 except that (E)-3-(2-methoxyphenyloxy)-2-methyl-N-(4-methylphenyl)-2-propenamide and 3-methylthiophenol were used as materials, the following 3-methylphenyl 3-(2-methoxyphenyloxy)-2-methyl-N-(4-methylphenyl)-2-propenimidothioate (hereinafter referred to as the present compound 119) was obtained.

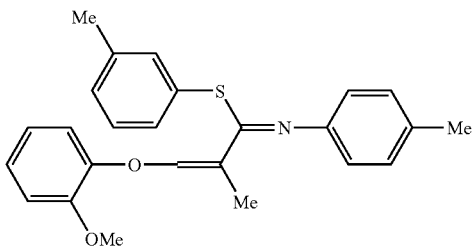

$^1$H-NMR (DMSO-D$_6$, 50° C.) δ: 1.92 (3H, br s), 2.23 (3H, s), 2.26 (3H, s), 3.75 (3H, s), 6.53 (1H, d, J=7.3 Hz), 6.67 (2H, d, J=8.3 Hz), 6.71-6.79 (2H, m), 6.81-6.87 (1H, m), 6.88-6.92 (1H, m), 6.97-7.12 (4H, m), 7.19 (1H, t, J=7.4 Hz), 7.26-7.39 (1H, br).

Production Example 120

In the same manner as in Production Example 14 except that (E)-N-(4-methoxyphenyl)-3-(2-methoxyphenyloxy)-2-methyl-2-propenamide was used as materials, the following phenyl N-(4-methoxyphenyl)-3-(2-methoxyphenyloxy)-2-methyl-2-propenimidothioate (hereinafter referred to as the present compound 120) was obtained.

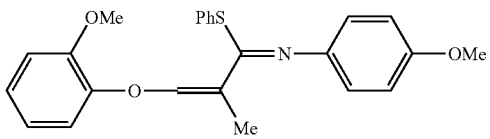

$^1$H-NMR (DMSO-D$_6$, 50° C.) δ: 1.94 (3H, br s), 3.73 (3H, s), 3.74 (3H, s), 6.49-6.60 (1H, br), 6.76 (2H, d, J=9.0 Hz), 6.80-6.91 (3H, m), 7.04-7.13 (2H, m), 7.16-7.46 (6H, m).

Production Example 121

In the same manner as in Production Example 14 except that (E)-N-(3,4-dimethylphenyl)-3-(2-methoxyphenyloxy)-2-methyl-2-propenamide was used as materials, the following phenyl N-(3,4-dimethylphenyl)-3-(2-methoxyphenyloxy)-2-methyl-2-propenimidothioate (hereinafter referred to as the present compound 121) was obtained.

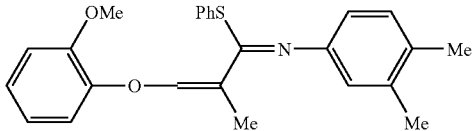

$^1$H-NMR (DMSO-D$_6$, 50° C.) δ: 1.92 (3H, br s), 2.17 (6H, s), 3.74 (3H, s), 6.48-6.59 (3H, m), 6.80-6.86 (1H, m), 7.00-7.12 (3H, m), 7.18-7.38 (6H, m).

Production Example 122

In the same manner as in Production Example 14 except that (E)-3-(3-methoxyphenyloxy)-2-methyl-N-phenyl-2-propenamide was used as materials, the following phenyl 3-(3-methoxyphenyloxy)-2-methyl-N-phenyl-2-propenimidothioate (hereinafter referred to as the present compound 122) was obtained.

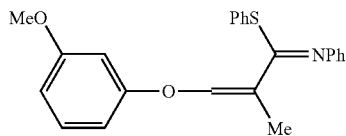

$^1$H-NMR (DMSO-D$_6$) δ: 1.92 (3H, br s), 3.74 (3H, s), 6.29 (1H, d, J=7.3 Hz), 6.46 (1H, t, J=2.2 Hz), 6.70 (1H, dd, J=8.3, 2.2 Hz), 6.81 (2H, d, J=7.6 Hz), 7.05 (1H, t, J=7.3 Hz), 7.20 (1H, t, J=8.3 Hz), 7.24-7.37 (7H, m), 7.45 (1H, br s).

Production Example 123

In the same manner as in Production Example 21 except that (E)-3-(3-methoxyphenyloxy)-2-methyl-N-phenyl-2-propenamide and 3-methylthiophenol were used as materials, the following 3-methylphenyl 3-(3-methoxyphenyloxy)-2-methyl-N-phenyl-2-propenimidothioate (hereinafter referred to as the present compound 123) was obtained.

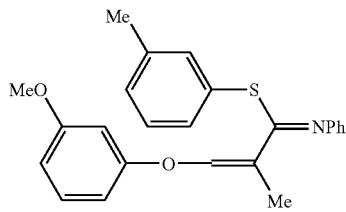

$^1$H-NMR (DMSO-D$_6$, 50° C.) δ: 1.91 (3H, br s), 2.25 (3H, s), 3.74 (3H, s), 6.29 (1H, d, J=8.3 Hz), 6.44 (1H, t, J=2.4 Hz), 6.70 (1H, dd, J=8.3, 2.4 Hz), 6.80 (2H, d, J=8.3 Hz), 6.99-7.16 (4H, m), 7.20 (2H, t, J=8.3 Hz), 7.29 (2H, t, J=7.8 Hz), 7.44 (1H, br s).

Production Example 124

In the same manner as in Production Example 14 except that (E)-3-(3-methoxyphenyloxy)-2-methyl-N-(4-methylphenyl)-2-propenamide was used as materials, the following phenyl 3-(3-methoxyphenyloxy)-2-methyl-N-(4-methylphenyl)-2-propenimidothioate (hereinafter referred to as the present compound 124) was obtained.

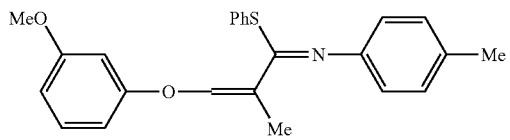

$^1$H-NMR (DMSO-D$_6$, 50° C.) δ: 1.91 (3H, br s), 2.27 (3H, s), 3.73 (3H, s), 6.26 (1H, d, J=6.3 Hz), 6.44 (1H, t, J=2.2 Hz), 6.65-6.75 (3H, m), 7.10 (2H, d, J=8.0 Hz), 7.19 (1H, t, J=8.3 Hz), 7.24-7.49 (6H, m).

Production Example 125

In the same manner as in Production Example 21 except that (E)-3-(3-methoxyphenyloxy)-2-methyl-N-(4-methylphenyl)-2-propenamide and 3-methylthiophenol were used as materials, the following 3-methylphenyl 3-(3-methoxyphenyloxy)-2-methyl-N-(4-methylphenyl)-2-propenimidothioate (hereinafter referred to as the present compound 125) was obtained.

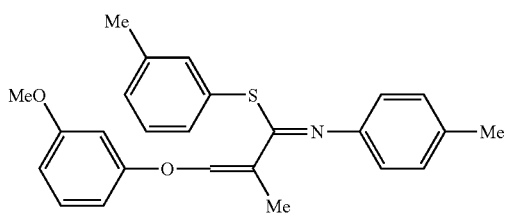

$^1$H-NMR (DMSO-D$_6$, 50° C.) δ: 1.91 (3H, br s), 2.25 (3H, s), 2.27 (3H, s), 3.74 (3H, s), 6.27 (1H, d, J=7.3 Hz), 6.42 (1H, t, J=2.3 Hz), 6.67-6.74 (3H, m), 7.02-7.14 (5H, m), 7.16-7.24 (2H, m), 7.42 (1H, br s).

Production Example 126

In the same manner as in Production Example 14 except that (E)-3-(4-methoxyphenyloxy)-2-methyl-N-phenyl-2-propenamide was used as materials, the following phenyl 3-(4-methoxyphenyloxy)-2-methyl-N-phenyl-2-propenimidothioate (hereinafter referred to as the present compound 126) was obtained.

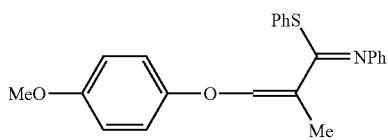

$^1$H-NMR (DMSO-D$_6$, 50° C.) δ: 1.91 (3H, br s), 3.72 (3H, s), 6.69 (2H, d, J=8.9 Hz), 6.79 (2H, d, J=7.4 Hz), 6.86 (2H, d, J=8.9 Hz), 7.05 (1H, t, J=7.4 Hz), 7.22-7.41 (8H, m).

Production Example 127

In the same manner as in Production Example 21 except that (E)-3-(4-methoxyphenyloxy)-2-methyl-N-phenyl-2-propenamide and 3-methylthiophenol were used as materials, the following 3-methylphenyl 3-(4-methoxyphenyloxy)-2-methyl-N-phenyl-2-propenimidothioate (hereinafter referred to as the present compound 127) was obtained.

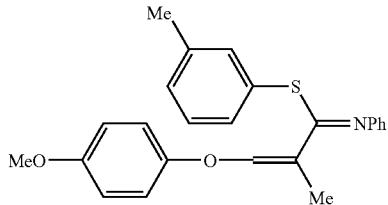

$^1$H-NMR (DMSO-D$_6$, 50° C.) δ: 1.90 (3H, br s), 2.25 (3H, s), 3.73 (3H, s), 6.70 (2H, d, J=9.2 Hz), 6.78 (2H, d, J=7.3 Hz), 6.86 (2H, d, J=9.2 Hz), 7.00-7.13 (4H, m), 7.22 (1H, t, J=7.6 Hz), 7.28 (2H, dd, J=8.3, 7.6 Hz), 7.35 (1H, s).

Production Example 128

In the same manner as in Production Example 21 except that (E)-3-(4-methoxyphenyloxy)-2-methyl-N-phenyl-2-propenamide and 4-methylthiophenol were used as materials, the following 4-methylphenyl 3-(4-methoxyphenyloxy)-2-methyl-N-phenyl-2-propenimidothioate (hereinafter referred to as the present compound 128) was obtained.

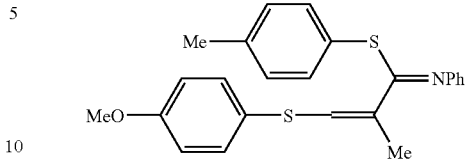

$^1$H-NMR (DMSO-D$_6$, 50° C.) δ: 1.88 (3H, br s), 2.29 (3H, s), 3.73 (3H, s), 6.70 (2H, d, J=8.8 Hz), 6.79 (2H, d, J=7.5 Hz), 6.86 (2H, d, J=8.8 Hz), 7.05 (1H, t, J=7.5 Hz), 7.10-7.24 (4H, m), 7.25-7.33 (3H, m).

Production Example 129

In the same manner as in Production Example 14 except that (E)-3-(4-methoxyphenyloxy)-2-methyl-N-(4-methylphenyl)-2-propenamide was used as materials, the following phenyl 3-(4-methoxyphenyloxy)-2-methyl-N-(4-methylphenyl)-2-propenimidothioate (hereinafter referred to as the present compound 129) was obtained.

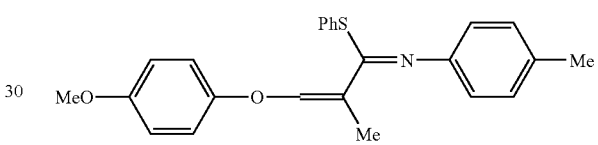

$^1$H-NMR (DMSO-D$_6$, 50° C.) δ: 1.91 (3H, br s), 2.27 (3H, s), 3.72 (3H, s), 6.61-6.76 (4H, m), 6.85 (2H, d, J=9.0 Hz), 7.10 (2H, d, J=8.0 Hz), 7.19-7.44 (6H, m).

Production Example 130

In the same manner as in Production Example 21 except that (E)-3-(4-methoxyphenyloxy)-2-methyl-N-(4-methylphenyl)-2-propenamide and 3-methylthiophenol were used as materials, the following 3-methylphenyl 3-(4-methoxyphenyloxy)-2-methyl-N-(4-methylphenyl)-2-propenimidothioate (hereinafter referred to as the present compound 130) was obtained.

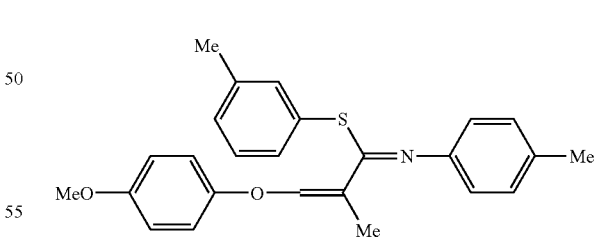

$^1$H-NMR (DMSO-D$_6$, 50° C.) δ: 1.90 (3H, br s), 2.25 (3H, s), 2.26 (3H, s), 3.73 (3H, s), 6.63-6.75 (4H, m), 6.85 (2H, d, J=9.0 Hz), 7.00-7.15 (5H, m), 7.22 (1H, t, J=7.6 Hz), 7.33 (1H, br s).

Production Example 131

In the same manner as in Production Example 21 except that (E)-3-(4-methoxyphenyloxy)-2-methyl-N-(4-methylphenyl)-2-propenamide and 4-methylthiophenol were used as materials, the following 4-methylphenyl 3-(4-methoxyphenyloxy)-2-methyl-N-(4-methylphenyl)-2-propenimidothioate (hereinafter referred to as the present compound 131) was obtained.

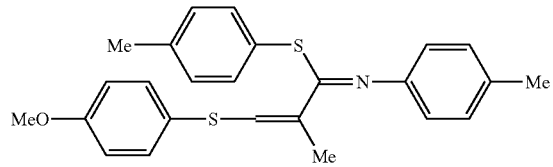

¹H-NMR (DMSO-D₆, 50° C.) δ: 1.88 (3H, br s), 2.27 (3H, s), 2.29 (3H, s), 3.73 (3H, s), 6.60-6.77 (4H, m), 6.85 (2H, d, J=9.0 Hz), 6.99-7.37 (8H, m).

Production Example 132

In the same manner as in Production Example 14 except that (E)-3-(4-ethoxyphenyloxy)-2-methyl-N-phenyl-2-propenamide was used as materials, the following phenyl 3-(4-ethoxyphenyloxy)-2-methyl-N-phenyl-2-propenimidothioate (hereinafter referred to as the present compound 132) was obtained.

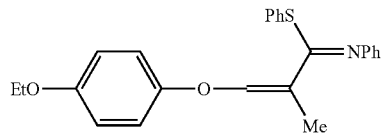

¹H-NMR (DMSO-D₆, 50° C.) δ: 1.30 (3H, t, J=7.0 Hz), 1.90 (3H, br s), 3.98 (2H, q, J=7.0 Hz), 6.67 (2H, d, J=8.9 Hz), 6.79 (2H, d, J=7.6 Hz), 6.84 (2H, d, J=8.9 Hz), 7.05 (1H, t, J=7.4 Hz), 7.20-7.42 (8H, m).

Production Example 133

In the same manner as in Production Example 14 except that (E)-2-methyl-N-phenyl-3-(4-phenylphenyloxy)-2-propenamide was used as materials, the following phenyl 2-methyl-N-phenyl-3-(4-phenylphenyloxy)-2-propenimidothioate (hereinafter referred to as the present compound 133) was obtained.

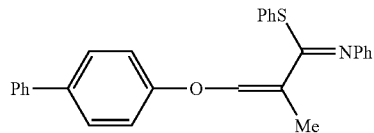

¹H-NMR (DMSO-D₆, 50° C.) δ: 1.94 (3H, br s), 6.78-6.89 (4H, m), 7.07 (1H, t, J=7.3 Hz), 7.23-7.53 (11H, m), 7.55-7.65 (4H, m).

Production Example 134

In the same manner as in Production Example 14 except that (E)-2-methyl-3-(4-phenoxyphenyloxy)-N-phenyl-2-propenamide was used as materials, the following phenyl 2-methyl-3-(4-phenoxyphenyloxy)-N-phenyl-2-propenimidothioate (hereinafter referred to as the present compound 134) was obtained.

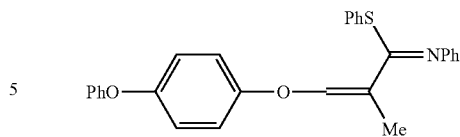

¹H-NMR (DMSO-D₆, 50° C.) δ: 1.92 (3H, br s), 6.75-6.84 (4H, m), 6.93-7.01 (4H, m), 7.05 (1H, t, J=7.4 Hz), 7.12 (1H, t, J=7.3 Hz), 7.22-7.50 (10H, m).

Production Example 135

In the same manner as in Production Example 14 except that (E)-3-(3,4-dimethylphenyloxy)-2-methyl-N-phenyl-2-propenamide was used as materials, the following phenyl 3-(3,4-dimethylphenyloxy)-2-methyl-N-phenyl-2-propenimidothioate (hereinafter referred to as the present compound 135) was obtained.

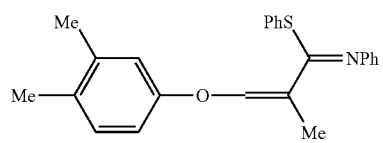

¹H-NMR (DMSO-D₆, 50° C.) δ: 1.92 (3H, br s), 2.16 (3H, s), 2.16 (3H, s), 6.47 (1H, d, J=8.3 Hz), 6.52 (1H, s), 6.80 (2H, d, J=8.3 Hz), 7.05 (2H, t, J=8.8 Hz), 7.20-7.46 (8H, m).

Production Example 136

In the same manner as in Production Example 14 except that (E)-3-(5-indolyloxy)-2-methyl-N-phenyl-2-propenamide was used as materials, the following phenyl 3-(5-indolyloxy)-2-methyl-N-phenyl-2-propenimidothioate (hereinafter referred to as the present compound 136) was obtained.

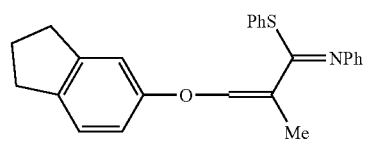

¹H-NMR (DMSO-D₆, 50° C.) δ: 1.92 (3H, s), 1.96-2.06 (2H, m), 2.73-2.86 (4H, m), 6.45 (1H, s), 6.51 (1H, d, J=8.2 Hz), 6.80 (2H, d, J=7.3 Hz), 7.06 (1H, t, J=7.3 Hz), 7.11 (1H, d, J=8.2 Hz), 7.22-7.43 (8H, m).

Production Example 137

In the same manner as in Production Example 21 except that (E)-2-methyl-3-phenoxy-N-phenyl-2-propenamide and 2-methylphenol were used as materials, the following 2-methylphenyl 2-methyl-3-phenoxy-N-phenyl-2-propenimidate (hereinafter referred to as the present compound 137) was obtained.

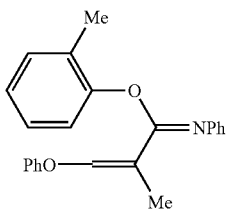

$^1$H-NMR (DMSO-D$_6$, 50° C.) δ: 1.89 (3H, br s), 2.19 (3H, br s), 6.82 (2H, d, J=7.7 Hz), 6.86 (2H, d, J=7.0 Hz), 6.92-7.05 (3H, m), 7.07-7.26 (6H, m), 7.32 (2H, t, J=7.7 Hz).

Production Example 138

In the same manner as in Production Example 21 except that (E)-2-methyl-3-phenoxy-N-phenyl-2-propenamide and 3-methylphenol were used as materials, 3-methylphenyl 2-methyl-3-phenoxy-N-phenyl-2-propenimidate (hereinafter referred to as the present compound 138) was obtained.

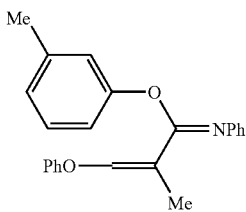

$^1$H-NMR (DMSO-D$_6$, 50° C.) δ: 1.92 (3H, br s), 2.25 (3H, s), 6.72-6.94 (7H, br m), 6.98 (1H, t, J=7.4 Hz), 7.09-7.29 (5H, m), 7.32 (2H, dd, J=8.5, 7.4 Hz).

Production Example 139

In the same manner as in Production Example 21 except that (E)-2-methyl-3-phenoxy-N-phenyl-2-propenamide and 4-methylphenol were used as materials, the following 4-methylphenyl 2-methyl-3-phenoxy-N-phenyl-2-propenimidate (hereinafter referred to as the present compound 139) was obtained.

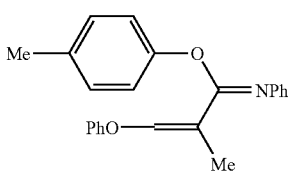

$^1$H-NMR (DMSO-D$_6$, 50° C.) δ: 1.90 (3H, s), 2.23 (3H, s), 6.82-6.95 (6H, m), 6.98 (1H, t, J=7.3 Hz), 7.05-7.16 (3H, m), 7.18-7.27 (3H, m), 7.32 (2H, t, J=7.9 Hz).

Production Example 140

In the same manner as in Production Example 21 except that (E)-2-methyl-3-phenoxy-N-phenyl-2-propenamide and 3-ethylphenol were used as materials, the following 3-ethylphenyl 2-methyl-3-phenoxy-N-phenyl-2-propenimidate (hereinafter referred to as the present compound 140) was obtained.

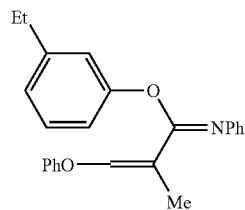

$^1$H-NMR (DMSO-D$_6$, 50° C.) δ: 1.12 (3H, t, J=7.4 Hz), 1.92 (3H, br s), 2.55 (2H, q, J=7.4 Hz), 6.74-7.01 (8H, m), 7.12 (1H, t, J=7.4 Hz), 7.15-7.25 (3H, m), 7.27 (1H, br s), 7.32 (2H, t, J=7.9 Hz).

Production Example 141

In the same manner as in Production Example 21 except that (E)-2-methyl-3-phenoxy-N-phenyl-2-propenamide and 2-fluorophenol were used as materials, the following 2-fluorophenyl 2-methyl-3-phenoxy-N-phenyl-2-propenimidate (hereinafter referred to as the present compound 141) was obtained.

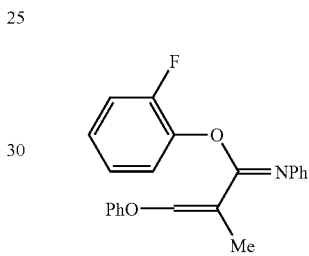

$^1$H-NMR (DMSO-D$_6$, 50° C.) δ: 1.83 (3H, br s), 6.80 (2H, d, J=7.6 Hz), 6.87 (2H, d, J=7.8 Hz), 6.99 (1H, t, J=7.4 Hz), 7.09-7.37 (10H, m).

Production Example 142

In the same manner as in Production Example 21 except that (E)-2-methyl-3-phenoxy-N-phenyl-2-propenamide and 3-fluorophenol were used as materials, the following 3-fluorophenyl 2-methyl-3-phenoxy-N-phenyl-2-propenimidate (hereinafter referred to as the present compound 142) was obtained.

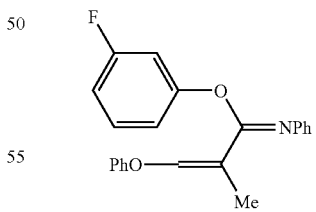

$^1$H-NMR (DMSO-D$_6$, 50° C.) δ: 1.93 (3H, br s), 6.78-7.03 (8H, m), 7.13 (1H, t, J=7.4 Hz), 7.23 (2H, t, J=7.8 Hz), 7.27-7.39 (4H, m).

Production Example 143

In the same manner as in Production Example 21 except that (E)-2-methyl-3-phenoxy-N-phenyl-2-propenamide and 4-fluorophenol were used as materials, the following 4-fluorophenyl 2-methyl-3-phenoxy-N-phenyl-2-propenimidate (hereinafter referred to as the present compound 143) was obtained.

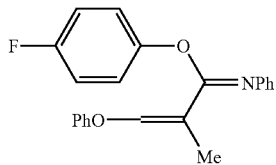

$^1$H-NMR (DMSO-D$_6$, 50° C.) δ: 1.88 (3H, br s), 6.85 (2H, d, J=7.6 Hz), 6.91 (2H, d, J=7.8 Hz), 6.98 (1H, t, J=7.6 Hz), 7.03-7.17 (5H, m), 7.22 (2H, t, J=7.6 Hz), 7.27-7.39 (3H, m).

Production Example 144

In the same manner as in Production Example 21 except that (E)-2-methyl-3-phenoxy-N-phenyl-2-propenamide and 2-chlorophenol were used as materials, the following 2-chlorophenyl 2-methyl-3-phenoxy-N-phenyl-2-propenimidate (hereinafter referred to as the present compound 144) was obtained.

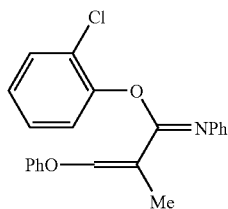

$^1$H-NMR (DMSO-D$_6$, 50° C.) δ: 1.86 (3H, br s), 6.83 (2H, d, J=7.6 Hz), 6.87 (2H, d, J=7.8 Hz), 6.99 (1H, t, J=7.4 Hz), 7.09-7.37 (9H, m), 7.47 (1H, d, J=7.8 Hz).

Production Example 145

In the same manner as in Production Example 21 except that (E)-2-methyl-3-phenoxy-N-phenyl-2-propenamide and 3-chlorophenol were used as materials, the following 3-chlorophenyl 2-methyl-3-phenoxy-N-phenyl-2-propenimidate (hereinafter referred to as the present compound 145) was obtained.

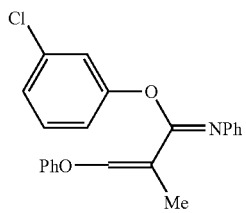

$^1$H-NMR (DMSO-D$_6$, 50° C.) δ: 1.92 (3H, br s), 6.88 (2H, d, J=7.6 Hz), 6.91-7.04 (4H, m), 7.06-7.17 (3H, m), 7.23 (2H, t, J=7.7 Hz), 7.27-7.39 (4H, m).

Production Example 146

In the same manner as in Production Example 21 except that (E)-2-methyl-3-phenoxy-N-phenyl-2-propenamide and 4-chlorophenol were used as materials, the following 4-chlorophenyl 2-methyl-3-phenoxy-N-phenyl-2-propenimidate (hereinafter referred to as the present compound 146) was obtained.

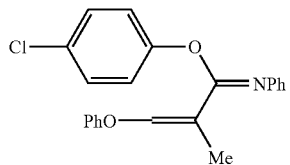

$^1$H-NMR (DMSO-D$_6$, 50° C.) δ: 1.91 (3H, br s), 6.87 (2H, d, J=7.6 Hz), 6.93 (2H, d, J=6.6 Hz), 6.99 (2H, t, J=7.5 Hz), 7.06 (1H, br s), 7.13 (1H, t, J=7.5 Hz), 7.23 (2H, t, J=7.5 Hz), 7.27-7.42 (5H, m).

Production Example 147

In the same manner as in Production Example 21 except that (E)-2-methyl-3-phenoxy-N-phenyl-2-propenamide and 3-bromophenol were used as materials, the following 3-bromophenyl 2-methyl-3-phenoxy-N-phenyl-2-propenimidate (hereinafter referred to as the present compound 147) was obtained.

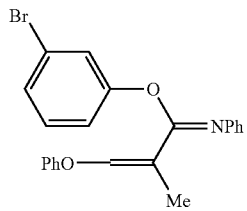

$^1$H-NMR (DMSO-D$_6$, 50° C.) δ: 1.91 (3H, br s), 6.87 (2H, d, J=7.3 Hz), 6.94 (2H, d, J=7.3 Hz), 6.99 (1H, t, J=7.4 Hz), 7.06 (1H, br s), 7.13 (1H, t, J=7.4 Hz), 7.19-7.40 (8H, m).

Production Example 148

In the same manner as in Production Example 21 except that (E)-2-methyl-3-phenoxy-N-phenyl-2-propenamide and 3-methoxyphenol were used as materials, the following 3-methoxyphenyl 2-methyl-3-phenoxy-N-phenyl-2-propenimidate (hereinafter referred to as the present compound 148) was obtained.

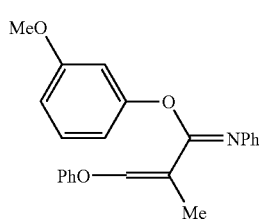

$^1$H-NMR (DMSO-D$_6$, 50° C.) δ: 1.93 (3H, br s), 3.70 (3H, s), 6.49-6.70 (3H, m), 6.85-6.95 (4H, m), 6.99 (1H, t, J=7.3 Hz), 7.09-7.26 (4H, m), 7.28-7.39 (3H, m).

Production Example 149

In the same manner as in Production Example 21 except that (E)-2-methyl-3-phenoxy-N-phenyl-2-propenamide and 4-methoxyphenol were used as materials, the following 4-methoxyphenyl 2-methyl-3-phenoxy-N-phenyl-2-propenimidate (hereinafter referred to as the present compound 149) was obtained.

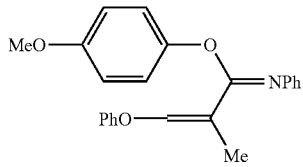

$^1$H-NMR (DMSO-D$_6$, 50° C.) δ: 1.86 (3H, br s), 3.70 (3H, s), 6.79-6.91 (6H, m), 6.93-7.05 (3H, m), 7.12 (1H, t, J=7.6 Hz), 7.18-7.27 (3H, m), 7.32 (2H, t, J=7.6 Hz).

Production Example 150

In the same manner as in Production Example 21 except that (E)-2-methyl-3-phenoxy-N-phenyl-2-propenamide and 4-(methylthio)phenol were used as materials, the following 4-(methylthio)phenyl 2-methyl-3-phenoxy-N-phenyl-2-propenimidate (hereinafter referred to as the present compound 150) was obtained.

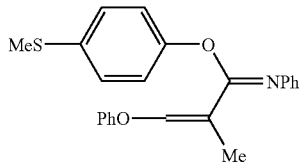

$^1$H-NMR (DMSO-D$_6$, 50° C.) δ: 1.90 (3H, br s), 2.42 (3H, s), 6.82-6.93 (4H, m), 6.95-7.08 (3H, m), 7.12 (1H, t, J=7.4 Hz), 7.18-7.29 (5H, m), 7.33 (2H, dd, J=8.7, 7.4 Hz).

Production Example 151

In the same manner as in Production Example 21 except that (E)-2-methyl-3-phenoxy-N-phenyl-2-propenamide and 4-cyanophenol were used as materials, the following 4-cyanophenyl 2-methyl-3-phenoxy-N-phenyl-2-propenimidate (hereinafter referred to as the present compound 151) was obtained.

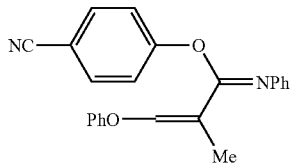

$^1$H-NMR (DMSO-D$_6$, 50° C.) δ: 1.97 (3H, br s), 6.88 (2H, d, J=7.3 Hz), 6.92-7.03 (3H, m), 7.09-7.27 (5H, m), 7.31-7.43 (3H, m), 7.67-7.78 (2H, m).

Production Example 152

In the same manner as in Production Example 21 except that (E)-2-methyl-3-phenoxy-N-phenyl-2-propenamide and 3-phenylphenol were used as materials, the following 3-phenylphenyl 2-methyl-3-phenoxy-N-phenyl-2-propenimidate (hereinafter referred to as the present compound 152) was obtained.

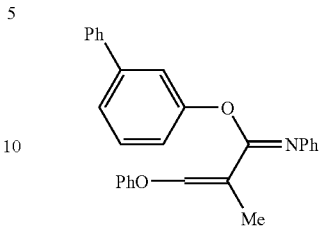

$^1$H-NMR (DMSO-D$_6$, 50° C.) δ: 1.94 (3H, br s), 6.84-7.15 (7H, m), 7.19-7.50 (11H, m), 7.59 (2H, d, J=7.3 Hz).

Production Example 153

In the same manner as in Production Example 21 except that (E)-2-methyl-3-phenoxy-N-phenyl-2-propenamide and 2-(trifluoromethyl)phenol were used as materials, the following 2-(trifluoromethyl)phenyl 2-methyl-3-phenoxy-N-phenyl-2-propenimidate (hereinafter referred to as the present compound 153) was obtained.

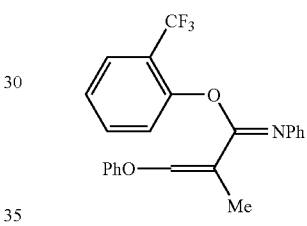

$^1$H-NMR (DMSO-D$_6$, 50° C.) δ: 1.90 (3H, br s), 6.80-6.92 (4H, m), 7.00 (1H, t, J=7.4 Hz), 7.13 (1H, t, J=7.4 Hz), 7.19-7.39 (7H, m), 7.57-7.71 (2H, m).

Production Example 154

In the same manner as in Production Example 21 except that (E)-2-methyl-3-phenoxy-N-phenyl-2-propenamide and 3-(trifluoromethyl)phenol were used as materials, the following 3-(trifluoromethyl)phenyl 2-methyl-3-phenoxy-N-phenyl-2-propenimidate (hereinafter referred to as the present compound 154) was obtained.

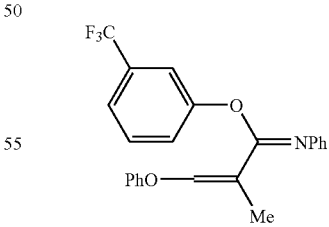

$^1$H-NMR (DMSO-D$_6$, 50° C.) δ: 1.91 (3H, br s), 6.86 (2H, d, J=7.6 Hz), 6.90-7.01 (3H, m), 7.13 (1H, t, J=7.3 Hz), 7.21 (2H, t, J=7.6 Hz), 7.26-7.46 (6H, m), 7.52 (1H, br s).

Production Example 155

In the same manner as in Production Example 21 except that (E)-2-methyl-3-phenoxy-N-phenyl-2-propenamide and 3-(trifluoromethoxy)phenol were used as materials, the following 3-(trifluoromethoxy)phenyl 2-methyl-3-phenoxy-N-phenyl-2-propenimidate (hereinafter referred to as the present compound 155) was obtained.

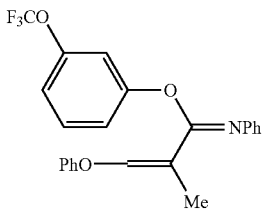

¹H-NMR (DMSO-D₆, 50° C.) δ: 1.92 (3H, br s), 6.87 (2H, d, J=7.6 Hz), 6.90-7.09 (6H, m), 7.13 (1H, t, J=7.4 Hz), 7.21 (2H, t, J=7.7 Hz), 7.29-7.45 (4H, m).

Production Example 156

In the same manner as in Production Example 21 except that (E)-2-methyl-3-phenoxy-N-phenyl-2-propenamide and 2,3-dimethylphenol were used as materials, the following 2,3-dimethylphenyl 2-methyl-3-phenoxy-N-phenyl-2-propenimidate (hereinafter referred to as the present compound 156) was obtained.

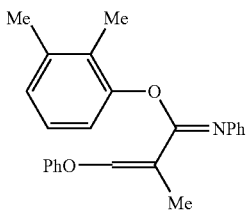

¹H-NMR (DMSO-D₆, 50° C.) δ: 1.88 (3H, br s), 2.09 (3H, s), 2.21 (3H, s), 6.74-7.07 (8H, m), 7.11 (1H, t, J=7.3 Hz), 7.15 (1H, br s), 7.22 (2H, t, J=7.7 Hz), 7.32 (2H, t, J=8.0 Hz).

Production Example 157

In the same manner as in Production Example 21 except that (E)-2-methyl-3-phenoxy-N-phenyl-2-propenamide and 2,4-dimethylphenol were used as materials, the following 2,4-dimethylphenyl 2-methyl-3-phenoxy-N-phenyl-2-propenimidate (hereinafter referred to as the present compound 157) was obtained.

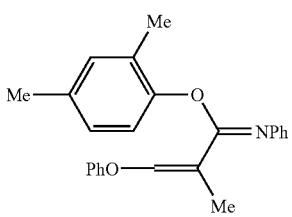

¹H-NMR (DMSO-D₆, 50° C.) δ: 1.86 (3H, br s), 2.16 (3H, s), 2.21 (3H, s), 6.75-7.04 (8H, m), 7.08-7.18 (2H, m), 7.22 (2H, t, J=7.7 Hz), 7.31 (2H, t, J=8.0 Hz).

Production Example 158

In the same manner as in Production Example 21 except that (E)-2-methyl-3-phenoxy-N-phenyl-2-propenamide and 2,5-dimethylphenol were used as materials, the following 2,5-dimethylphenyl 2-methyl-3-phenoxy-N-phenyl-2-propenimidate (hereinafter referred to as the present compound 158) was obtained.

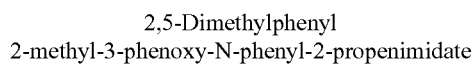

2,5-Dimethylphenyl 2-methyl-3-phenoxy-N-phenyl-2-propenimidate

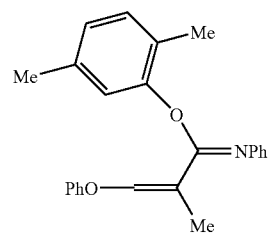

¹H-NMR (DMSO-D₆, 50° C.) δ: 1.88 (3H, br s), 2.14 (3H, s), 2.23 (3H, s), 6.74-6.92 (6H, m), 6.94-7.07 (2H, m), 7.11 (1H, t, J=7.4 Hz), 7.15-7.27 (3H, m), 7.32 (2H, t, J=7.9 Hz).

Production Example 159

In the same manner as in Production Example 21 except that (E)-2-methyl-3-phenoxy-N-phenyl-2-propenamide and 2,6-dimethylphenol were used as materials, the following (3E)-2,6-dimethylphenyl 2-methyl-3-phenoxy-N-phenyl-2-propenimidate (hereinafter referred to as the present compound 159) was obtained.

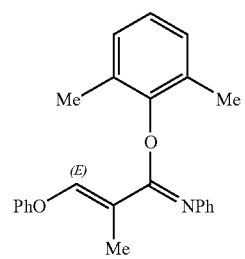

¹H-NMR (DMSO-D₆, 50° C.) δ: 1.83 (3H, d, J=1.2 Hz), 2.24 (6H, s), 6.70-6.77 (4H, m), 6.96-7.03 (2H, m), 7.04-7.13 (4H, m), 7.22-7.33 (4H, m).

Production Example 160

In the same manner as in Production Example 21 except that (E)-2-methyl-3-phenoxy-N-phenyl-2-propenamide and 2,3-dimethoxyphenol were used as materials, the following 2,3-dimethoxyphenyl 2-methyl-3-phenoxy-N-phenyl-2-propenimidate (hereinafter referred to as the present compound 160) was obtained.

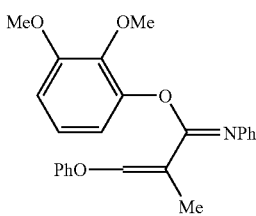

¹H-NMR (DMSO-D₆, 50° C.) δ: 1.85 (3H, br s), 3.74 (3H, s), 3.79 (3H, s), 6.69 (1H, br s), 6.77-6.90 (5H, m), 6.94-7.04 (2H, m), 7.11 (1H, t, J=7.4 Hz), 7.15 (1H, br s), 7.24 (2H, t, J=7.8 Hz), 7.31 (2H, dd, J=8.7, 7.4 Hz).

Production Example 161

In the same manner as in Production Example 21 except that (E)-2-methyl-3-phenoxy-N-phenyl-2-propenamide and 2,6-dimethoxyphenol were used as materials, the following 2,6-dimethoxyphenyl 2-methyl-3-phenoxy-N-phenyl-2-propenimidate (hereinafter referred to as the present compound 161) was obtained.

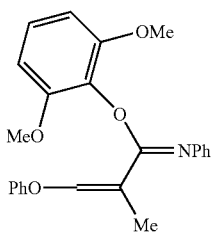

¹H-NMR (DMSO-D₆, 50° C.) δ: 1.79 (3H, br s), 3.79 (6H, s), 6.67 (2H, d, J=8.5 Hz), 6.71-6.83 (4H, m), 6.94 (1H, t, J=7.4 Hz), 7.01-7.14 (3H, m), 7.21 (2H, t, J=7.7 Hz), 7.31 (2H, dd, J=8.5, 7.4 Hz).

Production Example 162

In the same manner as in Production Example 21 except that (E)-2-methyl-3-phenoxy-N-phenyl-2-propenamide and 3,4-dimethoxyphenol were used as materials, the following 3,4-dimethoxyphenyl 2-methyl-3-phenoxy-N-phenyl-2-propenimidate (hereinafter referred to as the present compound 162) was obtained.

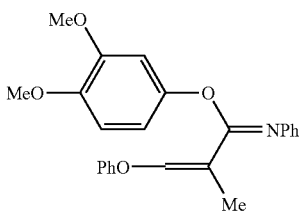

¹H-NMR (DMSO-D₆, 50° C.) δ: 1.88 (3H, br s), 3.69 (3H, s), 3.70 (3H, s), 6.55 (1H, br s), 6.68 (1H, br s), 6.81-6.94 (5H, m), 6.99 (1H, t, J=7.4 Hz), 7.12 (1H, t, J=7.4 Hz), 7.20-7.38 (5H, m).

Production Example 163

In the same manner as in Production Example 21 except that (E)-2-methyl-3-phenoxy-N-phenyl-2-propenamide and 5-hydroxyindan were used as materials, the following 5-indanyl 2-methyl-3-phenoxy-N-phenyl-2-propenimidate (hereinafter referred to as the present compound 163) was obtained.

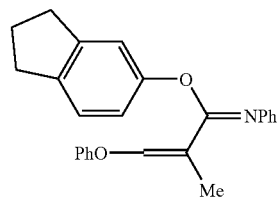

¹H-NMR (DMSO-D₆, 50° C.) δ: 1.79-2.07 (5H, m), 2.68-2.90 (4H, m), 6.69-6.95 (6H, m), 6.99 (1H, t, J=7.3 Hz), 7.08-7.17 (2H, m), 7.19-7.27 (3H, m), 7.32 (2H, t, J=8.0 Hz).

Production Example 164

In the same manner as in Production Example 21 except that (E)-2-methyl-3-phenoxy-N-phenyl-2-propenamide and 3-hydroxypyridine were used as materials, the following 3-pyridyl 2-methyl-3-phenoxy-N-phenyl-2-propenimidate (hereinafter referred to as the present compound 164) was obtained.

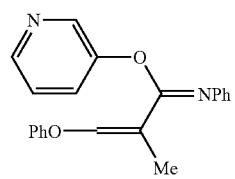

¹H-NMR (DMSO-D₆, 50° C.) δ: 1.89 (3H, br s), 6.86 (2H, d, J=7.5 Hz), 6.90-7.02 (3H, m), 7.13 (1H, t, J=7.4 Hz), 7.23 (2H, t, J=7.7 Hz), 7.28-7.41 (4H, m), 7.51 (1H, br s), 8.27 (1H, br s), 8.36 (1H, br s).

Production Example 165

In the same manner as in Production Example 21 except that (E)-N-(3-fluorophenyl)-2-methyl-3-phenoxy-2-propenamide and phenol were used as materials, phenyl N-(3-fluorophenyl)-2-methyl-3-phenoxy-2-propenimidate (hereinafter referred to as the present compound 165) was obtained.

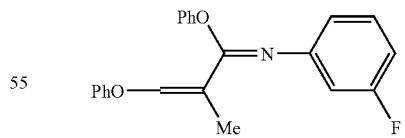

¹H-NMR (CDCl₃, 50° C.) δ: 2.02 (3H, s), 6.56-6.71 (3H, m), 6.81-6.94 (4H, m), 6.97 (1H, t, J=7.0 Hz), 7.04-7.13 (2H, m), 7.20 (2H, t, J=7.7 Hz), 7.27 (2H, dd, J=8.7, 7.4 Hz), 7.36 (1H, br s).

Production Example 166

In the same manner as in Production Example 21 except that (E)-N-(4-chlorophenyl)-2-methyl-3-phenoxy-2-propenamide and phenol were used as materials, the following phenyl N-(4-chlorophenyl)-2-methyl-3-phenoxy-2-propenimidate (hereinafter referred to as the present compound 166) was obtained.

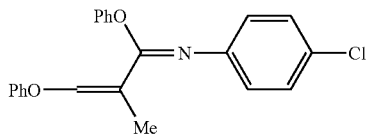

¹H-NMR (CDCl₃, 50° C.) δ: 2.03 (3H, br s), 6.77-6.93 (6H, m), 6.98 (1H, t, J=6.9 Hz), 7.07 (1H, t, J=7.7 Hz), 7.11 (2H, d, J=8.5 Hz), 7.20 (2H, t, J=6.9 Hz), 7.27 (2H, t, J=7.7 Hz), 7.33 (1H, br s).

Production Example 167

In the same manner as in Production Example 21 except that (E)-2-methyl-N-(2-methylphenyl)-3-phenoxy-2-propenamide and phenol were used as materials, the following phenyl 2-methyl-N-(2-methylphenyl)-3-phenoxy-2-propenimidate (hereinafter referred to as the present compound 167) was obtained.

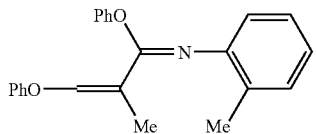

¹H-NMR (DMSO-D₆, 50° C.) δ: 1.93 (3H, br s), 2.10 (3H, s), 6.75 (1H, d, J=7.8 Hz), 6.84-6.92 (3H, m), 6.96-7.15 (6H, m), 7.21-7.38 (5H, m).

Production Example 168

In the same manner as in Production Example 21 except that (E)-N-(4-ethylphenyl)-2-methyl-3-phenoxy-2-propenamide was used as a material, the following phenyl N-(4-ethylphenyl)-2-methyl-3-phenoxy-2-propenimidate (hereinafter referred to as the present compound 168) was obtained.

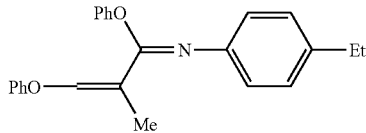

¹H-NMR (DMSO-D₆, 50° C.) δ: 1.13 (3H, t, J=7.6 Hz), 1.94 (3H, br s), 2.53 (2H, t, J=7.6 Hz), 6.75-6.93 (4H, m), 6.95-7.17 (6H, m), 7.19-7.45 (5H, m).

Production Example 169

In the same manner as in Production Example 21 except that (E)-N-(4-isopropylphenyl)-2-methyl-3-phenoxy-2-propenamide was used as a material, the following phenyl N-(4-isopropylphenyl)-2-methyl-3-phenoxy-2-propenimidate (hereinafter referred to as the present compound 169) was obtained.

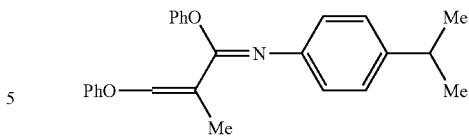

¹H-NMR (DMSO-D₆, 50° C.) δ: 1.15 (7H, d, J=6.8 Hz), 1.93 (3H, br s), 2.80 (1H, quint, J=6.8 Hz), 6.76-6.92 (4H, m), 6.94-7.17 (6H, m), 7.18-7.39 (5H, m).

Production Example 170

In the same manner as in Production Example 21 except that (E)-N-(4-methoxyphenyl)-2-methyl-3-phenoxy-2-propenamide was used as a material, the following phenyl N-(4-methoxyphenyl)-2-methyl-3-phenoxy-2-propenimidate (hereinafter referred to as the present compound 170) was obtained.

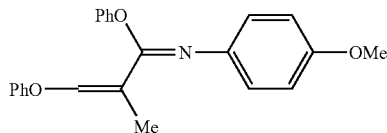

¹H-NMR (DMSO-D₆, 50° C.) δ: 1.97 (3H, br s), 3.68 (3H, s), 6.71-7.07 (9H, m), 7.12 (1H, t, J=7.3 Hz), 7.19-7.36 (5H, m).

Production Example 171

In the same manner as in Production Example 21 except that (E)-N-(4-methoxyphenyl)-2-methyl-3-phenoxy-2-propenamide and 3-methylphenol were used as materials, the following 3-methylphenyl N-(4-methoxyphenyl)-2-methyl-3-phenoxy-2-propenimidate (hereinafter referred to as the present compound 171) was obtained.

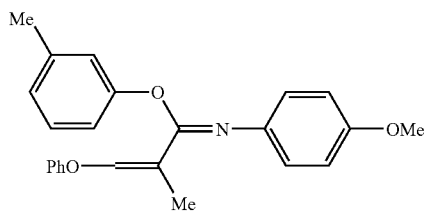

¹H-NMR (DMSO-D₆, 50° C.) δ: 1.97 (3H, br s), 2.24 (3H, s), 3.68 (3H, s), 6.61-7.06 (9H, m), 7.08-7.21 (2H, m), 7.27 (1H, br s), 7.32 (2H, t, J=7.9 Hz).

Production Example 172

In the same manner as in Production Example 21 except that (E)-2-methyl-3-phenoxy-N-(3-pyridyl)-2-propenamide and phenol were used as materials, the following phenyl 2-methyl-3-phenoxy-N-(3-pyridyl)-2-propenimidate (hereinafter referred to as the present compound 172) was obtained.

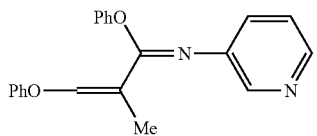

¹H-NMR (DMSO-D₆, 50° C.) δ: 1.95 (3H, br s), 6.94 (2H, d, J=8.0 Hz), 6.97-7.09 (3H, m), 7.14 (1H, t, J=7.4 Hz), 7.22 (1H, dd, J=8.0, 4.6 Hz), 7.26-7.42 (6H, m), 8.14-8.20 (2H, m).

Production Example 173

In the same manner as in Production Example 21 except that (E)-2-methyl-3-(2-methylphenyloxy)-N-phenyl-2-propenamide and phenol were used as materials, the following phenyl 2-methyl-3-(2-methylphenyloxy)-N-phenyl-2-propenimidate (hereinafter referred to as the present compound 173) was obtained.

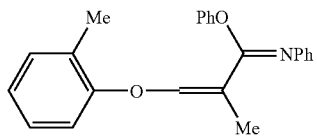

¹H-NMR (DMSO-D₆, 50° C.) δ: 1.95 (3H, br s), 2.16 (3H, s), 6.66 (1H, d, J=7.6 Hz), 6.88 (2H, d, J=7.6 Hz), 6.93-7.15 (6H, m), 7.16-7.38 (6H, m).

Production Example 174

In the same manner as in Production Example 21 except that (E)-2-methyl-3-(2-methylphenyloxy)-N-phenyl-2-propenamide and 2-methylphenol were used as materials, the following 2-methylphenyl 2-methyl-3-(2-methylphenyloxy)-N-phenyl-2-propenimidate (hereinafter referred to as the present compound 174) was obtained.

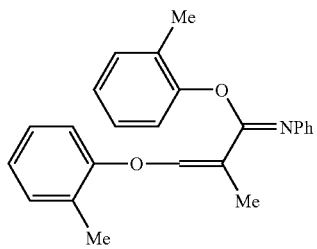

¹H-NMR (DMSO-D₆, 50° C.) δ: 1.92 (3H, br s), 2.17 (6H, s), 6.61 (1H, br), 6.81 (2H, d, J=7.8 Hz), 6.92-7.05 (4H, m), 7.07-7.26 (7H, m).

Production Example 175

In the same manner as in Production Example 21 except that (E)-2-methyl-3-(3-methylphenyloxy)-N-phenyl-2-propenamide and phenol were used as materials, the following phenyl 2-methyl-3-(3-methylphenyloxy)-N-phenyl-2-propenimidate (hereinafter referred to as the present compound 175) was obtained.

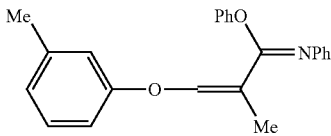

¹H-NMR (DMSO-D₆, 50° C.) δ: 1.92 (3H, br s), 2.24 (3H, s), 6.59 (1H, s), 6.68 (1H, d, J=8.0 Hz), 6.83-7.11 (7H, m), 7.15-7.26 (4H, m), 7.27-7.36 (2H, m).

Production Example 176

In the same manner as in Production Example 21 except that (E)-2-methyl-3-(3-methylphenyloxy)-N-phenyl-2-propenamide and 3-methylphenol were used as materials, the following 3-methylphenyl 2-methyl-3-(3-methylphenyloxy)-N-phenyl-2-propenimidate (hereinafter referred to as the present compound 176) was obtained.

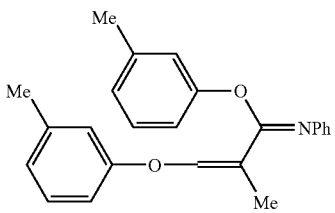

¹H-NMR (DMSO-D₆, 50° C.) δ: 1.92 (3H, br s), 2.25 (3H, s), 2.26 (3H, s), 6.58 (1H, br s), 6.68 (1H, d, J=7.6 Hz), 6.75-6.95 (6H, m), 6.99 (1H, t, J=7.4 Hz), 7.13-7.28 (5H, m).

Production Example 177

In the same manner as in Production Example 21 except that (E)-2-methyl-3-(3-methylphenyloxy)-N-phenyl-2-propenamide and 3-ethylphenol were used as materials, the following 3-ethylphenyl 2-methyl-3-(3-methylphenyloxy)-N-phenyl-2-propenimidate (hereinafter referred to as the present compound 177) was obtained.

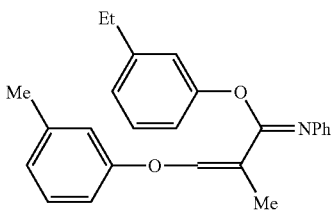

¹H-NMR (DMSO-D₆, 50° C.) δ: 1.12 (3H, t, J=7.5 Hz), 1.92 (3H, br s), 2.24 (3H, s), 2.55 (2H, q, J=7.5 Hz), 6.59 (1H, s), 6.66 (1H, d, J=8.0 Hz), 6.74-7.03 (7H, m), 7.11-7.28 (5H, m).

Production Example 178

In the same manner as in Production Example 21 except that (E)-2-methyl-3-(3-methylphenyloxy)-N-phenyl-2-propenamide and 3-isopropylphenol were used as materials, 3-isopropylphenyl 2-methyl-3-(3-methylphenyloxy)-N-phenyl-2-propenimidate (hereinafter referred to as the present compound 178) was obtained.

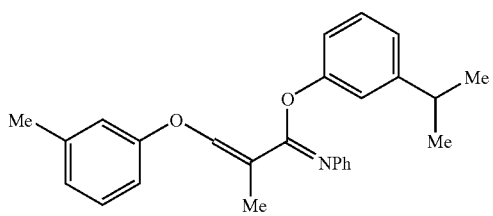

¹H-NMR (DMSO-D₆, 50° C.) δ: 1.14 (6H, d, J=6.8 Hz), 1.93 (3H, br s), 2.24 (3H, s), 2.78-2.88 (1H, m), 6.61 (1H, s), 6.65 (1H, d, J=8.0 Hz), 6.74-7.01 (7H, m), 7.13-7.29 (5H, m).

Production Example 179

In the same manner as in Production Example 21 except that (E)-2-methyl-3-(3-methylphenyloxy)-N-phenyl-2-propenamide and 3-ethoxyphenol were used as materials, the following 3-ethoxyphenyl 2-methyl-3-(3-methylphenyloxy)-N-phenyl-2-propenimidate (hereinafter referred to as the present compound 179) was obtained.

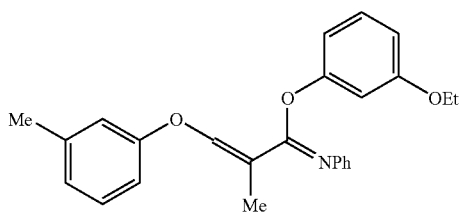

¹H-NMR (DMSO-D₆, 50° C.) δ: 1.28 (3H, t, J=6.9 Hz), 1.93 (3H, br s), 2.25 (3H, s), 3.97 (2H, q, J=6.9 Hz), 6.44-6.80 (5H, m), 6.85-7.08 (4H, m), 7.12-7.40 (5H, m).

Production Example 180

In the same manner as in Production Example 21 except that (E)-2-methyl-3-(3-methylphenyloxy)-N-phenyl-2-propenamide and 3-phenylphenol were used as materials, the following 3-phenylphenyl 2-methyl-3-(3-methylphenyloxy)-N-phenyl-2-propenimidate (hereinafter referred to as the present compound 180) was obtained.

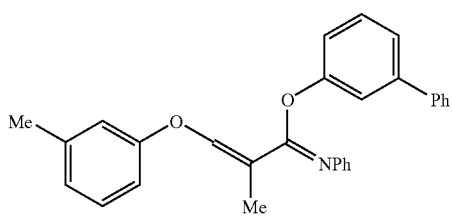

¹H-NMR (DMSO-D₆, 50° C.) δ: 1.94 (3H, br s), 2.21 (3H, s), 6.61 (1H, s), 6.69 (1H, d, J=8.0 Hz), 6.87-7.09 (5H, m), 7.13-7.50 (10H, m), 7.60 (2H, d, J=7.6 Hz).

Production Example 181

In the same manner as in Production Example 21 except that (E)-2-methyl-3-(3-methylphenyloxy)-N-phenyl-2-propenamide and 3-phenoxyphenol were used as materials, the following 3-phenoxyphenyl 2-methyl-3-(3-methylphenyloxy)-N-phenyl-2-propenimidate (hereinafter referred to as the present compound 181) was obtained.

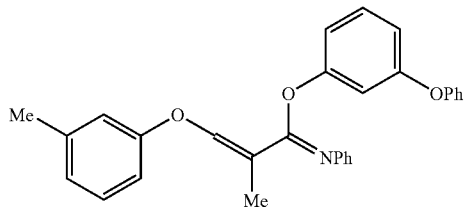

¹H-NMR (DMSO-D₆, 50° C.) δ: 1.91 (3H, br s), 2.27 (3H, s), 6.50-6.82 (5H, m), 6.85 (2H, d, J=7.6 Hz), 6.90-6.98 (3H, m), 7.01 (1H, t, J=7.2 Hz), 7.15 (1H, t, J=7.3 Hz), 7.18-7.32 (5H, m), 7.37 (2H, t, J=7.9 Hz).

Production Example 182

In the same manner as in Production Example 21 except that (E)-2-methyl-3-(3-methylphenyloxy)-N-phenyl-2-propenamide and 3,5-dimethylphenol were used as materials, the following 3,5-dimethylphenyl 2-methyl-3-(3-methylphenyloxy)-N-phenyl-2-propenimidate (hereinafter referred to as the present compound 182) was obtained.

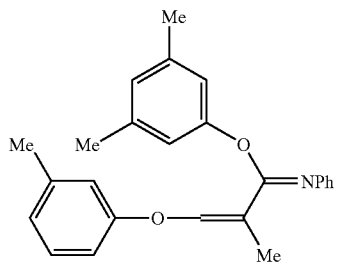

¹H-NMR (DMSO-D₆, 50° C.) δ: 1.92 (3H, br s), 2.21 (6H, s), 2.25 (3H, s), 6.51-6.79 (5H, m), 6.84-6.95 (3H, m), 6.99 (1H, t, J=7.3 Hz), 7.13-7.31 (4H, m).

Production Example 183

In the same manner as in Production Example 21 except that (E)-2-methyl-N-(4-methylphenyl)-3-(3-methylphenyloxy)-2-propenamide and phenol were used as materials, the following phenyl 2-methyl-N-(4-methylphenyl)-3-(3-methylphenyloxy)-2-propenimidate (hereinafter referred to as the present compound 183) was obtained.

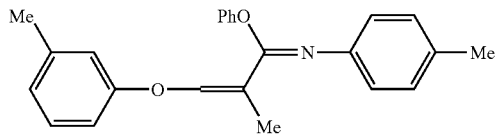

¹H-NMR (DMSO-D₆, 50° C.) δ: 1.94 (3H, br s), 2.21 (3H, s), 2.24 (3H, s), 6.59 (1H, s), 6.67 (1H, d, J=7.8 Hz), 6.77-6.89 (2H, m), 6.90-7.13 (6H, m), 7.15-7.25 (2H, m), 7.31 (2H, t, J=7.4 Hz).

Production Example 184

In the same manner as in Production Example 21 except that (E)-2-methyl-N-(4-methylphenyl)-3-(3-methylphenyloxy)-2-propenamide and 3-methylphenol were used as materials, the following 3-methylphenyl 2-methyl-N-(4-methylphenyl)-3-(3-methylphenyloxy)-2-propenimidate (hereinafter referred to as the present compound 184) was obtained.

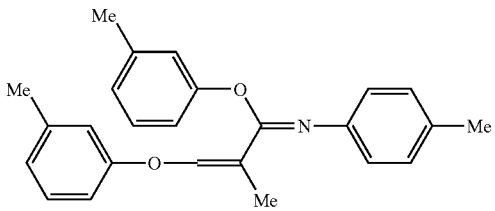

$^1$H-NMR (DMSO-D$_6$, 50° C.) δ: 1.93 (3H, br s), 2.22 (3H, s), 2.24 (3H, s), 2.25 (3H, s), 6.58 (1H, s), 6.67 (1H, d, J=8.0 Hz), 6.72-6.97 (6H, m), 7.04 (2H, d, J=8.0 Hz), 7.13-7.26 (3H, m).

Production Example 185

In the same manner as in Production Example 21 except that (E)-2-methyl-N-(4-methylphenyl)-3-(3-methylphenyloxy)-2-propenamide and 3-ethylphenol were used as materials, the following 3-ethylphenyl 2-methyl-N-(4-methylphenyl)-3-(3-methylphenyloxy)-2-propenimidate (hereinafter referred to as the present compound 185) was obtained.

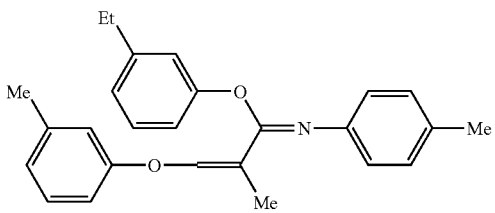

$^1$H-NMR (DMSO-D$_6$, 50° C.) δ: 1.12 (3H, t, J=7.5 Hz), 1.93 (3H, br s), 2.21 (3H, s), 2.24 (3H, s), 2.55 (2H, q, J=7.5 Hz), 6.59 (1H, s), 6.65 (1H, d, J=8.3 Hz), 6.72-6.97 (6H, m), 7.03 (2H, d, J=7.8 Hz), 7.14-7.29 (3H, m).

Production Example 186

In the same manner as in Production Example 21 except that (E)-2-methyl-N-(4-methylphenyl)-3-(3-methylphenyloxy)-2-propenamide and 3-ethoxyphenol were used as materials, the following 3-ethoxyphenyl 2-methyl-N-(4-methylphenyl)-3-(3-methylphenyloxy)-2-propenimidate (hereinafter referred to as the present compound 186) was obtained.

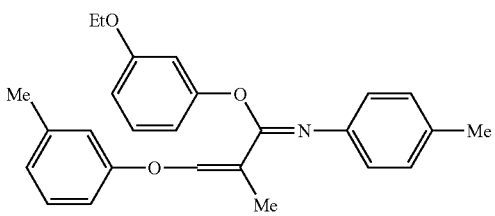

$^1$H-NMR (DMSO-D$_6$, 50° C.) δ: 1.27 (3H, t, J=7.1 Hz), 1.93 (3H, br s), 2.22 (3H, s), 2.24 (3H, s), 3.97 (2H, q, J=7.1 Hz), 6.38-6.75 (5H, m), 6.77-6.90 (2H, m), 6.93 (1H, d, J=7.6 Hz), 7.04 (2H, d, J=8.0 Hz), 7.13-7.34 (3H, m).

Production Example 187

In the same manner as in Production Example 21 except that (E)-2-methyl-N-(4-methylphenyl)-3-(3-methylphenyloxy)-2-propenamide and 3-phenoxyphenol were used as materials, the following 3-phenoxyphenyl 2-methyl-N-(4-methylphenyl)-3-(3-methylphenyloxy)-2-propenimidate (hereinafter referred to as the present compound 187) was obtained.

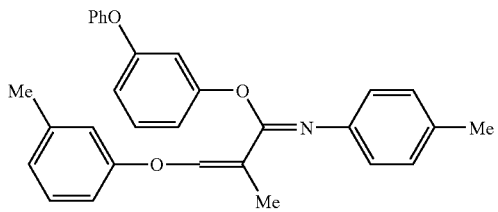

$^1$H-NMR (DMSO-D$_6$, 50° C.) δ: 1.91 (3H, br s), 2.23 (3H, s), 2.26 (3H, s), 6.44-6.86 (7H, m), 6.88-7.00 (3H, m), 7.04 (2H, d, J=8.0 Hz), 7.15 (1H, t, J=7.4 Hz), 7.21 (1H, t, J=7.8 Hz), 7.28 (2H, t, J=7.7 Hz), 7.36 (2H, dd, J=8.5, 7.6 Hz).

Production Example 188

In the same manner as in Production Example 21 except that (E)-N-(4-methoxyphenyl)-2-methyl-3-(3-methylphenyloxy)-2-propenamide and phenol were used as materials, the following phenyl N-(4-methoxyphenyl)-2-methyl-3-(3-methylphenyloxy)-2-propenimidate (hereinafter referred to as the present compound 188) was obtained.

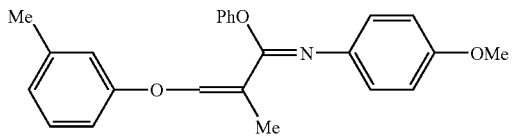

$^1$H-NMR (DMSO-D$_6$, 50° C.) δ: 1.96 (3H, br s), 2.24 (3H, s), 3.68 (3H, s), 6.60 (1H, s), 6.69 (1H, dd, J=8.2, 1.8 Hz), 6.80 (2H, d, J=8.3 Hz), 6.85-7.11 (6H, m), 7.15-7.37 (4H, m).

Production Example 189

In the same manner as in Production Example 21 except that (E)-N-(4-methoxyphenyl)-2-methyl-3-(3-methylphenyloxy)-2-propenamide and 3-methylphenol were used as materials, the following 3-methylphenyl N-(4-methoxyphenyl)-2-methyl-3-(3-methylphenyloxy)-2-propenimidate (hereinafter referred to as the present compound 189) was obtained.

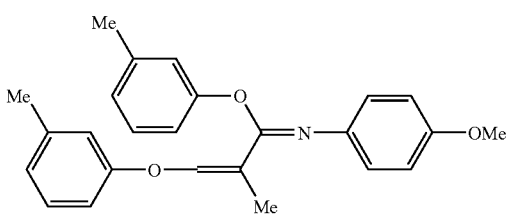

¹H-NMR (DMSO-D₆, 50° C.) δ: 1.96 (3H, br s), 2.24 (3H, s), 2.25 (3H, s), 3.69 (3H, s), 6.59 (1H, s), 6.64-7.08 (9H, m), 7.10-7.32 (3H, m).

Production Example 190

In the same manner as in Production Example 21 except that (E)-N-(4-methoxyphenyl)-2-methyl-3-(3-methylphenyloxy)-2-propenamide and 3-ethylphenol were used as materials, the following 3-ethylphenyl N-(4-methoxyphenyl)-2-methyl-3-(3-methylphenyloxy)-2-propenimidate (hereinafter referred to as the present compound 190) was obtained.

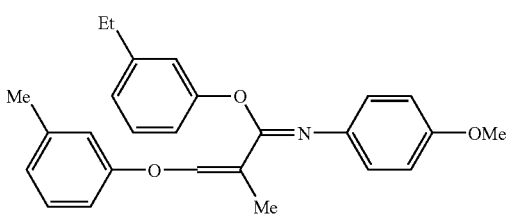

¹H-NMR (DMSO-D₆, 50° C.) δ: 1.12 (3H, t, J=7.6 Hz), 1.96 (3H, br s), 2.24 (3H, s), 2.55 (2H, q, J=7.6 Hz), 3.68 (3H, s), 6.60 (1H, br s), 6.67 (1H, d, J=8.3 Hz), 6.71-6.84 (3H, m), 6.85-7.03 (4H, m), 7.10-7.30 (3H, m).

Production Example 191

In the same manner as in Production Example 21 except that (E)-N-(4-methoxyphenyl)-2-methyl-3-(3-methylphenyloxy)-2-propenamide and 3-ethoxyphenol were used as materials, the following 3-ethoxyphenyl N-(4-methoxyphenyl)-2-methyl-3-(3-methylphenyloxy)-2-propenimidate (hereinafter referred to as the present compound 191) was obtained.

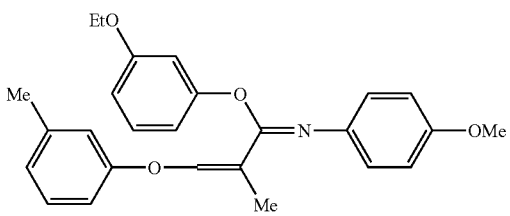

¹H-NMR (DMSO-D₆, 50° C.) δ: 1.27 (3H, t, J=6.9 Hz), 1.96 (3H, br s), 2.24 (3H, s), 3.69 (3H, s), 3.97 (2H, q, J=6.9 Hz), 6.36-6.66 (4H, m), 6.71 (1H, d, J=8.5 Hz), 6.81 (2H, d, J=8.5 Hz), 6.89-7.08 (3H, m), 7.12-7.38 (3H, m).

Production Example 192

In the same manner as in Production Example 21 except that (E)-N-(3,5-dimethylphenyl)-2-methyl-3-(3-methylphenyloxy)-2-propenamide and phenol were used as materials, the following phenyl N-(3,5-dimethylphenyl)-2-methyl-3-(3-methylphenyloxy)-2-propenimidate (hereinafter referred to as the present compound 192) was obtained.

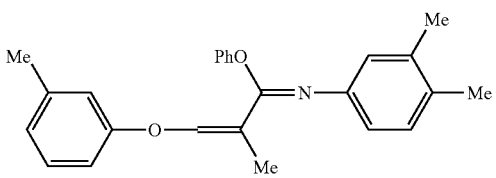

¹H-NMR (DMSO-D₆, 50° C.) δ: 1.93 (3H, br s), 2.13 (6H, s), 2.24 (3H, s), 6.58 (1H, br s), 6.66 (2H, d, J=7.2 Hz), 6.73 (1H, br s), 6.89-7.11 (5H, m), 7.14-7.24 (2H, m), 7.31 (2H, t, J=7.4 Hz).

Production Example 193

In the same manner as in Production Example 21 except that (E)-N-(3,5-dimethylphenyl)-2-methyl-3-(3-methylphenyloxy)-2-propenamide and 3-ethoxyphenol were used as materials, the following 3-ethoxyphenyl N-(3,5-dimethylphenyl)-2-methyl-3-(3-methylphenyloxy)-2-propenimidate (hereinafter referred to as the present compound 193) was obtained.

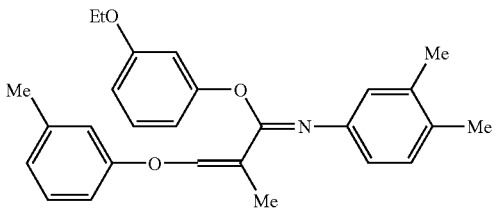

¹H-NMR (DMSO-D₆, 50° C.) δ: 1.27 (3H, t, J=7.0 Hz), 1.93 (3H, br s), 2.13 (3H, s), 2.14 (3H, s), 2.24 (3H, s), 3.97 (2H, q, J=7.0 Hz), 6.43-6.82 (7H, m), 6.93 (1H, d, J=7.3 Hz), 6.98 (1H, d, J=8.0 Hz), 7.14-7.32 (3H, m).

Production Example 194

In the same manner as in Production Example 21 except that (E)-2-methyl-3-(4-methylphenyloxy)-N-phenyl-2-propenamide and 2-methylphenol were used as materials, the following 2-methylphenyl 2-methyl-3-(4-methylphenyloxy)-N-phenyl-2-propenimidate (hereinafter referred to as the present compound 194) was obtained.

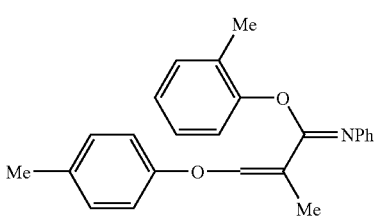

¹H-NMR (DMSO-D₆, 50° C.) δ: 1.88 (3H, br s), 2.18 (3H, s), 2.24 (3H, s), 6.73 (2H, d, J=7.6 Hz), 6.81 (2H, d, J=7.8 Hz), 6.91-7.05 (3H, m), 7.06-7.28 (7H, m).

Production Example 195

In the same manner as in Production Example 21 except that (E)-2-methyl-3-(4-methylphenyloxy)-N-phenyl-2-propenamide and 3-methylphenol were used as materials, the following 3-methylphenyl 2-methyl-3-(4-methylphenyloxy)-N-phenyl-2-propenimidate (hereinafter referred to as the present compound 195) was obtained.

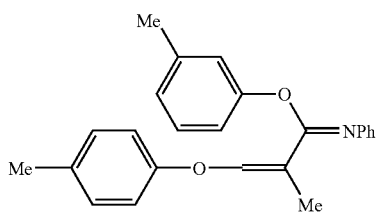

$^1$H-NMR (DMSO-D$_6$, 50° C.) δ: 1.91 (3H, br s), 2.24 (6H, s), 6.71-6.93 (7H, m), 6.97 (1H, t, J=7.4 Hz), 7.08-7.28 (6H, m).

Production Example 196

In the same manner as in Production Example 21 except that (E)-2-methyl-3-(4-methylphenyloxy)-N-phenyl-2-propenamide and 3-ethylphenol were used as materials, the following 3-ethylphenyl 2-methyl-3-(4-methylphenyloxy)-N-phenyl-2-propenimidate (hereinafter referred to as the present compound 196) was obtained.

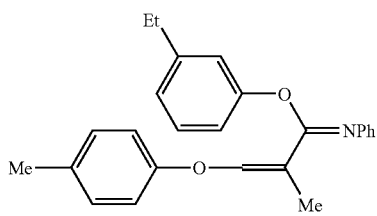

$^1$H-NMR (DMSO-D$_6$, 50° C.) δ: 1.12 (3H, t, J=7.6 Hz), 1.92 (3H, br s), 2.24 (3H, s), 2.54 (2H, q, J=7.6 Hz), 6.70-6.92 (7H, m), 6.97 (1H, t, J=7.4 Hz), 7.11 (2H, d, J=8.7 Hz), 7.14-7.28 (4H, m).

Production Example 197

In the same manner as in Production Example 21 except that (E)-2-methyl-3-(4-methylphenyloxy)-N-phenyl-2-propenamide and 2-fluorophenol were used as materials, the following 2-fluorophenyl 2-methyl-3-(4-methylphenyloxy)-N-phenyl-2-propenimidate (hereinafter referred to as the present compound 197) was obtained.

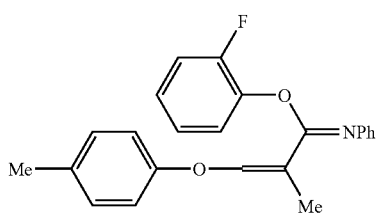

$^1$H-NMR (DMSO-D$_6$, 50° C.) δ: 1.82 (3H, br s), 2.25 (3H, s), 6.75 (2H, d, J=8.0 Hz), 6.79 (2H, d, J=7.6 Hz), 6.99 (1H, t, J=7.4 Hz), 7.08-7.30 (9H, m).

Production Example 198

In the same manner as in Production Example 21 except that (E)-2-methyl-3-(4-methylphenyloxy)-N-phenyl-2-propenamide and 3-fluorophenol were used as materials, the following 3-fluorophenyl 2-methyl-3-(4-methylphenyloxy)-N-phenyl-2-propenimidate (hereinafter referred to as the present compound 198) was obtained.

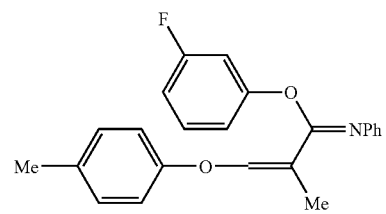

$^1$H-NMR (DMSO-D$_6$, 50° C.) δ: 1.91 (3H, br s), 2.25 (3H, s), 6.73-6.94 (7H, m), 6.98 (1H, t, J=7.2 Hz), 7.13 (2H, d, J=8.3 Hz), 7.17-7.36 (4H, m).

Production Example 199

In the same manner as in Production Example 21 except that (E)-2-methyl-3-(4-methylphenyloxy)-N-phenyl-2-propenamide and 4-fluorophenol were used as materials, the following 4-fluorophenyl 2-methyl-3-(4-methylphenyloxy)-N-phenyl-2-propenimidate (hereinafter referred to as the present compound 199) was obtained.

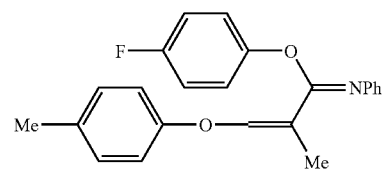

$^1$H-NMR (DMSO-D$_6$, 50° C.) δ: 1.87 (3H, br s), 2.25 (3H, s), 6.79 (2H, d, J=7.6 Hz), 6.84 (2H, d, J=7.3 Hz), 6.98 (1H, t, J=7.3 Hz), 7.02-7.17 (5H, m), 7.18-7.29 (4H, m).

Production Example 200

In the same manner as in Production Example 21 except that (E)-2-methyl-3-(4-methylphenyloxy)-N-phenyl-2-propenamide and 2-chlorophenol were used as materials, 2-chlorophenyl 2-methyl-3-(4-methylphenyloxy)-N-phenyl-2-propenimidate (hereinafter referred to as the present compound 200) was obtained.

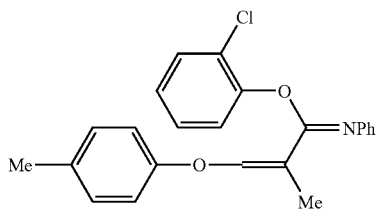

¹H-NMR (DMSO-D₆, 50° C.) δ: 1.84 (3H, br s), 2.25 (3H, s), 6.75 (2H, d, J=8.0 Hz), 6.82 (2H, d, J=7.6 Hz), 6.99 (1H, t, J=7.4 Hz), 7.08-7.36 (8H, m), 7.46 (1H, d, J=7.1 Hz).

Production Example 201

In the same manner as in Production Example 21 except that (E)-2-methyl-3-(4-methylphenyloxy)-N-phenyl-2-propenamide and 3-chlorophenol were used as materials, the following 3-chlorophenyl 2-methyl-3-(4-methylphenyloxy)-N-phenyl-2-propenimidate (hereinafter referred to as the present compound 201) was obtained.

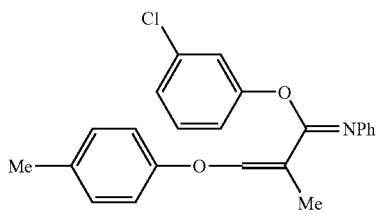

¹H-NMR (DMSO-D₆, 50° C.) δ: 1.90 (3H, br s), 2.25 (3H, s), 6.82 (2H, d, J=7.8 Hz), 6.87 (2H, d, J=7.3 Hz), 6.98 (1H, t, J=7.3 Hz), 7.05-7.17 (4H, m), 7.18-7.37 (5H, m).

Production Example 202

In the same manner as in Production Example 21 except that (E)-2-methyl-3-(4-methylphenyloxy)-N-phenyl-2-propenamide and 4-chlorophenol were used as materials, the following 4-chlorophenyl 2-methyl-3-(4-methylphenyloxy)-N-phenyl-2-propenimidate (hereinafter referred to as the present compound 202) was obtained.

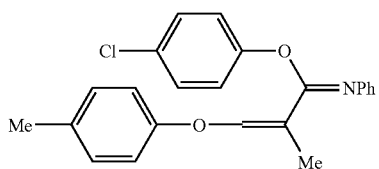

¹H-NMR (DMSO-D₆, 50° C.) δ: 1.89 (3H, br s), 2.25 (3H, s), 6.81 (2H, d, J=7.6 Hz), 6.85 (2H, d, J=7.8 Hz), 6.94-7.09 (2H, m), 7.12 (2H, d, J=8.5 Hz), 7.18-7.38 (6H, m).

Production Example 203

In the same manner as in Production Example 21 except that (E)-2-methyl-3-(4-methylphenyloxy)-N-phenyl-2-propenamide and 2-methoxyphenol were used as materials, the following 2-methoxyphenyl 2-methyl-3-(4-methylphenyloxy)-N-phenyl-2-propenimidate (hereinafter referred to as the present compound 203) was obtained.

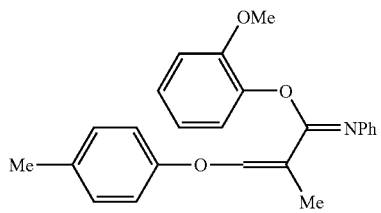

¹H-NMR (DMSO-D₆, 50° C.) δ: 1.81 (3H, br s), 2.24 (3H, s), 3.79 (3H, s), 6.68 (2H, d, J=8.5 Hz), 6.80 (2H, d, J=7.3 Hz), 6.88 (1H, t, J=6.8 Hz), 6.97 (1H, t, J=7.4 Hz), 7.01-7.16 (6H, m), 7.22 (2H, t, J=7.7 Hz).

Production Example 204

In the same manner as in Production Example 21 except that (E)-2-methyl-3-(4-methylphenyloxy)-N-phenyl-2-propenamide and 3-methoxyphenol were used as materials, the following 3-methoxyphenyl 2-methyl-3-(4-methylphenyloxy)-N-phenyl-2-propenimidate (hereinafter referred to as the present compound 204) was obtained.

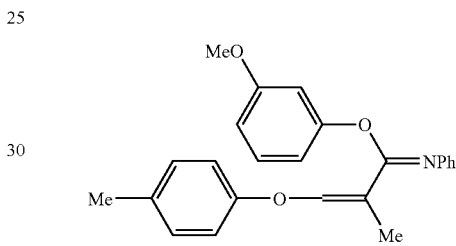

¹H-NMR (DMSO-D₆, 50° C.) δ: 1.92 (3H, br s), 2.25 (3H, s), 3.70 (3H, s), 6.43-6.69 (2H, m), 6.79 (2H, d, J=8.0 Hz), 6.90 (2H, d, J=7.7 Hz), 6.99 (1H, t, J=7.4 Hz), 7.07-7.41 (7H, m).

Production Example 205

In the same manner as in Production Example 21 except that (E)-2-methyl-3-(4-methylphenyloxy)-N-phenyl-2-propenamide and 4-methoxyphenol were used as materials, the following 4-methoxyphenyl 2-methyl-3-(4-methylphenyloxy)-N-phenyl-2-propenimidate (hereinafter referred to as the present compound 205) was obtained.

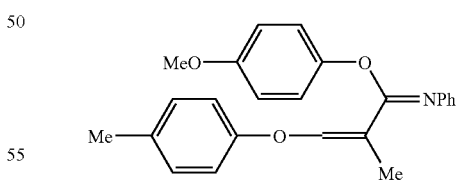

¹H-NMR (DMSO-D₆, 50° C.) δ: 1.85 (3H, br s), 2.25 (3H, s), 3.70 (3H, s), 6.75 (2H, d, J=8.3 Hz), 6.80-7.04 (7H, m), 7.11 (2H, d, J=8.0 Hz), 7.17 (1H, br s), 7.22 (2H, t, J=7.8 Hz).

Production Example 206

In the same manner as in Production Example 21 except that (E)-2-methyl-3-(4-methylphenyloxy)-N-phenyl-2-propenamide and 3-(trifluoromethyl)phenol were used as materials, the following 3-(trifluoromethyl)phenyl 2-methyl-3-(4- methylphenyloxy)-N-phenyl-2-propenimidate (hereinafter referred to as the present compound 206) was obtained.

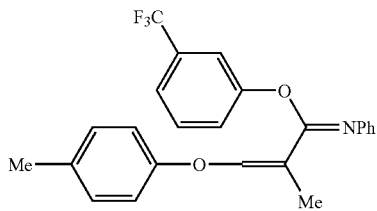

¹H-NMR (DMSO-D₆, 50° C.) δ: 1.91 (3H, br s), 2.25 (3H, s), 6.78-6.89 (4H, m), 6.96 (1H, t, J=7.3 Hz), 7.05-7.58 (9H, m).

Production Example 207

In the same manner as in Production Example 21 except that (E)-2-methyl-3-(4-methylphenyloxy)-N-phenyl-2-propenamide and 2-naphthol were used as materials, the following 2-naphthyl 2-methyl-3-(4-methylphenyloxy)-N-phenyl-2-propenimidate (hereinafter referred to as the present compound 207) was obtained.

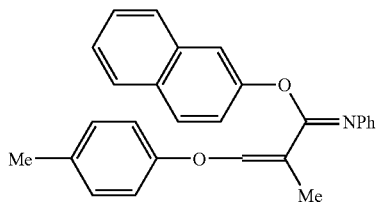

¹H-NMR (DMSO-D₆, 50° C.) δ: 1.95 (3H, br s), 2.22 (3H, s), 6.76 (2H, d, J=8.4 Hz), 6.87-6.99 (3H, m), 7.06 (2H, d, J=8.4 Hz), 7.13-7.54 (7H, m), 7.78-7.88 (3H, m).

Production Example 208

In the same manner as in Production Example 21 except that (E)-2-methyl-N-(4-methylphenyl)-3-(4-methylphenyloxy)-2-propenamide and phenol were used as materials, the following phenyl 2-methyl-N-(4-methylphenyl)-3-(4-methylphenyloxy)-2-propenimidate (hereinafter referred to as the present compound 208) was obtained.

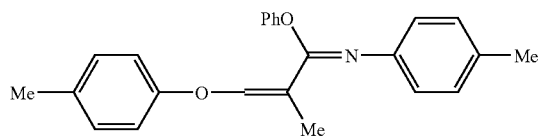

¹H-NMR (DMSO-D₆, 50° C.) δ: 1.93 (3H, br s), 2.21 (3H, s), 2.24 (3H, s), 6.76 (2H, d, J=8.3 Hz), 6.79-6.88 (2H, m), 6.90-7.38 (10H, m).

Production Example 209

In the same manner as in Production Example 21 except that (E)-2-methyl-N-(4-methylphenyl)-3-(4-methylphenyloxy)-2-propenamide and 2-methylphenol were used as materials, the following 2-methylphenyl 2-methyl-N-(4-methylphenyl)-3-(4-methylphenyloxy)-2-propenimidate (hereinafter referred to as the present compound 209) was obtained.

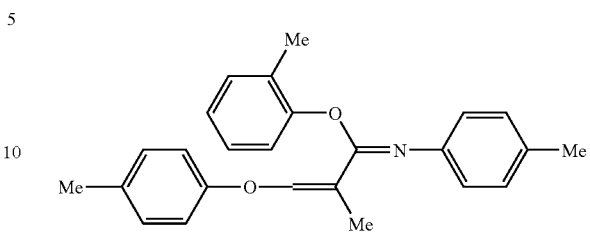

¹H-NMR (DMSO-D₆, 50° C.) δ: 1.87 (3H, br s), 2.18 (3H, s), 2.21 (3H, s), 2.24 (3H, s), 6.66-6.81 (4H, m), 6.86-7.27 (9H, m).

Production Example 210

In the same manner as in Production Example 21 except that (E)-2-methyl-N-(4-methylphenyl)-3-(4-methylphenyloxy)-2-propenamide and 3-methylphenol were used as materials, the following 3-methylphenyl 2-methyl-N-(4-methylphenyl)-3-(4-methylphenyloxy)-2-propenimidate (hereinafter referred to as the present compound 210) was obtained.

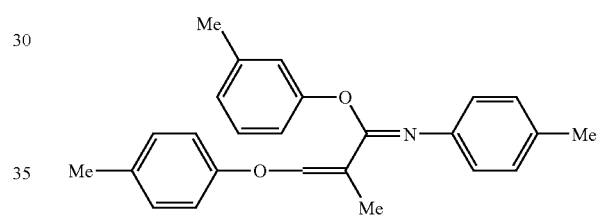

¹H-NMR (DMSO-D₆, 50° C.) δ: 1.91 (3H, br s), 2.21 (3H, s), 2.24 (6H, s), 6.61-6.92 (7H, m), 7.02 (2H, d, J=8.0 Hz), 7.07-7.26 (4H, m).

Production Example 211

In the same manner as in Production Example 21 except that (E)-2-methyl-N-(4-methylphenyl)-3-(4-methylphenyloxy)-2-propenamide and 4-methylphenol were used as materials, the following 4-methylphenyl 2-methyl-N-(4-methylphenyl)-3-(4-methylphenyloxy)-2-propenimidate (hereinafter referred to as the present compound 211) was obtained.

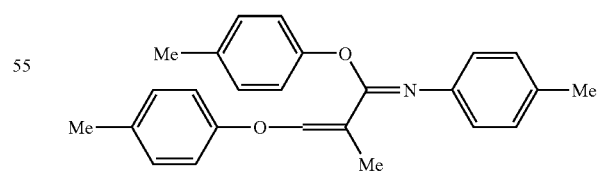

¹H-NMR (DMSO-D₆, 50° C.) δ: 1.89 (3H, br s), 2.21 (6H, s), 2.24 (3H, s), 6.68-6.94 (5H, m), 6.98-7.27 (8H, m).

Production Example 212

In the same manner as in Production Example 21 except that (E)-2-methyl-N-(4-methylphenyl)-3-(4-methylphenyloxy)-2-propenamide and 3-ethylphenol were used as materials, the following 3-ethylphenyl 2-methyl-N-(4-methylphenyl)-3-(4-methylphenyloxy)-2-propenimidate (hereinafter referred to as the present compound 212) was obtained.

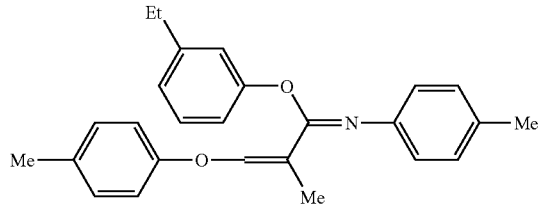

$^1$H-NMR (DMSO-D$_6$, 50° C.) δ: 1.11 (3H, t, J=7.6 Hz), 1.93 (3H, br s), 2.21 (3H, s), 2.24 (3H, s), 2.54 (2H, d, J=7.6 Hz), 6.63-6.95 (7H, m), 7.02 (2H, d, J=7.8 Hz), 7.10 (2H, d, J=8.3 Hz), 7.14-7.33 (2H, m).

Production Example 213

In the same manner as in Production Example 21 except that (E)-2-methyl-N-(4-methylphenyl)-3-(4-methylphenyloxy)-2-propenamide and 2-fluorophenol were used as materials, the following 2-fluorophenyl 2-methyl-N-(4-methylphenyl)-3-(4-methylphenyloxy)-2-propenimidate (hereinafter referred to as the present compound 213) was obtained.

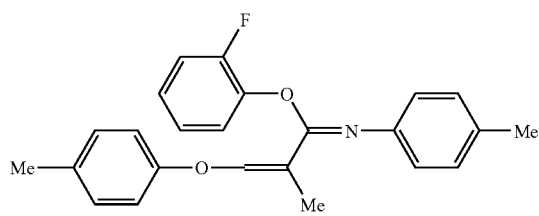

$^1$H-NMR (DMSO-D$_6$, 50° C.) δ: 1.82 (3H, br s), 2.23 (3H, s), 2.25 (3H, s), 6.70 (2H, d, J=7.8 Hz), 6.75 (2H, d, J=8.0 Hz), 7.04 (2H, d, J=8.0 Hz), 7.08-7.32 (7H, m).

Production Example 214

In the same manner as in Production Example 21 except that (E)-2-methyl-N-(4-methylphenyl)-3-(4-methylphenyloxy)-2-propenamide and 3-fluorophenol were used as materials, the following 3-fluorophenyl 2-methyl-N-(4-methylphenyl)-3-(4-methylphenyloxy)-2-propenimidate (hereinafter referred to as the present compound 214) was obtained.

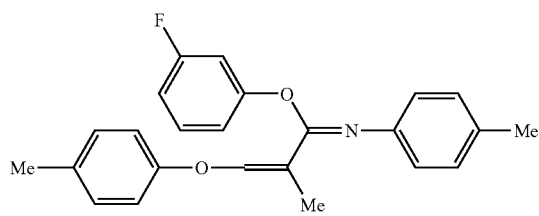

$^1$H-NMR (DMSO-D$_6$, 50° C.) δ: 1.92 (3H, br s), 2.21 (3H, s), 2.25 (3H, s), 6.70-6.94 (7H, m), 7.03 (2H, d, J=8.0 Hz), 7.12 (2H, d, J=8.3 Hz), 7.19-7.37 (2H, m).

Production Example 215

In the same manner as in Production Example 21 except that (E)-2-methyl-N-(4-methylphenyl)-3-(4-methylphenyloxy)-2-propenamide and 4-fluorophenol were used as materials, the following 4-fluorophenyl 2-methyl-N-(4-methylphenyl)-3-(4-methylphenyloxy)-2-propenimidate (hereinafter referred to as the present compound 215) was obtained.

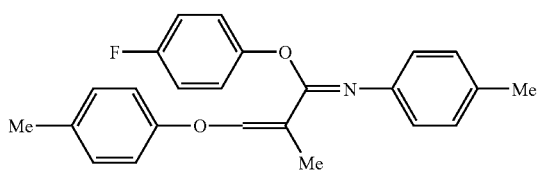

$^1$H-NMR (DMSO-D$_6$, 50° C.) δ: 1.87 (3H, br s), 2.22 (3H, s), 2.25 (3H, s), 6.71-6.87 (4H, m), 6.92-7.36 (9H, m).

Production Example 216

In the same manner as in Production Example 21 except that (E)-2-methyl-N-(4-methylphenyl)-3-(4-methylphenyloxy)-2-propenamide and 2-chlorophenol were used as materials, 2-chlorophenyl 2-methyl-N-(4-methylphenyl)-3-(4-methylphenyloxy)-2-propenimidate (hereinafter referred to as the present compound 216) was obtained.

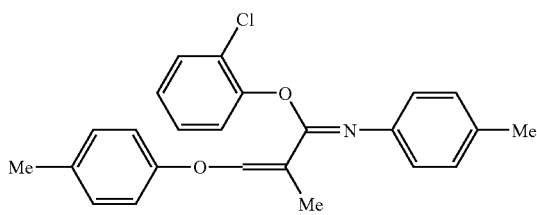

$^1$H-NMR (DMSO-D$_6$, 50° C.) δ: 1.84 (3H, br s), 2.22 (3H, s), 2.25 (3H, s), 6.67-6.81 (4H, m), 6.98-7.36 (8H, m), 7.46 (1H, d, J=7.3 Hz).

Production Example 217

In the same manner as in Production Example 21 except that (E)-2-methyl-N-(4-methylphenyl)-3-(4-methylphenyloxy)-2-propenamide and 3-chlorophenol were used as materials, the following 3-chlorophenyl 2-methyl-N-(4-methylphenyl)-3-(4-methylphenyloxy)-2-propenimidate (hereinafter referred to as the present compound 217) was obtained.

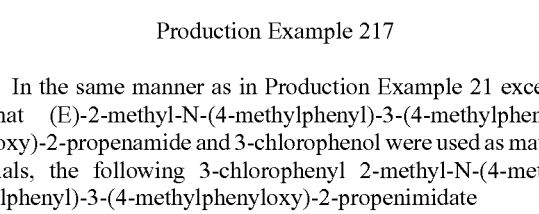

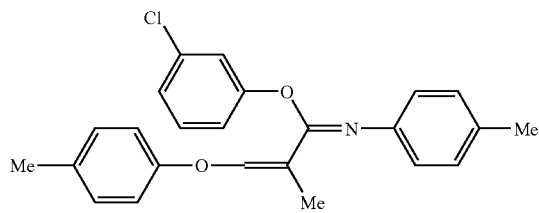

¹H-NMR (DMSO-D₆, 50° C.) δ: 1.91 (3H, br s), 2.21 (3H, s), 2.25 (3H, s), 6.74-6.88 (4H, m), 6.90-7.40 (9H, m).

Production Example 218

In the same manner as in Production Example 21 except that (E)-2-methyl-N-(4-methylphenyl)-3-(4-methylphenyloxy)-2-propenamide and 4-chlorophenol were used as materials, the following 4-chlorophenyl 2-methyl-N-(4-methylphenyl)-3-(4-methylphenyloxy)-2-propenimidate (hereinafter referred to as the present compound 218) was obtained.

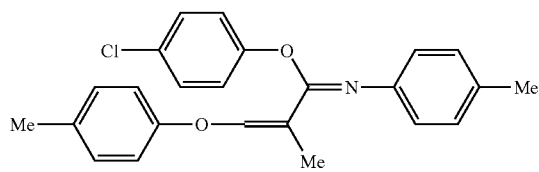

¹H-NMR (DMSO-D₆, 50° C.) δ: 1.90 (3H, br s), 2.22 (3H, s), 2.25 (3H, s), 6.73-6.87 (4H, m), 6.93-7.18 (6H, m), 7.19-7.27 (1H, br), 7.32 (2H, d, J=6.8 Hz).

Production Example 219

In the same manner as in Production Example 21 except that (E)-2-methyl-N-(4-methylphenyl)-3-(4-methylphenyloxy)-2-propenamide and 2-methoxyphenol were used as materials, 2-methoxyphenyl 2-methyl-N-(4-methylphenyl)-3-(4-methylphenyloxy)-2-propenimidate (hereinafter referred to as the present compound 219) was obtained.

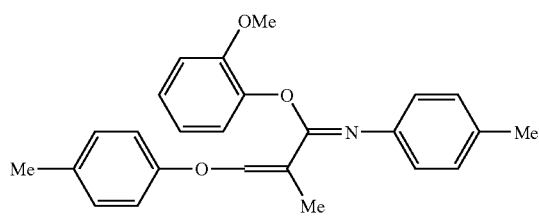

¹H-NMR (DMSO-D₆, 50° C.) δ: 1.81 (3H, br s), 2.23 (3H, s), 2.25 (3H, s), 3.78 (3H, s), 6.64-6.81 (4H, m), 6.88 (1H, t, J=6.7 Hz), 6.96-7.16 (8H, m).

Production Example 220

In the same manner as in Production Example 21 except that (E)-2-methyl-N-(4-methylphenyl)-3-(4-methylphenyloxy)-2-propenamide and 3-methoxyphenol were used as materials, the following 3-methoxyphenyl 2-methyl-N-(4-methylphenyl)-3-(4-methylphenyloxy)-2-propenimidate (hereinafter referred to as the present compound 220) was obtained.

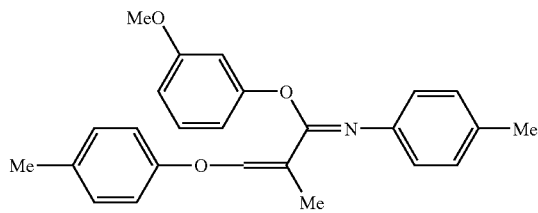

¹H-NMR (DMSO-D₆, 50° C.) δ: 1.93 (3H, br s), 2.22 (3H, s), 2.25 (3H, s), 3.70 (3H, s), 6.45-6.75 (5H, m), 6.78-6.90 (2H, m), 6.93 (1H, d, J=7.6 Hz), 7.05 (2H, d, J=8.3 Hz), 7.14-7.32 (3H, m).

Production Example 221

In the same manner as in Production Example 21 except that (E)-2-methyl-N-(4-methylphenyl)-3-(4-methylphenyloxy)-2-propenamide and 4-methoxyphenol were used as materials, the following 4-methoxyphenyl 2-methyl-N-(4-methylphenyl)-3-(4-methylphenyloxy)-2-propenimidate (hereinafter referred to as the present compound 221) was obtained.

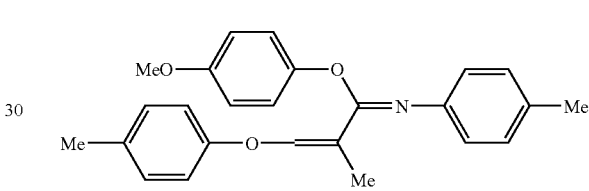

¹H-NMR (DMSO-D₆, 50° C.) δ: 1.86 (3H, br s), 2.22 (3H, s), 2.25 (3H, s), 3.70 (3H, s), 6.69-7.00 (8H, m), 7.04 (2H, d, J=8.0 Hz), 7.08-7.24 (3H, m).

Production Example 222

In the same manner as in Production Example 21 except that (E)-2-methyl-N-(4-methylphenyl)-3-(4-methylphenyloxy)-2-propenamide and 3-(trifluoromethoxy)phenol were used as materials, the following 3-(trifluoromethoxy)phenyl 2-methyl-N-(4-methylphenyl)-3-(4-methylphenyloxy)-2-propenimidate (hereinafter referred to as the present compound 222) was obtained.

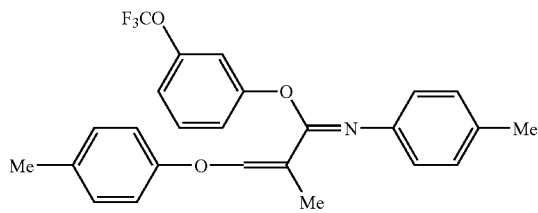

¹H-NMR (DMSO-D₆, 50° C.) δ: 1.92 (3H, br s), 2.20 (3H, s), 2.25 (3H, s), 6.74-6.87 (4H, m), 6.92-7.18 (7H, m), 7.23-7.47 (2H, m).

Production Example 223

In the same manner as in Production Example 21 except that (E)-2-methyl-N-(4-methylphenyl)-3-(4-methylphenyloxy)-2-propenamide and 2-naphthol were used as materials, the following 2-naphthyl 2-methyl-N-(4-methylphenyl)-3-(4-methylphenyloxy)-2-propenimidate (hereinafter referred to as the present compound 223) was obtained.

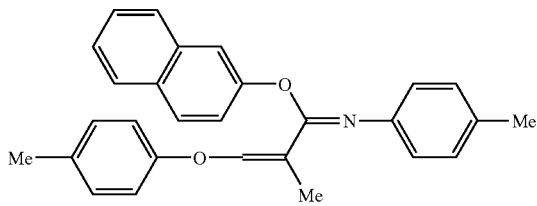

¹H-NMR (DMSO-D₆, 50° C.) δ: 1.97 (3H, br s), 2.17 (3H, s), 2.22 (3H, s), 6.76 (2H, d, J=8.5 Hz), 6.86 (2H, br s), 7.00 (2H, d, J=7.6 Hz), 7.06 (2H, d, J=8.0 Hz), 7.16-7.57 (5H, m), 7.77-7.91 (3H, m).

Production Example 224

In the same manner as in Production Example 21 except that (E)-N-(4-methoxyphenyl)-2-methyl-3-(4-methylphenyloxy)-2-propenamide and phenol were used as materials, the following phenyl N-(4-methoxyphenyl)-2-methyl-3-(4-methylphenyloxy)-2-propenimidate (hereinafter referred to as the present compound 224) was obtained.

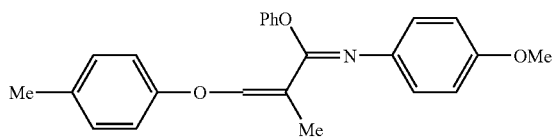

¹H-NMR (DMSO-D₆, 50° C.) δ: 1.96 (3H, br s), 2.24 (3H, s), 3.68 (3H, s), 6.73-6.85 (4H, m), 6.85-7.07 (4H, m), 7.11 (2H, d, J=8.0 Hz), 7.17-7.41 (3H, m).

Production Example 225

In the same manner as in Production Example 21 except that (E)-N-(4-methoxyphenyl)-2-methyl-3-(4-methylphenyloxy)-2-propenamide and 3-methylphenol were used as materials, the following 3-methylphenyl N-(4-methoxyphenyl)-2-methyl-3-(4-methylphenyloxy)-2-propenimidate (hereinafter referred to as the present compound 225) was obtained.

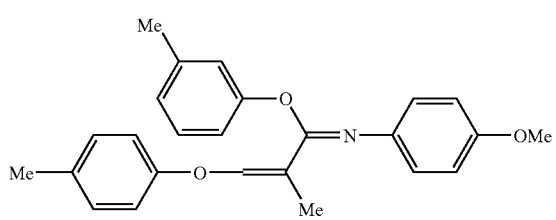

¹H-NMR (DMSO-D₆, 50° C.) δ: 1.95 (3H, br s), 2.25 (6H, s), 3.68 (3H, s), 6.61-7.05 (9H, m), 7.08-7.33 (4H, m).

Production Example 226

In the same manner as in Production Example 21 except that (E)-N-(4-methoxyphenyl)-2-methyl-3-(4-methylphenyloxy)-2-propenamide and 3-ethylphenol were used as materials, the following 3-ethylphenyl N-(4-methoxyphenyl)-2-methyl-3-(4-methylphenyloxy)-2-propenimidate (hereinafter referred to as the present compound 226) was obtained.

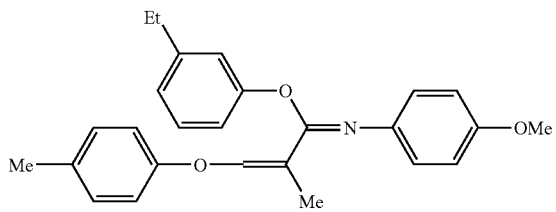

¹H-NMR (DMSO-D₆, 50° C.) δ: 1.11 (3H, t, J=7.5 Hz), 1.96 (3H, br s), 2.24 (3H, s), 2.54 (2H, d, J=7.5 Hz), 3.68 (3H, s), 6.61-7.02 (9H, m), 7.10 (2H, d, J=8.5 Hz), 7.14-7.32 (2H, m).

Production Example 227

In the same manner as in Production Example 21 except that (E)-N-(4-methoxyphenyl)-2-methyl-3-(4-methylphenyloxy)-2-propenamide and 3-methoxyphenol were used as materials, the following 3-methoxyphenyl N-(4-methoxyphenyl)-2-methyl-3-(4-methylphenyloxy)-2-propenimidate (hereinafter referred to as the present compound 227) was obtained.

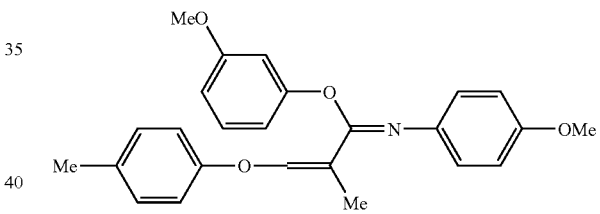

¹H-NMR (DMSO-D₆, 50° C.) δ: 1.97 (3H, br s), 2.25 (3H, s), 3.69 (3H, s), 3.70 (3H, s), 6.38-6.72 (3H, m), 6.76-6.88 (4H, m), 6.89-7.07 (2H, m), 7.09-7.40 (4H, m).

Production Example 228

In the same manner as in Production Example 21 except that (E)-3-(3-ethylphenyloxy)-2-methyl-N-phenyl-2-propenamide and phenol were used as materials, the following phenyl 3-(3-ethylphenyloxy)-2-methyl-N-phenyl-2-propenimidate (hereinafter referred to as the present compound 228) was obtained.

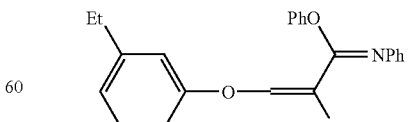

¹H-NMR (DMSO-D₆, 50° C.) δ: 1.13 (3H, t, J=7.6 Hz), 1.93 (3H, br s), 2.54 (2H, q, J=7.6 Hz), 6.61 (1H, s), 6.69 (1H, d, J=8.0 Hz), 6.90 (2H, d, J=7.5 Hz), 6.93-7.11 (5H, m), 7.16-7.26 (4H, m), 7.31 (2H, t, J=7.4 Hz).

Production Example 229

In the same manner as in Production Example 21 except that (E)-3-(4-ethylphenyloxy)-2-methyl-N-phenyl-2-propenamide and phenol were used as materials, the following phenyl 3-(4-ethylphenyloxy)-2-methyl-N-phenyl-2-propenimidate (hereinafter referred to as the present compound 229) was obtained.

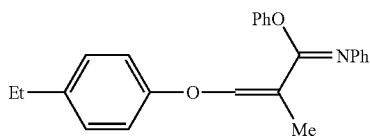

¹H-NMR (DMSO-D₆, 50° C.) δ: 1.14 (3H, t, J=7.6 Hz), 1.92 (3H, br s), 2.55 (2H, q, J=7.6 Hz), 6.79 (2H, d, J=8.4 Hz), 6.88 (2H, d, J=7.6 Hz), 6.93-7.09 (4H, m), 7.14 (2H, d, J=8.4 Hz), 7.18-7.36 (5H, m).

Production Example 230

In the same manner as in Production Example 21 except that (E)-3-(4-isopropylphenyloxy)-2-methyl-N-phenyl-2-propenamide and phenol were used as materials, the following phenyl 3-(4-isopropylphenyloxy)-2-methyl-N-phenyl-2-propenimidate (hereinafter referred to as the present compound 230) was obtained.

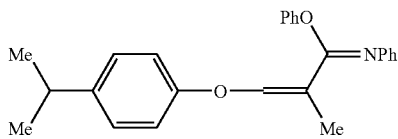

¹H-NMR (DMSO-D₆, 50° C.) δ: 1.16 (6H, d, J=6.8 Hz), 1.92 (3H, br s), 2.79-2.91 (1H, m), 6.80 (2H, d, J=8.5 Hz), 6.88 (2H, d, J=7.8 Hz), 6.93-7.10 (4H, m), 7.14-7.36 (7H, m).

Production Example 231

In the same manner as in Production Example 21 except that (E)-3-(4-chlorophenyloxy)-2-methyl-N-phenyl-2-propenamide and phenol were used as materials, the following phenyl 3-(4-chlorophenyloxy)-2-methyl-N-phenyl-2-propenimidate (hereinafter referred to as the present compound 231) was obtained.

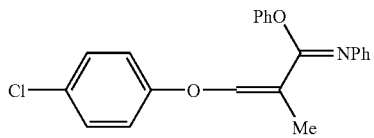

¹H-NMR (DMSO-D₆, 50° C.) δ: 1.90 (3H, br s), 6.88 (2H, d, J=7.6 Hz), 6.92 (2H, d, J=8.7 Hz), 6.95-7.11 (4H, m), 7.18-7.33 (5H, m), 7.36 (2H, d, J=8.7 Hz).

Production Example 232

In the same manner as in Production Example 21 except that (E)-3-(2-methoxyphenyloxy)-2-methyl-N-phenyl-2-propenamide and phenol were used as materials, the following phenyl 3-(2-methoxyphenyloxy)-2-methyl-N-phenyl-2-propenimidate (hereinafter referred to as the present compound 232) was obtained.

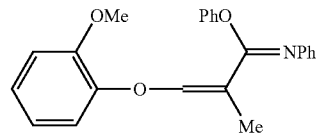

¹H-NMR (DMSO-D₆, 50° C.) δ: 1.93 (3H, br s), 3.71 (3H, s), 6.76-7.33 (15H, m).

Production Example 233

In the same manner as in Production Example 21 except that (E)-3-(2-methoxyphenyloxy)-2-methyl-N-phenyl-2-propenamide and 3-methylphenol were used as materials, the following 3-methylphenyl 3-(2-methoxyphenyloxy)-2-methyl-N-phenyl-2-propenimidate (hereinafter referred to as the present compound 233) was obtained.

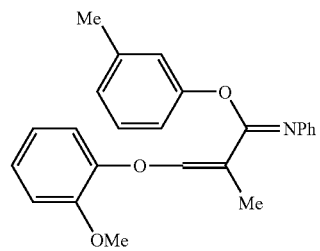

¹H-NMR (DMSO-D₆, 50° C.) δ: 1.93 (3H, br s), 2.23 (3H, s), 3.71 (3H, s), 6.65-6.92 (8H, m), 6.96 (1H, t, J=7.4 Hz), 7.04-7.17 (4H, m), 7.20 (2H, t, J=7.8 Hz).

Production Example 234

In the same manner as in Production Example 21 except that (E)-3-(2-methoxyphenyloxy)-2-methyl-N-phenyl-2-propenamide and 3-ethylphenol were used as materials, the following 3-ethylphenyl 3-(2-methoxyphenyloxy)-2-methyl-N-phenyl-2-propenimidate (hereinafter referred to as the present compound 234) was obtained.

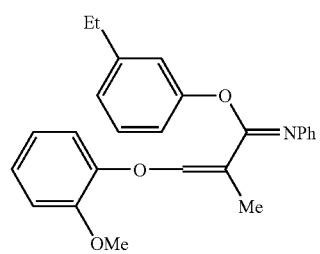

¹H-NMR (DMSO-D₆, 50° C.) δ: 1.10 (3H, t, J=7.6 Hz), 1.93 (3H, br s), 2.52 (2H, q, J=7.6 Hz), 3.71 (3H, s), 6.67-6.90 (7H, m), 6.95 (1H, t, J=7.4 Hz), 7.04-7.23 (6H, m).

Production Example 235

In the same manner as in Production Example 21 except that (E)-3-(2-methoxyphenyloxy)-2- propenamide and 2-methoxyphenol were used as materials, the following 2-methoxyphenyl 3-(2-methoxyphenyloxy)-2-methyl-N-phenyl-2-propenimidate (hereinafter referred to as the present compound 235) was obtained.

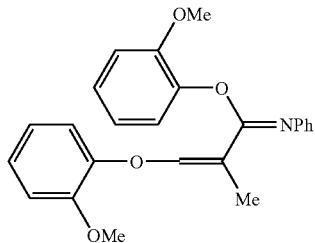

$^1$H-NMR (CDCl$_3$, 50° C.) δ: 1.93 (3H, br s), 3.81 (3H, s), 6.76-7.09 (10H, m), 7.15 (2H, t, J=7.6 Hz), 7.22-7.33 (4H, m).

Production Example 236

In the same manner as in Production Example 21 except that (E)-3-(2-methoxyphenyloxy)-2-methyl-N-phenyl-2-propenamide and 3-methoxyphenol were used as materials, the following 3-methoxyphenyl 3-(2-methoxyphenyloxy)-2-methyl-N-phenyl-2-propenimidate (hereinafter referred to as the present compound 236) was obtained.

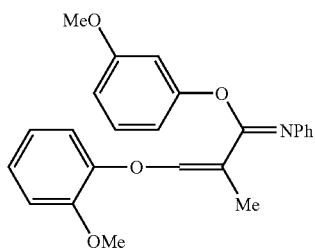

$^1$H-NMR (DMSO-D$_6$, 50° C.) δ: 1.94 (3H, br s), 3.68 (3H, s), 3.72 (3H, s), 6.51 (2H, br s), 6.59 (1H, d, J=7.1 Hz), 6.80-6.93 (4H, m), 6.97 (1H, t, J=7.4 Hz), 7.05-7.27 (6H, m).

Production Example 237

In the same manner as in Production Example 21 except that (E)-3-(2-methoxyphenyloxy)-2-methyl-N-phenyl-2-propenamide and 3-ethoxyphenol were used as materials, the following 3-ethoxyphenyl 3-(2-methoxyphenyloxy)-2-methyl-N-phenyl-2-propenimidate (hereinafter referred to as the present compound 237) was obtained.

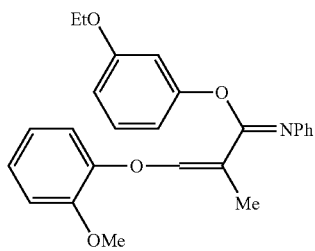

$^1$H-NMR (DMSO-D$_6$, 50° C.) δ: 1.26 (3H, t, J=7.0 Hz), 1.93 (3H, br s), 3.72 (3H, s), 3.95 (2H, q, J=7.0 Hz), 6.49 (2H, br s), 6.57 (1H, d, J=7.3 Hz), 6.80-6.93 (4H, m), 6.97 (1H, t, J=7.4 Hz), 7.04-7.25 (6H, m).

Production Example 238

In the same manner as in Production Example 21 except that (E)-3-(2-methoxyphenyloxy)-2-methyl-N-phenyl-2-propenamide and 3,5-dimethylphenol were used as materials, the following 3,5-dimethylphenyl 3-(2-methoxyphenyloxy)-2-methyl-N-phenyl-2-propenimidate (hereinafter referred to as the present compound 238) was obtained.

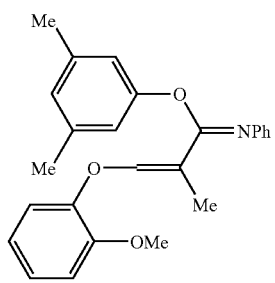

$^1$H-NMR (DMSO-D$_6$, 50° C.) δ: 1.93 (3H, br s), 2.18 (6H, s), 3.72 (3H, s), 6.55 (2H, br s), 6.65 (1H, br s), 6.76-6.92 (4H, m), 6.96 (1H, t, J=7.4 Hz), 7.04-7.16 (3H, m), 7.20 (2H, t, J=7.8 Hz).

Production Example 239

In the same manner as in Production Example 21 except that (E)-3-(2-methoxyphenyloxy)-2-methyl-N-(4-methylphenyl)-2-propenamide and phenol were used as materials, the following phenyl 3-(2-methoxyphenyloxy)-2-methyl-N-(4-methylphenyl)-2-propenimidate (hereinafter referred to as the present compound 239) was obtained.

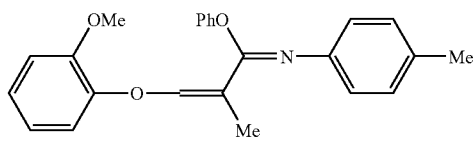

$^1$H-NMR (DMSO-D$_6$, 50° C.) δ: 1.94 (3H, br s), 2.20 (3H, s), 3.70 (3H, s), 6.71-7.17 (11H, m), 7.27 (2H, t, J=7.3 Hz).

Production Example 240

In the same manner as in Production Example 21 except that (E)-3-(2-methoxyphenyloxy)-2-methyl-N-(4-methylphenyl)-2-propenamide and 3-methylphenol were used as materials, the following 3-methylphenyl 3-(2-methoxyphenyloxy)-2-methyl-N-(4-methylphenyl)-2-propenimidate (hereinafter referred to as the present compound 240) was obtained.

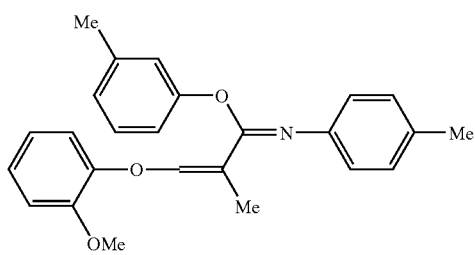

¹H-NMR (DMSO-D₆, 50° C.) δ: 1.94 (3H, br s), 2.20 (3H, s), 2.23 (3H, s), 3.70 (3H, s), 6.59-6.93 (7H, m), 6.97-7.22 (6H, m).

Production Example 241

In the same manner as in Production Example 21 except that (E)-3-(2-methoxyphenyloxy)-2-methyl-N-(4-methylphenyl)-2-propenamide and 3-ethylphenol were used as materials, the following 3-ethylphenyl 3-(2-methoxyphenyloxy)-2-methyl-N-(4-methylphenyl)-2-propenimidate (hereinafter referred to as the present compound 241) was obtained.

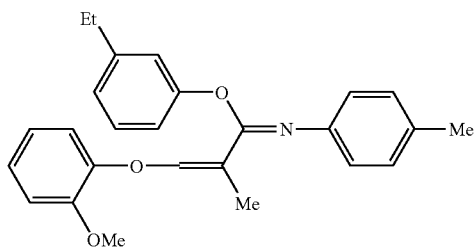

¹H-NMR (DMSO-D₆, 50° C.) δ: 1.10 (3H, t, J=7.6 Hz), 1.94 (3H, br s), 2.20 (3H, s), 2.52 (2H, q, J=7.6 Hz), 3.70 (3H, s), 6.65-6.92 (7H, m), 7.00 (2H, d, J=8.0 Hz), 7.04-7.22 (4H, m).

Production Example 242

In the same manner as in Production Example 21 except that (E)-3-(2-methoxyphenyloxy)-2-methyl-N-(4-methylphenyl)-2-propenamide and 3-methoxyphenol were used as materials, the following 3-methoxyphenyl 3-(2-methoxyphenyloxy)-2-methyl-N-(4-methylphenyl)-2-propenimidate (hereinafter referred to as the present compound 242) was obtained.

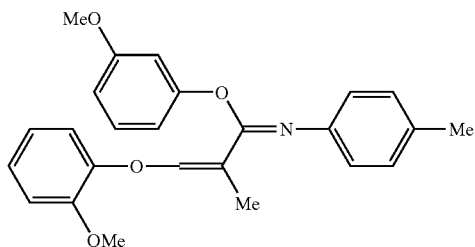

¹H-NMR (DMSO-D₆, 50° C.) δ: 1.94 (3H, br s), 2.20 (3H, s), 3.68 (3H, s), 3.70 (3H, s), 6.47 (2H, br s), 6.59 (1H, d, J=7.8 Hz), 6.78-6.90 (4H, m), 7.02 (2H, d, J=8.0 Hz), 7.05-7.22 (4H, m).

Production Example 243

In the same manner as in Production Example 21 except that (E)-3-(2-methoxyphenyloxy)-2-methyl-N-(4-methylphenyl)-2-propenamide and 3-ethoxyphenol were used as materials, the following 3-ethoxyphenyl 3-(2-methoxyphenyloxy)-2-methyl-N-(4-methylphenyl)-2-propenimidate (hereinafter referred to as the present compound 243) was obtained.

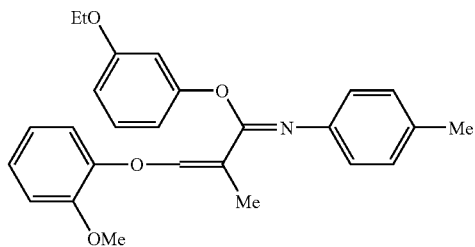

¹H-NMR (DMSO-D₆, 50° C.) δ: 1.26 (3H, t, J=7.0 Hz), 1.94 (3H, br s), 2.20 (3H, s), 3.71 (3H, s), 3.95 (2H, q, J=7.0 Hz), 6.46 (2H, br s), 6.57 (1H, d, J=6.1 Hz), 6.78-6.91 (4H, m), 7.02 (2H, d, J=8.0 Hz), 7.05-7.20 (4H, m).

Production Example 244

In the same manner as in Production Example 21 except that (E)-3-(2-methoxyphenyloxy)-2-methyl-N-(4-methylphenyl)-2-propenamide and 3,5-dimethylphenol were used as materials, the following 3,5-dimethylphenyl 3-(2-methoxyphenyloxy)-2-methyl-N-(4-methylphenyl)-2-propenimidate (hereinafter referred to as the present compound 244) was obtained.

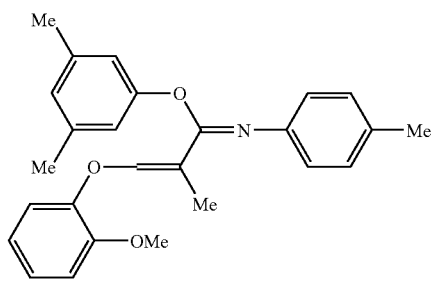

¹H-NMR (DMSO-D₆, 50° C.) δ: 1.93 (3H, br s), 2.18 (6H, s), 2.20 (3H, s), 3.71 (3H, s), 6.52 (2H, br s), 6.64 (1H, br s), 6.73-6.89 (4H, m), 7.01 (2H, d, J=7.6 Hz), 7.04-7.15 (3H, m).

Production Example 245

In the same manner as in Production Example 21 except that (E)-N-(4-methoxyphenyl)-3-(2-methoxyphenyloxy)-2-methyl-2-propenamide and phenol were used as materials, the following phenyl N-(4-methoxyphenyl)-3-(2-methoxyphenyloxy)-2-methyl-2-propenimidate (hereinafter referred to as the present compound 245) was obtained.

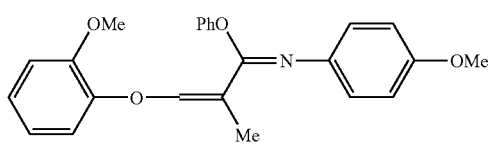

$^1$H-NMR (DMSO-D$_6$, 50° C.) δ: 1.97 (3H, br s), 3.67 (3H, s), 3.69 (3H, s), 6.71-7.18 (12H, m), 7.22-7.33 (2H, m).

Production Example 246

In the same manner as in Production Example 21 except that (E)-N-(4-methoxyphenyl)-3-(2-methoxyphenyloxy)-2-methyl-2-propenamide and 3-methylphenol were used as materials, the following 3-methylphenyl N-(4-methoxyphenyl)-3-(2-methoxyphenyloxy)-2-methyl-2-propenimidate (hereinafter referred to as the present compound 246) was obtained.

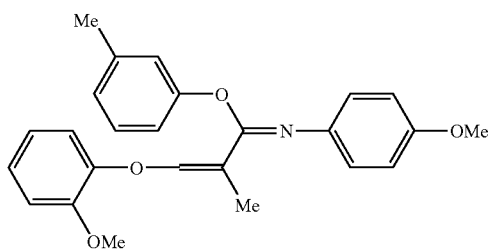

$^1$H-NMR (DMSO-D$_6$, 50° C.) δ: 1.97 (3H, br s), 2.23 (3H, s), 3.68 (3H, s), 3.70 (3H, s), 6.58-7.02 (9H, m), 7.04-7.22 (4H, m).

Production Example 247

In the same manner as in Production Example 21 except that (E)-N-(4-methoxyphenyl)-3-(2-methoxyphenyloxy)-2-methyl-2-propenamide and 3-ethylphenol were used as materials, the following 3-ethylphenyl N-(4-methoxyphenyl)-3-(2-methoxyphenyloxy)-2-methyl-2-propenimidate (hereinafter referred to as the present compound 247) was obtained.

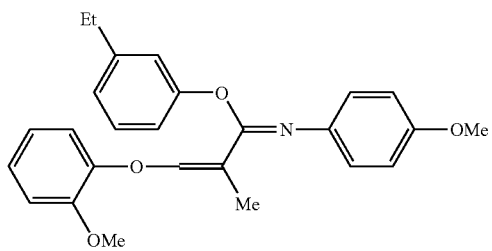

$^1$H-NMR (DMSO-D$_6$, 50° C.) δ: 1.10 (3H, t, J=7.7 Hz), 1.97 (3H, br s), 2.52 (2H, q, J=7.7 Hz), 3.67 (3H, s), 3.70 (3H, s), 6.61-7.00 (9H, m), 7.03-7.22 (4H, m).

Production Example 248

In the same manner as in Production Example 21 except that (E)-N-(4-methoxyphenyl)-3-(2-methoxyphenyloxy)-2-methyl-2-propenamide and 3-methoxyphenol were used as materials, the following 3-methoxyphenyl N-(4-methoxyphenyl)-3-(2-methoxyphenyloxy)-2-methyl-2-propenimidate (hereinafter referred to as the present compound 248) was obtained.

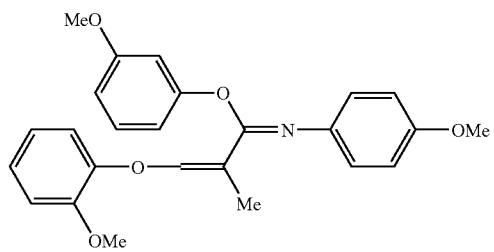

$^1$H-NMR (DMSO-D$_6$, 50° C.) δ: 1.97 (3H, br s), 3.68 (6H, s), 3.70 (3H, s), 6.45 (2H, br s), 6.58 (1H, br s), 6.79 (2H, d, J=8.8 Hz), 6.83-6.90 (2H, m), 6.94 (2H, br s), 7.04-7.23 (4H, m).

Production Example 249

In the same manner as in Production Example 21 except that (E)-N-(4-methoxyphenyl)-3-(2-methoxyphenyloxy)-2-methyl-2-propenamide and 3-ethoxyphenol were used as materials, the following 3-ethoxyphenyl N-(4-methoxyphenyl)-3-(2-methoxyphenyloxy)-2-methyl-2-propenimidate (hereinafter referred to as the present compound 249) was obtained.

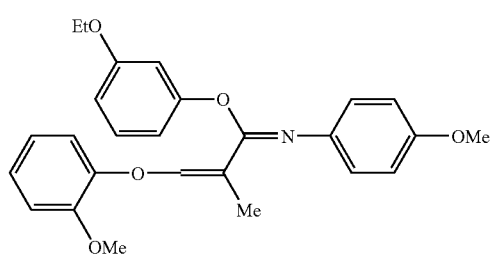

$^1$H-NMR (DMSO-D$_6$, 50° C.) δ: 1.26 (3H, t, J=6.9 Hz), 1.97 (3H, br s), 3.68 (3H, s), 3.70 (3H, s), 3.95 (2H, q, J=6.9 Hz), 6.43 (2H, br s), 6.56 (1H, s), 6.79 (2H, d, J=8.8 Hz), 6.86 (2H, d, J=4.4 Hz), 6.95 (2H, br s), 7.04-7.22 (4H, m).

Production Example 250

In the same manner as in Production Example 21 except that (E)-N-(4-methoxyphenyl)-3-(2-methoxyphenyloxy)-2-methyl-2-propenamide and 3,5-dimethylphenol were used as materials, the following 3,5-dimethylphenyl N-(4-methoxyphenyl)-3-(2-methoxyphenyloxy)-2-methyl-2-propenimidate (hereinafter referred to as the present compound 250) was obtained.

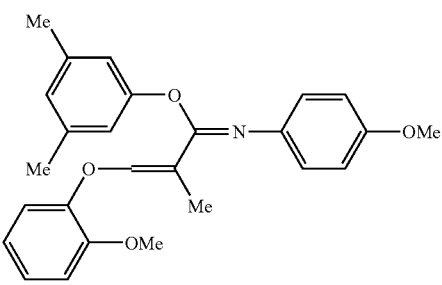

¹H-NMR (DMSO-D₆, 50° C.) δ: 1.93 (3H, br s), 2.12 (6H, s), 2.18 (6H, s), 3.71 (3H, s), 6.40-6.90 (7H, m), 6.94 (1H, d, J=8.0 Hz), 7.03-7.18 (3H, m).

Production Example 251

In the same manner as in Production Example 21 except that (E)-N-(3,4-dimethylphenyl)-3-(2-methoxyphenyloxy)-2-methyl-2-propenamide and phenol were used as materials, the following phenyl N-(3,4-dimethylphenyl)-3-(2-methoxyphenyloxy)-2-methyl-2-propenimidate (hereinafter referred to as the present compound 251) was obtained.

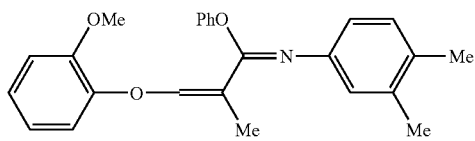

¹H-NMR (DMSO-D₆, 50° C.) δ: 1.93 (3H, br s), 2.11 (6H, s), 3.70 (3H, s), 6.58-6.81 (3H, m), 6.85 (1H, td, J=7.4, 1.7 Hz), 6.88-7.18 (7H, m), 7.27 (2H, t, J=7.0 Hz).

Production Example 252

In the same manner as in Production Example 21 except that (E)-N-(3,4-dimethylphenyl)-3-(2-methoxyphenyloxy)-2-methyl-2-propenamide and 3-methylphenol were used as materials, the following 3-methylphenyl N-(3,4-dimethylphenyl)-3-(2-methoxyphenyloxy)-2-methyl-2-propenimidate (hereinafter referred to as the present compound 252) was obtained.

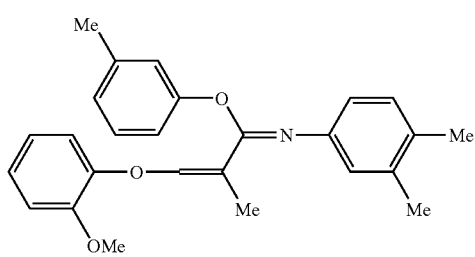

¹H-NMR (DMSO-D₆, 50° C.) δ: 1.93 (3H, br s), 2.11 (6H, s), 2.22 (3H, s), 3.70 (3H, s), 6.55-6.89 (7H, m), 6.94 (1H, d, J=7.8 Hz), 7.02-7.20 (4H, m).

Production Example 253

In the same manner as in Production Example 21 except that (E)-N-(3,4-dimethylphenyl)-3-(2-methoxyphenyloxy)-2-methyl-2-propenamide and 3-ethylphenol were used as materials, the following 3-ethylphenyl N-(3,4-dimethylphenyl)-3-(2-methoxyphenyloxy)-2-methyl-2-propenimidate (hereinafter referred to as the present compound 253) was obtained.

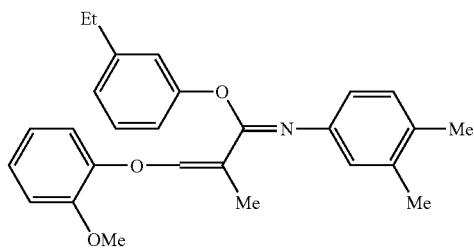

¹H-NMR (DMSO-D₆, 50° C.) δ: 1.10 (3H, t, J=7.6 Hz), 1.94 (3H, br s), 2.11 (6H, s), 2.52 (2H, q, J=7.6 Hz), 3.71 (3H, s), 6.56-6.80 (5H, m), 6.81-6.89 (2H, m), 6.94 (1H, d, J=8.0 Hz), 7.03-7.21 (4H, m).

Production Example 254

In the same manner as in Production Example 21 except that (E)-N-(3,4-dimethylphenyl)-3-(2-methoxyphenyloxy)-2-methyl-2-propenamide and 3-methoxyphenol were used as materials, the following 3-methoxyphenyl N-(3,4-dimethylphenyl)-3-(2-methoxyphenyloxy)-2-methyl-2-propenimidate (hereinafter referred to as the present compound 254) was obtained.

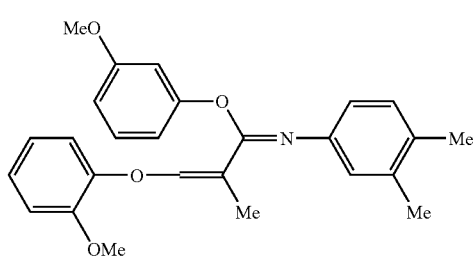

¹H-NMR (DMSO-D₆, 50° C.) δ: 1.93 (3H, br s), 2.12 (6H, s), 3.68 (3H, s), 3.71 (3H, s), 6.48 (2H, br s), 6.59 (1H, d, J=7.1 Hz), 6.65 (1H, d, J=7.1 Hz), 6.72 (1H, s), 6.77-6.90 (2H, m), 6.95 (1H, d, J=8.0 Hz), 7.04-7.22 (4H, m).

Production Example 255

In the same manner as in Production Example 21 except that (E)-N-(3,4-dimethylphenyl)-3-(2-methoxyphenyloxy)-2-methyl-2-propenamide and 3-ethoxyphenol were used as materials, the following 3-ethoxyphenyl N-(3,4-dimethylphenyl)-3-(2-methoxyphenyloxy)-2-methyl-2-propenimidate (hereinafter referred to as the present compound 255) was obtained.

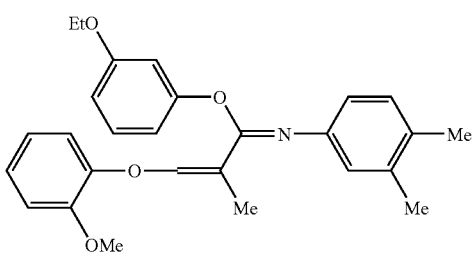

$^1$H-NMR (DMSO-D$_6$, 50° C.) δ: 1.26 (3H, t, J=7.0 Hz), 1.94 (3H, br s), 2.12 (6H, s), 3.71 (3H, s), 3.94 (2H, q, J=7.0 Hz), 6.47 (2H, br s), 6.57 (1H, d, J=6.6 Hz), 6.65 (1H, d, J=6.6 Hz), 6.70-6.77 (1H, m), 6.78-6.89 (2H, m), 6.95 (1H, d, J=8.0 Hz), 7.04-7.23 (4H, m).

Production Example 256

In the same manner as in Production Example 21 except that (E)-N-(3,4-dimethylphenyl)-3-(2-methoxyphenyloxy)-2-methyl-2-propenamide and 3,5-dimethylphenol were used as materials, the following 3,5-dimethylphenyl N-(3,4-dimethylphenyl)-3-(2-methoxyphenyloxy)-2-methyl-2-propenimidate (hereinafter referred to as the present compound 256) was obtained.

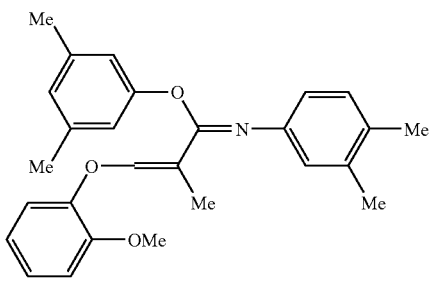

$^1$H-NMR (DMSO-D$_6$, 50° C.) δ: 1.97 (3H, br s), 2.18 (6H, s), 3.68 (3H, s), 3.70 (3H, s), 6.49 (2H, br s), 6.63 (1H, br s), 6.72-7.02 (6H, m), 7.04-7.20 (3H, m).

Production Example 257

In the same manner as in Production Example 21 except that (E)-3-(3-methoxyphenyloxy)-2-methyl-N-phenyl-2-propenamide and phenol were used as materials, the following phenyl 3-(3-methoxyphenyloxy)-2-methyl-N-phenyl-2-propenimidate (hereinafter referred to as the present compound 257) was obtained.

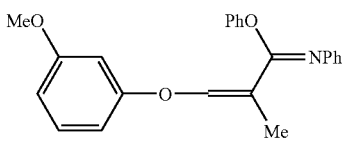

$^1$H-NMR (DMSO-D$_6$, 50° C.) δ: 1.93 (3H, br s), 3.71 (3H, s), 6.44 (1H, d, J=8.0 Hz), 6.48 (1H, t, J=2.3 Hz), 6.67-6.72 (1H, m), 6.85-7.08 (6H, m), 7.16-7.37 (6H, m).

Production Example 258

In the same manner as in Production Example 21 except that (E)-3-(3-methoxyphenyloxy)-2-methyl-N-phenyl-2-propenamide and 3-methylphenol were used as materials, the following 3-methylphenyl 3-(3-methoxyphenyloxy)-2-methyl-N-phenyl-2-propenimidate (hereinafter referred to as the present compound 258) was obtained.

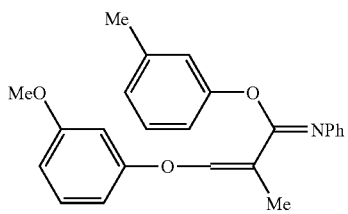

$^1$H-NMR (DMSO-D$_6$, 50° C.) δ: 1.93 (3H, br s), 2.25 (3H, s), 3.71 (3H, s), 6.44 (1H, d, J=8.1 Hz), 6.47 (1H, t, J=2.4 Hz), 6.70 (1H, dd, J=8.2, 2.4 Hz), 6.74-6.94 (5H, m), 6.98 (1H, t, J=7.4 Hz), 7.12-7.31 (5H, m).

Production Example 259

In the same manner as in Production Example 21 except that (E)-3-(3-methoxyphenyloxy)-2-methyl-N-phenyl-2-propenamide and 3-methoxyphenol were used as materials, the following 3-methoxyphenyl 3-(3-methoxyphenyloxy)-2-methyl-N-phenyl-2-propenimidate (hereinafter referred to as the present compound 259) was obtained.

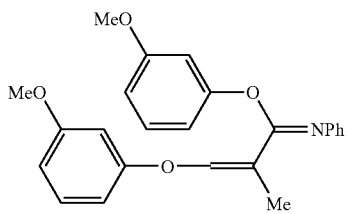

$^1$H-NMR (DMSO-D$_6$, 50° C.) δ: 1.94 (3H, br s), 3.70 (3H, s), 3.71 (3H, s), 6.42-6.51 (2H, m), 6.52-6.66 (3H, m), 6.67-6.75 (1H, m), 6.91 (2H, d, J=7.5 Hz), 6.99 (1H, t, J=7.5 Hz), 7.13-7.38 (5H, m).

Production Example 260

In the same manner as in Production Example 21 except that (E)-3-(3-methoxyphenyloxy)-2-methyl-N-(4-methylphenyl)-2-propenamide and phenol were used as materials, the following phenyl 3-(3-methoxyphenyloxy)-2-methyl-N-(4-methylphenyl)-2-propenimidate (hereinafter referred to as the present compound 260) was obtained.

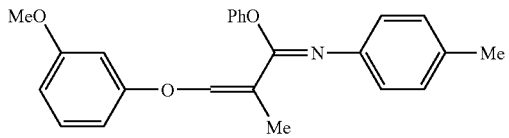

$^1$H-NMR (DMSO-D$_6$, 50° C.) δ: 1.94 (3H, br s), 2.21 (3H, s), 3.70 (3H, s), 6.40-6.49 (2H, m), 6.69 (1H, dd, J=8.2, 2.3 Hz), 6.76-6.89 (2H, m), 6.91-7.10 (5H, m), 7.17-7.36 (4H, m).

Production Example 261

In the same manner as in Production Example 21 except that (E)-3-(3-methoxyphenyloxy)-2-methyl-N-(4-methylphenyl)-2-propenamide and 3-methylphenol were used as materials, the following 3-methylphenyl 3-(3-methoxyphenyloxy)-2-methyl-N-(4-methylphenyl)-2-propenimidate (hereinafter referred to as the present compound 261) was obtained.

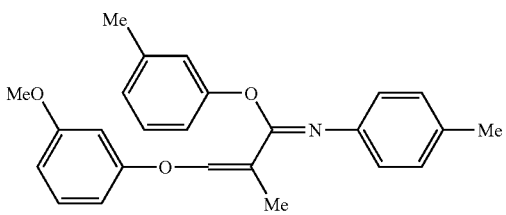

$^1$H-NMR (DMSO-D$_6$, 50° C.) δ: 1.93 (3H, br s), 2.21 (3H, s), 2.25 (3H, s), 3.70 (3H, s), 6.39-6.50 (2H, m), 6.64-6.94 (6H, m), 7.03 (2H, d, J=8.0 Hz), 7.11-7.33 (3H, m).

Production Example 262

In the same manner as in Production Example 21 except that (E)-3-(4-methoxyphenyloxy)-2-methyl-N-phenyl-2-propenamide and phenol were used as materials, phenyl 3-(4-methoxyphenyloxy)-2-methyl-N-phenyl-2-propenimidate (hereinafter referred to as the present compound 262) was obtained.

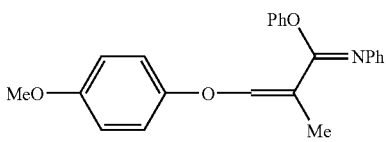

$^1$H-NMR (DMSO-D$_6$, 50° C.) δ: 1.91 (3H, br s), 3.71 (3H, s), 6.77-7.08 (10H, m), 7.14-7.34 (5H, m).

Production Example 263

In the same manner as in Production Example 21 except that (E)-3-(4-methoxyphenyloxy)-2-methyl-N-phenyl-2-propenamide and 3-methylphenol were used as materials, the following 3-methylphenyl 3-(4-methoxyphenyloxy)-2-methyl-N-phenyl-2-propenimidate (hereinafter referred to as the present compound 263) was obtained.

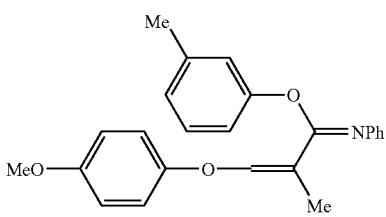

$^1$H-NMR (DMSO-D$_6$, 50° C.) δ: 1.91 (3H, br s), 2.24 (3H, s), 3.71 (3H, s), 6.70-6.92 (9H, m), 6.97 (1H, t, J=7.4 Hz), 7.11-7.25 (4H, m).

Production Example 264

In the same manner as in Production Example 21 except that (E)-3-(4-methoxyphenyloxy)-2-methyl-N-phenyl-2-propenamide and 4-methylphenol were used as materials, the following 4-methylphenyl 3-(4-methoxyphenyloxy)-2-methyl-N-phenyl-2-propenimidate (hereinafter referred to as the present compound 264) was obtained.

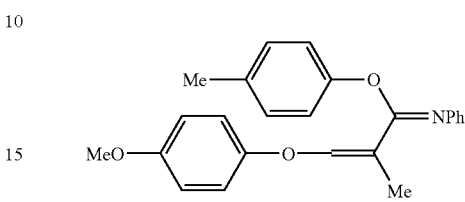

$^1$H-NMR (DMSO-D$_6$, 50° C.) δ: 1.89 (3H, br s), 2.22 (3H, s), 3.71 (3H, s), 6.78-6.94 (8H, m), 6.97 (1H, t, J=7.3 Hz), 7.08 (2H, d, J=7.6 Hz), 7.14-7.26 (3H, m).

Production Example 265

In the same manner as in Production Example 21 except that (E)-3-(4-methoxyphenyloxy)-2-methyl-N-phenyl-2-propenamide and 3-ethylphenol were used as materials, the following 3-ethylphenyl 3-(4-methoxyphenyloxy)-2-methyl-N-phenyl-2-propenimidate (hereinafter referred to as the present compound 265) was obtained.

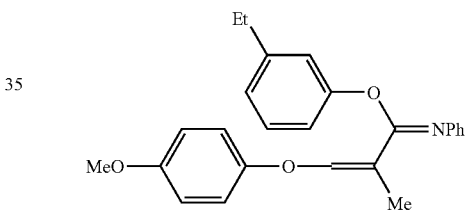

$^1$H-NMR (DMSO-D$_6$, 50° C.) δ: 1.11 (3H, t, J=7.6 Hz), 1.91 (3H, br s), 2.54 (2H, q, J=7.6 Hz), 3.71 (3H, s), 6.72-6.93 (9H, m), 6.96 (1H, t, J=7.4 Hz), 7.13-7.26 (4H, m).

Production Example 266

In the same manner as in Production Example 21 except that (E)-3-(4-methoxyphenyloxy)-2-methyl-N-phenyl-2-propenamide and 3-methoxyphenol were used as materials, the following 3-methoxyphenyl 3-(4-methoxyphenyloxy)-2-methyl-N-phenyl-2-propenimidate (hereinafter referred to as the present compound 266) was obtained.

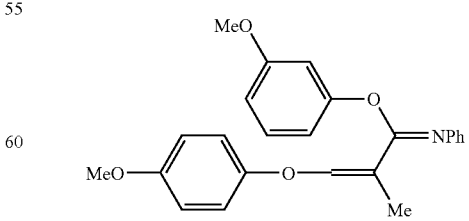

$^1$H-NMR (DMSO-D$_6$, 50° C.) δ: 1.92 (3H, br s), 3.69 (3H, s), 3.71 (3H, s), 6.45-6.67 (3H, m), 6.81-6.93 (6H, m), 6.98 (1H, t, J=7.3 Hz), 7.13-7.27 (4H, m).

Production Example 267

In the same manner as in Production Example 21 except that (E)-3-(4-methoxyphenyloxy)-2-methyl-N-phenyl-2-propenamide and 3-ethoxyphenol were used as materials, the following 3-ethoxyphenyl 3-(4-methoxyphenyloxy)-2-methyl-N-phenyl-2-propenimidate (hereinafter referred to as the present compound 267) was obtained.

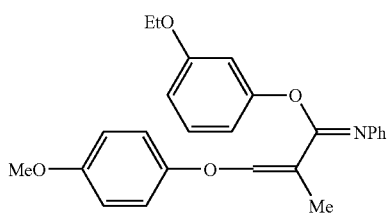

$^1$H-NMR (DMSO-D$_6$, 50° C.) δ: 1.27 (3H, t, J=7.0 Hz), 1.91 (3H, br s), 3.71 (3H, s), 3.96 (2H, q, J=7.0 Hz), 6.41-6.67 (3H, m), 6.81-6.95 (6H, m), 6.98 (1H, t, J=7.4 Hz), 7.11-7.29 (4H, m).

Production Example 268

In the same manner as in Production Example 21 except that (E)-3-(4-methoxyphenyloxy)-2-methyl-N-phenyl-2-propenamide and 3,5-dimethylphenol were used as materials, the following 3,5-dimethylphenyl 3-(4-methoxyphenyloxy)-2-methyl-N-phenyl-2-propenimidate (hereinafter referred to as the present compound 268) was obtained.

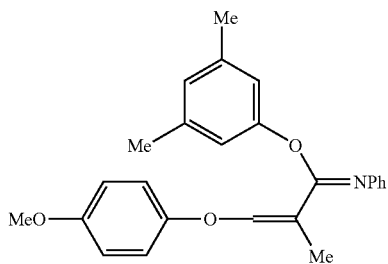

$^1$H-NMR (DMSO-D$_6$, 50° C.) δ: 1.90 (3H, br s), 2.19 (6H, s), 3.71 (3H, s), 6.58 (2H, br s), 6.66 (1H, br s), 6.80-6.94 (6H, m), 6.97 (1H, t, J=7.4 Hz), 7.13-7.28 (3H, m).

Production Example 269

In the same manner as in Production Example 21 except that (E)-3-(4-methoxyphenyloxy)-2-methyl-N-(4-methylphenyl)-2-propenamide and phenol were used as materials, the following phenyl 3-(4-methoxyphenyloxy)-2-methyl-N-(4-methylphenyl)-2-propenimidate (hereinafter referred to as the present compound 269) was obtained.

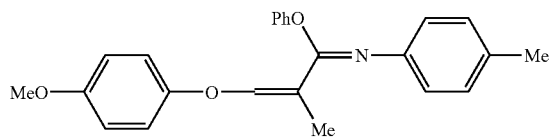

$^1$H-NMR (DMSO-D$_6$, 50° C.) δ: 1.92 (3H, br s), 2.20 (3H, s), 3.71 (3H, s), 6.71-7.09 (11H, m), 7.11-7.37 (3H, m).

Production Example 270

In the same manner as in Production Example 21 except that (E)-3-(4-methoxyphenyloxy)-2-methyl-N-(4-methylphenyl)-2-propenamide and 3-methylphenol were used as materials, the following 3-methylphenyl 3-(4-methoxyphenyloxy)-2-methyl-N-(4-methylphenyl)-2-propenimidate (hereinafter referred to as the present compound 270) was obtained.

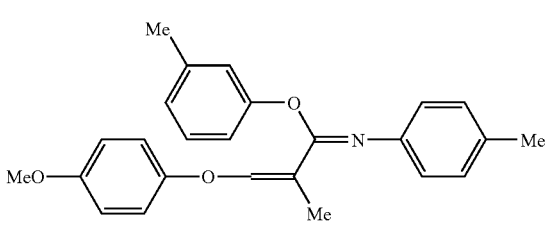

$^1$H-NMR (DMSO-D$_6$, 50° C.) δ: 1.92 (3H, br s), 2.21 (3H, s), 2.24 (3H, s), 3.71 (3H, s), 6.66-6.97 (9H, m), 7.02 (2H, d, J=8.0 Hz), 7.09-7.26 (2H, m).

Production Example 271

In the same manner as in Production Example 21 except that (E)-3-(4-methoxyphenyloxy)-2-methyl-N-(4-methylphenyl)-2-propenamide and 4-methylphenol were used as materials, the following 4-methylphenyl 3-(4-methoxyphenyloxy)-2-methyl-N-(4-methylphenyl)-2-propenimidate (hereinafter referred to as the present compound 271) was obtained.

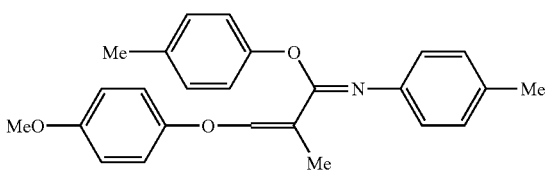

$^1$H-NMR (DMSO-D$_6$, 50° C.) δ: 1.89 (3H, br s), 2.21 (6H, s), 3.71 (3H, s), 6.72-6.96 (8H, m), 7.02 (2H, d, J=8.0 Hz), 7.08 (2H, d, J=7.3 Hz), 7.15 (1H, br s).

Production Example 272

In the same manner as in Production Example 21 except that (E)-3-(4-methoxyphenyloxy)-2-methyl-N-(4-methylphenyl)-2-propenamide and 3-ethylphenol were used as materials, the following 3-ethylphenyl 3-(4-methoxyphenyloxy)-2-methyl-N-(4-methylphenyl)-2-propenimidate (hereinafter referred to as the present compound 272) was obtained.

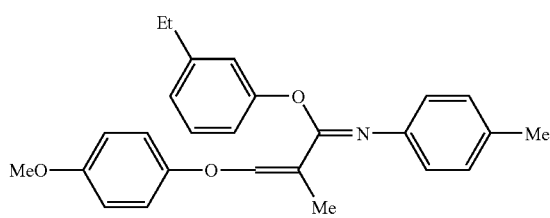

¹H-NMR (DMSO-D₆, 50° C.) δ: 1.11 (3H, t, J=7.6 Hz), 1.92 (3H, br s), 2.20 (3H, s), 2.54 (2H, q, J=7.6 Hz), 3.71 (3H, s), 6.68-6.93 (9H, m), 7.01 (2H, d, J=8.0 Hz), 7.13-7.23 (2H, m).

Production Example 273

In the same manner as in Production Example 21 except that (E)-3-(4-methoxyphenyloxy)-2-methyl-N-(4-methylphenyl)-2-propenamide and 3-methoxyphenol were used as materials, the following 3-methoxyphenyl 3-(4-methoxyphenyloxy)-2-methyl-N-(4-methylphenyl)-2-propenimidate (hereinafter referred to as the present compound 273) was obtained.

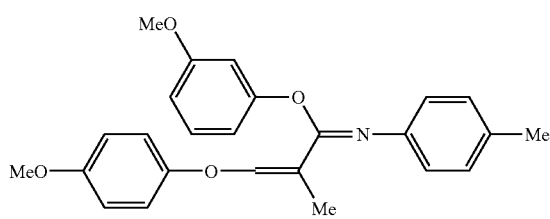

¹H-NMR (DMSO-D₆, 50° C.) δ: 1.93 (3H, br s), 2.21 (3H, s), 3.69 (3H, s), 3.71 (3H, s), 6.40-6.68 (3H, m), 6.77-6.92 (6H, m), 7.03 (2H, d, J=8.0 Hz), 7.12-7.28 (2H, m).

Production Example 274

In the same manner as in Production Example 21 except that (E)-3-(4-methoxyphenyloxy)-2-methyl-N-(4-methylphenyl)-2-propenamide and 3-ethoxyphenol were used as materials, the following 3-ethoxyphenyl 3-(4-methoxyphenyloxy)-2-methyl-N-(4-methylphenyl)-2-propenimidate (hereinafter referred to as the present compound 274) was obtained.

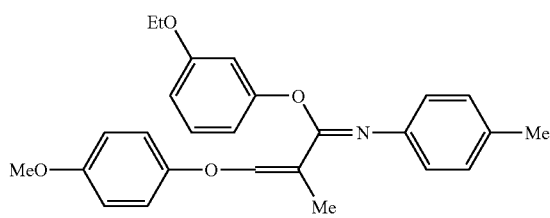

¹H-NMR (DMSO-D₆, 50° C.) δ: 1.27 (3H, t, J=7.0 Hz), 1.92 (3H, br s), 2.21 (3H, s), 3.71 (3H, s), 3.96 (2H, q, J=7.0 Hz), 6.37-6.67 (3H, m), 6.77-6.92 (6H, m), 7.03 (2H, d, J=8.0 Hz), 7.11-7.26 (2H, m).

Production Example 275

In the same manner as in Production Example 21 except that (E)-3-(4-methoxyphenyloxy)-2-methyl-N-(4-methylphenyl)-2-propenamide and 3,5-dimethylphenol were used as materials, the following 3,5-dimethylphenyl 3-(4-methoxyphenyloxy)-2-methyl-N-(4-methylphenyl)-2-propenimidate (hereinafter referred to as the present compound 275) was obtained.

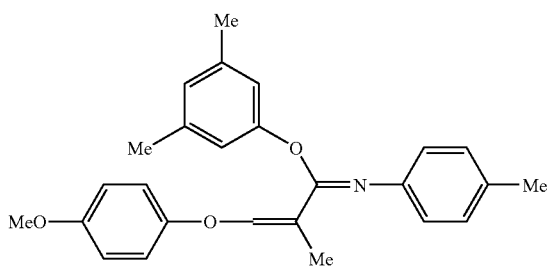

¹H-NMR (DMSO-D₆, 50° C.) δ: 1.91 (3H, br s), 2.19 (6H, s), 2.21 (3H, s), 3.71 (3H, s), 6.55 (2H, br s), 6.66 (1H, br s), 6.76-6.92 (6H, m), 7.02 (2H, d, J=7.8 Hz), 7.15 (1H, br s).

Production Example 276

In the same manner as in Production Example 21 except that (E)-N-(4-methoxyphenyl)-3-(4-methoxyphenyloxy)-2-methyl-2-propenamide and phenol were used as materials, the following phenyl N-(4-methoxyphenyl)-3-(4-methoxyphenyloxy)-2-methyl-2-propenimidate (hereinafter referred to as the present compound 276) was obtained.

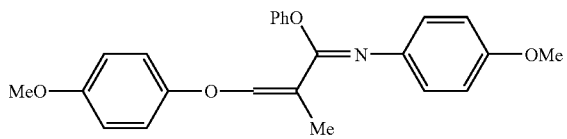

¹H-NMR (DMSO-D₆, 50° C.) δ: 1.95 (3H, br s), 3.68 (3H, s), 3.71 (3H, s), 6.72-7.10 (11H, m), 7.15-7.36 (3H, m).

Production Example 277

In the same manner as in Production Example 21 except that (E)-N-(4-methoxyphenyl)-3-(4-methoxyphenyloxy)-2-methyl-2-propenamide and 3-methylphenol were used as materials, the following 3-methylphenyl N-(4-methoxyphenyl)-3-(4-methoxyphenyloxy)-2-methyl-2-propenimidate (hereinafter referred to as the present compound 277) was obtained.

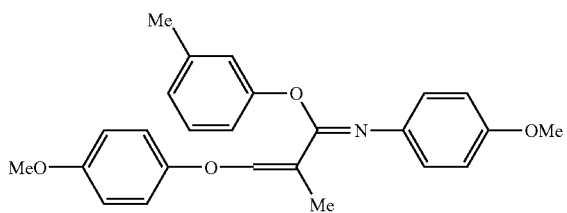

¹H-NMR (DMSO-D₆, 50° C.) δ: 1.95 (3H, br s), 2.23 (3H, s), 3.68 (3H, s), 3.71 (3H, s), 6.61-7.02 (11H, m), 7.09-7.25 (2H, m).

Production Example 278

In the same manner as in Production Example 21 except that (E)-N-(4-methoxyphenyl)-3-(4-methoxyphenyloxy)-2-methyl-2-propenamide and 3-ethylphenol were used as materials, the following 3-ethylphenyl N-(4-methoxyphenyl)-3-(4-methoxyphenyloxy)-2-methyl-2-propenimidate (hereinafter referred to as the present compound 278) was obtained.

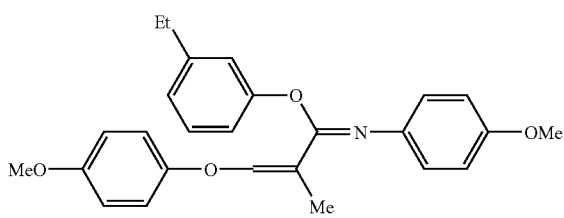

$^1$H-NMR (DMSO-D$_6$, 50° C.) δ: 1.11 (3H, t, J=7.6 Hz), 1.94 (3H, br s), 2.53 (2H, q, J=7.6 Hz), 3.67 (3H, s), 3.71 (3H, s), 6.63-7.01 (11H, m), 7.11-7.25 (2H, m).

Production Example 279

In the same manner as in Production Example 21 except that (E)-N-(4-methoxyphenyl)-3-(4-methoxyphenyloxy)-2-methyl-2-propenamide and 3-methoxyphenol were used as materials, 3-methoxyphenyl N-(4-methoxyphenyl)-3-(4-methoxyphenyloxy)-2-methyl-2-propenimidate (hereinafter referred to as the present compound 279) was obtained.

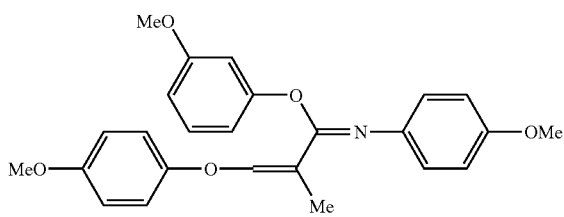

$^1$H-NMR (DMSO-D$_6$, 50° C.) δ: 1.96 (3H, br s), 3.68 (3H, s), 3.69 (3H, s), 3.71 (3H, s), 6.47 (2H, br s), 6.60 (1H, br s), 6.80 (2H, d, J=8.8 Hz), 6.85-7.02 (6H, m), 7.11-7.28 (2H, m).

Production Example 280

In the same manner as in Production Example 21 except that (E)-N-(4-methoxyphenyl)-3-(4-methoxyphenyloxy)-2-methyl-2-propenamide and 3-ethoxyphenol were used as materials, 3-ethoxyphenyl N-(4-methoxyphenyl)-3-(4-methoxyphenyloxy)-2-methyl-2-propenimidate (hereinafter referred to as the present compound 280) was obtained.

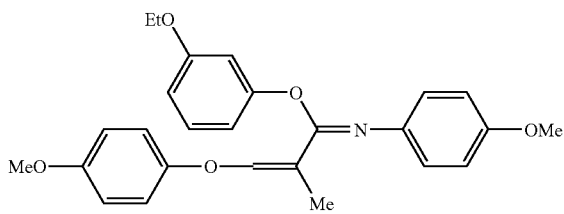

$^1$H-NMR (DMSO-D$_6$, 50° C.) δ: 1.27 (3H, t, J=6.9 Hz), 1.95 (3H, br s), 3.68 (3H, s), 3.71 (3H, s), 3.96 (2H, q, J=6.9 Hz), 6.45 (2H, br s), 6.58 (1H, br s), 6.79 (2H, d, J=8.8 Hz), 6.84-7.03 (6H, m), 7.15 (1H, t, J=7.9 Hz), 7.22 (1H, br s).

Production Example 281

In the same manner as in Production Example 21 except that (E)-N-(4-methoxyphenyl)-3-(4-methoxyphenyloxy)-2-methyl-2-propenamide and 3,5-dimethylphenol were used as materials, the following 3,5-dimethylphenyl N-(4-methoxyphenyl)-3-(4-methoxyphenyloxy)-2-methyl-2-propenimidate (hereinafter referred to as the present compound 281) was obtained.

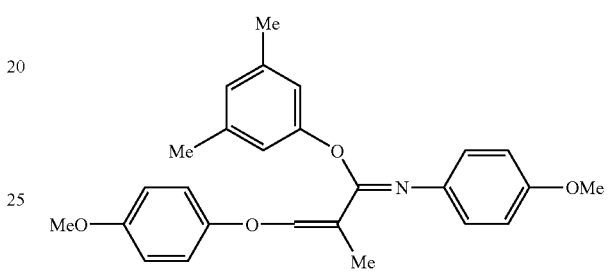

$^1$H-NMR (DMSO-D$_6$, 50° C.) δ: 1.95 (3H, br s), 2.19 (6H, s), 3.68 (3H, s), 3.71 (3H, s), 6.33-6.70 (4H, m), 6.74-7.05 (7H, m), 7.17 (1H, br s).

Production Example 282

In the same manner as in Production Example 21 except that (E)-N-(3,4-dimethylphenyl)-3-(4-methoxyphenyloxy)-2-methyl-2-propenamide and phenol were used as materials, the following phenyl N-(3,4-dimethylphenyl)-3-(4-methoxyphenyloxy)-2-methyl-2-propenimidate (hereinafter referred to as the present compound 282) was obtained.

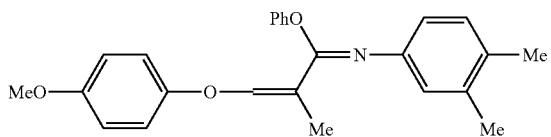

$^1$H-NMR (DMSO-D$_6$, 50° C.) δ: 1.92 (3H, br s), 2.12 (6H, s), 3.71 (3H, s), 6.59-6.68 (1H, br), 6.72 (1H, s), 6.78-7.10 (8H, m), 7.17 (1H, br s), 7.28 (2H, t, J=7.2 Hz).

Production Example 283

In the same manner as in Production Example 21 except that (E)-N-(3,4-dimethylphenyl)-3-(4-methoxyphenyloxy)-2-methyl-2-propenamide and 3-methylphenol were used as materials, the following 3-methylphenyl N-(3,4-dimethylphenyl)-3-(4-methoxyphenyloxy)-2-methyl-2-propenimidate (hereinafter referred to as the present compound 283) was obtained.

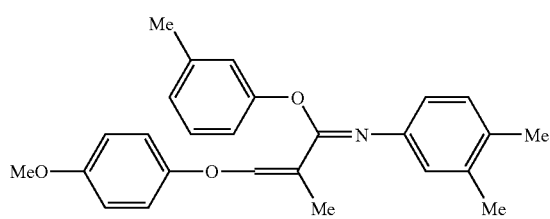

$^1$H-NMR (DMSO-D$_6$, 50° C.) δ: 1.91 (3H, br s), 2.12 (6H, s), 2.24 (3H, s), 3.71 (3H, s), 6.55-6.90 (9H, m), 6.94 (1H, s), 7.08-7.24 (2H, m).

Production Example 284

In the same manner as in Production Example 21 except that (E)-N-(3,4-dimethylphenyl)-3-(4-methoxyphenyloxy)-2-methyl-2-propenamide and 3-ethylphenol were used as materials, the following 3-ethylphenyl N-(3,4-dimethylphenyl)-3-(4-methoxyphenyloxy)-2-methyl-2-propenimidate (hereinafter referred to as the present compound 284) was obtained.

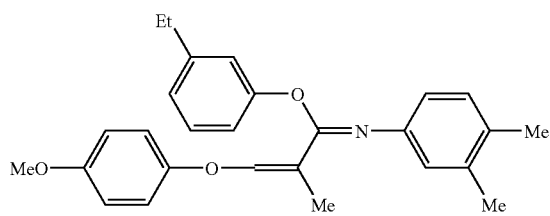

$^1$H-NMR (DMSO-D$_6$, 50° C.) δ: 1.11 (3H, t, J=7.6 Hz), 1.91 (3H, br s), 2.11 (6H, s), 2.53 (2H, q, J=7.6 Hz), 3.71 (3H, s), 6.57-6.91 (9H, m), 6.94 (1H, d, J=8.0 Hz), 7.10-7.24 (2H, m).

Production Example 285

In the same manner as in Production Example 21 except that (E)-N-(3,4-dimethylphenyl)-3-(4-methoxyphenyloxy)-2-methyl-2-propenamide and 3-methoxyphenol were used as materials, 3-methoxyphenyl N-(3,4-dimethylphenyl)-3-(4-methoxyphenyloxy)-2-methyl-2-propenimidate (hereinafter referred to as the present compound 285) was obtained.

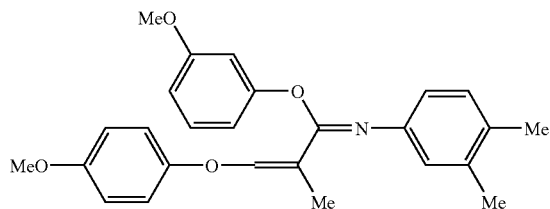

$^1$H-NMR (DMSO-D$_6$, 50° C.) δ: 1.92 (3H, br s), 2.13 (6H, s), 3.69 (3H, s), 3.71 (3H, s), 6.56 (4H, d, J=109.3 Hz), 6.73 (1H, s), 6.81-6.91 (4H, m), 6.96 (1H, d, J=8.0 Hz), 7.13-7.26 (2H, m).

Production Example 286

In the same manner as in Production Example 21 except that (E)-N-(3,4-dimethylphenyl)-3-(4-methoxyphenyloxy)-2-methyl-2-propenamide and 3-ethoxyphenol were used as materials, the following 3-ethoxyphenyl N-(3,4-dimethylphenyl)-3-(4-methoxyphenyloxy)-2-methyl-2-propenimidate (hereinafter referred to as the present compound 286) was obtained.

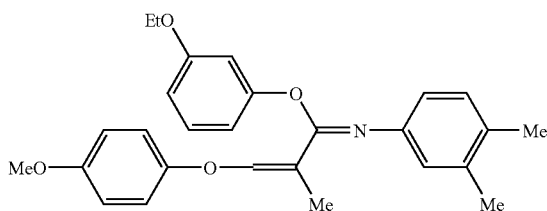

$^1$H-NMR (DMSO-D$_6$, 50° C.) δ: 1.27 (3H, t, J=7.0 Hz), 1.92 (3H, br s), 2.13 (6H, s), 3.71 (3H, s), 3.95 (2H, q, J=7.0 Hz), 6.49 (2H, br s), 6.55-6.62 (1H, m), 6.62-6.69 (1H, m), 6.73 (1H, s), 6.81-6.91 (4H, m), 6.96 (1H, d, J=8.0 Hz), 7.11-7.26 (2H, m).

Production Example 287

In the same manner as in Production Example 21 except that (E)-N-(3,4-dimethylphenyl)-3-(4-methoxyphenyloxy)-2-methyl-2-propenamide and 3,5-dimethylphenol were used as materials, the following 3,5-dimethylphenyl N-(3,4-dimethylphenyl)-3-(4-methoxyphenyloxy)-2-methyl-2-propenimidate (hereinafter referred to as the present compound 287) was obtained.

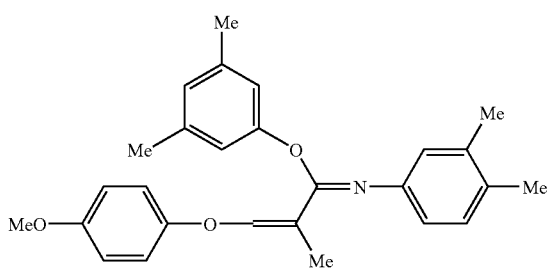

$^1$H-NMR (DMSO-D$_6$, 50° C.) δ: 1.91 (3H, br s), 2.12 (6H, s), 2.19 (6H, s), 3.71 (3H, s), 6.42-6.76 (5H, m), 6.78-6.91 (4H, m), 6.95 (1H, d, J=8.0 Hz), 7.15 (1H, br s).

Production Example 288

In the same manner as in Production Example 21 except that (E)-3-(3-ethoxyphenyloxy)-2-methyl-N-phenyl-2-propenamide and phenol were used as materials, the following phenyl 3-(3-ethoxyphenyloxy)-2-methyl-N-phenyl-2-propenimidate (hereinafter referred to as the present compound 288) was obtained.

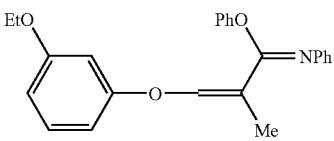

¹H-NMR (DMSO-D₆, 50° C.) δ: 1.30 (3H, t, J=7.0 Hz), 1.93 (3H, br s), 3.95 (2H, q, J=7.0 Hz), 6.39-6.48 (2H, m), 6.65-6.70 (1H, m), 6.89 (2H, d, J=7.6 Hz), 6.95-7.11 (4H, m), 7.16-7.35 (6H, m).

Production Example 289

In the same manner as in Production Example 21 except that (E)-3-(4-ethoxyphenyloxy)-2-methyl-N-phenyl-2-propenamide and phenol were used as materials, the following phenyl 3-(4-ethoxyphenyloxy)-2-methyl-N-phenyl-2-propenimidate (hereinafter referred to as the present compound 289) was obtained.

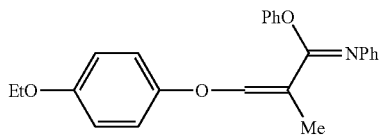

¹H-NMR (DMSO-D₆, 50° C.) δ: 1.29 (3H, t, J=7.0 Hz), 1.90 (3H, br s), 3.97 (2H, q, J=7.0 Hz), 6.77-6.91 (6H, m), 6.92-7.09 (4H, m), 7.14-7.23 (3H, m), 7.28 (2H, t, J=7.3 Hz).

Production Example 290

In the same manner as in Production Example 21 except that (E)-2-methyl-N-phenyl-3-(4-phenylphenyloxy)-2-propenamide and phenol were used as materials, the following phenyl 2-methyl-N-phenyl-3-(4-phenylphenyloxy)-2-propenimidate (hereinafter referred to as the present compound 290) was obtained.

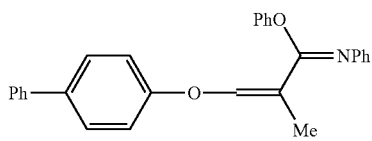

¹H-NMR (DMSO-D₆, 50° C.) δ: 1.95 (3H, br s), 6.84-7.14 (8H, m), 7.17-7.38 (6H, m), 7.43 (2H, t, J=7.7 Hz), 7.56-7.65 (4H, m).

Production Example 291

In the same manner as in Production Example 21 except that (E)-2-methyl-3-(4-phenoxyphenyloxy)-N-phenyl-2-propenamide and phenol were used as materials, the following phenyl 2-methyl-3-(4-phenoxyphenyloxy)-N-phenyl-2-propenimidate (hereinafter referred to as the present compound 291) was obtained.

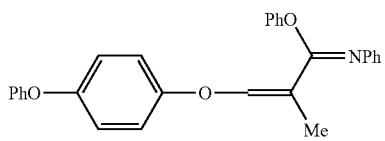

¹H-NMR (DMSO-D₆, 50° C.) δ: 1.92 (3H, br s), 6.84-7.08 (12H, m), 7.11 (1H, t, J=7.4 Hz), 7.21 (2H, t, J=7.8 Hz), 7.24-7.33 (3H, m), 7.36 (2H, dd, J=8.7, 7.4 Hz).

Production Example 292

In the same manner as in Production Example 21 except that (E)-3-(3,4-dimethylphenyloxy)-2-methyl-N-phenyl-2-propenamide and phenol were used as materials, the following phenyl 3-(3,4-dimethylphenyloxy)-2-methyl-N-phenyl-2-propenimidate (hereinafter referred to as the present compound 292) was obtained.

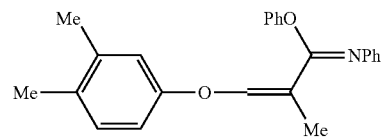

¹H-NMR (DMSO-D₆, 50° C.) δ: 1.91 (3H, br s), 2.15 (6H, s), 6.56-6.62 (2H, m), 6.88 (2H, d, J=7.3 Hz), 6.94-7.10 (5H, m), 7.13-7.25 (3H, m), 7.30 (2H, t, J=7.9 Hz).

Production Example 293

In the same manner as in Production Example 21 except that (E)-3-(5-indanyloxy)-2-methyl-N-phenyl-2-propenamide and phenol were used as materials, the following phenyl 3-(5-indanyloxy)-2-methyl-N-phenyl-2-propenimidate (hereinafter referred to as the present compound 293) was obtained.

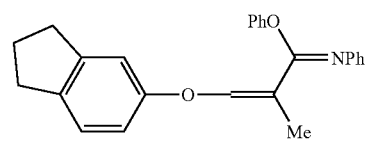

¹H-NMR (DMSO-D₆, 50° C.) δ: 1.91 (3H, s), 1.95-2.05 (2H, m), 2.72-2.83 (4H, m), 6.58-6.68 (2H, m), 6.88 (2H, d, J=7.5 Hz), 6.93-7.09 (4H, m), 7.12 (1H, d, J=8.9 Hz), 7.15-7.26 (3H, m), 7.30 (2H, t, J=7.1 Hz).

Production Example 294

In the same manner as in Production Example 21 except that (E)-3-(2,4-dimethoxyphenyloxy)-2-methyl-N-phenyl-2-propenamide and phenol were used as materials, the following phenyl 3-(2,4-dimethoxyphenyloxy)-2-methyl-N-phenyl-2-propenimidate (hereinafter referred to as the present compound 294) was obtained.

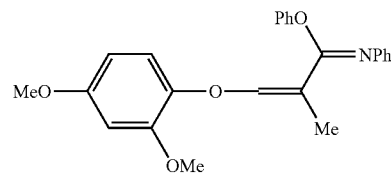

¹H-NMR (DMSO-D₆, 50° C.) δ: 1.91 (3H, br s), 3.68 (3H, s), 3.72 (3H, s), 6.40 (1H, dd, J=8.8, 2.8 Hz), 6.62 (1H, d, J=2.8 Hz), 6.79 (1H, d, J=8.8 Hz), 6.83-7.09 (7H, m), 7.18 (2H, t, J=7.8 Hz), 7.25 (2H, t, J=7.8 Hz).

Production Example 295

In the same manner as in Production Example 21 except that (E)-3-(2,6-dimethoxyphenyloxy)-2-methyl-N-phenyl- 2-propenamide and phenol were used as materials, the following phenyl 3-(2,6-dimethoxyphenyloxy)-2-methyl-N-phenyl-2-propenimidate (hereinafter referred to as the present compound 295) was obtained.

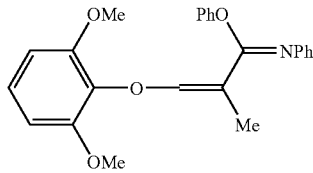

¹H-NMR (DMSO-D₆, 50° C.) δ: 1.94 (3H, br s), 3.66 (6H, s), 6.69 (2H, d, J=8.4 Hz), 6.78-7.02 (7H, m), 7.08 (1H, t, J=8.4 Hz), 7.17 (2H, t, J=7.7 Hz), 7.23 (2H, t, J=7.6 Hz).

Production Example 296

In the same manner as in Production Example 21 except that (E)-3-(3,4-(ethylenedioxy)phenyloxy)-2-methyl-N-phenyl-2-propenamide and phenol were used as materials, the following phenyl 3-(3,4-(ethylenedioxy)phenyloxy)-2-methyl-N-phenyl-2-propenimidate (hereinafter referred to as the present compound 296) was obtained.

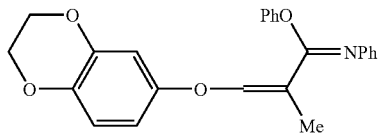

¹H-NMR (DMSO-D₆, 50° C.) δ: 1.89 (3H, br s), 4.14-4.24 (4H, m), 6.37 (1H, dd, J=8.8, 2.7 Hz), 6.43 (1H, d, J=2.7 Hz), 6.77 (1H, d, J=8.8 Hz), 6.87 (2H, d, J=7.6 Hz), 6.92-7.09 (4H, m), 7.13-7.24 (3H, m), 7.28 (2H, t, J=7.2 Hz).

Production Example 297

In the same manner as in Production Example 21 except that (E)-3-benzyloxy-2-methyl-N-phenyl-2-propenamide and phenol were used as materials, the following phenyl 3-benzyloxy-2-methyl-N-phenyl-2-propenimidate (hereinafter referred to as the present compound 297) was obtained.

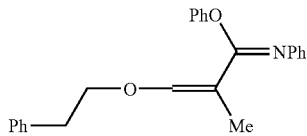

¹H-NMR (DMSO-D₆, 50° C.) δ: 1.75 (3H, br s), 5.00 (2H, s), 6.74-7.03 (6H, m), 7.14 (2H, t, J=7.8 Hz), 7.18-7.28 (5H, m), 7.30-7.38 (3H, m).

Production Example 298

In the same manner as in Production Example 21 except that (E)-3-(1-(4-chlorophenyl)pyrazol-3-yloxy)-2-methyl-N-phenyl-2-propenamide and phenol were used as materials, the following phenyl 3-(1-(4-chlorophenyl)pyrazol-3-yloxy)-2-methyl-N-phenyl-2-propenimidate (hereinafter referred to as the present compound 298) was obtained.

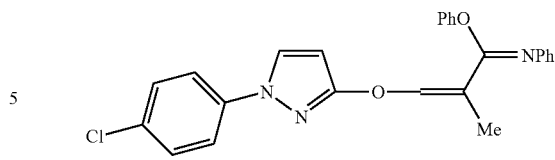

¹H-NMR (DMSO-D₆, 50° C.) δ: 1.94 (3H, br s), 6.19 (1H, d, J=2.6 Hz), 6.90 (2H, d, J=7.8 Hz), 6.95-7.11 (4H, m), 7.22 (2H, t, J=7.8 Hz), 7.30 (2H, t, J=7.6 Hz), 7.52 (2H, d, J=9.0 Hz), 7.69 (2H, d, J=9.0 Hz), 7.73 (1H, br s), 8.40 (1H, d, J=2.6 Hz).

Production Example 299

In the same manner as in Production Example 21 except that (E)-2-methyl-3-(2-naphthyl)-N-phenyl-2-propenamide and phenol were used as materials, the following phenyl 2-methyl-3-(2-naphthyl)-N-phenyl-2-propenimidate (hereinafter referred to as the present compound 299) was obtained.

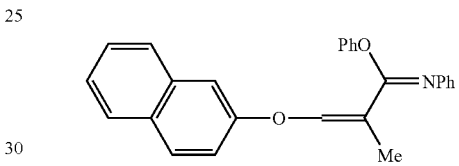

¹H-NMR (DMSO-D₆, 50° C.) δ: 1.99 (3H, br s), 6.93 (2H, d, J=7.6 Hz), 6.99-7.15 (5H, m), 7.20 (1H, dd, J=9.0, 2.4 Hz), 7.26 (2H, t, J=7.6 Hz), 7.30-7.47 (4H, m), 7.48-7.54 (1H, m), 7.76 (1H, d, J=8.0 Hz), 7.88 (1H, d, J=8.0 Hz), 7.90 (1H, d, J=9.0 Hz).

Production Example 300

In the same manner as in Production Example 14 except that 2-ethyl-3-phenoxy-N-phenyl-2-propenamide were used as a material, the following phenyl 2-ethyl-3-phenoxy-N-phenyl-2-propenimidothioate (hereinafter referred to as the present compound 300) was obtained.

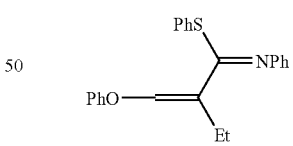

¹H-NMR (DMSO-D₆, 50° C.) δ: 1.07 (3H, t, J=7.2 Hz), 2.35-2.53 (2H, br m), 6.73 (2H, d, J=7.6 Hz), 6.82 (2H, d, J=7.6 Hz), 7.06 (1H, t, J=7.4 Hz), 7.11 (1H, t, J=7.4 Hz), 7.26-7.39 (10H, m).

Production Example 301

In the same manner as in Production Example 21 except that 2-ethyl-3-phenoxy-N-phenyl-2-propenamide and phenol were used as materials, phenyl 2-ethyl-3-phenoxy-N-phenyl-2-propenimidate (hereinafter referred to as the present compound 301) was obtained.

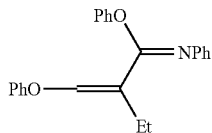

¹H-NMR (DMSO-D₆, 50° C.) δ: 1.15 (3H, t, J=7.4 Hz), 2.38-2.54 (2H, br m), 6.83 (2H, d, J=6.6 Hz), 6.89 (2H, d, J=7.7 Hz), 6.95-7.19 (6H, m), 7.23 (2H, t, J=7.7 Hz), 7.27-7.36 (4H, m).

Production Example 302

In the same manner as in Production Example 21 except that 2-ethyl-N-(4-methylphenyl)-3-phenoxy-2-propenamide and phenol were used as materials, phenyl 2-ethyl-N-(4-methylphenyl)-3-phenoxy-2-propenimidate (hereinafter referred to as the present compound 302) was obtained.

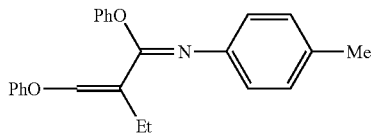

¹H-NMR (DMSO-D₆, 50° C.) δ: 1.15 (3H, t, J=7.3 Hz), 2.20-2.23 (3H, br m), 2.38-2.56 (3H, m), 6.74-6.90 (4H, m), 6.92-7.21 (7H, m), 7.24-7.43 (4H, m).

Production Example 303

In the same manner as in Production Example 21 except that 2-ethyl-N-(4-methylphenyl)-3-phenoxy-2-propenamide and 3-methylphenol were used as materials, 3-methyl phenyl 2-ethyl-N-(4-methylphenyl)-3-phenoxy-2-propenimidate (hereinafter referred to as the present compound 302) was obtained.

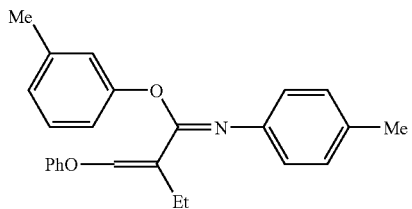

¹H-NMR (DMSO-D₆, 50° C.) δ: 1.14 (3H, t, J=7.3 Hz), 2.22 (3H, s), 2.25 (3H, s), 2.39-2.55 (3H, m), 6.69-6.96 (7H, m), 6.99-7.23 (5H, m), 7.31 (2H, t, J=8.0 Hz).

Production Example 304

In the same manner as in Production Example 21 except that 2-ethyl-3-(3-methylphenyloxy)-N-phenyl-2-propenamide and phenol were used as materials, phenyl 2-ethyl-3-(3-methylphenyloxy)-N-phenyl-2-propenimidate (hereinafter referred to as the present compound 304) was obtained.

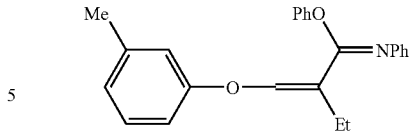

¹H-NMR (DMSO-D₆, 50° C.) δ: 1.15 (3H, t, J=7.4 Hz), 2.24 (3H, s), 2.39-2.52 (2H, br), 6.48-6.57 (1H, br), 6.59-6.68 (1H, br), 6.81-6.94 (3H, m), 6.94-7.13 (5H, m), 7.17 (1H, t, J=7.8 Hz), 7.24 (2H, t, J=7.5 Hz), 7.32 (2H, t, J=7.5 Hz).

Production Example 305

In the same manner as in Production Example 21 except that 2-ethyl-3-(3-methylphenyloxy)-N-phenyl-2-propenamide and 3-methylphenol were used as materials, 3-methylphenyl 2-ethyl-3-(3-methylphenyloxy)-N-phenyl-2-propenimidate (hereinafter referred to as the present compound 305) was obtained.

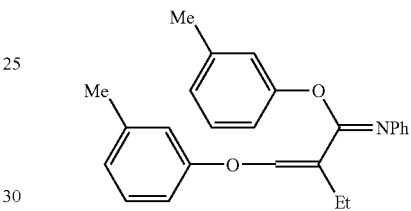

¹H-NMR (DMSO-D₆, 50° C.) δ: 1.15 (3H, t, J=7.4 Hz), 2.24 (3H, s), 2.26 (3H, s), 2.39-2.54 (3H, br), 6.47-6.57 (1H, br), 6.59-6.69 (1H, br), 6.74-6.96 (6H, m), 7.00 (1H, t, J=7.4 Hz), 7.18 (2H, t, J=7.7 Hz), 7.24 (2H, t, J=7.7 Hz).

Production Example 306

In the same manner as in Production Example 21 except that 2-ethyl-3-(3-methylphenyloxy)-N-phenyl-2-propenamide and 4-methylphenol were used as materials, 4-methylphenyl 2-ethyl-3-(3-methylphenyloxy)-N-phenyl-2-propenimidate (hereinafter referred to as the present compound 306) was obtained.

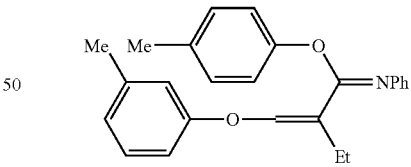

¹H-NMR (DMSO-D₆, 50° C.) δ: 1.14 (3H, t, J=7.5 Hz), 2.24 (6H, s), 2.37-2.51 (4H, br m), 6.45-6.54 (1H, br m), 6.58-6.68 (1H, br m), 6.80-7.20 (10H, m), 7.24 (2H, t, J=7.7 Hz).

Production Example 307

In the same manner as in Production Example 21 except that 2-ethyl-N-(4-methylphenyl)-3-(3-methylphenyloxy)-2-propenamide and phenol were used as materials, phenyl 2-ethyl-N-(4-methylphenyl)-3-(3-methylphenyloxy)-2-propenimidate (hereinafter referred to as the present compound 307) was obtained.

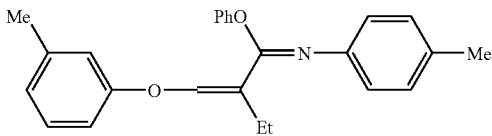

¹H-NMR (DMSO-D₆, 50° C.) δ: 1.15 (3H, t, J=7.4 Hz), 2.22 (3H, s), 2.23 (3H, s), 2.40-2.56 (2H, br m), 6.48-6.58 (1H, br m), 6.59-6.69 (1H, br m), 6.75-7.22 (10H, m), 7.32 (2H, t, J=7.3 Hz).

Production Example 308

In the same manner as in Production Example 21 except that 2-ethyl-N-(4-methylphenyl)-3-(3-methylphenyloxy)-2-propenamide and 3-methylphenol were used as materials, 3-methylphenyl 2-ethyl-N-(4-methylphenyl)-3-(3-methylphenyloxy)-2-propenimidate (hereinafter referred to as the present compound 308) was obtained.

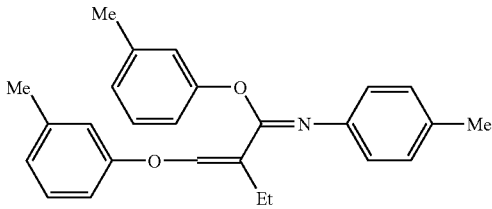

¹H-NMR (DMSO-D₆, 50° C.) δ: 1.14 (3H, t, J=7.4 Hz), 2.22 (3H, s), 2.23 (3H, s), 2.26 (3H, s), 2.38-2.54 (2H, br m), 6.47-6.57 (1H, br m), 6.59-6.68 (1H, br m), 6.70-6.97 (6H, m), 7.01-7.13 (3H, m), 7.14-7.24 (2H, m).

Production Example 309

In the same manner as in Production Example 21 except that 2-ethyl-3-(4-methylphenyloxy)-N-phenyl-2-propenamide and phenol were used as materials, phenyl 2-ethyl-3-(4-methylphenyloxy)-N-phenyl-2-propenimidate (hereinafter referred to as the present compound 309) was obtained.

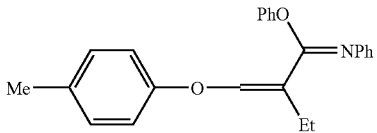

¹H-NMR (DMSO-D₆, 50° C.) δ: 1.15 (3H, t, J=7.3 Hz), 2.24 (3H, s), 2.38-2.54 (2H, br), 6.71 (2H, d, J=6.8 Hz), 6.88 (2H, d, J=7.6 Hz), 6.95-7.14 (7H, m), 7.22 (2H, t, J=7.8 Hz), 7.30 (2H, t, J=7.3 Hz).

Production Example 310

In the same manner as in Production Example 21 except that 2-ethyl-3-(4-methylphenyloxy)-N-phenyl-2-propenamide and 3-methylphenol were used as materials, 3-methylphenyl 2-ethyl-3-(4-methylphenyloxy)-N-phenyl-2-propenimidate (hereinafter referred to as the present compound 310) was obtained.

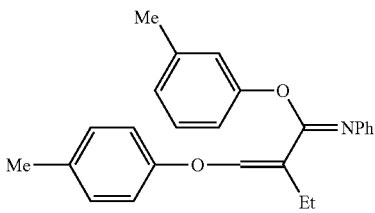

¹H-NMR (DMSO-D₆, 50° C.) δ: 1.14 (3H, t, J=7.3 Hz), 2.24 (3H, s), 2.25 (3H, s), 2.38-2.50 (2H, br), 6.64-6.95 (7H, m), 6.98 (1H, t, J=7.4 Hz), 7.05-7.29 (6H, m).

Production Example 311

In the same manner as in Production Example 21 except that 2-ethyl-N-(4-methylphenyl)-3-(4-methylphenyloxy)-2-propenamide and phenol were used as materials, phenyl 2-ethyl-N-(4-methylphenyl)-3-(4-methylphenyloxy)-2-propenimidate (hereinafter referred to as the present compound 311) was obtained.

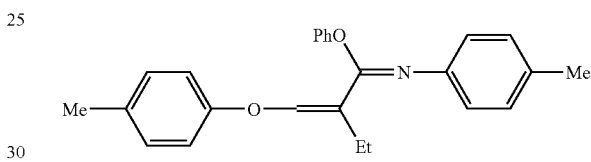

¹H-NMR (DMSO-D₆, 50° C.) δ: 1.14 (3H, t, J=7.3 Hz), 2.22 (3H, s), 2.24 (3H, s), 2.39-2.52 (2H, br m), 6.66-6.75 (2H, br m), 6.77-6.87 (2H, br m), 6.91-7.20 (8H, m), 7.30 (2H, t, J=7.0 Hz).

Production Example 312

In the same manner as in Production Example 21 except that 2-ethyl-N-(4-methylphenyl)-3-(4-methylphenyloxy)-2-propenamide and 3-methylphenol were used as materials, 3-methylphenyl 2-ethyl-N-(4-methylphenyl)-3-(4-methylphenyloxy)-2-propenimidate (hereinafter referred to as the present compound 312) was obtained.

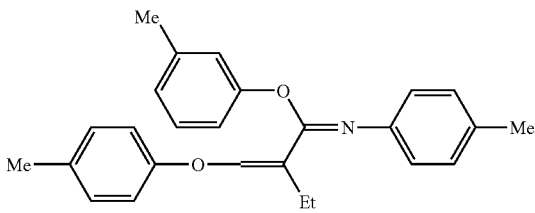

¹H-NMR (DMSO-D₆, 50° C.) δ: 1.14 (3H, t, J=7.3 Hz), 2.22 (3H, s), 2.24 (6H, s), 2.36-2.52 (2H, br m), 6.61-6.92 (7H, m), 6.98-7.22 (6H, m).

Production Example 313

In the same manner as in Production Example 21 except that 2-ethyl-3-(2-methoxyphenyloxy)-N-phenyl-2-propenamide and phenol were used as materials, phenyl 2-ethyl-3-(2-methoxyphenyloxy)-N-phenyl-2-propenimidate (hereinafter referred to as the present compound 313) was obtained.

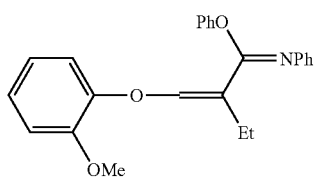

¹H-NMR (DMSO-D₆, 50° C.) δ: 1.17 (3H, t, J=7.4 Hz), 2.42-2.53 (3H, br), 3.70 (3H, s), 6.75 (1H, br s), 6.82-6.91 (3H, m), 6.92-7.12 (7H, m), 7.20 (2H, t, J=7.8 Hz), 7.27 (2H, t, J=7.4 Hz).

Production Example 314

In the same manner as in Production Example 21 except that 2-ethyl-3-(2-methoxyphenyloxy)-N-phenyl-2-propenamide and 3-methylphenol were used as materials, 3-methylphenyl 2-ethyl-3-(2-methoxyphenyloxy)-N-phenyl-2-propenimidate (hereinafter referred to as the present compound 314) was obtained.

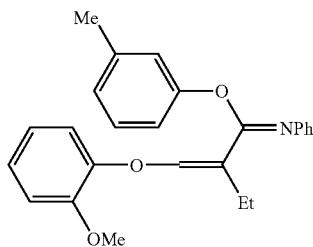

¹H-NMR (DMSO-D₆, 50° C.) δ: 1.16 (3H, t, J=7.3 Hz), 2.23 (3H, s), 2.42-2.54 (2H, br), 3.71 (3H, s), 6.67-6.80 (2H, br), 6.81-6.93 (4H, m), 6.94-7.27 (8H, m).

Production Example 315

In the same manner as in Production Example 21 except that 2-ethyl-3-(2-methoxyphenyloxy)-N-(4-methylphenyl)-2-propenamide and phenol were used as materials, phenyl 2-ethyl-3-(2-methoxyphenyloxy)-N-(4-methylphenyl)-2-propenimidate (hereinafter referred to as the present compound 315) was obtained.

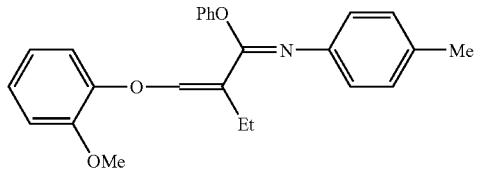

¹H-NMR (DMSO-D₆, 50° C.) δ: 1.16 (3H, t, J=7.3 Hz), 2.20 (3H, s), 2.40-2.57 (2H, br), 3.69 (3H, s), 6.62-7.14 (12H, m), 7.27 (2H, t, J=7.0 Hz).

Production Example 316

In the same manner as in Production Example 21 except that 2-ethyl-3-(2-methoxyphenyloxy)-N-(4-methylphenyl)-2-propenamide and 3-methylphenol were used as materials, 3-methylphenyl 2-ethyl-3-(2-methoxyphenyloxy)-N-(4-methylphenyl)-2-propenimidate (hereinafter referred to as the present compound 316) was obtained.

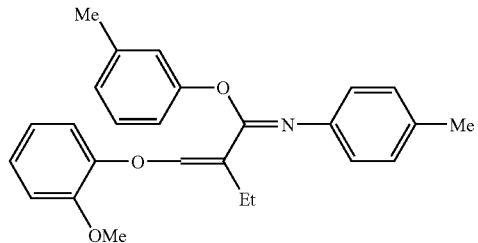

¹H-NMR (DMSO-D₆, 50° C.) δ: 1.16 (3H, t, J=7.9 Hz), 2.21 (3H, s), 2.23 (3H, s), 2.40-2.57 (2H, br), 3.70 (3H, s), 6.61-6.91 (7H, m), 6.96-7.21 (6H, m).

Production Example 317

In the same manner as in Production Example 21 except that 2-ethyl-3-(4-methoxyphenyloxy)-N-phenyl-2-propenamide and phenol were used as materials, phenyl 2-ethyl-3-(4-methoxyphenyloxy)-N-phenyl-2-propenimidate (hereinafter referred to as the present compound 317) was obtained.

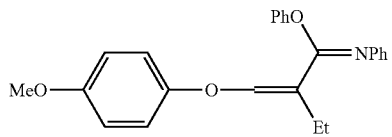

¹H-NMR (DMSO-D₆, 50° C.) δ: 1.15 (3H, t, J=7.3 Hz), 2.37-2.53 (2H, br m), 3.71 (3H, s), 6.72-6.82 (2H, m), 6.83-6.91 (4H, m), 6.93-7.14 (5H, m), 7.22 (2H, t, J=7.8 Hz), 7.29 (2H, t, J=7.4 Hz).

Production Example 318

In the same manner as in Production Example 21 except that 2-ethyl-3-(4-methoxyphenyloxy)-N-phenyl-2-propenamide and 3-methylphenol were used as materials, 3-methylphenyl 2-ethyl-3-(4-methoxyphenyloxy)-N-phenyl-2-propenimidate (hereinafter referred to as the present compound 318) was obtained.

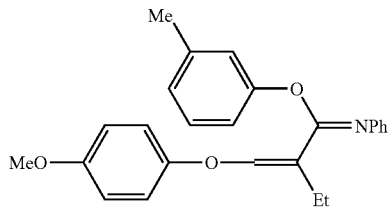

¹H-NMR (DMSO-D₆, 50° C.) δ: 1.14 (3H, t, J=7.2 Hz), 2.24 (3H, s), 2.38-2.53 (2H, br m), 3.71 (3H, s), 6.71-6.93 (9H, m), 6.98 (1H, t, J=7.3 Hz), 7.06 (1H, br s), 7.16 (1H, t, J=7.7 Hz), 7.22 (2H, t, J=7.8 Hz).

Production Example 319

In the same manner as in Production Example 21 except that 2-ethyl-3-(4-methoxyphenyloxy)-N-(4-methylphenyl)-

2-propenamide and phenol were used as materials, phenyl 2-ethyl-3-(4-methoxyphenyloxy)-N-(4-methylphenyl)-2-propenimidate (hereinafter referred to as the present compound 319) was obtained.

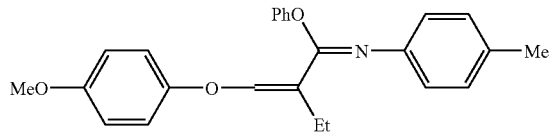

$^1$H-NMR (DMSO-D$_6$, 50° C.) δ: 1.14 (3H, t, J=7.4 Hz), 2.21 (3H, s), 2.38-2.53 (2H, br m), 3.71 (3H, s), 6.72-6.88 (6H, m), 6.90-7.15 (6H, m), 7.29 (2H, t, J=7.2 Hz).

Production Example 320

In the same manner as in Production Example 21 except that 2-ethyl-3-(4-methoxyphenyloxy)-N-(4-methylphenyl)-2-propenamide and 3-methylphenol were used as materials, 3-methylphenyl 2-ethyl-3-(4-methoxyphenyloxy)-N-(4-methylphenyl)-2-propenimidate (hereinafter referred to as the present compound 320) was obtained.

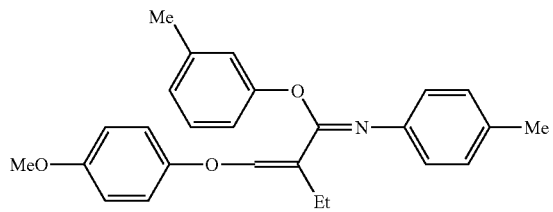

$^1$H-NMR (DMSO-D$_6$, 50° C.) δ: 1.14 (3H, t, J=7.4 Hz), 2.21 (3H, s), 2.24 (3H, s), 2.38-2.51 (2H, br m), 3.71 (3H, s), 6.67-6.92 (9H, m), 6.98-7.10 (3H, m), 7.16 (1H, t, J=7.4 Hz).

Production Example 321

In the same manner as in Production Example 14 except that 3-phenoxy-N-phenyl-2-n-propyl-2-propenamide was used as materials, the following phenyl 3-phenoxy-N-phenyl-2-n-propyl-2-propenimidothioate (hereinafter referred to as the present compound 321) was obtained.

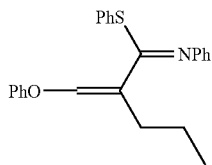

$^1$H-NMR (DMSO-D$_6$, 50° C.) δ: 0.87 (3H, t, J=7.4 Hz), 1.45-1.60 (2H, m), 2.42 (2H, br s), 6.74 (2H, d, J=7.8 Hz), 6.80 (2H, d, J=8.3 Hz), 7.06 (1H, t, J=7.4 Hz), 7.12 (1H, t, J=7.3 Hz), 7.24-7.47 (10H, m).

Production Example 322

In the same manner as in Production Example 21 except that 3-phenoxy-N-phenyl-2-n-propyl-2-propenamide and phenol were used as materials, the following phenyl 3-phenoxy-N-phenyl-2-n-propyl-2-propenimidate (hereinafter referred to as the present compound 322) was obtained.

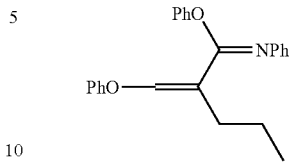

$^1$H-NMR (DMSO-D$_6$, 50° C.) δ: 0.93 (3H, t, J=7.3 Hz), 1.53-1.68 (2H, m), 2.36-2.47 (2H, br m), 6.83 (2H, d, J=7.3 Hz), 6.87 (2H, d, J=7.8 Hz), 6.95-7.15 (5H, m), 7.18-7.26 (3H, m), 7.27-7.36 (4H, m).

Production Example 323

In the same manner as in Production Example 21 except that (E)-2-cyclopropyl-3-phenoxy-N-phenyl-2-propenamide and phenol were used as materials, the following phenyl 2-cyclopropyl-3-phenoxy-N-phenyl-2-propenimidate (hereinafter referred to as the present compound 323) was obtained.

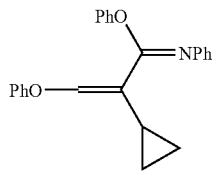

$^1$H-NMR (DMSO-D$_6$, 50° C.) δ: 0.68-0.88 (4H, m), 1.46-1.61 (1H, br), 6.70-6.90 (4H, m), 6.97-7.42 (12H, m).

Production Example 324

In the same manner as in Production Example 21 except that (E)-2-methyl-3-phenoxy-N-phenyl-2-propenamide and N-methylaniline were used as materials, the following N,N'-diphenyl-2,N'-dimethyl-3-phenoxy-2-propenimidamide (hereinafter referred to as the present compound 324) was obtained.

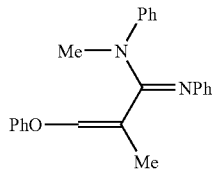

$^1$H-NMR (CDCl$_3$) δ: 1.38 (3H, s), 3.47 (3H, s), 6.24 (2H, d, J=8.5 Hz), 6.30 (1H, s), 6.85 (2H, d, J=8.5 Hz), 6.92-7.01 (2H, m), 7.11 (2H, t, J=7.7 Hz), 7.16-7.23 (3H, m), 7.27 (2H, t, J=7.2 Hz), 7.36 (2H, t, J=7.7 Hz).

Next, examples of processes of producing the materials for the compounds of the present invention are shown.

Reference Production Example 1-(1)

A suspension of 2.5 g (12.8 mmol) of (E)-2-methyl-3-(phenylthio)-2-propenoic acid and 3.5 g (25.7 mmol) of thionyl chloride in 25 ml of toluene was refluxed for 1 hour and then concentrated under vacuum. The residue was dissolved in 25 ml of ethyl acetate and cooled in ice bath. To the solution was added dropwise 2.9 g (32 mmol) of aniline and stirred at room temperature for 30 minutes. The reaction mixture was washed sequentially with 1N HCl solution, a saturated NaHCO$_3$ solution, and a saturated NaCl solution. The organic layer was dried over anhydrous MgSO$_4$ and concentrated to obtain 3.0 g of (E)-2-Methyl-N-phenyl-3-(phenylthio)-2-propenamide.

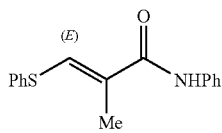

$^1$H-NMR (CDCl$_3$) δ: 2.11 (3H, d, J=1.0 Hz), 7.11 (1H, t, J=7.5 Hz), 7.29-7.39 (6H, m), 7.45-7.50 (3H, m), 7.54 (2H, d, J=8.5 Hz).

Reference Production Example 1-(2) to (89)

In the same manner as in Reference Production Example 1-(1), the following compounds were produced.

2-Methyl-N-(2-methylphenyl)-3-(phenylthio)-2-propenamide

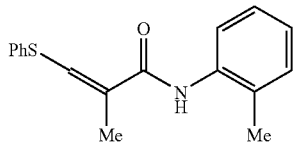

$^1$H-NMR (CDCl$_3$) δ: 2.14 (3H, s), 2.28 (3H, s), 7.08 (1H, t, J=7.5 Hz), 7.17-7.25 (3H, m), 7.29-7.39 (3H, m), 7.44-7.49 (2H, m), 7.54 (1H, s), 7.89 (1H, d, J=8.0 Hz).

(E)-2-Methyl-N-(3-methylphenyl)-3-(phenylthio)-2-propenamide

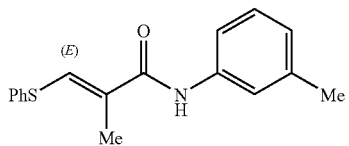

$^1$H-NMR (CDCl$_3$) δ: 2.10 (3H, d, J=1.0 Hz), 2.34 (3H, s), 6.93 (1H, d, J=7.6 Hz), 7.21 (1H, t, J=7.6 Hz), 7.29-7.39 (5H, m), 7.41 (1H, s), 7.45-7.49 (3H, m).

2-Methyl-N-(4-methylphenyl)-3-(phenylthio)-2-propenamide

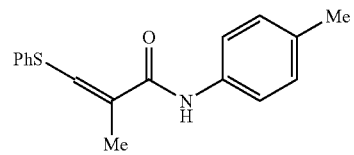

$^1$H-NMR (CDCl$_3$) δ: 2.10 (3H, s), 2.32 (3H, s), 7.13 (2H, d, J=8.5 Hz), 7.27-7.39 (4H, m), 7.42 (2H, d, J=8.5 Hz), 7.45-7.49 (3H, m).

(E)-N-(4-Ethylphenyl)-2-methyl-3-(phenylthio)-2-propenamide

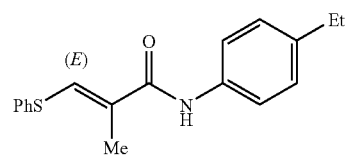

$^1$H-NMR (CDCl$_3$) δ: 1.21 (3H, t, J=7.6 Hz), 2.10 (3H, d, J=1.0 Hz), 2.61 (2H, q, J=7.6 Hz), 7.15 (2H, d, J=8.5 Hz), 7.28-7.39 (4H, m), 7.41-7.49 (5H, m).

(E)-N-(4-Isopropylphenyl)-2-methyl-3-(phenylthio)-2-propenamide

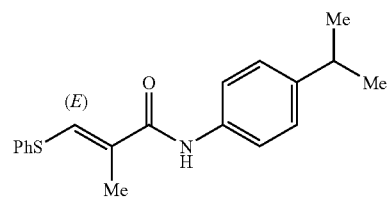

$^1$H-NMR (CDCl$_3$) δ: 1.23 (6H, d, J=6.8 Hz), 2.10 (3H, d, J=1.0 Hz), 2.88 (1H, sept, J=6.8 Hz), 7.18 (2H, d, J=8.5 Hz), 7.28-7.39 (4H, m), 7.43-7.49 (5H, m).

(E)-N-(5-Indanyl)-2-methyl-3-(phenylthio)-2-propenamide

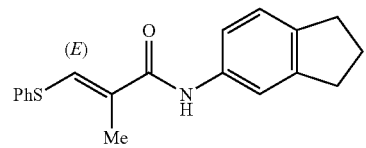

$^1$H-NMR (CDCl$_3$) δ: 2.07 (2H, quint, J=7.5 Hz), 2.10 (3H, d, J=0.7 Hz), 2.86 (2H, t, J=7.5 Hz), 2.89 (2H, t, J=7.5 Hz), 7.15 (1H, d, J=8.1 Hz), 7.20 (1H, dd, J=8.1, 1.9 Hz), 7.28-7.39 (4H, m), 7.44-7.48 (3H, m), 7.49 (1H, br s).

(E)-3-(4-Fluorophenylthio)-2-methyl-N-phenyl-2-propenamide

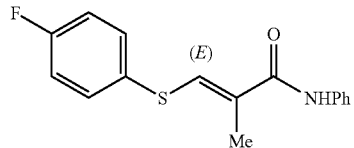

¹H-NMR (CDCl₃) δ: 2.09 (3H, d, J=0.7 Hz), 7.06 (2H, t, J=8.8 Hz), 7.11 (1H, t, J=7.6 Hz), 7.32 (2H, t, J=7.6 Hz), 7.36-7.41 (2H, m), 7.45 (2H, dd, J=8.8, 5.1 Hz), 7.53 (2H, d, J=7.6 Hz).

(E)-3-(4-Fluorophenylthio)-2-methyl-N-(4-methylphenyl)-2-propenamide

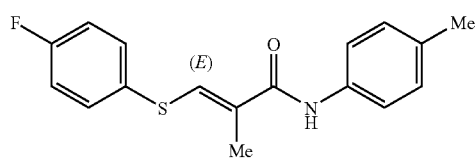

¹H-NMR (CDCl₃) δ: 2.08 (3H, d, J=0.7 Hz), 2.31 (3H, s), 7.05 (2H, t, J=8.9 Hz), 7.12 (2H, d, J=7.9 Hz), 7.34-7.38 (2H, m), 7.40 (2H, t, J=7.9 Hz), 7.44 (2H, dd, J=8.9, 5.2 Hz).

(E)-3-(4-Chlorophenylthio)-2-methyl-N-phenyl-2-propenamide

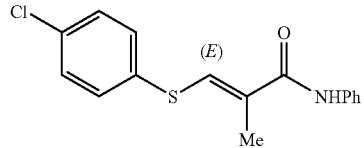

¹H-NMR (CDCl₃) δ: 2.11 (3H, d, J=1.0 Hz), 7.12 (1H, t, J=7.4 Hz), 7.30-7.43 (8H, m), 7.51-7.56 (2H, m).

(E)-3-(4-Chlorophenylthio)-2-methyl-N-(4-methylphenyl)-2-propenamide

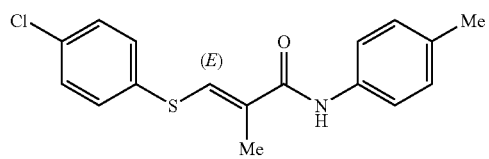

¹H-NMR (CDCl₃) δ: 2.10 (3H, d, J=1.0 Hz), 2.32 (3H, s), 7.13 (2H, d, J=8.2 Hz), 7.29-7.45 (8H, m).

(E)-2-Methyl-3-(4-methylphenylthio)-N-phenyl-2-propenamide

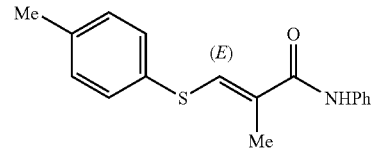

¹H-NMR (CDCl₃) δ: 2.10 (3H, d, J=1.0 Hz), 2.36 (3H, s), 7.11 (1H, t, J=7.5 Hz), 7.17 (2H, d, J=7.8 Hz), 7.29-7.39 (5H, m), 7.43 (1H, q, J=1.0 Hz), 7.53 (2H, d, J=7.5 Hz).

(E)-2-Methyl-N-(4-methylphenyl)-3-(4-methylphenylthio)-2-propenamide

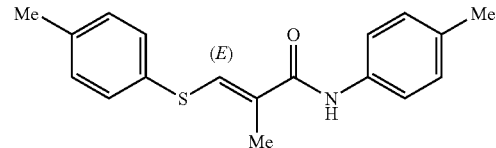

¹H-NMR (CDCl₃) δ: 2.08 (3H, d, J=1.0 Hz), 2.31 (3H, s), 2.35 (3H, s), 7.12 (2H, d, J=8.0 Hz), 7.17 (2H, d, J=7.8 Hz), 7.30 (1H, br s), 7.36 (2H, d, J=8.0 Hz), 7.39-7.44 (3H, m).

2-Ethyl-N-phenyl-3-(phenylthio)-2-propenamide

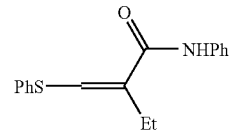

¹H-NMR (CDCl₃) δ: 1.20 (3H, t, J=7.6 Hz), 2.56 (2H, q, J=7.6 Hz), 7.11 (1H, t, J=7.4 Hz), 7.28-7.41 (7H, m), 7.44-7.49 (2H, m), 7.54 (2H, d, J=7.7 Hz).

N-phenyl-3-(phenylthio)-2-n-propyl-2-propenamide

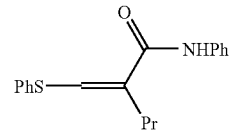

¹H-NMR (CDCl₃) δ: 1.03 (3H, t, J=7.4 Hz), 1.55-1.68 (2H, m), 2.53 (2H, t, J=7.7 Hz), 7.10 (1H, t, J=7.4 Hz), 7.28-7.41 (7H, m), 7.43-7.48 (2H, m), 7.53 (2H, d, J=7.6 Hz).

2-n-Butyl-N-phenyl-3-(phenylthio)-2-propenamide

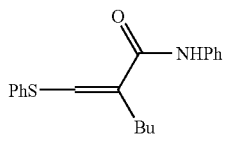

¹H-NMR (CDCl₃) δ: 0.98 (3H, t, J=7.2 Hz), 1.36-1.62 (4H, m), 2.55 (2H, t, J=7.6 Hz), 7.11 (1H, t, J=7.5 Hz), 7.28-7.41 (7H, m), 7.43-7.48 (2H, m), 7.51-7.57 (2H, m).

2-n-Butyl-3-(4-fluorophenylthio)-N-phenyl-2-propenamide

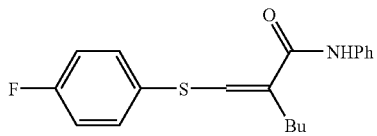

¹H-NMR (CDCl₃) δ: 0.98 (3H, t, J=7.2 Hz), 1.37-1.63 (4H, m), 2.53 (2H, t, J=7.7 Hz), 7.06 (2H, t, J=8.8 Hz), 7.11 (1H, t, J=7.9 Hz), 7.25 (1H, s), 7.32 (2H, t, J=7.9 Hz), 7.37 (1H, br s), 7.44 (2H, dd, J=8.8, 5.1 Hz), 7.53 (2H, d, J=7.9 Hz).

2-Fluoro-N-phenyl-3-(phenylthio)-2-propenamide

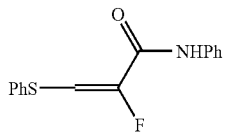

¹H-NMR (CDCl₃) δ: 7.16 (1H, t, J=7.5 Hz), 7.17 (1H, d, J=35.2 Hz), 7.31-7.41 (5H, m), 7.48 (2H, d, J=7.5 Hz), 7.58 (2H, d, J=8.5 Hz), 7.80 (1H, br s).

2-Fluoro-3-(4-fluorophenylthio)-N-phenyl-2-propenamide

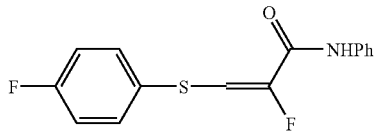

¹H-NMR (CDCl₃) δ: 7.06 (1H, d, J=35.6 Hz), 7.08 (2H, t, J=8.6 Hz), 7.16 (1H, t, J=7.9 Hz), 7.36 (2H, t, J=7.9 Hz), 7.48 (2H, dd, J=8.6, 5.2 Hz), 7.57 (2H, d, J=7.9 Hz), 7.79 (1H, br s).

2-(Methylthio)-N-phenyl-3-(phenylthio)-2-propenamide

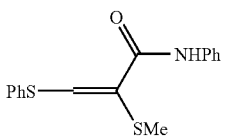

¹H-NMR (CDCl₃) δ: 2.38 (3H, s), 7.13 (1H, t, J=7.5 Hz), 7.32-7.42 (5H, m), 7.50-7.55 (2H, m), 7.63 (2H, d, J=7.5 Hz), 8.43 (1H, s), 9.12 (1H, br s).

3-(4-Fluorophenylthio)-2-(methylthio)-N-phenyl-2-propenamide

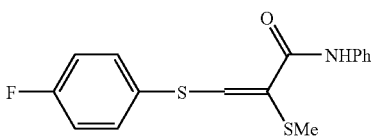

¹H-NMR (CDCl₃) δ: 2.37 (3H, s), 7.09 (2H, t, J=8.7 Hz), 7.13 (1H, t, J=7.9 Hz), 7.35 (2H, t, J=7.9 Hz), 7.51 (2H, dd, J=8.7, 5.1 Hz), 7.62 (2H, d, J=7.9 Hz), 8.31 (1H, s), 9.10 (1H, br s).

2,3-Bis(phenylthio)-N-phenyl-2-propenamide

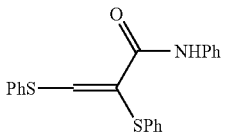

¹H-NMR (CDCl₃) δ: 7.09 (1H, t, J=7.5 Hz), 7.19-7.42 (10H, m), 7.46-7.55 (4H, m), 8.71 (1H, s), 8.79 (1H, br s).

3-(4-Fluorophenylthio)-N-phenyl-2-(phenylthio)-2-propenamide

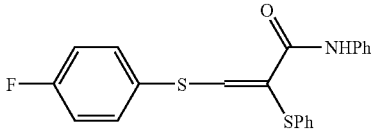

¹H-NMR (CDCl₃) δ: 7.05-7.13 (3H, m), 7.20-7.41 (7H, m), 7.46-7.54 (4H, m), 8.59 (0.8H, s), 8.71 (0.2H, s), 8.78 (1H, br s).

2-Phenoxy-N-phenyl-3-(phenylthio)-2-propenamide

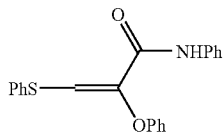

¹H-NMR (CDCl₃) δ: 7.07-7.17 (4H, m), 7.27-7.46 (9H, m), 7.51 (2H, d, J=7.6 Hz), 7.69 (1H, s), 7.94 (1H, s).

3-(4-Fluorophenylthio)-2-phenoxy-N-phenyl-2-propenamide

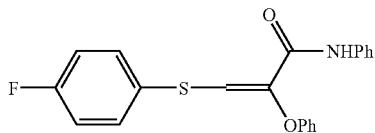

¹H-NMR (CDCl₃) δ: 7.04 (2H, t, J=8.7 Hz), 7.08-7.16 (4H, m), 7.30 (2H, t, J=8.0 Hz), 7.35-7.45 (4H, m), 7.48-7.53 (2H, m), 7.56 (1H, s), 7.94 (1H, s).

N-Phenyl-3-(phenylthio)-2-(2-thienyl)-2-propenamide

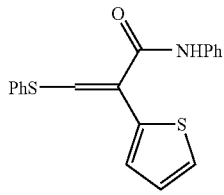

¹H-NMR (CDCl₃) δ: 7.10 (1H, t, J=7.4 Hz), 7.19-7.24 (2H, m), 7.27-7.40 (5H, m), 7.44-7.52 (5H, m), 7.56 (1H, dd, J=4.3, 1.9 Hz), 8.14 (1H, s).

3-(4-Fluorophenylthio)-N-phenyl-2-(2-thienyl)-2-propenamide

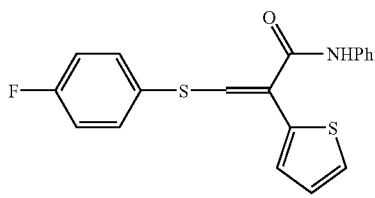

¹H-NMR (CDCl₃) δ: 7.03-7.14 (3H, m), 7.19-7.24 (2H, m), 7.30 (2H, t, J=8.0 Hz), 7.42-7.51 (5H, m), 7.56 (1H, dd, J=3.5, 2.8 Hz), 8.03 (1H, s).

N-Phenyl-3-(phenylthio)-2-(3-thienyl)-2-propenamide

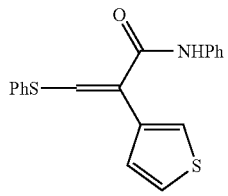

¹H-NMR (CDCl₃) δ: 7.09 (1H, t, J=7.4 Hz), 7.20-7.58 (13H, m), 8.06 (1H, s).

3-(4-Fluorophenylthio)-N-phenyl-2-(3-thienyl)-2-propenamide

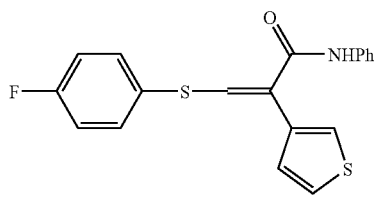

¹H-NMR (CDCl₃) δ: 7.03-7.12 (3H, m), 7.22 (1H, dd, J=4.9, 1.4 Hz), 7.27-7.33 (3H, m), 7.43-7.48 (4H, m), 7.50 (1H, dd, J=2.9, 1.4 Hz), 7.55 (1H, dd, J=4.9, 2.9 Hz), 7.94 (1H, s).

2,N-Diphenyl-3-(phenylthio)-2-propenamide

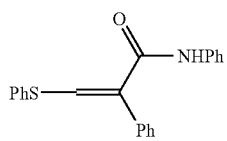

¹H-NMR (CDCl₃) δ: 7.03-7.13 (2H, m), 7.25-7.58 (14H, m), 8.10 (1H, s).

(E)-2-Methyl-3-phenoxy-N-phenyl-2-propenamide

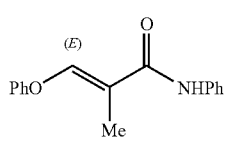

¹H-NMR (CDCl₃) δ: 7.05-7.13 (3H, m), 7.20-7.41 (7H, m), 7.46-7.54 (4H, m), 8.59 (0.8H, s), 8.71 (0.2H, s), 8.78 (1H, br s).

¹H-NMR (CDCl₃) δ: 2.08 (3H, d, J=1.2 Hz), 7.06-7.18 (4H, m), 7.29-7.41 (5H, m), 7.54-7.59 (2H, m), 7.74 (1H, q, J=1.2 Hz).

(E)-2-Methyl-N-(2-methylphenyl)-3-phenoxy-2-propenamide

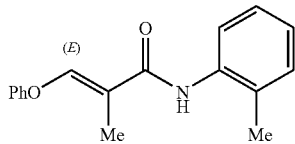

¹H-NMR (CDCl₃) δ: 2.09 (3H, d, J=1.2 Hz), 2.29 (3H, s), 7.04-7.11 (3H, m), 7.14 (1H, t, J=7.5 Hz), 7.18-7.26 (3H, m), 7.36 (2H, dd, J=8.7, 7.5 Hz), 7.76 (1H, q, J=1.2 Hz), 7.92 (1H, d, J=8.0 Hz).

(E)-2-Methyl-N-(3-methylphenyl)-3-phenoxy-2-propenamide

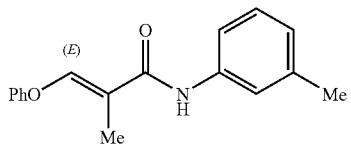

¹H-NMR (CDCl₃) δ: 2.07 (3H, d, J=1.2 Hz), 2.35 (3H, s), 6.93 (1H, d, J=7.5 Hz), 7.06-7.11 (2H, m), 7.12-7.17 (1H, m), 7.22 (1H, t, J=7.5 Hz), 7.29 (1H, br s), 7.32-7.39 (3H, m), 7.44 (1H, s), 7.73 (1H, q, J=1.2 Hz).

(E)-2-Methyl-N-(4-methylphenyl)-3-phenoxy-2-propenamide

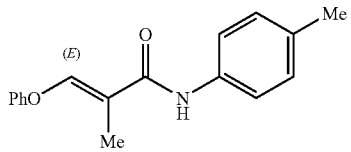

¹H-NMR (CDCl₃) δ: 2.07 (3H, d, J=1.1 Hz), 2.32 (3H, s), 7.09 (2H, d, J=8.3 Hz), 7.12-7.17 (3H, m), 7.28 (1H, br s), 7.36 (2H, dd, J=8.3, 7.6 Hz), 7.45 (2H, d, J=8.5 Hz), 7.73 (1H, q, J=1.1 Hz).

(E)-N-(2-Ethylphenyl)-2-methyl-3-phenoxy-2-propenamide

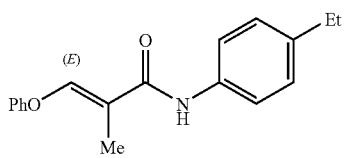

¹H-NMR (CDCl₃) δ: 1.22 (3H, t, J=7.6 Hz), 2.07 (3H, d, J=1.2 Hz), 2.62 (2H, q, J=7.6 Hz), 7.09 (2H, d, J=8.2 Hz), 7.13 (1H, d, J=7.6 Hz), 7.17 (2H, d, J=8.5 Hz), 7.29 (1H, br s), 7.36 (2H, dd, J=8.2, 7.6 Hz), 7.47 (2H, d, J=8.5 Hz), 7.73 (1H, q, J=1.2 Hz).

(E)-N-(2-Isopropylphenyl)-2-methyl-3-phenoxy-2-propenamide

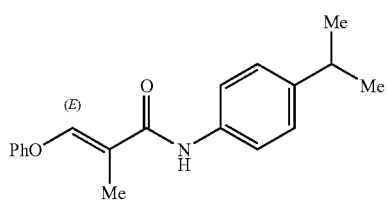

¹H-NMR (CDCl₃) δ: 1.24 (6H, d, J=6.8 Hz), 2.06 (3H, d, J=1.2 Hz), 2.85-2.92 (1H, quint, J=6.8 Hz), 7.08 (2H, d, J=8.7 Hz), 7.14 (1H, t, J=7.3 Hz), 7.19 (2H, d, J=8.5 Hz), 7.31 (1H, br s), 7.36 (2H, dd, J=8.7, 7.3 Hz), 7.47 (2H, d, J=8.5 Hz), 7.73 (1H, q, J=1.2 Hz).

(E)-N-(3-Fluorophenyl)-2-methyl-3-phenoxy-2-propenamide

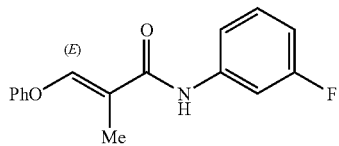

¹H-NMR (CDCl₃) δ: 2.06 (3H, d, J=1.3 Hz), 6.81 (1H, td, J=8.2, 2.3 Hz), 7.08 (2H, d, J=8.1 Hz), 7.12-7.21 (2H, m), 7.27 (1H, td, J=8.2, 6.5 Hz), 7.36 (2H, dd, J=8.1, 7.4 Hz), 7.41 (1H, br s), 7.56 (1H, dt, J=11.1, 2.3 Hz), 7.74 (1H, q, J=1.3 Hz).

(E)-N-(4-Fluorophenyl)-2-methyl-3-phenoxy-2-propenamide

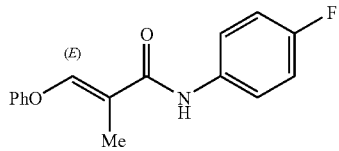

¹H-NMR (CDCl₃) δ: 2.06 (3H, d, J=1.0 Hz), 7.02 (2H, t, J=9.0 Hz), 7.08 (2H, d, J=8.5 Hz), 7.15 (1H, t, J=7.4 Hz), 7.31-7.41 (3H, m), 7.52 (2H, dd, J=9.0, 4.8 Hz), 7.72 (1H, q, J=1.0 Hz).

(E)-N-(4-Chlorophenyl)-2-methyl-3-phenoxy-2-propenamide

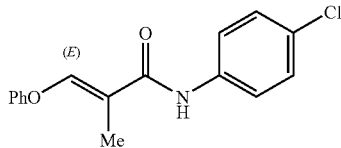

$^1$H-NMR (CDCl$_3$) δ: 2.07 (3H, d, J=1.2 Hz), 7.09 (2H, d, J=8.2 Hz), 7.16 (1H, t, J=7.5 Hz), 7.30 (2H, d, J=8.8 Hz), 7.32 (1H, br s), 7.37 (2H, dd, J=8.2, 7.5 Hz), 7.53 (2H, d, J=8.8 Hz), 7.74 (1H, q, J=1.2 Hz).

(E)-N-(4-Methoxyphenyl)-2-methyl-3-phenoxy-2-propenamide

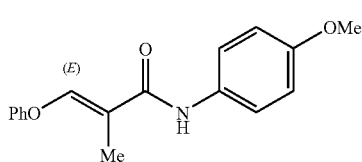

$^1$H-NMR (CDCl$_3$) δ: 2.06 (3H, d, J=1.2 Hz), 3.80 (3H, s), 6.87 (2H, d, J=9.0 Hz), 7.08 (2H, d, J=8.5 Hz), 7.14 (1H, t, J=7.3 Hz), 7.28 (1H, br s), 7.35 (2H, dd, J=8.5, 7.3 Hz), 7.46 (2H, d, J=9.0 Hz), 7.72 (1H, q, J=1.2 Hz).

(E)-N-(3,4-dimethylphenyl)-2-methyl-3-phenoxy-2-propenamide

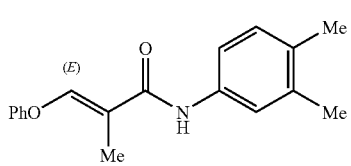

$^1$H-NMR (CDCl$_3$) δ: 2.06 (3H, d, J=1.2 Hz), 2.23 (3H, s), 2.25 (3H, s), 7.05-7.10 (3H, m), 7.14 (1H, t, J=7.4 Hz), 7.22-7.30 (2H, m), 7.32-7.39 (3H, m), 7.72 (1H, q, J=1.2 Hz).

(E)-N-(5-Indanyl)-2-methyl-3-phenoxy-2-propenamide

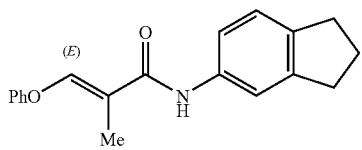

$^1$H-NMR (CDCl$_3$) δ: 2.06 (3H, d, J=1.2 Hz), 2.07 (2H, quint, J=7.5 Hz), 2.87 (2H, t, J=7.5 Hz), 2.88 (2H, t, J=7.5 Hz), 7.06-7.24 (5H, m), 7.28-7.39 (3H, m), 7.52 (1H, s), 7.72 (1H, q, J=1.2 Hz).

(E)-2-Methyl-3-phenoxy-N-(3-pyridyl)-2-propenamide

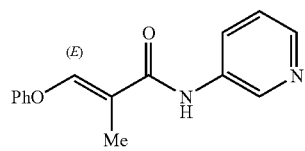

$^1$H-NMR (CDCl$_3$) δ: 2.07 (3H, d, J=1.3 Hz), 7.07 (2H, d, J=8.6 Hz), 7.15 (1H, t, J=7.5 Hz), 7.26 (1H, dd, J=8.3, 4.7 Hz), 7.35 (2H, dd, J=8.6, 7.5 Hz), 7.74 (1H, q, J=1.3 Hz), 7.82 (1H, br s), 8.20 (1H, ddd, J=8.3, 2.6, 1.3 Hz), 8.33 (1H, dd, J=4.7, 1.3 Hz), 8.61 (1H, d, J=2.6 Hz).

(E)-2-Methyl-3-(2-methylphenyloxy)-N-phenyl-2-propenamide

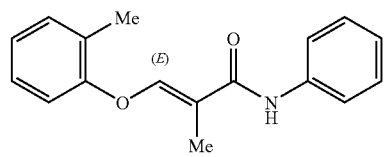

$^1$H-NMR (CDCl$_3$) δ: 2.07 (3H, d, J=1.2 Hz), 2.29 (3H, s), 6.98 (1H, d, J=7.6 Hz), 7.04 (1H, t, J=7.6 Hz), 7.10 (1H, t, J=7.9 Hz), 7.16 (1H, d, J=7.6 Hz), 7.19 (1H, d, J=7.6 Hz), 7.31 (2H, t, J=7.9 Hz), 7.45 (1H, s), 7.56 (2H, d, J=7.9 Hz), 7.66 (1H, q, J=1.2 Hz).

(E)-2-Methyl-3-(3-methylphenyloxy)-N-phenyl-2-propenamide

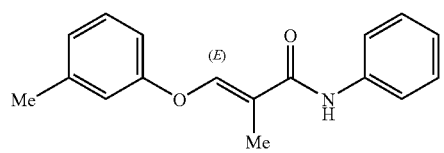

$^1$H-NMR (CDCl$_3$) δ: 2.07 (3H, d, J=1.3 Hz), 2.36 (3H, s), 6.87-6.93 (2H, m), 6.96 (1H, d, J=7.8 Hz), 7.12 (1H, t, J=7.7

Hz), 7.24 (1H, t, J=7.8 Hz), 7.31 (1H, br s), 7.34 (2H, t, J=7.7 Hz), 7.57 (2H, d, J=7.7 Hz), 7.73 (1H, q, J=1.3 Hz).

(E)-2-Methyl-N-(4-methylphenyl)-3-(3-methylphenyloxy)-2-propenamide

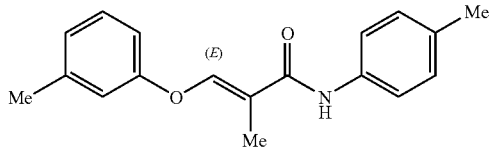

$^1$H-NMR (CDCl$_3$) δ: 2.06 (3H, d, J=1.2 Hz), 2.32 (3H, s), 2.36 (3H, s), 6.86-6.93 (2H, m), 6.95 (1H, d, J=7.6 Hz), 7.14 (2H, d, J=8.3 Hz), 7.20-7.31 (2H, m), 7.45 (2H, d, J=8.3 Hz), 7.72 (1H, q, J=1.2 Hz).

(E)-N-(4-Methoxyphenyl)-2-methyl-3-(3-methylphenyloxy)-2-propenamide

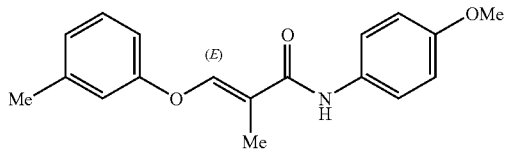

$^1$H-NMR (CDCl$_3$) δ: 2.05 (3H, d, J=1.3 Hz), 2.36 (3H, s), 3.80 (3H, s), 6.86-6.93 (4H, m), 6.95 (1H, d, J=7.6 Hz), 7.20-7.27 (2H, m), 7.47 (2H, d, J=9.1 Hz), 7.72 (1H, d, J=1.3 Hz).

(E)-N-(3,5-Dimethylphenyl)-2-methyl-3-(3-methylphenyloxy)-2-propenamide

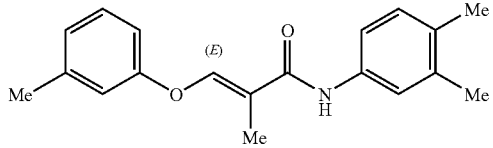

$^1$H-NMR (CDCl$_3$) δ: 2.05 (3H, d, J=1.2 Hz), 2.23 (3H, s), 2.25 (3H, s), 2.35 (3H, s), 6.85-6.93 (2H, m), 6.95 (1H, d, J=7.5 Hz), 7.08 (1H, d, J=8.2 Hz), 7.20-7.30 (3H, m), 7.37 (1H, d, J=1.9 Hz), 7.72 (1H, q, J=1.2 Hz).

(E)-2-Methyl-3-(4-methylphenyloxy)-N-phenyl-2-propenamide

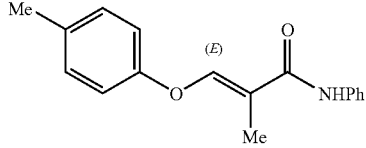

$^1$H-NMR (CDCl$_3$) δ: 2.06 (3H, d, J=1.2 Hz), 2.33 (3H, s), 6.98 (2H, d, J=8.5 Hz), 7.11 (1H, t, J=7.6 Hz), 7.15 (2H, d, J=8.5 Hz), 7.31 (1H, br s), 7.34 (2H, t, J=7.6 Hz), 7.56 (2H, d, J=7.6 Hz), 7.70 (1H, q, J=1.2 Hz).

(E)-2-Methyl-N-(4-methylphenyl)-3-(4-methylphenyloxy)-2-propenamide

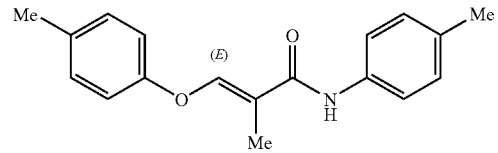

$^1$H-NMR (CDCl$_3$) δ: 2.05 (3H, d, J=1.2 Hz), 2.32 (3H, s), 2.33 (3H, s), 6.97 (2H, d, J=8.5 Hz), 7.14 (2H, d, J=8.3 Hz), 7.14 (2H, d, J=8.5 Hz), 7.26 (1H, br s), 7.44 (2H, d, J=8.3 Hz), 7.69 (1H, q, J=1.2 Hz).

(E)-N-(4-Methoxyphenyl)-2-methyl-3-(4-methylphenyloxy)-2-propenamide

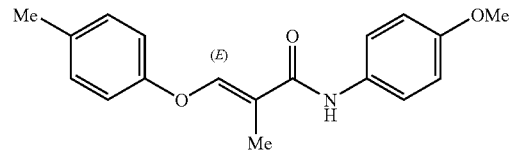

$^1$H-NMR (CDCl$_3$) δ: 2.05 (3H, d, J=1.3 Hz), 2.33 (3H, s), 3.80 (3H, s), 6.88 (2H, d, J=8.9 Hz), 6.98 (2H, d, J=8.5 Hz), 7.15 (2H, d, J=8.5 Hz), 7.22 (1H, br s), 7.46 (2H, d, J=8.9 Hz), 7.69 (1H, q, J=1.3 Hz).

(E)-3-(3-Ethylphenyloxy)-2-methyl-N-phenyl-2-propenamide

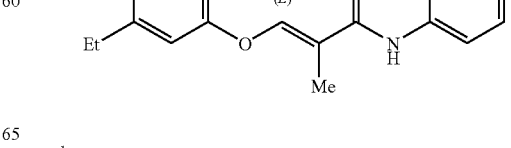

$^1$H-NMR (CDCl$_3$) δ: 1.24 (3H, t, J=7.6 Hz), 2.07 (3H, d, J=1.2 Hz), 2.65 (2H, q, J=7.6 Hz), 6.87-6.95 (2H, m), 6.98

(1H, d, J=7.6 Hz), 7.11 (1H, t, J=7.4 Hz), 7.26 (1H, t, J=7.8 Hz), 7.30-7.40 (3H, m), 7.57 (2H, d, J=8.5 Hz), 7.74 (1H, q, J=1.2 Hz).

(E)-3-(4-Ethylphenyloxy)-2-methyl-N-phenyl-2-propenamide

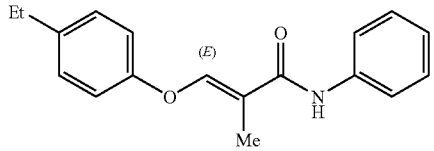

¹H-NMR (CDCl₃) δ: 1.23 (3H, t, J=7.6 Hz), 2.07 (3H, d, J=1.3 Hz), 2.63 (2H, q, J=7.6 Hz), 7.01 (2H, d, J=8.6 Hz), 7.11 (1H, t, J=7.6 Hz), 7.18 (2H, d, J=8.6 Hz), 7.31 (1H, br s), 7.34 (2H, t, J=7.6 Hz), 7.56 (2H, d, J=7.6 Hz), 7.71 (1H, q, J=1.3 Hz).

(E)-3-(4-Isopropylphenyloxy)-2-methyl-N-phenyl-2-propenamide

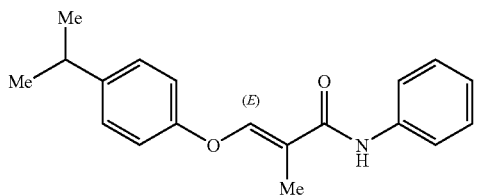

¹H-NMR (CDCl₃) δ: 1.24 (6H, d, J=6.8 Hz), 2.06 (3H, d, J=1.2 Hz), 2.84-2.96 (1H, m), 7.01 (2H, d, J=8.7 Hz), 7.11 (1H, t, J=7.4 Hz), 7.21 (2H, d, J=8.7 Hz), 7.30-7.37 (3H, m), 7.56 (2H, d, J=8.5 Hz), 7.71 (1H, q, J=1.2 Hz).

(E)-3-(4-Chlorophenyloxy)-2-methyl-N-phenyl-2-propenamide

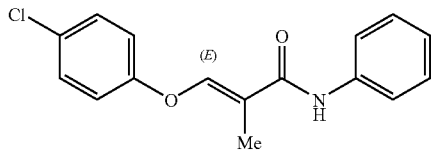

¹H-NMR (CDCl₃) δ: 2.05 (3H, d, J=1.2 Hz), 7.01 (2H, d, J=8.9 Hz), 7.12 (1H, t, J=7.5 Hz), 7.30 (2H, d, J=8.9 Hz), 7.33 (2H, t, J=7.5 Hz), 7.41 (1H, br s), 7.56 (2H, d, J=7.5 Hz), 7.65 (1H, q, J=1.2 Hz).

(E)-3-(2-Methoxyphenyloxy)-2-methyl-N-phenyl-2-propenamide

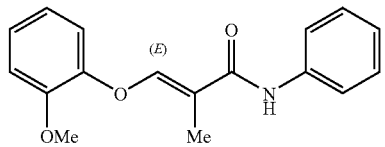

¹H-NMR (CDCl₃) δ: 2.10 (3H, d, J=1.2 Hz), 3.88 (3H, s), 6.90-6.99 (2H, m), 7.06-7.16 (3H, m), 7.29-7.36 (3H, m), 7.53-7.59 (3H, m).

(E)-3-(2-Methoxyphenyloxy)-2-methyl-N-(4-methylphenyl)-2-propenamide

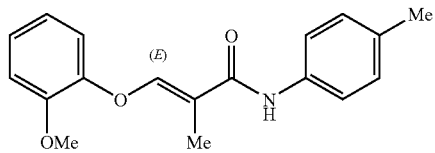

¹H-NMR (CDCl₃) δ: 2.09 (3H, d, J=1.2 Hz), 2.32 (3H, s), 3.88 (3H, s), 6.93 (1H, td, J=8.0, 1.5 Hz), 6.97 (1H, dd, J=8.0, 1.5 Hz), 7.07 (1H, dd, J=8.0, 1.5 Hz), 7.10-7.16 (3H, m), 7.25 (1H, br s), 7.43 (2H, d, J=8.5 Hz), 7.56 (1H, q, J=1.2 Hz).

(E)-N-(4-Methoxyphenyl)-3-(2-methoxyphenyloxy)-2-methyl-2-propenamide

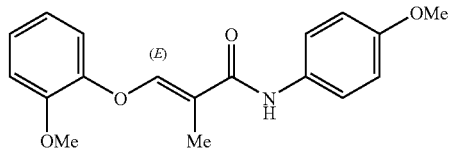

¹H-NMR (CDCl₃) δ: 2.09 (3H, d, J=1.3 Hz), 3.80 (3H, s), 3.88 (3H, s), 6.87 (2H, d, J=8.9 Hz), 6.93 (1H, ddd, J=8.4, 7.0, 1.2 Hz), 6.97 (1H, dd, J=8.4, 1.3 Hz), 7.07 (1H, dd, J=8.3, 1.2 Hz), 7.12 (1H, ddd, J=8.3, 7.0, 1.3 Hz), 7.21 (1H, br s), 7.46 (2H, d, J=8.9 Hz), 7.56 (1H, q, J=1.3 Hz).

(E)-N-(3,4-Dimethylphenyl)-3-(2-methoxyphenyloxy)-2-methyl-2-propenamide

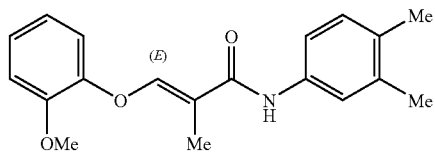

¹H-NMR (CDCl₃) δ: 2.08 (3H, d, J=1.2 Hz), 2.22 (3H, s), 2.25 (3H, s), 3.88 (3H, s), 6.90-6.95 (1H, m), 6.97 (1H, dd,

J=8.2, 1.3 Hz), 7.05-7.09 (2H, m), 7.11-7.13 (1H, m), 7.21 (1H, br s), 7.26 (2H, dd, J=7.8, 2.1 Hz), 7.36 (1H, d, J=2.1 Hz), 7.56 (1H, q, J=1.2 Hz).

(E)-3-(3-Methoxyphenyloxy)-2-methyl-N-phenyl-2-propenamide

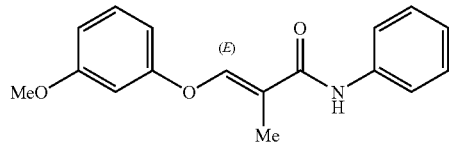

¹H-NMR (CDCl₃) δ: 2.07 (3H, d, J=1.2 Hz), 3.81 (3H, s), 6.64 (1H, t, J=2.3 Hz), 6.66-6.73 (2H, m), 7.12 (1H, t, J=7.5 Hz), 7.25 (1H, t, J=8.2 Hz), 7.29-7.40 (3H, m), 7.57 (2H, d, J=7.5 Hz), 7.73 (1H, q, J=1.2 Hz).

(E)-3-(3-Methoxyphenyloxy)-2-methyl-N-(4-methylphenyl)-2-propenamide

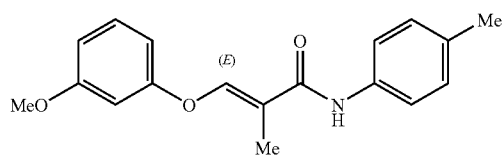

¹H-NMR (CDCl₃) δ: 2.06 (3H, d, J=1.2 Hz), 2.32 (3H, s), 3.81 (3H, s), 6.64 (1H, t, J=2.3 Hz), 6.66-6.72 (2H, m), 7.14 (2H, d, J=8.5 Hz), 7.21-7.30 (2H, m), 7.45 (2H, d, J=8.5 Hz), 7.71 (1H, q, J=1.2 Hz).

(E)-3-(4-Methoxyphenyloxy)-2-methyl-N-phenyl-2-propenamide

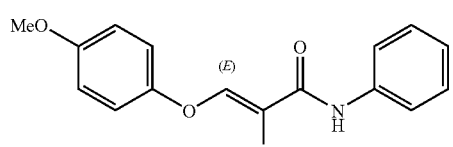

¹H-NMR (CDCl₃) δ: 2.06 (3H, d, J=1.2 Hz), 3.80 (3H, s), 6.87 (2H, d, J=9.2 Hz), 7.02 (2H, d, J=9.2 Hz), 7.11 (1H, t, J=7.9 Hz), 7.29 (1H, br s), 7.34 (2H, t, J=7.9 Hz), 7.56 (2H, d, J=7.9 Hz), 7.66 (1H, q, J=1.2 Hz).

(E)-3-(4-Methoxyphenyloxy)-2-methyl-N-(4-methylphenyl)-2-propenamide

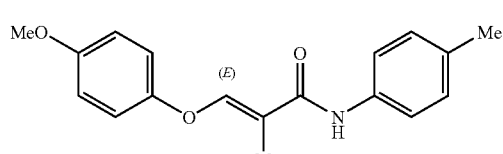

¹H-NMR (CDCl₃) δ: 2.03 (3H, d, J=1.2 Hz), 2.31 (3H, s), 3.78 (3H, s), 6.85 (2H, d, J=9.1 Hz), 7.00 (2H, d, J=9.1 Hz), 7.12 (2H, d, J=8.4 Hz), 7.36 (1H, br s), 7.44 (2H, d, J=8.4 Hz), 7.63 (1H, q, J=1.2 Hz).

(E)-N-(4-Methoxyphenyl)-3-(4-methoxyphenyloxy)-2-methyl-2-propenamide

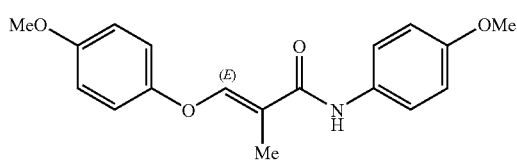

¹H-NMR (CDCl₃) δ: 2.04 (3H, d, J=1.0 Hz), 3.79 (6H, s), 6.86 (2H, d, J=9.0 Hz), 6.87 (2H, d, J=9.0 Hz), 7.01 (2H, d, J=9.0 Hz), 7.26 (1H, br s), 7.45 (2H, d, J=9.0 Hz), 7.63 (1H, d, J=1.0 Hz).

(E)-N-(3,4-Dimethylphenyl)-3-(4-methoxyphenyloxy)-2-methyl-2-propenamide

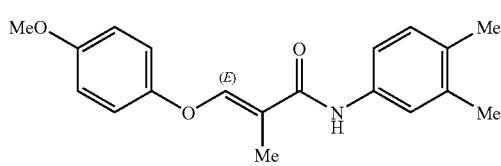

¹H-NMR (CDCl₃) δ: 2.03 (3H, d, J=1.0 Hz), 2.22 (3H, s), 2.24 (3H, s), 3.79 (3H, s), 6.86 (2H, d, J=9.3 Hz), 7.00 (2H, d, J=9.3 Hz), 7.07 (1H, d, J=8.0 Hz), 7.23-7.30 (2H, m), 7.36 (1H, s), 7.63 (1H, d, J=1.0 Hz).

(E)-3-(3-Ethoxyphenyloxy)-2-methyl-N-phenyl-2-propenamide

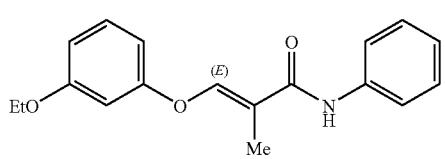

¹H-NMR (CDCl₃) δ: 1.41 (3H, t, J=7.0 Hz), 2.05 (3H, d, J=1.2 Hz), 4.02 (2H, q, J=7.0 Hz), 6.60-6.71 (3H, m), 7.11

(1H, t, J=7.6 Hz), 7.23 (1H, t, J=8.2 Hz), 7.33 (2H, t, J=7.6 Hz), 7.39 (1H, br s), 7.56 (2H, d, J=7.6 Hz), 7.71 (1H, q, J=1.2 Hz).

(E)-3-(4-Ethoxyphenyloxy)-2-methyl-N-phenyl-2-propenamide

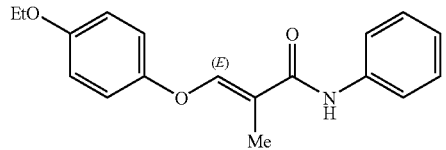

$^1$H-NMR (CDCl$_3$) δ: 1.41 (3H, t, J=7.0 Hz), 2.06 (3H, d, J=1.2 Hz), 4.01 (2H, q, J=7.0 Hz), 6.86 (2H, d, J=9.2 Hz), 7.00 (2H, d, J=9.2 Hz), 7.11 (1H, t, J=7.4 Hz), 7.27-7.37 (3H, m), 7.56 (2H, d, J=8.5 Hz), 7.65 (1H, q, J=1.2 Hz).

(E)-2-Methyl-N-phenyl-3-(4-phenylphenyloxy)-2-propenamide

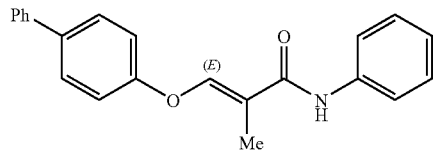

$^1$H-NMR (CDCl$_3$) δ: 2.10 (3H, d, J=1.2 Hz), 7.13 (1H, t, J=7.4 Hz), 7.17 (2H, d, J=8.8 Hz), 7.30-7.38 (4H, m), 7.44 (2H, t, J=7.6 Hz), 7.54-7.62 (6H, m), 7.79 (1H, q, J=1.2 Hz).

(E)-2-Methyl-3-(4-phenoxyphenyloxy)-N-phenyl-2-propenamide

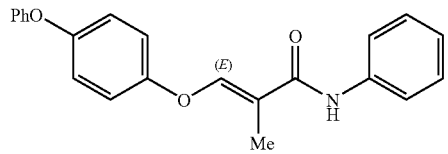

$^1$H-NMR (CDCl$_3$) δ: 2.07 (3H, d, J=1.4 Hz), 6.95-7.16 (8H, m), 7.29-7.39 (5H, m), 7.56 (2H, d, J=8.3 Hz), 7.69 (1H, q, J=1.4 Hz).

(E)-3-(3,4-Dimethylphenyloxy)-2-methyl-N-phenyl-2-propenamide

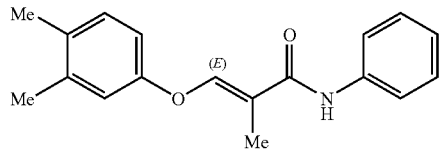

$^1$H-NMR (CDCl$_3$) δ: 2.05 (3H, d, J=1.2 Hz), 2.23 (3H, s), 2.25 (3H, s), 6.82 (1H, dd, J=8.3, 2.7 Hz), 6.88 (1H, d, J=2.7 Hz), 7.03-7.16 (2H, m), 7.33 (3H, t, J=8.0 Hz), 7.56 (2H, d, J=8.3 Hz), 7.70 (1H, q, J=1.2 Hz).

(E)-3-(5-Indanyloxy)-2-methyl-N-phenyl-2-propenamide

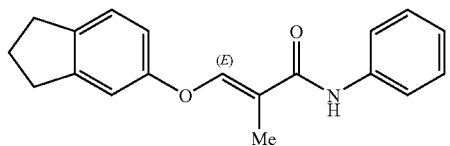

$^1$H-NMR (CDCl$_3$) δ: 2.06 (3H, d, J=1.2 Hz), 2.10 (2H, t, J=7.4 Hz), 2.83-2.94 (4H, m), 6.85 (1H, dd, J=8.0, 2.4 Hz), 6.96 (1H, d, J=2.4 Hz), 7.11 (1H, t, J=7.4 Hz), 7.16 (1H, d, J=8.0 Hz), 7.27-7.39 (3H, m), 7.56 (2H, d, J=8.0 Hz), 7.70 (1H, q, J=1.2 Hz).

(E)-3-(2,4-Dimethoxyphenyloxy)-2-methyl-N-phenyl-2-propenamide

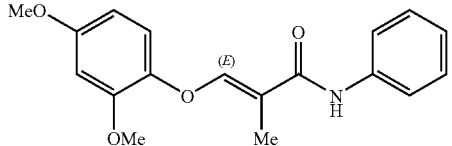

$^1$H-NMR (CDCl$_3$) δ: 2.08 (3H, d, J=1.2 Hz), 3.80 (3H, s), 3.84 (3H, s), 6.41 (1H, dd, J=8.8, 2.7 Hz), 6.53 (1H, d, J=2.7 Hz), 6.99 (1H, d, J=8.8 Hz), 7.10 (1H, t, J=7.6 Hz), 7.28 (1H, br s), 7.32 (2H, t, J=7.6 Hz), 7.48 (1H, q, J=1.2 Hz), 7.55 (2H, d, J=7.6 Hz).

(E)-3-(2,6-Dimethoxyphenyloxy)-2-methyl-N-phenyl-2-propenamide

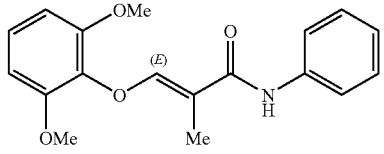

$^1$H-NMR (CDCl$_3$) δ: 2.11 (3H, d, J=1.2 Hz), 3.84 (6H, s), 6.61 (2H, d, J=8.3 Hz), 7.09 (2H, t, J=8.3 Hz), 7.27 (1H, br s), 7.31 (2H, t, J=8.3 Hz), 7.35 (1H, q, J=1.2 Hz), 7.54 (2H, d, J=8.3 Hz).

(E)-3-(3,4-(Ethylenedioxy)phenyloxy)-2-methyl-N-phenyl-2-propenamide

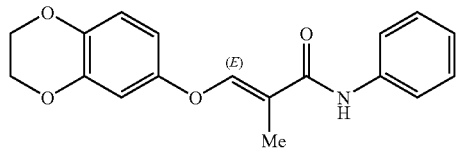

$^1$H-NMR (CDCl$_3$) δ: 2.04 (3H, d, J=1.2 Hz), 4.20-4.29 (4H, m), 6.58 (1H, dd, J=8.8, 2.9 Hz), 6.64 (1H, d, J=2.9 Hz), 6.82 (1H, d, J=8.8 Hz), 7.11 (1H, t, J=7.7 Hz), 7.30 (1H, br s), 7.33 (2H, t, J=7.7 Hz), 7.56 (2H, d, J=7.7 Hz), 7.62 (1H, q, J=1.2 Hz).

(E)-3-Benzyloxy-2-methyl-N-phenyl-2-propenamide

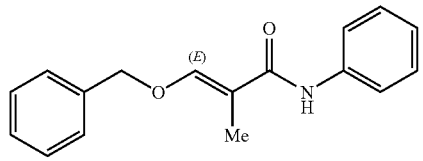

$^1$H-NMR (CDCl$_3$) δ: 1.93 (3H, d, J=1.1 Hz), 5.01 (2H, s), 7.08 (1H, t, J=7.6 Hz), 7.23 (1H, br s), 7.28-7.41 (7H, m), 7.48 (1H, q, J=1.1 Hz), 7.53 (2H, d, J=7.6 Hz).

(E)-3-(1-(4-chlorophenyl)pyrazol-3-yloxy)-2-methyl-N-phenyl-2-propenamide

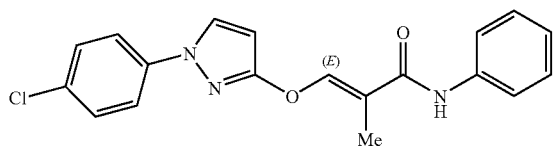

$^1$H-NMR (CDCl$_3$) δ: 2.08 (3H, d, J=1.5 Hz), 6.11 (1H, d, J=2.7 Hz), 7.12 (1H, t, J=7.4 Hz), 7.31-7.45 (5H, m), 7.54-7.62 (4H, m), 7.77 (1H, d, J=2.7 Hz), 8.12 (1H, q, J=1.5 Hz).

(E)-2-methyl-3-(2-naphthyloxy)-N-phenyl-2-propenamide

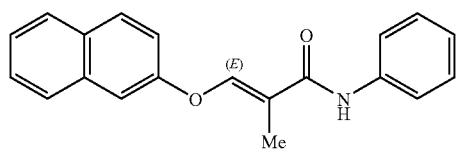

$^1$H-NMR (CDCl$_3$) δ: 2.13 (3H, d, J=1.4 Hz), 7.13 (1H, t, J=7.5 Hz), 7.29 (1H, dd, J=9.0, 2.4 Hz), 7.32-7.39 (3H, m), 7.41-7.47 (2H, m), 7.47-7.52 (1H, m), 7.59 (2H, d, J=7.5 Hz), 7.78 (1H, d, J=8.0 Hz), 7.82 (1H, d, J=8.0 Hz), 7.84 (1H, d, J=8.8 Hz), 7.89 (1H, q, J=1.4 Hz).

2-Ethyl-3-phenoxy-N-phenyl-2-propenamide

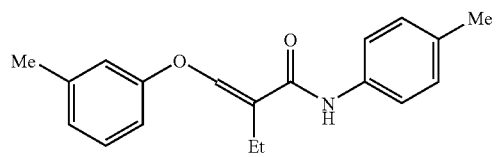

$^1$H-NMR (CDCl$_3$) δ: 1.21 (3H, t, J=7.6 Hz), 2.56 (2H, q, J=7.6 Hz), 7.09 (2H, d, J=7.8 Hz), 7.11-7.18 (2H, m), 7.31-7.40 (5H, m), 7.56 (2H, d, J=7.6 Hz), 7.61 (1H, s).

2-Ethyl-N-(4-methylphenyl)-3-phenoxy-2-propenamide $^1$H-NMR (CDCl$_3$) δ: 1.19 (3H, t, J=7.5 Hz), 2.31 (3H, s), 2.53 (2H, q, J=7.5 Hz), 6.99-7.18 (5H, m), 7.34 (2H, t, J=7.8 Hz), 7.38-7.49 (3H, m), 7.57 (1H, s).

2-Ethyl-N-(4-methylphenyl)-3-(3-methylphenyloxy)-2-propenamide $^1$H-NMR (CDCl$_3$) δ: 1.19 (3H, t, J=7.6 Hz), 2.32 (3H, s), 2.35 (3H, s), 2.53 (2H, q, J=7.6 Hz), 6.85-6.91 (2H, m), 6.95 (1H, d, J=7.6 Hz), 7.13 (2H, d, J=8.3 Hz), 7.22 (1H, t, J=7.8 Hz), 7.33 (1H, s), 7.44 (2H, d, J=8.3 Hz), 7.58 (1H, s).

2-Ethyl-3-(4-methylphenyloxy)-N-phenyl-2-propenamide

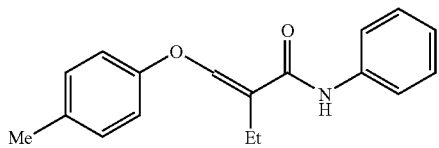

$^1$H-NMR (CDCl$_3$) δ: 1.21 (3H, t, J=7.6 Hz), 2.54 (2H, q, J=7.6 Hz), 6.98 (2H, d, J=8.7 Hz), 7.11 (1H, d, J=7.2 Hz), 7.15 (2H, d, J=8.7 Hz), 7.29-7.37 (3H, m), 7.54-7.59 (3H, m).

2-Ethyl-N-(4-methylphenyl)-3-(4-methylphenyloxy)-2-propenamide

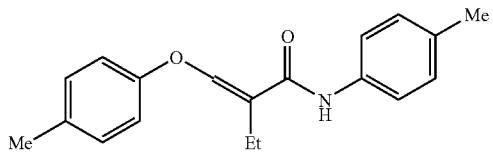

$^1$H-NMR (CDCl$_3$) δ: 1.20 (3H, t, J=7.6 Hz), 2.31 (3H, s), 2.32 (3H, s), 2.53 (2H, q, J=7.6 Hz), 6.97 (2H, d, J=8.7 Hz), 7.14 (2H, d, J=8.5 Hz), 7.15 (2H, d, J=8.7 Hz), 7.39-7.46 (3H, m), 7.56 (1H, s).

2-Ethyl-3-(2-methoxyphenyloxy)-N-(4-methylphenyl)-2-propenamide

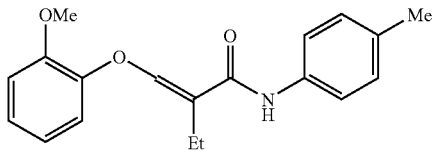

$^1$H-NMR (CDCl$_3$) δ: 1.22 (3H, t, J=7.6 Hz), 2.32 (3H, s), 2.57 (2H, q, J=7.6 Hz), 3.87 (3H, s), 6.90-6.99 (2H, m), 7.07 (1H, dd, J=7.9, 1.3 Hz), 7.10-7.16 (3H, m), 7.26 (1H, br s), 7.40-7.45 (3H, m).

2-Ethyl-3-(4-methoxyphenyloxy)-N-phenyl-2-propenamide

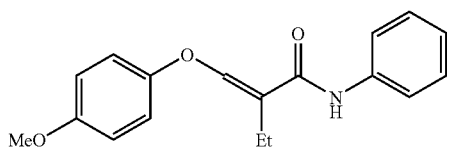

$^1$H-NMR (CDCl$_3$) δ: 1.21 (3H, t, J=7.5 Hz), 2.54 (2H, q, J=7.5 Hz), 3.80 (3H, s), 6.87 (2H, d, J=9.1 Hz), 7.02 (2H, d, J=9.1 Hz), 7.11 (1H, t, J=7.4 Hz), 7.29-7.38 (3H, m), 7.51-7.59 (3H, m).

2-Ethyl-3-(4-methoxyphenyloxy)-N-(4-methylphenyl)-2-propenamide

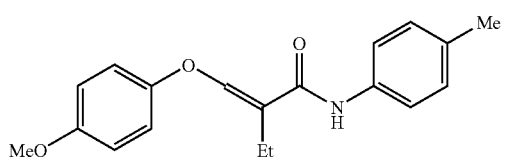

$^1$H-NMR (CDCl$_3$) δ: 1.20 (3H, t, J=7.6 Hz), 2.32 (3H, s), 2.53 (2H, q, J=7.6 Hz), 3.80 (3H, s), 6.87 (2H, d, J=9.1 Hz), 7.01 (2H, d, J=9.1 Hz), 7.14 (2H, d, J=8.2 Hz), 7.26 (1H, br s), 7.43 (2H, d, J=8.2 Hz), 7.51 (1H, s).

3-Phenoxy-N-phenyl-2-n-propyl-2-propenamide

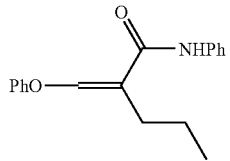

$^1$H-NMR (CDCl$_3$) δ: 1.03 (3H, t, J=7.5 Hz), 1.56-1.69 (2H, m), 2.52 (2H, t, J=7.5 Hz), 7.04-7.19 (4H, m), 7.29-7.43 (5H, m), 7.55 (2H, d, J=7.6 Hz), 7.65 (1H, s).

(E)-2-Cyclopropyl-3-phenoxy-N-phenyl-2-propenamide

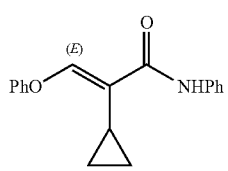

$^1$H-NMR (CDCl$_3$) δ: 0.77-0.82 (2H, m, 0.98-1.05 (2H, m), 1.44-1.53 (1H, m), 7.04-7.16 (4H, m), 7.28-7.37 (4H, m), 7.59 (2H, d, J=7.8 Hz), 7.84 (1H, d, J=1.5 Hz), 8.27 (1H, br s).

N-Phenyl-4,4,4-trifluoro-3-(phenylthio)-2-butenamide

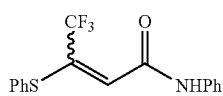

$^1$H-NMR (CDCl$_3$) δ: 6.90 (1H, s), 7.16 (1H, t, J=7.4 Hz), 7.29-7.38 (5H, m), 7.44-7.54 (4H, m), 8.04 (1H, br s).

N-(4-Methylphenyl)-3-(phenylthio)-4,4,4-trifluoro-2-butenamide

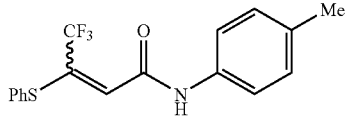

$^1$H-NMR (CDCl$_3$) δ: 2.32 (3H, s), 6.87-6.91 (1H, m), 7.13 (2H, d, J=8.4 Hz), 7.28-7.35 (3H, m), 7.37 (2H, d, J=8.4 Hz), 7.46-7.53 (2H, m), 8.02 (1H, br s).

Reference Production Example 2-(1)

A solution of 4.39 g (19.8 mmol) of (E)-methyl 2-ethyl-3-(phenylthio)-2-propenoate and 20 ml of an aqueous 2N NaOH solution in 40 ml of ethanol was stirred at 80° C. for 2 hours and then cooled to room temperature. To the reaction mixture was added 100 ml of water and washed with t-butyl methyl ether. The aqueous layer was acidified to pH 2 with concentrated HCl and extracted with tert-butyl methyl ether. The organic layer was washed with a saturated NaCl solution, dried over anhydrous MgSO$_4$, and concentrated to obtain 4.07 g of 2-ethyl-3-(phenylthio)-2-propenoic acid.

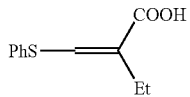

$^1$H-NMR (CDCl$_3$) δ: 1.12 (3H, t, J=7.5 Hz), 2.43 (2H, q, J=7.5 Hz), 7.30-7.41 (3H, m), 7.44-7.49 (2H, m), 7.79 (1H, s).

Reference Production Exampled 2-(2) to (49)

In the same manner as in Reference Production Example 2-(1), the following compounds were produced.

(E)-2-Methyl-3-(phenylthio)-2-propenoic acid

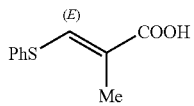

$^1$H-NMR (CDCl$_3$) δ: 1.96 (3H, d, J=1.1 Hz), 7.31-7.40 (3H, m), 7.43-7.50 (2H, m), 7.82 (1H, q, J=1.1 Hz).

(E)-2-Methyl-3-(4-methylphenylthio)-2-propenoic acid

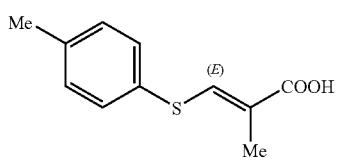

$^1$H-NMR (CDCl$_3$) δ: 1.94 (3H, d, J=1.0 Hz), 2.36 (3H, s), 7.18 (2H, d, J=8.1 Hz), 7.35 (2H, d, J=8.1 Hz), 7.78 (1H, q, J=1.0 Hz).

(E)-3-(4-Fluorophenylthio)-2-methyl-2-propenoic acid

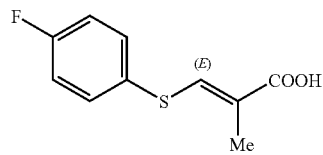

$^1$H-NMR (CDCl$_3$) δ: 1.95 (3H, d, J=1.0 Hz), 7.08 (2H, t, J=8.8 Hz), 7.45 (2H, dd, J=8.8, 5.1 Hz), 7.70 (1H, d, J=1.0 Hz).

(E)-3-(4-Chlorophenylthio)-2-methyl-2-propenoic acid

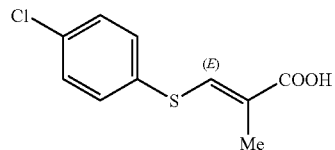

$^1$H-NMR (CDCl$_3$) δ: 1.96 (3H, d, J=1.1 Hz), 7.35 (2H, d, J=8.9 Hz), 7.40 (2H, d, J=8.9 Hz), 7.73 (1H, q, J=1.1 Hz).

3-(Phenylthio)-2-n-propyl-2-propenoic acid

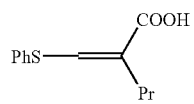

$^1$H-NMR (CDCl$_3$) δ: 0.98 (3H, t, J=7.4 Hz), 1.50-1.65 (2H, m), 2.39 (2H, t, J=7.6 Hz), 7.29-7.40 (3H, m), 7.42-7.50 (2H, m), 7.83 (1H, s).

2-n-Butyl-3-(phenylthio)-2-propenoic acid

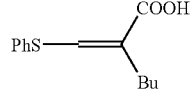

$^1$H-NMR (CDCl$_3$) δ: 0.95 (3H, t, J=7.2 Hz), 1.34-1.57 (4H, m), 2.41 (2H, t, J=7.6 Hz), 7.29-7.40 (3H, m), 7.43-7.48 (2H, m), 7.81 (1H, s).

2-n-Butyl-3-(4-fluorophenylthio)-2-propenoic acid

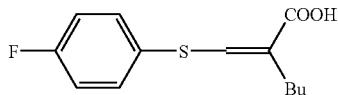

$^1$H-NMR (CDCl$_3$) δ: 0.95 (3H, t, J=7.2 Hz), 1.32-1.56 (4H, m), 2.39 (2H, t, J=7.7 Hz), 7.07 (2H, t, J=8.7 Hz), 7.44 (2H, dd, J=8.7, 5.2 Hz), 7.69 (1H, s).

2-Fluoro-3-(phenylthio)-2-propenoic acid

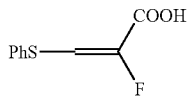

$^1$H-NMR (CDCl$_3$) δ: 7.25 (1H, d, J=31.2 Hz), 7.35-7.43 (3H, m), 7.46-7.53 (2H, m), 10.39 (1H, br s).

2-Fluoro-3-(4-fluorophenylthio)-2-propenoic acid

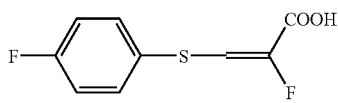

$^1$H-NMR (CDCl$_3$) δ: 7.10 (2H, t, J=8.8 Hz), 7.14 (1H, d, J=31.2 Hz), 7.49 (2H, dd, J=8.8, 5.1 Hz), 9.74 (1H, br s).

2-(Methylthio)-3-(phenylthio)-2-propenoic acid

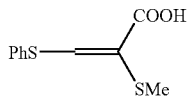

$^1$H-NMR (CDCl$_3$) δ: 2.40 (3H, s), 7.35-7.44 (3H, m), 7.46-7.54 (2H, m), 8.31 (1H, s).

3-(4-Fluorophenylthio)-2-(methylthio)-2-propenoic acid

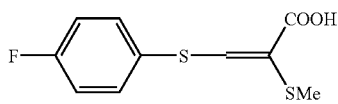

$^1$H-NMR (CDCl$_3$) δ: 2.40 (3H, s), 7.10 (2H, t, J=8.7 Hz), 7.49 (2H, dd, J=8.7, 5.1 Hz), 8.19 (1H, s).

2,3-Bis(phenylthio)-2-propenoic acid

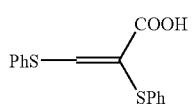

$^1$H-NMR (CDCl$_3$) δ: 7.16-7.23 (1H, m), 7.24-7.35 (4H, m), 7.36-7.43 (3H, m), 7.45-7.52 (2H, m), 8.58 (1H, s).

3-(4-Fluorophenylthio)-2-(phenylthio)-2-propenoic acid

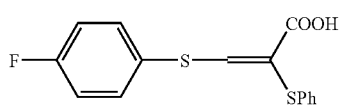

$^1$H-NMR (CDCl$_3$) δ: 7.10 (2H, t, J=8.7 Hz), 7.17-7.41 (5H, m), 7.48 (2H, dd, J=8.7, 5.1 Hz), 8.46 (0.8H, s), 8.58 (0.2H, s).

2-Phenoxy-3-(phenylthio)-2-propenoic acid

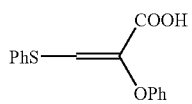

$^1$H-NMR (CDCl$_3$) δ: 6.96-7.02 (2H, m), 7.03-7.08 (1H, m), 7.27-7.40 (5H, m), 7.43-7.49 (2H, m), 7.70 (1H, s).

3-(4-Fluorophenylthio)-2-phenoxy-2-propenoic acid

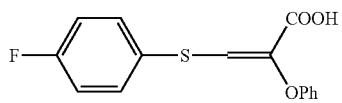

$^1$H-NMR (CDCl$_3$) δ: 6.95-7.00 (2H, m), 7.02-7.11 (3H, m), 7.27-7.34 (2H, m), 7.45 (2H, dd, J=8.7, 5.1 Hz), 7.58 (1H, s).

3-(Phenylthio)-2-(2-thienyl)-2-propenoic acid

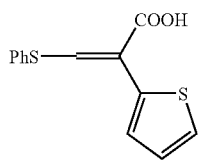

$^1$H-NMR (CDCl$_3$) δ: 7.12 (1H, dd, J=5.1, 3.6 Hz), 7.36-7.44 (5H, m), 7.48-7.54 (2H, m), 8.20 (1H, s).

3-(4-Fluorophenylthio)-2-(2-thienyl)-2-propenoic acid

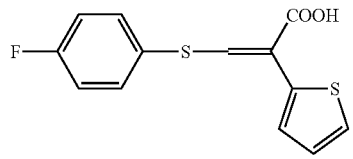

¹H-NMR (CDCl₃) δ: 7.05-7.16 (3H, m), 7.36 (1H, d, J=3.4 Hz), 7.43 (1H, d, J=5.1 Hz), 7.49 (2H, dd, J=8.1, 5.2 Hz), 8.08 (1H, s).

3-(Phenylthio)-2-(3-thienyl)-2-propenoic acid

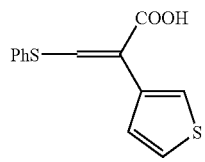

¹H-NMR (CDCl₃) δ: 7.31 (1H, dd, J=5.1, 1.2 Hz), 7.34-7.42 (4H, m), 7.46-7.50 (2H, m), 7.53 (1H, dd, J=2.9, 1.2 Hz), 8.13 (1H, s).

3-(4-Fluorophenylthio)-2-(3-thienyl)-2-propenoic acid

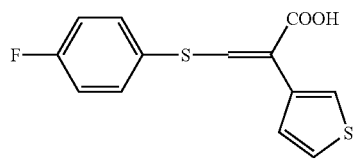

¹H-NMR (CDCl₃) δ: 7.09 (2H, t, J=8.8 Hz), 7.29 (1H, dd, J=5.1, 1.3 Hz), 7.37 (1H, dd, J=5.1, 3.0 Hz), 7.47 (2H, dd, J=8.8, 5.1 Hz), 7.51 (1H, dd, J=3.0, 1.3 Hz), 8.01 (1H, s).

(E)-2-Methyl-3-phenoxy-2-propenoic acid

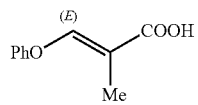

¹H-NMR (CDCl₃) δ: 1.93 (3H, d, J=1.2 Hz), 7.09 (2H, d, J=7.7 Hz), 7.17 (1H, t, J=7.7 Hz), 7.38 (2H, t, J=7.7 Hz), 7.85 (1H, q, J=1.2 Hz).

(E)-2-Methyl-3-(2-methylphenyloxy)-2-propenoic acid

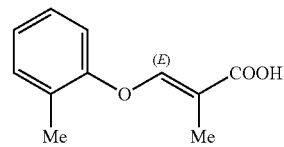

¹H-NMR (CDCl₃) δ: 1.94 (3H, d, J=1.2 Hz), 2.30 (3H, s), 7.00 (1H, d, J=8.0 Hz), 7.08 (1H, t, J=7.4 Hz), 7.17-7.24 (2H, m), 7.79 (1H, q, J=1.2 Hz).

(E)-2-Methyl-3-(3-methylphenyloxy)-2-propenoic acid

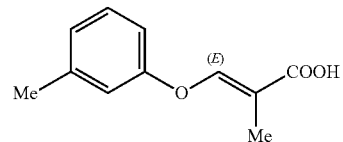

¹H-NMR (CDCl₃) δ: 1.92 (3H, d, J=1.2 Hz), 2.37 (3H, s), 6.86-6.93 (2H, m), 6.98 (1H, d, J=7.6 Hz), 7.25 (2H, t, J=7.6 Hz), 7.83 (1H, q, J=1.2 Hz).

(E)-2-Methyl-3-(4-methylphenyloxy)-2-propenoic acid

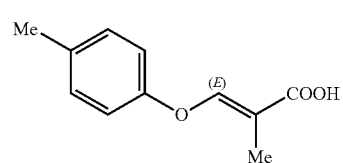

¹H-NMR (CDCl₃) δ: 1.91 (3H, d, J=1.2 Hz), 2.34 (3H, s), 6.97 (2H, d, J=8.5 Hz), 7.16 (2H, d, J=8.5 Hz), 7.81 (1H, q, J=1.2 Hz).

(E)-3-(3-Ethylphenyloxy)-2-methyl-2-propenoic acid

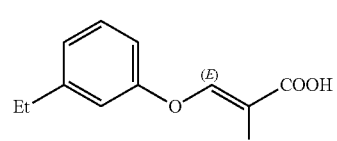

¹H-NMR (CDCl₃) δ: 1.25 (3H, t, J=7.6 Hz), 1.92 (3H, d, J=1.0 Hz), 2.66 (2H, q, J=7.6 Hz), 6.88-6.94 (2H, m), 7.01

(1H, d, J=7.8 Hz), 7.27 (1H, t, J=7.8 Hz), 7.85 (1H, q, J=1.0 Hz).

(E)-3-(4-Ethylphenyloxy)-2-methyl-2-propenoic acid

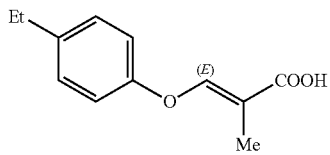

$^1$H-NMR (CDCl$_3$) δ: 1.23 (3H, t, J=7.6 Hz), 1.92 (3H, d, J=1.4 Hz), 2.64 (2H, q, J=7.6 Hz), 7.00 (2H, d, J=8.7 Hz), 7.19 (2H, d, J=8.7 Hz), 7.82 (1H, q, J=1.4 Hz).

(E)-3-(4-Isopropylphenyloxy)-2-methyl-2-propenoic acid

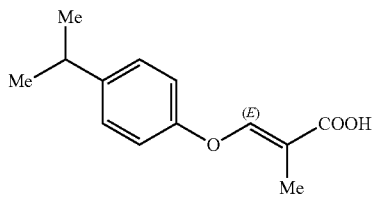

$^1$H-NMR (CDCl$_3$) δ: 1.24 (6H, d, J=7.1 Hz), 1.91 (3H, d, J=1.4 Hz), 2.84-2.97 (1H, m), 7.01 (2H, d, J=8.4 Hz), 7.22 (2H, d, J=8.4 Hz), 7.82 (1H, q, J=1.4 Hz).

(E)-3-(4-Chlorophenyloxy)-2-methyl-2-propenoic acid

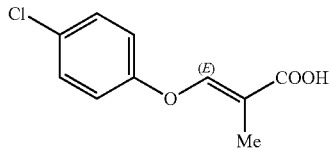

$^1$H-NMR (CDCl$_3$) δ: 1.92 (3H, d, J=1.4 Hz), 7.03 (2H, d, J=9.0 Hz), 7.34 (2H, d, J=9.0 Hz), 7.77 (1H, q, J=1.4 Hz).

(E)-3-(2-Methoxyphenyloxy)-2-methyl-2-propenoic acid

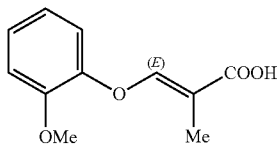

$^1$H-NMR (CDCl$_3$) δ: 1.94 (3H, d, J=1.2 Hz), 3.87 (3H, s), 6.90-7.01 (2H, m), 7.07 (1H, dd, J=7.9, 1.6 Hz), 7.11-7.18 (1H, m), 7.68 (1H, d, J=1.2 Hz).

(E)-3-(3-Methoxyphenyloxy)-2-methyl-2-propenoic acid

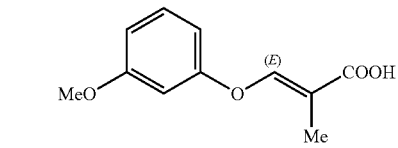

$^1$H-NMR (CDCl$_3$) δ: 1.92 (3H, d, J=1.4 Hz), 3.82 (3H, s), 6.64 (1H, t, J=2.3 Hz), 6.68 (1H, dd, J=8.3, 2.3 Hz), 6.72 (1H, dd, J=8.3, 2.3 Hz), 7.26 (1H, t, J=8.3 Hz), 7.84 (1H, q, J=1.4 Hz).

(E)-3-(4-Methoxyphenyloxy)-2-methyl-2-propenoic acid

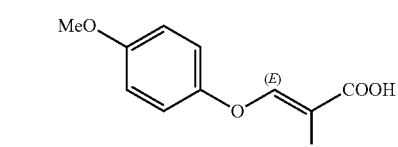

$^1$H-NMR (CDCl$_3$) δ: 1.91 (3H, d, J=1.2 Hz), 3.80 (3H, s), 6.88 (2H, d, J=9.3 Hz), 7.02 (2H, d, J=9.3 Hz), 7.75 (1H, q, J=1.2 Hz).

(E)-3-(3-Ethoxyphenyloxy)-2-methyl-2-propenoic acid

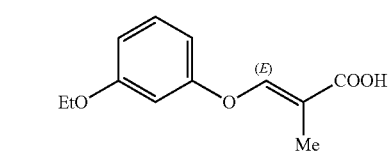

$^1$H-NMR (CDCl$_3$) δ: 1.42 (3H, t, J=7.1 Hz), 1.92 (3H, d, J=1.5 Hz), 4.04 (2H, q, J=7.1 Hz), 6.63 (1H, t, J=2.3 Hz), 6.65-6.72 (2H, m), 7.25 (1H, t, J=8.2 Hz), 7.83 (1H, d, J=1.5 Hz).

(E)-3-(4-Ethoxyphenyloxy)-2-methyl-2-propenoic acid

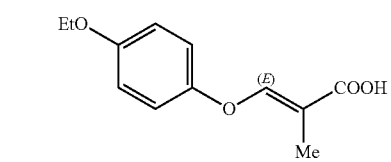

$^1$H-NMR (CDCl$_3$) δ: 1.41 (3H, t, J=7.0 Hz), 1.90 (3H, d, J=1.5 Hz), 4.01 (2H, q, J=7.0 Hz), 6.87 (2H, d, J=8.9 Hz), 7.00 (2H, d, J=8.9 Hz), 7.76 (1H, d, J=1.5 Hz).

(E)-2-Methyl-3-(4-phenylphenyloxy)-2-propenoic acid

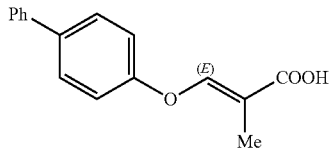

¹H-NMR (CDCl₃) δ: 1.95 (3H, d, J=1.4 Hz), 7.17 (2H, d, J=8.8 Hz), 7.35 (1H, t, J=7.3 Hz), 7.44 (2H, t, J=7.6 Hz), 7.54-7.63 (4H, m), 7.88 (1H, q, J=1.4 Hz).

(E)-2-Methyl-3-(4-phenoxyphenyloxy)-2-propenoic acid

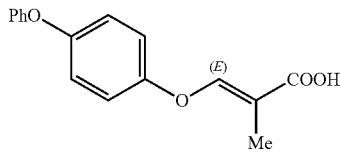

¹H-NMR (CDCl₃) δ: 1.92 (3H, d, J=1.2 Hz), 6.96-7.13 (7H, m), 7.34 (2H, dd, J=8.5, 7.3 Hz), 7.79 (1H, q, J=1.2 Hz).

(E)-3-(3,4-dimethylphenyloxy)-2-methyl-2-propenoic acid

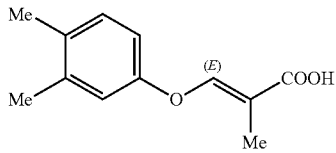

¹H-NMR (CDCl₃) δ: 1.91 (3H, d, J=1.2 Hz), 2.23 (3H, s), 2.26 (3H, s), 6.82 (1H, dd, J=8.2, 2.6 Hz), 6.87 (1H, d, J=2.6 Hz), 7.10 (1H, d, J=8.2 Hz), 7.81 (1H, q, J=1.2 Hz).

(E)-3-(5-indanyloxy)-2-methyl-2-propenoic acid

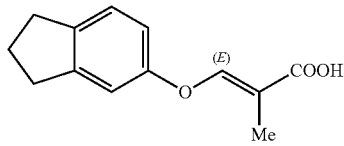

¹H-NMR (CDCl₃) δ: 1.91 (3H, d, J=1.3 Hz), 2.10 (2H, quint), 2.83-2.95 (4H, m), 6.85 (1H, dd, J=8.1, 2.4 Hz), 6.95 (1H, d, J=2.4 Hz), 7.17 (1H, d, J=8.1 Hz), 7.81 (1H, q, J=1.3 Hz).

(E)-3-(2,4-Dimethoxyphenyloxy)-2-methyl-2-propenoic acid

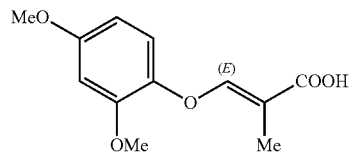

¹H-NMR (CDCl₃) δ: 1.92 (3H, d, J=1.2 Hz), 3.80 (3H, s), 3.84 (3H, s), 6.41 (1H, dd, J=8.8, 2.9 Hz), 6.53 (1H, d, J=2.9 Hz), 6.98 (1H, d, J=8.8 Hz), 7.59 (1H, q, J=1.2 Hz).

(E)-3-(2,6-Dimethoxyphenyloxy)-2-methyl-2-propenoic acid

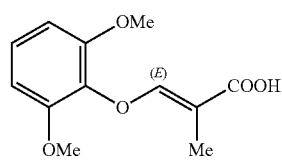

¹H-NMR (CDCl₃) δ: 1.95 (3H, d, J=1.1 Hz), 3.83 (6H, s), 6.60 (2H, d, J=8.5 Hz), 7.09 (1H, t, J=8.5 Hz), 7.47 (1H, q, J=1.2 Hz).

(E)-3-(3,4-(Ethlenedioxy)phenyloxy)-2-methyl-2-propenoic acid

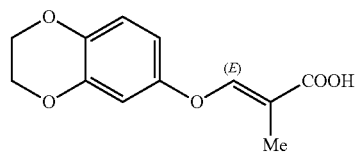

¹H-NMR (CDCl₃) δ: 1.89 (3H, d, J=1.2 Hz), 4.21-4.29 (4H, m), 6.58 (1H, dd, J=8.8, 2.9 Hz), 6.63 (1H, d, J=2.9 Hz), 6.83 (1H, d, J=8.8 Hz), 7.73 (1H, q, J=1.2 Hz).

(E)-3-Benzyloxy-2-methyl-2-propenoic acid

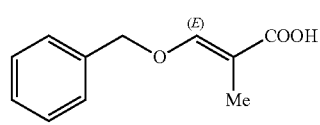

¹H-NMR (CDCl₃) δ: 1.77 (3H, d, J=1.1 Hz), 5.04 (2H, s), 7.30-7.42 (5H, m), 7.55 (1H, q, J=1.1 Hz).

(E)-3-(1-(4-Chlorophenyl)pyrazol-3-yloxy)-2-methyl-2-propenoic acid

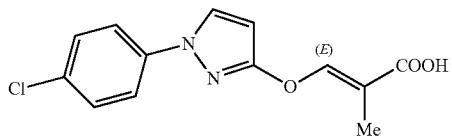

¹H-NMR (CDCl₃) δ: 1.95 (3H, d, J=1.5 Hz), 6.11 (1H, d, J=2.6 Hz), 7.41 (2H, d, J=9.0 Hz), 7.58 (2H, d, J=9.0 Hz), 7.78 (1H, d, J=2.6 Hz), 8.30 (1H, q, J=1.5 Hz).

(E)-2-Methyl-3-(2-naphthyloxy)-2-propenoic acid

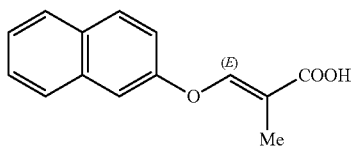

¹H-NMR (CDCl₃) δ: 1.99 (3H, d, J=1.2 Hz), 7.29 (1H, dd, J=9.0, 2.4 Hz), 7.41-7.54 (3H, m), 7.77-7.89 (3H, m), 8.00 (1H, q, J=1.2 Hz).

2-Ethyl-3-phenoxy-2-propenoic acid

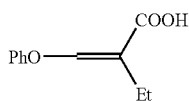

¹H-NMR (CDCl₃) δ: 1.12 (3H, t, J=7.4 Hz), 2.44 (2H, q, J=7.4 Hz), 7.09 (2H, d, J=8.6 Hz), 7.17 (1H, t, J=7.4 Hz), 7.38 (2H, dd, J=8.6, 7.4 Hz), 7.80 (1H, s).

2-Ethyl-3-(3-methylphenyloxy)-2-propenoic acid

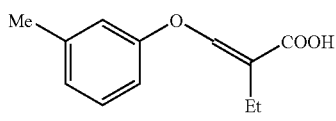

¹H-NMR (DMSO-D₆) δ: 1.02 (3H, t, J=7.4 Hz), 2.30 (3H, q, J=7.4 Hz), 2.32 (3H, s), 6.92-7.04 (3H, m), 7.29 (1H, t, J=8.0 Hz), 7.63 (1H, s), 12.21 (1H, br s).

2-Ethyl-3-(4-methylphenyloxy)-2-propenoic acid

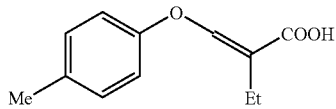

¹H-NMR (CDCl₃) δ: 1.11 (3H, t, J=7.2 Hz), 2.34 (3H, s), 2.42 (2H, q, J=7.2 Hz), 6.97 (2H, d, J=7.9 Hz), 7.16 (2H, d, J=7.9 Hz), 7.78 (1H, s).

2-Ethyl-3-(2-methoxyphenyloxy)-2-propenoic acid

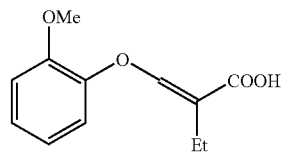

¹H-NMR (CDCl₃) δ: 1.13 (3H, t, J=7.4 Hz), 2.45 (2H, q, J=7.4 Hz), 3.86 (3H, s), 6.91-6.99 (2H, m), 7.07 (1H, dd, J=7.8, 1.3 Hz), 7.11-7.18 (1H, m), 7.65 (1H, s).

2-Ethyl-3-(4-methoxyphenyloxy)-2-propenoic acid

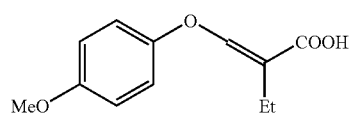

¹H-NMR (CDCl₃) δ: 1.11 (3H, t, J=7.5 Hz), 2.42 (2H, q, J=7.5 Hz), 3.80 (3H, s), 6.88 (2H, d, J=9.1 Hz), 7.02 (2H, d, J=9.1 Hz), 7.72 (1H, s).

3-Phenoxy-2-n-propyl-2-propenoic acid

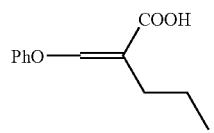

¹H-NMR (CDCl₃) δ: 0.96 (3H, t, J=7.4 Hz), 1.30-1.70 (2H, m), 2.40 (2H, t, J=7.4 Hz), 7.09 (2H, d, J=8.7 Hz), 7.17 (1H, t, J=7.4 Hz), 7.37 (2H, dd, J=8.7, 7.4 Hz), 7.85 (1H, s).

(E)-2-Cyclopropyl-3-phenoxy-2-propenoic acid

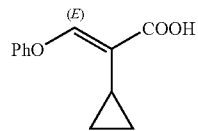

¹H-NMR (CDCl₃) δ: 0.78-0.83 (2H, m), 0.92-0.97 (2H, m), 1.62-1.71 (1H, m), 7.08 (2H, d, J=8.7 Hz), 7.17 (1H, t, J=7.4 Hz), 7.37 (2H, dd, J=8.7, 7.4 Hz), 7.84 (1H, d, J=0.7 Hz).

Reference Production Example 3-(1)

11.0 g (40.7 mmol) of (E)-methyl 2-methyl-3-(p-toluenesulfonyloxy)-2-propenoate was dissolved in 100 ml of chloroform and 6.3 g (57.0 mmol) of thiophenol and 33 ml of triethylamine were added. The solution was stirred at 50° C. for 9 hours. To the reaction mixture was added tert-butyl methyl ether and washed sequentially with an aqueous 1N NaOH solution and a saturated NaCl solution, dried, and concentrated. The residue was purified by silica gel column chromatography (hexane/ethyl acetate=10/1) to obtain 6.5 g of (E)-methyl 2-methyl-3-(phenylthio)-2-propenoate.

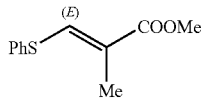

$^1$H-NMR (CDCl$_3$) δ: 1.97 (3H, d, J=1.0 Hz), 3.74 (3H, s), 7.31-7.40 (3H, m), 7.44-7.46 (1H, m), 7.46-7.48 (1H, m), 7.65 (1H, q, J=1.0 Hz).

Reference Production Examples 3-(2) to (8)

In the same manner as in Reference Production Example 3-(1), the following compounds were produced.

(E)-Methyl 2-methyl-3-(4-methylphenylthio)-2-propenoate

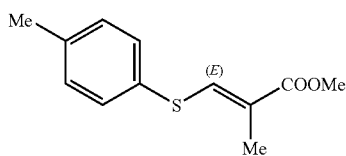

$^1$H-NMR (CDCl$_3$) δ: 1.96 (3H, d, J=1.2 Hz), 2.36 (3H, s), 3.72 (3H, s), 7.18 (2H, d, J=8.0 Hz), 7.35 (2H, d, J=8.0 Hz), 7.60 (1H, q, J=1.2 Hz).

(E)-Methyl 3-(4-fluorophenylthio)-2-methyl-2-propenoate

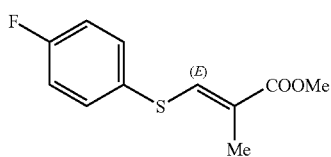

$^1$H-NMR (CDCl$_3$) δ: 1.96 (3H, d, J=1.0 Hz), 3.73 (3H, s), 7.07 (2H, t, J=8.8 Hz), 7.45 (2H, dd, J=8.8, 5.1 Hz), 7.53 (1H, q, J=1.0 Hz).

(E)-Methyl 3-(4-chlorophenylthio)-2-methyl-2-propenoate

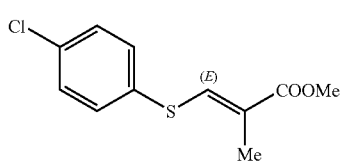

$^1$H-NMR (CDCl$_3$) δ: 1.96 (3H, d, J=1.0 Hz), 3.74 (3H, s), 7.34 (2H, d, J=8.8 Hz), 7.39 (2H, d, J=8.8 Hz), 7.56 (1H, q, J=1.0 Hz).

Methyl 2-ethyl-3-(phenylthio)-2-propenoate

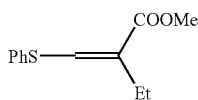

$^1$H-NMR (CDCl$_3$) δ: 1.11 (3H, t, J=7.5 Hz), 2.44 (2H, q, J=7.5 Hz), 3.74 (3H, s), 7.30-7.40 (3H, m), 7.44-7.49 (2H, m), 7.62 (1H, s).

Methyl 3-(phenylthio)-2-n-propyl-2-propenoate

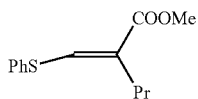

$^1$H-NMR (CDCl$_3$) δ: 0.98 (3H, t, J=7.3 Hz), 1.49-1.61 (2H, m), 2.40 (2H, t, J=7.7 Hz), 3.73 (3H, s), 7.29-7.40 (3H, m), 7.43-7.48 (2H, m), 7.65 (1H, s).

Methyl 2-n-butyl-3-(phenylthio)-2-propenoate

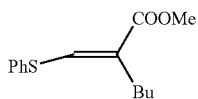

$^1$H-NMR (CDCl$_3$) δ: 0.95 (3H, t, J=7.2 Hz), 1.34-1.54 (4H, m), 2.42 (2H, t, J=7.6 Hz), 3.73 (3H, s), 7.29-7.40 (3H, m), 7.43-7.48 (2H, m), 7.63 (1H, s).

Methyl 2-n-butyl-3-(4-fluorophenylthio)-2-propenoate

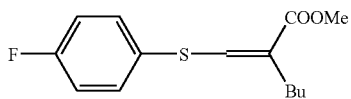

$^1$H-NMR (CDCl$_3$) δ: 0.95 (3H, t, J=7.2 Hz), 1.33-1.53 (4H, m), 2.40 (2H, t, J=7.6 Hz), 3.73 (3H, s), 7.07 (2H, t, J=8.6 Hz), 7.44 (2H, dd, J=8.6, 5.1 Hz), 7.52 (1H, s).

Reference Production Example 4-(1)

3.50 g (11.6 mmol) of methyl 2-(methylthio)-3-(p-toluenesulfonyloxy)-2-propenoate was dissolved in 20 ml of chloroform and cooled to 0° C. To the solution was added 1.28 g (11.6 mmol) of thiophenol and 2 ml (14.3 mmol) of triethylamine and stirred at room temperature for 1 hour. To the reaction mixture was added tert-butyl methyl ether and washed sequentially with an aqueous 1N NaOH solution and a saturated NaCl solution. The organic layer was dried and then concentrated. The residue was purified by silica gel column chromatography (hexane/ethyl acetate=10/1) to obtain 1.64 g of methyl 2-(methylthio)-3-(phenylthio)-2-propenoate.

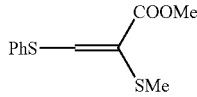

$^1$H-NMR (CDCl$_3$) δ: 2.39 (3H, s), 3.79 (3H, s), 7.35-7.42 (3H, m), 7.46-7.54 (2H, m), 8.12 (1H, s).

Reference Production Examples 4-(2) to (13)

In the same manner as in Reference Production Example 4-(1), the following compounds were produced.

Methyl 3-(4-fluorophenylthio)-2-(methylthio)-2-propenoate

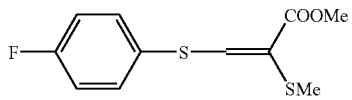

$^1$H-NMR (CDCl$_3$) δ: 2.38 (3H, s), 3.79 (3H, s), 7.09 (2H, t, J=8.5 Hz), 7.49 (2H, dd, J=8.5, 5.1 Hz), 8.00 (1H, s). Methyl 2,3-bis(phenylthio)-2-propenoate

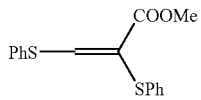

$^1$H-NMR (CDCl$_3$) δ: 3.71 (3H, s), 7.16-7.22 (1H, m), 7.25-7.34 (4H, m), 7.36-7.43 (3H, m), 7.48-7.54 (2H, m), 8.43 (1H, s).

Methyl 3-(4-fluorophenylthio)-2-(phenylthio)-2-propenoate

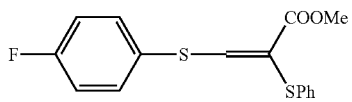

$^1$H-NMR (CDCl$_3$) δ: 3.70 (2.4H, s), 3.71 (0.6H, s), 7.10 (2H, t, J=8.9 Hz), 7.17-7.42 (5H, m), 7.49 (2H, dd, J=8.9, 5.1 Hz), 8.31 (0.8H, s), 8.44 (0.2H, s). Methyl 2-phenoxy-3-(phenylthio)-2-propenoate

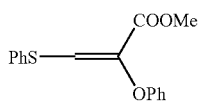

$^1$H-NMR (CDCl$_3$) δ: 3.73 (3H, s), 6.98-7.02 (2H, m), 7.03-7.09 (1H, m), 7.29-7.41 (5H, m), 7.45-7.50 (2H, m), 7.57 (1H, s).

Methyl 3-(4-fluorophenylthio)-2-phenoxy-2-propenoate

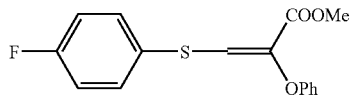

$^1$H-NMR (CDCl$_3$) δ: 3.72 (3H, s), 6.96-7.01 (2H, m), 7.03-7.11 (3H, m), 7.32 (2H, dd, J=8.7, 7.4 Hz), 7.42-7.50 (3H, m).

Methyl 3-(phenylthio)-2-(2-thienyl)-2-propenoate

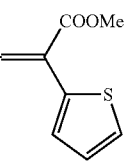

$^1$H-NMR (CDCl$_3$) δ: 3.81 (3H, s), 7.11 (1H, dd, J=4.8, 3.9 Hz), 7.34-7.44 (5H, m), 7.48-7.53 (2H, m), 8.00 (1H, s). Methyl 3-(4-fluorophenylthio)-2-(2-thienyl)-2-propenoate

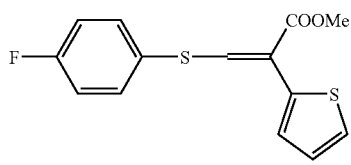

$^1$H-NMR (CDCl$_3$) δ: 3.80 (3H, s), 7.06-7.14 (3H, m), 7.34 (1H, dd, J=3.6, 1.0 Hz), 7.43 (1H, dd, J=5.1, 1.0 Hz), 7.50 (2H, dd, J=8.7, 5.1 Hz), 7.88 (1H, s). Methyl 3-(phenylthio)-2-(3-thienyl)-2-propenoate

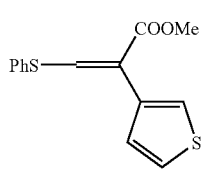

$^1$H-NMR (CDCl$_3$) δ: 3.78 (3H, s), 7.28 (1H, dd, J=5.1, 1.2 Hz), 7.34-7.41 (4H, m), 7.46-7.51 (3H, m), 7.96 (1H, s).

Methyl 3-(4-fluorophenylthio)-2-(3-thienyl)-2-propenoate

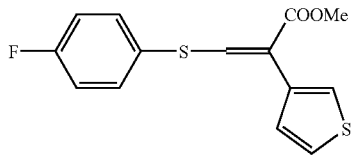

¹H-NMR (CDCl₃) δ: 3.77 (3H, s), 7.08 (2H, t, J=8.7 Hz), 7.25-7.28 (1H, m), 7.37 (1H, dd, J=5.1, 2.9 Hz), 7.44-7.50 (3H, m), 7.84 (1H, s). Ethyl 2-fluoro-3-(phenylthio)-2-propenoate

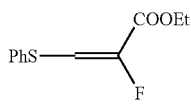

¹H-NMR (CDCl₃) δ: 1.33 (3H, t, J=7.2 Hz), 4.29 (2H, q, J=7.2 Hz), 7.05 (1H, d, J=31.5 Hz), 7.32-7.42 (3H, m), 7.45-7.51 (2H, m). Ethyl 2-fluoro-3-(4-fluorophenylthio)-2-propenoate

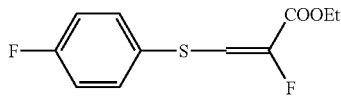

¹H-NMR (CDCl₃) δ: 1.32 (3H, t, J=7.2 Hz), 4.28 (2H, q, J=7.2 Hz), 6.94 (1H, d, J=31.5 Hz), 7.09 (2H, t, J=8.8 Hz), 7.47 (2H, dd, J=8.8, 5.0 Hz). Ethyl 3-phenylthio-4,4,4-trifluoro-2-butenoate

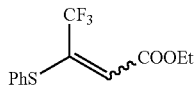

¹H-NMR (CDCl₃) δ: 1.31 (3H, t, J=7.1 Hz), 4.24 (2H, q, J=7.1 Hz), 6.61 (1H, s), 7.31-7.41 (3H, m), 7.56 (2H, d, J=6.5 Hz).

Reference Production Example 5

3.50 g (11.6 mmol) of methyl 2-(methylthio)-3-(p-toluenesulfonyloxy)-2-propenoate was dissolved in 20 ml of chloroform and cooled to 0° C. To the solution was added 1.28 g (11.6 mmol) of thiophenol and 2 ml (14.3 mmol) of triethylamine and stirred at room temperature for 1 hour. To the reaction mixture was added tert-butyl methyl ether and washed sequentially with an aqueous 1N NaOH solution and a saturated NaCl solution. The organic layer was dried and then concentrated. The residue was purified by silica gel column chromatography (hexane/ethyl acetate=4/1) to obtain 1.64 g of methyl 3-(4-fluorophenylthio)-2-(methylthio)-2-propenoate.

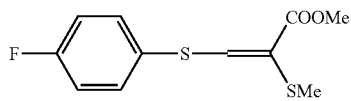

Reference Production Example 6

To a suspension of 1.3 g (32.5 mmol) of sodium hydride (60% in oil) in 45 ml of DMF was added dropwise a mixture of 4.2 g (27.9 mmol) of methyl phenylacetate and 3.2 g (53.4 mmol) of methyl formate under ice cooling and stirred at room temperature for 5 hours. The reaction mixture was poured into ice-water and washed with tert-butyl methyl ether. The aqueous layer was acidified with concentrated HCl solution to pH 2, and then extracted with tert-butyl methyl ether. The organic layer was washed with a saturated NaCl solution, dried over anhydrous MgSO₄, and then concentrated to obtain 4.3 g of a residue. 3.3 g of the residue was dissolved in 27 ml of DMF, and to the solution was added 3.2 g (22.2 mmol) of iodomethane and 3.0 g (22.2 mmol) of potassium carbonate under ice cooling and stirred at room temperature for 15 hours. The reaction mixture was poured into water and extracted with ethyl acetate. The organic layer was washed with water, dried over anhydrous MgSO₄, and concentrated. The residue was purified by silica gel column chromatography (hexane/ethyl acetate=5/1) to obtain 2.0 g of methyl 3-methoxy-2-phenyl-2-propenoate.

¹H-NMR (CDCl₃) δ: 3.74 (3H, s), 3.85 (3H, s), 7.24-7.38 (5H, m), 7.56 (1H, s).

A solution of 2.0 g (10.4 mmol) of methyl 3-methoxy-2-phenyl-2-propenoate 1.26 g (11.4 mmol) of thiophenol and 10 mg of p-toluenesulfonic acid monohydrate in 28 ml of toluene was stirred at 90° C. for 9 hours. The reaction mixture was cooled to room temperature and then concentrated. The residue was purified by silica gel column chromatography (hexane/ethyl acetate=10/1) to obtain 1.75 g of methyl 2-phenyl-3-(phenylthio)-2-propenoate.

¹H-NMR (CDCl₃) δ: 3.75 (3H, s), 7.30-7.48 (10H, m), 8.01 (1H, s).

Reference Production Example 7-(1)

To a suspension of 10.6 g (250 mmol) of sodium hydride (60% in oil) in 150 ml of DMF was added dropwise a mixture of 20 g (226 mmol) of methyl propionate and 20.4 g (340 mmol) of methyl formate under ice cooling and stirred at room temperature overnight. To the reaction mixture was added portionwise 34.6 g (181 mmol) of p-toluenesulfonyl chloride under ice cooling and stirred at room temperature for 1 hour. After dilution with tert-butyl methyl ether, the solution was washed sequentially with water and saturated NaCl solution, dried over anhydrous MgSO₄, and concentrated. The residue was purified by silica gel column chromatography (hexane/ethyl acetate=5/1 to obtain 11.0 g of (E)-methyl 2-methyl-3-(p-toluenesulfonyloxy)-2-propenoate.

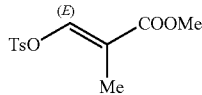

¹H-NMR (CDCl₃) δ: 1.73 (3H, d, J=1.5 Hz), 2.47 (3H, s), 3.73 (3H, s), 7.38 (2H, d, J=8.4 Hz), 7.60 (1H, q, J=1.5 Hz), 7.82 (2H, d, J=8.4 Hz).

Reference Production Examples 7-(2) to (7)

In the same manner as in Reference Production Example 7-(1), the following compounds were produced.

Methyl 2-ethyl-3-(p-toluenesulfonyloxy)-2-propenoate

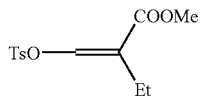

¹H-NMR (CDCl₃) δ: 0.87 (3H, t, J=7.5 Hz), 2.22 (2H, q, J=7.5 Hz), 2.47 (3H, s), 3.73 (3H, s), 7.26 (1H, s), 7.38 (2H, d, J=8.2 Hz), 7.82 (2H, d, J=8.2 Hz). Methyl 2-n-propyl-3-(p-toluenesulfonyloxy)-2-propenoate

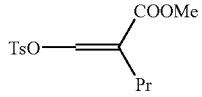

¹H-NMR (CDCl₃) δ: 0.77 (3H, t, J=7.4 Hz), 1.23-1.34 (2H, m), 2.18 (2H, dd, J=8.7, 6.3 Hz), 2.47 (3H, s), 3.72 (3H, s), 7.38 (2H, d, J=8.4 Hz), 7.62 (1H, s), 7.82 (2H, d, J=8.4 Hz).

Methyl 2-n-butyl-3-(p-toluenesulfonyloxy)-2-propenoate

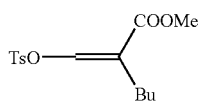

¹H-NMR (CDCl₃) δ: 0.80 (3H, t, J=7.0 Hz), 1.09-1.24 (4H, m), 2.19 (2H, t, J=7.0 Hz), 2.47 (3H, s), 3.72 (3H, s), 7.38 (2H, d, J=8.4 Hz), 7.60 (1H, s), 7.82 (2H, d, J=8.4 Hz).

Methyl 2-phenoxy-3-(p-toluenesulfonyloxy)-2-propenoate

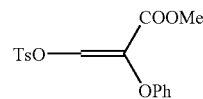

¹H-NMR (CDCl₃) δ: 2.46 (3H, s), 3.73 (3H, s), 6.70-6.75 (2H, m), 6.97-7.03 (1H, m), 7.14-7.21 (2H, m), 7.32 (2H, d, J=8.3 Hz), 7.69 (1H, s), 7.73 (2H, d, J=8.3 Hz).

Methyl 2-(2-thienyl)-3-(p-toluenesulfonyloxy)-2-propenoate

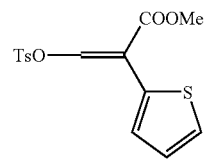

¹H-NMR (CDCl₃) δ: 2.17 (2H, s), 2.45 (3H, s), 3.83 (3H, s), 7.02 (1H, dd, J=5.1, 3.8 Hz), 7.36 (1H, dd, J=5.1, 1.0 Hz), 7.37 (2H, d, J=8.4 Hz), 7.49 (1H, dd, J=3.8, 1.0 Hz), 7.85 (1H, s), 7.85 (2H, d, J=8.4 Hz).

Methyl 2-(3-thienyl)-3-(p-toluenesulfonyloxy)-2-propenoate

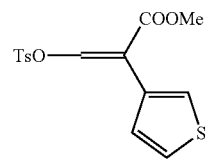

¹H-NMR (CDCl₃) δ: 2.45 (3H, s), 3.80 (3H, s), 7.18 (1H, dd, J=5.1, 1.2 Hz), 7.25 (1H, dd, J=5.1, 2.9 Hz), 7.36 (2H, d, J=8.3 Hz), 7.47 (1H, dd, J=2.9, 1.2 Hz), 7.79 (2H, d, J=8.3 Hz), 7.81 (1H, s).

Reference Production Example 8-(1) and (2)

To a suspension of 21.4 g (535 mmol) of sodium hydride (60% in oil) in 200 ml of DMF was added dropwise a mixture of 25.8 g (214 mmol) of methyl 2-(methylthio)acetate and 26.5 g (428 mmol) of methyl formate under ice cooling and stirred at room temperature overnight. To the reaction mixture was added portionwise 27.0 g (141 mmol) of p-toluenesulfonyl chloride under ice cooling and stirred at room temperature for 1 hour. After dilution with tert-butyl methyl ether, the solution was washed sequentially with water and saturated NaCl solution, dried over anhydrous MgSO₄, and concentrated. The residue was purified by silica gel column chromatography (hexane/ethyl acetate=5/1) to obtain 9.72 g of methyl 2-(methylthio)-3-(p-toluenesulfonyloxy)-2-propenoate and 1.88 g of methyl 3-chloro-2-(methylthio)-2-propenoate.

Methyl 2-(methylthio)-3-(p-toluenesulfonyloxy)-2-propenoate

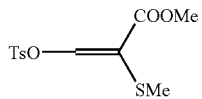

$^1$H-NMR (CDCl$_3$) δ: 2.23 (3H, s), 2.47 (3H, s), 3.79 (3H, s), 7.39 (2H, d, J=8.3 Hz), 7.85 (2H, d, J=8.3 Hz), 7.93 (1H, s).

Methyl 3-chloro-2-(methylthio)-2-propenoate

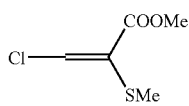

$^1$H-NMR (CDCl$_3$) δ: 2.42 (3H, s), 3.82 (3H, s), 7.94 (1H, s).

Reference Production Examples 8-(3) to (4)

In the same manner as in Reference Production Example 8-(1) and (2), the following compounds were produced.

Methyl 2-(phenylthio)-3-(p-toluenesulfonyloxy)-2-propenoate

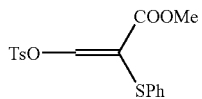

$^1$H-NMR (CDCl$_3$) δ: 2.47 (3H, s), 3.69 (3H, s), 7.09-7.13 (2H, m), 7.14-7.19 (3H, m), 7.34 (2H, d, J=8.3 Hz), 7.76 (2H, d, J=8.3 Hz), 8.13 (1H, s).

Methyl 3-chloro-2-(phenylthio)-2-propenoate

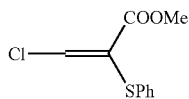

$^1$H-NMR (CDCl$_3$) δ: 3.73 (3H, s), 7.11-7.21 (3H, m), 7.26-7.31 (2H, m), 8.11 (1H, s).

Reference Production Example 9

To a solution of 2.0 g of phenyl N-phenyl-3-(phenylthio)-2-propenimidothioate in THF (45 mL) was added 1.61 g of thiophenol and 88.9 mg of potassium tert-butoxide at room temperature and stirred for 10 hours. To the reaction mixture was added 50 ml of a saturated NaCl solution and extracted with 100 ml of ethyl acetate. The organic layer was dried over anhydrous MgSO$_4$, and then concentrated. The residue was purified by silica gel column chromatography (hexane:ethyl acetate=30:1 to hexane:ethyl acetate=10:1) to obtain 2.0 g of phenyl 3,3-bis(phenylthio)-N-phenylpropanimidothioate as a yellow oil.

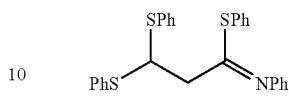

$^1$H-NMR (CDCl$_3$) δ: 2.80 (2H, d, J=7.2 Hz), 5.02 (1H, t, J=7.2 Hz), 7.11-7.40 (20H, m).

Reference Production Example 10

To a solution of 2.0 g (10.8 mmol) of ethyl 4,4,4-trifluoroacetoacetate in 10 ml of DMF was added 2.28 g of p-toluenesulfonyl chloride and 4.24 g of cesium carbonate and stirred at room temperature overnight. The reaction solution was poured into water and extracted with tert-butyl methyl ether. The organic layer was washed with a saturated NaCl solution, dried over anhydrous MgSO$_4$, and concentrated. The residue was purified by silica gel column chromatography (hexane:ethyl acetate=10:1) to obtain 2.27 g of ethyl 4,4,4-trifluoro-3-p-toluenesulfonyloxy-2-butenoate.

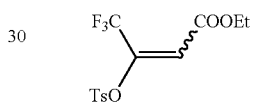

$^1$H-NMR (CDCl$_3$) δ: 1.36 (3H, t, J=7.2 Hz), 2.47 (3H, s), 4.31 (2H, q, J=7.2 Hz), 6.38 (1H, s), 7.37 (2H, d, J=8.3 Hz), 7.86 (2H, d, J=8.3 Hz).

Reference Production Example 11

To a solution of 6.98 g (25.8 mmol) of methyl 2-methyl-3-(p-toluenesulfonyloxy)-2-propenoate in 30 ml of DMF was added 2.67 g (28.3 mmol) of phenol and 10 g (30.6 mmol) of cesium carbonate and stirred at room temperature for 12 hours. The reaction solution was poured into water and extracted with tert-butyl methyl ether (twice). The combined organic layer was washed sequentially with a 1N aqueous NaOH solution, water, and a saturated NaCl solution, dried over anhydrous MgSO$_4$, and then concentrated. The residue was purified by silica gel column chromatography (hexane:ethyl acetate=10:1) to obtain 657 mg of (E)-methyl 2-methyl-3-phenoxy-2-propenoate.

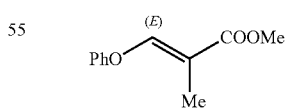

$^1$H-NMR (CDCl$_3$) δ: 1.93 (3H, d, J=1.4 Hz), 3.75 (3H, s), 7.05-7.10 (2H, m), 7.13-7.18 (1H, m), 7.34-7.39 (2H, m), 7.72 (1H, q, J=1.4 Hz).

Reference Production Example 12-(1)

To a solution of 28.5 g (147 mmol) of (E)-ethyl 3-bromo-2-methyl-2-propenoate in 130 ml of DMF was added 15.3 g (162 mmol) of phenol and 57.7 g (177 mmol) of cesium carbonate and stirred at 70° C. for 2 hours. After cooling to room temperature, the reaction solution was poured into water and extracted with tert-butyl methyl ether (twice). The combined organic layer was washed sequentially with water and a saturated NaCl solution, dried over anhydrous MgSO$_4$, and concentrated under vacuum to obtain 29.0 g of (E)-ethyl 2-methyl-3-phenoxy-2-propenoate

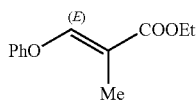

$^1$H-NMR (CDCl$_3$) δ: 1.30 (3H, t, J=7.2 Hz), 1.92 (3H, d, J=1.4 Hz), 4.22 (2H, q, J=7.2 Hz), 7.08 (2H, d, J=8.7 Hz), 7.15 (1H, t, J=7.4 Hz), 7.37 (2H, dd, J=8.7, 7.4 Hz), 7.71 (1H, q, J=1.4 Hz).

Reference Production Examples 12-(2) to (28)

In the same manner as in Reference Production Example 12-(1), the following compounds were produced.

(E)-Ethyl 2-methyl-3-(2-methylphenyloxy)-2-propenoate

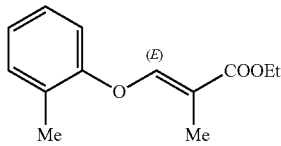

$^1$H-NMR (CDCl$_3$) δ: 1.29 (3H, t, J=7.1 Hz), 1.94 (3H, d, J=1.3 Hz), 2.29 (3H, s), 4.21 (2H, q, J=7.1 Hz), 6.99 (1H, d, J=8.2 Hz), 7.06 (1H, t, J=7.4 Hz), 7.16-7.23 (2H, m), 7.66 (1H, q, J=1.3 Hz).

(E)-Ethyl 2-methyl-3-(3-methylphenyloxy)-2-propenoate

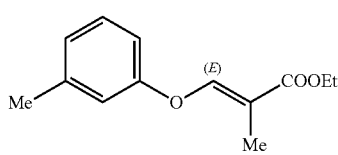

$^1$H-NMR (CDCl$_3$) δ: 1.30 (3H, t, J=7.2 Hz), 1.91 (3H, d, J=1.5 Hz), 2.37 (3H, s), 4.22 (2H, q, J=7.2 Hz), 6.88 (1H, d, J=7.6 Hz), 6.89 (1H, s), 6.96 (1H, d, J=7.6 Hz), 7.24 (1H, t, J=7.6 Hz), 7.69 (1H, q, J=1.5 Hz).

(E)-Ethyl 2-methyl-3-(4-methylphenyloxy)-2-propenoate

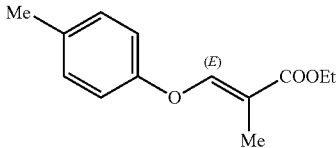

$^1$H-NMR (CDCl$_3$) δ: 1.29 (3H, t, J=7.1 Hz), 1.91 (3H, d, J=1.2 Hz), 2.33 (3H, s), 4.21 (2H, q, J=7.1 Hz), 6.97 (2H, d, J=8.4 Hz), 7.15 (2H, d, J=8.4 Hz), 7.67 (1H, q, J=1.2 Hz).

(E)-Ethyl 3-(3-ethylphenyloxy)-2-methyl-2-propenoate

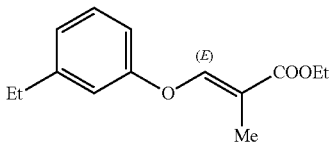

$^1$H-NMR (CDCl$_3$) δ: 1.25 (3H, t, J=7.6 Hz), 1.30 (3H, t, J=7.2 Hz), 1.92 (3H, d, J=1.5 Hz), 2.66 (2H, q, J=7.6 Hz), 4.22 (2H, q, J=7.2 Hz), 6.87-6.93 (2H, m), 6.97-7.01 (1H, m), 7.26 (1H, t, J=7.8 Hz), 7.71 (1H, q, J=1.5 Hz).

(E)-Ethyl 3-(4-ethylphenyloxy)-2-methyl-2-propenoate

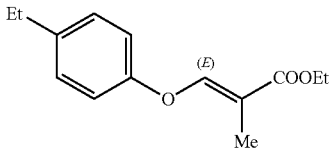

$^1$H-NMR (CDCl$_3$) δ: 1.23 (3H, t, J=7.6 Hz), 1.29 (3H, t, J=7.2 Hz), 1.91 (3H, d, J=1.2 Hz), 2.63 (2H, q, J=7.6 Hz), 4.21 (2H, q, J=7.2 Hz), 6.99 (2H, d, J=8.5 Hz), 7.18 (2H, d, J=8.5 Hz), 7.68 (1H, q, J=1.2 Hz).

(E)-Ethyl 3-(4-isopropylphenyloxy)-2-methyl-2-propenoate

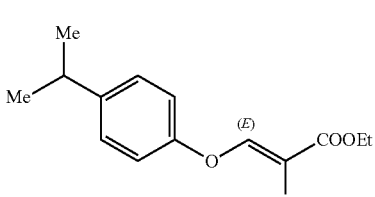

$^1$H-NMR (CDCl$_3$) δ: 1.24 (6H, d, J=6.8 Hz), 1.29 (3H, t, J=7.1 Hz), 1.91 (3H, d, J=1.2 Hz), 2.84-2.97 (1H, m), 4.21

(2H, q, J=7.1 Hz), 7.00 (2H, d, J=8.7 Hz), 7.21 (2H, d, J=8.7 Hz), 7.69 (1H, q, J=1.2 Hz).

(E)-Ethyl 3-(4-chlorophenyloxy)-2-methyl-2-propenoate

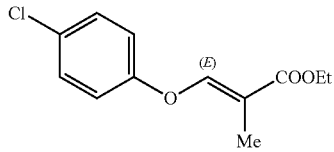

¹H-NMR (CDCl₃) δ: 1.30 (3H, t, J=7.1 Hz), 1.91 (3H, d, J=1.5 Hz), 4.22 (2H, q, J=7.1 Hz), 7.01 (2H, d, J=8.9 Hz), 7.32 (2H, d, J=8.9 Hz), 7.63 (1H, q, J=1.5 Hz).

(E)-Ethyl 3-(2-methoxyphenyloxy)-2-methyl-2-propenoate

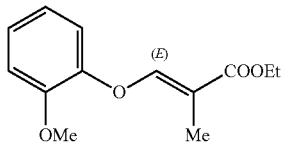

¹H-NMR (CDCl₃) δ: 1.28 (3H, t, J=7.2 Hz), 1.94 (3H, d, J=1.2 Hz), 3.87 (3H, s), 4.20 (2H, q, J=7.2 Hz), 6.91-7.00 (2H, m), 7.06 (1H, dd, J=8.0, 1.7 Hz), 7.10-7.17 (1H, m), 7.56 (1H, q, J=1.2 Hz).

(E)-Ethyl 3-(3-methoxyphenyloxy)-2-methyl-2-propenoate

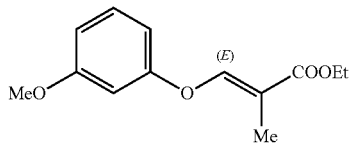

¹H-NMR (CDCl₃) δ: 1.30 (3H, t, J=7.2 Hz), 1.92 (3H, d, J=1.4 Hz), 3.81 (3H, s), 4.22 (2H, q, J=7.2 Hz), 6.63 (1H, t, J=2.4 Hz), 6.65-6.72 (2H, m), 7.25 (1H, t, J=8.2 Hz), 7.70 (1H, q, J=1.4 Hz).

(E)-Ethyl 3-(4-methoxyphenyloxy)-2-methyl-2-propenoate

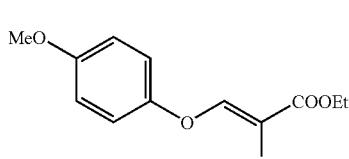

¹H-NMR (CDCl₃) δ: 1.29 (3H, t, J=7.2 Hz), 1.90 (3H, d, J=1.5 Hz), 3.80 (3H, s), 4.21 (2H, q, J=7.2 Hz), 6.87 (2H, d, J=9.0 Hz), 7.01 (2H, d, J=9.0 Hz), 7.62 (1H, q, J=1.5 Hz).

(E)-Ethyl 3-(3-ethoxyphenyloxy)-2-methyl-2-propenoate

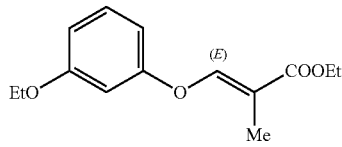

¹H-NMR (CDCl₃) δ: 1.30 (3H, t, J=7.1 Hz), 1.42 (3H, t, J=7.0 Hz), 1.91 (3H, d, J=1.5 Hz), 4.03 (2H, q, J=7.0 Hz), 4.22 (2H, q, J=7.1 Hz), 6.62 (1H, t, J=2.3 Hz), 6.64-6.70 (2H, m), 7.24 (1H, t, J=8.3 Hz), 7.69 (1H, q, J=1.5 Hz).

(E)-Ethyl 3-(4-ethoxyphenyloxy)-2-methyl-2-propenoate

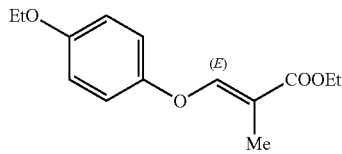

¹H-NMR (CDCl₃) δ: 1.29 (3H, t, J=7.1 Hz), 1.41 (3H, t, J=7.0 Hz), 1.90 (3H, d, J=1.5 Hz), 4.00 (2H, q, J=7.0 Hz), 4.20 (2H, q, J=7.1 Hz), 6.86 (2H, d, J=8.9 Hz), 6.99 (2H, d, J=8.9 Hz), 7.62 (1H, q, J=1.5 Hz).

(E)-Ethyl 2-methyl-3-(4-phenylphenyloxy)-2-propenoate

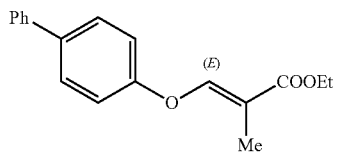

¹H-NMR (CDCl₃) δ: 1.31 (3H, t, J=7.2 Hz), 1.94 (3H, d, J=1.4 Hz), 4.23 (2H, q, J=7.2 Hz), 7.15 (2H, d, J=8.8 Hz), 7.35 (1H, t, J=7.4 Hz), 7.40-7.50 (2H, m), 7.54-7.61 (4H, m), 7.75 (1H, q, J=1.4 Hz).

(E)-Ethyl 2-methyl-3-(4-phenoxyphenyloxy)-2-propenoate

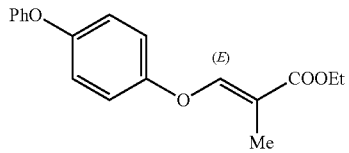

¹H-NMR (CDCl₃) δ: 1.30 (3H, t, J=7.2 Hz), 1.92 (3H, d, J=1.4 Hz), 4.22 (2H, q, J=7.2 Hz), 6.91-7.13 (8H, m), 7.33 (2H, dd, J=8.7, 7.4 Hz), 7.65 (1H, q, J=1.4 Hz).

(E)-Ethyl 3-(3,4-dimethylphenyloxy)-2-methyl-2-propenoate

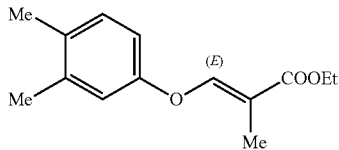

$^1$H-NMR (CDCl$_3$) δ: 1.29 (3H, t, J=7.2 Hz), 1.91 (3H, d, J=1.3 Hz), 2.23 (3H, s), 2.26 (3H, s), 4.21 (2H, q, J=7.2 Hz), 6.80 (1H, dd, J=8.2, 2.2 Hz), 6.86 (1H, d, J=2.2 Hz), 7.09 (1H, d, J=8.2 Hz), 7.67 (1H, q, J=1.3 Hz).

(E)-Ethyl 3-(5-indolyloxy)-2-methyl-2-propenoate

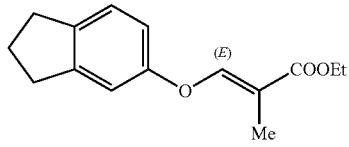

$^1$H-NMR (CDCl$_3$) δ: 1.29 (3H, t, J=7.1 Hz), 1.91 (3H, d, J=1.3 Hz), 2.10 (2H, quint, J=7.4 Hz), 2.82-2.93 (4H, m), 4.21 (2H, q, J=7.1 Hz), 6.83 (1H, dd, J=8.0, 2.3 Hz), 6.93 (1H, d, J=2.3 Hz), 7.16 (1H, d, J=8.0 Hz), 7.67 (1H, q, J=1.3 Hz).

(E)-Ethyl 3-(2,4-dimethoxyphenyloxy)-2-methyl-2-propenoate

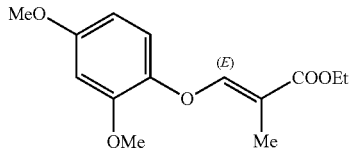

$^1$H-NMR (CDCl$_3$) δ: 1.27 (3H, t, J=7.1 Hz), 1.92 (3H, d, J=1.3 Hz), 3.80 (3H, s), 3.84 (3H, s), 4.18 (2H, q, J=7.1 Hz), 6.42 (1H, dd, J=8.8, 2.7 Hz), 6.53 (1H, d, J=2.7 Hz), 6.97 (1H, d, J=8.8 Hz), 7.47 (1H, q, J=1.3 Hz).

(E)-Ethyl 3-(2,6-dimethoxyphenyloxy)-2-methyl-2-propenoate

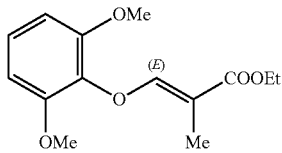

$^1$H-NMR (CDCl$_3$) δ: 1.25 (3H, t, J=7.1 Hz), 1.96 (3H, d, J=1.4 Hz), 3.84 (6H, s), 4.17 (2H, q, J=7.1 Hz), 6.61 (2H, d, J=8.4 Hz), 7.09 (1H, t, J=8.4 Hz), 7.35 (1H, q, J=1.4 Hz).

(E)-Ethyl 3-(3,4-(ethylenedioxy)phenyloxy)-2-methyl-2-propenoate

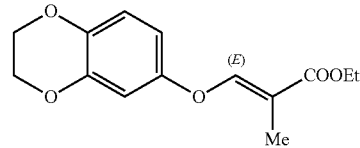

$^1$H-NMR (CDCl$_3$) δ: 1.29 (3H, t, J=7.2 Hz), 1.89 (3H, d, J=1.3 Hz), 4.20 (2H, q, J=7.2 Hz), 4.22-4.28 (4H, m), 6.57 (1H, dd, J=8.8, 2.8 Hz), 6.62 (1H, d, J=2.8 Hz), 6.83 (1H, d, J=8.8 Hz), 7.60 (1H, q, J=1.3 Hz).

(E)-Ethyl 3-(1-(4-chlorophenyl)pyrazol-3-yloxy)-2-methyl-2-propenoate

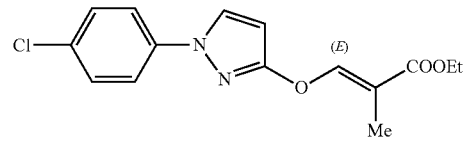

$^1$H-NMR (CDCl$_3$) δ: 1.32 (3H, t, J=7.2 Hz), 1.94 (3H, d, J=1.5 Hz), 4.24 (2H, q, J=7.2 Hz), 6.10 (1H, d, J=2.7 Hz), 7.41 (2H, d, J=9.0 Hz), 7.58 (2H, d, J=9.0 Hz), 7.77 (1H, d, J=2.7 Hz), 8.14 (1H, q, J=1.5 Hz).

(E)-Ethyl 3-(2-naphthyloxy)-2-methyl-2-propenoate

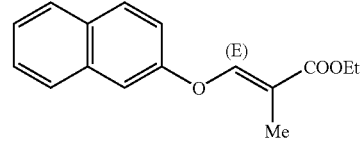

$^1$H-NMR (CDCl$_3$) δ: 1.32 (3H, t, J=7.2 Hz), 1.97 (3H, d, J=1.5 Hz), 4.25 (2H, q, J=7.2 Hz), 7.28 (1H, dd, J=8.9, 2.6 Hz), 7.41-7.46 (2H, m), 7.47-7.53 (1H, m), 7.77-7.88 (4H, m).

Methyl 2-ethyl-3-phenoxy-2-propenoate

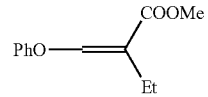

$^1$H-NMR (CDCl$_3$) δ: 1.10 (3H, t, J=7.5 Hz), 2.44 (2H, q, J=7.5 Hz), 3.75 (3H, s), 7.08 (2H, d, J=8.7 Hz), 7.15 (1H, t, J=7.3 Hz), 7.37 (2H, dd, J=8.7, 7.3 Hz), 7.68 (1H, s).

Methyl 2-ethyl-3-(3-methylphenyloxy)-2-propenoate

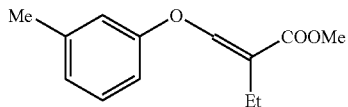

¹H-NMR (CDCl₃) δ: 1.09 (3H, t, J=7.5 Hz), 2.36 (3H, s), 2.43 (2H, q, J=7.5 Hz), 3.75 (3H, s), 6.85-6.91 (2H, m), 6.96 (1H, d, J=7.0 Hz), 7.24 (1H, t, J=7.8 Hz), 7.67 (1H, s).

Methyl 2-ethyl-3-(4-methylphenyloxy)-2-propenoate

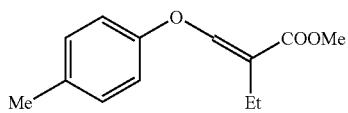

¹H-NMR (CDCl₃) δ: 1.09 (3H, t, J=7.5 Hz), 2.33 (3H, s), 2.43 (2H, q, J=7.5 Hz), 3.74 (3H, s), 6.96 (2H, d, J=8.5 Hz), 7.15 (2H, d, J=8.5 Hz), 7.64 (1H, s).

Methyl 2-ethyl-3-(2-methoxyphenyloxy)-2-propenoate

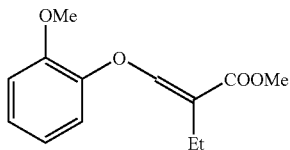

¹H-NMR (CDCl₃) δ: 1.12 (3H, t, J=7.5 Hz), 2.47 (2H, q, J=7.5 Hz), 3.72 (3H, s), 3.85 (3H, s), 6.90-6.98 (2H, m), 7.05 (1H, dd, J=7.8, 1.6 Hz), 7.09-7.15 (1H, m), 7.52 (1H, s).

Methyl 2-ethyl-3-(4-methoxyphenyloxy)-2-propenoate

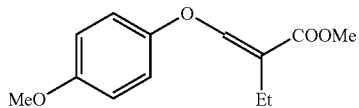

¹H-NMR (CDCl₃) δ: 1.09 (3H, t, J=7.5 Hz), 2.42 (2H, q, J=7.5 Hz), 3.74 (3H, s), 3.80 (3H, s), 6.87 (2H, d, J=8.9 Hz), 7.00 (2H, d, J=8.9 Hz), 7.59 (1H, s).

Methyl 3-phenoxy-2-n-propyl-2-propenoate

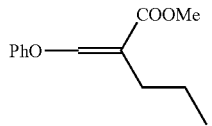

¹H-NMR (CDCl₃) δ: 0.95 (3H, t, J=7.4 Hz), 1.47-1.58 (2H, m), 2.40 (2H, t, J=7.4 Hz), 3.74 (3H, s), 7.07 (2H, d, J=8.1 Hz), 7.15 (1H, t, J=7.4 Hz), 7.36 (2H, dd, J=8.1, 7.4 Hz), 7.72 (1H, s).

Reference Production Example 13-(1)

To a solution of 50 g (438 mmol) of ethyl methacrylate in 300 ml of tert-butyl methyl ether was added dropwise 70 g (438 mmol) of bromine under ice cooling and stirred at room temperature for 1 hours. The reaction mixture was washed sequentially with a aqueous NaHSO₃ solution, a saturated NaHCO₃ solution, and saturated NaCl solution, dried over anhydrous MgSO₄, and concentrated under vacuum to obtain 120 g of ethyl 2,3-dibromo-2-methylpropanoate.

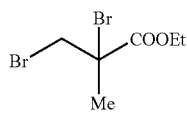

¹H-NMR (CDCl₃) δ: 1.33 (3H, t, J=7.1 Hz), 2.03 (3H, s), 3.73 (1H, d, J=9.8 Hz), 4.24 (1H, d, J=9.8 Hz), 4.29 (2H, q, J=7.1 Hz).

To a solution of 37.7 g (137 mmol) of ethyl 2,3-dibromo-2-methylpropanoate in 176 ml of THF was added 25 ml of 1,8-diazabicyclo[5.4.0]-7-undecene and refluxed for 2 hours. After cooling to room temperature, to the mixture was added 1N HCl and extracted with tert-butyl methyl ether. The organic layer was washed sequentially with a saturated NaHCO₃ solution and a saturated NaCl solution, dried over anhydrous MgSO₄, and then concentrated under vacuum to obtain 23.8 g of (E)-ethyl 3-bromo-2-methyl-2-propenoate.

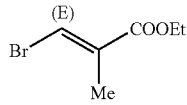

¹H-NMR (CDCl₃) δ: 1.31 (3H, t, J=7.2 Hz), 2.01 (3H, d, J=1.4 Hz), 4.22 (2H, q, J=7.2 Hz), 7.52 (1H, q, J=1.4 Hz).

Reference Production Examples 13-(2) to (3)

In the same manner as in Reference Production Example 13-(1), the following compounds were produced.
Methyl 3-bromo-2-ethyl-2-propenoate

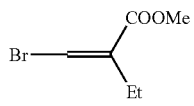

¹H-NMR (CDCl₃) δ: 1.06 (3H, t, J=7.5 Hz), 2.50 (2H, q, J=7.5 Hz), 3.77 (3H, s), 7.48 (1H, s).

Methyl 3-bromo-2-n-propyl-2-propenoate

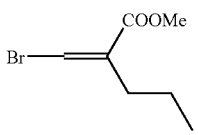

¹H-NMR (CDCl₃) δ: 0.95 (3H, t, J=7.5 Hz), 1.43-1.55 (2H, m), 2.46 (2H, t, J=7.5 Hz), 3.76 (3H, s), 7.52 (1H, s).

Reference Production Example 14

To a suspension of 1.0 g (6.20 mmol) of N-phenyl-methacrylamide in 4 ml of toluene was added 1.30 g (6.24 mmol) of phosphorus pentachloride and stirred at room temperature for 1 hour. The reaction mixture was concentrated under reduced pressure. The residue was dissolved in 5 ml of DMF and then cooled to 0° C. To a solution of 1.17 g (12.4 mmol) of phenol in 5 ml of DMF was added 546 mg (13.6 mmol) of sodium hydride (60% in oil) under ice cooling and stirred for 5 minutes. The mixture was added portionwise to the above-described DMF solution of the residue under ice cooling and stirred at room temperature for 1 hour. The reaction mixture was poured into water wad extracted with tert-butyl methyl ether (twice). The combined organic layer was washed sequentially with water and saturated NaCl, dried over anhydrous MgSO₄, and then concentrated. The residue was purified by silica gel column chromatography (hexane/ethyl acetate=20/1) to obtain 1.28 g of phenyl 2-methyl-N-phenyl-2-propenimidate.

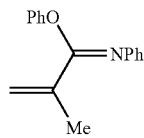

¹H-NMR (DMSO-D₆, 50° C.) δ: 1.96 (3H, br s), 5.52 (2H, br s), 6.78-6.89 (2H, m), 6.90-7.10 (4H, m), 7.21 (2H, dd, J=8.3, 7.6 Hz), 7.25-7.35 (2H, m).

Reference Production Example 15

To a solution of 1.27 g (5.35 mmol) of phenyl 2-methyl-N-phenyl-2-propenimidate in 10 ml of tert-butyl methyl ether was added dropwise 860 mg (5.38 mmol) of bromine at room temperature and stirred for 2 hours. The reaction mixture was concentrated under vacuum. The residue was purified by silica gel column chromatography (hexane/ethyl acetate=20/1) to obtain 1.82 g of phenyl 2,3-dibromo-2-methylpropanimidate.

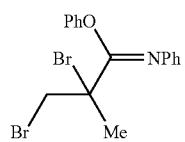

¹H-NMR (CDCl₃) δ: 2.18-2.26 (3H, m), 3.89-3.96 (1H, m), 4.50-4.58 (1H, m), 6.55-6.90 (6H, m), 6.95-7.12 (4H, m).

Reference Production Example 16

To a solution of 1.83 g (4.59 mmol) of phenyl 2,3-dibromo-2-methyl-N-phenylpropanimidate in 10 ml of THF was added 770 mg (5.05 mmol) of 1,8-diazabicyclo[5.4.0]-7-undecene and stirred at room temperature for 2 hours. To the mixture was added 1N HCl and extracted with tert-butyl methyl ether. The combined organic layer was washed sequentially with a saturated aqueous NaHCO₃ solution and a saturated NaCl solution, dried over anhydrous MgSO₄, and then concentrated under vacuum. The residue was purified by silica gel column chromatography (hexane/ethyl acetate=20/1) to obtain 1.26 g of phenyl 3-bromo-2-methyl-N-phenyl-2-propenimidate.

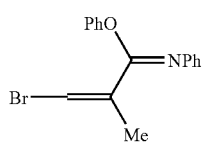

¹H-NMR (DMSO-D₆, 50° C.) δ: 1.95 (3H, s), 6.85 (2H, d, J=7.6 Hz), 6.95-7.47 (11H, m).

Next, Formulation Examples are described. Herein, the term "part(s)" means "part(s) by weight".

Formulation Example 1

Ten parts of any one of the present compounds 1 to 324 is dissolved in a mixture of 35 parts of xylene and 35 parts of N,N-dimethylformamide. Thereto 14 parts of polyoxyethylene styryl phenyl ether and 6 parts of calcium dodecylbenzenesulfonate are added, and mixed by stirring thoroughly to obtain a 10% emulsifiable concentrate.

Formulation Example 2

Twenty parts of any one of the present compounds 1 to 324 is added to a mixture of 4 parts of sodium lauryl sulfate, 2 parts of calcium lignin sulfonate, 20 parts of synthetic hydrous silicon oxide fine powder and 54 parts of diatomaceous earth, and mixed by stirring thoroughly to obtain a 20% wettable powder.

Formulation Example 3

To 2 parts of any one of the present compounds 1 to 324 are added 1 part of synthetic hydrous silicon oxide fine powder, 2 parts of calcium lignin sulfonate, 30 parts of bentonite and 65 parts of kaoline clay, and mixed by stirring thoroughly. To the mixture, an appropriate amount of water is added. The mixture is further stirred, granulated with a granulator, and then air-dried to obtain a 2% granule.

Formulation Example 4

One part of any one of the present compounds 1 to 324 is dissolved in an appropriate amount of acetone. Thereto parts of synthetic hydrous silicon oxide fine powder, 0.3 part of PAP (isopropyl acid phosphate) and 93.7 parts of agalmatolite clay are added, and mixed by stirring thoroughly. The acetone is evaporated to obtain a 1% dust.

Formulation Example 5

Ten parts of any one of the present compounds 1 to 324, parts of a mixture of cyclohexanone with dimethylsulfoxide (weight ratio 90/10), 35 parts of a mixture of white carbon with polyoxyethylene alkylether sulfate ammonium salt (weight ratio 50/50), and 25 parts of water are mixed and then finely-divided by a wet grinding method to obtain a 10% flowable formulation.

Formulation Example 6

Zero point one part of any one of the present compounds 1 to 324 is dissolved in a mixture of 5 parts of xylene and 5 parts of trichloroethane. This solution is mixed with 89.9 parts of deodorized kerosene to obtain a 0.1% oil solution.

Formulation Example 7

Ten milligrams of any one of the present compounds 1 to 324 is dissolved in 0.5 mL of acetone. This solution is mixed homogeneously with 5 g of a powdered solid animal feed (powdered solid feed for breeding, CE-2 manufactured by Clea Japan Inc.). The acetone was eveporated to obtain a poison bait.

Formulation Example 8

Ten parts of any one of the present compounds 1 to 324, parts of a mixture of white carbon with polyoxyethylene alkylether sulfate ammonium salt (weight ratio 50/50), and 55 parts of water are mixed and then finely-divided by a wet grinding method to obtain a 10% flowable formulation.

The following Test Examples show that the compound of the present invention is effective for pest control.

In Test Examples 1 to 9, the formulation obtained in Formulation Example 5 was diluted with ion-exchanged water so that the concentration of the active ingredient could be 500 ppm to prepare a test solution.

Test Example 1

Spodoptera litura

A filter paper having a diameter of 5.5 cm was spread on the bottom of a polyethylene cup having the same diameter, and an artificial diet, Insecta LF (Nosan Kogyo Corp.) which was sliced into 6 mm pieces in thickness and further cut into half, was placed on the filter paper. Then, 2 mL of the test solution was poured onto the filter paper. After the filter paper was air-dried, 5 fourth-instar larvae of Spodoptera litura were released into the polyethylene cup, and the cup was sealed with a lid. After 6 days, the number of dead insects was counted.

The death rate was calculated by the following equation, and evaluated with indexes of 4: 100%, 3: 80 to 99%, 2: 60 to 79%, 1: 30 to 59% and 0: 0 to 29% in terms of death rate.

Death rate (%)=(Number of dead insects/Number of tested insects)×100

As a result, the present compounds 1, 2, 3, 5, 6, 7, 8, 9, 10, 14, 15, 16, 17, 19, 21, 22, 23, 24, 25, 26, 27, 28, 29, 33, 34, 35, 36, 37, 38, 41, 46, 47, 49, 50, 51, 52, 53, 54, 55, 56, 57, 58, 59, 60, 61, 62, 63, 64, 65, 66, 67, 68, 69, 70, 72, 73, 74, 75, 76, 77, 78, 79, 80, 81, 82, 83, 84, 86, 87, 88, 89, 90, 91, 92, 93, 94, 95, 96, 97, 99, 101, 102, 103, 104, 105, 107, 108, 109, 110, 111, 112, 113, 114, 115, 116, 118, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 152, 153, 154, 155, 156, 157, 158, 159, 160, 161, 162, 163, 165, 166, 167, 168, 170, 171, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 296, 298, 299, 300, 301, 302, 303, 304, 305, 306, 307, 308, 309, 310, 311, 312, 313, 314, 315, 316, 317, 318, 319, 320, 321, 322 and 323 were evaluated as index 3 or greater.

Test Example 2

Adoxophyes orana

A filter paper having a diameter of 5.5 cm was spread on the bottom of a polyethylene cup having the same diameter, and an artificial diet, Silkmate 2S (Nosan Kogyo Corp.) which was sliced into 2 mm pieces in thickness, was placed on the filter paper. Then, 1 mL of the test solution was poured onto the filter paper. Immediately after the filter paper was air-dried, a filter paper having a diameter of 5.5 cm was placed thereon. Then, 30 first-instar larvae of Adoxophyes orana were released into the polyethylene cup, and the cup was sealed with a lid. After 7 days, the number of surviving insects was counted.

The death rate was calculated by the following equation, and evaluated with indexes of 4: 100%, 3: 80 to 99%, 2: 60 to 79%, 1: 30 to 59% and 0: 0 to 29% in terms of death rate.

Death rate (%)=(Number of dead insects/Number of tested insects)×100

As a result, the present compounds 1, 2, 3, 5, 6, 7, 8, 9, 10, 13, 14, 15, 16, 17, 19, 21, 22, 23, 24, 25, 26, 27, 28, 29, 30, 31, 32, 33, 34, 35, 36, 37, 38, 41, 44, 45, 46, 47, 49, 50, 51, 52, 53, 54, 55, 56, 57, 58, 59, 60, 61, 62, 63, 64, 65, 66, 67, 68, 69, 70, 72, 73, 74, 75, 76, 77, 78, 79, 80, 81, 82, 83, 84, 86, 87, 88, 89, 90, 91, 92, 93, 94, 95, 96, 97, 99, 101, 102, 103, 104, 105, 106, 107, 108, 109, 110, 111, 112, 113, 114, 115, 116, 118, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 152, 153, 154, 155, 156, 157, 158, 159, 160, 161, 162, 163, 165, 166, 167, 168, 169, 170, 171, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 296, 298, 299, 300, 301, 302, 303, 304, 305, 306, 307, 308, 309, 310, 311, 312, 313, 314, 315, 316, 317, 318, 319, 320, 321, 322 and 323 were evaluated as index 3 or greater.

Test Example 3

Aphis gossypii

On the leaves of cucumber at a one-leaf stage grown in a one-ounce cup, 30 individuals of Aphis gossypii (including imagoes and larvae) were released. The next day, 20 mL of the test solution was sprayed on the leaves. After 6 days, the number of surviving insects was counted.

The survival rate of tested insects on the basis of the number of insects provided in an untreated cup was calculated by the following equation, and evaluated with indexes of 4: 0%, 3: 1 to 10%, 2: 11 to 40%, 1: 41 to 70%, and 0: >70% in terms of a survival rate.

Survival rate (%)=(Number of surviving insects in test cup/Number of insects provided in untreated cup)×100

As a result, the present compounds 1, 3, 7, 8, 9, 13, 14, 21, 22, 23, 24, 25, 26, 27, 28, 29, 30, 32, 34, 38, 41, 47, 49, 50, 51, 52, 53, 55, 56, 57, 59, 60, 61, 62, 63, 64, 65, 66, 67, 68, 69, 70, 72, 73, 75, 76, 77, 78, 79, 80, 81, 82, 83, 84, 86, 87, 88, 89, 90, 91, 92, 93, 94, 95, 96, 99, 101, 102, 103, 104, 105, 107, 108, 109, 110, 111, 112, 113, 114, 115, 116, 118, 120, 121, 122, 123, 124, 125, 126, 127, 128, 129, 130, 131, 132, 133, 134, 135, 136, 137, 138, 139, 140, 142, 143, 145, 146, 147, 148, 149, 150, 152, 154, 155, 156, 157, 158, 160, 161, 162, 163, 165, 166, 167, 168, 170, 171, 173, 175, 176, 177, 178, 179, 180, 182, 183, 184, 185, 186, 187, 188, 189, 190, 191, 192, 193, 194, 195, 196, 197, 198, 199, 201, 203, 204, 205, 206, 207, 208, 209, 210, 211, 212, 213, 214, 215, 217, 218, 219, 220, 221, 222, 224, 225, 226, 227, 228, 229, 230, 231, 232, 233, 234, 237, 239, 240, 241, 242, 243, 244, 245, 246, 247, 250, 251, 252, 253, 254, 255, 257, 258, 259, 260, 261, 262, 263, 264, 265, 267, 268, 269, 270, 271, 272, 273, 274, 275, 276, 277, 278, 279, 280, 281, 282, 283, 284, 285, 286, 287, 288, 289, 290, 292, 293, 294, 296, 298, 300, 301, 302, 303, 304, 305, 306, 307, 308, 309, 310, 311, 312, 313, 314, 315, 316, 317, 318, 319, 320, 321 and 322 were evaluated as index 3 or greater.

Test Example 4

Nilaparvata lugens

A rice plant was grown in a 90 mL plastic cup, and at a two- or three-leaf stage, the stem was cut at 5 cm from the base. Then, 20 mL/pot of the test solution was sprayed on the plant. After air-dried, 30 first-instar larvae of Nilaparvata lugens were released into the cup, and the cup was sealed with a lid. After 6 days, the number of surviving insects was counted.

The survival rate of tested insects on the basis of the number of insects provided in an untreated cup was calculated by the following equation, and evaluated with indexes of 4: 0%, 3: 1 to 10%, 2: 11 to 40%, 1: 41 to 70%, and 0: >70% in terms of a survival rate.

Survival rate (%)=(Number of surviving insects in test cup/Number of insects provided in untreated cup)×100

As a result, the present compounds 1, 9, 14, 22, 23, 25, 28, 29, 32, 47, 49, 51, 55, 57, 59, 61, 62, 65, 66, 67, 68, 69, 70, 72, 73, 75, 76, 77, 78, 79, 80, 81, 82, 87, 89, 91, 92, 93, 95, 101, 103, 104, 105, 107, 108, 109, 110, 111, 112, 114, 115, 116, 118, 120, 121, 122, 123, 124, 125, 127, 128, 129, 130, 132, 133, 134, 135, 136, 137, 138, 139, 140, 141, 142, 143, 144, 145, 146, 147, 148, 149, 152, 154, 155, 156, 157, 158, 159, 163, 165, 166, 167, 170, 171, 173, 174, 175, 176, 177, 178, 179, 180, 182, 183, 184, 185, 186, 187, 188, 189, 190, 191, 192, 193, 194, 195, 196, 197, 198, 199, 200, 201, 203, 204, 205, 206, 208, 209, 210, 212, 213, 214, 215, 217, 222, 223, 226, 228, 229, 230, 232, 233, 234, 237, 239, 240, 241, 243, 245, 246, 247, 248, 251, 252, 253, 257, 258, 259, 260, 261, 263, 265, 267, 268, 270, 272, 275, 278, 282, 283, 284, 288, 289, 291, 292, 293, 294, 298, 300, 301, 302, 303, 304, 305, 306, 307, 308, 309, 310, 311, 312, 313, 314, 315, 316, 317, 318, 319, 320, 321, 322 and 323 were evaluated as index 3 or greater.

Test Example 5

Musca domestica

A filter paper having a diameter of 5.5 cm was spread on the bottom of a polyethylene cup having a diameter of 5.5 cm, and 0.7 ml of the test solution was added dropwise onto the filter paper. As a bait, 30 mg of sucrose was uniformly placed on the filter paper. Into the polyethylene cup, 10 female imagoes of Musca domestica were released and the cup was sealed with a lid. After 24 hours, the number of dead insects was counted.

The death rate was calculated by the following equation, and evaluated with indexes of 4: 100%, 3: 70 to 99%, 2: 40 to 69%, 1: 10 to 39% and 0: 0 to 9% in terms of a death rate.

Death rate (%)=(Number of dead insects/Number of tested insects)×100

As a result, the present compounds 1, 2, 14, 22, 26, 28, 29, 34, 44, 46, 49, 51, 53, 55, 56, 57, 59, 61, 62, 63, 64, 65, 66, 67, 68, 69, 75, 76, 77, 78, 79, 80, 81, 82, 83, 86, 87, 89, 91, 92, 93, 94, 95, 99, 101, 102, 103, 104, 105, 106, 107, 108, 109, 110, 111, 112, 113, 114, 115, 116, 118, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 152, 153, 154, 155, 156, 157, 158, 159, 160, 161, 162, 163, 164, 165, 167, 168, 170, 171, 173, 175, 176, 177, 178, 179, 182, 183, 184, 185, 186, 188, 189, 190, 191, 192, 193, 194, 195, 196, 197, 198, 199, 201, 202, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 296, 298, 300, 301, 302, 303, 304, 305, 306, 307, 308, 309, 310, 311, 312, 313, 314, 315, 316, 317, 318, 319, 320, 321, 322 and 323 were evaluated as index 3 or greater.

Test Example 6

Blattalla germanica

A filter paper having a diameter of 5.5 cm was spread on the bottom of a polyethylene cup having a diameter of 5.5 cm, and 0.7 ml of the test solution was added dropwise onto the filter paper. As a bait, 30 mg of sucrose was uniformly placed on the filter paper. Into the polyethylene cup, 2 male imagoes of Blattalla germanica were released and the cup was sealed with a lid. After 6 days, the number of dead insects was counted.

The death rate was calculated by the following equation, and evaluated with indexes of 4: 100%, 2: 50%, and 0: 0% in terms of a death rate.

Death rate (%)=(Number of dead insects/Number of tested insects)×100

As a result, the present compounds 1, 2, 3, 5, 12, 14, 15, 21, 22, 25, 34, 44, 49, 51, 53, 55, 57, 59, 63, 64, 65, 66, 68, 69, 75, 76, 77, 78, 79, 80, 81, 82, 83, 87, 89, 91, 92, 93, 95, 101, 103, 104, 105, 107, 108, 109, 110, 111, 112, 113, 114, 115, 116, 118, 120, 121, 122, 123, 124, 125, 126, 127, 128, 129, 130, 131, 132, 133, 134, 135, 136, 137, 138, 139, 140, 141, 142, 143, 144, 145, 146, 147, 148, 152, 154, 155, 156, 157, 158, 160, 163, 165, 166, 167, 170, 171, 173, 175, 176, 177, 178, 179, 182, 183, 184, 185, 186, 188, 189, 190, 192, 194, 195, 196, 197, 198, 199, 201, 203, 204, 206, 208, 210, 211, 212, 214, 215, 217, 218, 220, 222, 224, 225, 226, 228, 229, 230, 231, 232, 233, 234, 236, 237, 238, 239, 240, 241, 244, 245, 246, 247, 248, 250, 251, 252, 253, 257, 258, 259, 260, 261, 262, 263, 264, 265, 267, 268, 269, 270, 271, 272, 275, 277, 278, 282, 283, 287, 289, 290, 291, 292, 293, 294, 296, 298, 300, 301, 302, 303, 304, 305, 307, 308, 309, 310, 311, 312, 313, 314, 315, 316, 317, 318, 319, 321, 322 and 323 were evaluated as index 4.

Test Example 7

Culex pipiens pallens

To 100 mL of ion-exchanged water was added 0.7 mL of the test solution (the active ingredient concentration: 3.5 ppm). Into the solution, 20 last-instar larvae of Culex pipiens pallens were released. After 1 day, the number of dead insects was counted.

The death rate was calculated by the following equation, and evaluated with indexes of 4: 91 to 100%, 2: 11 to 90%, and 0: 0 to 10% in terms of a death rate. Death rate (%)= (Number of dead insects/Number of tested insects)×100

As a result, the present compounds 1, 2, 3, 5, 9, 10, 21, 22, 23, 24, 25, 26, 32, 33, 34, 35, 37, 38, 44, 46, 47, 48, 49, 50, 51, 52, 53, 54, 55, 56, 57, 59, 60, 61, 62, 63, 64, 65, 66, 67, 68, 69, 70, 72, 75, 76, 77, 78, 79, 80, 81, 82, 83, 84, 85, 86, 87, 89, 90, 91, 92, 93, 94, 95, 96, 97, 98, 99, 100, 101, 102, 103, 104, 105, 106, 107, 108, 109, 110, 111, 112, 113, 114, 115, 116, 118, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 152, 153, 154, 155, 156, 157, 158, 159, 160, 161, 162, 163, 165, 166, 167, 168, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 296, 298, 300, 301, 302, 303, 304, 305, 306, 307, 308, 309, 310, 311, 312, 313, 314, 315, 316, 317, 318, 319, 320, 321, 322 and 323 were evaluated as index 4.

Test Example 8

Tetranychus urticae

A leaf of a bean plant with many individuals of Tetranychus urticae being parasitizing thereon was cut out, and then placed on a leaf of a bean plant which was grown for a week after seeding in a 3 ounce cup. It was left for a day so that the insects could move from the cut leaf to the leaf of the bean plant planted in the cup. The next day, the leaf used for inoculation was removed using a pair of tweezers, and 20 mL of the test solution was sprayed on the plant. After 8 days, the number of female imagoes surviving on a primary leaf of the bean plant in the cup was counted.

The effect of the tested compound was evaluated with 5 stages of index 4: 0 to 3; index 3: 4 to 10; index 2: 11 to 20; index 1: 21 to 30, and index 0: 31 or more in terms of the surviving number.

As a result, the present compounds 1, 7, 8, 14, 21, 24, 25, 26, 28, 29, 32, 34, 35, 36, 49, 51, 53, 55, 59, 60, 61, 62, 64, 65, 66, 67, 68, 73, 75, 76, 77, 78, 79, 80, 83, 84, 86, 87, 89, 90, 91, 93, 95, 97, 101, 103, 104, 105, 107, 108, 109, 110, 111, 112, 116, 118, 120, 121, 122, 123, 124, 125, 128, 129, 130, 131, 132, 135, 137, 138, 139, 140, 142, 143, 145, 146, 147, 148, 149, 150, 151, 155, 156, 157, 158, 163, 166, 171, 173, 174, 175, 176, 177, 178, 182, 183, 184, 185, 186, 188, 189, 192, 193, 194, 195, 197, 199, 201, 205, 206, 210, 215, 222, 228, 229, 230, 231, 232, 233, 234, 237, 240, 244, 245, 246, 250, 252, 253, 255, 257, 258, 259, 261, 263, 270, 271, 272, 288, 292, 300, 301, 310, 312, 313, 314, 316, 317, 318, 320, 321 and 323 were evaluated as index 3 or greater.

Test Example 9

Plutella xylostella

On cabbage (Brassicae oleacea) at a 4-leaf stage, 20 mL of the test solution was sprayed. After the test solution was dried, the aboveground part of the cabbage was cut off, and then placed in a polyethylene cup (volume: 100 mL) together with 5 second-instar larvae of *Plutella xylostella*. The cup was kept at 25° C. After 5 days, the number of dead insects was counted.

The death rate was calculated by the following equation, and evaluated with indexes of 4: 100%, 3: 80 to 99%, 2: 60 to 79%, 1: 30 to 59% and 0: 0 to 29% in terms of a death rate.

Death rate (%)=(Number of dead insects/Number of tested insects)×100

As a result, the present compounds 1, 2, 5, 6, 7, 8, 9, 10, 13, 14, 15, 16, 17, 21, 22, 23, 24, 25, 26, 27, 28, 29, 32, 33, 35, 36, 38, 41, 42, 46, 47, 49, 50, 51, 53, 54, 55, 57, 58, 59, 60, 61, 62, 63, 64, 65, 66, 67, 68, 69, 70, 71, 72, 73, 74, 75, 76, 77, 78, 79, 80, 81, 82, 83, 84, 86, 87, 88, 89, 90, 91, 92, 93, 94, 95, 96, 97, 99, 101, 102, 103, 104, 105, 107, 108, 109, 110, 111, 112, 113, 114, 115, 116, 118, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 152, 153, 154, 155, 156, 157, 158, 159, 160, 161, 162, 163, 165, 166, 167, 168, 170, 171, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 296, 298, 299, 300, 301, 303, 304, 305, 306, 307, 308, 309, 310, 311, 312, 313, 314, 315, 316, 317, 318, 319, 320, 321, 322 and 323 were evaluated as index 3 or greater.

Test Example 10

Haemaphysalis longicornis

In 1 mL of acetone, 0.5 mg of any one of the present compounds 1 to 48 was dissolved, and the solution was spread uniformly on one side of a filter paper (TOYO No. 2; 5×10 cm). After dried, the filter paper was folded into two, and the sides were clipped to make a pouch. Into the pouch, tested ticks (Haemaphysalis longicornis, non-blood sucking nymphal ticks, 10 ticks in a group) were placed. The pouch was clipped and sealed. After 2 days, the number of dead ticks was counted.

As a result, the present compounds 1, 3, 25, 30, 49, 51, 55, 57, 59, 64, 65, 66, 68, 69, 70, 75, 76, 77, 78, 79, 80, 81, 82, 89, 91, 92, 93, 101, 103, 104, 107, 108, 109, 110, 111, 115, 116, 118, 122, 128, 131, 134, 136, 137, 138, 139, 140, 141, 142, 143, 144, 145, 146, 147, 148, 149, 152, 153, 154, 155, 156, 157, 163, 165, 166, 167, 170, 175, 176, 177, 178, 179, 182, 183, 184, 185, 186, 188, 189, 194, 195, 198, 199, 202, 205, 206, 207, 210, 214, 215, 220, 221, 225, 229, 230, 231, 232, 233, 234, 236, 237, 238, 239, 240, 241, 242, 243, 244, 245, 246, 247, 252, 257, 261, 262, 266, 270, 271, 272, 273, 275, 279, 281, 284, 291, 292, 300, 301 and 322 gave a death rate of 100%.

Industrial Applicability

The compound of the present invention has an excellent controlling effect on pests, and thus it is useful as an active ingredient of a pesticidal composition.

The invention claimed is:

1. A compound represented by the formula (I):

(I)

wherein,
A and E independently represent a —$R^1$ group, a -$L^1$-$R^1$ group, a —S—C(=O)—$R^1$ group, a —O—C(=O)—$R^1$ group, a —O—S(O)$_2$—$R^1$ group, a —C(=O)—$R^1$ group, a —C(=O)—O—$R^1$ group, a —N($R^2$)—$R^3$ group, a halogen atom, a cyano group, a nitro group, or a hydrogen atom, provided that at least one of A and E is a —$R^1$ group, a -$L^1$-$R^1$ group, a —S—C(=O)—$R^1$ group, a —O—C(=O)—$R^1$ group, a —O—S(O)$_2$—$R^1$ group, a —C(=O)—$R^1$ group, a —C(=O)—O—$R^1$ group, a —N($R^2$)—$R^3$ group, a halogen atom, a cyano group, or a nitro group;
G represents a -$L^2$-$R^1$ group, a —S(O)$_2$—$R^4$ group, or a —N($R^2$)—$R^3$ group;
X represents a —S—$R^5$ group or a —O—$R^6$ group;
Z represents a carbocyclic group having 3 to 14 ring-constituting atoms which is optionally substituted with a group selected from the group a;
$R^1$ represents a C1-C20 chain hydrocarbon group which is optionally substituted with a group selected from the group b, a carbocyclic group having 3 to 14 ring-constituting atoms which is optionally substituted with a group selected from the group a, or a heterocyclic group having 3 to 14 ring-constituting atoms which is optionally substituted with a group selected from the group a;
$R^2$ represents a hydrogen atom or a —$R^1$ group;
$R^3$ represents a —$R^1$ group, a —O—$R^1$ group, a mono(C1-C6 alkyl)amino group, a di(C1-C6 alkyl)amino group, a (C1-C6 alkyl)phenylamino group, a —C(=O)—$R^1$ group, or a —C(=O)—O—$R^1$ group;
$R^4$ represents a C1-C10 hydrocarbon group;
$R^5$ represents a C1-C4 alkyl group substituted with a group selected from the group b, a C5-C10 alkyl group which is optionally substituted with a group selected from the group b, a C3-C10 alkenyl group which is optionally substituted with a group selected from the group c, a C3-C10 alkynyl group which is optionally substituted with a group selected from the group c, a carbocyclic group having 3 to 14 ring-constituting atoms which is optionally substituted with a group selected from the group a, or a heterocyclic group having 3 to 14 ring-constituting atoms which is optionally substituted with a group selected from the group a;
$R^6$ represents a C1-C2 alkyl group substituted with a group selected from the group b, a C3-C10 alkyl group which is optionally substituted with a group selected from the group b, a C3-C10 alkenyl group which is optionally substituted with a group selected from the group c, a C3-C10 alkynyl group which is optionally substituted with a group selected from the group c, a carbocyclic group having 3 to 14 ring-constituting atoms which is optionally substituted with a group selected from the group a, a heterocyclic group having 3 to 14 ring-constituting atoms which is optionally substituted with a group selected from the group a, or a —S(O)$_2$—$R^1$ group;
$L^1$ represents a an oxygen atom, a sulfur atom, a —S(O)— group, or a —S(O)$_2$— group;
$L^2$ represents an oxygen atom or a sulfur atom;
the group a represents the group consisting of a halogen atom, a cyano group, a nitro group, a -$Q^3$ group, a -$L^1$-$Q^3$ group, a —C(=O)-$Q^3$ group, a —C(=O)—O-$Q^3$ group, a —C(=O)—N($Q^1$)-$Q^3$ group, a —O—C(=O)-$Q^3$ group, a —N($Q^3$)—C(=O)-$Q^3$ group, a —N($Q^1$)-$Q^3$ group, and a -$L^1$-T-$Q^3$ group;
the group b represents the group consisting of a halogen atom, a cyano group, a nitro group, a -$Q^2$ group, a -$L^1$-$Q^3$ group, a —C(=O)-$Q^3$ group, a —C(=O)—O-$Q^3$ group, a —C(=O)—N($Q^1$)-$Q^3$ group, a —O—C(=O)-$Q^3$ group, a —N($Q^3$)—C(=O)-$Q^3$ group, a —N($Q^1$)-$Q^3$ group, and a -$L^1$-T-$Q^3$ group;
the group c represents the group consisting of a halogen atom, a -$Q^2$ group, a —C(=O)-$Q^3$ group, a —C(=O)—O-$Q^3$ group, and a —C(=O)—N($Q^1$)-$Q^3$ group;
$Q^1$ represents a C1-C6 chain hydrocarbon group which is optionally substituted with a halogen atom;
$Q^2$ represents a carbocyclic group having 3 to 14 ring-constituting atoms which is optionally substituted with a group selected from the group d, or a heterocyclic group having 3 to 14 ring-constituting atoms which is optionally substituted with a group selected from the group d;
the group d represents the group consisting of a C1-C6 chain hydrocarbon group which is optionally substituted with a halogen atom, a phenyl group which is optionally substituted with a halogen atom, a C1-C6 alkoxy group which is optionally substituted with a halogen atom, a C1-C6 alkylthio group which is optionally substituted with a halogen atom, a halogen atom, a cyano group, and a nitro group;
$Q^3$ represents a -$Q^1$ group or a -$Q^2$ group; and
T represents a C1-C6 alkanediyl group which is optionally substituted with a halogen atom.

2. The compound according to claim 1, wherein
E is a hydrogen atom; and
A is a —$R^1$ group, a -$L^1$-$R^1$ group, a —S—C(=O)—$R^1$ group, a —O—C(=O)—$R^1$ group, a —O—S(O)$_2$—$R^1$ group, a —C(=O)—$R^1$ group, a —C(=O)—O—$R^1$ group, a —N($R^2$)—$R^3$ group, a halogen atom, a cyano group, or a nitro group.

3. The compound according to claim 1, wherein
A is a hydrogen atom; and
E is a —$R^1$ group, a -$L^1$-$R^1$ group, or a halogen atom.

4. The compound according to claim 1, wherein
A is a hydrogen atom; and
E is a methyl group, an ethyl group, or a propyl group.

5. The compound according to claim 1, wherein
G is a —S—$R^{1g}$ group or a —O—$R^{1g}$ group;
X is a —S—$R^{5x}$ group or a —O—$R^{6x}$ group;
Z is a phenyl group which is optionally substituted with a group selected from the group a;
A is a hydrogen atom;
E is a —$R^1$ group or a -$L^1$-$R^1$ group;
$L^1$ is an oxygen atom or a sulfur atom;
$R^1$ is a C1-C10 alkyl group which is optionally substituted with a group selected from the group b, a phenyl group which is optionally substituted with a group selected from the group a, or a thienyl group which is optionally substituted with a group selected from the group a;
$R^{1g}$ is a C1-C10 alkyl group which is optionally substituted with a group selected from the group b, a phenyl group which is optionally substituted with a group selected from the group a, a naphthyl group which is optionally substituted with a group selected from the group a, or a thienyl group which is optionally substituted with a group selected from the group a; and
$R^{6x}$ and $R^{5x}$ independently represent a phenyl group which is optionally substituted with a group selected from the group a, or a naphthyl group which is optionally substituted with a group selected from the group a.

6. The compound according to claim 1, wherein
G is a —S—$R^{1g}$ group or a —O—$R^{1g}$ group;
X is a —O—$R^{6x}$ group;
Z is a phenyl group which is optionally substituted with a group selected from the group a;
A is a hydrogen atom;
E is a —$R^1$ group;
$R^1$ is a C1-C10 alkyl group which is optionally substituted with a group selected from the group b, a phenyl group which is optionally substituted with a group selected from the group a, or a thienyl group which is optionally substituted with a group selected from the group a; $R^{1g}$ is a C1-C10 alkyl group which is optionally substituted with a group selected from the group b, a phenyl group which is optionally substituted with a group selected from the group a, a naphthyl group which is optionally substituted with a group selected from the group a, or a thienyl group which is optionally substituted with a group selected from the group a; and
$R^{6x}$ is a phenyl group which is optionally substituted with a group selected from the group a, or a naphthyl group which is optionally substituted with a group selected from the group a.

7. The compound according to claim 1, wherein
G is a —S—$R^{1g}$ group;
X is a —O—$R^{6x}$ group;
Z is a phenyl group which is optionally substituted with a group selected from the group a;
A is a hydrogen atom;
E is a —$R^1$ group;
$R^1$ is a C1-C10 alkyl group which is optionally substituted with a group selected from the group b, a phenyl group which is optionally substituted with a group selected from the group a, or a thienyl group which is optionally substituted with a group selected from the group a;
$R^{1g}$ is a C1-C10 alkyl group which is optionally substituted with a group selected from the group b, a phenyl group which is optionally substituted with a group selected from the group a, a naphthyl group which is optionally substituted with a group selected from the group a, or a thienyl group which is optionally substituted with a group selected from the group a; and
$R^{6x}$ is a phenyl group which is optionally substituted with a group selected from the group a, or a naphthyl group which is optionally substituted with a group selected from the group a.

8. The compound according to claim 1, wherein
G is a —O—$R^{1g}$ group;
X is a —O—$R^{6x}$ group;
Z is a phenyl group which is optionally substituted with a group selected from the group a;
A is a hydrogen atom;
E is a —$R^1$ group;
$R^1$ is a C1-C10 alkyl group which is optionally substituted with a group selected from the group b, a phenyl group which is optionally substituted with a group selected from the group a, or a thienyl group which is optionally substituted with a group selected from the group a;
$R^{1g}$ is a C1-C10 alkyl group which is optionally substituted with a group selected from the group b, a phenyl group which is optionally substituted with a group selected from the group a, a naphthyl group which is optionally substituted with a group selected from the group a, or a thienyl group which is optionally substituted with a group selected from the group a; and
$R^{6x}$ is a phenyl group which is optionally substituted with a group selected from the group a, or a naphthyl group which is optionally substituted with a group selected from the group a.

9. The compound according to claim 1, wherein
G is a —S—$R^{1g}$ group;
X is a —O—$R^{6x}$ group;
Z is a phenyl group which is optionally substituted with a group selected from the group a;
A is a hydrogen atom;
E is a methyl group, an ethyl group, or a propyl group;
$R^{1g}$ is a C1-C10 alkyl group which is optionally substituted with a group selected from the group b, a phenyl group which is optionally substituted with a group selected from the group a, a naphthyl group which is optionally substituted with a group selected from the group a, or a thienyl group which is optionally substituted with a group selected from the group a; and
$R^{6x}$ is a phenyl group which is optionally substituted with a group selected from the group a; or a naphthyl group which is optionally substituted with a group selected from the group a.

10. The compound according to claim 1, wherein
G is a —S—$R^{1g}$ group;
X is a —O—$R^{6x}$ group;
Z is a phenyl group which is optionally substituted with a group selected from the group a;
A is a hydrogen atom;
E is a —$R^1$ group;
$R^1$ is a C1-C10 alkyl group which is optionally substituted with a group selected from the group b, a phenyl group which is optionally substituted with a group selected from the group a, or a thienyl group which is optionally substituted with a group selected from the group a;
$R^{1g}$ is a phenyl group which is optionally substituted with a group selected from the group a, or a naphthyl group which is optionally substituted with a group selected from the group a; and
$R^{6x}$ is a phenyl group which is optionally substituted with a group selected from the group a, or a naphthyl group which is optionally substituted with a group selected from the group a.

11. The compound according to claim 1, wherein
G is a —S—$R^{1g}$ group;
X is a —O—$R^{6x}$ group;
Z is a phenyl group which is optionally substituted with a group selected from the group a;
A is a hydrogen atom;
E is a methyl group, an ethyl group, or a propyl group;
$R^{1g}$ is a phenyl group which is optionally substituted with a group selected from the group a, or a naphthyl group which is optionally substituted with a group selected from the group a; and
$R^{6x}$ is a phenyl group which is optionally substituted with a group selected from the group a; or a naphthyl group which is optionally substituted with a group selected from the group a.

12. The compound according to claim 1, wherein
G is a —O—$R^{1g}$ group;
X is a —O—$R^{6x}$ group;
Z is a phenyl group which is optionally substituted with a group selected from the group a;
A is a hydrogen atom;
E is a methyl group, an ethyl group, or a propyl group;
$R^{1g}$ is a C1-C10 alkyl group which is optionally substituted with a group selected from the group b, a phenyl group which is optionally substituted with a group selected from the group a, a naphthyl group which is optionally substituted with a group selected from the group a, or a thienyl group which is optionally substituted with a group selected from the group a; and
$R^{6x}$ is a phenyl group which is optionally substituted with a group selected from the group a, or a naphthyl group which is optionally substituted with a group selected from the group a.

13. The compound according to claim 1, wherein
G is a —O—$R^{1g}$ group;
X is a —O—$R^{6x}$ group;
Z is a phenyl group which is optionally substituted with a group selected from the group a;
A is a hydrogen atom;
E is a —$R^1$ group;
$R^1$ is a C1-C10 alkyl group which is optionally substituted with a group selected from the group b, a phenyl group which is optionally substituted with a group selected from the group a, or a thienyl group which is optionally substituted with a group selected from the group a;
$R^{1g}$ is a phenyl group which is optionally substituted with a group selected from the group a, or a naphthyl group which is optionally substituted with a group selected from the group a; and
$R^{6x}$ is a phenyl group which is optionally substituted with a group selected from the group a, or a naphthyl group which is optionally substituted with a group selected from the group a.

14. The compound according to claim 1, wherein
G is a —O—$R^{1g}$ group;
X is a —O—$R^{6x}$ group;
Z is a phenyl group which is optionally substituted with a group selected from the group a;
A is a hydrogen atom;
E is a methyl group, an ethyl group, or a propyl group;
$R^{1g}$ is a phenyl group which is optionally substituted with a group selected from the group a; or a naphthyl group which is optionally substituted with a group selected from the group a; and
$R^{6x}$ is a phenyl group which is optionally substituted with a group selected from the group a; or a naphthyl group which is optionally substituted with a group selected from the group a.

15. The compound according to claim 1, wherein
A is a hydrogen atom;
E is a —$R^1$ group, a —S—$R^1$ group, or a halogen atom;
G is a —S—$R^{1g}$ group or a —O—$R^{1g}$ group;
X is a —S—$R^{5x}$ group or a —O—$R^{6x}$ group;
Z is a phenyl group which is optionally substituted with a group selected from the group a;
$R^1$ is a C1-C10 alkyl group, a phenyl group, or a thienyl group;
$R^{1g}$ is a C1-C20 chain hydrocarbon group which is optionally substituted with a group selected from the group b, or a phenyl group which is optionally substituted with a group selected from the group a; and
$R^{6x}$ and $R^{5x}$ independently represent a phenyl group which is optionally substituted with a group selected from the group a.

16. A pesticidal composition comprising the compound according to claim 1 as an active ingredient.

17. A method of controlling a pest, which comprises applying the compound according to claim 1 to the pest or a place where the pest inhabits.

* * * * *